(12) United States Patent
Lawrence et al.

(10) Patent No.: US 9,681,646 B2
(45) Date of Patent: Jun. 20, 2017

(54) DOSAGE COMPENSATING TRANSGENES AND CELLS

(71) Applicant: UNIVERSITY OF MASSACHUSETTS, Boston, MA (US)

(72) Inventors: Jeanne B. Lawrence, Mapleville, RI (US); Jun Jiang, Shrewsbury, MA (US); Lisa L. Hall, Framingham, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/215,997

(22) Filed: Mar. 17, 2014

(65) Prior Publication Data

US 2014/0294785 A1  Oct. 2, 2014

Related U.S. Application Data

(60) Provisional application No. 61/790,917, filed on Mar. 15, 2013.

(51) Int. Cl.
| | |
|---|---|
| *C12N 15/113* | (2010.01) |
| *C12N 15/63* | (2006.01) |
| *A01K 67/027* | (2006.01) |
| *C07K 14/47* | (2006.01) |
| *C12N 5/0789* | (2010.01) |
| *C12N 9/12* | (2006.01) |

(52) U.S. Cl.
CPC ...... *A01K 67/0275* (2013.01); *C07K 14/4703* (2013.01); *C12N 5/0647* (2013.01); *C12N 9/12* (2013.01); *C12N 2510/00* (2013.01)

(58) Field of Classification Search
None
See application file for complete search history.

(56) References Cited

U.S. PATENT DOCUMENTS

| | | |
|---|---|---|
| 9,297,023 B2 | 3/2016 | Lawrence et al. |
| 2010/0160417 A1 | 6/2010 | Lawrence et al. |
| 2012/0142758 A1 | 6/2012 | Collard et al. |
| 2012/0252123 A1 | 10/2012 | Lawrence et al. |
| 2016/0143951 A1 | 5/2016 | Lawrence et al. |
| 2016/0264994 A1 | 9/2016 | Lawrence et al. |

OTHER PUBLICATIONS

Fotaki et al., Dyrk1A haploinsufficiency affects viability and causes developmental delay and abnormal brain morphology in mice. Mol Cell Biol. Sep. 2002;22(18):6636-47.*
Song et al., Isolation of Human and Murine Homologues of the Drosophila Minibrain Gene: Human Homologue Maps to 21q22.2 in the Down Syndrome "Critical Region". Genomics 38, 331-339 (1996).*
Song et al., Modeling Disease in Human ESCs Using an Efficient BAC-Based Homologous Recombination System. Cell Stem Cell 6, 80-89, Jan. 8, 2010.*
Dragatsis et al., Huntingtin-associated protein 1 (Hap1) mutant mice bypassing the early postnatal lethality are neuroanatomically normal and fertile but display growth retardation. Human Molecular Genetics, 2004, vol. 13, No. 24 3115-3125.*
Antonarakis et al., "The challenge of Down syndrome", Trends Mol Med., vol. 12:473-479 (2006).
Bailey et al., "Molecular evidence for a relationship between LINE-1 elements and X chromosome inactivation: The Lyon repeat hypothesis", PNAS, vol. 97:6634-6639 (2000).
Biancotti et al., "Human Embryonic Stem Cells as Models for Aneuploid Chromosomal Syndromes", Stem Cells, vol. 28:1530-1540 (2010).
Brockdorff et al., "X Chromosome Inactivation and the Xist Gene", Cell. Mol. Life Sci., 1998, vol. 54, pp. 104-112.
Brockdorff, N, "Chromosome silencing mechanisms in X-chromosome inactivation: unknown unknowns", Development, vol. 138:5057-5065 (2011).
Brown et al., "Expression of genes from the human active and inactive X chromosomes", Am J Hum Genet, vol. 60:1333-1343 (1997).
Brown, C. J. et al. The human XIST gene: analysis of a 17 kb inactive X-specific RNA that contains conserved repeats and is highly localized within the nucleus, Cell 71:527-542 (1992).
Carrel et al., "X-inactivation profile reveals extensive variability in X-linked gene expression in females", Nature, vol. 434:400-404 (2005).
Cathomen et al., "Zinc-finger Nucleases: The Next Generation Emerges", Molecular Therapy, vol. 16:1200-1207 (2008).
Chow et al., "Characterization of expression at the human *XIST* locus in somatic, embryonal carcinoma, and transgenic cell lines", Genomics, vol. 82:309-322 (2003).
Chow et al., "Inducible XIST-dependent X-chromosome inactivation in human somatic cells is reversible", Proc. Natl. Acad. Sci. USA, vol. 104:10104-10109 (2007).
Clemson et al., "The X chromosome is organized into a gene-rich outer rim and an internal core containing silenced nongenic sequences", Proc Natl Acad Sci USA 103, 7688-7693 (2006).
Clemson et al., "XIST RNA Paints the Inactive X Chromosome at Interphase: Evidence for a Novel RNA Involved in Nuclear/Chromosome Structure", J. Cell Biol., vol. 132:259-275 (1996).
Cotton et al., "Chromosome-wide DNA methylation analysis predicts human tissue-specific X inactivation", Human Genetics, vol. 130:187-201 (2011).
Csankovszki et al., "Synergism of Xist RNA, DNA Methylation, and Histone Hypoacetylation in Maintaining X Chromosome Inactivation", J. of Cell Biol., vol. 153:773-783 (2001).
Debrand et al., "Functional Analysis of the DXPas34 Locus, a 3' Regulator of Xist Expression", Mol. Cell. Bio., vol. 19:8513-8525 (1999).
DeKelver et al., "Functional genomics, proteomics, and regulatory DNA analysis in isogenic settings using zinc finger nuclease-driven transgenesis into a safe harbor locus in the human genome", Genome Research, vol. 20:1133-1142 (2010).

(Continued)

*Primary Examiner* — Kevin Hill
*Assistant Examiner* — Arthur S Leonard
(74) *Attorney, Agent, or Firm* — Fish & Richardson P.C.

(57) ABSTRACT

Methods and compositions for reducing expression of genes on Chromosome 21 ("Chr 21") by targeting an XIST transgene to the Dual specificity tyrosine-phosphorylation-regulated kinase 1A (DYRK1A) gene or a Regulator of calcineurin 1 (RCAN1) gene, and cells and transgenic animals comprising an XIST transgene inserted into a DYRK1A or RCAN1 allele, e.g., cells and animals trisomic for human Chr 21 and mouse Chr 16.

17 Claims, 74 Drawing Sheets

(56) References Cited

OTHER PUBLICATIONS

Douillard-Guilloux et al., "Partial phenotypic correction and immune tolerance induction to enzyme replacement therapy after hematopoietic stem cell gene transfer of alpha-glucosidase in Pompe disease", J Gene Med., vol. 11:279-287 (2009).
Gardiner, "Molecular basis of pharmacotherapies for cognition in Down syndrome", Trends Pharmacol Sci., vol. 31:66-73 (2010).
Goodrich et al. "From bacteria to humans, chromatin to elongation, and activation to repression: The expanding roles of nonconding RNAs in regulating transcription", Crit. Rev. Biochem. Mol. Biol., vol. 44:3-15 (2009).
Greene et al., "The Human Xist Gene Promoter Prevents Silencing of an Integrated Reporter Gene", Blood, vol. 104(11), Abstract #2114 (2004).
Guidi, et al., "Widespread Proliferation Impairment and Hypocellularity in the Cerebellum of Fetuses with Down Syndrome", Brain Pathol., vol. 21:361-373 (2011).
Hall et al., "An ectopic human XIST gene can induce chromosome inactivation in postdifferentiation human HT-1080 cells", Proc. Natl. Acad. Sci. USA, vol. 99:8677-8682 (2002).
Hall et al., "Unbalanced X;autosome translocations provide evidence for sequence specificity in the association of XIST RNA with chromatin", Hum Mol Genet., vol. 11:3157-3165 (2002).
Hall et al., "The cell biology of a novel chromosomal RNA: chromosome painting by XIST/Xist RNA initiates a remodeling cascade", Semin Cell Dev Biol, vol. 14:369-378 (2003).
Haydar et al., "Trisomy and early brain development", Trends Neurosci, vol. 35:81-91 (2012).
Heard, "Delving into the diversity of facultative heterochromatin: the epigenetics of the inactive X chromosome", Curr Opin Genet Dev., vol. 15:482-489 (2005).
Hockemeyer et al., "Efficient targeting of expressed and silent genes in human ESCs and iPSCs using zinc-finger nucleases", Nat Biotechnol, vol. 27:851-857 (2009).
Khalil et al., "Many human large intergenic noncoding RNAs associate with chromatin-modifying complexes and affect gene expression", PNAS, vol. 106:11667-11672 (2009).
Lau et al., "Skewed X-Chromosome Inactivation is Common in Fetuses or Newborns Associated with Confined Placental Mosaicism", Am. J. Hum. Genet., vol. 61:1353-1361 (1997).
Lavon et al., "Derivation of Euploid Human Embryonic Stem Cells from Aneuploid Embryos", Stem Cells, vol. 26:1874-1882 (2008).
Lee et al., "A 450 kb Transgene Displays Properties of the Mammalian X-Inactivation Center", Cell, vol. 86:83-94 (1996).
Lee, "Gracefully ageing at 50, X-chromosome inactivation becomes a paradigm for RNA and chromatin control", Nat Rev Mol Cell Bioll, vol. 12:815-826 (2011).
Li et al., "Trisomy correction in down syndrome induced pluripotent stem cells", Cell Stem Cell, vol. 11:615-619 (2012).
Liu et al., "Mouse Models for Down Syndrome-Associated Developmental Cognitive Disabilities", Dev Neurosci, vol. 33:404-413 (2011).
Lockstone et al., "Gene expression profiling in the adult Down syndrome brain", Genomics, vol. 90:647-660 (2007).
Lyon, "Gene Action in the X-chromosome of the Mouse (*Mus musculus* L.)," Nature, vol. 190:372-373 (1961).
McNeil et al., "Word frequency analysis reveals enrichment of dinucleotide repeats on the human X chromosome and [GATA]$_n$ in the X escape region", Genome Research, vol. 16:477-484 (2006).
Megarbane, et al., "The 50th anniversary of the discovery of trisomy 21: The past, present, and future of research and treatment of Down syndrome", Genetics in medicine: official journal of the American College of Medical Genetics, vol. 11:611-616 (2009).
Migeon et al., "X Inactivation in Triploidy and Trisomy: The Search for Autosomal Transfactors That Choose the Active X", European Journal of Human Genetics, published on-line Oct. 31, 2007, vol. 16:153-162 (2008).

Miller et al., "An improved zinc-finger nuclease architecture for highly specific genome editing", Nat Biotechnol, vol. 25:778-785 (2007).
Moehle et al., "Targeted gene addition into a specified location in the human genome using designed zinc finger nucleases", Proc. Natl. Acad. Sci. USA, vol. 104:3055-3060 (2007).
O'Doherty et al., "An Aneuploid Mouse Strain Carrying Human Chromosome 21 with Down Syndrome Phenotypes", Science, vol. 309:2033-2037 (2005).
Park et al., "Function and regulation of Dyrk1A: towards understanding Down syndrome", Cellular and molecular life sciences: CMLS, vol. 66:3235-3240 (2009).
Porteus, "Mammalian Gene Targeting with Designed Zinc Finger Nucleases", Molecular Therapy, 2006, vol. 13(2), pp. 438-446.
Prandini et al., "Natural Gene-Expression Variation in Down Syndrome Modulates the Outcome of Gene-Dosage Imbalance", Am J Hum Genet., vol. 81:252-263 (2007).
Reeves, "Down syndrome mouse models are looking up", Trends Mol Med., vol. 12:237-240 (2006).
Savarese et al., "Hematopoietic Precursor Cells Transiently Reestablish Permissiveness for X Inactivation", Molecular and Cellular Biology, 2006, vol. 26(19), pp. 7167-7177.
Sharp et al., "DNA methylation profiles of human active and inactive X chromosomes", Genome research, vol. 21:1592-1600 (2011).
Tam et al., "The 4q subtelomere harboring the FSHD locus is specifically anchored with peripheral heterochromatic unlike most human telomeres",. Journal of Cell Biology, vol. 167:269-279 (2004).
Tanzi et al., "Twenty Years of the Alzheimer's Disease Amyloid Hypothesis: A Genetic Perspective", Cell, vol. 120:545-555 (2005).
Urnov et al., Genome editing with engineered zinc finger nucleases, Nat Rev Genet., vol. 11:636-646 (2010).
Webb et al., "β-Secretases, Alzheimer's Disease, and Down Syndrome", Curr Gerontol Geriatr Res, vol. 2012, Article ID 362839, 8 pp. (2012).
Wutz et al., "A shift from reversible to irreversible X inactivation is triggered during ES cell differentiation", Mol Cell, vol. 5:695-705 (2000).
Wutz et al., "Chromosomal silencing and localization are mediated by different domains of Xist RNA", Nat. Genetics, vol. 30:167-174 (2002).
Wutz et al., "Xinactivation Xplained", Curr. Opin. Genet Dev., vol. 17:387-393 (2007).
Wutz, "Gene silencing in X-chromosome inactivation: advances in understanding facultative heterochromatin formation", Nat Rev Genet, vol. 12:542-553 (2011).
Yabut et al., "Dyrk1A Overexpression Inhibits Proliferation and Induces Premature Neuronal Differentiation of Neural Progenitor Cells", J Neurosci, vol. 30:4004-4014 (2010).
Yahya-Graison et al., "Classification of Human Chromosome 21 Gene-Expression Variations in Down Syndrome: Impact on Disease Phenotypes", Am J Hum Genet, vol. 81:475-491 (2007).
International Preliminary Report on Patentability (IPRP) mailed in Application No. PCT/US2009/052318 on Feb. 1, 2011, Written Opinion dated Apr. 30, 2010.
International Search Report and Written Opinion for PCT/US2009/052318, mailed Apr. 30, 2010 (17 pages).
Copenheaver, Brian R., "Notification of Transmittal of the International Search Report and the Written Opinion of the International Searching Authority, or the Declaration", International Application No. PCT/US2010/027525, mailed on Sep. 12, 2014, 17 pages.
Lepagnol-Bestel, Aude-Marie et al., "DYRK1A interacts with the REST/NRSF-SWI/SNF chromatin remodeling complex to deregulate gene clusters involved in the neuronal phenotypic traits of Down syndrome", Human Molecular Genetics, vol. 18(8):1405-1414, 2009.
Canzonetta et al., DYRK1A-Dosage Imbalance Perturbs NRSF/REST Levels, Deregulating Pluripotency and Embryonic Stem Cell Fate in Down Syndrome, The American Journal of Human Genetics, vol. 83:388-400, 2008.
Jiang, Jun et al., "Translating dosage compensation to trisomy 21", Nature, vol. 500:296-300, 2013.

(56) References Cited

OTHER PUBLICATIONS

Fish & Richardson P.C., Preliminary Amendment in Response to Restriction Requirement of Jan. 23, 2015 in U.S. Appl. No. 14/045,057, filed Mar. 20, 2015, 6 pages.

Fish & Richardson P.C., Preliminary Amendment in U.S. Appl. No. 13/483,240, filed Nov. 16, 2012.

Fish & Richardson P.C., Response to Final Office Action in U.S. Appl. No. 13/483,240, filed Jun. 24, 2013, 6 pages.

Fish & Richardson P.C., Response to Final Office Action in U.S. Appl. No. 14/045,057, filed Oct. 21, 2015, 4 pages.

Fish & Richardson P.C., Response to Office Action in U.S. Appl. No. 13/483,240, filed Mar. 26, 2013, 8 pages.

Fish & Richardson P.C., Response to Office Action in U.S. Appl. No. 14/045,057, filed Aug. 27, 2015, 8 pages.

Fish & Richardson P.C., Response to Office Action in U.S. Appl. No. 12/512,964, filed Jan. 23, 2012 (10 pages).

Fish & Richardson P.C., Response to Restriction Requirement in U.S. Appl. No. 12/512,964, filed Jul. 6, 2011 (8 pages).

Fish & Richardson P.C., Response to Restriction Requirement in U.S. Appl. No. 13/483,240, filed Nov. 7, 2012 (6 pages).

International Preliminary Report on Patentability (IPRP) mailed in Application No. PCT/US2014/027525 on Sep. 15, 2015, 10 pages.

International Search Report and Written Opinion for PCT/US2014/027525, mailed Sep. 12, 2014 (13 pages).

U.S. Patent and Trademark Office Notice of Allowability in U.S. Appl. No. 12/512,964, mailed Apr. 24, 2012 (5 pages).

U.S. Patent and Trademark Office Notice of Allowance in U.S. Appl. No. 12/512,964, mailed Mar. 5, 2012 (9 pages).

U.S. Patent and Trademark Office, Final Office Action in U.S. Appl. No. 13/483,240, mailed May 28, 2013, 6 pages.

U.S. Patent and Trademark Office, Final Office Action in U.S. Appl. No. 14/045,057, mailed Sep. 15, 2015, 6 pages.

U.S. Patent and Trademark Office, Non Final Office Action in U.S. Appl. No. 12/512,964, mailed Sep. 21, 2011 (12 pages).

U.S. Patent and Trademark Office, Office Action in U.S. Appl. No. 14/045,057, mailed Apr. 27, 2015, 11 pages.

U.S. Patent and Trademark Office, Office Action in U.S. Appl. No. 13/483,240, mailed Jan. 9, 2013 (9 pages).

U.S. Patent and Trademark Office, Restriction Requirement in U.S. Appl. No. 14/045,057, mailed Jan. 23, 2015, 9 pages.

U.S. Patent and Trademark Office, Restriction Requirement in U.S. Appl. No. 12/512,964, mailed Apr. 6, 2011 (9 pages).

U.S. Patent and Trademark Office, Restriction Requirement in U.S. Appl. No. 13/483,240, mailed Oct. 11, 2012 (9 pages).

U.S. Patent and Trademark Office, Notice of Allowance in U.S. Appl. No. 13/483,240, mailed Jul. 3, 2013, 6 pages.

U.S. Patent and Trademark Office, Notice of Allowance in U.S. Appl. No. 14/045,057, mailed Nov. 19, 2015, 5 pages.

\* cited by examiner

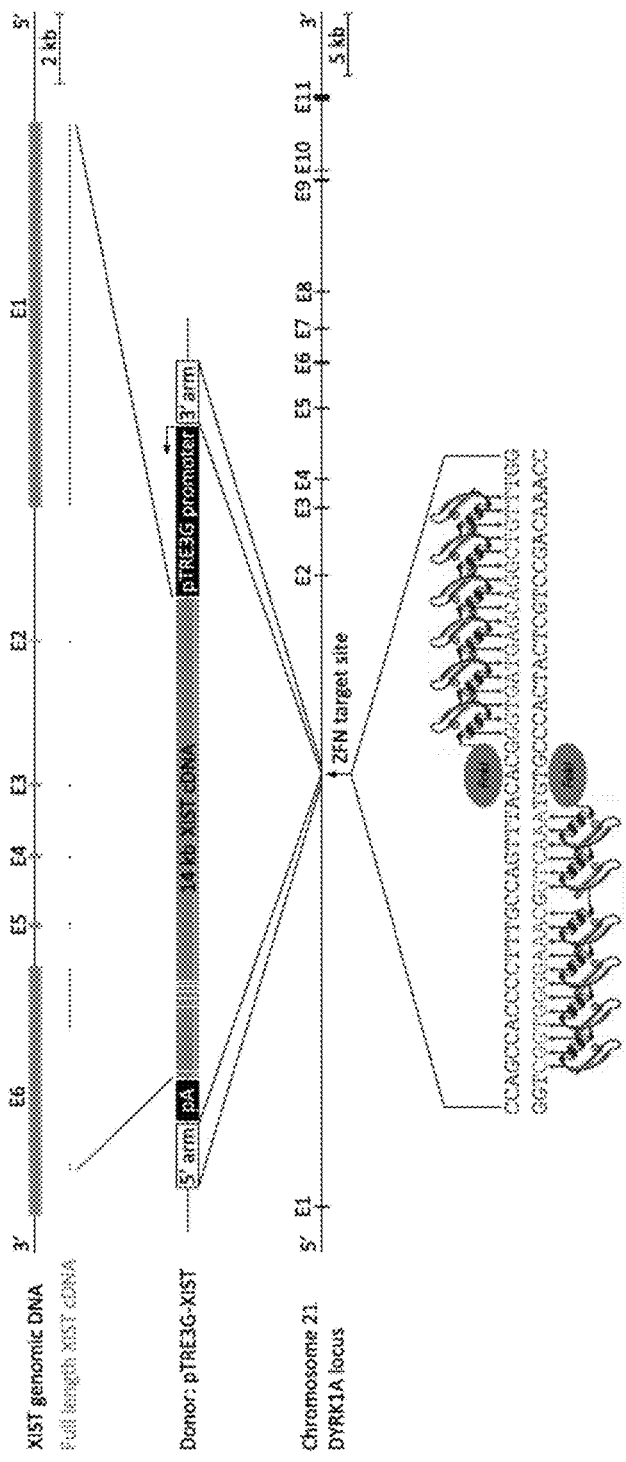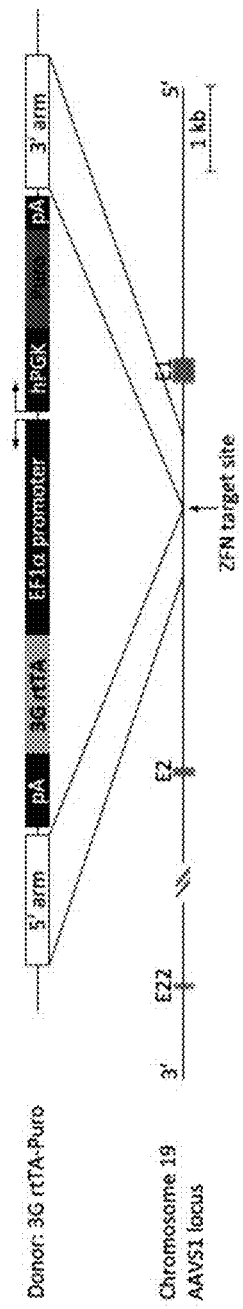
FIG. 2A
FIG. 2B

FIG. 10A sequence of construct 1

```
LOCUS       pTRE3G/DYRK1A LA & RA/BglII/KpnI linker/FL XIST 18515 bp    DNA    SYN
            29-Nov-2012
DEFINITION  pTRE3G/DYRK1A LA & RA/BglII/KpnI linker/FL XIST
ACCESSION
KEYWORDS
SOURCE
  ORGANISM  other sequences; artificial sequences; vectors.
FEATURES            Location/Qualifiers
     source          1..18515
                     /organism="pTRE3G/DYRK1A LA & RA/BglII/KpnI linker/FL XIST"
                     /mol_type="other DNA"
     promoter        7..382
                     /label="pTRE3G promoter"
     misc_feature    289..308
                     /label="pCEP_fwd_primer"
     misc_feature    291..315
                     /label="LNCX_primer"
     misc_feature    454..14183
                     /label="human FL XIST"
     misc_feature    14460..14475
                     /label="SV40_int"
     misc_feature    14481..14528
                     /label="SV40_3_splice"
     misc_feature    14385..15182
                     /label="SV40_pA"
     terminator      15104..15223
                     /label="SV40_PA_terminator"
     misc_feature    15192..15211
                     /label="EBV_rev_primer"
     misc_feature    15423..16112
                     /label="DYRK1A left arm"
     rep_origin      complement(16158..16777)
                     /label="pBR322_origin"
     CDS             complement(16932..17792)
                     /label="Ampicillin"
                     /gene="Ampicillin"
                     /note="ORF frame 3"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"
     gene            complement(16932..17792)
                     /label="Ampicillin"
                     /gene="Ampicillin"
     promoter        complement(17834..17862)
                     /label="AmpR_promoter"
     misc_feature    18003..18510
                     /label="DYRK1A right arm"
ORIGIN
    1 CTCGAGTTTA CTCCCTATCA GTGATAGAGA ACGTATGAAG AGTTTACTCC CTATCAGTGA
   61 TAGAGAACGT ATGCAGACTT TACTCCCTAT CAGTGATAGA GAACGTATAA GGAGTTTACT
  121 CCCTATCAGT GATAGAGAAC GTATGACCAG TTTACTCCCT ATCAGTGATA GAGAACGTAT
  181 CTACAGTTTA CTCCCTATCA GTGATAGAGA ACGTATATCC AGTTTACTCC CTATCAGTGA
  241 TAGAGAACGT ATAAGCTTTA GGCGTGTACG GTGGGCGCCT ATAAAAGCAG AGCTCGTTTA
  301 GTGAACCGTC AGATCGCCTG GAGCAATTCC ACAACACTTT GTCTTATAC CAACTTTCCG
  361 TACCACTTCC TACCCTCGTA AAGTCGACAC CGGGGCCCAG ATCTGGTACC GAGCTCGGAT
  421 CCACTAGTCC AGTGTGGTGG AATTCTGCAG ATtctagaac attttctagt cccccaacac
  481 cctttatggc gtatttcttt aaaaaaatca cctaaattcc ataaaatatt tttttaaatt
  541 ctatactttc tcctagtgtc ttcttgacac gtcctccata ttttttttaaa gaaagtattt
  601 ggaatatttt gaggcaattt ttaatattta aggaattttt ctttggaatc attttggtg
  661 acatctctgt ttttgtggaa tcagttttttt actcttccac tctcttttct atattttgcc
```

FIG. 10A sequence of construct 1 (continued)

```
 721 catcgggct gcggatacct ggttttatta ttttttcttt gcccaacggg gccgtggata
 781 cctgccttt  aattctttt  tattcgccca tcgggccgc  ggatacctgc tttttatttt
 841 tttttcctta gcccatcggg gtatcggata cctgctgatt cccttcccct ctgaaccccc
 901 aacactctgg cccatcgggg tgacggatat ctgcttttta aaaatttct  tttttggcc
 961 catcgggct  tcggatacct gcttttttt  ttttatttt  ccttgcccat cggggcctcg
1021 gatacctgct ttaatttttg ttttttctgcc catcgggcc  gcggatacct gctttgattt
1081 ttttttttca tcgccatcg  gtgctttta  tggatgaaaa aatgttggtt ttgtgggttg
1141 ttgcactctc tggaatatct acactttttt ttgctgctga tcatttggtg gtgtgtgagt
1201 gtaccctaccg ctttggcaga gaatgactct gcagttaagc taagggcgtg ttcagattgt
1261 ggaggaaaag tggccgccat tttagacttg ccgcataact cggcttaggg ctagtcgttt
1321 gtgctaagtt aaactaggga ggcaagatgg atgatagcag gtcaggcaga ggaagtcatg
1381 tgcattgcat gagctaaacc tatctgaatg aattgatttg gggcttgtta ggagctttgc
1441 gtgattgttg tatcgggagg cagtaagaat catctttat  cagtacaagg gactagttaa
1501 aaatgaagg  ttaggaaaga ctaaggtgca gggcttaaaa tggcgatttt gacattgcgg
1561 cattgctcag catggcggc  tgtgctttgt taggttgtcc aaaatggcgg atccagttct
1621 gtcgcagtgt tcaagtggcg ggaaggccac atcatgatgg gcgaggcttt gttaagtggt
1681 tagcatggtg gtggacatgt gcggtcacac aggaaaagat ggcggctgaa ggtcttgccg
1741 cagtgtaaaa catggcggc  ctctttgtct ttgctgtgtg cttttcgtgt tgggttttgc
1801 cgcagggaca atatggcagg cgttgtcata tgtatatcat ggctttttgtc acgtggacat
1861 catggcgggc ttgccgcatt gttaaagatg gcgggttttg ccgcctagtg ccacgcagag
1921 cgggagaaaa ggtgggatgg acagtgctgg attgctgcat aacccaacca attagaaatg
1981 ggggtggaat tgatcacagc caattagagc agaagatgga attagactga tgacacactg
2041 tccagctact cagcgaagac ctgggtgaat tagcatggca cttcgcagct gtctttagcc
2101 agtcaggaga aagaagtgga ggggccacgt gtatgtctcc cagtgggcgg tacaccaggt
2161 gttttcaagg tcttttcaag gacatttagc ctttccacct ctgtccctc  ttatttgtcc
2221 cctcctgtcc agtgctgcct cttgcagtgc tggatatctg gctgtgtggt ctgaacctcc
2281 ctccattcct ctgtattggt gcctcaccta aggctaagta tacctccccc cccaccccc
2341 aacccccca  actcccacc  cccacccccc acccccacc  tcccaccccc cctacccccc
2401 taccccccta cccccctctg gtctgccctg cactgcactg ttgccatggg cagtgctcca
2461 ggcctgcttg gtgtggacat ggtggtgagc cgtggcaagg accagaatgg atcacagatg
2521 atcgttggcc aacaggtggc agaagaggaa ttcctgcctt cctcaagagg aacacctacc
2581 ccttggctaa tgctggggtc ggatttgat  ttatatttat cttttggatg tcagtcatac
2641 agtctgattt tgtggtttgc tagtgtttga atttaagtct taagtgacta ttatagaaat
2701 gtattaagag gctttatttg tagaattcac tttaattaca tttaatgagt ttttgttttg
2761 agttccttaa aattccttaa agtttttagc ttctcattac aaattcctta acttttttt
2821 ggcagtagat agtcaaagtc aaatcatttc taatgtttta aaaatgtgct ggtcattttc
2881 tttgaaattg acttaactat tttcctttga agagtctgta gcacagaaac agtaaaaaat
2941 ttaacttcat gacctaatgt aaaaaagagt gtttgaaggt ttacacaggt ccaggccttg
3001 ctttgttccc atccttgatg ctgcactaat tgactaatca cctacttatc agacaggaaa
3061 cttgaattgc tgtggtctgg tgtcctctat tcagacttat tatattggag tatttcaatt
3121 tttcgttgta tcctgcctgc ctagcatcca gttcctcccc agccctgctc ccagcaaacc
3181 cctagtctag ccccagccct actcccaccc ggcccagcc  ctgcccagg  cccagtcccc
3241 taacccccca gccctaggcc cagtcccagt cctagttcct cagtctgtcc agcttctcc
3301 gaaagtcact ctaattttca ttgattcagt gctcaaaata agttgtccat tggtatccta
3361 ttatactggg atattccgtt taccttggc  attgctgatc ttcagtactg actccttgac
3421 catttttcagt taagcataca atcccatttg tctgtgatct caggacaaag aatttcctta
3481 ctcggtacgt tgaagttagg gaatgtcaat tgagagcttt ctatcagagc attattgccc
3541 acaatttgag ttacttatca ttttctcgat cccctgccct taaaggagaa accatttctc
3601 tgtcattgct tctgtagtca cagtcccaat tttgagtagt gatcttttct tgtgtactgt
3661 gttggccacc taaaactctt tgcattgagt aaaattctaa ttgccaataa tcctacccat
3721 tggattagac agcactctga accccatttg cattcagcag ggggtcgcag acaacccgtc
3781 ttttgttgga cagttaaaat gctcagtccc aattgtcata gctttgccta ttaaacaaag
3841 gcaccctact gcgctttttg ctgtgcttct ggagaatcct gctgttcttg gacaattaaa
3901 gaacaaagta gtaattgcta attgtctcac ccattaatca tgaagactac cagtcgccct
3961 tgcatttgcc ttgaggcagc gctgactacc tgagatttaa gagtttctta aattattgag
4021 taaaatccca attatccata gttctgttag ttacactatg gcctttgcaa acatctttgc
4081 ataacagcag tgggactgac tcattcttag agcccctttcc cttggaatat taatggatac
4141 aatgtaatt  atcatggtt  ctgcgtaaca gagaagaccc acttatgtgt atgcctttat
4201 cattgctcct agatagtgtg aactacctca cacccttgcat taatatgtaa aacactaatt
4261 gcccatagtc ccactcatta gtctaggatg tcctctttgc cattgctgct gagttctgac
4321 tacccaagtt tccttctctt aaacagttga tatgcataat tgcatatatt catggttctg
4381 tgcaataaaa atggattctc accccatccc accttctgtg ggatgttgct aacgagtgca
4441 gattattcaa taacagctct tgaacagtta atttgcacag ttgcaattgt ccagagtcct
4501 gtccattaga aagggactct gtatcctatt tgcacgctac aatgtgggct gatcacccaa
4561 ggactcttct tgtgcattga tgttcataat tgtatttgtc cacgatcttg tgcactaacc
```

FIG. 10A sequence of construct 1 (continued)

```
4621 cttccactcc ctttgtattc cagcagggga cccttactac tcaagacctc tgtactagga
4681 cagtttatgt gcacaatcct aattgattag aactgagtct tttatatcaa ggtccctgca
4741 tcatctttgc tttacatcaa gagggtgctg gttactaat gccctcctc cagaaattat
4801 tgatgtgcaa aatgcaattt ccctatctgc tgttagtctg gggtctcatc ccctcatatt
4861 cctttgtct tacagcaggg ggtacttggg actgttaatg cgcataattg caattatggt
4921 cttttccatt aaattaagat cccaactgct cacaccctct tagcattaca gtagagggtg
4981 ctaatcacaa ggacatttct tttgtactgt taatgtgcta cttgcatttg tccctcttcc
5041 tgtgcactaa agaccccact cacttcccta gtgttcagca gtggatgacc tctagtcaag
5101 accttgcac taggatagtt aatgtgaacc atggcaactg atcacaacaa tgtcttcag
5161 atcagatcca ttttatcctc cttgttttac agcaagggat attaattacc tatgttacct
5221 ttccctggga ctatgaatgt gcaaaattcc aatgttcatg gtctctccct ttaaacctat
5281 attctacccc ttttacatta tagaaaggga tgctggaaac ccagagtcct tctcttggga
5341 ctcttaatgt gtatttctaa ttatccatga ctcttaatgt gcatattttc aattgcctaa
5401 ttgatttcaa ttgtctaaga catttcaaat gtctaattga ttagaactga gtcttttata
5461 tcaagctaat atctagcttt tatatcaagc taatatcttg acttctcagc atcatagaag
5521 ggggtactga tttcctaaag tcttcttga attctatta tgcaaaattg ccctgaggcc
5581 gggtgtggtg gctcacacct gtaatcccag cactttggga ggctgaggtg ggaagatccc
5641 ttactgccag gagtttgaga ccagcctggc caacattaaa aaaaaaaaaa aaagtaagac
5701 aattgccctg gaatcccatc ccctcacac ctccttggca aagcagcagg agtgctaact
5761 agctagtgct tcttctctta tactgcttaa atgcgcataa ttagcagtag ttgatgtgcc
5821 cctatgttag agtagaatcc cgcttccttg ctccatttgc attactgcag gagcttctaa
5881 ctagcctgaa ttcactctct tggactgtta atgtgcatac ttatatttgc tgctgtactt
5941 ttttaccatg taaggacccc acccactgta tttacatccc agctggaagt acctactact
6001 taagacccctt agactagtaa agttagcgtg cataatctta ggtgttatat acacatttc
6061 agttgcatac agttgtgcct tttatcagga ctcctgtact tatcaaagca gagagtgcta
6121 atcaatatta agccctctc ttcgaactgt agatgccatg taattgcagt tgtcaatggt
6181 ccttcaatta gacttgggtt tctgacctat cacacctct ttgctttatt gcatgggta
6241 ctattcactt aaggccctt tctcaaactg ttaatgtgcc taatgacaat tacatcagta
6301 tccttccttt tgaaggacag catggttggt gacacctaag gccccattc ttggcctccc
6361 aatatgtgtg attgtatttg tcgaggttgc tatgcactag agaaggaaag tgctcccctc
6421 atcccactt ttcccttcca gcaggaagtg cccacccat aagaccctt tatttggaga
6481 gtctaggtgc acaattgtaa gtgacacaa gcatgcatct tggacattta tgtgcgtaat
6541 cgcacactgc tcattccatg tgaataaggt cctactctcc gacccctttt gcaatacaga
6601 agggttgctg ataacgcagt ccccttttct tggcatgttg tgtgtgatta taatcgtctg
6661 ggatcctatg cactagaaaa ggagggtcct ctccacatac ctcagtctca cctttccctt
6721 ccagcaggga gtgcccactc cataagactc tcacatttgg acagtcaagg tgcgtaattg
6781 ttaagtgaac acaaccatgc acttagaca tggatttgca taactacaca cagctcaacc
6841 tatctgaata aaatcctact ctcagacccc ttttgcagta cagcaggggt gctgatcacc
6901 aaggcccttt ttcctggcct ggtatgcgtg tgattatgtt tgtcccggtt cctgtgtatt
6961 agacatggaa gctccctg ccacactcca ccccaatct tcctttcct tccggcagga
7021 gtgccctctc cataagacgc ttacgtttgg acaatcaagg tgcacagttg taagtgacca
7081 caggcataca ccttggacat taatgtgcat aaccactttg cccattccat ctgaataagg
7141 tcctactctc agacccctt tgcagtacag caggggtgct gatcaccaag gccctttc
7201 ttggcctgtt atgtgcgtga ttatattgt ctgggttcct gtgtattaga caaggaagcc
7261 ttccccgc cccaccccc actcccagtc ttcctttccc ttccagcagg gagtgccccc
7321 tccataagat cattcatttt ggacaatcaa ggtgcacaat tataagtgac cacagccatg
7381 caccttggac attattggac attaatgtgc gtaactgcac atggcccatc ccatctgaat
7441 aaggacctac tctcagatgc ctttgcagta cagcagggt actgaatcac caaggccctt
7501 tttcttggcc tgttatgtgt gtgattatat ttatcccagt ttctgtgtaa tagacatgaa
7561 agcctccct gccacacccc acctccaatc ttcctttccc ttccaccag gagtgtccac
7621 tccatatacc cttacatttg gacaatcaag gtgcacaatt gtaagtgagc ataggcactc
7681 accttggaca tgaatgtgca taactgcaca tggcccatcc catctgaata aggtcctact
7741 ctcagaccct ttttgcagta cagcagggt gctgatcacc aaggccctt ttcctggcct
7801 gttatgtgtg tgattatatt tgttccagtt cctgtgtaat agacatggaa gcctccctg
7861 ccacactcca ccccaatct tcctttcct ctggcaggaa gtaccgctc cataagaccc
7921 ttacatttgg acagtcaagg tgcacaattg tatgtgacca caacaatgca ccttggacat
7981 aaatgtgtgt aactgcacat ggcccatccc atctgaatag gtcctactc tcagaccct
8041 tttgcagtac agtaggtgtg ctgataacca aggccctct tctggcctg ttaacgtatg
8101 tgattatatt tgtctgggtt ccagtgtata agacatggaa gcctccct ccccaccca
8161 ccctcaatct tcctttccct tctggcaggg agtgccagct ccataagaac cttacatttg
8221 gacagtcaag gtgcacaatt ctaagtgacc gcagccatgc accttggtca ataatgtgtg
8281 taactgcaca cggcctact catctgaccc ctcagaccct cttttgcagta
8341 cagcaggggt gctgataacc aaggccatt ttcctggcct gttatgtgtg tgattatatt
8401 tgtccaggtt tctgtgtact agacaaggaa gcctcctctg ccccatccca tctacgcata
8461 atctttcttt tcctccagc agggagtgct cactccataa gacccttaca tttggacaat
```

FIG. 10A  sequence of construct 1 (continued)

```
 8521 caaggtgcac aattgtaagt gaccacaacc atgcatcttg gaaatttatg tgcataactg
 8581 cacatggctt atcctatttg aataaagtcc tactctcaga cccccttttgc agtatagctg
 8641 gggtgctgat cactgaggcc tctttgcttg gcttgtctat attcttgtgt actagataag
 8701 ggcaccttct catggactcc ctttgctttt caacaaggag tacccactac tttttaagat
 8761 tcttatattt gtccaaagta catggtttta attgaccaca acaatgtccc ttgacatta
 8821 atgtatgtaa tcaccacatg gttcatccta attaaacaaa gttctacctt ctcaccctcc
 8881 atttgcagta taccagggtt gctgacccc taagtcccct tttcttggct tgttgacatg
 8941 cataattgca tttatgttgg ttcttgtgcc ctagacaagg atgcccacc tcttttcaat
 9001 agtgggtgcc cactccttat gatctttaca tttgaacagt taatgtgaat aattgcagtt
 9061 gtccacaacc ctatcacttc taggaccatt ataccctctt tgcattactg tggggtatac
 9121 tgtttccctc caaggccct tctggtggac tatcaacata taattgaaat tttcttttgt
 9181 ctttgtcagt agattaaggt cataccccat caccttcct ttgtagtaca acagggtgtc
 9241 ctgatcaacc aaagtcctgt tgttttggac tgttaatatg tgcaattaca tttgctcctg
 9301 atctgtgcac tagataagga tcctacctac tttcttagtg tttttagcag gtagtgccca
 9361 ctactcaaga ctgtcacttg gaatgttcat gtgcacaaac tcaattctct aagcatgttc
 9421 ctgtaccacc tttgctttag agcaggggga tgatattcac taagtgcccc ttcttttgga
 9481 cttaatatgc attaatgcaa ttgtccacct cttcttttag actaagagtt gatctccaca
 9541 tattcccctt gcatcagggg catgttaatt atgaatgaac ccttttcttt taatattaat
 9601 gtcataattg tatttgtgga cctgtgtagg agaaaaagac cctatgttcc tcccattacc
 9661 ctttggattg ctgctgagaa gtgttaacta ctcataatct cagctcttgg acaattaata
 9721 gcattaataa caattatcaa gggcactgat cattagataa gactcctgct tcctcgttgc
 9781 ttacatcggg ggtactgacc cactaaggcc cctttgtactg ttaatgtgaa tatttgcaat
 9841 tatatatgtc tccttctggt agagtgggat attatgcccct agtatccct ttgcattact
 9901 gcaggggctg ctgactactc aaaacttctc ctgggactgt taataggcac aatgcagtt
 9961 atcaatggtt ttctccctcc ctgaccttgt taagcaagcg cccccacccca cccttagttt
10021 cccatggcat aataaagtat aagcattgga gtattccatg cacttgtcta tcaaacagtg
10081 gtccatactc ccaacccttt tgcattgcgc cagtgtgtaa aatcacaggt agccatggtg
10141 tcatgcttta tatacgaagt cttccctctc tctgcccctt gtgtgccctt ggccccctttt
10201 tacagactat tgctcacaat ctcaggtgtc catatttgca gctattaggt aagattgtgc
10261 tgtctccctc ttcccttccc tctgccctgc cccttttgcc tctttgctgg gtaatgttga
10321 ccagacaagg ccctttctct tggacttaaa caattctcag ttgcacttcc ttggtccac
10381 ccattataca tgaaccctc tacttccttt cgcattgctt ctgagtatgc tgactaccca
10441 aagcccctc tgtgttatta ataaacacag tactgactgt cccattttc agcccatcag
10501 tccaagatct ccctaccact tggtgtgtt ggtgcagtgt tgactatgaa aagcaggcct
10561 gaactaggtg gataagcctt cactcatttt ctttcattta ttaatgatcc tagtttcaat
10621 tattgtcaga ttctggggac aagaaccatt cttgccacc tgtgttactg ctttactgtg
10681 caaaatactg aaggcaagtc agacccaggg agctggattg ccatccttta ttttgtgttt
10741 ccagtgtaca ctataaaatt gtctccccag gaaggaaggt tggcactttc tctgcattct
10801 tcttccaga gcagattgcc tggttaagaa tctcttgttg tccctctgt atattgttat
10861 tgtaaagtgc caaatgccag gatacagcca gaaaaattgc ttattattat taaaaaaatt
10921 ttttaagaa agacatctgg attgtagggt ggactcgata acctggtcat tatttttttg
10981 aagccaaaat atccatttat actatgtacc tggtgaccag tgtctctcat tttaactgag
11041 ggtggtgggt ctgtggatag aacactgact cttgctattt taatatcaaa gatattctag
11101 ATCCAGCACA GTGGCggccg ctctagagtg gaactcttaa gaccagtatc tttgtgtggg
11161 ctttaccagc attcacttt agaaaaacta cctaaatttt ataatcctt aatttcttca
11221 tctggagcac ctgccctac ttatttcaag aagattgcag taaaacgatt aaatgaggga
11281 acatatgcag aggtgctttt aaaaagcata tgccaccttt tttattaatt attatataaa
11341 atgaagcatt taattatagt aataatttga agtagtttga agtaccacac tgaggtgagg
11401 acttaaaaat gataagacga gttccctatt ttataagaaa aataagccaa aattaaatat
11461 tctttttggat ataaatttca acagtgagat agctgcctag tggaaatgaa taatatccca
11521 gccactagtg tacagggtgt tttgtggcac aggattatgt aatatggaac tgctcaagca
11581 aataactagt catcacaaca gcagttcttt gtaataactg aaaaagaata ttgtttctcg
11641 gagaaggatg tcaaaagatc ggccagctc agggagcagt ttgccctact agctcctcgg
11701 acagctgtaa agaagagtct ctggcattgaa ggaatactga tcccattaga gataccacgc
11761 tgcatgtgtc cttagtagtc atgtctcctt aggctcctct tggacattct gagcatgtga
11821 gacctgagga ctgcaaacag ctataagagg ctccaaatta atcatatctt tcccttttgag
11881 aatctggcca agctccagct aatctacttg gatgggttgc cagctatctg gagaaaaaga
11941 tcttcctcag aagaataggc ttgttgttt acagtgttag tgatccatcc ccttgacga
12001 tccctaggtg gagatggggc atgaggacta tccaggggaa aagctcacta ccactgggca
12061 acaaccctag gtcaggaggt tctgtcaaga tactttcctg gtcccagata ggaagataaa
12121 gtctcaaaaa caaccaccac acgtcaagct cttcattgtt cctatctgcc aaatcattat
12181 acttcctaca agcagtgcag agagctgagt cttcagcagg tccaagaaat ttgaacacac
12241 tgaaggaagt cagccttccc acctgaagat caacatgcct ggcactctag cacttgagga
12301 tagctgaatg aatgtgtatt tcttgtctc tttctttctt gtctttgctc tttgttctct
12361 atctaaagtg tgtcttaccc atttccatgt ttctcttgct aatttctttc gtgtgtgcct
```

FIG. 10A sequence of construct 1 (continued)

```
12421 ttgcctcatt ttctcttttt gttcacaaga gtggtctgtg tcttgtctta gacatatctc
12481 tcatttttca ttttgttgct atttctcttt gctctcctag atgtggctct tctttcacgc
12541 tttatttcat gtctcctttt tgggtcacat gctgtgtgct ttttgtcctt ttcttgttct
12601 gtctacctct cctttctctg cctacctctc ttttctcttt gtgaactgtg attatttgtt
12661 accccttccc cttctcgttc gttttaaatt tcaccttttt tctgagtctg gcctcctttc
12721 tgctgtttct acttttatc tcacatttct catttctgca tttcctttct gcctctcttg
12781 ggctattctc tctctcctcc cctgcgtgcc tcagcatctc ttgctgtttg tgattttcta
12841 tttcagtatt aatctctgtt ggcttgtatt tgttctctgc ttcttccctt tctactcacc
12901 tttgagtatt tcagcctctt catgaatcta tctccctctc tttgatttca tgtaatctct
12961 cctaaatat ttctttgcat atgtgggcaa gtgtacgtgt gtgtgtgtca tgtgtggcag
13021 aggggcttcc taaccctgc ctgataggtc cagaacgtcg gctatcagag caagcattgt
13081 ggagcggttc cttatgccag gctgccatgt gagatgatcc aagaccaaaa caaggccta
13141 gactgcagta aaacccagaa ctcaagtagg gcagaaggtg gaaggctcat atggatagaa
13201 ggcccaaagt ataagacaga tggtttgaga cttgagaccc gaggactaag atggaaagcc
13261 catgttccaa gatagataga agcctcaggc ctgaaaccaa caaaagcctc aagagccaag
13321 aaaacagagg gtggcctgaa ttggaccgaa ggcctgagtt ggatggaagt ctcaaggctt
13381 gagttagaag tcttaagacc tgggacagga cacatggaag gcctaagaac tgagacttgt
13441 gacacaaggc caacgaccta agattagccc agggttgtag ctggaagacc tacaacccaa
13501 ggatggaagg ccctgtcac aaagcctacc tagatggata gaggacccaa gcgaaaaagg
13561 tatctcaaga ctaacggccg gaatctggag gccatgacc cagaacccag gaaggataga
13621 agcttgaaga cctggggaaa tcccaagatg agaaccctaa accctacctc ttttctattg
13681 tttacacttc ttactcttag atatttccag ttctcctgtt tatctttaag cctgattctt
13741 ttgagatgta ctttttgatg ttgccggtta cctttagatt gacagtatta tgcctgggcc
13801 agtcttgagc cagctttaaa tcacagcttt tacctatttg ttaggctata gtgttttgta
13861 aacttctgtt tctattcaca tcttctccac ttgagagaga caccaaaatc cagtcagtat
13921 ctaatctggc ttttgttaac ttccctcagg agcagacatt catataggtg atactgtatt
13981 tcagtccttt cttttgaccc cagaagacct agactggaga gataaaatgg tcaggttgtt
14041 ggggaaaaaa aaagtgccag gctctctaga gaaaaatgtg aagagatgct ccaggccaat
14101 gagaagaatt agacaagaaa tacacagatg tgccagactt ctgagaagca cctgccagca
14161 acagcttcct tctttgagct tagATTTTCC TAGTCCATCC CTCATGAAAA ATGACTGACC
14221 ACTGCTGGGC AGCAGGAGGG ATGATGACCA ACTAATTCCC AAACCCCAGT CTCATTGGTA
14281 CCATCGATCG GCCGGATATC ACGCGTCATA TGGCTAGCCT GCAGGGATCC AATGTAACTG
14341 TATTCAGCGA TGACGAAATT CTTAGCTATT GTAATACTCT AGAGGGATCTT TGTGAAGGAA
14401 CCTTACTTCT GTGGTGTGAC ATAATTGGAC AAACTACCTA CAGAGATTTA AAGCTCTAAG
14461 GTAAATATAA AATTTTTAAG TGTATAATGT GTTAAACTAC TGATTCTAAT TGTTTGTGTA
14521 TTTTAGATTC CAACCTATGG AACTGATGAA TGGGAGCAGT GGTGGAATGC CTTTAATGAG
14581 GAAAACCTGT TTTGCTCAGA AGAAATGCCA TCTAGTGATG ATGAGGCTAC TGCTGACTCT
14641 CAACATTCTA CTCCTCCAAA AAAGAAGAGA AAGGTAGAAG ACCCCAAGGA CTTTCCTTCA
14701 GAATTGCTAA GTTTTTTGAG TCATGCTGTG TTTAGTAATA GAACTCTTGC TTGCTTTGCT
14761 ATTTACACCA CAAAGGAAAA AGCTGCACTG CTATACAAGA AAATTATGGA AAAATATTCT
14821 GTAACCTTTA TAAGTAGGCA TAACAGTTAT AATCATAACA TACTGTTTTT TCTTACTCCA
14881 CACAGGCATA GAGTGTCTGC TATTAATAAC TATGCTCAAA AATTGTGTAC CTTTAGCTTT
14941 TTAATTTGTA AAGGGGTTAA TAAGGAATAT TTGATCTATA GTGCCTTGAC TAGAGATCAT
15001 AATCAGCCAT ACCACATTTG TAGAGGTTTT ACTTGCTTTA AAAAACCTCC CACACCTCCC
15061 CCTGAACCTG AAACATAAAA TGAATGCAAT TGTTGTTGTT AACTTGTTTA TTGCAGCTTA
15121 TAATGGTTAC AAATAAAGCA ATAGCATCAC AAATTTCACA AATAAAGCAT TTTTTTCACT
15181 GCATTCTAGT TGTGGTTTGT CCAAACTCAT CAATGTATCT TATCATGTCT GCGGCTCTAG
15241 AGCTGCATTA ATGAATCGGC CAACGCGCGG GGAGAGGCGG TTTGCGTATT GGGCGCTCTT
15301 CCGCTTCCTC GCTCACTGAC TCGCTGCGCT CGGTCGTTCG GCTGCGGCGA GCGGTATCAG
15361 CTCACTCAAA GGCGGTAATA CGGTTATCCA CAGAATCAGG GGATAACGCA GGAAAGAACA
15421 TGTacgtaaa ctggcaaagg ggtggctggg ccaaaagaca gaggaattaa gtaagaagtc
15481 caggaaaaat gaacttcaca tcaattttta gagcacggta gccatgaatc ttgtgaatag
15541 ctcccaaaaa tgtcctgtgg aagacaacta gaaagcattc tacaatcagg cacccacctc
15601 cacctgcagc ctctgtgtt gttctcatgt ggctccagct cctccaaggc
15661 acctccacac tctctcaagt acactcttca ctcttcccca aacatgattc ccctactgct
15721 ctgcctaact cccacttctc tttcaagtag cagcttaaac gtcacctcat atttggctgg
15781 aaaatagaat atagacagag gggtaagtta aggctagaaa ggcaggctgg gtcaacagaa
15841 tggcaagcta aaacatggga ttttctaaaa cagcctaaga gggtgacaga taaagtgtg
15901 caaggagtgg cacaactcca gtttcatctt tagctatagc aattaacacc ataaggagtc
15961 tggattcaat tttgccattt actagctagc taccaacttc tgtgtcgctt tgggcaaatc
16021 aattaaatcc ataccctcct ttccatctgc agaatgggtt tataacagta cttaaacctc
16081 aagtactaa gaacagtaaa gagttaatgg taCATGTGAG CAAAAGGCCA GCAAAAGGCC
16141 AGGAACCGTA AAAAGGCCGC GTTGCTGGCG TTTTTCCATA GGCTCCGCCC CCCTGACGAG
16201 CATCACAAAA ATCGACGCTC AAGTCAGAGG TGGCGAAACC CGACAGGACT ATAAAGATAC
16261 CAGGCGTTTC CCCCTGGAAG CTCCCTCGTG CGCTCTCCTG TTCCGACCCT GCCGCTTACC
```

FIG. 10A sequence of construct 1 (continued)

```
16321 GGATACCTGT CCGCCTTTCT CCCTTCGGGA AGCGTGGCGC TTTCTCATAG CTCACGCTGT
16381 AGGTATCTCA GTTCGGTGTA GGTCGTTCGC TCCAAGCTGG GCTGTGTGCA CGAACCCCCC
16441 GTTCAGCCCG ACCGCTGCGC CTTATCCGGT AACTATCGTC TTGAGTCCAA CCCGGTAAGA
16501 CACGACTTAT CGCCACTGGC AGCAGCCACT GGTAACAGGA TTAGCAGAGC GAGGTATGTA
16561 GGCGGTGCTA CAGAGTTCTT GAAGTGGTGG CCTAACTACG GCTACACTAG AAGAACAGTA
16621 TTTGGTATCT GCGCTCTGCT GAAGCCAGTT ACCTTCGGAA AAAGAGTTGG TAGCTCTTGA
16681 TCCGGCAAAC AAACCACCGC TGGTAGCGGT GGTTTTTTTG TTTGCAAGCA GCAGATTACG
16741 CGCAGAAAAA AAGGATCTCA AGAAGATCCT TTGATCTTTT CTACGGGGTC TGACGCTCAG
16801 TGGAACGAAA ACTCACGTTA AGGGATTTTG GTCATGAGAT TATCAAAAAG GATCTTCACC
16861 TAGATCCTTT TAAATTAAAA ATGAAGTTTT AAATCAATCT AAAGTATATA TGAGTAAACT
16921 TGGTCTGACA GTTACCAATG CTTAATCAGT GAGGCACCTA TCTCAGCGAT CTGTCTATTT
16981 CGTTCATCCA TAGTTGCCTG ACTCCCCGTC GTGTAGATAA CTACGATACG GGAGGGCTTA
17041 CCATCTGGCC CCAGTGCTGC AATGATACCG CGAGACCCAC GCTCACCGGC TCCAGATTTA
17101 TCAGCAATAA ACCAGCCAGC CGGAAGGGCC GAGCGCAGAA GTGGTCCTGC AACTTTATCC
17161 GCCTCCATCC AGTCTATTAA TTGTTGCCGG GAAGCTAGAG TAAGTAGTTC GCCAGTTAAT
17221 AGTTTGCGCA ACGTTGTTGC CATTGCTACA GGCATCGTGG TGTCACGCTC GTCGTTTGGT
17281 ATGGCTTCAT TCAGCTCCGG TTCCCAACGA TCAAGGCGAG TTACATGATC CCCCATGTTG
17341 TGCAAAAAAG CGGTTAGCTC CTTCGGTCCT CCGATCGTTG TCAGAAGTAA GTTGGCCGCA
17401 GTGTTATCAC TCATGGTTAT GGCAGCACTG CATAATTCTC TTACTGTCAT GCCATCCGTA
17461 AGATGCTTTT CTGTGACTGG TGAGTACTCA ACCAAGTCAT TCTGAGAATA GTGTATGCGG
17521 CGACCGAGTT GCTCTTGCCC GGCGTCAATA CGGGATAATA CCGCGCCACA TAGCAGAACT
17581 TTAAAAGTGC TCATCATTGG AAAACGTTCT TCGGGGCGAA AACTCTCAAG GATCTTACCG
17641 CTGTTGAGAT CCAGTTCGAT GTAACCCACT CGTGCACCCA ACTGATCTTC AGCATCTTTT
17701 ACTTTCACCA GCGTTTCTGG GTGAGCAAAA ACAGGAAGGC AAAATGCCGC AAAAAAGGGA
17761 ATAAGGGCGA CACGGAAATG TTGAATACTC ATACTCTTCC TTTTTCAATA TTATTGAAGC
17821 ATTTATCAGG GTTATTGTCT CATGAGCGGA TACATATTTG AATGTATTTA GAAAAATAAA
17881 CAAATAGGGG TTCCGCGCAC ATTTCCCCGA AAAGTGCCAC CTGACGTCTA AGAAACCATT
17941 ATTATCATGA CATTAACCTA TAAAAATAGG CGTATCACGA GGCCCTTTCG TCTTCAAGAA
18001 TTcgaaaacc agaaagtatt ctcagtaatg atagtatgga taaagcaggt ttctatgacc
18061 ctttattaca gaatctgtga gttttttcaca attaaaaagt aataaaaagt agtgacaaca
18121 ttcactgaac tcttattcta tgccaacttg ttccggtatg ccctt acacc cacaaaagcc
18181 ctatgcataa ggtggcatta ttcagcatg tattgcattg tacacacaaa gaggtcaagc
18241 actccaccac ggccctaagc atggtggctg aggtgggaag gcagaggta ggtgggccg
18301 cgcccttttc cactctgaac catgcctcca agataggagg gtgggaaagt gctcaagaca
18361 cattagaaat tccccataaa agacaagatt gttgaacacc tgcaagtgaa taaagataaa
18421 ctgatctcag agggga aaaa gacgcagggt taggaaacag caccctgctc gaggacgttc
18481 tttccaaaca gcctgctcat caccogttcg AATTC
//
```

FIG. 10B sequence of construct 2

```
LOCUS       AAVS1/ PEF1α-Tet3G/hPGK-PuroR-pA      9789 bpDNA     SYN      14-Mar-2013
DEFINITION  AAVS1/ PEF1α-Tet3G/hPGK-PuroR-pA
ACCESSION
KEYWORDS
SOURCE
  ORGANISM  other sequences; artificial sequences; vectors.
FEATURES             Location/Qualifiers
     source          1..9789
                     /organism="AAVS1/ PEF1α-Tet3G/hPGK-PuroR-pA"
                     /mol_type="other DNA"
     promoter        143..172
                     /label="lac_promoter"
     misc_feature    186..208
                     /label="M13_pUC_rev_primer"
     misc_feature    207..225
                     /label="M13_reverse_primer"
     promoter        242..261
                     /label="T3_promoter"
     misc_feature    295..1095
                     /label="Left arm"
     misc_feature    1120..1562
                     /label="SV40 pA signal"
     terminator      1444..1575
                     /label="SV40_PA_terminator"
     misc_feature    1532..1551
                     /label="EBV_rev_primer"
     CDS             complement(1585..2331)
                     /label="ORF frame 1"
                     /translation="MSRLDKSKVINSALELLNGVGIEGLTTRKLAQKLGVEQPTLYWH
                     VKNKRALLDALPIEMLDRHHTHSCPLEGESWQDFLRNNAKSYRCALLSHRDGAKVHLG
                     TRPTEKQYETLENQLAFLCQQGFSLENALYALSAVGHFTLGCVLEEQEHQVAKEERET
                     PTTDSMPPLLKQAIELFDRQGAEPAFLFGLELIICGLEKQLKCESGGPTDALDDFDLD
                     MLPADALDDFDLDMLPADALDDFDLDMLPG*"
     misc_feature    1585..2331
                     /label="Tet3G"
     misc_feature    complement(2413..2437)
                     /label="LNCX_primer"
     misc_feature    complement(2469..2489)
                     /label="EF1a_fwd_primer"
     CDS             2697..3344
                     /label="ORF frame 3"
                     /translation="MKRRLRTERPFSFVWVTHPPALPSAASSILSSLQQGREAAIFPL
                     TQLVPTGPALPPRAGRYTAARGQAPEQAGQLETTPVRFSVAALAGPASPNMCAGTHGP
                     RRRPRPQKPKYQCADLGPHLQDYLARKKASQQVIKNFKWLETYRKQRDRREGATRFAR
                     GGPSAQARPQLKHEAKGLLKRKASNSPTHFQPEARDQESRTAARGVEVIQGTQGP*"
     promoter        complement(2437..3624)
                     /label="EF1a_promoter"
     promoter        2437..3771
                     /label="EF1x promoter"
     misc_feature    3913..4419
                     /label="hPGK"
     CDS             4201..5040
                     /label="puro(variant)"
                     /gene="puro(variant)"
                     /note="ORF frame 1"
                     /translation="MAARRPRWAVANSGCSAGRAESSGREGAVREAGCGAVVWALFLP
                     ARCSAFCKPPERTSAVGSLVDRITDLSPQGDPPELTMTEYKPTVRLATRDDVPRAVRT
                     LAAAFADYPATRHTVDPDRHIERVTELQELFLTRVGLDIGKVWVADDGAAVAVWTTPE
                     SVEAGAVFAEIGPRMAELSGSRLAAQQMEGLLAPHRPKEPAWFLATVGVSPDHQGKG
                     LGSAVVLPGVEAAERAGVPAFLETSAPRNLPFYERLGFTVTADVEVPEGFRTWCMTRK
                     PGA*"
     gene            4441..5040
                     /label="puro(variant)"
```

FIG. 10B sequence of construct 2 (continued)

```
                    /gene="puro(variant)"
     misc_feature   4441..5040
                    /label="Puro"
     misc_feature   5047..5271
                    /label="BGH pA"
     terminator     5056..5271
                    /label="bGH_PA_terminator"
     misc_feature   5287..6126
                    /label="Right arm"
     promoter       complement(6162..6180)
                    /label="T7_promoter"
     misc_feature   complement(6187..6203)
                    /label="M13_forward20_primer"
     misc_feature   complement(6196..6218)
                    /label="M13_pUC_fwd_primer"
     misc_feature   6184..6327
                    /label="lacZ_a"
     misc_feature   6350..6643
                    /label="ccdB"
     promoter       6854..6903
                    /label="NEOKAN_promoter"
     CDS            6992..7786
                    /label="NeoR/KanR"
                    /gene="NeoR/KanR"
                    /note="ORF frame 2"
                    /translation="MIEQDGLHAGSPAAWVERLFGYDWAQQTIGCSDAAVFRLSAQGR
                    PVLFVKTDLSGALNELQDEAARLSWLATTGVPCAAVLDVVTEAGRDWLLLGEVPGQDL
                    LSSHLAPAEKVSIMADAMRRLHTLDPATCPFDHQAKHRIERARTRMEAGLVDQDDLDE
                    EHQGLAPAELFARLKASMPDGEDLVVTHGDACLPNIMVENGRFSGFIDCGRLGVADRY
                    QDIALATRDIAEELGGEWADRFLVLYGIAAPDSQRIAFYRLLDEFF*"
     gene           6995..7783
                    /label="NeoR/KanR"
                    /gene="NeoR/KanR"
     promoter       7919..7942
                    /label="AmpR_promoter"
     CDS            complement(8036..8896)
                    /label="Ampicillin"
                    /gene="Ampicillin"
                    /note="ORF frame 2"
                    /translation="MSIQHFRVALIPFFAAFCLPVFAHPETLVKVKDAEDQLGARVGY
                    IELDLNSGKILESFRPEERFPMMSTFKVLLCGAVLSRIDAGQEQLGRRIHYSQNDLVE
                    YSPVTEKHLTDGMTVRELCSAAITMSDNTAANLLLTTIGGPKELTAFLHNMGDHVTRL
                    DRWEPELNEAIPNDERDTTMPVAMATTLRKLLTGELLTLASRQQLIDWMEADKVAGPL
                    LRSALPAGWFIADKSGAGERGSRGIIAALGPDGKPSRIVVIYTTGSQATMDERNRQIA
                    EIGASLIKHW*"
     gene           complement(8036..8896)
                    /label="Ampicillin"
                    /gene="Ampicillin"
     rep_origin     9004..9623
                    /label="pBR322_origin"
ORIGIN
        1 agcgcccaat acgcaaaccg cctctccccg cgcgttggcc gattcattaa tgcagctggc
       61 acgacaggtt tcccgactgg aaagcgggca gtgagcgcaa cgcaattaat gtgagttagc
      121 tcactcatta ggcaccccag gctttacact ttatgcttcc ggctcgtatg ttgtgtggaa
      181 ttgtgagcgg ataacaattt cacacaggaa acagctatga ccatgattac gccaagctca
      241 gaattaaccc tcactaaagg gactagtcct gcaggtttaa acgaattcgc cctttgcttt
      301 ctctgaccag cattctctcc ctgggcctg tgccgctttc tgtctgcagc ttgtggcctg
      361 ggtcacctct acggctggcc cagatccttc cctcaggttc ccgtcttcct
      421 ccactccctc ttcccttgc tctctgctgt gttgctgccc aaggatgctc tttccggagc
      481 acttccttct cggcgctgca ccacgtgatg tcctctgagc ggatcctccc cgtgtctggg
      541 tcctctccgg gcatctctcc tccctcaccc aacccatgc cgtcttcact cgctgggttc
      601 ccttttcctt ctccttctgg ggcctgtgcc atctctcgtt tcttaggatg gccttctccg
      661 acggatgtct cccttgcgtc ccgcctcccc ttcttgtagg cctgcatcgt caccgttttt
      721 ctggacaacc ccaaagtacc ccgtctccct ggctttagcc acctctccat cctcttgctt
      781 tctttgcctg gacacccgt tctcctgtgg attcgggtca cctctcactc ctttcatttg
```

FIG. 10B sequence of construct 2 (continued)

```
 841 ggcagctccc ctacccccct tacctctcta gtctgtgcta gctcttccag cccctgtca
 901 tggcatcttc caggggtccg agagctcagc tagtcttctt cctccaaccc gggccctat
 961 gtccacttca ggacagcatg tttgctgcct ccagggatcc tgtgtcccg agctgggacc
1021 acctattatt cccagggccg gttaatgtgg ctctggttct gggtactttt atctgtcccc
1081 tccaccccac agtggggcaa gctAGCTTGG TCGAGCTGGA TACTTCCCGT CCGCCAGGGG
1141 GACATGCCGG CGATGCTGAA GGTCGCGCGC ATTCCCGATG AAGAGGCCGG TTACCGCCTG
1201 TTGACCTGGT GGGACGGGCA GGGCGCCGCC CGAGTCTTCG CCTCGGCGGC GGGCGCTCTG
1261 CTCATGGAGC GCGCGTCCGG GGCGCGGGAC CTTGCACAGA TAGCGTGGTC CGGCCAGGAC
1321 GACGAGGCTT GCAGGATCAT AATCAGCCAT ACCACATTTG TAGAGGTTTT ACTTGCTTTA
1381 AAAAACCTCC CACACCTCCC CCTGAACCTG AAACATAAAA TGAATGCAAT TGTTGTTGTT
1441 AACTTGTTTA TTGCAGCTTA TAATGGTTAC AAATAAAGCA ATAGCATCAC AAATTTCACA
1501 AATAAAGCAT TTTTTTCACT GCATTCTAGT TGTGGTTTGT CCAAACTCAT CAATGTATCT
1561 TATCATGTCT GGATCCTTAC TTAGTTACCC GGGGAGCATG TCAAGGTCAA AATCGTCAAG
1621 AGCGTCAGCA GGCAGCATAT CAAGGTCAAA GTCGTCAAGG GCATCGGCTG GGAGCATGTC
1681 TAAGTCAAAA TCGTCAAGGG CGTCGGTCGG CCCGCCGCTT TCGCACTTTA GCTGTTTCTC
1741 CAGGCCACAT ATGATTAGTT CCAGGCCGAA AAGGAAGGCA GGTTCGGCTC CCTGCCGGTC
1801 GAACAGCTCA ATTGCTTGTT TCAGAAGTGG GGGCATAGAA TCGGTGGTAG GTGTCTCTCT
1861 TTCCTCTTTT GCTACTTGAT GCTCCTGTTC CTCCAATACG CAGCCCAGTG TAAAGTGGCC
1921 CACGGCGGAC AGAGCGTACA GTGCGTTCTC CAGGGAGAAG CCTTGCTGAC ACAGGAACGC
1981 GAGCTGATTT TCCAGGGTTT CGTACTGTTT CTCTGTTGGG CGGGTGCCGA GATGCACTTT
2041 AGCCCCGTCG CGATGTGAGA GGAGAGCACA GCGGTATGAC TTGGCGTTGT TCCGCAGAAA
2101 GTCTTGCCAT GACTCGCCTT CCAGGGGGCA GGAGTGGGTA TGATGCCTGT CCAGCATCTC
2161 GATTGGCAGG GCATCGAGCA GGGCCCGCTT GTTCTTCACG TGCCAGTACA GGGTAGGCTG
2221 CTCAACTCCC AGCTTTTGAG CGAGTTTCCT TGTCGTCAGG CCTTCGATAC CGACTCCATT
2281 GAGTAATTCC AGAGCAGAGT TTATGACTTT GCTCTTGTCC AGTCTAGACA TGGTGAATTC
2341 GGGGCCGCGG AGGCTGGATC GGTCCCGGTG TCTTCTATGG AGGTCAAAAC AGCGTGGATG
2401 GCGTCTCCAG GCGATCTGAC GGTTCACTAA ACGAGCTCAC GACACCTGAA ATGGAAGAAA
2461 AAAACTTTGA ACCACTGTCT GAGGCTTGAG AATGAACCAA GATCCAAACT CAAAAGGGC
2521 AAATTCCAAG GAGAATTACA TCAAGTGCCA AGCTGGCCTA ACTTCAGTCT CCACCCACTC
2581 AGTGTGGGGA AACTCCATCG CATAAAACCC CTCCCCCCAA CCTAAGACG ACGTACTCCA
2641 AAAGCTCGGA AACTAATCGA GGTGCCTGGA CGGCGCCCGG TACTCCGTGG AGTCACATGA
2701 AGCGACGGCT GAGGACGGAA AGGCCCTTTT CCTTTGTGTG GGTGACTCAT CCGCCCGCTC
2761 TCCCGAGCGC CGCGTCCTCC ATTTTGAGCT CCCTGCAGCA GGGCCGGGAA GCGGCCATCT
2821 TTCCGCTCAC GCAACTGGTG CCGACCGGGC CAGCCTTGCC GCCCAGGGCG GGGCGATACA
2881 CGGCGGCGCG AGGCCAGGCA CCAGAGCAGG CCGGCCAGCT TGAGACTACC CCCGTCCGAT
2941 TCTCGGTGGC CGCGCTCGCA GGCCCCGCCT CGCCGAACAT GTGCGCTGGG ACGCACGGGC
3001 CCCGTCGCCG CCCGCGGCCC CAAAAACCGA AATACCAGTG TGCAGATCTT GGCCCGCATT
3061 TACAAGACTA TCTTGCCAGA AAAAAAGCGT CGCAGCAGGT CATCAAAAAT TTTAAATGGC
3121 TAGAGACTTA TCGAAAGCAG CGAGACAGGC GCGAAGGTGC CACCAGATTC GCACGCGGCG
3181 GCCCCAGCGC CAAGCCAGG CCTCAACTCA AGCACGAGGC GAAGGGGCTC CTTAAGCGCA
3241 AGGCCTCGAA CTCTCCCACC CACTTCCAAC CCGAAGCTCG GGATCAAGAA TCACGTACTG
3301 CAGCCAGGGG CGTGGAAGTA ATTCAAGGCA CGCAAGGGCC ATAACCCGTA AAGAGGCCAG
3361 GCCGCGGGA ACCACACACG GCACTTACCT GTGTTCTGGC GGCAAACCCG TTGCGAAAAA
3421 GAACGTTCAC GGCGACTACT GCACTTATAT ACGGTTCTCC CCCACCCTCG GGAAAAAGGC
3481 GGAGCCAGTA CACGACATCA CTTTCCCAGT TTACCCCGCG CCACCTTCTC TAGGCACCGG
3541 TTCAATTGCC GACCCCTCCC CCCAACTTCT CGGGGACTGT GGGCGATGTG CGCTCTGCCC
3601 ACTGACGGGC ACCGGAGCCT CACGCATGCT CTTCTCCACC TCAGTGATGA CGAGAGCGGG
3661 CGGGTGAGGG GGCGGGAACG CAGCGATCTC TGGGTTCTAC GTTAGTGGGA GTTTAACGAC
3721 GGTCCTCGGG ATTCCCCAAG GCAGGGGCGA GTCCTTTTGT ATGAATTACT CATGCGGTA
3781 ATGTTGGACA TGAGCCAATA TAAATGTACA TATTATGATA TGGATACAAC GTATGCAATG
3841 GGCCAAGCTC CTCGAGGTGG TGCACTCTCA GTACAATCTG CTCTGATGCC GCATAGTTAA
3901 GCCAGTAagc ttttgggtt gcgccttttc caaggcagcc ctgggtttgc gcagggacgc
3961 ggctgctctg ggcgtggttc cgggaaacgc agcggcgccg acctgggtc tcgcacattc
4021 ttcacgtccg ttcgcagcgt caccgggatc ttcgcgcta ccttgtggg cccccggcg
4081 acgcttcctg ctccgccct aagtcgggaa ggttccttgc ggttcgcggc gtgcgggacg
4141 tgacaaacgg aagccgcacg tctcactagt acccctcgcag acggacgcg ccagggagca
4201 atggcagcgc gccgacgcg atgggctgtg gccaatagcg gctgctcagc agggcgcgcc
4261 gagagcagcg gcgggaagg ggcggtgcgg gaggcggggt gtgggcggt agtgtgggcc
4321 ctgttcctgc ccgcgcggtg ttccgcattc tgcaagcctc cggagcgcac gtcggcagtc
4381 ggctccctcg ttgaccgaat caccgacctc tctcccagg gggatccacc ggagcttacc
4441 atgaccgagt acaagcccac ggtgcgcctc gccaccccgc acgacgtccc cagggccgta
4501 cgcacccctcg ccgccgcgtt gccgactac ccgccacgc gccacaccgt cgatccggac
4561 cgccacatcg agcgggtcac cgagctgcaa gaactcttcc tcacgcgcgt cgggctcgac
4621 atcggcaagg tgtgggtcgc ggacgacggc gccgcggtgg cggtctggac cacgccggag
4681 agcgtcgaag cgggggcggt gttcgccgag atcggccgc gcatggccga gttgagcggt
```

FIG. 10B  sequence of construct 2 (continued)

```
4741 tccggctgg ccgcgcagca acagatggaa ggcctcctgg cgccgcaccg gcccaaggag
4801 cccgcgtggt tcctggccac cgtcggcgtc tcgccgacc accagggcaa gggtctgggc
4861 agcgccgtcg tgctcccgg agtggaggcg gccgagcgcg cggggtgcc cgccttcctg
4921 gagacctccg cgcccgcaa cctcccttc tacgagcggc tcggcttcac cgtcaccgcc
4981 gacgtcgagg tgcccgaagg accgcgcacc tggtgcatga cccgcaagcc cggtgcctga
5041 ggtaccctgt gccttctagt tgccagccat ctgttgtttg ccctccccc gtgccttcct
5101 tgaccctgga aggtgccact cccactgtcc tttcctaata aaatgaggaa attgcatcgc
5161 attgtctgag taggtgtcat tctattctgg ggggtggggt ggggcaggac agcaagggg
5221 aggattggga agacaatagc aggcatgctg gggatgcggt gggctctatg gggtaccaag
5281 ctttactagg gacaggattg gtgacagaaa agcccatcc ttaggcctcc tccttcctag
5341 tctcctgata ttgggtctaa cccccacctc ctgttaggca gattccttat ctggtgacac
5401 acccccattt cctggagcca tctctctcct tgccagaacc tctaaggttt gcttacgatg
5461 gagccagaga ggatcctggg agggagagct tggcagggg tgggagggaa gggggggatg
5521 cgtgacctgc ccggttctca gtggccaccc tgcgctaccc tctcccagaa cctgagctgc
5581 tctgacgcgg ctgtctggtg cgtttcactg atcctggtgc tgcagcttcc ttacacttcc
5641 caagaggaga agcagtttgg aaaaacaaaa tcagaataag ttggtcctga gttctaactt
5701 tggctcttca cctttctagt ccccaattta tattgttcct ccgtgcgtca gttttacctg
5761 tgagataagg ccagtagcca gcccgtcct ggcaggctg tggtgaggag gggggtgtcc
5821 gtgtggaaaa ctcccttgt gagaatggtg cgtcctaggt gttcaccagg tcgtggccgc
5881 ctctactccc tttctcttc tccatccttc tttccttaaa gagtccccag tgctatctgg
5941 gacatattcc tccgccaga gcagggtccc gcttccctaa ggcctgctc tgggcttctg
6001 ggtttgagtc cttggcaagc ccaggagagg cgctcaggct tccctgtccc cctcctcgt
6061 ccaccatctc atgccctgc ctctcctgcc cctcctac aggggttcct ggctctgctc
6121 taagggcaag ggcgaattcg cggccgctaa attcaattcg ccctatagtg agtcgtatta
6181 caattcactg gccgtcgttt tacaacgtcg tgactgggaa aaccctggcg ttacccaact
6241 taatcgcctt gcagcacatc cccctttcgc cagctggcgt aatagcgaag aggcccgcac
6301 cgatcgccct tcccaacagt tgcgcagcct atacgtacgg cagtttaagg tttacaccta
6361 taaaagagag agccgttatc gtctgttttgt ggatgtacag agtgatatta ttgacacgcc
6421 ggggcgacgg atggtgatcc cctggccag tgcacgtctg ctgtcagata aagtctccg
6481 tgaactttac ccggtggtgc atatcgggga tgaaagctgg cgcatgatga ccaccgatat
6541 ggccagtgtg ccggtctccg ttatcgggga agaagtggct gatctcagcc accgcgaaaa
6601 tgacatcaaa aacgccatta acctgatgtt ctggggaata taatgtcag gcatgagatt
6661 atcaaaaagg atcttcacct agatccttttt cacgtagaaa gccagtcgc agaaacggtg
6721 ctgaccccgg atgaatgtca gctactgggc tatctggaca agggaaaacg caagcgcaaa
6781 gagaaagcag gtagcttgca gtgggcttac atggcgatag ctagactggg cggttttatg
6841 gacagcaagc gaaccggaat tgccagctgg ggcgccctct ggtaaggttg ggaagccctg
6901 caaagtaaac tggatggctt tcttgccgcc aaggatctga tggcgcaggg atcaagctc
6961 tgatcaagag acaggatgag gatcgtttcg catgattgca caagatgat tgcacgcagg
7021 ttctccggcc gcttgggtgg agaggctatt cggctatgac tgggcacaac agacaatcgg
7081 ctgtctgat gccgccgtgt tccggctgtc agcgcagggg cgcccggttc tttttgtcaa
7141 gaccgacctg tccggtgccc tgaatgaact gcaagacgag gcagcgcggc tatcgtggct
7201 ggccacgacg ggcgttcctt gcgcagctgt gctcgacgtt gtcactgaag cggaaggga
7261 ctggctgcta ttgggcgaag tgccggggca ggatctcctg tcatctcacc ttgctcctgc
7321 cgagaaagta tccatcatgg ctgatgcaat gcggcggctg catacgcttg atccggctac
7381 ctgcccattc gaccaccaag cgaaacatcg catcgagcga gcacgtactc ggatggaagc
7441 cggtcttgtc gatcaggatg atctgacga agagcatcag gggctcgcgc cagccgaact
7501 gttcgccagg ctcaaggcga gcatgcccga cggcgaggat ctcgtcgtga cccatggcga
7561 tgcctgcttg ccgaatatca tggtgaaaa tggccgcttt tctggattca tcgactgtgg
7621 ccggctgggt gtggcggacc gctatcagga catagcgttg gctacccgtg atattgctga
7681 agagcttggc ggcgaatggg ctgaccgctt cctcgtgctt tacggtatcg ccgctcccga
7741 ttcgcagcgc atcgccttct atcgccttct tgacgagttc ttctgaatta ttaacgctta
7801 caatttcctg atgcggtatt ttctccttac gcatctgtgc ggtatttcac accgcatcag
7861 gtggcactt tcgggaaat gtgcgcggaa cccctatttg tttatttttc taaatacatt
7921 caaatatgta tccgctcatg agattatcaa aaaggatctt cacctagatc cttttaaatt
7981 aaaaatgaag ttttaaatca atctaaagta tatatgagta aacttggtct gacagttacc
8041 aatgcttaat cagtgaggca cctatctcag cgatctgtct atttcgttca tccatagttg
8101 cctgactccc cgtcgtgtag ataactacga tacgggaggg cttaccatct ggccccagtg
8161 ctgcaatgat accgcgagac ccacgctcac cggctccaga tttatcagca ataaaccagc
8221 cagccggaag ggccgagcgc agaagtggtc ctgcaacttt atccgcctcc atccagtcta
8281 ttaattgttg ccgggaagct agagtaagta gttcgccagt taatagtttg cgcaacgttg
8341 ttgccattgc tacaggcatc gtggtgtcac gctcgtcgtt tggtatggct tcattcagct
8401 ccggttccca acgatcaagg cgagttacat gatccccat gttgtgcaaa aaagcggtta
8461 gctccttcgg tcctccgatc gttgtcagaa gtaagttggc cgcagtgtta tcactcatgg
8521 ttatggcagc actgcataat tctcttactg tcatgccatc cgtaagatgc ttttctgtga
8581 ctggtgagta ctcaaccaag tcattctgag aatagtgtat gcggcgaccg agttgctctt
```

FIG. 10B sequence of construct 2 (continued)

```
8641 gcccggcgtc aatacgggat aataccgcgc cacatagcag aactttaaaa gtgctcatca
8701 ttggaaaacg ttcttcgggg cgaaaactct caaggatctt accgctgttg agatccagtt
8761 cgatgtaacc cactcgtgca cccaactgat cttcagcatc ttttactttc accagcgttt
8821 ctgggtgagc aaaaacagga aggcaaaatg ccgcaaaaaa gggaataagg gcgacacgga
8881 aatgttgaat actcatactc ttcctttttc aatattattg aagcatttat cagggttatt
8941 gtctcatgac caaatccct taacgtgagt tttcgttcca ctgagcgtca gaccccgtag
9001 aaaagatcaa aggatcttct tgagatcctt ttttctgcg cgtaatctgc tgcttgcaaa
9061 caaaaaaacc accgctacca gcggtggttt gtttgccgga tcaagagcta ccaactcttt
9121 ttccgaaggt aactggcttc agcagagcgc agataccaaa tactgttctt ctagtgtagc
9181 cgtagttagg ccaccacttc aagaactctg tagcaccgcc tacataccto gctctgctaa
9241 tcctgttacc agtggctgct gccagtggcg ataagtcgtg tcttaccggg ttggactcaa
9301 gacgatagtt accggataag gcgcagcggt cgggctgaac ggggggttcg tgcacacagc
9361 ccagcttgga gcgaacgacc tacaccgaac tgagatacct acagcgtgag ctatgagaaa
9421 gcgccacgct tcccgaaggg agaaaggcgg acaggtatcc ggtaagcggc agggtcggaa
9481 caggagagcg cacgagggag cttccagggg gaaacgcctg gtatctttat agtcctgtcg
9541 ggtttcgcca cctctgactt gagcgtcgat ttttgtgatg ctcgtcaggg gggcggagcc
9601 tatggaaaaa cgccagcaac gcggccttttt tacggttcct ggccttttgc tggccttttg
9661 ctcacatgtt ctttcctgcg ttatcccctg attctgtgga taacgtatt accgcctttg
9721 agtgagctga taccgctcgc cgcagccgaa cgaccgagcg cagcgagtca gtgagcgagg
9781 aagcggaag
//
//
```

FIG. 10C sequence of construct 3

```
LOCUS       pcDNA5/TO/RCAN1 LA & RA/FL human XIST   21055 bp    DNA    SYN    29-Nov-
2012
DEFINITION  pcDNA5/TO/RCAN1 LA & RA/FL human XIST
ACCESSION
KEYWORDS
SOURCE
  ORGANISM  other sequences; artificial sequences; vectors.
FEATURES             Location/Qualifiers
     source          1..21055
                     /organism="pcDNA5/TO/RCAN1 LA & RA/FL human XIST"
                     /mol_type="other DNA"
     misc_feature    209..966
                     /label="RCAN1 right arm"
     misc_feature    1073..1360
                     /label="CAG_enhancer"
     promoter        994..1570
                     /label="CMV_immearly_promoter"
     misc_feature    1527..1547
                     /label="CMV_fwd_primer"
     promoter        1528..1651
                     /label="CMV_promoter"
     misc_feature    1578..1617
                     /label="tetO"
     promoter        1540..1713
                     /label="CMV2_promoter"
     misc_feature    1627..1651
                     /label="LNCX_primer"
     misc_feature    1790..15520
                     /label="Full length human XIST"
     misc_feature    complement(15719..15736)
                     /label="BGH_rev_primer"
     terminator      15722..15949
                     /label="bGH_PA_terminator"
     rep_origin      16012..16318
                     /label="f1_origin"
     misc_feature    complement(16432..16452)
```

FIG. 10C  sequence of construct 3 (continued)

```
     misc_feature    /label="pBABE_3_primer"
                     complement(16438..16653)
                     /label="SV40_enhancer"
     promoter        16450..16718
                     /label="SV40_promoter"
     rep_origin      16617..16694
                     /label="SV40_origin"
     misc_feature    16679..16698
                     /label="SV40pro_F_primer"
     CDS             complement(16752..17573)
                     /label="ORF frame 3"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNRERGRCKVPINITIFVETIGAAIYPQDISTPSYIEAES
                     TRFFALRELHQVGDAVELFDQKLLDRRRGEFRLFHHVLIRSENGYTSSRELFAKA*"
     CDS             16815..17840
                     /label="hygroB"
                     /gene="hygroB"
                     /note="ORF frame 3"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRFWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"
     gene            16830..17837
                     /label="hygroB"
                     /gene="hygroB"
     terminator      17973..18092
                     /label="SV40_PA_terminator"
     misc_feature    18061..18080
                     /label="EBV_rev_primer"
     misc_feature    18102..18860
                     /label="RCAN1_left_arm"
     misc_feature    complement(18894..18912)
                     /label="M13_reverse_primer"
     misc_feature    complement(18911..18933)
                     /label="M13_pUC_rev_primer"
     promoter        complement(18947..18976)
                     /label="lac_promoter"
     rep_origin      complement(19285..19904)
                     /label="pBR322_origin"
     CDS             complement(20059..20919)
                     /label="Ampicillin"
                     /gene="Ampicillin"
                     /note="ORF frame 1"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"
     gene            complement(20059..20919)
                     /label="Ampicillin"
                     /gene="Ampicillin"
     promoter        complement(20961..20989)
                     /label="AmpR_promoter"
ORIGIN
        1 GACGGATCGG GAGATCTCCC GATCCCCTAT GGTGCACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TAAGCTACA ACAAGGCAAG CTTGACCGA CAATTGCATG AAGAATCTGC
      181 TTAGGGTTAG GCGTTTTGCG CTGCTTCGCg acaatgtttt cagaaatgta atcttttcaa
      241 tatgaaactg ctgatggacc aagaaaacaa aaccctcaac ccaagggaac atcagattgc
```

FIG. 10C sequence of construct 3 (continued)

```
 301 tggtcaagga gaaatgagga gctgacggtc tcagcattta tttgacttgc tccacggaca
 361 gagcaggaga aggctcaaac ctcttcaccc caagactctc cctcacacct gcctcctcac
 421 ccaaacccta gaggacagga caggaaccac caacatttta tggttttcaa aaatcctgca
 481 ttgaacactg actgtgagcc aggtgctgat ggaagtgcct ttcactcgat gatctcatct
 541 actgctcaca attccaccag ttaaggccca cattttggac aaagagcctg aggaacctac
 601 ccctccccg cagtgctcac acttttgtcc ctccagagga cgggaacttc ctctttcttt
 661 agcaagctct gtaggggacc agcccacagg ccctggggta gggcagcccg accgcggccc
 721 ttccctcacc atggcctatg gttctcttc cctttcctt taagaaggcc aggtgagaat
 781 cacaggaaag ggagaattta ttttgattaa aaataacatt tcttaaaggg ggcatcgatt
 841 ttcccttcc aaagtccaat cactcatccc tatccggagc gacagaacct ggggccgggg
 901 ctcaggcctc ccacgcagge tgtgctcagt ggacacagga atggattcct gggacactgc
 961 gggtcgCGAT GTACGGGCCA GATATACGCG TTGACATTGA TTATTGACTA GTTATTAATA
1021 GTAATCAATT ACGGGGTCAT TAGTTCATAG CCCATATATG GAGTTCCGCG TTACATAACT
1081 TACGGTAAAT GGCCCGCCTG GCTGACCGCC CAACGACCCC CGCCCATTGA CGTCAATAAT
1141 GACGTATGTT CCCATAGTAA CGCCAATAGG GACTTTCCAT TGACGTCAAT GGGTGGAGTA
1201 TTTACGGTAA ACTGCCCACT TGGCAGTACA TCAAGTGTAT CATATGCCAA GTACGCCCCC
1261 TATTGACGTC AATGACGGTA AATGGCCCGC CTGGCATTAT GCCCAGTACA TGACCTTATG
1321 GGACTTTCCT ACTTGGCAGT ACATCTACGT ATTAGTCATC GCTATTACCA TGGTGATGCG
1381 GTTTTGGCAG TACATCAATG GGCGTGGATA GCGGTTTGAC TCACGGGGAT TTCCAAGTCT
1441 CCACCCCATT GACGTCAATG GGAGTTTGTT TTGGCACCAA AATCAACGGG ACTTTCCAAA
1501 ATGTCGTAAC AACTCCGCCC CATTGACGCA AATGGGCGGT AGGCGTGTAC GGTGGGAGGT
1561 CTATATAAGC AGAGCTCTCC CTATCAGTGA TAGAGATCTC CCTATCAGTG ATAGAGATCG
1621 TCGACGAGCT CGTTTAGTGA ACCGTCAGAT CGCCTGGAGA CGCCATCCAC GCTGTTTTGA
1681 CCTCCATAGA AGACACCGGG ACCGATCCAG CCTCCGGACT CTAGCGTTTA AACTTAAGCT
1741 TGGTACCGAG CTCGGATCCA CTAGTCCAGT GTGGTGGAAT TCTGCAGATt ctagaacatt
1801 ttctagtccc ccaacaccct ttatggcgta tttcttttaaa aaaatcacct aaattccata
1861 aaatatttt ttaaattcta tactttctcc tagtgtcttc ttgacacgtc ctccatattt
1921 ttttaaagaa agtatttgga atattttgag gcaattttta atattttaagg aattttttctt
1981 tggaatcatt tttggtgaca tctctgtttt ttgtgaatca gttttttact cttccactct
2041 cttttctata ttttgcccat cggggctgcg gatacctggt tttattattt tttctttgcc
2101 caacgggcc gtggatacct gccttttaat tcttttttat tcgcccatcg gggccgcgga
2161 tacctgcttt ttatttttt ttccttagcc catcggggta tcggatacct gctgattccc
2221 ttccctctg aaccccaac actctggccc atcgggtga cggatatctg cttttaaaa
2281 atttttcttt tttggcccat cgggctcg gatacctgct tttttttt ttatttcct
2341 tgcccatcgg ggcctcggat acctgcttta atttttgttt ttctgcccat cggggccgcg
2401 gatacctgct ttgatttttt tttttcatcg cccatcggtg cttttatgg atgaaaaaat
2461 gttggttttg tgggttgttg cactctctgg aatatctaca cttttttttg ctgctgatca
2521 tttggtgtg tgtgagtgta cctaccgctt ggcagagaa tgactctgca gttaagctaa
2581 gggcgtgttc agattgtgga ggaaaagtgg ccgccatttt agacttgccg cataactcgg
2641 cttagggcta gtcgtttgtg ctaagttaaa ctagggaggc aagatggatg atagcaggtc
2701 aggcagagga agtcatgtgc attgcatgaa ctaaacctat ctgaatgaat tgatttgggg
2761 cttgttagga gctttgcgtg attgttgtat cgggaggcag taagaatcat cttttatcag
2821 tacaagggac tagttaaaaa tggaaggtta ggaaagacta aggtgcaggg cttaaaatgg
2881 cgattttgac attgcggcat tgctcagcat ggcgggctgt gctttgttag gttgtccaaa
2941 atggcggatc cagttctgtc gcagtgttca agtggcggga aggccacatc atgatgggcg
3001 aggctttgtt aagtggttag catggtggtg gacatgtgcg gtcacacagg aaaagatggc
3061 ggctgaaggt cttgccgcag tgtaaaacat ggcgggcctc tttgtcttg ctgtgtgctt
3121 ttcgtgttgg gttttgccgc agggacaata tggcaggcgt tgtcatatgt atatcatggc
3181 ttttgtcacg tggacatcat ggcgggcttg ccgcattgtt aaagatggcg ggttttgccg
3241 cctagtgcca cgcagagcgg gagaaaaggt gggatggaca gtgctggatt gctgcataac
3301 ccaaccaatt agaaatgggg gtggaattga tcacagccaa ttagagcaga agatggaatt
3361 agactgatga cacactgtcc agctactcag cgaagacctg ggtgaattag catggcactt
3421 cgcagtgtc tttagccagt caggagaaag aagtggaggg gccacgtgta tgtctcccag
3481 tgggcggtac accaggtgtt tccaaggtct tttcaaggac atttagcctt tccacctctg
3541 tcccctctta tttgtccct cctgtccagt gctgcctctt gcagtgctgg atatctggct
3601 gtgtggtctg aacctccctc cattcctctg tattggtgcc tcacctaagg ctaagtatac
3661 ctccccccc acccccaac cccccaact cccacccc accccccacc cccaccctcc
3721 ccaccccct acccccctac ccccctaccc ccctctggtc tgccctgcac tgcactgttg
3781 ccatggcag tgctccaggc ctgcttggcg tggacatggt ggtgagccgt gcaggtgacc
3841 agaatggatc acagatgatc gttggccaac aggtggcaga agaggaattc ctgccttcct
3901 caagaggaac acctaccct tggctaatgc tggggtcgga ttttgattta tatttatctt
3961 ttggatgtca gtcatacagt ctgattttgt ggttgctag tgtttgaatt taagtcttaa
4021 gtgactatta tagaaatgta ttaagaggct ttatttgtag aattcacttt aattacattt
4081 aatgagtttt tgtttgagt tccttaaaat tccttaaagt ttttagcttc tcattacaaa
4141 ttccttaacc tttttttggc agtagatagt caaagtcaaa tcatttctaa tgttttaaaa
```

FIG. 10C sequence of construct 3 (continued)

```
4201 atgtgctggt catttctttt gaaattgact taactatttt cctttgaaga gtctgtagca
4261 cagaaacagt aaaaaattta acttcatgac ctaatgtaaa aagagtgtt tgaaggttta
4321 cacaggtcca ggccttgctt tgttcccatc cttgatgctg cactaattga ctaatcacct
4381 acttatcaga caggaaactt gaattgctgt ggtctgtgt cctctattca gacttattat
4441 attggagtat ttcaattttt cgttgtatcc tgcctgccta gcatccagtt cctcccagc
4501 cctgctccca gcaaacccct agtctagccc cagccctact cccacccggc cccagccctg
4561 cccaggccc agtccctaa ccccccagcc ctaggccag tccagtcct agttcctcag
4621 tctgtccagc ttctctcgaa agtcactcta attttcattg attcagtgct caaaataagt
4681 tgtccattgg tatcctatta tactgggata ttccgtttac ccttggcatt gctgatcttc
4741 agtactgact ccttgaccat tttcagttaa gcataccatc ccatttgtct gtgatctcag
4801 gacaagaat ttccttactc ggtacgttga agttagggaa tgtcaattga gagctttcta
4861 tcagagcatt attgcccaca atttgagtta cttatcattt tctcgatccc ctgcccttaa
4921 aggagaaacc atttctctgt cattgcttct gtagtcacag tccaatttt gagtagtgat
4981 cttttcttgt gtactgtgtt ggccacctaa aactctttgc attgagtaaa attctaattg
5041 ccaataatcc tacccattgg attagacagc actctgaacc ccatttgcat tcagcagggg
5101 gtcgcagaca acccgtcttt tgttggacag ttaaaatgct cagtcccaat tgtcatagct
5161 ttgcctatta aacaaaggca ccctactgcg cttttgctg tgctctgga gaatcctgct
5221 gttcttggac aattaaagaa caaagtagta attgctaatt gtctcaccca ttaatcatga
5281 agactaccag tcgcccttgc atttgccttg aggcagcgct gactacctga gatttaagag
5341 tttcttaaat tattgagtaa aatcccaatt atccatagtt ctgttagtta cactatggcc
5401 tttgcaaaca tctttgcata acagcagtgg gactgactca ttcttagagc cccttccctt
5461 ggaatattaa tggatacaat agtaattatt catggttctg cgtaacagag aagacccact
5521 tatgtgtatg cctttatcat tgctcctaga tagtgtgaac tacctaccac cttgcattaa
5581 tatgtaaaac actaattgcc catagtccca ctcattagtc taggatgtcc tctttgccat
5641 tgctgctgag ttctgactac ccaagtttcc ttctcttaaa cagttgatat gcataattgc
5701 atatattcat ggttctgtgc aataaaaatg gattctcacc ccatcccacc ttctgtggga
5761 tgttgctaac gagtgcagat tattcaataa cagctcttga acagttaatt tgcacagttg
5821 caattgtcca gagtcctgtc cattagaaag ggactctgta tcctatttgc acgctacaat
5881 gtgggctgat cacccaagga ctcttcttgt gcattgatgt tcataattgt atttgtccac
5941 gatcttgtgc actaaccctt ccactccctt tgtattccag caggggacc ttactactca
6001 agacctctgt actaggacga tttatgtgca caatcctaat tgattagaac tgagtctttt
6061 atatcaaggt ccctgcatca tctttgcttt acatcaagag ggtgctggtt acctaatgcc
6121 cctcctccag aaattattga tgtgcaaaat gcaatttccc tatctgctgt tagtctgggg
6181 tctcatcccc tcatattcct tttgtcttac agcagggggt acttgggact gttaatgcgc
6241 ataattgcaa ttatggtctt ttccattaaa ttaagatccc aactgctcac accctcttag
6301 cattacagta gagggtgcta atcacaagga catttcttt gtactgttaa tgtgctactt
6361 gcatttgtcc ctcttcctgt gcactaaaga ccccactcac ttccctagtg ttcagcagtg
6421 gatgacctct agtcaagacc tttgcactag gatagttaat gtgaaccatg gcaactgatc
6481 acaacaatgt ctttcagatc agatccattt tatcctcctt gttttacagc aagggatatt
6541 aattacctat gttacctttc cctgggacta tgaatgtgca aaattccaat gttcatggtc
6601 tctcccttta aacctatatt ctacccttt tacattatag aaagggatgc tgaaaccca
6661 gagtccttct cttgggactc ttaatgtgta tttctaatta tccatgactc ttaatgtgca
6721 tattttcaat tgcctaattg atttcaattg tctaagacat ttcaaatgtc taattgatta
6781 gaactgagtc ttttatatca agctaatatc tagcttttat atcaagctaa tatcttgact
6841 tctcagcatc atagaagggg gtactgattt cctaaagtct ttcttgaatt tctattatgc
6901 aaaattgccc tgaggccggg tgtggtggct cacacctgta atcccagcac tttgggaggc
6961 tgaggtggga agatcccta ctgccaggag tttgagacca gcctggccaa cattaaaaaa
7021 aaaaaaaaa gtaagacaat tgccctggaa tcccatcccc ctcacacctc cttggcaaag
7081 cagcaggagt gctaaatagc tagtgctct tctcttatac tgcttaaatg cgcataatta
7141 gcagtagttg atgtgccct atgttagagt agaatcccgc ttccttgctc catttgcatt
7201 actgcaggag cttctaacta gcctgaattc actctcttgg actgttaatg tgcatactta
7261 tatttgctgc tgtactttt taccatgtaa ggaccccacc cactgtattt acatcccagc
7321 tggaagtacc tactacttaa gaccttaga ctagtaaagt tagcgtgcat aatcttaggt
7381 gttatataca catttccagt tgcatacagt tgtgccttt atcaggactc ctgtacttat
7441 caaagcagag agtgctaatc aatattagac ccttctcttc gaactgtaga tggcatgtaa
7501 ttgcagttgt caatggtcct tcaattgac ttggtttct gacctatcac acctcttg
7561 ctttattgca tggggtacta ttcacttaag gccccttct caaactgtta atgtgcctaa
7621 tgacaattac atcagtatcc ttcctttga aggacagcat ggttggtgac acctaaggcc
7681 ccatttcttg gcctcccaat atgtgtgatt gtatttgtcg aggttgctat gcactagaga
7741 aggaaagtgc tccctcatc cccactttc ccttccagca ggaagtgccc acccataag
7801 acccttttat ttggagagtc taggtgcaca attgtaagtg accacaagca tgcatcttgg
7861 acatttatgt gcgtaatcgc acactgctca ttccatgtga ataaggtcct actctccgac
7921 ccctttgca atacagaagg gttgctgata acgcagtccc cttttcttgg catgttgtgt
7981 gtgattataa tcgtctggga tcctatgcac tagaaaagga gggtcctctc cacatacctc
8041 agtctcacct ttcccttcca gcagggagtg cccactccat aagactctca catttggaca
```

FIG. 10C  sequence of construct 3 (continued)

```
 8101 gtcaaggtgc gtaattgtta agtgaacaca accatgcacc ttagacatgg atttgcataa
 8161 ctacacacag ctcaacctat ctgaataaaa tcctactctc agaccccttt tgcagtacag
 8221 cagggtgct gatcaccaag gccctttttc ctggcctggt atgcgtgtga ttatgtttgt
 8281 cccggttcct gtgtattaga catggaagcc tgtccaccca cactccacca ccaatcttcc
 8341 tttccttcc ggcaggagtg ccctctccat aagacgctta cgtttggaca atcaaggtgc
 8401 acagttgtaa gtgaccacag gcatacacct tggacattaa tgtgcataac cactttgccc
 8461 attccatctg aataaggtcc tactctcaga ccccttttgc agtacagcag gggtgctgat
 8521 caccaaggcc ccttttcttg gcctgttatg tgcgtgatta tatttgtctg ggttcctgtg
 8581 tattagacaa ggaagccttc ccccgcccc cacccccact ccagtcttc ctttcccttc
 8641 cagcagggag tgcccctcc ataagatcat tacatttgga caatcaaggt gcacaattat
 8701 aagtgaccac agccatgcac cttggacatt attggacatt aatgtgcgta actgcacatg
 8761 gcccatccca tctgaataag gacctactct cagatgcctt tgcagtacag cagggtact
 8821 gaatcaccaa ggcccttttt cttggcctgt tatgtgtgtg attatattta tcccagtttc
 8881 tgtgtaatag acatgaaagc ctccctgcc acacccacc tccaatcttc ctttcccttc
 8941 caccaggagg tgtccactcc atatacccctt acatttggac aatcaaggtg cacaattgta
 9001 agtgagcata ggcactcacc ttggacatga atgtgcataa ctgcacatgg cccatcccat
 9061 ctgaataagg tcctactctc agacccttt tgcagtacag cagggtgct gatcaccaag
 9121 gccctttc ctggcctgtt atgtgtgtga ttatattgt tccagttcct gtgtaataga
 9181 catggaagcc tccctgcca cactccacc ccaatcttcc tttccttctg gcaggaagta
 9241 cccgctccat aagacccta catttggaca gtcaaggtgc acaattgtat gtgaccacaa
 9301 ccatgcacct tggacataaa tgtgtgtaac tgcacatggc ccatcccatc tgaataaggt
 9361 cctactctca gacccctttt gcagtacagt aggtgtgctg ataaccaagg ccctcttcc
 9421 tggcctgtta acgtatgtga ttatattgt ctgggttcca gtgtataaga catggaagcc
 9481 tccctgccc caccccaccc tcaatcttcc ttcccttct ggcagggagt gccagctcca
 9541 taagaaccttt acatttggac agtcaaggtg cacaattcta agtgaccgca gccatgcacc
 9601 ttggtcaata atgtgtgtaa ctgcacacgg cctatctcat ctgaatagg ccttactctc
 9661 agacccctt tgcagtacag caggggtgct gataaccaag gcccattttc ctggcctgtt
 9721 atgtgtgtga ttatattgt ccaggtttct gtgtactaga caaggaagcc tcctctgccc
 9781 catcccatct acgcataatc tttctttcc tcccagcagg gagtgctcac tccataagac
 9841 ccttacattt ggacaatcaa ggtgcacaat tgtaagtgac cacaaccatg catcttggaa
 9901 attatgtgc ataactgcac atggcttatc ctatttgaat aaagtcctac tctcagaccc
 9961 cctttgcagt atagctgggg tgctgatcac tgaggcctct tgcttggct tgtctatatt
10021 cttgtgtact agataaggc acctcctcat ggactccctt tgcttttcaa caaggagtac
10081 ccactccctt taagattct tatatttgtc caaagtacat ggttttaatt gaccacaaca
10141 atgtcccttg gacattaatg tatgtaatca ccacatggtt catcctaatt aaacaaagtt
10201 ctaccttctc acctccatt tgcagtatac caggttgct gacccctaa gtcccctttt
10261 cttggcttgt tgacatgcat aattgcattt atgttggttc ttgtgcccta gacaaggatg
10321 cccacctct tttcaatagt gggtgcccac tcttatgat ctttacattt gaacagttaa
10381 tgtgaataat tgcagttgtc cacaacccta tcacttctag gaccattata cctcttttgc
10441 attactgtgg ggtatactgt ttcctccaa ggcccttct ggtggactat caacatataa
10501 ttgaaatttt ctttttgtctt tgtcagtaga ttaaggtcat acccccatcac ctttccttg
10561 tagtacaaca gggtgtcctg atcaaccaaa gtcctgttgt tttggactgt taatatgtgc
10621 aattacattt gctcctgatc tgtgcactag ataaggatcc tacctacttt cttagtgttt
10681 ttagcaggta gtgccacta ctcaagactg tcacttggaa tgttcatgtg cacaaactca
10741 attctctaag catgttcctg taccaccttt gcttagagc aggggatga tattcactaa
10801 gtgccccttc ttttggactt aatatgcatt aatgcaattg tccacctctt cttttagact
10861 aagagttgat ctccacatat tcccttgca tcagggcat gttaattatg aatgaaccct
10921 tttcttttaa tattaatgtc ataattgtat ttgtggacct gtgtaggaga aaaagaccct
10981 atgttcctc cattacctt tggattgctg ctgagaagtg ttaactactc ataatctcag
11041 ctcttggaca attaatagca ttaataacaa ttatcaaggg cactgatcat tagataagac
11101 tcctgcttcc tcgttgctta catcgggggt actgacccac taaggcccct tgtactgtta
11161 atgtgaatat tgcaattat atatgtctcc ttctggtaga gtgggatatt atgccctagt
11221 atcccctttg cattactgca ggggctgctg actactcaaa actctcctg ggactgttaa
11281 taggcacaat ggcagttatc aatggttttc tccctccctg accttgttaa gcaagcgccc
11341 cacccccacc ttagtttccc atggcataat aaagtataag cattggagta tccatgcac
11401 ttgtctatca aacagtggtc catactccca accttttgc attgcgccag tgtgtaaaat
11461 cacaggtagc catggtgtca tgctttatat acgaagtctt ccctctctct gcccttgtg
11521 tgccttggc cccttttac agactattgc tcacaatctc aggtgtccat atttgcagct
11581 attaggtaag attgtgctgt ctccctcttc ccttccctct gccctgcccc ttttgcctct
11641 tgctgggta atgttgacca gacaaggcc tttctcttgg acttaaacaa ttctcagttg
11701 cacttcctt ggtccaccca ttatacatga acccctctac ttcctttcgc attgcttctg
11761 agtatgctga ctacccaag cccttctgt gttattaata aacacagtac tgattgtccc
11821 atttttcagc ccatcagtcc aagatctccc taccactttg gtgtgttggt gcagtgttga
11881 ctatgaaaag caggcctgaa ctaggtggat aagccttcac tcatttcttt tcatttatta
11941 atgatcctag tttcaattat tgtcagattc tggggacaag aaccattctt gccccacctgt
```

FIG. 10C sequence of construct 3 (continued)

```
12001 gttactgctt tactgtgcaa aatactgaag gcaagtcaga cccagggagc tggattgcca
12061 tcctttattt tgtgtttcca gtgtacacta taaaattgtc tccccaggaa ggaaggttgg
12121 cactttctct gcattcttct ttccagagca gattgcctgg ttaagaatct cttgttgtcc
12181 cttctgtata ttgttattgt aaagtgccaa atgccaggat acagccagaa aaattgctta
12241 ttattattaa aaaaatttt ttaagaaaga catctgcgatt gtagggtgga ctcgataacc
12301 tggtcattat ttttttgaag ccaaaatatc catttatact atgtacctgg tgaccagtgt
12361 ctctcatttt aactgagggt ggtgggtctg tggatagaac actgactctt gctattttaa
12421 tatcaaagat attctagATC CAGCACAGTG GCggccgctc tagagtggaa ctcttaagac
12481 cagtatcttt gtgtgggctt taccagcatt cactttttaga aaaactacct aaattttata
12541 atcctttaat ttcttcatct ggagcacctg ccctactta tttcaagaag attgcagtaa
12601 aacgattaaa tgaggaaaca tatgcagagg tgcttttaaa aagcatatgc cacctttttt
12661 attaattatt atataaaatg aagcatttaa ttatagtaat aatttgaagt agtttgaagt
12721 accacactga ggtgaggact taaaaatgat aagacgagtt ccctatttta taagaaaat
12781 aagccaaaat taaatattct tttggatata aatttcaaca gtgagatagc tgcctagtgg
12841 aaatgaataa tatcccagcc actagtgtac agggtgtttt gtggcacagg attatgtaat
12901 atggaactgc tcaagcaaat aactagtcat cacaacagca gttctttgta ataactgaaa
12961 aagaatattg tttctcggag aaggatgtca aaagatcggc ccagctcagg gagcagtttg
13021 ccctactagc tcctcggaca gctgtaaaga agagtctctg gctctttaga atactgatcc
13081 cattgaagat accacgctgc atgtgtcctt agtagtcatg tctccttagg ctcctcttgg
13141 acattctgag catgtgagac ctgaggactg caaacagcta taagaggctc caaattaatc
13201 atatctttcc ctttgagaat ctggccaagc tccagctaat ctacttggat gggttgccag
13261 ctatctggag aaaaagatct tcctcagaag aataggcttg ttgttttaca gtgttagtga
13321 tccattccct ttgacgatcc ctaggtgag atggggcatg aggatcctcc aggggaaaag
13381 ctcactacca ctgggcaaca accctaggtc aggaggttct gtcaagatac tttcctggtc
13441 ccagatagga agataaagtc tcaaaaacaa ccaccacacg tcaagctctt cattgttcct
13501 atctgccaaa tcattatact tcctacaagc agtgcagaga gctgagtctt cagcaggtcc
13561 aagaaatttg aacacactga aggaagtcag ccttcccacc tgaagatcaa catgcctggc
13621 actctagcac ttgaggatag ctgaatgaat gtgtatttct ttgtctcttt ctttcttgtc
13681 tttgctcttt gttctctatc taaagtgtgt cttacccatt tccatgtttc tcttgctaat
13741 tccttcgtg tgtgcctttg cctcattttc tcttttgtt cacaagagtg gtctgtgtct
13801 tgtcttagac atatctctca ttttttcattt tgttgctatt tctctttgct ctcctagatg
13861 tggctcttct ttcacgcttt atttcatgtc tccttttgg gtcacatgct gtgtgcttt
13921 tgtccttttc ttgtctgtc tacctctcct ttctctgcct acctctcttt tctctttgtg
13981 aactgtgatt atttgttacc ccttcccctt ctcgttcgtt ttaaatttca cctttttct
14041 gagtctggcc tcctttctgc tgtttctact ttttatctca catttctcat ttctgcattt
14101 cctttctgcc tctcttgggc tattctctct ctcctcccct gcgtgcctca gcatctcttg
14161 ctgtttgtga ttttctattt cagtattaat ctctgttggc ttgtatttgt tctctgcttc
14221 ttccctttct actcacctttt gagtatttca gcctcttcat gaatctatct ccctctcttt
14281 gatttcatgt aatctctcct taaatatttc tttgcatatg tggcaagtg tacgtgtgtg
14341 tgtgtcatgt gtggcagagg ggcttcctaa ccctgcctg ataggtcag aacgtcggct
14401 atcagagcaa gcattgtgga gcggttcctt atgccaggct gccatgtgag atgatccaag
14461 accaaaacaa ggccctagac tgcagtaaaa cccagaactc aagtagggca gaaggtggaa
14521 ggctcatatg gatagaaggc ccaaagtata agacagatgg tttgagactt gagacccgag
14581 gactaagatg gaaagcccat gttccaagat agatagaagc ctcaggcctg aaaccaacaa
14641 aagcctcaag agccaagaaa acagagggtg gcctgaattg gaccgaaggc ctgagttgga
14701 tggaagtctc aaggcttgag ttagaagtct taagacctgg gacaggacac atggaaggcc
14761 taagaactga gacttgtgac acaaggccaa cgacctaaga ttagcccagg gttgtagctg
14821 gaagcctac aaccaagga tggaaggccc ctgtcaacaa gcctacctag atggatagag
14881 gacccaagcg aaaaaggtat ctcaagacta acggccggaa tctggaggcc catgacccag
14941 aacccaggaa ggatagaagc ttgaagacct ggggaaatcc caagatgaga accctaaacc
15001 ctacctcttt tctattgttt acacttctta ctcttagata tttccagttc tctgtttat
15061 ctttaagcct gattcttttg agatgtactt tttgatgttg ccggttacct ttagattgac
15121 agtattatgc ctgggccagt cttgagccag ctttaaatca cagcttttac ctatttgtta
15181 ggctatagtg ttttgtaaac ttctgtttct attcacatct tctccacttg agagagacac
15241 caaaatccag tcagtatcta atctgtgttt tgttaactc cctcaggagc agacattcat
15301 ataggtgata ctgtatttca gtcctttctt ttgacccag aagccctaga ctgagaagat
15361 aaaatggtca ggttgttggg gaaaaaaaaa gtgccaggct ctctagaaa aaatgtgaag
15421 agatgctcca ggccaatgag aagaattaga caagaaatac acagatgtgc cagacttctg
15481 agaagcacct gccagcaaca gcttccttct ttgagcttag ATTTTCCTAG TCCATCCCTC
15541 ATGAAAAATG ACTGACCACT GCTGGGCAGC AGGAGGGATG ATGACCAACT AATTCCCAAA
15601 CCCCAGTCTC ATTGGTACCG AGCTCGGATC CACTAGTCCA GTGTGGTGGA ATTCTGCAGA
15661 TATCCAGCAC AGTGGCGGCC GCTCGAGTCT AGAGGGCCCG TTTAAACCCG CTGATCAGCC
15721 TCGACTGTGC CTTCTAGTTG CCAGCCATCT GTTGTTTGCC CCTCCCCCGT GCCTTCCTTG
15781 ACCCTGGAAG GTGCCACTCC CACTGTCCTT TCCTAATAAA ATGAGGAAAT TGCATCGCAT
15841 TGTCTGAGTA GGTGTCATTC TATTCTGGGG GGTGGGGTGG GGCAGGACAG CAAGGGGGAG
```

FIG. 10C sequence of construct 3 (continued)

```
15901 GATTGGGAAG ACAATAGCAG GCATGCTGGG GATGCGGTGG GCTCTATGGC TTCTGAGGCG
15961 GAAAGAACCA GCTGGGGCTC TAGGGGGTAT CCCCACGCGC CCTGTAGCGG CGCATTAAGC
16021 GCGGCGGGTG TGGTGGTTAC GCGCAGCGTG ACCGCTACAC TTGCCAGCGC CCTAGCGCCC
16081 GCTCCTTTCG CTTTCTTCCC TTCCTTTCTC GCCACGTTCG CCGGCTTTCC CCGTCAAGCT
16141 CTAAATCGGG GGCTCCCTTT AGGGTTCCGA TTTAGTGCTT TACGGCACCT CGACCCCAAA
16201 AAACTTGATT AGGGTGATGG TTCACGTAGT GGGCCATCGC CCTGATAGAC GGTTTTTCGC
16261 CCTTTGACGT TGGAGTCCAC GTTCTTTAAT AGTGGACTCT TGTTCCAAAC TGGAACAACA
16321 CTCAACCCTA TCTCGGTCTA TTCTTTTGAT TTATAAGGGA TTTTGCCGAT TTCGGCCTAT
16381 TGGTTAAAAA ATGAGCTGAT TTAACAAAAA TTTAACGCGA ATTAATTCTG TGGAATGTGT
16441 GTCAGTTAGG GTGTGGAAAG TCCCCAGGCT CCCCAGCAGG CAGAAGTATG CAAAGCATGC
16501 ATCTCAATTA GTCAGCAACC AGGTGTGGAA AGTCCCCAGG CTCCCCAGCA GGCAGAAGTA
16561 TGCAAAGCAT GCATCTCAAT TAGTCAGCAA CCATAGTCCC GCCCCTAACT CCGCCCATCC
16621 CGCCCCTAAC TCCGCCCAGT TCCGCCCATT CTCCGCCCCA TGGCTGACTA ATTTTTTTTA
16681 TTTATGCAGA GGCCGAGGCC GCCTCTGCCT CTGAGCTATT CCAGAAGTAG TGAGGAGGCT
16741 TTTTTGGAGG CCTAGGCTTT TGCAAAAAGC TCCCGGGAGC TTGTATATCC ATTTTCGGAT
16801 CTGATCAGCA CGTGATGAAA AAGCCTGAAC TCACCGCGAC GTCTGTCGAG AAGTTTCTGA
16861 TCGAAAAGTT CGACAGCGTC TCCGACCTGA TGCAGCTCTC GGAGGGCGAA GAATCTCGTG
16921 CTTTCAGCTT CGATGTAGGA GGGCGTGGAT ATGTCCTGCG GGTAAATAGC TGCGCCGATG
16981 GTTTCTACAA AGATCGTTAT GTTTATCGGC ACTTTGCATC GGCCGCGCTC CCGATTCCGG
17041 AAGTGCTTGA CATTGGGGAA TTCAGCGAGA GCCTGACCTA TTGCATCTCC CGCCGTGCAC
17101 AGGGTGTCAC GTTGCAAGAC CTGCCTGAAA CCGAACTGCC CGCTGTTCTG CAGCCGGTCG
17161 CGGAGGCCAT GGATGCGATC GCTGCGGCCG ATCTTAGCCA GACGAGCGGG TTCGGCCCAT
17221 TCGGACCGCA AGGAATCGGT CAATACACTA CATGGCGTGA TTTCATATGC GCGATTGCTG
17281 ATCCCCATGT GTATCACTGG CAAACTGTGA TGGACGACAC CGTCAGTGCG TCCGTCGCGC
17341 AGGCTCTCGA TGAGCTGATG CTTTGGGCCG AGGACTGCCC CGAAGTCCGG CACCTCGTGC
17401 ACGCGGATTT CGGCTCCAAC AATGTCCTGA CGGACAATGG CCGCATAACA GCGGTCATTG
17461 ACTGGAGCGA GGCGATGTTC GGGGATTCCC AATACGAGGT CGCCAACATC TTCTTCTGGA
17521 GGCCGTGGTT GGCTTGTATG GAGCAGCAGA CGCGCTACTT CGAGCGGAGG CATCCGGAGC
17581 TTGCAGGATC GCCGCGGCTC CGGGCGTATA TGCTCCGCAT TGGTCTTGAC CAACTCTATC
17641 AGAGCTTGGT TGACGGCAAT TTCGATGATG CAGCTTGGGC GCAGGGTCGA TGCGACGCAA
17701 TCGTCCGATC CGGAGCCGGG ACTGTCGGGC GTACACAAAT CGCCCGCAGA AGCGCGGCCG
17761 TCTGGACCGA TGGCTGTGTA GAAGTACTCG CCGATAGTGG AAACCGACGC CCCAGCACTC
17821 GTCCGAGGGC AAAGGAATAG CACGTGCTAC GAGATTTCGA TTCCACCGCC GCCTTCTATG
17881 AAAGGTTGGG CTTCGGAATC GTTTTCCGGG ACGCCGGCTG GATGATCCTC CAGCGCGGGG
17941 ATCTCATGCT GGAGTTCTTC GCCCACCCCA ACTTGTTTAT TGCAGCTTAT AATGGTTACA
18001 AATAAAGCAA TAGCATCACA AATTTCACAA ATAAAGCATT TTTTTCACTG CATTCTAGTT
18061 GTGGTTTGTC CAAACTCATC AATGTATCTT ATCATGTCTG TAtacgggtg gagggcgtg
18121 atgcagggtc cccacgatca gccgcagtct ctctaacact gcaggtggtg ccaagaggca
18181 ggcatgctcc cagcacaagg gacggtggcg cagaagaata cagagaagct cacaaaacat
18241 gccggcatgg gtcaggaga gctacggggg tagtgctgt actgctccct ggtgcagggc
18301 agcagctgtg tctccccctg cctcctccc accgagggc cctgctcacc tggcccagc
18361 ttggagatgg catataagag atcatagttt atgactgggg tgcatcttc cacttgtttc
18421 catcccactg gcggagaggc gggagggag atcagaaact gcttgtctgg atttggcgga
18481 gccaggtgtg agcttcctat gtgtaaggtc tgaggagaga aaataagcac aggtcagttg
18541 ttgccaggga agaactgcag tgaggcaaca gcacctaacg ccagttccgg gagatgggca
18601 ggtcaatgtc caggcgtcag gacaggtgtg attccaggac caattgtaag atggtctgta
18661 atggggaggg caaaaggaca tatgaactct ggttgtggca cagataggat gacagcccc
18721 tcccagggct atgggagtca caggcacagg gactgcaaat aattacgctt gacctagatg
18781 gacagaaaat cagcagaggt gactttagta tatatggaaa tttaagtcac tgtcattgag
18841 gtcaggaggg ctcttgggta TACCGTCGAC CTCTAGCTAG AGCTTGGCGT AATCATGGTC
18901 ATAGCTGTTT CCTGTGTGAA ATTGTTATCC GCTCACAATT CCACACAACA TACGAGCCGG
18961 AAGCATAAAG TGTAAAGCCT GGGGTGCCTA ATGAGTGAGC TAACTCACAT TAATTGCGTT
19021 GCGCTCACTG CCCGCTTTCC AGTCGGGAAA CCTGTCGTGC CAGCTGCATT AATGAATCGG
19081 CCAACGCGCG GGGAGAGGCG GTTTGCGTAT TGGGCGCTCT TCCGCTTCCT CGCTCACTGA
19141 CTCGCTGCGC TCGGTCGTTC GGCTGCGGCG AGCGGTATCA GCTCACTCAA AGGCGGTAAT
19201 ACGGTTATCC ACAGAATCAG GGGATAACGC AGGAAAGAAC ATGTGAGCAA AAGGCCAGCA
19261 AAAGGCCAGG AACCGTAAAA AGGCCGCGTT GCTGGCGTTT TTCCATAGGC TCCGCCCCCC
19321 TGACGAGCAT CACAAAAATC GACGCTCAAG TCAGAGGTGG CGAAACCCGA CAGGACTATA
19381 AAGATACCAG GCGTTTCCCC CTGGAAGCTC CCTCGTGCGC TCTCCTGTTC CGACCCTGCC
19441 GCTTACCGGA TACCTGTCCG CCTTTCTCCC TTCGGGAAGC GTGGCGCTTT CTCATAGCTC
19501 ACGCTGTAGG TATCTCAGTT CGGTGTAGGT CGTTCGCTCC AAGCTGGGCT GTGTGCACGA
19561 ACCCCCCGTT CAGCCCGACC GCTGCGCCTT ATCCGGTAAC TATCGTCTTG AGTCCAACCC
19621 GGTAAGACAC GACTTATCGC CACTGGCAGC AGCCACTGGT AACAGGATTA GCAGAGCGAG
19681 GTATGTAGGC GGTGCTACAG AGTTCTTGAA GTGGTGGCCT AACTACGGCT ACACTAGAAG
19741 AACAGTATTT GGTATCTGCG CTCTGCTGAA GCCAGTTACC TTCGGAAAAA GAGTTGGTAG
```

FIG. 10C sequence of construct 3 (continued)

```
19801 CTCTTGATCC GGCAAACAAA CCACCGCTGG TAGCGGTTGG TTTTTTGTTT GCAAGCAGCA
19861 GATTACGCGC AGAAAAAAAG GATCTCAAGA AGATCCTTTG ATCTTTTCTA CGGGGTCTGA
19921 CGCTCAGTGG AACGAAAACT CACGTTAAGG GATTTTGGTC ATGAGATTAT CAAAAAGGAT
19981 CTTCACCTAG ATCCTTTTAA ATTAAAAATG AAGTTTTAAA TCAATCTAAA GTATATATGA
20041 GTAAACTTGG TCTGACAGTT ACCAATGCTT AATCAGTGAG GCACCTATCT CAGCGATCTG
20101 TCTATTTCGT TCATCCATAG TTGCCTGACT CCCCGTCGTG TAGATAACTA CGATACGGGA
20161 GGGCTTACCA TCTGGCCCCA GTGCTGCAAT GATACCGCGA GACCCACGCT CACCGGCTCC
20221 AGATTTATCA GCAATAAACC AGCCAGCCGG AAGGGCCGAG CGCAGAAGTG GTCCTGCAAC
20281 TTTATCCGCC TCCATCCAGT CTATTAATTG TTGCCGGGAA GCTAGAGTAA GTAGTTCGCC
20341 AGTTAATAGT TTGCGCAACG TTGTTGCCAT TGCTACAGGC ATCGTGGTGT CACGCTCGTC
20401 GTTTGGTATG GCTTCATTCA GCTCCGGTTC CCAACGATCA AGGCGAGTTA CATGATCCCC
20461 CATGTTGTGC AAAAAAGCGG TTAGCTCCTT CGGTCCTCCG ATCGTTGTCA GAAGTAAGTT
20521 GGCCGCAGTG TTATCACTCA TGGTTATGGC AGCACTGCAT AATTCTCTTA CTGTCATGCC
20581 ATCCGTAAGA TGCTTTTCTG TGACTGGTGA GTACTCAACC AAGTCATTCT GAGAATAGTG
20641 TATGCGGCGA CCGAGTTGCT CTTGCCCGGC GTCAATACGG GATAATACCG CGCCACATAG
20701 CAGAACTTTA AAAGTGCTCA TCATTGGAAA ACGTTCTTCG GGGCGAAAAC TCTCAAGGAT
20761 CTTACCGCTG TTGAGATCCA GTTCGATGTA ACCCACTCGT GCACCCAACT GATCTTCAGC
20821 ATCTTTTACT TTCACCAGCG TTTCTGGGTG AGCAAAAACA GGAAGGCAAA ATGCCGCAAA
20881 AAAGGGAATA AGGGCGACAC GGAAATGTTG AATACTCATA CTCTTCCTTT TTCAATATTA
20941 TTGAAGCATT TATCAGGGTT ATTGTCTCAT GAGCGGATAC ATATTTGAAT GTATTTAGAA
21001 AAATAAACAA ATAGGGGTTC CGCGCACATT TCCCCGAAAA GTGCCACCTG ACGTC
//
```

FIG. 10D sequence of construct 4

```
LOCUS       pcDNA5/TO/DYRK1A LA & RA/FL human XIST   20737 bp    DNA     SYN    29-Nov-
2012
DEFINITION  pcDNA5/TO/DYRK1A LA & RA/FL human XIST
ACCESSION
KEYWORDS
SOURCE
  ORGANISM  other sequences; artificial sequences; vectors.
FEATURES             Location/Qualifiers
     source          1..20737
                     /organism="pcDNA5/TO/DYRK1A LA & RA/FL human XIST"
                     /mol_type="other DNA"
     misc_feature    209..716
                     /label="DYRK1A right arm"
     misc_feature    823..1110
                     /label="CAG_enhancer"
     promoter        744..1320
                     /label="CMV_immearly_promoter"
     misc_feature    1277..1297
                     /label="CMV_fwd_primer"
     promoter        1278..1401
                     /label="CMV_promoter"
     misc_feature    1328..1367
                     /label="tetO"
     promoter        1290..1463
                     /label="CMV2_promoter"
     misc_feature    1377..1401
                     /label="LNCX_primer"
     misc_feature    1540..15270
                     /label="Full length human XIST"
     misc_feature    complement(15469..15486)
                     /label="BGH_rev_primer"
     terminator      15472..15699
                     /label="bGH_PA_terminator"
     rep_origin      15762..16068
                     /label="f1_origin"
     misc_feature    complement(16182..16202)
```

FIG. 10D sequence of construct 4 (continued)

```
                    /label="pBABE_3_primer"
    misc_feature    complement(16188..16403)
                    /label="SV40_enhancer"
    promoter        16290..16468
                    /label="SV40_promoter"
    rep_origin      16367..16444
                    /label="SV40_origin"
    misc_feature    16429..16448
                    /label="SV40pro_F_primer"
    CDS             complement(16502..17323)
                    /label="ORF frame 2"
                    /translation="MPPLEVARLLLHTSQPRPPEEDVGDLVLGIPEHRLAPVNDRCYA
                    AIVRQDIVGAEIRVHEVPDFGAVLGPKHQLIESLRDGRTDGVVHHSLPVIHMGISNRA
                    YEITPCSVLTDSLRSEWAEPARLAKIGRSDRIHGLRDRLQNSGQFGFRQVLQRDTLCT
                    AGDAIGQALAEFPNVKHFRNRERGRCKVPINITIFVETIGAAIYPQDISTPSYIEAES
                    TRFFALRELHQVGDAVELFDQKLLDRERGEFRLFHHVLIRSENGYTSSRELFAKA*"
    CDS             16565..17590
                    /label="hygroB"
                    /gene="hygroB"
                    /note="ORF frame 2"
                    /translation="MKKPELTATSVEKFLIEKFDSVSDLMQLSEGEESRAFSFDVGGR
                    GYVLRVNSCADGFYKDRYVYRHFASAALPIPEVLDIGEFSESLTYCISRRAQGVTLQD
                    LPETELPAVLQPVAEAMDAIAAADLSQTSGFGPFGPQGIGQYTTWRDFICAIADPHVY
                    HWQTVMDDTVSASVAQALDELMLWAEDCPEVRHLVHADFGSNNVLTDNGRITAVIDWS
                    EAMFGDSQYEVANIFFWRPWLACMEQQTRYFERRHPELAGSPRLRAYMLRIGLDQLYQ
                    SLVDGNFDDAAWAQGRCDAIVRSGAGTVGRTQIARRSAAVWTDGCVEVLADSGNRRPS
                    TRPRAKE*"
    gene            16580..17587
                    /label="hygroB"
                    /gene="hygroB"
    terminator      17723..17842
                    /label="SV40_PA_terminator"
    misc_feature    17811..17830
                    /label="EBV_rev_primer"
    misc_feature    17853..18542
                    /label="DYRK1A left arm"
    misc_feature    complement(18576..18594)
                    /label="M13_reverse_primer"
    misc_feature    complement(18593..18615)
                    /label="M13_pUC_rev_primer"
    promoter        complement(18629..18658)
                    /label="lac_promoter"
    rep_origin      complement(18967..19586)
                    /label="pBR322_origin"
    CDS             complement(19741..20601)
                    /label="Ampicillin"
                    /gene="Ampicillin"
                    /note="ORF frame 1"
                    /translation="MSIQHFRVALIPFFAAFCLPVFAHPETLVKVKDAEDQLGARVGY
                    IELDLNSGKILESFRPEERFPMMSTFKVLLCGAVLSRIDAGQEQLGRRIHYSQNDLVE
                    YSPVTEKHLTDGMTVRELCSAAITMSDNTAANLLLTTIGGPKELTAFLHNMGDHVTRL
                    DRWEPELNEAIPNDERDTTMPVAMATTLRKLLTGELLTLASRQQLIDWMEADKVAGPL
                    LRSALPAGWFIADKSGAGERGSRGIIAALGPDGKPSRIVVIYTTGSQATMDERNRQIA
                    EIGASLIKHW*"
    gene            complement(19741..20601)
                    /label="Ampicillin"
                    /gene="Ampicillin"
    promoter        complement(20643..20671)
                    /label="AmpR_promoter"
ORIGIN
    1 GACGGATCGG GAGATCTCCC GATCCCCTAT GGTGCACTCT CAGTACAATC TGCTCTGATG
   61 CCGCATAGTT AAGCCAGTAT CTGCTCCCTG CTTGTGTGTT GGAGGTCGCT GAGTAGTGCG
  121 CGAGCAAAAT TTAAGCTACA ACAAGGCAAG GCTTGACCGA CAATTGCATG AAGAATCTGC
  181 TTAGGGTTAG GCGTTTTGCG CTGCTTCGcg aaaaccagaa agtattctca gtaatgatag
  241 tatggataaa gcaggttttct atgacccttt attacagaat ctgtgagttt ttcacaatta
```

FIG. 10D sequence of construct 4 (continued)

```
 301 aaaagtaata aaaagtagtg acaacattca ctgaactctt attctatgcc aacttgttcc
 361 ggtatgccct tacacccaca aagccctat gcataaggtg gcattattcc agcatgtatt
 421 gcattgtaca cacaaagagg tcaagcactc caccacggcc ctaagcatgg tggctgaggt
 481 gggaaggcca gaggtaggtg ggcccgcgcc cttttccact ctgaaccatg cctccaagat
 541 aggagggtgg gaaagtgctc aagacacatt agaaattccc cataaaagac aagattgttg
 601 aacacctgca agtgaataaa gataaactga tctcagaggg gaaaaagacg cagggttagg
 661 aaacagcacc ctgctcgagg acgttctttc caaacagcct gctcatcacc cgttcgCGAT
 721 GTACGGGCCA GATATACGCG TTGACATTGA TTATTGACTA GTTATTAATA GTAATCAATT
 781 ACGGGGTCAT TAGTTCATAG CCCATATATG GAGTTCCGCG TTACATAACT TACGGTAAAT
 841 GGCCCGCCTG GCTGACCGCC CAACGACCCC CGCCCATTGA CGTCAATAAT GACGTATGTT
 901 CCCATAGTAA CGCCAATAGG GACTTTCCAT TGACGTCAAT GGGTGGAGTA TTTACGGTAA
 961 ACTGCCCACT TGGCAGTACA TCAAGTGTAT CATATGCCAA GTACGCCCCC TATTGACGTC
1021 AATGACGGTA AATGGCCCGC CTGGCATTAT GCCCAGTACA TGACCTTATG GGACTTTCCT
1081 ACTTGGCAGT ACATCTACGT ATTAGTCATC GCTATTACCA TGGTGATGCG GTTTTGGCAG
1141 TACATCAATG GGCGTGGATA GCGGTTTGAC TCACGGGGAT TTCCAAGTCT CCACCCCATT
1201 GACGTCAATG GGAGTTTGTT TTGCACCAA AATCAACGGG ACTTTCCAAA ATGTCGTAAC
1261 AACTCCGCCC CATTGACGCA AATGGGCGGT AGGCGTGTAC GGTGGGAGGT CTATATAAGC
1321 AGAGCTCTCC CTATCAGTGA TAGAGATCTC CCTATCAGTG ATAGAGATCG TCGACGAGCT
1381 CGTTTAGTGA ACCGTCAGAT CGCCTGGAGA CGCCATCCAC GCTGTTTTGA CCTCCATAGA
1441 AGACACCGGG ACCGATCAG CCTCCGGACT CTAGCGTTTA AACTTAAGCT TGGTACCGAG
1501 CTCGGATCCA CTAGTCCAGT GTGGTGGAAT TCTGCAGATt ctagaacatt ttctagtccc
1561 ccaacaccct ttatggcgta tttctttaaa aaaatcacct aaattccata aatattttt
1621 ttaaattcta tactttctcc tagtgtcttc ttgacacgtc ctccatattt ttttaaagaa
1681 agtgttgga atattttgag gcaatttta atatttaagg aattttctt tggaatcatt
1741 tttggtgaca tctctgtttt ttgtggatca gttttttact cttccactct cttttctata
1801 ttttgcccat cggggctgcg gatacctggt tttattattt ttctttgcc caacggggcc
1861 gtggatacct gcctttaat tcttttttat tcgcccatcg gggccgcgga tacctgcttt
1921 ttatttttt ttccttagcc catcggggta tcggatacct gctgattccc ttccctctg
1981 aaccccaac actctggccc atcgggtga cggatatctg ctttttaaa attttctttt
2041 tttggccat cggggcttcg gatacctgct ttttttttt ttatttctt tgcccatcgg
2101 ggcctcggat acctgcttta atttttgttt ttctgcccat cggggccgcg gataccgct
2161 ttgattttt tttttcatcg cccatcggtg cttttatgg atgaaaaaat gttggttttg
2221 tgggttgttg cactctctgg aatatctaca cttttttttg ctgctgatca tttggtggtg
2281 tgtgagtgta cctaccgctt tggcagagaa tgactctgca gttaagctaa gggcgtgttc
2341 agattgtgga ggaaaagtgg ccgccatttt agacttgccg cataactcgg cttagggcta
2401 gtcgtttgtg ctaagttaaa ctaggcaggc aagatggatg atagccaggt agcagagga
2461 agtcatgtgc attgcatgag ctaaacctat ctgaatgaat tgatttgggg cttgttagga
2521 gctttgcgtg attgttgtat cgggaggcag taagaatcat cttttatcag tacaagggac
2581 tagttaaaaa tggaaggtta ggaagacta aggtgcaggg cttaaaatgg cgattttgac
2641 attgcggcat tgctcagcat ggcgggctgt gctttgttag gttgtccaaa atggcggatc
2701 cagttctgtc gcagtgttca agtggcggga aggccacatc atgatgggcg aggctttgtt
2761 aagtggttag catgtggtg gacatgtgcg gtcacagg aaaagatggc ggctgaaggt
2821 cttgccgcag tgtaaaacat ggcgggcctc tttgtcttg ctgtgtgctt ttcgtgttgg
2881 gttttgcgc agggacaata tggcaggcgt tgtcatatgt atatcatggc ttttgtcacg
2941 tggacatcat ggcgggcttg ccgcattgtt aaagatggcg gttttgccg cctagtgcca
3001 cgcagagcgg gagaaaaggt gggatggaca gtgctggatt gctgcataac caaccaatt
3061 agaaatgggg gtggaattga tcacagccaa ttagagcaga agatggaatt agactgatga
3121 cacactgtcc agctactcag cgaagacctg ggtgaattag catgcacatt cgcagctgtc
3181 tttagccagt caggagaaag aagtggaggg gccacgtgta tgtctcccag tgggcggtac
3241 accaggtgtt tcaaggtct tttcaaggac atttagcctt tccacctctg tccctctta
3301 tttgtccct cctgtccagt gctgcctctt gcagtgctgg atatctggct gtgtggtctg
3361 aacctccctc cattcctctg tattggtgcc tcacctaagg ctaagtatac ctccccccc
3421 accccaac ccccaact ccccaccc acccccacc cccacctcc ccaccccct
3481 accccctac ccctacc ccctctggtc tgccctgcac tgcactgttg ccatgggcag
3541 tgctccagge ctgcttgtg tggacatggt ggtgagcgt ggcaaggacc agaatggatc
3601 acagatgatc gttggccaac agtgtggcaga agaggaattc ctgccttcct caagaggaac
3661 acctaccct tggctaatgc tggggtcgga ttttgattta tatttatctt ttggatgtca
3721 gtcatacagt ctgatttgt ggtttgctag tgtttgaatt taagtcttaa gtgactatta
3781 tagaaatgta ttaagaggct ttatttgtag aattcacttt aattacattt aatgagtttt
3841 tgttttgagt tccttaaaat tccttaaagt ttttagcttc tcattacaaa ttccttaacc
3901 tttttctgc agtagatagt caagtttcaa tcattctaa tgttttaaaa atgtgctggt
3961 cattttcttt gaaattgact taactatttt ccttgaaga gtcgtagca cagaaacagt
4021 aaaaaattta acttcatgac ctaatgtaaa aagagtgtt tgaaggttta cacaggtcca
4081 ggccttgctt tgttcccatc cttgatgctg cactaattga ctaatcacct acttatcaga
4141 caggaaactt gaattgctgt ggtctggtgt cctctattca gacttattat attggagtat
```

FIG. 10D sequence of construct 4 (continued)

```
4201 ttcaattttt cgttgtatcc tgcctgccta gcatccagtt cctcccagc cctgctccca
4261 gcaaaccct agtctagccc cagccctact ccaccggc cccagccctg cccaggccc
4321 agtcccctaa ccccccagcc ctaggcccag tcccagtcct agttcctcag tctgtccagc
4381 ttctctcgaa agtcactcta attttcattg attcagtgct caaaataagt tgtccattgg
4441 tatcctatta tactgggata ttccgtttac ccttggcatt gctgatcttc agtactgact
4501 ccttgaccat tttcagttaa gcatacaatc ccatttgtct gtgatctcag gacaaagaat
4561 ttccttactc ggtacgttga agttagggaa tgtcaattga gagctttcta tcagagcatt
4621 attgcccaca atttgagtta cttatcattt tctcgatccc ctgcccttaa aggagaaacc
4681 atttctctgt cattgcttct gtagtcacag tcccaatttt gagtagtgat cttttcttgt
4741 gtactgtgtt ggccacctaa aactctttgc attgagtaaa attctaattg ccaataatcc
4801 tacccattgg attagacagc actctgaacc ccatttgcat tcagcagggg gtcgcagaca
4861 acccgtcttt tgttggacag ttaaaatgct cagtcccaat tgtcatagct ttgcctatta
4921 aacaaaggca ccctactgcg cttttgctg tgcttctgga gaatcctgct gttcttggac
4981 aattaaagaa caaagtagta attgctaatt gtctcaccca ttaatcatga agactaccag
5041 tcgcccttgc atttgccttg aggcagcgct gactaccgta gatttaagag tttcttaaat
5101 tattgagtaa aatcccaatt atccatagtt ctgttagtta cactatggcc tttgcaaaca
5161 tctttgcata acagcagtgg gactgactca ttcttagagc ccctccctt ggaatattaa
5221 tggatacaat agtaattatt catggttctg cgtaacagag aagacccact tatgtgtatg
5281 cctttatcat tgctcctaga tagtgtgaac tacctaccac cttgcattaa tatgtaaaac
5341 actaattgcc catagtccca ctcattagtc taggatgtcc tctttgccat tgctgctgag
5401 ttctgactac ccaagtttcc ttctcttaaa cagttgatat gcataattgc atatattcat
5461 ggttctgtgc aataaaaatg gattctcacc catcccacc ttctgtggga tgttgctaac
5521 gagtgcagat tattcaataa cagctcttga acagttaatt tgcacagttg caattgtcca
5581 gagtcctgtc cattagaaag ggactctgta tcctatttgc acgctacaat gtgggctgat
5641 caccccaagga ctcttcttgt gcattgatgt tcataattgt atttgtccac gatcttgtgc
5701 actaaccctt ccactccctt tgtattccag caggggaccc ttactactca agacctctgt
5761 actaggacag tttatgtgca caatcctaat tgattagaac tgagtctttt atatcaaggt
5821 ccctgcatca tctttgcttt acatcaagag ggtgctggtt acctaatgcc cctcctccag
5881 aaattattga tgtgcaaaat gcaattccc tatctgtgt tagtctgggg tctcatcccc
5941 tcatattcct tttgtcttac agcagggggt acttgggact gttaatgcgc ataattgcaa
6001 ttatggtctt ttccattaaa ttaagatccc aactgctcac accctcttag cattacagta
6061 gagggtgcta atcacaagga catttctttt gtactgttaa tgtgctactt gcatttgtcc
6121 ctcttcctgt gcactaaaga ccccactcac ttcccctagtg ttcagcagtg gatgacctct
6181 agtcaagacc tttgcactag gatagttaat gtgaaccatg gcaactgatc acaacaatgt
6241 ctttcagatc agatccattt tatcctcctt gttttacagc aagggatatt aattacctat
6301 gttacctttc cctgggacta tgaatgtgca aaattccaat gttcatgtc tctcccttta
6361 aacctatatt ctacccctttt tacattatag aaagggatgc tggaaaccca gagtccttct
6421 cttgggactc ttaatgtgta tttctaatta tccatgactc ttaatgtgca tattttcaat
6481 tgcctaattg atttcaattg tctaagacat ttcaaatgtc taattgatta gaactgagtc
6541 ttttatatca agctaatatc tagcttttat atcaagctaa tatcttgact tctcagcatc
6601 atagaagggg gtactgattt cctaaagtct ttcttgaatt tctattatgc aaaattgccc
6661 tgaggccggg tgtggtggct cacacctgta atcccagcac tttgggaggc tgaggtggga
6721 agatccctta ctgccaggag tttgagacca gcctggccaa cattaaaaaa aaaaaaaaaa
6781 gtaagacaat tgccctggaa tcccatcccc ctcacacctc cttggcaaag cagcaggagt
6841 gctaactagc tagtgcttct tctcttatac tgcttaaatg cgcataatta gcagtagttg
6901 atgtgcccct atgttagagt agaatcccgc ttccttgctc catttgcatt actgcaggag
6961 cttctaacta gcctgaattc actctcttgg actgttaatg tgcatactta tatttgctgc
7021 tgtacttttt taccatgtaa ggaccccacc cactgtattt acatcccagc tggaagtacc
7081 tactacttaa gaccccttaga ctagtaaagt tagcgtgcat aatcttaggt gttatataca
7141 cattttcagt tgcatacagt tgtgcctttt atcaggactc ctgtacttat caaagcagag
7201 agtgctaatc aatattaagc ccttctcttc gaactgtaga tggcatgtaa ttgcagttgt
7261 caatggtcct tcaattagac ttgggtttct gacctatcac accctctttg ctttattgca
7321 tggggtacta ttcacttaag gccccttctt caaactgtta atgtgcctaa tgacaattac
7381 atcagtatcc ttccttttga aggacagcat ggttggtgac cctaaggcc ccatttcttg
7441 gcctcccaat atgtgtgatt gtatttgtcg aggttgctat gcactagaga aggaaagtgc
7501 tccccctcatc cccactttc ccttccagca ggaatgccc acccccataag accctttat
7561 ttggagagtc taggtgcaca attgtaagtg accacaagca tgcatcttgg acatttatgt
7621 gcgtaatcgc acactgctca ttccatgtga ataaggtcct actctccgac cccttttgca
7681 atacagaagg gttgctgata acgcagtccc cttttcttgg catgttgtgt gtgattataa
7741 tcgtctggga tcctatgcac tagaaaagga gggtcctctc cacataccct agtctcacct
7801 ttccttcca gcaggggagtg cccactccat aagactctca catttggaca gtcaaggtgc
7861 gtaattgtta agtgaacaca accatgcacc ttagacatgg atttgcataa ctacacacag
7921 ctcaacctat ctgaataaaa tcctactctc agaccccttt tgcagtacag caggggtgct
7981 gatcaccaag gccctttttc ctggcctggt atgcgtgtga ttatgtttgt cccggttcct
8041 gtgtattaga catggaagcc tcccctgcca cactccaccc ccaatcttcc tttcccttcc
```

FIG. 10D sequence of construct 4 (continued)

```
 8101 ggcaggagtg ccctctccat aagacgctta cgtttggaca atcaaggtgc acagttgtaa
 8161 gtgaccacag gcatacacct tggacattaa tgtgcataac cactttgccc attccatctg
 8221 aataaggtcc tactctcaga cccctttgc agtacagcag gggtgctgat caccaaggcc
 8281 ccttttcttg gcctgttatg tgcgtgatta tatttgtctg ggttcctgtg tattagacaa
 8341 ggaagccttc ccccgcccc caccccact cccagtcttc ctttccttc cagcagggag
 8401 tgcccctcc ataagatcat tacatttgga caatcaaggt gcacaattat aagtgaccac
 8461 agccatgcac cttggacatt attggacatt aatgtgcgta actgcacatg gccatccca
 8521 tctgaataag gacctactct cagatgcctt tgcagtacag caggggtact gaatcaccaa
 8581 ggccctttt cttggcctgt tatgtgtgtg attatattta tcccagtttc tgtgtaatag
 8641 acatgaaagc ctccctgcc acacccacc tccaatcttc ctttccttc caccagggag
 8701 tgtccactcc atataccctt acatttggac aatcaaggtg cacaattgta agtgagcata
 8761 ggcactcacc ttggacatga atgtgcataa ctgcacatgg cccatcccat ctgaataagg
 8821 tcctactctc agaccctttt tgcagtacag caggggtgct gatcaccaag gcccttttc
 8881 ctggcctgtt atgtgtgtga ttatatttgt tccagttcct gtgtaataga catggaagcc
 8941 tccctgcca cactccaccc ccaatcttcc tttccttctg gcaggaagta ccgctccat
 9001 aagcccctta catttggaca gtcaaggtgc acaattgtat gtgaccacaa ccatgcacct
 9061 tggacataaa tgtgtgtaac tgcacatggc ccatcccatc tgaataaggt cctactctca
 9121 gaccccttttt gcagtacagt aggtgtgctg ataaccaagg ccctcttcc tggcctgtta
 9181 acgtatgtga ttatatttgt ctgggttcca gtgtataaga catggaagcc tccctgccc
 9241 caccccaccc tcaatcttcc tttccttct ggcagggagt gccagctcca taagaaccctt
 9301 acatttggac agtcaaggtg cacaattcta agtgaccgca gccatgcacc ttggtcaata
 9361 atgtgtgtaa ctgcacacgg cctatctcat ctgaataagg ccttactctc agacccttt
 9421 tgcagtacag caggggtgct gataaccaag gcccattttc ctggcctgtt atgtgtgtga
 9481 ttatatttgt ccaggtttct gtgtactaga caaggaagcc tcctctgccc catcccatct
 9541 acgcataatc tttcttttcc tcccagcagg gagtgctcac tccataagac ccttacattt
 9601 ggacaatcaa ggtgcacaat tgtaagtgac cacaaccatg catcttggaa atttatgtgc
 9661 ataactgcac atggcttatc ctatttgaac tctcagaccc cctttgcagt
 9721 atagctgggg tgctgatcac tgaggcctct ttgcttggct tgtctatatt cttgtgtact
 9781 agataagggc accttctcat ggactccctt tgcttttcaa caaggagtac ccactactt
 9841 ttaagattct tatatttgtc caaagtacat ggttttaatt gaccacaaca atgtcccttg
 9901 gacattaatg tatgtaatca ccacatggtt catcctaatt aaacaaagtt ctaccttctc
 9961 accctccatt tgcagtatac cagggttgct gaccccctaa gtcccctttt cttggcttgt
10021 tgacatgcat aattgcattt atgttggttc ttgtgcccta gacaaggatg cccacctct
10081 tttcaatagt gggtgcccac tccttatgat cttacatttt gaacagttaa tgtgaataat
10141 tgcagttgtc cacaacccta tcacttctag gaccattata cctcttttgc attactgtgg
10201 ggtatactgt ttccctccaa ggcccccttct ggtggactat caacatataa ttgaaatttt
10261 cttttgtctt tgtcagtaga ttaaggtcat accccatcac ctttccttg tagtacaaca
10321 gggtgtcctg atcaaccaaa gtcctgttgt tttggactgt taatatgtgc aattacattt
10381 gctcctgatc tgtgcactag ataaggatcc tacctacttt cttagtgttt ttagcaggta
10441 gtgcccacta ctcaagactg tcacttggaa tgttcatgtg cacaaactca attctctaag
10501 catgttcctg taccacctt gctttagagc aggggatga tattcactaa gtgcccttc
10561 ttttggactt aatatgcatt aatgcaattg tccacctctt cttttagact aagagttgat
10621 ctccacatat tcccttgca tcaggggcat gttaattatg aatgaaccct tttcttttaa
10681 tattaatgtc ataattgtat ttgtggacct gtgtaggaga aaaagaccct atgttcctcc
10741 cattacccctt tggattgctg ctgagaagtg ttaactactc ataatctcag ctcttggaca
10801 attaatagca ttaataacaa ttatcaagga cactgatcat tagataagac tcctgcttcc
10861 tcgttgctta catcgggggt actgacccac taaggcccct tgtactgtta atgtgaatat
10921 ttgcaattat atatgtctcc ttctggtaga gtgggatatt atgccctagt atccccttg
10981 cattactgca gggctgctg actactcaaa acttctcctg ggactgttaa taggcacaat
11041 ggcagttatc aatggtttc tccctccctg accttgttaa gcaagcgccc cacccacc
11101 ttagtttccc atggcataat aaagtataag cattggagta ttccatgcac ttgtctatca
11161 aacagtggtc catactccca accctttgc attgcgccag tgtgtaaaat cacaggtagc
11221 catggtgtca tgctttatat acgaagtctt ccctctctct gccccttgtg tgcccttggc
11281 ccttttac agactattgc tcacaatctc aggtgtccat atttgcagct attaggtaag
11341 attgtgctgt ctccctcttc cctccctct gccctgcccc ttttgcctct tgctgggta
11401 atgttgacca gacaaggcc tttctcttgg acttaaacaa ttctcagttg cactttcctt
11461 ggtccaccca ttatacatga acccctctac ttcctttcgc attgcttctg agtatgctga
11521 ctaccaaaag cccttctgt gttattaata aacacagtac tgattgtccc attttcagc
11581 ccatcagtcc aagatctccc taccacttgg tgtgttggt gcagtgttga ctatgaaaag
11641 caggcctgaa ctaggtggat aagccttcac tcattttctt tcatttatta atgatcctag
11701 tttcaattat tgtcagattc tggggacaag aaccattctt gcccacctgt gttactgctt
11761 tactgtgcaa aatactgaag gcaagtcaga cccagggagc tggattgcca tcctttattt
11821 tgtgtttcca gtgtacacta taaaattgtc tccccaggaa ggaaggttgg cactttctct
11881 gcattcttct ttccagagca gattgcctgg ttaagaatct cttgttgtcc cttctgtata
11941 ttgttattgt aaagtgccaa atgccaggat acagccagaa aaattgctta ttattattaa
```

FIG. 10D sequence of construct 4 (continued)

```
12001 aaaaattttt ttaagaaaga catctggatt gtagggtgga ctcgataacc tggtcattat
12061 tttttgaag ccaaaatatc catttatact atgtacctgg tgaccagtgt ctctcatttt
12121 aactgagggt ggtgggtctg tggatagaac actgactctt gctattttaa tatcaaagat
12181 attctagATC CAGCACAGTG GCggccgctc tagagtggaa ctcttaagac cagtatcttt
12241 gtgtgggctt taccagcatt cactttagaa aaaactacct aaattttata atcctttaat
12301 ttcttcatct ggagcacctg ccctactta tttcaagaag attgcagtaa aacgattaaa
12361 tgagggaaca tatgcagagg tgcttttaaa aagcatatgc caccttttt attaattatt
12421 atataaatg aagcatttaa ttatagtaat aatttgaagt agtttgaagt accacactga
12481 ggtgaggact taaaaatgat aagacgagtt ccctatttta taagaaaaat aagccaaaat
12541 taaatattct tttggatata aatttcaaca gtgagatagc tgcctagtgg aaatgaataa
12601 tatcccagcc actagtgtac agggtgtttt gtggcacagg attatgtaat atggaactgc
12661 tcaagcaaat aactagtcat cacaacagca gttctttgta ataactgaaa aagaatattg
12721 tttctcggag aaggatgtca aaagatcggc ccagctcagg gagcagtttg ccctactagc
12781 tcctcggaca gctgtaaaga agagtctctg gctctttaga atactgatcc cattgaagat
12841 accacgctgc atgtgtcctt agtagtcatg tctccttagg ctcctcttgg acattctgag
12901 catgtgagac ctgaggactg caaacagcta taagaggctc caaattaatc atatctttcc
12961 ctttgagaat ctggccaagc tccagctaat ctacttggat gggttgccag ctatctggag
13021 aaaaagatct tcctcagaag aataggcttg ttgtttaca gtgttagtga tccattccct
13081 ttgacgatcc ctaggtggag atggggcatg aggatcctcc agcggaaaag ctcactacca
13141 ctgggcaaca acctaggtc aggaggttct gtcaagatac tttcctggtc ccagatagga
13201 agataaagtc tcaaaaacaa ccaccacacg tcaagctctt cattgttcct atctgccaaa
13261 tcattatact tcctacaagc agtgcagaga gctgagtctt cagcaggtcc aagaaatttg
13321 aacacactga aggaagtcag ccttcccacc tgaagatcaa catgcctggc actctagcac
13381 ttgaggatag ctgaatgaat gtgtatttct ttgtctcttt ctttcttgtc tttgctcttt
13441 gttctctatc taaagtgtgt cttacccatt tccatgtttc tcttgctaat ttctttcgtg
13501 tgtgcctttg cctcatttc tcttttgtt cacaagagtg gtctgtgtct tgtcttagac
13561 atatctctca tttttcattt tgttgctatt tctctttgct ctcctagatg tggctcttct
13621 ttcacgcttt atttcatgtc tccttttg gtcacagtgc gtgtgctttt tgtcctttc
13681 ttgttctgtc tacctctcct ttctctgcct acctctcttt tctctttgtg aactgtgatt
13741 atttgttacc ccttcccctt ctcgttcgtt ttaaatttca ccttttttct gagtctggcc
13801 tcctttctgc tgtttctact ttttatctca catttctcat ttctgcattt cctttctgcc
13861 tctcttggc tattctctct ctcctcccct gcgtgcctca gcatctcttg ctgtttgtga
13921 tttttctattt cagtattaat ctctgttggc ttgtatttgt tctctgcttc ttcccttct
13981 actcaccttt gagtatttca gcctcttcat gaatctatct ccctctcttt gatttcatgt
14041 aatctctcct taaatatttc tttgcatatg tgggcaagtg tacgtgtgtg tgtgtcatgt
14101 gtgcagagg ggcttcctaa cccctgcctg ataggtgcag aacgtcggct atcagagcaa
14161 gcattgtgga gcggttcctt atgccagget gccatgtgag atgatccaag accaaaacaa
14221 ggccctagac tgcagtaaaa cccagaactc aagtagggca gaaggtggaa ggctcatatg
14281 gataaggc ccaaagtata agacagatgg tttgagactt gagacccgag gactaagatg
14341 gaaagcccat gttccaagat agatagaagc ctcaggcctg aaaccaacaa aagcctcaag
14401 agccaagaaa acagagggtg gcctgaattg gaccgaaggc ctgagttgga tggaagtctc
14461 aaggcttgag ttagaagtct taagacctgg gacaggacac atggaaggcc taagaactga
14521 gacttgtgac acaaggccaa cgacctaaga ttagcccagg gttgtagctg gaagacctac
14581 aacccaagga tggaaggcc ctgtcacaaa gcctacctag atggatagag gacccaagcg
14641 aaaaaggtat ctcaagacta acggccggaa tctggaggcc catgacccag acccaggas
14701 ggatagaagc ttgaagacct ggggaaatcc caagatgaga accctaaacc ctaccctctt
14761 tctattgttt acacttctta ctcttagata tttccagttc tcctgtttat ctttaagcct
14821 gattctttg agatgtactt tttgatgttg ccggttacct ttagattgac agtattatgc
14881 ctgggccagt cttgagccag ctttaaatca cagcttttac ctatttgtta ggctatagtg
14941 ttttgtaaac ttctgtttct attcacatct tctccactg agagagacac caaaatccag
15001 tcagtatcta atctggcttt tgttaacttc cctcaggagc agacattcat ataggtgata
15061 ctgtatttca gtcctttctt ttgaccccag aagccctaga ctgagaagat aaaatggtca
15121 ggttgttggg gaaaaaaaa gtgccaggct ctctagagaa aaatgtgaag agatgctcca
15181 ggccaatgag aagaattaga caagaaatac acagatgtgc cagacttctg agaagcacct
15241 gccagcaaca gttccttct ttgagcttag ATTTTCCTAG TCCATCCCTC ATGAAAAATG
15301 ACTGACCACT GCTGGGCAGC AGGAGGGATG ATGACCAACT AATTCCCAAA CCCCAGTCTC
15361 ATTGGTACCG AGCTCGGATC CACTAGTCCA GTGTGGTGGA ATTCTGCAGA TATCCAGCAC
15421 AGTGGCGGCC GCTCGAGTCT AGAGGGCCCG TTTAAACCCG CTGATCAGCC TCGACTGTGC
15481 CTTCTAGTTG CCAGCCATCT GTTGTTTGCC CCTCCCCCGT GCCTTCCTTG ACCCTGGAAG
15541 GTGCCACTCC CACTGTCCTT TCCTAATAAA ATGAGGAAAT TGCATCGCAT TGTCTGAGTA
15601 GGTGTCATTC TATTCTGGGG GGTGGGGTGG GGCAGGACAG CAAGGGGGAG GATTGGGAAG
15661 ACAATAGCAG GCATGCTGGG GATGCGGTGG GCTCTATGGC TTCTGAGGCG GAAAGAACCA
15721 GCTGGGGCTC TAGGGGGTAT CCCCACGCGC CCTGTAGCGG CGCATTAAGC GCGGCGGGTG
15781 TGGTGGTTAC GCGCAGCGTG ACCGCTACAC TTGCCAGCGC CCTAGCGCCC GCTCCTTTCG
15841 CTTTCTTCCC TTCCTTTCTC GCCACGTTCG CCGGCTTTCC CCGTCAAGCT CTAAATCGGG
```

FIG. 10D  sequence of construct 4 (continued)

```
15901 GGCTCCCTTT AGGGTTCCGA TTTAGTGCTT TACGGCACCT CGACCCCAAA AAACTTGATT
15961 AGGGTGATGG TTCACGTAGT GGGCCATCGC CCTGATAGAC GGTTTTTCGC CCTTTGACGT
16021 TGGAGTCCAC GTTCTTTAAT AGTGGACTCT TGTTCCAAAC TGGAACAACA CTCAACCCTA
16081 TCTCGGTCTA TTCTTTTGAT TTATAAGGGA TTTTGCCGAT TTCGGCCTAT TGGTTAAAAA
16141 ATGAGCTGAT TTAACAAAAA TTTAACGCGA ATTAATTCTG TGGAATGTGT GTCAGTTAGG
16201 GTGTGGAAAG TCCCCAGGCT CCCCAGCAGG CAGAAGTATG CAAAGCATGC ATCTCAATTA
16261 GTCAGCAACC AGGTGTGGAA AGTCCCCAGG CTCCCCAGCA GGCAGAAGTA TGCAAAGCAT
16321 GCATCTCAAT TAGTCAGCAA CCATAGTCCC GCCCCTAACT CCGCCCATCC CGCCCCTAAC
16381 TCCGCCCAGT TCCGCCCATT CTCCGCCCCA TGGCTGACTA ATTTTTTTTA TTTATGCAGA
16441 GGCCGAGGCC GCCTCTGCCT CTGAGCTATT CCAGAAGTAG TGAGGAGGCT TTTTTGGAGG
16501 CCTAGGCTTT TGCAAAAAGC TCCCGGGAGC TTGTATATCC ATTTTCGGAT CTGATCAGCA
16561 CGTGATGAAA AAGCCTGAAC TCACCGCGAC GTCTGTCGAG AAGTTTCTGA TCGAAAAGTT
16621 CGACAGCGTC TCCGACCTGA TGCAGCTCTC GGAGGGCGAA GAATCTCGTG CTTTCAGCTT
16681 CGATGTAGGA GGGCGTGGAT ATGTCCTGCG GGTAAATAGC TGCGCCGATG GTTTCTACAA
16741 AGATCGTTAT GTTTATCGGC ACTTTGCATC GGCCGCGCTC CCGATTCCGG AAGTGCTTGA
16801 CATTGGGGAA TTCAGCGAGA GCCTGACCTA TTGCATCTCC CGCCGTGCAC AGGGTGTCAC
16861 GTTGCAAGAC CTGCCTGAAA CCGAACTGCC CGCTGTTCTG CAGCCGGTCG CGGAGGCCAT
16921 GGATGCGATC GCTGCGGCCG ATCTTAGCCA GACGAGCGGG TTCGGCCCAT TCGGACCGCA
16981 AGGAATCGGT CAATACACTA CATGGCGTGA TTTCATATGC GCGATTGCTG ATCCCCATGT
17041 GTATCACTGG CAAACTGTGA TGGACGACAC CGTCAGTGCG TCCGTCGCGC AGGCTCTCGA
17101 TGAGCTGATG CTTTGGGCCG AGGACTGCCC CGAAGTCCGG CACCTCGTGC ACGCGGATTT
17161 CGGCTCCAAC AATGTCCTGA CGGACAATGG CCGCATAACA GCGGTCATTG ACTGGAGCGA
17221 GGCGATGTTC GGGGATTCCC AATACGAGGT CGCCAACATC TTCTTCTGGA GGCCGTGGTT
17281 GGCTTGTATG GAGCAGCAGA CGCGCTACTT CGAGCGGAGG CATCCGGAGC TTGCAGGATC
17341 GCCGCGGCTC CGGGCGTATA TGCTCCGCAT TGGTCTTGAC CAACTCTATC AGAGCTTGGT
17401 TGACGGCAAT TTCGATGATG CAGCTTGGGC GCAGGGTCGA TGCGACGCAA TCGTCCGATC
17461 CGGAGCCGGG ACTGTCGGGC GTACACAAAT CGCCCGCAGA AGCGCGGCCG TCTGGACCGA
17521 TGGCTGTGTA GAAGTACTCG CCGATAGTGG AAACCGACGC CCCAGCACTC GTCCGAGGGC
17581 AAAGGAATAG CACGTGCTAC GAGATTTCGA TTCCACCGCC GCCTTCTATG AAAGGTTGGG
17641 CTTCGGAATC GTTTTCCGGG ACGCCGGCTG GATGATCCTC CAGCGCGGGG ATCTCATGCT
17701 GGAGTTCTTC GCCCACCCCA ACTTGTTTAT TGCAGCTTAT AATGGTTACA AATAAAGCAA
17761 TAGCATCACA AATTTCACAA ATAAAGCATT TTTTTCACTG CATTCTAGTT GTGGTTTGTC
17821 CAAACTCATC AATGTATCTT ATCATGTCTG TAtacgtaaa ctggcaaagg ggtggctggg
17881 ccaaaagaca gaggaattaa gtaagaagtc caggaaaaat gaacttcaca tcaaatttta
17941 gagcacggta gccatgaatc ttgtgaatag ctcccaaaaa tgtcctgtgg aagacaacta
18001 gaaagcattc tacaatcagg cacccacctc cacctgcagc ctcctgtgtt gttctcatgg
18061 ggcacctctg ggctccagct cctccaaggc acctccacac tctctcaagt acactcttca
18121 ctcttcccca aacatgattc ccctactgct ctgcctaact cccacttctc tttcaagtag
18181 cagcttaaac gtcacctcat atttggctgg aaaatagaat atagacagag gggtaagtta
18241 aggctagaaa ggcaggctgg gtcaacagaa tggcaagcta aaacatggga tttttctaaaa
18301 cagcctaaga gggtgacaga taaaagtgtg caaggagtgg cacaactcca gtttcatctt
18361 tagctatagc aattaacacc ataaggagtc tggattcaat tttgccattt actagctagc
18421 taccaacttc tgtgtcgctt tgggcaaatc aattaaatcc atacctccct ttccatctgc
18481 agaatgggtt tataacagta cttaaacctc aaggtactaa gaacagtaaa gagttaatgg
18541 taTACCGTCG ACCTCTAGCT AGAGCTTGGC GTAATCATGG TCATAGCTGT TTCCTGTGTG
18601 AAATTGTTAT CCGCTCACAA TTCCACACAA CATACGAGCC GGAAGCATAA AGTGTAAAGC
18661 CTGGGGTGCC TAATGAGTGA GCTAACTCAC ATTAATTGCG TTGCGCTCAC TGCCCGCTTT
18721 CCAGTCGGGA AACCTGTCGT GCCAGCTGCA TTAATGAATC GGCCAACGCG CGGGGAGAGG
18781 CGGTTTGCGT ATTGGGCGCT CTTCCGCTTC CTCGCTCACT GACTCGCTGC GCTCGGTCGT
18841 TCGGCTGCGG CGAGCGGTAT CAGCTCACTC AAAGGCGGTA ATACGGTTAT CCACAGAATC
18901 AGGGGATAAC GCAGGAAAGA ACATGTGAGC AAAAGGCCAG CAAAAGGCCA GGAACCGTAA
18961 AAAGGCCGCG TTGCTGGCGT TTTTCCATAG GCTCCGCCCC CCTGACGAGC ATCACAAAAA
19021 TCGACGCTCA AGTCAGAGGT GGCGAAACCC GACAGGACTA TAAAGATACC AGGCGTTTCC
19081 CCCTGGAAGC TCCCTCGTGC GCTCTCCTGT TCCGACCCTG CCGCTTACCG GATACCTGTC
19141 CGCCTTTCTC CCTTCGGGAA GCGTGGCGCT TTCTCATAGC TCACGCTGTA GGTATCTCAG
19201 TTCGGTGTAG GTCGTTCGCT CCAAGCTGGG CTGTGTGCAC GAACCCCCCG TTCAGCCCGA
19261 CCGCTGCGCC TTATCCGGTA ACTATCGTCT TGAGTCCAAC CCGGTAAGAC ACGACTTATC
19321 GCCACTGGCA GCAGCCACTG GTAACAGGAT TAGCAGAGCG AGGTATGTAG GCGGTGCTAC
19381 AGAGTTCTTG AAGTGGTGGC CTAACTACGG CTACACTAGA AGAACAGTAT TTGGTATCTG
19441 CGCTCTGCTG AAGCCAGTTA CCTTCGGAAA AAGAGTTGGT AGCTCTTGAT CCGGCAAACA
19501 AACCACCGCT GGTAGCGGTT GGTTTTTTGT TTGCAAGCAG CAGATTACGC GCAGAAAAAA
19561 AGGATCTCAA GAAGATCCTT TGATCTTTTC TACGGGGTCT GACGCTCAGT GGAACGAAAA
19621 CTCACGTTAA GGGATTTTGG TCATGAGATT ATCAAAAAGG ATCTTCACCT AGATCCTTTT
19681 AAATTAAAAA TGAAGTTTTA AATCAATCTA AAGTATATAT GAGTAAACTT GGTCTGACAG
19741 TTACCAATGC TTAATCAGTG AGGCACCTAT CTCAGCGATC TGTCTATTTC GTTCATCCAT
```

FIG. 10D sequence of construct 4 (continued)

```
19801 AGTTGCCTGA CTCCCCGTCG TGTAGATAAC TACGATACGG GAGGGCTTAC CATCTGGCCC
19861 CAGTGCTGCA ATGATACCGC GAGACCCACG CTCACCGGCT CCAGATTTAT CAGCAATAAA
19921 CCAGCCAGCC GGAAGGGCCG AGCGCAGAAG TGGTCCTGCA ACTTTATCCG CCTCCATCCA
19981 GTCTATTAAT TGTTGCCGGG AAGCTAGAGT AAGTAGTTCG CCAGTTAATA GTTTGCGCAA
20041 CGTTGTTGCC ATTGCTACAG GCATCGTGGT GTCACGCTCG TCGTTTGGTA TGGCTTCATT
20101 CAGCTCCGGT TCCCAACGAT CAAGGCGAGT TACATGATCC CCCATGTTGT GCAAAAAAGC
20161 GGTTAGCTCC TTCGGTCCTC CGATCGTTGT CAGAAGTAAG TTGGCCGCAG TGTTATCACT
20221 CATGGTTATG GCAGCACTGC ATAATTCTCT TACTGTCATG CCATCCGTAA GATGCTTTTC
20281 TGTGACTGGT GAGTACTCAA CCAAGTCATT CTGAGAATAG TGTATGCGGC GACCGAGTTG
20341 CTCTTGCCCG GCGTCAATAC GGGATAATAC CGCGCCACAT AGCAGAACTT TAAAAGTGCT
20401 CATCATTGGA AAACGTTCTT CGGGGCGAAA ACTCTCAAGG ATCTTACCGC TGTTGAGATC
20461 CAGTTCGATG TAACCCACTC GTGCACCCAA CTGATCTTCA GCATCTTTTA CTTTCACCAG
20521 CGTTTCTGGG TGAGCAAAAA CAGGAAGGCA AAATGCCGCA AAAAAGGGAA TAAGGGCGAC
20581 ACGGAAATGT TGAATACTCA TACTCTTCCT TTTTCAATAT TATTGAAGCA TTTATCAGGG
20641 TTATTGTCTC ATGAGCGGAT ACATATTTGA ATGTATTTAG AAAAATAAAC AAATAGGGGT
20701 TCCGCGCACA TTTCCCCGAA AAGTGCCACC TGACGTC
//
```

FIG. 10E sequence of construct 5

```
LOCUS       pcDNA5/TO/RCAN1 LA & RA/6.8kb human XIST 14026 bp    DNA     SYN     29-Nov-
2012
DEFINITION  pcDNA5/TO/RCAN1 LA & RA/6.8kb human XIST
ACCESSION
KEYWORDS
SOURCE
  ORGANISM  other sequences; artificial sequences; vectors.
FEATURES             Location/Qualifiers
     source          1..14026
                     /organism="pcDNA5/TO/RCAN1 LA & RA/6.8kb human XIST"
                     /mol_type="other DNA"
     misc_feature    209..966
                     /label="RCAN1 right arm"
     misc_feature    1073..1360
                     /label="CAG_enhancer"
     promoter        994..1570
                     /label="CMV_immearly_promoter"
     misc_feature    1527..1547
                     /label="CMV_fwd_primer"
     promoter        1528..1651
                     /label="CMV_promoter"
     misc_feature    1578..1617
                     /label="tetO"
     promoter        1540..1713
                     /label="CMV2_promoter"
     misc_feature    1627..1651
                     /label="LNCX_primer"
     misc_feature    1790..8620
                     /label="6.8kb human XIST"
     misc_feature    complement(8641..8657)
                     /label="pBluescriptKS_primer"
     misc_feature    complement(8690..8707)
                     /label="BGH_rev_primer"
     terminator      8693..8920
                     /label="bGH_PA_terminator"
     rep_origin      8983..9289
                     /label="f1_origin"
     misc_feature    complement(9403..9423)
                     /label="pBABE_3_primer"
     misc_feature    complement(9409..9624)
                     /label="SV40_enhancer"
```

FIG. 10E sequence of construct 5 (continued)

```
     promoter        9421..9689
                     /label="SV40_promoter"
     rep_origin      9588..9665
                     /label="SV40_origin"
     misc_feature    9650..9669
                     /label="SV40pro_F_primer"
     CDS             complement(9723..10544)
                     /label="ORF frame 3"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNRERGRCKVPINITIFVETIGAAIYPQDISTPSYIEAES
                     TRFFALRELHQVGDAVELFDQKLLDRRRGEFRLFHHVLIRSENGYTSSRELFAKA*"
     CDS             9786..10811
                     /label="hygroB"
                     /gene="hygroB"
                     /note="ORF frame 3"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"
     gene            9801..10808
                     /label="hygroB"
                     /gene="hygroB"
     terminator      10944..11063
                     /label="SV40_PA_terminator"
     misc_feature    11032..11051
                     /label="EBV_rev_primer"
     misc_feature    11074..11831
                     /label="RCAN1 left arm"
     misc_feature    complement(11865..11883)
                     /label="M13_reverse_primer"
     misc_feature    complement(11882..11904)
                     /label="M13_pUC_rev_primer"
     promoter        complement(11918..11947)
                     /label="lac_promoter"
     rep_origin      complement(12256..12875)
                     /label="pBR322_origin"
     CDS             complement(13030..13890)
                     /label="Ampicillin"
                     /gene="Ampicillin"
                     /note="ORF frame 1"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"
     gene            complement(13030..13890)
                     /label="Ampicillin"
                     /gene="Ampicillin"
     promoter        complement(13932..13960)
                     /label="AmpR_promoter"
ORIGIN
        1 GACGGATCGG GAGATCTCCC GATCCCCTAT GGTGCACTCT CAGTACAATC TGCTCTGATG
       61 CCGCATAGTT AAGCCAGTAT CTGCTCCCTG CTTGTGTGTT GGAGGTCGCT GAGTAGTGCG
      121 CGAGCAAAAT TTAAGCTACA ACAAGGCAAG GCTTGACCGA CAATTGCATG AAGAATCTGC
      181 TTAGGGTTAG GCGTTTTGCG CTGCTTCGcg acaatgtttt cagaaatgta atctttcaa
      241 tatgaaactg ctgatggacc aagaaaacaa aaccctcaac ccaagggaac atcagattgc
      301 tggtcaagga gaaatgagga gctgacggtc tcagcattta tttgacttgc tccacggaca
      361 gagcaggaga aggctcaaac ctcttcaccc caagactctc cctcacacct gcctcctcac
      421 ccaaaccctc gaggacagga caggaaccac caacatttta tggttttcaa aaatcctgca
```

FIG. 10E sequence of construct 5 (continued)

```
 481 ttgaacactg actgtgagcc aggtgctgat ggaagtgcct ttcactcgat gatctcatct
 541 actgctcaca attccaccag ttaaggccca cattttggac aaagagcctg aggaacctac
 601 cccctccccg cagtgctcac acttttgtcc ctccagagga cggaacttc ctctttcttt
 661 agcaagctct gtagggacc agcccacagg ccctgggta gggcagcccg acgcggccc
 721 ttccctcacc atggcctatg ttctccttc ccttttcctt taagaaggcc aggtgagaat
 781 cacaggaaag ggagaattta ttttgattaa aaataacatt tcttaaaggg ggcatcgatt
 841 ttcccttttcc aaagtccaat cactcatccc tatccggagc gacagaacct ggggccgggg
 901 ctcaggcctc ccaacgcagc tgtgctcagt ggacacagga atggattcct gggacactgc
 961 gggtcgCGAT GTACGGGCCA GATATACGCG TTGACATTGA TTATTGACTA GTTATTAATA
1021 GTAATCAATT ACGGGGTCAT TAGTTCATAG CCCATATATG GAGTTCCGCG TTACATAACT
1081 TACGGTAAAT GGCCCGCCTG GCTGACCGCC CAACGACCCC CGCCCATTGA CGTCAATAAT
1141 GACGTATGTT CCCATAGTAA CGCCAATAGG GACTTTCCAT TGACGTCAAT GGGTGGAGTA
1201 TTTACGGTAA ACTGCCCACT TGGCAGTACA TCAAGTGTAT CATATGCCAA GTACGCCCCC
1261 TATTGACGTC AATGACGGTA AATGGCCCGC CTGGCATTAT GCCCAGTACA TGACCTTATG
1321 GGACTTTCCT ACTTGGCAGT ACATCTACGT ATTAGTCATC GCTATTACCA TGGTGATGCG
1381 GTTTTGGCAG TACATCAATG GGCGTGGATA GCGGTTTGAC TCACGGGGAT TTCCAAGTCT
1441 CCACCCCATT GACGTCAATG GGAGTTTGTT TTGGCACCAA AATCAACGGG ACTTTCCAAA
1501 ATGTCGTAAC AACTCCGCCC CATTGACGCA AATGGGCGGT AGGCGTGTAC GGTGGGAGGT
1561 CTATATAAGC AGAGCTCTCC CTATCAGTGA TAGAGATCTC CCTATCAGTG ATAGAGATCG
1621 TCGACGAGCT CGTTTAGTGA ACCGTCAGAT CGCCTGGAGA CGCCATCCAC GCTGTTTTGA
1681 CCTCCATAGA AGACACCGGG ACCGATCCAG CCTCGGACT CTAGCGTTTA AACTTAAGCT
1741 TGGTACCGAG CTCGGATCCA CTAGTCCAGT GTGGTGGAAT TCTGCAGATt ctagaacatt
1801 ttctagtccc caacaccct ttatggcgta tttctttaaa aaaatcacct aaattccata
1861 aaatatttt ttaaattcta tactttctcc tagtgtcttc ttgacacgtc ctccatattt
1921 ttttaaagaa agtatttgga atatttgag gcaattttta atatttaagg aattttttctt
1981 tggaatcatt tttggtgaca tctctgtttt ttgtggatca gtttttact cttccactct
2041 cttttctata ttttgcccat cggggcgtga gatacctgct tttattattt tttcttttgcc
2101 caacgggcc gtggatacct gccttttaat tcttttttat tcgcccatcg gggcgcgga
2161 tacctgcttt ttattttttt ttccttagcc catcgggta tcggataccct gctgattccc
2221 ttccctctg aacccccaac actctggcc atcggggtga cggatatctg cttttaaaa
2281 attttctttt tttggcccat cggggcttcg gataacctgct ttttttttt ttattttcct
2341 tgcccatcgg ggcctcggat acctgcttta attttgttt tctgcccat cggggccgcg
2401 gatacctgct ttgattttt ttttcatcg cccatcggtg cttttatgg atgaaaaat
2461 gttggttttg tgggttgttg cactctctgg aatatctaca cttttttttg ctgctgatca
2521 tttggtggtg tgtgagtgta cctaccgctt tggcagagaa tgactctgca gttaagctaa
2581 gggcgtgttc agattgtgga ggaaagtgg ccgccatttt agacttgccg cataactcgg
2641 cttagggcta gtcgtttgtg ctaagttaaa ctaggggaggc aagatggatg atagcaggtc
2701 aggcagagga agtcatgtgc attgcatgag ctaaacctat ctgaatgaat tgatttgggg
2761 cttgttagga gctttgcgtg attgttgtat cgggaggcag taagaatcat cttttatcag
2821 tacaagggac tagttaaaaa tggaaggtta ggaaagacta aggtgcaggg cttaaaatgg
2881 cgatttgac attgcggcat tgctcagcat ggcgggctgt gcttttgttag gttgtccaaa
2941 atggcggatc cagttctgtc gcagtgttca agtggcggga aggccacatc atgatgggcg
3001 aggctttgtt aagtggttag catggtggtg gacatgtgcg gtcacacagg aaaagatggc
3061 ggctgaaggt cttgccgcag tgtaaaacat ggcgggcctc tttgtctttg ctgtgtgctt
3121 ttcgtgttgg gttttgccgc agggacaata tggcaggcgt tgtcatatgt atatcatggc
3181 ttttgtcacg tggacatcat ggcgggcttg ccgcattgtt aaagatggcg ggttttgccg
3241 cctagtgcca cgcagagcgg gagaaaaggt ggattggaca gtgctggatt gctgcataac
3301 ccaaccaatt agaaatgggg gtggaattga tcacagccaa ttagagcaga agatggaatt
3361 agactgatga cacactgtcc agctactcag cgaagacctg ggtgaattag catggcactt
3421 cgcagctgtc tttagccagt caggagaaag aagtggaggg gccacgtgta tgtctccag
3481 tgggcggtac accaggtgtt ttcaaggtct tttcaaggac atttagcctt tccacctctg
3541 tcccctctta tttgtccct cctgtccagt gctgcctctt gcagtgctgg atatctggct
3601 gtgtggtctg aacctccctc cattcctctg tattggtgcc tcacctaagg ctaagtatac
3661 ctcccccaac cccccaact cccccaact accccccacc cccacctcc
3721 ccacccccct accccctac cccctaccc cctctggtc tgccctgcac tgcactgttg
3781 ccatgggcag tgctccaggc ctgcttggtg tggacatggt ggtgagccgt ggcaaggacc
3841 agaatggatc acagatgatc gttggccaat tggcctccca atatgtgtga ttgtatttgt
3901 cgaggttgct atgcactaga gaaggaaagt gctccctca tccccacttt tccttccag
3961 caggaagtgc ccacccata agaccctttt atttggagag tctaggtgca caattgtaag
4021 tgaccacaag catgcatctt ggacatttat gtgcgtaatc gcacactgct cattccatgt
4081 gcctaccgca ctactctccg accccttttg caatacagaa gggtgctga taacgcagtc
4141 cccttttctt ggcatgttgt gtgtgattat aatcgtctgg gatcctatgc actagaaaag
4201 gagggtcctc tccacatacc tcagtctcac ctttccctttc cagcaggag tgcccactcc
4261 ataagactct cacatttgga cagtcaaggt gcgtaattgt taagtgaaca caaccatgca
4321 ccttagacat ggatttgcat aactacacac agctcaacct atctgaataa aatcctactc
```

FIG. 10E  sequence of construct 5 (continued)

```
4381 tcagacccct tttgcagtac agcaggggtg ctgatcacca aggcccttt tcctggcctg
4441 gtatgcgtgt gattatgttt gtcccggttc ctgtgtatta gacatggaag cctccctgc
4501 cacactccac cccaatctt ccttccctt ccggcaggag tgccctctcc ataagacgct
4561 tacgtttgga caatcaaggt gcacagttgt aagtgaccac aggcatacac cttggacatt
4621 aatgtgcata accactttgc ccattccatc tgaataaggt cctactctca gacccctttt
4681 gcagtacagc agggtgctg atcaccaagg cccttttct tggcctgtta tgtgcgtgat
4741 tatattgtc tgggttcctg tgtattagac aaggaagcct tcccccgcc cccacccccc
4801 ctcccagtct tccttccct tccagcaggg agtgccccct ccataagatc attacatttg
4861 gacaatcaag gtgcacaatt ataagtgacc acagccatgc accttggaca ttattggaca
4921 ttaatgtgcg taactgcaca tggcccatcc catctgaata aggacctact ctcagatgcc
4981 tttgcagtac agcagggta ctgaatcacc aaggccctt tcttggcct gttatgtgtg
5041 tgattatatt tatcccagtt tctgtgtaat agacatgaaa gcctccctg ccacacccca
5101 cctccaatct tcctttcct tccaccaggg agtgtccact ccatatacccc ttacatttgg
5161 acaatcaagg tgcacaattg taagtgagca taggcactca ccttggacat gaatgtgcat
5221 aactgcacat ggcccatccc atctgaataa ggtcctactc tcagacccct tttgcagtac
5281 agcaggggtg ctgatcacca aggcccttt tcctggcctg ttatgtgtgt gattatattt
5341 gttccagttc ctgtgtaata gacatggaag cctccctgc cacactccac cccaatctt
5401 ccttccttc tggcaggaag taccggctcc ataagaccct tacatttgga cagtcaaggt
5461 gcacaattgt atgtgaccac aaccatgcac cttggacata aatgtgtgta actgcacatg
5521 gcccatccca tctgaataag gtcctactct cagacccctt ttgcagtaca gtaggtgtgc
5581 tgataaccaa ggccctctt cctggcctgt taacgtatgt gattatattt gtctgggttc
5641 cagtgtataa gacatggaag cctccctgc cccacccac cctcaatctt ccttccctt
5701 ctggcaggga gtgccagctc cataagaacc ttacatttgg acagtcaagg tgcacaattc
5761 taagtgaccg cagccatgca ccttggtcaa taatgtgtgt aactgcacac ggcctatctc
5821 atctgaataa ggccttactc tcagacccct tttgcagtac agcaggggtg ctgataacca
5881 aggcccattt tcctggcctg ttatgtgtgt gattatattt gtccaggttt ctgtgtacta
5941 gacaaggaag cctcctctgc cccatccat ctacgcataa tctttctttt cctcccagca
6001 gggagtgctc actccataag cccttacat ttggacaatc aaggtgcaca attgtaagtg
6061 accacaacca tgcatcttgg aaattatgt gcataactgc acatggctta tcctatttga
6121 ataaagtcct actctcagac cccctttgca gtagctgg ggtgctgatc actgaggcct
6181 ctttgcttgg cttgtctata ttcttgtgta ctagataagg gcaccttctc atggactccc
6241 tttgctttc aacaaggagt acccactact ttttaagatt cttatatttg tccaaagtac
6301 atggttttaa ttgaccacaa caatgtccct tggacattaa tgtatgtaat caccacatgg
6361 ttcatcctaa ttaaacaaag ttctaccttc tcaccctcca tttgcagtat accaggttg
6421 ctgaccccct aagtcccctt ttcttggctt gttgacatgc ataattgcat ttatgttggt
6481 tcttgtgccc tagacaagga tgccccacct cttttcaata gtgggtgccc actccttatg
6541 atctttacat ttgaacagtt aatgtgaata attgcagttg tccacaaccc tatcacttct
6601 aggaccatta tacctctttt gcattactgt ggggtatact gtttcctcc aaggccctt
6661 ctggtggact atcaacatat aattgaaatt ttcttttgtc tttgtcagta gattaaggtc
6721 atacccccatc aactttcctt tgtagtacaa cagggtgtcc tgatcaacca aagtcctgtt
6781 gttttggact gttaatatgt gcaattacat ttgctcctga tctgtgcact agataaggat
6841 cctactact ttcttagtgt ttttagcagg tagtgcccac tactcaagac tgtcacttgg
6901 aatgttcatg tgcacaaact caattctcta agcatgttcc tgtaccacct ttgctttaga
6961 gcaggggat gatattcact aagtgccct tcttttggac ttaatatgca ttaatgcaat
7021 tgtccacctc ttcttttaga ctaagagttg atctccacat attccccttg catcaggggc
7081 atgttaatta tgaatgaacc ctttctttt aatattaatg tcataattgt atttgtggac
7141 ctgtgtagga gaaaaagacc ctatgttcct cccattaccc tttggattgc tgctgagaag
7201 tgttaactac tcataatctc agctcttgga caattaatag cattaataac aattatcaag
7261 ggcactgatc attagataag atcctgctt cctcgttgct tacatcgggg gtactgaccc
7321 actaaggccc cttgtactgt taatgtgaat atttgcaatt atatatgtct ccttctggta
7381 gagtgggata ttatgcccta gtatcccctt tgcattactg caggggctgc tgactactca
7441 aaacttctcc tgggactgtt aataggcaca atggcagtta tcaatggttt tctccctccc
7501 tgaccttgtt aagcaagcgc cccacccac ccttagtttc ccatggcata ataaagtata
7561 agcattggag tattccatgc acttgtctat caaacagtgg tccatactcc caaccctttt
7621 gcattgcgcc agtgtgtaaa atcacaggta gccatggtgt catgctttat atacgaagtc
7681 ttccctctct ctgcccttc tgtgccttg gcccctttct acagactatt gctcacaatc
7741 tcaggtgtcc atatttgcag ctattaggta agattgtgct gtctccctct tccttccct
7801 ctgccctgcc ccttttgcct ctttgctggg taatgttgac cGgacaaggc cctttctctt
7861 ggacttaaac aattctcagt tgcactttcc ttggtccCac ccattataca tgaaccctc
7921 tacttccttt cgcattgctt ctgagtatgc tgactaccca agcccctcc tgtgttatta
7981 ataaacacag tactgattgt cccattttc agccatcag tccagatct ccctaccact
8041 ttggtgtgtt ggtgcagtgt tgactatgaa aagcaggcct gaactaggtg gataagcctt
8101 cactcatttt ctttcattta ttaatgatcc tagtttcaat tattgtcaga ttctgggac
8161 aagaaccatt cttgcccacc tgtgttactg ctttactgtg caaaatactg aaggcaagtc
8221 agacccaggg agctggattg ccatccttta ttttgtgttt ccagtgtaca ctataaaatt
```

FIG. 10E sequence of construct 5 (continued)

```
8281 gtctccccag gaaggaaggt tggcactttc tctgcattct tctttccaga gcagattgcc
8341 tggttaagaa tctcttgttg tcccCtTtgt atattgttat tgtaaagtgc caaatgccag
8401 gatacagcca gaaaaattgc ttattattat taaaaaaatt tttttaagaa agacatctgg
8461 attgtagggt ggactcgata acctggtcat tattttttg aagccaaaat atccatttat
8521 actatgtacc tggtgaccag tgtctctcat tttaactgag ggtggtgggt ctgtggatag
8581 aacactgact cttgctattt taatatcaaa gatattctag ATCCAGCACA GTGGCggccc
8641 gataccgtcg accTCGAGTC TAGAGGGCCC GTTTAAACCC GCTGATCAGC CTCGACTGTG
8701 CCTTCTAGTT GCCAGCCATC TGTTGTTTGC CCCTCCCCCG TGCCTTCCTT GACCCTGGAA
8761 GGTGCCACTC CCACTGTCCT TTCCTAATAA AATGAGGAAA TTGCATCGCA TTGTCTGAGT
8821 AGGTGTCATT CTATTCTGGG GGGTGGGGTG GGGCAGGACA GCAAGGGGGA GGATTGGGAA
8881 GACAATAGCA GGCATGCTGG GGATGCGGTG GGCTCTATGG CTTCTGAGGC GGAAAGAACC
8941 AGCTGGGGCT CTAGGGGGTA TCCCCACGCG CCCTGTAGCG GCGCATTAAG CGCGGCGGGT
9001 GTGGTGGTTA CGCGCAGCGT GACCGCTACA CTTGCCAGCG CCCTAGCGCC CGCTCCTTTC
9061 GCTTTCTTCC CTTCCTTTCT CGCCACGTTC GCCGGCTTTC CCCGTCAAGC TCTAAATCGG
9121 GGGCTCCCTT TAGGGTTCCG ATTTAGTGCT TTACGGCACC TCGACCCCAA AAAACTTGAT
9181 TAGGGTGATG GTTCACGTAG TGGGCCATCG CCCTGATAGA CGGTTTTTCG CCCTTTGACG
9241 TTGGAGTCCA CGTTCTTTAA TAGTGGACTC TTGTTCCAAA CTGGAACAAC ACTCAACCCT
9301 ATCTCGGTCT ATTCTTTTGA TTTATAAGGG ATTTTGCCGA TTTCGGCCTA TTGGTTAAAA
9361 AATGAGCTGA TTTAACAAAA ATTTAACGCG AATTAATTCT GTGGAATGTG TGTCAGTTAG
9421 GGTGTGGAAA GTCCCCAGGC TCCCCAGCAG GCAGAAGTAT GCAAAGCATG CATCTCAATT
9481 AGTCAGCAAC CAGGTGTGGA AAGTCCCCAG GCTCCCCAGC AGGCAGAAGT ATGCAAAGCA
9541 TGCATCTCAA TTAGTCAGCA ACCATAGTCC CGCCCCTAAC TCCGCCCATC CCGCCCCTAA
9601 CTCCGCCCAG TTCCGCCCAT TCTCCGCCCC ATGGCTGACT AATTTTTTTT ATTTATGCAG
9661 AGGCCGAGGC CGCCTCTGCC TCTGAGCTAT TCCAGAAGTA GTGAGGAGGC TTTTTTGGAG
9721 GCCTAGGCTT TTGCAAAAAG CTCCCGGGAG CTTGTATATC CATTTTCGGA TCTGATCAGC
9781 ACGTGATGAA AAAGCCTGAA CTCACCGCGA CGTCTGTCGA GAAGTTTCTG ATCGAAAAGT
9841 TCGACAGCGT CTCCGACCTG ATGCAGCTCT CGGAGGGCGA AGAATCTCGT GCTTTCAGCT
9901 TCGATGTAGG AGGGCGTGGA TATGTCCTGC GGGTAAATAG CTGCGCCGAT GGTTTCTACA
9961 AAGATCGTTA TGTTTATCGG CACTTTGCAT CGGCCGCGCT CCCGATTCCG GAAGTGCTTG
10021 ACATTGGGGA ATTCAGCGAG AGCCTGACCT ATTGCATCTC CCGCCGTGCA CAGGGTGTCA
10081 CGTTGCAAGA CCTGCCTGAA ACCGAACTGC CCGCTGTTCT GCAGCCGGTC GCGGAGGCCA
10141 TGGATGCGAT CGCTGCGGCC GATCTTAGCC AGACGAGCGG GTTCGGCCCA TTCGGACCGC
10201 AAGGAATCGG TCAATACACT ACATGGCGTG ATTTCATATG CGCGATTGCT GATCCCCATG
10261 TGTATCACTG GCAAACTGTG ATGGACGACA CCGTCAGTGC GTCCGTCGCG CAGGCTCTCG
10321 ATGAGCTGAT GCTTTGGGCC GAGGACTGCC CCGAAGTCCG GCACCTCGTG CACGCGGATT
10381 TCGGCTCCAA CAATGTCCTG ACGGACAATG GCCGCATAAC AGCGGTCATT GACTGGAGCG
10441 AGGCGATGTT CGGGGATTCC CAATACGAGG TCGCCAACAT CTTCTTCTGG AGGCCGTGGT
10501 TGGCTTGTAT GGAGCAGCAG ACGCGCTACT TCGAGCGGAG GCATCCGGAG CTTGCAGGAT
10561 CGCCGCGGCT CCGGGCGTAT ATGCTCCGCA TTGGTCTTGA CCAACTCTAT CAGAGCTTGG
10621 TTGACGGCAA TTTCGATGAT GCAGCTTGGG CGCAGGGTCG ATGCGACGCA ATCGTCCGAT
10681 CCGGAGCCGG GACTGTCGGG CGTACACAAA TCGCCCGCAG AAGCGCGGCC GTCTGGACCG
10741 ATGGCTGTGT AGAAGTACTC GCCGATAGTG GAAACCGACG CCCCAGCACT CGTCCGAGGG
10801 CAAAGGAATA GCACGTGCTA CGAGATTTCG ATTCCACCGC CGCCTTCTAT GAAAGGTTGG
10861 GCTTCGGAAT CGTTTTCCGG GACGCCGGCT GGATGATCCT CCAGCGCGGG GATCTCATGC
10921 TGGAGTTCTT CGCCCACCCC AACTTGTTTA TTGCAGCTTA TAATGGTTAC AAATAAAGCA
10981 ATAGCATCAC AAATTTCACA AATAAAGCAT TTTTTCACT GCATTCTAGT TGTGGTTTGT
11041 CCAAACTCAT CAATGTATCT TATCATGTCT GTAtacgggg ggaggggcgt gatgcagggt
11101 cccacgatc agccgcagtc tctctaacac tgcaggtggt gccaagaggc aggcatgctc
11161 ccagcacaag ggacggtggc gcagaagaat acagagaagc tcacaaaaca tgccggcatg
11221 ggctcaggag agctacgggg gtagtggtgg tactgctccc tggtgcaggg cagcagctgt
11281 gtctcccct gcctccctcc caccccgaggg ccctgctcac ctggcccag cttggagatg
11341 gcatataaga gatcatagtt tatgactggg gtcgcatctt ccacttgttt ccatcccact
11401 ggcggagagg cgggagggga gatcagaaac tgcttgtctg gatttggcgg agccaggtgt
11461 gagcttccta tgtgtaaggt ctgaggagag aaaataagca caggtcagtt gttgccaggg
11521 aagaactgca gtgaggcaac agcacctcag gccagttccg ggagatgggc aggtcaatgt
11581 ccaggcgtca ggacaggtgt gattccagga ccaattgtaa gatggtctgt aatggggagg
11641 gcaaaaggac atatgaactc tggttgtggc acagatagga tgacagcccc ctcccagggc
11701 tatgggagtc acaggcacag ggactgcaaa taattacgct tgacctagat ggacagaaaa
11761 tcagcagagg tgactttagt atatatgaa atttaagtca ctgtcattga ggtcaggagg
11821 gctcttgggt aTACCGTCGA CCTCTAGCTA GAGCTTGGCG TAATCATGGT CATAGCTGTT
11881 TCCTGTGTGA AATTGTTATC CGCTCACAAT TCCACACAAC ATACGAGCCG GAAGCATAAA
11941 GTGTAAAGCC TGGGGTGCCT AATGAGTGAG CTAACTCACA TTAATTGCGT TGCGCTCACT
12001 GCCCGCTTTC CAGTCGGGAA ACCTGTCGTG CCAGCTGCAT TAATGAATCG GCCAACGCGC
12061 GGGGAGAGGC GGTTTGCGTA TTGGGCGCTC TTCCGCTTCC TCGCTCACTG ACTCGCTGCG
12121 CTCGGTCGTT CGGCTGCGGC GAGCGGTATC AGCTCACTCA AAGGCGGTAA TACGGTTATC
```

FIG. 10E sequence of construct 5 (continued)

```
12181 CACAGAATCA GGGGATAACG CAGGAAAGAA CATGTGAGCA AAAGGCCAGC AAAAGGCCAG
12241 GAACCGTAAA AAGGCCGCGT TGCTGGCGTT TTTCCATAGG CTCCGCCCCC CTGACGAGCA
12301 TCACAAAAAT CGACGCTCAA GTCAGAGGTG GCGAAACCCG ACAGGACTAT AAAGATACCA
12361 GGCGTTTCCC CCTGGAAGCT CCCTCGTGCG CTCTCCTGTT CCGACCCTGC CGCTTACCGG
12421 ATACCTGTCC GCCTTTCTCC CTTCGGGAAG CGTGGCGCTT TCTCATAGCT CACGCTGTAG
12481 GTATCTCAGT TCGGTGTAGG TCGTTCGCTC CAAGCTGGGC TGTGTGCACG AACCCCCCGT
12541 TCAGCCCGAC CGCTGCGCCT TATCCGGTAA CTATCGTCTT GAGTCCAACC CGGTAAGACA
12601 CGACTTATCG CCACTGGCAG CAGCCACTGG TAACAGGATT AGCAGAGCGA GGTATGTAGG
12661 CGGTGCTACA GAGTTCTTGA AGTGGTGGCC TAACTACGGC TACACTAGAA GAACAGTATT
12721 TGGTATCTGC GCTCTGCTGA AGCCAGTTAC CTTCGGAAAA AGAGTTGGTA GCTCTTGATC
12781 CGGCAAACAA ACCACCGCTG GTAGCGGTTG GTTTTTTGTT TGCAAGCAGC AGATTACGCG
12841 CAGAAAAAAA GGATCTCAAG AAGATCCTTT GATCTTTTCT ACGGGGTCTG ACGCTCAGTG
12901 GAACGAAAAC TCACGTTAAG GGATTTTGGT CATGAGATTA TCAAAAAGGA TCTTCACCTA
12961 GATCCTTTTA AATTAAAAAT GAAGTTTTAA ATCAATCTAA AGTATATATG AGTAAACTTG
13021 GTCTGACAGT TACCAATGCT TAATCAGTGA GGCACCTATC TCAGCGATCT GTCTATTTCG
13081 TTCATCCATA GTTGCCTGAC TCCCCGTCGT GTAGATAACT ACGATACGGG AGGGCTTACC
13141 ATCTGGCCCC AGTGCTGCAA TGATACCGCG AGACCCACGC TCACCGGCTC CAGATTTATC
13201 AGCAATAAAC CAGCCAGCCG GAAGGGCCGA GCGCAGAAGT GGTCCTGCAA CTTTATCCGC
13261 CTCCATCCAG TCTATTAATT GTTGCCGGGA AGCTAGAGTA AGTAGTTCGC CAGTTAATAG
13321 TTTGCGCAAC GTTGTTGCCA TTGCTACAGG CATCGTGGTG TCACGCTCGT CGTTTGGTAT
13381 GGCTTCATTC AGCTCCGGTT CCCAACGATC AAGGCGAGTT ACATGATCCC CCATGTTGTG
13441 CAAAAAAGCG GTTAGCTCCT TCGGTCCTCC GATCGTTGTC AGAAGTAAGT TGGCCGCAGT
13501 GTTATCACTC ATGGTTATGG CAGCACTGCA TAATTCTCTT ACTGTCATGC CATCCGTAAG
13561 ATGCTTTTCT GTGACTGGTG AGTACTCAAC CAAGTCATTC TGAGAATAGT GTATGCGGCG
13621 ACCGAGTTGC TCTTGCCCGG CGTCAATACG GGATAATACC GCGCCACATA GCAGAACTTT
13681 AAAAGTGCTC ATCATTGGAA AACGTTCTTC GGGGCGAAAA CTCTCAAGGA TCTTACCGCT
13741 GTTGAGATCC AGTTCGATGT AACCCACTCG TGCACCCAAC TGATCTTCAG CATCTTTTAC
13801 TTTCACCAGC GTTTCTGGGT GAGCAAAAAC AGGAAGGCAA AATGCCGCAA AAAAGGGAAT
13861 AAGGGCGACA CGGAAATGTT GAATACTCAT ACTCTTCCTT TTTCAATATT ATTGAAGCAT
13921 TTATCAGGGT TATTGTCTCA TGAGCGGATA CATATTTGAA TGTATTTAGA AAAATAAACA
13981 AATAGGGGTT CCGCGCACAT TTCCCCGAAA AGTGCCACCT GACGTC
//
```

FIG. 10F sequence of construct 6

```
LOCUS       pcDNA5/TO/DYRK1A LA & RA/6.8kb human XIST    13708 bp    DNA    SYN
       29-Nov-2012
DEFINITION  pcDNA5/TO/DYRK1A LA & RA/6.8kb human XIST
ACCESSION
KEYWORDS
SOURCE
  ORGANISM  other sequences; artificial sequences; vectors.
FEATURES            Location/Qualifiers
     source         1..13708
                    /organism="pcDNA5/TO/DYRK1A LA & RA/6.8kb human XIST"
                    /mol_type="other DNA"
     misc_feature   209..716
                    /label="DYRK1A right arm"
     misc_feature   823..1110
                    /label="CAG_enhancer"
     promoter       744..1320
                    /label="CMV_immearly_promoter"
     misc_feature   1277..1297
                    /label="CMV_fwd_primer"
     promoter       1278..1401
                    /label="CMV_promoter"
     misc_feature   1328..1367
                    /label="tetO"
     promoter       1290..1463
                    /label="CMV2_promoter"
     misc_feature   1377..1401
```

FIG. 10F  sequence of construct 6 (continued)

```
                    /label="LNCX_primer"
    misc_feature    1540..8403
                    /label="6.8kb human XIST"
    misc_feature    complement(8391..8407)
                    /label="pBluescriptKS_primer"
    misc_feature    complement(8440..8457)
                    /label="BGH_rev_primer"
    terminator      8443..8670
                    /label="bGH_PA_terminator"
    rep_origin      8733..9039
                    /label="f1_origin"
    misc_feature    complement(9153..9173)
                    /label="pBABE_3_primer"
    misc_feature    complement(9159..9374)
                    /label="SV40_enhancer"
    promoter        9171..9439
                    /label="SV40_promoter"
    rep_origin      9338..9415
                    /label="SV40_origin"
    misc_feature    9400..9419
                    /label="SV40pro_F_primer"
    CDS             complement(9473..10294)
                    /label="ORF frame 2"
                    /translation="MPPLEVARLLLHTSQPRPPEEDVGDLVLGIPEHRLAPVNDRCYA
                    AIVRQDIVGAEIRVHEVPDFGAVLGPKHQLIESLRDGRTDGVVHHSLPVIHMGISNRA
                    YEITPCSVLTDSLRSEWAEPARLAKIGRSDRIHGLRDRLQNSGQFGFRQVLQRDTLCT
                    AGDAIGQALAEFPNVKHFRNRERGRCKVPINITIFVETIGAAIYPQDISTPSYIEAES
                    TRFFALRELHQVGDAVELFDQKLLDRRRGEFRLFHHVLIRSENGYTSSRELFAKA*"
    CDS             9536..10561
                    /label="hygroB"
                    /gene="hygroB"
                    /note="ORF frame 2"
                    /translation="MKKPELTATSVEKFLIEKFDSVSDLMQLSEGEESRAFSFDVGGR
                    GYVLRVNSCADGFYKDRYVYRHFASAALPIPEVLDIGEFSESLTYCISRRAQGVTLQD
                    LPETELPAVLQPVAEAMDAIAAADLSQTSGFGPFGPQGIGQYTTWRDFICAIADPHVY
                    HWQTVMDDTVSASVAQALDELMLWAEDCPEVRHLVHADFGSNNVLTDNGRITAVIDWS
                    EAMFGDSQYEVANIFFWRPWLACMEQQTRYFERRHPELAGSPRLRAYMLRIGLDQLYQ
                    SLVDGNFDDAAWAQGRCDAIVRSGAGTVGRTQIARRSAAVWTDGCVEVLADSGNRRPS
                    TRPRAKE*"
    gene            9551..10558
                    /label="hygroB"
                    /gene="hygroB"
    terminator      10694..10813
                    /label="SV40_PA_terminator"
    misc_feature    10782..10801
                    /label="EBV_rev_primer"
    misc_feature    10824..11513
                    /label="DYRK1A left arm"
    misc_feature    complement(11547..11565)
                    /label="M13_reverse_primer"
    misc_feature    complement(11564..11586)
                    /label="M13_pUC_rev_primer"
    promoter        complement(11600..11629)
                    /label="lac_promoter"
    rep_origin      complement(11938..12557)
                    /label="pBR322_origin"
    CDS             complement(12712..13572)
                    /label="Ampicillin"
                    /gene="Ampicillin"
                    /note="ORF frame 1"
                    /translation="MSIQHFRVALIPFFAAFCLPVFAHPETLVKVKDAEDQLGARVGY
                    IELDLNSGKILESFRPEERFPMMSTFKVLLCGAVLSRIDAGQEQLGRRIHYSQNDLVE
                    YSPVTEKHLTDGMTVRELCSAAITMSDNTAANLLLTTIGGPKELTAFLHNMGDHVTRL
                    DRWEPELNEAIPNDERDTTMPVAMATTLRKLLTGELLTLASRQQLIDWMEADKVAGPL
                    LRSALPAGWFIADKSGAGERGSRGIIAALGPDGKPSRIVVIYTTGSQATMDERNRQIA
```

FIG. 10F  sequence of construct 6 (continued)

```
                        EIGASLIKHW*"
        gene            complement(12712..13572)
                        /label="Ampicillin"
                        /gene="Ampicillin"
        promoter        complement(13614..13642)
                        /label="AmpR_promoter"
ORIGIN
     1 GACGGATCGG GAGATCTCCC GATCCCCTAT GGTGCACTCT CAGTACAATC TGCTCTGATG
    61 CCGCATAGTT AAGCCAGTAT CTGCTCCCTG CTTGTGTGTT GGAGGTCGCT GAGTAGTGCG
   121 CGAGCAAAAT TTAAGCTACA ACAAGGCAAG GCTTGACCGA CAATTGCATG AAGAATCTGC
   181 TTAGGGTTAG GCGTTTTGCG CTGCTTCGcg aaaaccagaa agtattctca gtaatgatag
   241 tatggataaa gcaggtttct atgacccttt attacagaat ctgtgagttt tcacaatta
   301 aaaagtaata aaaagtagtg acaacattca ctgaactctt attctatgcc aacttgttcc
   361 ggtatgccct tacacccaca aagccctat gcataaggtg gcattattcc agcatgtatt
   421 gcattgtaca cacaaagagg tcaagcactc caccacggcc ctaagcatgg tggctgaggt
   481 gggaaggcca gaggtaggtg ggcccgcgcc cttttccact ctgaaccatg cctccaagat
   541 aggagggtgg gaaagtgctc aagacacatt agaaattccc cataaaagac aagattgttg
   601 aacacctgca agtgaataaa gataaactga tctcagaggg gaaaagacg cagggttagg
   661 aaacagcacc ctgctcgagg acgttctttc caaacagcct gctcatcacc cgttcgCGAT
   721 GTACGGGCCA GATATACGCG TTGACATTGA TTATTGACTA GTTATTAATA GTAATCAATT
   781 ACGGGGTCAT TAGTTCATAG CCCATATATG GAGTTCCGCG TTACATAACT TACGGTAAAT
   841 GGCCCGCCTG GCTGACCGCC CAACGACCCC CGCCCATTGA CGTCAATAAT GACGTATGTT
   901 CCCATAGTAA CGCCAATAGG GACTTTCCAT TGACGTCAAT GGGTGGAGTA TTTACGGTAA
   961 ACTGCCCACT TGGCAGTACA TCAAGTGTAT CATATGCCAA GTACGCCCCC TATTGACGTC
  1021 AATGACGGTA AATGGCCCGC CTGGCATTAT GCCCAGTACA TGACCTTATG GGACTTTCCT
  1081 ACTTGGCAGT ACATCTACGT ATTAGTCATC GCTATTACCA TGGTGATGCG GTTTTGGCAG
  1141 TACATCAATG GGCGTGGATA GCGGTTTGAC TCACGGGGAT TTCCAAGTCT CCACCCCATT
  1201 GACGTCAATG GGAGTTTGTT TTGGCACCAA AATCAACGGG ACTTTCCAAA ATGTCGTAAC
  1261 AACTCCGCCC CATTGACGCA AATGGGCGGT AGGCGTGTAC GGTGGGAGGT CTATATAAGC
  1321 AGAGCTCTCC CTATCAGTGA TAGAGATCG CCTATCAGTG ATAGAGATCG TCGACGAGCT
  1381 CGTTTAGTGA ACCGTCAGAT CGCCTGGAGA CGCCATCCAC GCTGTTTGA CCTCCATAGA
  1441 AGACACCGGG ACCGATCCAG CCTCCGGACT CTAGCGTTTA AACTTAAGCT TGGTACCGAG
  1501 CTCGGATCCA CTAGTCCAGT GTGGTGGAAT TCTGCAGATt ctagaacatt ttctagtccc
  1561 ccaacaccct ttatggcgta tttctttaaa aaaatcacct aaattccata aaatattttt
  1621 ttaaattcta tactttctcc tagtgtcttc ttgacacgtc ctccatattt ttttaaagaa
  1681 agtatttgga atattttgag gcaattttta atatttaagg aattttttctt tggaatcatt
  1741 tttggtgaca tctctgtttt tgtggatca gttttttact cttccactct cttttctata
  1801 ttttggccat cggggctgcg gatactggt tttattattt tttcttttcc caacggggcc
  1861 gtggatacct gccttttaat tctttttttat tcgcccatcg gggccgcgca tacctgcttt
  1921 ttatttttttt ttccttagcc catcgggta tcggataccgt gctgattccc ttcccctctg
  1981 aaccccccaac actctggccc atcggggtga cggatatctg cttttttaaa attttctttt
  2041 tttggcccat cggggcttcg gatacctgct ttttttttt tatttttcct tgcccatcgg
  2101 ggcctcggat acctgcttta atttttgttt ttctgcccat cggggccgcg gatacctgct
  2161 ttgatttttt tttttcatcg cccatcggtg cttttatgg atgaaaaat gttggttttg
  2221 tgggttgttg cactctctgg aatatctaca cttttttttg ctgctgatca tttggtggtg
  2281 tgtgagtgta cctaccgctt tggcagagaa tgactctgca gttaagctaa gggcgtgttc
  2341 agattgtgga ggaaaagtgg ccgccattt agacttgccg cataactcgg cttagggcta
  2401 gtcgtttgtg ctaagttaaa ctaggagggc aagatggatg atagcaggtc aggcagagga
  2461 agtcatgtgc attgcatgag ctaaacctat ctgaatgaat tgatttgggg cttgttagga
  2521 gctttgcgtg attgttgtat cgggaggcag taagaatcat cttttatcag tacaagggac
  2581 tagttaaaaa tggaaggtta ggaaagacta aggtgcaggc cttaaaatgc cgatttgac
  2641 attgcggcat tgctcagcat ggcgggctgt gctttgttag gttgtccaaa atggcggatc
  2701 cagttcgtc gcagtgttca agtgcgggga aggccacatc atgatggggg aggctttgt
  2761 aagtggttag catggtggtg gacatgtgcg gtcacacagg aaaagatggc ggctgaaggt
  2821 cttgccgcag tgtaaaacat ggcgggcctc tttgtctttg ctgtgtgctt tcgtgtttgg
  2881 gtttttgccgc agggacaata tggcaggcgt tgtcatatgt atatcatggc ttttgtcacg
  2941 tggacatcat ggcgggcttg ccgcattgtt aaagatggcg ggttttgccg cctagtgcca
  3001 cgcagagcgg gagaaaaggt gggatggaca gtgctggatt gctgcataac caaccaatt
  3061 agaaatgggg gtggaattga tcacagccaa ttagagcaga agatggaatt agactgatga
  3121 cacactgtcc agctactcag cgaagacctg ggtgaattga catggcactt cgcagctgtc
  3181 tttagccagt caggagaaag aagtggaggg gccacgtgta tgtctcccag tgggcggtac
  3241 accaggtgtt ttcaaggtct tttcaaggac atttagcctt tccacctctg tcccctctta
  3301 tttgtcccct cctgtccagt gctgcctctt gcagtgctgg atatctggct gtgtggtctg
  3361 aacctccctc cattcctctg tattggtgcc tcacctaagg ctaagtatac ctcccccccc
  3421 accccccaac ccccccaact ccccacccccc acccccaccc cccacccctcc ccacccccct
```

FIG. 10F sequence of construct 6 (continued)

```
3481 acccccctac ccccctaccc ccctctggtc tgcctgcac tgcactgttg ccatgggcag
3541 tgctccaggc ctgcttggtg tggacatggt ggtgagccgt ggcaaggacc agaatggatc
3601 acagatgatc gttggccaat tggcctccca atatgtgtga ttgtatttgt cgaggttgct
3661 atgcactaga gaaggaaagt gctcccctca tccccacttt tcccttccag caggaagtgc
3721 ccacccata agacccttt atttggagag tctaggtgca caattgtaag tgaccacaag
3781 catgcatctt ggacatttat gtgcgtaatc gcacactgct cattccatgt gaataaggtc
3841 ctactctccg acccctttg caatacagaa gggttgctga taacgcagtc ccctttctt
3901 ggcatgttgt gtgtgattat aatcgtctgg gatcctatgc actagaaaag gagggtcctc
3961 tccacatacc tcagtctcac ctttcccttc cagcagggag tgcccactcc ataagactct
4021 cacatttgga cagtcaaggt gcgtaattgt taagtgaaca caaccatgca ccttagacat
4081 ggatttgcat aactacacac agctcaacct atctgaataa aatcctactc tcagaccct
4141 tttgcagtac agcaggggtg ctgatcacca aggccctttt tcctggcctg gtatgcgtgt
4201 gattatgttt gtcccggttc ctgtgtatta gacatggaag cctccctgc cacactccac
4261 cccaatctt ccttccctt ccggcaggag tgccctctcc ataagacgct tacgtttgga
4321 caatcaaggt gcacagttgt aagtgaccac aggcatacac cttggacatt aatgtgcata
4381 accactttgc ccattccatc tgaataaggt cctactctca gaccccttt gcagtacagc
4441 aggggtgctg atcaccaagg cccctttct tggcctgtta tgtgcgtgat tatatttgtc
4501 tgggttcctg tgtattagac aaggaagcct tcccccgcc cccacccca ctcccagtct
4561 tcctttcct tccagcaggg agtgccccct ccataagatc attacatttg gacaatcaag
4621 gtgcacaatt ataagtgacc acagccatgc accttggaca ttattggaca ttaatgtgcg
4681 taactgcaca tggcccatcc catctgaata aggacctact ctcagatgcc tttgcagtac
4741 agcaggggta ctgaatcacc aaggcccttt tccttggcct gttatgtgtg tgattatatt
4801 tatcccagtt tctgtgtaat agacatgaaa gcctccctg ccacacccca cctccaatct
4861 tcctttccct tccaccaggg agtgtccact ccatatacc ttacatttgg acaatcaagg
4921 tgcacaattg taagtgagca taggcactca ccttggacat gaatgtgcat aactgcacat
4981 ggcccatccc atctgaataa ggtcctactc tcagaccctt tttgcagtac agcagggtg
5041 ctgatcacca aggccccttt tcctggcctg ttatgtgtgt gattatattt gttccagttc
5101 ctgtgtaata gacatggaag cctccctgc cacactccac cccaatctt ccttccttc
5161 tggcaggaag tacccgctcc ataagaccct tacatttgga cagtcaaggt gcacaattgt
5221 atgtgaccac aaccatgcac cttggacata aatgtgtgta actgcacatg gcccatcca
5281 tctgaataag gtcctactct cagaccctt ttgcagtaca gtaggtgtgc tgataaccaa
5341 ggcccctctc cctggcctgt taacgtatgt gattatattt gtctgggttc cagtgtataa
5401 gacatggaag cctccctgc cccacccac cctcaatctt cctttcctt ctggcaggga
5461 gtgccagctc cataagaacc ttacatttgg acagtcaagg tgcacaattc taagtgaccg
5521 cagccatgca ccttggtcaa taatgtgtgt aactgcacac ggcctatctc atctgaataa
5581 ggccttactc tcagacccct tttgcagtac agcaggggtg ctgataacca aggcccattt
5641 tcctggcctg ttatgtgtgt gattatattt gtccaggttt ctgtgtacta gacaaggaag
5701 cctcctctgc cccatcccat ctacgcataa tctttctttt cctccagca gggagtgctc
5761 actccataag acccttacat tggacaatc aaggtgcaca attgtaagtg accacaacca
5821 tgcatcttgg aaatttatgt gcataactgc acatggctta tcctatttga ataaagtcct
5881 actctcagac cccctttgca gtagctgg ggtgctgatc actgaggcct ctttgcttgg
5941 cttgtctata ttcttgtgta ctagataagg gcaccttctc atggactccc tttgcttttc
6001 aacaaggagt acccactact ttttaagatt cttatatttg tccaaagtac atggttttaa
6061 ttgaccacaa caatgtccct tggacattaa tgtatgtaat caccacatgg ttcatcctaa
6121 ttaaacaaag ttctaccttc tcacctcca tttgcagtat accaggggtg ctgacccct
6181 aagtcccctt ttcttggctt gttgacatgc ataattgcat ttatgttggt tcttgtgcc
6241 tagacaagga tgccccacct cttttcaata gtgggtgcc actccttatg atctttacat
6301 ttgaacagtt aatgtgaata attgcagttg tccacaaccc tatcacttct aggaccatta
6361 tacctctttt gcattactgt ggggtatact gtttccctcc aaggcccctt ctggtggact
6421 atcaacatat aattgaaatt ttcttttgtc tttgtcagta gattaaggtc atacccatc
6481 aacctttctt tgtgtagtacaa caggggtgtc tgatcaacca aagtcctgtt gttttggact
6541 gttaatatgt gcaattacat ttgctcctga tctgtgcact agataaggat cctacctact
6601 ttctagtgt ttttagcagg tagtgcccac tactcaagac tgtcacttgg aatgttcatg
6661 tgcacaaact caattctcta agcatgttcc tgtaccacct ttgctttaga gcaggggat
6721 gatattcact aagtgccct tcttttggac ttaatatgca ttaatgcaat tgtccacctc
6781 ttctttttaga ctaagagttg atctccacat attcccttg catcagggc atgttaatta
6841 tgaatgaacc cttttcttt aatattaatg tcataattgt atttgtggac ctgtgtagga
6901 gaaaagacc ctatgttcct cccattaccc tttggattgc tgctgagaag tgttaactac
6961 tcataatctc agctcttgga caattaatag cattaataac aattatcaag ggcactgatc
7021 attagataag actcctgctt cctcgttgct tacatcgggt gtactgaccc actaaggcccc
7081 cttgtactgt taatgtgaat atttgcaatt atatatgtct cctctggta gagtgggata
7141 ttatgcccta gtatcccctt tgcattactg caggggctgc tgactactca aaacttctcc
7201 tgggactgtt aataggcaca atggcagtta tcaatggttt tctccctcc tgaccttgtt
7261 aagcaagcgc cccacccac ccttagtttc ccatggcata ataaagtata agcattggag
7321 tattccatgc acttgtctat caaacagtgg tccatactcc caacccttt gcattgcgcc
```

FIG. 10F sequence of construct 6 (continued)

```
7381 agtgtgtaaa atcacaggta gccatggtgt catgctttat atacgaagtc ttccctctct
7441 ctgcccttg tgtgcccttg gcccttttt acagactatt gctcacaatc tcaggtgtcc
7501 atatttgcag ctattaggta agattgtgct gtctccctct tcccttcct ctgccctgcc
7561 ccttttgcct ctttgctggg taatgttgac cGgacaaggc cctttctctt ggacttaaac
7621 aattctcagt tgcactttcc ttggtccCac ccattataca tgaaccctc tacttccttt
7681 cgcattgctt ctgagtatgc tgactaccca aagcccttc tgtgttatta ataaacacag
7741 tactgattgt cccatttttc agcccatcag tccaagatct ccctaccact ttggtgtgtt
7801 ggtgcagtgt tgactatgaa aagcaggcct gaactaggtg gataagcctt cactcatttt
7861 ctttcattta ttaatgatcc tagtttcaat tattgtcaga ttctggggac aagaaccatt
7921 cttgcccacc tgtgttactg ctttactgtg caaaatactg aaggcaagtc agacccaggg
7981 agctggattg ccatccttta ttttgtgttt ccagtgtaca ctataaaatt gtctccccag
8041 gaaggaaggt tggcactttc tctgcattct tctttccaga gcagattgcc tggttaagaa
8101 tctcttgttg tcccCtTtgt atattgttat tgtaaagtgc caaatgccag gatacagcca
8161 gaaaaattgc ttattattat taaaaaaatt tttttaagaa agacatctgg attgtagggt
8221 ggactcgata acctggtcat tatttttag aagccaaaat atccatttat actatgtacc
8281 tggtgaccag tgtctctcat tttaactgag ggtggtgggt ctgtggatag aacactgact
8341 cttgctattt taatatcaaa gatattctag ATCAGCACA GTGGCggccc gataccgtcg
8401 accTCGAGTC TAGAGGGCCC GTTTAAACCC GCTGATAGC CTCGACTGTG CCTTCTAGTT
8461 GCCAGCCATC TGTTGTTTGC CCCTCCCCG TGCCTTCCTT GACCCTGGAA GGTGCCACTC
8521 CCACTGTCCT TTCCTAATAA AATGAGGAAA TTGCATCGCA TTGTCTGAGT AGGTGTCATT
8581 CTATTCTGGG GGGTGGGGTG GGGCAGGACA GCAAGGGGGA GGATTGGGAA GACAATAGCA
8641 GGCATGCTGG GGATGCGGTG GGCTCTATGG CTTCTGAGGC GGAAAGAACC AGCTGGGGCT
8701 CTAGGGGGTA TCCCCACGCG CCCTGTAGCG GCGCATTAAG CGCGGCGGGT GTGGTGGTTA
8761 CGCGCAGCGT GACCGCTACA CTTGCCAGCG CCCTAGCGCC CGCTCCTTTC GCTTTCTTCC
8821 CTTCCTTTCT CGCCACGTTC GCCGGCTTTC CCCGTCAAGC TCTAAATCGG GGGCTCCCTT
8881 TAGGGTTCCG ATTTAGTGCT TTACGGCACT TCGACCCCAA AAAACTTGAT TAGGGTGATG
8941 GTTCACGTAG TGGGCCATCG CCCTGATAGA CGGTTTTCG CCCTTTGACG TTGGAGTCCA
9001 CGTTCTTTAA TAGTGGACTC TTGTTCCAAA CTGGAACAAC ACTCAACCCT ATCTCGGTCT
9061 ATTCTTTTGA TTTATAAGGG ATTTTGCCGA TTTCGGCCTA TTGGTTAAAA AATGAGCTGA
9121 TTTAACAAAA ATTTAACGCG AATTAATTCT GTGGAATGTG TGTCAGTTAG GGTGTGGAAA
9181 GTCCCCAGGC TCCCCAGCAG CAGAAGTAT GCAAAGCATG CATCTCAATT AGTCAGCAAC
9241 CAGGTGTGGA AAGTCCCCAG GCTCCCCAGC AGGCAGAAGT ATGCAAAGCA TGCATCTCAA
9301 TTAGTCAGCA ACCATAGTCC CGCCCCTAAC TCCGCCCATC CCGCCCCTAA CTCCGCCCAG
9361 TTCCGCCCAT TCTCCGCCCC ATGGCTGACT AATTTTTTTT ATTTATGCAG AGGCCGAGGC
9421 CGCCTCTGCC TCTGAGCTAT TCCAGAAGTA GTGAGGAGGC TTTTTTGGAG GCCTAGGCTT
9481 TTGCAAAAAG CTCCCGGGAG CTTGTATATC CATTTTCGGA TCTGATCAGC ACGTGATGAA
9541 AAAGCCTGAA CTCACCGCGA CGTCTGTCGA GAAGTTTCTG ATCGAAAAGT TCGACAGCGT
9601 CTCCGACCTG ATGCAGCTCT CGGAGGGCGA AGAATCTCGT GCTTTCAGCT TCGATGTAGG
9661 AGGGCGTGGA TATGTCCTGC GGGTAAATAG CTGCGCCGAT GGTTTCTACA AAGATCGTTA
9721 TGTTTATCGG CACTTTGCAT CGGCCGCGCT CCCGATTCCG GAAGTGCTTG ACATTGGGGA
9781 ATTCAGCGAG AGCCTGACCT ATTGCATCTC CCGCCGTGCA CAGGGTGTCA CGTTGCAAGA
9841 CCTGCCTGAA ACCGAACTGC CCGCTGTTCT GCAGCCGGTC GCGGAGGCCA TGGATGCGAT
9901 CGCGTCGGCC GATCTTAGCC AGACGAGCGG GTTCGGCCCA TTCGGACCGC AAGGAATCGG
9961 TCAATACACT ACATGGCGTG ATTTCATATG CGCGATTGCT GATCCCCATG TGTATCACTG
10021 GCAAACTGTG ATGGACGACA CCGTCAGTGC GTCCGTCGCG CAGGCTCTCG ATGAGCTGAT
10081 GCTTTGGGCC GAGGACTGCC CCGAAGTCCG GCACCTCGTG CACGCGGATT TCGGCTCCAA
10141 CAATGTCCTG ACGGACAATG GCCGCATAAC AGCGGTCATT GACTGGAGCG AGGCGATGTT
10201 CGGGGATTCC CAATACGAGG TCGCCAACAT CTTCTTCTGG AGGCCGTGGT TGGCTTGTAT
10261 GGATGCAGCAG ACGCGCTACT TCGAGCGGAG GCATCCGGAG CTTGCAGGAT CGCCGCGGCT
10321 CCGGGCGTAT ATGCTCCGCA TTGGTCTTGA CCAACTCTAT CAGAGCTTGG TTGACGGCAA
10381 TTTCGATGAT GCAGCTTGGG CGCAGGGTCG ATGCGACGCA ATCGTCCGAT CCGGAGCCGG
10441 GACTGTCGGG CGTACACAAA TCGCCCGCAG AAGCGCGGCC GTCTGGACCG ATGGCTGTGT
10501 AGAAGTACTC GCCGATAGTG GAAACCGACG CCCCAGCACT CGTCCGAGGG CAAAGGAATA
10561 GCACGTGCTA CGAGATTTCG ATTCCACCGC CGCCTTCTAT GAAAGGTTGG GCTTCGGAAT
10621 CGTTTTCCGG GACGCCGGCT GGATGATCCT CCAGCGCGGG GATCTCATGC TGGAGTTCTT
10681 CGCCCACCCC AACTTGTTTA TTGCAGCTTA TAATGGTTAC AAATAAAGCA ATAGCATCAC
10741 AAATTTCACA AATAAAGCAT TTTTTTCACT GCATTCTAGT TGTGGTTTGT CCAAACTCAT
10801 CAATGTATCT TATCATGTCT GTAtacgtaa actggcaaag gggtggctgg gccaaaagac
10861 agaggaatta agtaagaagt ccaggaaaaa tgaacttcac atcaaatttt agagcacgt
10921 agccatgaat cttgtgaata gctcccaaaa atgtcctgtg gaagacaact agaaagcatt
10981 ctacaatcag gcaccacct ccacctgccc cctcctgtgt tgttctcatg gggcacctct
11041 gggctccagc tcctccaagg cacctccaca ctctctcaag tacactcttc actcttcccc
11101 aaacatgatt cccctactgc tctgcctaac tcccacttct ctttcaagta gcagcttaaa
11161 cgtcacctca tatttggctg gaaaatagaa tatagacaga ggggtaagtt aaggctagaa
11221 aggcaggctg ggtcaacaga atggcaagct aaaacatggg attttctaaa acagcctaag
```

FIG. 10F sequence of construct 6 (continued)

```
11281 agggtgacag ataaaagtgt gcaaggagtg gcacaactcc agtttcatct ttagctatag
11341 caattaacac cataaggagt ctggattcaa ttttgccatt tactagctag ctaccaactt
11401 ctgtgtcgct ttgggcaaat caattaaatc catacctccc tttccatctg cagaatgggt
11461 ttataacagt acttaaacct caaggtacta agaacagtaa agagttaatg gtaTACCGTC
11521 GACCTCTAGC TAGAGCTTGG CGTAATCATG GTCATAGCTG TTTCCTGTGT GAAATTGTTA
11581 TCCGCTCACA ATTCCACACA ACATACGAGC CGGAAGCATA AAGTGTAAAG CCTGGGGTGC
11641 CTAATGAGTG AGCTAACTCA CATTAATTGC GTTGCGCTCA CTGCCCGCTT TCCAGTCGGG
11701 AAACCTGTCG TGCCAGCTGC ATTAATGAAT CGGCCAACGC GCGGGGAGAG GCGGTTTGCG
11761 TATTGGGCGC TCTTCCGCTT CCTCGCTCAC TGACTCGCTG CGCTCGGTCG TTCGGCTGCG
11821 GCGAGCGGTA TCAGCTCACT CAAAGGCGGT AATACGGTTA TCCACAGAAT CAGGGGATAA
11881 CGCAGGAAAG AACATGTGAG CAAAAGGCCA GCAAAAGGCC AGGAACCGTA AAAAGGCCGC
11941 GTTGCTGGCG TTTTTCCATA GGCTCCGCCC CCCTGACGAG CATCACAAAA ATCGACGCTC
12001 AAGTCAGAGG TGGCGAAACC CGACAGGACT ATAAAGATAC CAGGCGTTTC CCCCTGGAAG
12061 CTCCCTCGTG CGCTCTCCTG TTCCGACCCT GCCGCTTACC GGATACCTGT CCGCCTTTCT
12121 CCCTTCGGGA AGCGTGGCGC TTTCTCATAG CTCACGCTGT AGGTATCTCA GTTCGGTGTA
12181 GGTCGTTCGC TCCAAGCTGG GCTGTGTGCA CGAACCCCCC GTTCAGCCCG ACCGCTGCGC
12241 CTTATCCGGT AACTATCGTC TTGAGTCCAA CCCGGTAAGA CACGACTTAT CGCCACTGGC
12301 AGCAGCCACT GGTAACAGGA TTAGCAGAGC GAGGTATGTA GGCGGTGCTA CAGAGTTCTT
12361 GAAGTGGTGG CCTAACTACG GCTACACTAG AAGAACAGTA TTTGGTATCT GCGCTCTGCT
12421 GAAGCCAGTT ACCTTCGGAA AAAGAGTTGG TAGCTCTTGA TCCGGCAAAC AAACCACCGC
12481 TGGTAGCGGT TGGTTTTTTG TTTGCAAGCA GCAGATTACG CGCAGAAAAA AAGGATCTCA
12541 AGAAGATCCT TTGATCTTTT CTACGGGGTC TGACGCTCAG TGGAACGAAA ACTCACGTTA
12601 AGGGATTTTG GTCATGAGAT TATCAAAAAG GATCTTCACC TAGATCCTTT TAAATTAAAA
12661 ATGAAGTTTT AAATCAATCT AAAGTATATA TGAGTAAACT TGGTCTGACA GTTACCAATG
12721 CTTAATCAGT GAGGCACCTA TCTCAGCGAT CTGTCTATTT CGTTCATCCA TAGTTGCCTG
12781 ACTCCCCGTC GTGTAGATAA CTACGATACG GGAGGGCTTA CCATCTGGCC CCAGTGCTGC
12841 AATGATACCG CGAGACCCAC GCTCACCGGC TCCAGATTTA TCAGCAATAA ACCAGCCAGC
12901 CGGAAGGGCC GAGCGCAGAA GTGGTCCTGC AACTTTATCC GCCTCCATCC AGTCTATTAA
12961 TTGTTGCCGG GAAGCTAGAG TAAGTAGTTC GCCAGTTAAT AGTTTGCGCA ACGTTGTTGC
13021 CATTGCTACA GGCATCGTGG TGTCACGCTC GTCGTTTGGT ATGGCTTCAT TCAGCTCCGG
13081 TTCCCAACGA TCAAGGCGAG TTACATGATC CCCCATGTTG TGCAAAAAAG CGGTTAGCTC
13141 CTTCGGTCCT CCGATCGTTG TCAGAAGTAA GTTGGCCGCA GTGTTATCAC TCATGGTTAT
13201 GGCAGCACTG CATAATTCTC TTACTGTCAT GCCATCCGTA AGATGCTTTT CTGTGACTGG
13261 TGAGTACTCA ACCAAGTCAT TCTGAGAATA GTGTATGCGG CGACCGAGTT GCTCTTGCCC
13321 GGCGTCAATA CGGGATAATA CCGCGCCACA TAGCAGAACT TTAAAAGTGC TCATCATTGG
13381 AAAACGTTCT TCGGGGCGAA AACTCTCAAG GATCTTACCG CTGTTGAGAT CCAGTTCGAT
13441 GTAACCCACT CGTGCACCCA ACTGATCTTC AGCATCTTTT ACTTTCACCA GCGTTTCTGG
13501 GTGAGCAAAA ACAGGAAGGC AAAATGCCGC AAAAAAGGGA ATAAGGGCGA CACGGAAATG
13561 TTGAATACTC ATACTCTTCC TTTTTCAATA TTATTGAAGC ATTTATCAGG GTTATTGTCT
13621 CATGAGCGGA TACATATTTG AATGTATTTA GAAAAATAAA CAAATAGGGG TTCCGCGCAC
13681 ATTTCCCCGA AAAGTGCCAC CTGACGTC
//
```

FIG. 10G sequence of construct 7

```
LOCUS       AAVS1 HindIII/pcDNA5/TO/6.8kb human XIST    15721 bp    DNA    SYN    29-Nov-
2012
DEFINITION  AAVS1 HindIII/pcDNA5/TO/6.8kb human XIST
ACCESSION
KEYWORDS
SOURCE
  ORGANISM  other sequences; artificial sequences; vectors.
FEATURES             Location/Qualifiers
     source          1..15721
                     /organism="AAVS1 HindIII/pcDNA5/TO/6.8kb human XIST"
                     /mol_type="other DNA"
     promoter        143..172
                     /label="lac_promoter"
     misc_feature    186..208
                     /label="M13_pUC_rev_primer"
     misc_feature    207..225
                     /label="M13_reverse_primer"
     promoter        242..261
                     /label="T3_promoter"
```

FIG. 10G  sequence of construct 7 (continued)

```
misc_feature    295..1095
                /label="Left arm"
misc_feature    complement(1126..1145)
                /label="EBV_rev_primer"
terminator      complement(1112..1231)
                /label="SV40_PA_terminator"
gene            complement(1369..2376)
                /label="hygroB"
                /gene="hygroB"
CDS             complement(1366..2391)
                /label="ORF frame 1"
                /translation="MKKPELTATSVEKFLIEKFDSVSDLMQLSEGEESRAFSFDVGGR
                GYVLRVNSCADGFYKDRYVYRHFASAALPIPEVLDIGEFSESLTYCISRRAQGVTLQD
                LPETELPAVLQPVAEAMDAIAAADLSQTSGFGPFGPQGIGQYTTWRDFICAIADPHVY
                HWQTVMDDTVSASVAQALDELMLWAEDCPEVRHLVHADFGSNNVLTDNGRITAVIDWS
                EAMFGDSQYEVANIFFWRPWLACMEQQTRYFERRHPELAGSPRLRAYMLRIGLDQLYQ
                SLVDGNFDDAAWAQGRCDAIVRSGAGTVGRTQIARRSAAVWTDGCVEVLADSGNRRPS
                TRPRAKE*"
CDS             1633..2454
                /label="ORF frame 1"
                /translation="MPPLEVARLLLHTSQPRPPEEDVGDLVLGIPEHRLAPVNDRCYA
                AIVRQDIVGAEIRVHEVPDFGAVLGPKHQLIESLRDGRTDGVVHHSLPVIHMGISNRA
                YEITPCSVLTDSLRSEWAEPARLAKIGRSDRIHGLRDRLQNSGQFGFRQVLQRDTLCT
                AGDAIGQALAEFPNVKHFRNRERGRCKVPINITIFVETIGAAIYPQDISTPSYIEABS
                TRFFALRELHQVGDAVELFDQKLLDRRRGEFRLFHHVLIRSENGYTSSRELFAKA*"
misc_feature    complement(2508..2527)
                /label="SV40pro_F_primer"
rep_origin      complement(2512..2589)
                /label="SV40_origin"
promoter        complement(2488..2756)
                /label="SV40_promoter"
misc_feature    2559..2774
                /label="SV40_enhancer"
misc_feature    2754..2774
                /label="pBABE_3_primer"
rep_origin      complement(2888..3194)
                /label="f1_origin"
terminator      complement(3257..3484)
                /label="bGH_PA_terminator"
misc_feature    3470..3487
                /label="BGH_rev_primer"
misc_feature    3520..3536
                /label="pBluescriptKS_primer"
misc_feature    complement(3524..10387)
                /label="6.8kb human XIST"
misc_feature    complement(10526..10550)
                /label="LNCX_primer"
promoter        complement(10464..10637)
                /label="CMV2_promoter"
misc_feature    complement(10560..10599)
                /label="tetO"
promoter        complement(10526..10651)
                /label="CMV_promoter"
misc_feature    complement(10630..10650)
                /label="CMV_fwd_primer"
promoter        complement(10603..11183)
                /label="CMV_immearly_promoter"
misc_feature    complement(10816..11103)
                /label="CAG_enhancer"
misc_feature    11219..12058
                /label="Right arm"
promoter        complement(12094..12112)
                /label="T7_promoter"
misc_feature    complement(12119..12135)
                /label="M13_forward20_primer"
```

FIG. 10G sequence of construct 7 (continued)

```
    misc_feature    complement(12128..12150)
                    /label="M13_pUC_fwd_primer"
    misc_feature    12116..12259
                    /label="lacZ_a"
    misc_feature    12282..12575
                    /label="ccdB"
    promoter        12786..12835
                    /label="NEOKAN_promoter"
    CDS             12924..13718
                    /label="NeoR/KanR"
                    /gene="NeoR/KanR"
                    /note="ORF frame 3"
                    /translation="MIEQDGLHAGSPAAWVERLFGYDWAQQTIGCSDAAVFRLSAQGR
                    PVLFVKTDLSGALNELQDEAARLSWLATTGVPCAAVLDVVTEAGRDWLLLGEVPGQDL
                    LSSHLAPAEKVSIMADAMRRLHTLDPATCPFDHQAKHRIERARTRMEAGLVDQDDLDE
                    EHQGLAPAELFARLKASMPDGEDLVVTHGDACLPNIMVENGRFSGFIDCGRLGVADRY
                    QDIALATRDIAEELGGEWADRFLVLYGIAAPDSQRIAFYRLLDEFF*"
    gene            12927..13715
                    /label="NeoR/KanR"
                    /gene="NeoR/KanR"
    promoter        13851..13874
                    /label="AmpR_promoter"
    CDS             complement(13968..14828)
                    /label="Ampicillin"
                    /gene="Ampicillin"
                    /note="ORF frame 3"
                    /translation="MSIQHFRVALIPFFAAFCLPVFAHPETLVKVKDAEDQLGARVGY
                    IELDLNSGKILESFRPEERFPMMSTFKVLLCGAVLSRIDAGQEQLGRRIHYSQNDLVE
                    YSPVTEKHLTDGMTVRELCSAAITMSDNTAANLLLTTIGGPKELTAFLHNMGDHVTRL
                    DRWEPELNEAIPNDERDTTMPVAMATTLRKLLTGELLTLASRQQLIDWMEADKVAGPL
                    LRSALPAGWFIADKSGAGERGSRGIIAALGPDGKPSRIVVIYTTGSQATMDERNRQIA
                    EIGASLIKHW*"
    gene            complement(13968..14828)
                    /label="Ampicillin"
                    /gene="Ampicillin"
    rep_origin      14936..15555
                    /label="pBR322_origin"
ORIGIN
        1 AGCGCCCAAT ACGCAAACCG CCTCTCCCCG CGCGTTGGCC GATTCATTAA TGCAGCTGGC
       61 ACGACAGGTT TCCCGACTGG AAAGCGGGCA GTGAGCGCAA CGCAATTAAT GTGAGTTAGC
      121 TCACTCATTA GGCACCCCAG GCTTTACACT TTATGCTTCC GGCTCGTATG TTGTGTGGAA
      181 TTGTGAGCGG ATAACAATTT CACACAGGAA ACAGCTATGA CCATGATTAC GCCAAGCTCA
      241 GAATTAACCC TCACTAAAGG GACTAGTCCT GCAGGTTTAA ACGAATTCGC CCTTTGCTTT
      301 CTCTGACCAG CATTCTCTCC CCTGGGCCTG TGCCGCTTTC TGTCTGCAGC TTGTGGCCTG
      361 GGTCACCTCT ACGGCTGGCC CAGATCCTTC CCTGCCGCCT CCTTCAGGTT CCGTCTTCCT
      421 CCACTCCCTC TTCCCCTTGC TCTCTGCTGT GTTGCTGCCC AAGGATGCTC TTTCCGGAGC
      481 ACTTCCTTCT CGGCGCTGCA CCACGTGATG TCCTCTGAGC GGATCCTCCC CGTGTCTGGG
      541 TCCTCTCCGG GCATCTCTCC TCCCTCACCC AACCCCATGC CGTCTTCACT CGCTGGGTTC
      601 CCTTTTCCTT CTCCTTCTGG GGCCTGTGCC ATCTCTCGTT TCTTAGGATG GCCTTCTCCG
      661 ACGGATGTCT CCCTTGCGTC CCGCCTCCCC TTCTTGTAGG CCTGCATCAT CACCGTTTTT
      721 CTGGACAACC CCAAAGTACC CCGTCTCCCT GGCTTAGCC ACCTCTCCAT CCTCTTGCTT
      781 TCTTTGCCTG GACACCCCGT TCTCCTGTGG ATTCGGGTCA CCTCTCACTC CTTTCATTTG
      841 GGCAGCTCCC CTACCCCCCT TACCTCTCTA GTCTGTGCTA GCTCTTCCAG CCCCCTGTCA
      901 TGGCATCTTC CAGGGGTCCG AGAGCTCAGC TAGTCTTCTT CCTCCAACCC GGGCCCCTAT
      961 GTCCACTTCA GGACAGCATG TTTGCTGCCT CCAGGGATCC TGTGTCCCCG AGCTGGGACC
     1021 ACCTTATATT CCCAGGGCCG GTTAATGTGG CTCTGGTTCT GGGTACTTTT ATCTGTCCCC
     1081 TCCACCCCAC AGTGGGGCAA GCTTACAGAC ATGATAAGAT ACATTGATGA GTTTGGACAA
     1141 ACCACAACTA GAATGCAGTG AAAAAAATGC TTTATTTGTG AAATTTGTGA TGCTATTGCT
     1201 TTATTTGTAA CCATTATAAG CTGCAATAAA CAAGTTGGGG TGGGCGAAGA ACTCCAGCAT
     1261 GAGATCCCCG CGCTGGAGGA TCATCCAGCC GGCGTCCCGG AAAACGATTC CGAAGCCCAA
     1321 CCTTTCATAG AAGGCGGCGG TGGAATCGAA ATCTCGTAGC ACGTGCTATT CCTTTGCCCT
     1381 CGGACGAGTG CTGGGGCGTC GGTTTCCACT ATCGGCGAGT ACTTCTACAC AGCCATCGGT
     1441 CCAGACGGCC GCGCTTCTGC GGGCGATTTG TGTACGCCCG ACAGTCCCGG CTCCGGATCA
     1501 GACGATTGCG TCGCATCGAC CCTGCGCCCA AGCTGCATCA TCGAAATTGC CGTCAACCAA
     1561 GCTCTGATAG AGTTGGTCAA GACCAATGCG GAGCATATAC GCCCGGAGCC GCGGCGATCC
```

FIG. 10G sequence of construct 7 (continued)

```
1621 TGCAAGCTCC GGATGCCTCC GCTCGAAGTA GCGCGTCTGC TGCTCCATAC AAGCCAACCA
1681 CGGCCTCCAG AAGAAGATGT TGGCGACCTC GTATTGGGAA TCCCCGAACA TCGCCTCGCT
1741 CCAGTCAATG ACCGCTGTTA TGCGGCCATT GTCCGTCAGG ACATTGTTGG AGCCGAAATC
1801 CGCGTGCACG AGGTGCCGGA CTTCGGGGCA GTCCTCGGCC CAAAGCATCA GCTCATCGAG
1861 AGCCTGCGCG ACGGACGCAC TGACGGTGTC GTCCATCACA GTTTGCCAGT GATACACATG
1921 GGGATCAGCA ATCGCGCATA TGAAATCACG CCATGTAGTG TATTGACCGA TTCCTTGCGG
1981 TCCGAATGGG CCGAACCCGC TCGTCTGGCT AAGATCGGCC GCAGCGATCG CATCCATGGC
2041 CTCCGCGACC GGCTGCAGAA CAGCGGGCAG TTCGGTTTCA GGCAGGTCTT GCAACGTGAC
2101 ACCCTGTGCA CGGCGGGAGA TGCAATAGGT CAGGCTCTCG CTGAATTCCC CAATGTCAAG
2161 CACTTCCGGA ATCGGAGCG CGGCCGATGC AAAGTGCCGA TAAACATAAC GATCTTTGTA
2221 GAAACCATCG GCGCAGCTAT TTACCCGCAG GACATATCCA CGCCCTCCTA CATCGAAGCT
2281 GAAAGCACGA GATTCTTCGC CCTCCGAGAG CTGCATCAGG TCGGAGACGC TGTCGAACTT
2341 TTCGATCAGA AACTTCTCGA CAGACGTCGC GGTGAGTTCA GGCTTTTTCA TCACGTGCTG
2401 ATCAGATCCG AAAATGGATA TACAAGCTCC CGGGAGCTTT TTGCAAAAGC CTAGGCCTCC
2461 AAAAAAGCCT CCTCACTACT TCTGGAATAG CTCAGAGGCA GAGGCGGCCT CGGCCTCTGC
2521 ATAAATAAAA AAAATTAGTC AGCCATGGGG CGGAGAATGG GCGGAACTGG GCGGAGTTAG
2581 GGGCGGGATG GGCGGAGTTA GGGGCGGGAC TATGGTTGCT GACTAATTGA GATGCATGCT
2641 TTGCATACTT CTGCCTGCTG GGAGCCTGG GGACTTTCCA CACCTGGTTG CTGACTAATT
2701 GAGATGCATG CTTTGCATAC TTCTGCCTGC TGGGGAGCCT GGGGACTTTC CACACCCTAA
2761 CTGACACACA TTCCACAGAA TTAATTCGCG TTAAATTTTT GTTAAATCAG CTCATTTTTT
2821 AACCAATAGG CCGAAATCGG CAAATCCCT TATAAATCAA AAGAATAGAC CGAGATAGGG
2881 TTGAGTGTTG TTCCAGTTTG GAACAAGAGT CCACTATTAA AGAACGTGGA CTCCAACGTC
2941 AAAGGGCGAA AAACCGTCTA TCAGGGCGAT GGCCCACTAC GTGAACCATC ACCCTAATCA
3001 AGTTTTTTGG GGTCGAGGTG CCGTAAAGCA CTAAATCGGA ACCCTAAAGG GAGCCCCCGA
3061 TTTAGAGCTT GACGGGGAAA GCCGGCGAAC GTGGCGAGAA AGGAAGGGAA GAAAGCGAAA
3121 GGAGCGGGCG CTAGGGCGCT GGCAAGTGTA GCGGTCACGC TGCGCGTAAC CACCACACCC
3181 GCCGCGCTTA ATGCGCCGCT ACAGGGCGCG TGGGGATACC CCTAGAGCC CCAGCTGGTT
3241 CTTTCCGCCT CAGAAGCCAT AGAGCCCACC GCATCCCAG CATGCCTGCT ATTGTCTTCC
3301 CAATCCTCCC CCTTGCTGTC CTGCCCCACC CCACCCCCA GAATAGAATG ACACCTACTC
3361 AGACAATGCG ATGCAATTTC CTCATTTTAT TAGGAAAGGA CAGTGGGAGT GGCACCTTCC
3421 AGGGTCAAGG AAGCACGGG GGAGGGGCAA ACAACAGGTG GCTGGCAACT AGAAGGCACA
3481 GTCGAGGCTG ATCAGCGGGT TTAAACGGGC CCTCTAGACT CGAggtcgac ggtatcgggc
3541 cGCCACTGTG CTGGATCtag aatatctttg atattaaaat agcaagagtc agtgttctat
3601 ccacagaccc accaccctca gttaaaatga gagacactgg tcaccaggta catagtataa
3661 atggatattt tggcttcaaa aaaataatga ccaggttatc gagtccaccc tacaatccag
3721 atgtctttct taaaaaaatt tttttaataa taataagcaa tttttctggc tgtatcctgg
3781 catttggcac tttacaataa caatatacaa aggggacaac aagagattct taaccaggca
3841 atctgctctg gaaagaagaa tgcagagaaa gtgccaacct tccttcctgg ggagacaatt
3901 ttatagtgta cactggaaac acaaaataaa ggatggcaat ccagctccc gggtctgact
3961 tgccttcagt attttgcaca gtaaagcagt aacacaggtg ggcaagaatg gttcttgtcc
4021 ccagaatctg acaataattg aaactaggat cattaataaa tgaagaaaa tgagtgaagg
4081 cttatccacc tagttcaggc ctgcttttca tagtcaacac tgcaccaaca caccaaagtg
4141 gtaggagat cttggactga tgggctgaaa aatgggacaa tcagtactgt gtttattaat
4201 aacacagaag gggctttggg tagtcagcat actcagaagc aatgcgaaag gaagtagagg
4261 ggttcatgta taatgggtgg gaccaaggaa agtgcaactg agaattgttt aagtccaaga
4321 gaaagggcct tgtccggtca acattaccca gcaaagaggc aaaagggca gggcagaggg
4381 aagggaagag ggagacagca caatcttacc taatagctgc aaatatggac acctgagatt
4441 gtgagcaata gtctgtaaaa aggggccaag ggcacacaag gggcagagag agggaagact
4501 tcgtatataa agcatgacac catggctacc tgtgatttta cacactggcg caatgcaaaa
4561 gggttggag tatggaccac tgtttgatag acaagtgcat ggaatactcc aatgcttata
4621 ctttattatg ccatgggaaa ctaagggtgg ggtggggcgc ttgcttaaca aggtcaggga
4681 gggagaaaac cattgataac tgccattgtg cctattaaca gtcccaggag aagttttgag
4741 tagtcagcag ccctgcagt aatgcaaagg ggatactagg gcataatatc ccactctacc
4801 agaaggagac atatataatt gcaaatattc acattaacag tacaagggc cttagtgggt
4861 cagtaccccc gatgtaagca acgaggaagc aggagtctta tctaatgatc agtgcccttg
4921 ataattgtta ttaatgctat taattgtcca agagctgaga ttatgagtag ttaacacttc
4981 tcagcagcaa tccaaagggt aatgggagga acataggggtc tttttctcct acacaggtcc
5041 acaaatacaa ttatgacatt aatattaaaa gaaaagggtt cattcataat taacatgccc
5101 ctgatgcaag gggaatatgt ggagatcaac tcttagtcta aagaagagg tggacaattg
5161 cattaatgca tattaagtcc aaaagaaggg gcacttagtg aatatcatcc ccctgctcta
5221 aagcaaaggt ggtacaggaa catgcttaga gaattgagtt tgtgcacatg aacattccaa
5281 gtgacagtct tgagtagtgg gcactacctg ctaaaacac taagaaagta ggtaggatcc
5341 ttatctagtg cacagatcag gagcaaatgt aattgcacat attaacagtc caaaacaaca
5401 ggactttggt tgatcaggac ccctgttgt actacaaagg aaggtgatg gggtatgacc
5461 ttaatctact gacaaagaca aagaaaatt tcaattatat gttgatagtc caccagaagg
```

FIG. 10G sequence of construct 7 (continued)

```
5521 ggccttggag ggaaacagta taccccacag taatgcaaaa gaggtataat ggtcctagaa
5581 gtgatagggt tgtggacaac tgcaattatt cacattaact gttcaaatgt aaagatcata
5641 aggagtgggc accactatt gaaagaggt gggcatcct tgtctagggc acaagaacca
5701 acataaatgc aattatgcat gtcaacaagc caagaaaagg ggacttaggg ggtcagcaac
5761 cctggtatac tgcaaatgga gggtgagaag gtagaacttt gtttaattag gatgaaccat
5821 gtggtgatta catacattaa tgtccaaggg acattgttgt ggtcaattaa aaccatgtac
5881 tttggacaaa tataagaatc ttaaaaagta gtgggtactc cttgttgaaa agcaaaggga
5941 gtccatgaga aggtgccctt atctagtaca caagaatata gacaagccaa gcaaagaggc
6001 ctcagtgatc agcacccag ctatactgca aagggggtct gagagtagga ctttattcaa
6061 ataggataag ccatgtgcag ttatgcacat aaatttccaa gatgcatggt tgtggtcact
6121 tacaattgtg caccttgatt gtccaaatgt aagggtctta tggagtgagc actcctgct
6181 gggaggaaaa gaaagattat gcgtagatgg gatggggcag aggaggcttc cttgtctagt
6241 acacagaaac ctggacaaat ataatcacac ataacagg ccaggaaaat gggccttggt
6301 tatcagcacc cctgctgtac tgcaaaaggg gtctgagagt aaggccttat tcagatgaga
6361 taggccgtgt gcagttacac acattattga ccaaggtgca tggctgcggt cacttagaat
6421 tgtgcacctt gactgtccaa atgtaaggtt cttatggagc tggcactccc tgccagaagg
6481 gaaaggaaga ttgagggtgg ggtggggcag gggaggcttc catgtcttat acactggaac
6541 ccagacaaat ataatcacat acgttaacag gccaggaaga ggggccttgg ttatcagcac
6601 acctactgta ctgcaaaagg ggtctgagag taggaccta ttcagatggg atgggccatg
6661 tgcagttaca cacatttatg tccaaggtgc atggttgtgt tcacatacaa ttgtgcacct
6721 tgactgtcca aatgtaaggg tcttatggag cgggtacttc ctgccagaag gaaaggaaga
6781 ttgggggtgg agtgtggcag gggaggcttc catgtctatt acacaggaac tggaacaaat
6841 ataatcacac acataacagg ccaggaaaag gggccttggt gatcagcacc cctgctgtac
6901 tgcaaaaagg gtctgagagt aggaccttat tcagatggga tgggccatgt gcagttatgc
6961 acattcatgt ccaaggtgag tgcctatgct cacttacaat tgtgcacctt gattgtccaa
7021 atgtaagggt atatggagtg gacactccct ggtggaaggg aaaggaagat tggaggtggg
7081 gtgtggcagg ggaggctttc atgtctatta cacagaaact gggataaata taatcacaca
7141 cataacaggc caagaaaag ggccttggt attcagtacc cctgctgtac tgcaaaggca
7201 tctgagagta ggtccttatt cagatgggat gggccatgtg cagttacgca cattaatgtc
7261 caataagtc caaggtgcat ggctgtggtc acttataatt gtgcaccttg attgtccaaa
7321 tgtaatgatc ttatggaggg ggcactccc gctggaaggg aaaggaagac tgggagtggg
7381 ggtggggcg gggggaaggc ttccttgtct aatacacagg aaccagaca aatataatca
7441 cgcacataac aggccaagaa aagggggcctt ggtgatcagc acccctgctg tactgcaaaa
7501 ggggtctgag agtaggacct tattcagatg aatgggcaa agtggttatg cacattaatg
7561 tccaaggtgt atgcctgtgg tcacttacaa ctgtgcacct tgattgtcca aacgtaagcg
7621 tcttatggag agggcactcc tgccggaagg gaaaggaaga ttgggggtgg agtgtggcag
7681 gggaggcttc catgtctaat acacaggaac cgggacaaac ataatcacac gcataccagg
7741 ccaggaaaaa gggccttggt gatcagcacc cctgctgtac tgcaaaaggg gtctgagagt
7801 aggattttat tcagataggt tgagctgtgt gtagttatgc aaatccatgt ctaaggtgca
7861 tggttgtgtt cacttaacaa ttacgcacct tgactgtcca aatgtgagag tcttatggag
7921 tgggcactcc ctgctggaag ggaaaggtga gactgaggta tgtggagagg accctccttt
7981 tctagtgcat aggatcccag acgattataa tcacacacaca catgccaaga aaggggact
8041 gcgttatcag caaccttct gtattgcaaa aggggtcgga gagtaggacc ttattcacat
8101 ggaatgagca gtgtgcgatt acgcacataa atgtccaaga tgcatgcttg tggtcactta
8161 caattgtcca cctagactct ccaaataaa gggtcttatg gggtgggcac ttcctgctgg
8221 aagggaaaag tggggatgag gggagcactt tccttctcta gtgcatagca acctcgacaa
8281 atacaatcac acatattggg aggccaattg ccaacgatc atctgtgatc cattctggtc
8341 cttgccacgg ctcaccacca tgtccacacc aagcaggcct ggagcactgc ccatggcaac
8401 agtgcagtgc agggcagacc agaggggggt aggggggtag ggggtaggg ggtggggag
8461 gtggggggtg gggggtggg gtgggagtt gggggggttg ggggtgggg gggaggtat
8521 acttagcctt agtgaggca ccaatacaga ggaatggagg gaggttcaga ccacacagcc
8581 agatatccag cactgcaaga ggcagcactg gacaggaggg gacaaataag aggggacaga
8641 ggtggaaagg ctaaatgtcc ttgaaaagac cttgaaaaca cctgctgtac cgcccactgg
8701 gagacataca cgtggcccct ccacttcttt ctcctgactg ctaaagaca gctgcgaagt
8761 gccatgctaa ttcacccagg tcttcgctga gtagctggac agtgtgtcat cagtctaatt
8821 ccatcttctg ctctaattgg ctgtgatcaa ttccaccccc atttctaatt ggtgggtta
8881 tgcagcaatc cagcactgtc catccacct tttctcccgc tctgcgtggc actaggcggc
8941 aaaacccgcc atctttaaca atgcggcaag cccgccatga tgtccacgtg acaaaagcca
9001 tgatatacat atgacaacgc ctgccatatt gtcctgcgg caaaacccaa cacgaaaagc
9061 acaacaaa gacaaagagg cccgccatgt tttacactgc ggcaagacct tcagccgcaa
9121 tcttttcctg tgtgaccgca catgtccacc accatgctaa ccacttaaca aagcctcgcc
9181 catcatgatg tggccttccc gccacttgaa cactgcgaca gaactggatc cgccattttg
9241 gacaacctaa caaagcacag ccgccatgc tgagcaatgc cgcaatgtca aaatcgccat
9301 tttaagccct gcaccttagt ctttcctaac cttccatttt taactagtcc cttgtactga
9361 taaaagatga ttcttactgc ctcccgatac aacaatcacg caaagctcct aacaagcccc
```

FIG. 10G sequence of construct 7 (continued)

```
 9421 aaatcaattc attcagatag gtttagctca tgcaatgcac atgacttcct ctgcctgacc
 9481 tgctatcatc catcttgcct ccctagttta acttagcaca aacgactagc cctaagccga
 9541 gttatgcggc aagtctaaaa tggcggccac ttttcctcca caatctgaac acgcccttag
 9601 cttaactgca gagtcattct ctgccaaagc ggtaggtaca ctcacacacc accaaatgat
 9661 cagcagcaaa aaaaagtgta gatattccag agagtgcaac aacccacaaa accaacattt
 9721 tttcatccat aaaaagcacc gatgggcgat gaaaaaaaaa aatcaaagca ggtatccgcg
 9781 gccccgatgg gcagaaaaac aaaaattaaa gcaggtatcc gaggcccga tgggcaagga
 9841 aaataaaaaa aaaaaaagca ggtatccgaa gccccgatgg gccaaaaaaa gaaaattttt
 9901 aaaaagcaga tatccgtcac cccgatgggc cagagtgttg ggggttcaga ggggaaggga
 9961 atcagcaggt atccgatacc ccgatgggct aaggaaaaaa aaataaaaag caggtatccg
10021 cggcccgat gggcgaataa aaaagcaggt atccacgcc ccgttgggca
10081 aagaaaaaat aataaaaacca ggtatccgca gccccgatgg gcaaaatata gaaagagag
10141 tggaagagta aaaaactgat ccacaaaaaa cagagatgtc accaaaaatg attccaaaga
10201 aaaattcctt aaatattaaa aattgcctca aatattcca aatactttct ttaaaaaaat
10261 atggaggacg tgtcaagaag acactaggag aaagtatagc atttaaasaaa atattttatg
10321 gaatttaggt gatttttta aagaaatacg ccataaaggg tgttgggga ctagaaaatg
10381 ttctagaATC TGCAGAATTC CACCACACTG GACTAGTGGA TCCGAGCTCG GTACCAAGCT
10441 TAAGTTTAAA CGCTAGAGTC CGGAGGCTGG ATCGGTCCCG GTGTCTTCTA TGGAGGTCAA
10501 AACAGCGTGG ATGGCGTCTC CAGGCGATCT GACGGTTCAC TAAACGAGCT CGTCGACGAT
10561 CTCTATCACT GATAGGGAGA TCTCTATCAC TGATAGGGAG AGCTCTGCTT ATATAGACCT
10621 CCCACCGTAC ACGCCTACCG CCCATTTGCG TCAATGGGGC GGAGTTGTTA CGACATTTTG
10681 GAAAGTCCCG TTGATTTTGG TGCCAAAACA AACTCCCATT GACGTCAATG GGGTGGAGAC
10741 TTGGAAATCC CCGTGAGTCA AACCGCTATC CACGCCCATT GATGTACTGC CAAAACCGCA
10801 TCACCATGGT AATAGCGATG ACTAATACGT AGATGTACTG CCAAGTAGGA AAGTCCCATA
10861 AGGTCATGTA CTGGGCATAA TGCCAGGCGG GCCATTTACC GTCATTGACG TCAATAGGGG
10921 GCGTACTTGG CATATGATAC ACTTGATGTA CTGCCAAGTG GGCAGTTTAC CGTAAATACT
10981 CCACCCATTG ACGTCAATGG AAAGTCCCTA TTGGCGTTAC TATGGGAACA TACGTCATTA
11041 TTGACGTCAA TGGGCGGGGG TCGTTGGGCG GTCAGCCAGG CGGGCCATTT ACCGTAAGTT
11101 ATGTAACGCG GAACTCCATA TATGGGCTAT GAACTAATGA CCCCGTAATT GATTACTATT
11161 AATAACTAGT CAATAATCAA TGTCACATCG CCGTACATCG AGCTTTACTA
11221 GGGACAGGAT TGGTGACAGA AAAGCCCCAT CCTTAGGCCT CCTCCTTCCT AGTCTCCTGA
11281 TATTGGGTCT AACCCCCACC TCCTGTTAGG CAGATTCCTT ATCTGGTGAC ACACCCCAT
11341 TTCCTGGAGC CATCTCTCTC CTTGCCAGAA CCTCTAAGGT TTGCTTACGA TGGAGCCAGA
11401 GAGGATCCTG GGAGGGAGAG CTTGGCAGGG GGTGGAGGG AAGGGGGGA TGCGTGACCT
11461 GCCCGGTTCT CAGTGGCCAC CCTGCGCTAC CCTCTCCCAG AACCTGAGCT GCTCTGACGC
11521 GGCTGTCTGG TGCGTTTCAC TGATCCTGGT GCTGCAGCTT CCTTACACTT CCCAAGAGGA
11581 GAAGCAGTTT GGAAAAACAA AATCAGAATA AGTTGGTCCT GAGTTCTAAC TTTGGCTCTT
11641 CACCTTTCTA GTCCCCAATT TATATTGTTC CTCCGTGCGT CAGTTTTACC TGTGAGATAA
11701 GGCCAGTAGC CAGCCCCGTC CTGGCAGGGC TGTGGTGAGG AGGGGGGGTGT CCGTGTGGAA
11761 AACTCCCTTT GTGAGAATGG TGCGTCCTAG GTGTTCACCA GGTCGTGGCC GCCTCTACTC
11821 CCTTTCTCTT TCTCCATCCT TCTTTCCTTA AAGAGTCCCC AGTGCTATCT GGGACATATT
11881 CCTCCGCCCA GAGCAGGGTC CCGCTTCCCT AAGGCCCTGC TCTGGGCTTC TGGGTTTGAG
11941 TCCTTGGCAA GCCCAGGAGA GGCGCTCAGG CTTCCCTGTC CCCCTTCCTC GTCCACCATC
12001 TCATGCCCCT GGCTCTCCTG CCCCTTCCCT ACAGGGGTTC CTGGCTCTGC TCTAAGGGCA
12061 AGGGCGAATT CGCGGCCGCT AAATTCAATT CGCCCTATAG TGAGTCGTAT TACAATTCAC
12121 TGGCCGTCGT TTTACAACGT CGTGACTGGG AAAACCCTGG CGTTACCCAA CTTAATCGCC
12181 TTGCAGCACA TCCCCCTTTC GCCAGCTGGC GTAATAGCGA AGAGGCCCGC ACCGATCGCC
12241 CTTCCCAACA GTTGCGCAGC CTATACGTAC GGCAGTTTAA GGTTTACACC TATAAAGAG
12301 AGAGCCGTTA TCGTCTGTTT GTGGATGTAC AGAGTGATAT TATTGACACG CCGGGGCGAC
12361 GGATGGTGAT CCCCCTGGCC AGTGCACGTC TGCTGTCAGA TAAAGTCTCC CGTGAACTTT
12421 ACCCGGTGGT GCATATCGGG GATGAAAGCT GGCGCATGAT GACCACCGAT ATGGCCAGTG
12481 TGCCGGTCTC CGTTATCGGG GAAGAAGTGG CTGATCTCAG CCACCGCGAA AATGACATCA
12541 AAAACGCCAT TAACCTGATG TTCTGGGGAA TATAAATGTC AGGCATGAGA TTATCAAAAA
12601 GGATCTTCAC CTAGATCCTT TTCACGTAGA AAGCCAGTCC GCAGAAACGG TGCTGACCCC
12661 GGATGAATGT CAGCTACTGG GCTATCTGGA CAAGGGAAAA CGCAAGCGCA AAGAGAAAGC
12721 AGGTAGCTTG CAGTGGGCTT ACATGGCGAT AGCTAGACTG GGCGGTTTTA TGGACAGCAA
12781 GCGAACCGGA ATTGCCAGCT GGGGCGCCCT CTGGTAAGGT TGGGAAGCCC TGCAAAGTAA
12841 ACTGGATGGC TTTCTTGCCG CCAAGGATCT GATGGCGCAG GGGATCAAGC TCTGATCAAG
12901 AGACAGGATG AGGATCGTTT CGCATGATTG AACAAGATGG ATTGCACGCA GGTTCTCCGG
12961 CCGCTTGGGT GGAGAGGCTA TTCGGCTATG ACTGGGCACA ACAGACAATC GGCTGCTCTG
13021 ATGCCGCCGT GTTCCGGCTG TCAGCGCAGG GGCGCCCGGT TCTTTTTGTC AAGACCGACC
13081 TGTCCGGTGC CCTGAATGAA CTGCAAGACG AGGCAGCGCG GCTATCGTGG CTGGCCACGA
13141 CGGGCGTTCC TTGCGCAGCT GTGCTCGACG TTGTCACTGA AGCGGGAAGG GACTGGCTGC
13201 TATTGGGCGA AGTGCCGGGG CAGGATCTCC TGTCATCTCA CCTTGCTCCT GCCGAGAAAG
13261 TATCCATCAT GGCTGATGCA ATGCGGCGGC TGCATACGCT TGATCCGGCT ACCTGCCCAT
```

FIG. 10G sequence of construct 7 (continued)

```
13321 TCGACCACCA AGCGAAACAT CGCATCGAGC GAGCACGTAC TCGGATGGAA GCCGGTCTTG
13381 TCGATCAGGA TGATCTGGAC GAAGAGCATC AGGGGCTCGC GCCAGCCGAA CTGTTCGCCA
13441 GGCTCAAGGC GAGCATGCCC GACGGCGAGG ATCTCGTCGT GACCCATGGC GATGCCTGCT
13501 TGCCGAATAT CATGGTGGAA AATGGCCGCT TTTCTGGATT CATCGACTGT GGCCGGCTGG
13561 GTGTGGCGGA CCGCTATCAG GACATAGCGT TGGCTACCCG TGATATTGCT GAAGAGCTTG
13621 GCGGCGAATG GGCTGACCGC TTCCTCGTGC TTTACGGTAT CGCCGCTCCC GATTCGCAGC
13681 GCATCGCCTT CTATCGCCTT CTTGACGAGT TCTTCTGAAT TATTAACGCT TACAATTTCC
13741 TGATGCGGTA TTTTCTCCTT ACGCATCTGT GCGGTATTTC ACACCGCATC AGGTGGCACT
13801 TTTCGGGGAA ATGTGCGCGG AACCCCTATT TGTTTATTTT TCTAAATACA TTCAAATATG
13861 TATCCGCTCA TGAGATTATC AAAAAGGATC TTCACCTAGA TCCTTTTAAA TTAAAAATGA
13921 AGTTTTAAAT CAATCTAAAG TATATATGAG TAAACTTGGT CTGACAGTTA CCAATGCTTA
13981 ATCAGTGAGG CACCTATCTC AGCGATCTGT CTATTTCGTT CATCCATAGT TGCCTGACTC
14041 CCCGTCGTGT AGATAACTAC GATACGGGAG GGCTTACCAT CTGGCCCCAG TGCTGCAATG
14101 ATACCGCGAG ACCCACGCTC ACCGGCTCCA GATTTATCAG CAATAAACCA GCCAGCCGGA
14161 AGGGCCGAGC GCAGAAGTGG TCCTGCAACT TTATCCGCCT CCATCCAGTC TATTAATTGT
14221 TGCCGGGAAG CTAGAGTAAG TAGTTCGCCA GTTAATAGTT TGCGCAACGT TGTTGCCATT
14281 GCTACAGGCA TCGTGGTGTC ACGCTCGTCG TTTGGTATGG CTTCATTCAG CTCCGGTTCC
14341 CAACGATCAA GGCGAGTTAC ATGATCCCCC ATGTTGTGCA AAAAAGCGGT TAGCTCCTTC
14401 GGTCCTCCGA TCGTTGTCAG AAGTAAGTTG GCCGCAGTGT TATCACTCAT GGTTATGGCA
14461 GCACTGCATA ATTCTCTTAC TGTCATGCCA TCCGTAAGAT GCTTTTCTGT GACTGGTGAG
14521 TACTCAACCA AGTCATTCTG AGAATAGTGT ATGCGGCGAC CGAGTTGCTC TTGCCCGGCG
14581 TCAATACGGG ATAATACCGC GCCACATAGC AGAACTTTAA AAGTGCTCAT CATTGGAAAA
14641 CGTTCTTCGG GGCGAAAACT CTCAAGGATC TTACCGCTGT TGAGATCCAG TTCGATGTAA
14701 CCCACTCGTG CACCCAACTG ATCTTCAGCA TCTTTTACTT TCACCAGCGT TTCTGGGTGA
14761 GCAAAAACAG GAAGGCAAAA TGCCGCAAAA AAGGGAATAA GGGCGACACG GAAATGTTGA
14821 ATACTCATAC TCTTCCTTTT TCAATATTAT TGAAGCATTT ATCAGGGTTA TTGTCTCATG
14881 ACCAAAATCC CTTAACGTGA GTTTTCGTTC CACTGAGCGT CAGACCCCGT AGAAAAGATC
14941 AAAGGATCTT CTTGAGATCC TTTTTTTCTG CGCGTAATCT GCTGCTTGCA AACAAAAAAA
15001 CCACCGCTAC CAGCGGTGGT TTGTTTGCCG GATCAAGAGC TACCAACTCT TTTTCCGAAG
15061 GTAACTGGCT TCAGCAGAGC GCAGATACCA AATACTGTTC TTCTAGTGTA GCCGTAGTTA
15121 GGCCACCACT TCAAGAACTC TGTAGCACCG CCTACATACC TCGCTCTGCT AATCCTGTTA
15181 CCAGTGGCTG CTGCCAGTGG CGATAAGTCG TGTCTTACCG GGTTGGACTC AAGACGATAG
15241 TTACCGGATA AGGCGCAGCG GTCGGGCTGA ACGGGGGGTT CGTGCACACA GCCCAGCTTG
15301 GAGCGAACGA CCTACACCGA ACTGAGATAC CTACAGCGTG AGCTATGAGA AAGCGCCACG
15361 CTTCCCGAAG GGAGAAAGGC GGACAGGTAT CCGGTAAGCG GCAGGGTCGG AACAGGAGAG
15421 CGCACGAGGG AGCTTCCAGG GGGAAACGCC TGGTATCTTT ATAGTCCTGT CGGGTTTCGC
15481 CACCTCTGAC TTGAGCGTCG ATTTTTGTGA TGCTCGTCAG GGGGGCGGAG CCTATGGAAA
15541 AACGCCAGCA ACGCGGCCTT TTTACGGTTC CTGGCCTTTT GCTGGCCTTT TGCTCACATG
15601 TTCTTTCCTG CGTTATCCCC TGATTCTGTG GATAACCGTA TTACCGCCTT TGAGTGAGCT
15661 GATACCGCTC GCCGCAGCCG AACGACCGAG CGCAGCGAGT CAGTGAGCGA GGAAGCGGAA
15721 G
//
```

FIG. 10H sequence of construct 8

```
LOCUS       Runx1/pcDNA5/TO/6.3kb mouse Xist-right direction     20607 bp
     DNA   SYN   29-Nov-2012
DEFINITION  Runx1/pcDNA5/TO/6.3kb mouse Xist-right direction
ACCESSION
KEYWORDS
SOURCE
  ORGANISM  other sequences; artificial sequences; vectors.
FEATURES             Location/Qualifiers
     source          1..20607
                     /organism="Runx1/pcDNA5/TO/6.3kb mouse Xist-right
direction"
                     /mol_type="other DNA"
```

FIG. 10H sequence of construct 8 (continued)

```
misc_feature    49..4008
                /label="Left arm"
misc_feature    complement(4037..4056)
                /label="EBV_rev_primer"
terminator      complement(4023..4142)
                /label="SV40_PA_terminator"
gene            complement(4280..5287)
                /label="hygroB"
                /gene="hygroB"
CDS             complement(4277..5302)
                /label="ORF frame 2"
```

/translation="MKKPELTATSVEKFLIEKFDSVSDLMQLSEGEESRAFSFDVGGR

GYVLRVNSCADGFYKDRYVYRHFASAALPIPEVLDIGEFSESLTYCISRRAQGVTLQD

LPETELPAVLQPVAEAMDAIAAADLSQTSGFGPFGPQGIGQYTTWRDFICAIADPHVY

HWQTVMDDTVSASVAQALDELMLWAEDCPEVRHLVHADFGSNNVLTDNGRITAVIDWS

EAMFGDSQYEVANIFFWRPWLACMEQQTRYFERRHPELAGSPRLRAYMLRIGLDQLYQ

SLVDGNFDDAAWAQGRCDAIVRSGAGTVGRTQIARRSAAVWTDGCVEVLADSGNRRPS

```
                TRPRAKE*"
CDS             4544..5365
                /label="ORF frame 2"
```

/translation="MPPLEVARLLLHTSQPRPPEEDVGDLVLGIPEHRLAPVNDRCYA

AIVRQDIVGAEIRVHEVPDFGAVLGPKHQLIESLRDGRTDGVVHHSLPVIHMGISNRA

YEITPCSVLTDSLRSEWAEPARLAKIGRSDRIHGLRDRLQNSGQFGFRQVLQRDTLCT

AGDAIGQALAEFPNVKHFRNRERGRCKVPINITIFVETIGAAIYPQDISTPSYIEAES

TRFFALRELHQVGDAVELFDQKLLDRRRGEFRLFHHVLIRSENGYTSSRELFAKA*"

```
    misc_feature    complement(5419..5438)
                    /label="SV40pro_F_primer"
    rep_origin      complement(5423..5500)
                    /label="SV40_origin"
    promoter        complement(5399..5667)
                    /label="SV40_promoter"
    misc_feature    5470..5685
                    /label="SV40_enhancer"
    misc_feature    5665..5685
                    /label="pBABE_3_primer"
    rep_origin      complement(5799..6105)
                    /label="f1_origin"
    terminator      complement(6168..6395)
                    /label="bGH_PA_terminator"
    misc_feature    6381..6398
                    /label="BGH_rev_primer"
```

FIG. 10H sequence of construct 8 (continued)

```
    misc_feature     complement(6637..12936)
                     /label="6.3kb mouse Xist"
    misc_feature     complement(13105..13129)
                     /label="LNCX_primer"
    promoter         complement(13043..13216)
                     /label="CMV2_promoter"
    misc_feature     complement(13139..13178)
                     /label="tetO"
    promoter         complement(13105..13230)
                     /label="CMV_promoter"
    misc_feature     complement(13209..13229)
                     /label="CMV_fwd_primer"
    promoter         complement(13182..13762)
                     /label="CMV_immearly_promoter"
    misc_feature     complement(13395..13682)
                     /label="CAG_enhancer"
    CDS              13759..14364
                     /label="ORF frame 1"
/translation="MSTRISGPYIGPRGQEHSLCPTHPPTVGRGTLGNPVCPEPQHSG

SLGSLCLPDHTLMPSLPLPAHSGSGPDRLRRPTPVPYSAVHLRPAHALPRRLHLLAAR

HVGHRHRHVSHELGLSLPHRPAAALPRLITGAGRALPDRLALLPSILRRLGRFLPVLH
                     GGRREIAPAHPAALHQRIHRRRAAQPQPPQPERRGGDRGQP*"
    misc_feature     13796..17681
                     /label="Right arm"
    misc_feature     complement(17733..17750)
                     /label="Sp6_primer"
    misc_feature     complement(17764..17782)
                     /label="M13_reverse_primer"
    misc_feature     complement(17781..17803)
                     /label="M13_pUC_rev_primer"
    promoter         complement(17817..17846)
                     /label="lac_promoter"
    rep_origin       complement(18155..18774)
                     /label="pBR322_origin"
    CDS              complement(18929..19789)
                     /label="Ampicillin"
                     /gene="Ampicillin"
                     /note="ORF frame 2"
/translation="MSIQHFRVALIPFFAAFCLPVFAHPETLVKVKDAEDQLGARVGY

IELDLNSGKILESFRPEERFPMMSTFKVLLCGAVLSRIDAGQEQLGRRIHYSQNDLVE

YSPVTEKHLTDGMTVRELCSAAITMSDNTAANLLLTTIGGPKELTAFLHNMGDHVTRL

DRWEPELNEAIPNDERDTTMPVAMATTLRKLLTGELLTLASRQQLIDWMEADKVAGPL

LRSALPAGWFIADKSGAGERGSRGIIAALGPDGKPSRIVVIYTTGSQATMDERNRQIA
                     EIGASLIKHW*"
```

FIG. 10H sequence of construct 8 (continued)

```
       gene            complement(18929..19789)
                       /label="Ampicillin"
                       /gene="Ampicillin"
       promoter        complement(19831..19859)
                       /label="AmpR_promoter"
       rep_origin      complement(20104..20410)
                       /label="f1_origin"
       misc_feature    complement(20439..20587)
                       /label="lacZ_a"
       misc_feature    20553..20575
                       /label="M13_pUC_fwd_primer"
       misc_feature    20568..20584
                       /label="M13_forward20_primer"
       promoter        20591..2
                       /label="T7_promoter"
ORIGIN
    1 GGGCGAATTG GGCCCGACGT CGCATGCTCC CGGCCGCCAT GGCCGCGGGG CATCTCTCTC
   61 CTTCCTCCAG TGTCTGCAAG CACACACACA CACACACACA CACACACACA CACACACACA
  121 CACACACATG CGCGCGAGCA CCTAACTAAA AATAAAATAG CTGTAAATGA GAACACGTAT
  181 TCGAATAGAG CACTTGAATT TGAACATATC TAAAAGGCCC ATGTCTTTTT TATTACAGAG
  241 CGTATACAAA GCGAGACAGG GAGGGATGGA AGGAGAAGGG GAGGAGGGAG AGAGAACCTG
  301 ACCTCTCGTA GAAAGACGCC ACACTATCTC AGATCTTCCA CATACTCTGC CCCCAGCAGC
  361 TGAGACTGTA ACATTACTCC TGCGCTTATG CCCATGACAA ATCACGGACT CACTCGGGAT
  421 TCCGGTAACG TGGTACCATT ACCACATTAC CATGTAAGAA CTGGGACAGA CTGGCAGAGC
  481 ATGTTCAGAC ACGGCTCTGA ACGTGGTGA CCTCTCCTTC ATTTTTTTCC AGTGGATTCA
  541 CCTTTTTTGT CTCAGGACAA ATGAAGCAAG AGGGATAATG GGCAGAGTCA CTTGTTTGTG
  601 TCCAGTGTAT TGCATCAGAT GACAACAGGC CGATTGTGTG TGTGCCTAAT GCTCTCCCTC
  661 CTGCCTCGGC TTCTCCCTAG ACTGTATAAA TCTAACTGGA AAAAAAAAAT GGAGTAGAGC
  721 TTCCTGTTAA CTCTCAAGCA TGTCATGGCT CTCTGTAAGC AAAACAAGTG ACACAGAGTT
  781 TGCTCATAGA GGTCCCCGGT GAGGGCGCAG AGATGAACCC TGAGGAATGA GGTGTGGCCT
  841 GCTGGCTGGA GGAGAGGCTA GAGGGCAGCC TACCAGGGCA GCCTACCAGA GCCACTGTTG
  901 GTTTACAGCC TTTGCCTGCC CACATGTCTG ACTTGCTTTG AAAAGATTAA CAGGAGTGTT
  961 TGTTTGAAAG TCAGACTCCT GGTTTCCTCA TTAGTAAGAG GATTTGCTGC AGACTTGGGC
 1021 TGTGCTTATA AACTCTAATT ACCTCTCTGA TGAGGAGTCT ATTTCTCTCA CATTCAGCCC
 1081 AAATGTACAC AAGAGTTCCT TTTGTAAAAT CGTGTTAGAG CAATAAAAGA TTATTGAGAG
 1141 GGGGTGGAGG GGGAGAGGGA GAAACAAGAA CACAAGCCCG AGCTCTCCGT GCTGAAATAA
 1201 TAGGCTTGGA ACAGAAAGAA GTTGATCACA GCCCATGCCT TCCAAAAAAA AAAAAAGATT
 1261 AATCCACCCG GGTAGCTTTC CTTTCAAAGG AAGCTTTTCG ATCCCCTCAA GTTTCTCTCT
 1321 AGCAGGCTCA ACTCTGTACC TGAATTTGAG AATTTAACAT TTTGAACACT TAGTTCGTGC
 1381 CTCTGCCCTG TGTTGTTGCT GCTGCTGAGC CGTGCTGGTG CGAACAGTAT AGTCGCAGCC
 1441 TGCCCTCCTC TGACTGACAG ACACAAGCTA CCCGAAACAC CGTCCTAACT CACTGTGGCA
 1501 GCTGGTGGGC GGATGTGCAT CCCTTCCTAA CCATTCTCAG TTATTTCGCA ATGTCTGGAG
 1561 ATTCTTTTGG ATGTCAAAGT AGCGGGCAGG GGGTCGGCAG GGAGGCCACT AGAGGCATCT
 1621 TGTGGGTAAA GAAGGAAGAT GCCACCAAAC AGTTATCAGT CTCCAAACAC CCGCTAGACA
 1681 TAATACAGCC CAAAGATGCC AGCAGTGGCA CTTTTGGCAA GGGAACCCTC CTGTCCCTCC
 1741 TGTCCCCTGG TCTGCCTCAA AGGCAGCATG CACACGTGCC AAGTGCAGAG GGAGCCGGTG
 1801 AAGCAAGGGC AGTCTGTAGA ACTGTAAATT CAAAATGAAT CTTGTAAAGA AAGTCTGTCA
 1861 TTTCTGGACA AAACAAGTTT TGCTATCCAT TTGTGTTAGA AGCTAGTGAG TGACACAGCA
 1921 GCTGGAGCCA TGACTCAGTG GTTAGAGCA TGCACTGCTC TGGGGATGT TGGCACCCAC
 1981 TTCTAGCCTC TGGGGGCACT GCACACACAC AGGCTCATAA CCACACAAGC ATAATCACAA
 2041 GTAAAATTAC CTTTAAGAAG AAAACAGTGA CTCAGGTCTT AGATAAAGAC GAGACATGAA
 2101 GTCAAATGTC TAAGGTTACT ATAGATGGGA ACAAGTCAGA AGGCAGAGAC AGAGGCAAGT
```

FIG. 10H  sequence of construct 8 (continued)

```
2161 GATGTGTCAA TCACCGACAT TCACGTCGTC CCTACCACAA CACGCACTGC ACCTAATAAT
2221 AGGAAATTAG CCAACTTTCA AGGGATCAGA GTCTACAAAA ATGACAGTTT TCTATTATCC
2281 AACCTGACTA CTAAGTGCAA TGACATAATA TTGTTATTAT AACATACTTA ACATATAATA
2341 TTCTACTATC AACATATCAG TGGATGCATG ACCTCAGTTA TTTTAATGTT ATGCCATTGT
2401 ATATTGTTAT ATTAATATTG TTATGCCAAT GTACTGATTA TATTAGCAAT ATACCAGTCA
2461 GTATTGATGC TTTCATTAGA GGATAGGCTT TTTTTTCTCC CCCAGTAAAG GACCAAAGAG
2521 AAGTTGTTAA GCTTTGGACA CTCTGTTGTC CTGGTCACTC AACAGCAATA GGAGCTACTT
2581 AGCGCCCATG AAAGTGCACA CAGGTGCCAA CTTGTGCTAT AGGTTGAAGC TATGTCGCAA
2641 CAGAGTAGAA ATACAATTTT TGTGTGTTTT TATTTTTAGT CTTACAACCA TTTGAAAAGG
2701 TAAAATTCAT TCTTAATTCC TAGAACACAT AAAACTTCTC CCCAGCCAGA CTTAGCCAAT
2761 GAGCTACAGT TTGCCAACCT GGGATCTAAC ATTTATGTGT ATTGGAAACT TTACACTACA
2821 GTGTGTGTGA CAGGTACCTA TATGGTACAT ATGCTACGGC GTGTCAGGAT ACATACCATA
2881 TGCCGCCCAC CACTCCCTGC AATGCATCTG CCATTGCTCT GTGTCACACT GTTTGACATC
2941 TGTCATGTCA AACATGCTGG GGGAAGCCCA CTTCTTGCTA GATAGTCCCC GCCACCCACC
3001 ATTCCCTGGC AGCAGCCCTC TGCATAGAAT CTCATCTTCT TAAGTGACAG TATCTTGGGT
3061 AGTTATCTGT CCTGTTGACT TCTAGGTAAG TGTACATCTC AGGCAGGAAT ATTCTCAGTG
3121 GTTCCCTCCT CCCTGGGCAG GGAGCTGTGG GCAGTCCAGT CTGTTGGGTG GGTGCACTCT
3181 CCGTGCTCCC TCCTCCATGG TCAGGGCCAG TCTGGGCACT CTTCTGTGTC CTGAGTAGGA
3241 GCACTCCCTG TGCCACCCCC ATCCCCCACC CATAGTCATT CTGTGCAATC TTGTGTGACC
3301 TGGTTGGAAA CAGTCTTGGT GGTCTGGGAC ACTCTGAGCA GTCCTGTGTC CTGGGTGGGA
3361 GCAATTTTGC GGTCCCCCCT TCCACAGGCA GGGGCAGTGT GTTGTGGGGG GAGCACTCTC
3421 TGTGTAGCCC CCTACATGGG CAGAGGCACT CTCCGTGGTC CCCCCCCCC GGGCAGAAGC
3481 ACTCTGGGTA GTCCTGTGTG TTAGGGCAGG ATCACATGCT GTGCCCCCAC TCCGTGGGCA
3541 GGAGCACTCT GGGTAGTCCT GTGTCTTAGG GCAGGTGCAC TTGCCGTGCT CCCCTCCCCG
3601 TGGGCAGGGT CACTCTCTGT GGCCCCCCCC TCCATGGGCA GGGGTACTCT GGGTAGTCCA
3661 GTATTTGGGG CAGGGGTATT CTCTATGCCC CCCCCCCCA TGAGCAGGGC CAGTCTGGGC
3721 AATCCTGTGT CCTAGGTGGG AGCACTTCCG GTTTCCCCCT CCATGGATGG GGCACTTTTG
3781 GCAGTCAGTG TGTTGGGGTG GGAGCACTCT CTGGGTCGCT CCCTCCATGG GCAGAAGCAC
3841 TCTGATTAGT CCTTTGTCAT AGGGCAGGAG CACTCGCTGT GCCCCCCCCC CCGCCCCCGG
3901 GGCAAGGGCA CTCTCTGTGG TCCCTCTCCA TGGGCAGGGA CACTCTCTGG GCAAGTCCAG
3961 TGTGTTGGAG AGGGAGCACT CTTTGTGTCA GAGGCACTCT CCGTGATCGC GGCCTACAGA
4021 CATGATAAGA TACATTGATG AGTTTGGACA AACCACAACT AGAATGCAGT GAAAAAAATG
4081 CTTTATTTGT GAAATTTGTG ATGCTATTGC TTTATTTGTA ACCATTATAA GCTGCAATAA
4141 ACAAGTTGGG GTGGGCGAAG AACTCCAGCA TGAGATCCCC GCGCTGGAGG ATCATCCAGC
4201 CGGCGTCCCG GAAAACGATT CCGAAGCCCA ACCTTTCATA GAAGGCGGCG GTGGAATCGA
4261 AATCTCGTAG CACGTGCTAT TCCTTTGCCC TCGGACGAGT GCTGGGGCGT CGGTTTCCAC
4321 TATCGGCGAG TACTTCTACA CAGCCATCGG TCCAGACGGC CGCGCTTCTG CGGGCGATTT
4381 GTGTACGCCC GACAGTCCCG GCTCCGGATC GGACGATTGC GTCGCATCGA CCCTGCGCCC
4441 AAGCTGCATC ATCGAAATTG CCGTCAACCA AGCTCTGATA GAGTTGGTCA AGACCAATGC
4501 GGAGCATATA CGCCCGGAGC CGCGGCGATC CTGCAAGCTC CGGATGCCTC CGCTCGAAGT
4561 AGCGCGTCTG CTGCTCCATA CAAGCCAACC ACGGCCTCCA GAAGAAGATG TTGGCGACCT
4621 CGTATTGGGA ATCCCCGAAC ATCGCCTCGC TCCAGTCAAT GACCGCTGTT ATGCGGCCAT
4681 TGTCCGTCAG GACATTGTTG GAGCCGAAAT CCGCGTGCAC GAGGTGCCGG ACTTCGGGGC
4741 AGTCCTCGGC CCAAAGCATC AGCTCATCGA GAGCCTGCGC GACGACGCA CTGACGGTGT
4801 CGTCCATCAC AGTTTGCCAG TGATACACAT GGGGATCAGC AATCGCGCAT ATGAAATCAC
4861 GCCATGTAGT GTATTGACCG ATTCCTTGCG GTCCGAATGG GCCGAACCCG CTCGTCTGGC
4921 TAAGATCGGC CGCAGCGATC GCATCCATGG CCTCCGCGAC CGGCTGCAGA ACAGCGGGCA
4981 GTTCGGTTTC AGGCAGGTCT TGCAACGTGA CACCCTGTGC ACGGCGGGAG ATGCAATAGG
5041 TCAGGCTCTC GCTGAATTCC CCAATGTCAA GCACTTCCGG AATCGGGAGC GCGGCCGATG
5101 CAAAGTGCCG ATAAACATAA CGATCTTTGT AGAAACCATC GGCGCAGCTA TTTACCCGCA
5161 GGACATATCC ACGCCCTCCT ACATCGAAGC TGAAAGCACG AGATTCTTCG CCCTCCGAGA
5221 GCTGCATCAG GTCGGAGACG CTGTCGAACT TTTCGATCAG AAACTTCTCG ACAGACGTCG
```

FIG. 10H  sequence of construct 8 (continued)

```
5281 CGGTGAGTTC AGGCTTTTTC ATCACGTGCT GATCAGATCC GAAAATGGAT ATACAAGCTC
5341 CCGGGAGCTT TTTGCAAAAG CCTAGGCCTC CAAAAAAGCC TCCTCACTAC TTCTGGAATA
5401 GCTCAGAGGC AGAGGCGGCC TCGGCCTCTG CATAAATAAA AAAAATTAGT CAGCCATGGG
5461 GCGGAGAATG GCGGAACTG GCGGAGTTA GGGGCGGGAT GGGCGGAGTT AGGGGCGGGA
5521 CTATGGTTGC TGACTAATTG AGATGCATGC TTTGCATACT TCTGCCTGCT GGGGAGCCTG
5581 GGGACTTTCC ACACCTGGTT GCTGACTAAT TGAGATGCAT GCTTTGCATA CTTCTGCCTG
5641 CTGGGGAGCC TGGGGACTTT CCACACCCTA ACTGACACAC ATTCCACAGA ATTAATTCGC
5701 GTTAAATTTT TGTTAAATCA GCTCATTTTT TAACCAATAG GCCGAAATCG GCAAAATCCC
5761 TTATAAATCA AAAGAATAGA CCGAGATAGG GTTGAGTGTT GTTCCAGTTT GGAACAAGAG
5821 TCCACTATTA AAGAACGTGG ACTCCAACGT CAAAGGGCGA AAAACCGTCT ATCAGGGCGA
5881 TGGCCCACTA CGTGAACCAT CACCCTAATC AAGTTTTTTG GGGTCGAGGT GCCGTAAAGC
5941 ACTAAATCGG AACCCTAAAG GGAGCCCCCG ATTTAGAGCT TGACGGGGAA AGCCGGCGAA
6001 CGTGGCGAGA AAGGAAGGGA AGAAAGCGAA AGGAGCGGGC GCTAGGGCGC TGGCAAGTGT
6061 AGCGGTCACG CTGCGCGTAA CCACCACACC CGCCGCGCTT AATGCGCCGC TACAGGGCGC
6121 GTGGGGATAC CCCCTAGAGC CCCAGCTGGT TCTTTCCGCC TCAGAAGCCA TAGAGCCCAC
6181 CGCATCCCCA GCATGCCTGC TATTGTCTTC CCAATCCTCC CCCTTGCTGT CCTGCCCCAC
6241 CCCACCCCCC AGAATAGAAT GACACCTACT CAGACAATGC GATGCAATTT CCTCATTTTA
6301 TTAGGAAAGG ACAGTGGGAG TGGCACCTTC CAGGGTCAAG GAAGGCACGG GGGAGGGGCA
6361 AACAACAGAT GGCTGGCAAC TAGAAGGCAC AGTCGAGGCT GATCAGCGGG TTTAAACGGG
6421 CCCTCTAGAC TCGAGCGGCC CGAAGTCGGC CATATCCAGA GCGCCGTAGG GGGCGGAGTC
6481 GTGGGGGGTA AATCCCGGAC CCGGGGAATC CCCGTCCCCC AACATGTCCA GATCGAAATC
6541 GTCTAGCGCG TCGGCATGCG CCATCGCCAC GTCCTCGCCG TCTAAGTGGA GCTCGTCCCC
6601 CAGGCTGACA TCGGTCGGGG GGGCCGTCGA CGGTATCGCG CGCAGCAACA TGCATGTACA
6661 CACACACATA CATACACTCA TACACAATAG CTCCCAAAAA AGACCTAAGT ACTCGGCGGC
6721 TACAAAGCAC CCTTCACACT AGAGAAAGCT CTTTTCTTAC TAGGAAAATC TCTCTTTGAA
6781 GTGTACGTTT AAAGGAATGA TTAGATCCTG GCAGACATAT TTTAAAATGT AAAGTGGGGA
6841 AACAGGTTCT ATCATCTCTA AATAAATTC CCACTTTAGG AATTTTCAAG CTACTTCAAA
6901 TTATTGCAGG AGTTTAATGG TGGATAGAAT GAATTAATTA AATGTGATGG CCTATATAAT
6961 TTTCAAAGGC GACTTGACAT GTTCTCAAAT TTAATCCATC CAGTCACCTT TTAAAAATAA
7021 GCAAGGACTG GTGACCAATG TCAGACAAAA TATAATGATT AGAAGGCTTA GGTCATCTTC
7081 CAAAAAGTTA ATCATACTAA AGGCCACACA AAGATTGACT TTTTCGTTTT GTTAAACTTG
7141 TAGTAAAGAC CAAGCAAAGA TACTTGTCTT AAACATTCTG CAATAGTTGC ACTGATCTTT
7201 CCACAGACTC ATCACCCTCA GTACACTGAG ACACTGCTTA GTCTTCAGAA ACATGACACA
7261 AATGGCTATT TTTACTTCAC AAAAGCTAAT GATCTCACAG TCAATCCACC TTGCAATCCA
7321 AATGCCTTTC TTAAGGAATA AAATTATCAA TAACTTTTCT GGCAGTTGGT CCTGTACAGT
7381 AGCAATATAC AAAATCGGGC TTAAAGTTTC TTAAGCAGAC AGTTGGCTCC TTCCTGGAGG
7441 AAGAATGGAA AGAAAGTGC TAAGCTTCCT TCTCAGGAAG ACAATTTTCA GTTCATACTG
7501 TAAAGGAAAG CCCCAAGTAA AAGGTGGCAA TCCAACTCCC TGAGCTACTT GCCTGCAATA
7561 TTTTGCACAA TAAAGCATTA ATAAAGGTAG GCAAGAATGG TTCCTGGCCC TAGAATGTGC
7621 CAGCAGTTGG AATTGGAATA ATTTAGAAGT GCAAGTTAAA GATTGAAGGC TCATCCACCT
7681 AGTTTTGGCC TGCTTTTGCT ATTCAGTGTA TAAATACACC AAAATTTATT AATGACACAT
7741 AGGGTGTTTG GGGTAATTAA CATTACCCAG AATAATGTAA GAATTCGAGG TGTCTCTGTT
7801 CAGTGGGAGC AAGGAGAAGG CAACTGAGAC ACTGTAGCCA TATGAAGTGA GTAAACTGGT
7861 GTTGTTGACT TTAAGTCAAG AGAAGGGCTT TGCCCAGTCA ATACTGTTCA AACAAAGAGG
7921 CAAAAGGGAT GGCATGATGG AATTGAGAAA GGGCACAAAC TCTTCCTTAA TGATGGGTTT
7981 GTGAGAATTA GTGATTCAGA AAAGTGGTCA ATGGACAAAC TAGAGGCCGG GCAAAAGGAA
8041 CACTATAAAG TGTGAGATTG TGACTATTTA GGATTGTATA TATTAAAGCA ATGCAAAAAG
8101 GGTCGAAATC CGGGTCATTG TTGGGTGTAC ATACTGCTGT ACTTTATTAT ATCATTGGGA
8161 AACTAGCAGG GGATTGCTC AAGTTGGAGT AGAAAATAAA CCATCCAGAA CTGCCATTGT
8221 GCCTATTAAG AGTCCCAAAA TCAGTTTAAG GAAGAGAGCA GGTCATTCGT CAGAGCCCCT
8281 GTGCTCATTG ACAGTACCGG GTAGTTTCGG GGGCTCAGCA ACCTCTGCAA TAATGTAAAG
8341 GGGACAAAAT ATTCCAGACA TTCATAGTTA TAAATACGCA TAACTTAGCA ATTAATTCTG
```

FIG. 10H sequence of construct 8 (continued)

```
8401 GGACTCAGTA GCCTTGATGG TATGCAAAGA GAGCACACAG GTCCTTGACA TTTTTGCATA
8461 GTAATCATCC AAATGCTGAG GTTACTAATA GTTACTACCA CTCAGCAGCC CCAGTCAAAA
8521 GGTAGGCATT TCAGAACCTT TGCTGCCGCA CAGGTCATAT GTGTAAGGGT ACAGATTAAT
8581 ATTGACAAGA GAAGTGCTCA GAAATAATTA ATATGCCTCT GGTGTCAAAA GAGTACAAGG
8641 ATGTAAAATC CAACTCCAAA GGTAATGATG GACAACTAAC TGCATTAATG CACTTAAGTC
8701 CAAATGAAGA GCACTTCGTA CAACCCTCTT TCTGCTTTAA AGCGGAGAAG AGGGTACAGT
8761 AGTTCTTAGA GAAGTGCTTA GACATGTGAA CTTTCCAAAT GAAAGTCTTG AGCTTATTAT
8821 CACTTCCTGC TGAAGGTGCT AAGGAAGTGA GTGGGATCCT TTCAAGTGCA CAGAGCAGGT
8881 GGCAGTGCAT ACGCATACAT TTAATATATG ATAACAGTCC AAAAGAATGC GGCCTTGTTG
8941 ATCAGCATAT CCTGATATAG TGCAAATGAA AGGCGAAGGA GTATGGCCTT TGTTTACTGG
9001 CAAAGACAAA GGAAGATTCA CTGTATATTA ATGGTCCACT AGCAGGGACC TTGGGAGATA
9061 AACGGTATCC CTTGCAGGAG TGCAAGAGAT ACAATGGTCC GAAAAGTAAT AAGGTTGTGG
9121 ATAAGTGTAA TTTTACACAT TAACTGGCCA AGTATTTTTA TTAAAATGAA TGGATCATGT
9181 CCCTGTTATA TACATTAATG TTCAAGGGAC ATGTTATCAA TTAAAACCCC CATCCTTTAT
9241 GCAAATATTA AGTCTTTAAA GTAATAGTCC TGGAAATTAA AGAGTGGAAA GGAGGGGACA
9301 GCCTTATCCA GTGTCCAGGA AGATGAAGAA GCCAAAAGAT TAGTGACCCT TGCTGTACTG
9361 CAAAAGGGTT TGAGAGTAGG ATCGTATCCA AATGGAATGA GATGTGTGCA GTAAATGCAT
9421 ACTAATATGC AAGGTACATG TTTATGGCCA TTACAGTTTT ACGCTGTTCA GGTTCCTTC
9481 TGTAGTGAAC AGAAAAGGCC TACTACAATC AGTCATTATT ATTAGCAAGC CACAAAATGG
9541 GACCTTATAG GTCAACACCA CTTCTGTACT TCAAAGTTAA GAGTAAAATT GATCCTACTA
9601 AAATTGCCAG TATGTACATA AATAGTTTGA GGAAGGGGTT TCAAGTGCAC AGCACATACA
9661 TAATTCCATA AAGCAAAGAG GATATGAATG ATCAGAGACA GAAGTCTTAC CTTGAAGGAC
9721 CATTGACCGT ATTGGAATCG TTTCAATCTA TAGTCTCATG AAAGAAGCTT TATATTAGTG
9781 AGCCTCTTTG CTTTGCTAAG TACAGGAGTC CTGATCTAAA AGGCACAACT GTGGACATGA
9841 GAATATGTAC AATAGAGTTA ACACTGTGCA CATTTACTAT GTTAAGGATC TTAAATACTG
9901 CTGCAATACA AATAAGTCTT CACCAGATGC AGATTACTAC AGTGAAATGA CATATGCACA
9961 TTCACAATAT GAAAGACTGC ATGCAGGGCA TAGTGGTAGG AACCAGATAT GCCAACACTT
10021 GTTAAACGCA GGCTAGATCC TGAGCTCAAG GCTAGCCTGG GTTATATGCT AAGTTCCAGG
10081 CCAGCCTGGA AGTTAAAAAC AGGACAGATC AAAGGTCTTC TTGATTACCA ACAAAATGAC
10141 TTGACTTAGT TTGGTTTCTT TATCCAATGC TTAGGAAGAG GGACAAATGC AGCTGTGCAC
10201 ACAACAGGCA CAAATATGTT TACATTACAG GTGGCAATGC CTGTAAGTCC CGCCCAGCCC
10261 AGGCTACATA AGAGGCTGTT CTCTCAAACC ACCACACGGT GGGGCTGTAG CTCTATGACA
10321 GTGCTTTACT AGCGTACACA AGACTCAAGG TTTGATTCCC CAGCACAGCA GAAAGACCAG
10381 AACAGAGAAG TGGTCTCATT GGTTGGCACC CTTGATTGTC ACCCATTAGG GTATGAGGGT
10441 ATGGGATCTT GGTTACTAAC AGAAGGGGAC TTGAACAACT GCAATTTGC ACAATTGTGT
10501 AAGAGGCATT AAGTAATCAG CACCCTCTTT ACATAAAGCA AGGGTAGTAT TAGGACCTTG
10561 AGAAAAGACT CAATTCCTAG TCAGGATTAT CCACATAAAA TGTTCCAGTG CAGAGGTTTT
10621 TGGCTGAAAT AAGAAAGCAT GTGAGACTAG TATACAATAT CATGAGCAAA TAAATGTATC
10681 TCCATCAGTT AGAAAGATGT GACCTGGGGC GATAGCACCC ATGACAGCAT GCCAACAGTA
10741 TATAGTATTC TACCCCCTTT AATGGCCAAT GCCTTGAAAA TTGGGACTGA GCACTTTAAC
10801 TGTCTGATAA CAGACCTGTG TTTGCCCCTT TGCTAAATGC ACACAGGGCT GGACTAGCTA
10861 AAGTCTAATC CAATGGACAA AATATTTCTG ACAGAATTAT TCAGTACTCA AGGTAATACA
10921 TGAGAAAAGA CGACTGAACA CTGCTTAGAA ACTTGGGACT GTGACTACTA CAGCAATGAC
10981 AGAATGGTTT TCTTTCCTTA AAGGAAAGGA GACTTGAGAG ATGATACCTC CATGGATCCG
11041 ACATCATCCA ACACTTCAGT GTTAGAATTG CAAGCATGCG CTCTCCCGAC CTGGGCAGGC
11101 ACTTCGAAAA AATGATGACT AAAGACACAC GTGAAGTACC AAGCGAAACT CACGTCCTTA
11161 TGGGACAGTG ACTCATCACA GTCTAATTCC ATCCTGGCCA CCAAGCAATA ATGCACATTT
11221 CTAACTGGAA GTCAAGCAAA CACCAACACT TTCACACTTG TGCCCATTTC TGACGAGTTA
11281 CGTCAAGTGG CAACCAACAC TTCCACTTAG CCTTGCCTCA GCTTCGAGTG GCACAAGGTA
11341 GGACCAACCA CACCCTACCA TAATGCACCA AGTGTACCCT CGGGCAAAGC CCGCCAAGTA
11401 GCTAAAGCCC GCCAAAAAAA AAATCACTGA AGAAACCAC TAGAGGGCAG GTCACATGAC
11461 TTCCGCCATC TTAGACACAT TCAAGAGCAT GTGCCACCTC TCCAGGCTAA CTCAGACATG
```

FIG. 10H sequence of construct 8 (continued)

```
11521 AAGCTGACAT GTGACACACA AAGCCCTTTG CGTTATACCG CACCAAGAAC TTGAGCCGCC
11581 ATCTTTTCCT GTACGACCTA AATGTCCTAT AATCCATTGC TACACACCAG AACAAAGATT
11641 GGGCTGTCGA GCCTCGGGTG GAGCCCCCGA GCCGCCATTT TATAGACTTC TGAGCAGCCC
11701 TTAAAGCCAC GGGGGACCGC GCCAGGGGTC CATATGCACA CACACCCTGC CCAATCCCCA
11761 CACCCACGCT GAGCCCTATC CCCTAGTCCT CTGCGGCTTC CGCGCAACAC CGCACACTAA
11821 TACGAGCACT CCTTGGCTTT CTACTTCCGG CTAGCACAAC CCCGCAAATG CTACCACAAA
11881 TCAAGGCGAA TCCCGCAACC CCGCACATAT AAAGAAAGCC TTTAGCTAGC GCAGCGCAAT
11941 TGGTTGCTTT TATCCAGTCC GCTGTGCTCC TCGGTGTCCT AATTCTTGGC GTAACTGGCT
12001 CGAGAATAGC CGTATCACGC AGAAGCCATA ATGGCGGACG CGGGCTCTCC ACGCCCTGAA
12061 CACCCACTCA GTTTAAGAGC AAAGTCGTTT TTCTAAGCCA TAGGTTCACT CACACAGCAC
12121 CAAACGATCA GCAGCAACAG TACACGCAAA TAAGAGGCAT AGATATTCCA GGTAGTGCAA
12181 TAACTCACAA AACCATATTT CCATCCACCA AGCGCCCCGT TGGGCCGTGA AAAAAAAAAT
12241 TTAAAGCAGG TATCCACAGC CCCGATGGGC AAAAGAAAAA GAAAAAAAAA TAATAACAGC
12301 AGGTATCCGA GGCCCCGTTG GGCATGGGAA AAAAGACTA AACGCAGGTA TCCGAGGTCC
12361 CGATGGACCG AGAAGGTTT TTTTTTTTT TTTTTTTTT TTACAAAAAG CAGGTATCCA
12421 TGGCCCCGAT GGGCTAAGGA GAAGAAAAAA AGAATAAAAG CAGGTATCCA CAGCCCAGAT
12481 GGGCAAGTTT AGAAAAAAAA ATAATAAGAA AAAAAAAGAA TGAAAAGGCA GGTAAGTATC
12541 CAAAACCCCG TTGGGCATGG AATGGCGGGG AGGACACACA GGTATCCGTG GCCCCGATGG
12601 GCAAGAATAT ATAAACAATG AAAGAAAGGT AAGTCCACCA TACACACACA AGTATCAACC
12661 AAAAGGCACA ACAAAGAAAT ATTCCTTAAA AATGAAAAAT TGACTGAAAA TATTACAAAT
12721 ATCAAAAAGT ATGGAGGACA TGTCAAAAAA AAAATCTTAC CAGAACATAT CAAAACGTCA
12781 AAAATCTCGT GGAATTTTGA TATGTTTTCT TAAATAAGCC ATAAGGCTTG GTGGTAGGGG
12841 AACTAAAAAT GTTCCCCCAA AGCTCCTTAG ATGGAGAGAA ACCACGGAAG AACCGCACAT
12901 CCACGGGAAA CGAGCAAACA TGGCTGGAGC AAGCCGTTGC ACGCCTTTAA CTGATCCGCG
12961 GAGGCTGGAT CGGTCCCGGT GTCTTCTATG GAGGTCGGAT CCGAGCTCGG TACCAAGCTT
13021 AAGTTTAAAC GCTAGAGTCC GGAGGCTGGA TCGGTCCCGG TGTCTTCTAT GGAGGTCAAA
13081 ACAGCGTGGA TGGCGTCTCC AGGCGATCTG ACGGTTCACT AAACGAGCTC GTCGACGATC
13141 TCTATCACTG ATAGGGAGAT CTCTATCACT GATAGGGAGA GCTCTGCTTA TATAGACCTC
13201 CCACCGTACA CGCCTACCGC CCATTTGCGT CAATGGGGCG GAGTTGTTAC GACATTTTGG
13261 AAAGTCCCGT TGATTTTGGT GCCAAAACAA ACTCCCATTG ACGTCAATGG GGTGGAGACT
13321 TGGAAATCCC CGTGAGTCAA ACCGCTATCC ACGCCCATTG ATGTACTGCC AAAACCGCAT
13381 CACCATGGTA ATAGCGATGA CTAATACGTA GATGTACTGC CAAGTAGGAA AGTCCCATAA
13441 GGTCATGTAC TGGGCATAAT GCCAGGCGGG CCATTTACCG TCATTGACGT CAATAGGGGG
13501 CGTACTTGGC ATATGATACA CTTGATGTAC TGCCAAGTGG GCAGTTTACC GTAAATACTC
13561 CACCCATTGA CGTCAATGGA AAGTCCCTAT TGGCGTTACT ATGGGAACAT ACGTCATTAT
13621 TGACGTCAAT GGGCGGGGGT CGTTGGGCGG TCAGCCAGGC GGGCCATTTA CCGTAAGTTA
13681 TGTAACGCGG AACTCCATAT ATGGGCTATG AACTAATGAC CCCGTAATTG ATTACTATTA
13741 ATAACTAGTC AATAATCAAT GTCAACGCGT ATATCTGGCC CGTACATCGG GCCGCGTGGG
13801 CAGGAGCACT CGCTGTGCCC CACCCACCCA CCCACCGTGG GCAGGGGCAC CCTGGGCAAT
13861 CCTGTGTGTC CTGAGCCGCA GCACTCTGGC AGTCTAGGAA GCCTGTGCCT CCCTGACCAC
13921 ACACTCATGC CTTCTCTTCC TCTGCCCGCC CACAGCGGCT CCGGACCTGA CCGCCTTCGG
13981 CGACCCACGC CAGTTCCCTA CTCTGCCGTC CATCTCCGAC CCGCGCATGC ACTACCCAGG
14041 CGCCTTCACC TACTCGCCGC CCGTCACGTC GGGCATCGGC ATCGGCATGT CAGCCATGAG
14101 CTCGGCCTCT CGCTACCACA CCGCCCTGCC GCCGCCCTAC CCCGGCTCAT CACAGGCGCA
14161 GGCCGGGCCC TTCCAGACCG GCTCGCCCTC CTACCATCTA TACTACGGCG CCTCGGCCGG
14221 TTCCTACCAG TTCTCCATGG TGGGCGGAGA GAGATCGCCC CGCGCATCC TGCCGCCCTG
14281 CACCAACGCA TCCACCGGCG CCGCGCTGCT CAACCCCAGC CTCCCCAGCC AGAGCGACGT
14341 GGTGGAGACC GAGGGCAGCC ATAGCAACTC GCCCACCAAC ATGCCCCCG CGCGCCTGGA
14401 GGAGGCCGTG TGGCGGCCCT ACTGAGCTGA GCGCCATCGC CATCGAGGGA CTGGGCCTGC
14461 CGTCCATGCA CAGACCCCGC CAGGAGGGCC TTGGAGGCC ACCAGGAAGA ATCCGGAGG
14521 GAAACTGTGA ATGCTTCTGA TTTAGCAATG CTGTGAATAA AAGAAAGATT TTATACCCTT
14581 GACTTCACTT TTTAACCACG TTGTTTATTC CAAAGAGTGT GGAATGTTTT CGGTTCGGGG
```

FIG. 10H sequence of construct 8 (continued)

```
14641 TGGGGAAGAC GCAGCCCATC CTGTTTGGCA TCTATTTCTT ATTTCGGAGT TTTCTTTTCC
14701 GCACCTTATC GATTGCAAAA ATGCCTGTTT GCATCTGGGT GGTCATTTAT TTTTAAGTGT
14761 GTATAGATTT GAGCTTGCTT TTTTTTCTTC CTTTGACCAA CTCAAAGAAA TAAAATTCCC
14821 TTCTCTGTAA GGTTTATTTA ACTTTTAGAC TTTCATGTAG CTGGGGGTTT TATTTGTGTT
14881 TGGTTTTTGT TTTTATTTTT AAAGAGACAG CTACAGCTTT GGGTCATTTT TTAACTACTG
14941 TATTTCCACA AAGAAATCCC TAGATATTTA TGTATCTTGA TGTTTGAACA TTTACATATG
15001 TGTTGATACT TTTTTAATTA TTTAAATGTA CTTATATTAA GAAAGATATC AAGTACTACA
15061 TTTTTCTTTA TAATAGCCAA AGTTAAATAT TATTGCGTTG AAGATGTCTG GAAAAAAAAG
15121 AGATCGCTTG GTTAACTAGA AATATTGTTT ACATTAAACT CCCTTTATGT TATTCAAACA
15181 AGTTGGTAGG TAACGCAGCA ATGTTTTTAA TTGGATTGTA GACACTGAGG GTCACTCCAA
15241 GGTCAGAAGT ACAAAATTTT CTGCTAGGCT CAACAAATAG TCTCATACCT GGCTCCTTCC
15301 CTTCAAAAAG AGAGGCAAAC TCTGTCCTGA AAGGGTTCAG AGAGGTGCCA AGGATTTGCT
15361 CTGAAGAGGA TTTCATTTTG GCCTGGAGAT ATACTTGCCC CAAGGCCTCC TCATTCTGGC
15421 ATGCTTTATC ACAGAGCTCA ACCAAGTAAG CTGTTGGTCA GGGGTTTACT TACATAGTAT
15481 TTACATAGAC CCAAACCACT GAATGTGATT TTTAAATTGC CTTCCATTAA TAGTACCCGT
15541 TCATTGATGA AAACCAAAAC TTGAGGCTGT ACCCCAAAGA TCCAAATAGA AGAGTTAAGA
15601 CCAGGTGTCT TTGAGGCCTA AAGGCTGAGT TTTAAGAGAG TGTACCCCAA AAGTCTGAAG
15661 GAGCCGGTTT CCTTCTCCCA GTCTTAGTGG AATCAGTCAT GGGAGGCAGA TGCCACGCCC
15721 ACCTGTGCAG GATGCTCCTC AGAAGCTGCC CCTTCACCAG CATCTTCTCC CACCAGGCCG
15781 AGCCCCTGAC CTTTGGGGTG CATCAGTGTG ATAGATCCTG GTCTCTGCAG TCCGCCATGG
15841 CTACGGTTCA GATGTGCATC GTGTCACTGT AAATGTAATG GTACTGTTGT TACAGTGGAG
15901 GACTTGGTCA AAATCCAGTT GTTCTACAAC GTATGAAGCC TAACCGCTGG TTCTGACATA
15961 CATGTGCTCA AAATGATCTG GTTGTTTGGA TTTTTCTTTT GTTGTTTTGT TTTTAATGT
16021 ACCTCTTAAA TTAGTTGAAG TGATGTCAGG TCAACTCCGA AGAGCGTTTG AAAGCAGGAC
16081 TTCAGCACAG TGTTTGATTT TTTTATTATT ATTAATATTA TTTTATAAAT TTAAGCATTC
16141 AGATTAGATC TTTGGCTGCA GGCAGCAAAA ACGGCTGGAC TTATTTAAAA AAAATACAGC
16201 TTGTTTTTTG AGTTATCTAT ATCTATATCT ATATGTTGAT TCTTTGTCTT ACATAGAGCA
16261 GCAGCACTTT GGTAACCTGT GATACCAGGT TGCTCTTGTC TGGAGAAGAG CGCTAGCAGG
16321 ATTCAGAGAA ACTCAGAATA GATCTTCATA TCAGCCATAC CTTCCTCCTC CATCCGGTCT
16381 CCACTCAGTT ATTCCACAGA ACACTTTGAC AGCTGTGTTG TCAGAAAAAT AAAAAAAAAT
16441 TTAATTTCTC AAAAGGAGTT TGTTTCTCCA ACATTAAATG TTCCTCTTAC CATAGGCTGC
16501 CGTATCTGGC CTGAGAAAAC GGTAGGGAAG GACGAAGGAA AGAGATTTCT ATTTTTTCAT
16561 ATTAATTTTG ATATCTAAAG ATACGCTAGC CCTCAGAGGA GCATATAATC TCACACATTG
16621 AATTTTCGCC CTGGGCACCA TGCATCAAGA AGGCTTGTCA CTGTGTTAGA GCCATTTAGT
16681 GCTTCCTAAA CTTTTATCAA CATAGGCAGT ATTTAGTCTC AGAGAAAAAA AAATCCATCA
16741 GGCACATGTA GTCTTGGAGA TAGATTCCAC GGGGCAGGTA TTTCTCTACC TGAGAAATTG
16801 TGTTCATTGC CTTCGGGTGC TTCCAGCGGT CTCCTCATTC GCTGTCTTCA AGGAAGACCC
16861 ATAAGCCAAT TCTGAGATAA TGGAGCTGTT GGGAATACTG GTCCAGAGAA AGAAAAATGG
16921 GATAAGCCAT TCTTACTGCT TATTCAAGCC CCTATTTATA ATTTAACAC ACTTTCCATT
16981 CCTTCTGGTT TTCTCGCCGT CTATATCCTC CAATAGCCC TTCTCACTTT TCTTTTCCCT
17041 CCTGCAAACA CACACACACA CACACACACA CACACACATA AGGCACACAC ACACACATCC
17101 TCTCCCCCAT ACCAAGTGTC CAGAACACAG AAAGTCCAGT TCTTCTCCGT TTATTAAAGA
17161 ACAGGGTGAG TCAGCCATTC TCTTGCTCAC GGGTTTTTTT CCCCAACAGA ACAGAGGCGT
17221 TGCCAGCCAT TTTGGGTCTG CTTTCTGTCC AGATACTGCA GCAAAAACTC TTGAGGATCA
17281 CAACCCGTTG GCTGAGCAGC TGTGCTGCTG CCCAAACGTC CTGCGCAGAC AAACGCACGC
17341 TGGGACCGGA AGGGGTGTCT CTCCTTCTGC CTCTTTTCTT TCATACGTTT CTCTCGAAAG
17401 GCCTCAACTG AGGACTGCAA ATTCTTTCT TGAAATAACT TTCCCCCAGG ACATTCGGT
17461 CTTAGGGATT TTTTGGTTTT GATGGGTTTT GTTTTGTTTT GGTTTTTTG GTTCTTCTCA
17521 TTTTCTTTGT AGGAGAAGGC ATGAGATGTT GAGGGTCTTT CATACATGAA AATAAATAGT
17581 TTGACAGCAA TCTCAGAATA TATTTTTTCC TTATTTGAAC AAAGTACTGT TTTGTTTACT
17641 CTACAGTACA CCTTTATTTG GTGGGTTTGG CTGTTGGTCG GGTCGACCAT ATGGGAGAGC
17701 TCCCAACGCG TTGGATGCAT AGCTTGAGTA TTCTATAGTG TCACCTAAAT AGCTTGGCGT
```

FIG. 10H  sequence of construct 8 (continued)

```
17761 AATCATGGTC ATAGCTGTTT CCTGTGTGAA ATTGTTATCC GCTCACAATT CCACACAACA
17821 TACGAGCCGG AAGCATAAAG TGTAAAGCCT GGGGTGCCTA ATGAGTGAGC TAACTCACAT
17881 TAATTGCGTT GCGCTCACTG CCCGCTTTCC AGTCGGGAAA CCTGTCGTGC CAGCTGCATT
17941 AATGAATCGG CCAACGCGCG GGGAGAGGCG GTTTGCGTAT TGGGCGCTCT TCCGCTTCCT
18001 CGCTCACTGA CTCGCTGCGC TCGGTCGTTC GGCTGCGGCG AGCGGTATCA GCTCACTCAA
18061 AGGCGGTAAT ACGGTTATCC ACAGAATCAG GGGATAACGC AGGAAAGAAC ATGTGAGCAA
18121 AAGGCCAGCA AAAGGCCAGG AACCGTAAAA AGGCCGCGTT GCTGGCGTTT TTCCATAGGC
18181 TCCGCCCCCC TGACGAGCAT CACAAAAATC GACGCTCAAG TCAGAGGTGG CGAAACCCGA
18241 CAGGACTATA AAGATACCAG GCGTTTCCCC CTGGAAGCTC CCTCGTGCGC TCTCCTGTTC
18301 CGACCCTGCC GCTTACCGGA TACCTGTCCG CCTTTCTCCC TTCGGGAAGC GTGGCGCTTT
18361 CTCATAGCTC ACGCTGTAGG TATCTCAGTT CGGTGTAGGT CGTTCGCTCC AAGCTGGGCT
18421 GTGTGCACGA ACCCCCCGTT CAGCCCGACC GCTGCGCCTT ATCCGGTAAC TATCGTCTTG
18481 AGTCCAACCC GGTAAGACAC GACTTATCGC CACTGGCAGC AGCCACTGGT AACAGGATTA
18541 GCAGAGCGAG GTATGTAGGC GGTGCTACAG AGTTCTTGAA GTGGTGGCCT AACTACGGCT
18601 ACACTAGAAG AACAGTATTT GGTATCTGCG CTCTGCTGAA GCCAGTTACC TTCGGAAAAA
18661 GAGTTGGTAG CTCTTGATCC GGCAAACAAA CCACCGCTGG TAGCGGTGGT TTTTTTGTTT
18721 GCAAGCAGCA GATTACGCGC AGAAAAAAAG GATCTCAAGA AGATCCTTTG ATCTTTTCTA
18781 CGGGGTCTGA CGCTCAGTGG AACGAAAACT CACGTTAAGG GATTTTGGTC ATGAGATTAT
18841 CAAAAAGGAT CTTCACCTAG ATCCTTTTAA ATTAAAAATG AAGTTTTAAA TCAATCTAAA
18901 GTATATATGA GTAAACTTGG TCTGACAGTT ACCAATGCTT AATCAGTGAG GCACCTATCT
18961 CAGCGATCTG TCTATTTCGT TCATCCATAG TTGCCTGACT CCCCGTCGTG TAGATAACTA
19021 CGATACGGGA GGGCTTACCA TCTGGCCCCA GTGCTGCAAT GATACCGCGA GACCCACGCT
19081 CACCGGCTCC AGATTTATCA GCAATAAACC AGCCAGCCGG AAGGGCCGAG CGCAGAAGTG
19141 GTCCTGCAAC TTTATCCGCC TCCATCCAGT CTATTAATTG TTGCCGGGAA GCTAGAGTAA
19201 GTAGTTCGCC AGTTAATAGT TTGCGCAACG TTGTTGCCAT TGCTACAGGC ATCGTGGTGT
19261 CACGCTCGTC GTTTGGTATG GCTTCATTCA GCTCCGGTTC CCAACGATCA AGGCGAGTTA
19321 CATGATCCCC CATGTTGTGC AAAAAAGCGG TTAGCTCCTT CGGTCCTCCG ATCGTTGTCA
19381 GAAGTAAGTT GGCCGCAGTG TTATCACTCA TGGTTATGGC AGCACTGCAT AATTCTCTTA
19441 CTGTCATGCC ATCCGTAAGA TGCTTTTCTG TGACTGGTGA GTACTCAACC AAGTCATTCT
19501 GAGAATAGTG TATGCGGCGA CCGAGTTGCT CTTGCCCGGC GTCAATACGG GATAATACCG
19561 CGCCACATAG CAGAACTTTA AAAGTGCTCA TCATTGGAAA ACGTTCTTCG GGGCGAAAAC
19621 TCTCAAGGAT CTTACCGCTG TTGAGATCCA GTTCGATGTA ACCCACTCGT GCACCCAACT
19681 GATCTTCAGC ATCTTTTACT TTCACCAGCG TTTCTGGGTG AGCAAAAACA GGAAGGCAAA
19741 ATGCCGCAAA AAAGGGAATA AGGGCGACAC GGAAATGTTG AATACTCATA CTCTTCCTTT
19801 TTCAATATTA TTGAAGCATT TATCAGGGTT ATTGTCTCAT GAGCGGATAC ATATTTGAAT
19861 GTATTTAGAA AAATAAACAA ATAGGGGTTC CGCGCACATT TCCCCGAAAA GTGCCACCTG
19921 ATGCGGTGTG AAATACCGCA CAGATGCGTA AGGAGAAAAT ACCGCATCAG GAAATTGTAA
19981 GCGTTAATAT TTTGTTAAAA TTCGCGTTAA ATTTTGTTA AATCAGCTCA TTTTTTAACC
20041 AATAGGCCGA AATCGGCAAA ATCCCTTATA AATCAAAAGA ATAGACCGAG ATAGGGTTGA
20101 GTGTTGTTCC AGTTTGGAAC AAGAGTCCAC TATTAAAGAA CGTGGACTCC AACGTCAAAG
20161 GGCGAAAAAC CGTCTATCAG GGCGATGGCC CACTACGTGA ACCATCACCC TAATCAAGTT
20221 TTTTGGGGTC GAGGTGCCGT AAAGCACTAA ATCGGAACCC TAAAGGGAGC CCCCGATTTA
20281 GAGCTTGACG GGGAAAGCCG GCGAACGTGG CGAGAAAGGA AGGGAAGAAA GCGAAAGGAG
20341 CGGGCGCTAG GGCGCTGGCA AGTGTAGCGG TCACGCTGCG CGTAACCACC ACACCCGCCG
20401 CGCTTAATGC GCCGCTACAG GGCGCGTCCA TTCGCCATTC AGGCTGCGCA ACTGTTGGGA
20461 AGGGCGATCG GTGCGGGCCT CTTCGCTATT ACGCCAGCTG GCGAAAGGGG GATGTGCTGC
20521 AAGGCGATTA AGTTGGGTAA CGCCAGGGTT TTCCCAGTCA CGACGTTGTA AAACGACGGC
20581 CAGTGAATTG TAATACGACT CACTATA
//
```

DOSAGE COMPENSATING TRANSGENES AND CELLS

CROSS-REFERENCE TO RELATED APPLICATIONS

This application claims the benefit of U.S. Provisional Patent Application Ser. No. 61/790,917, filed on Mar. 15, 2013, the entire contents of which are hereby incorporated by reference.

STATEMENT OF FEDERALLY SPONSORED RESEARCH

This invention was made with government support under Grant No. GM053234, GM085548 and GM096400 awarded by the National Institutes of Health. The Government has certain rights in the invention.

TECHNICAL FIELD

This invention relates to methods of effecting dosage compensation in cells trisomic for chromosome 21, and cells produced by said methods.

BACKGROUND

In the U.S., about 1 in 300 live births carry a trisomy, roughly half of which are trisomy for chromosome 21 (Chr21), which causes Down syndrome (DS). DS is the leading genetic cause of cognitive disability with increasing prevalence, and millions of patients worldwide experience congenital and progressive medical issues that impact multiple organ systems[1,2]. In addition to progressive intellectual impairment and early onset Alzheimer disease, there is greatly increased risk of myeloproliferative disorder, childhood leukemia, heart defects, and both immune and endocrine system dysfunction. DS researchers have sought to define the more "DS critical" genes on Chr21, but this has proven difficult due to high genetic complexity and phenotypic variability of DS, confounded by normal variation between any individuals[1-3]. Much progress has been made in developing DS mouse models[4-6], however there remains a critical need for better ways to understand the underlying cell and developmental pathology of human DS, so key to rationale design of therapeutics of any kind[7].

The last decade has seen great advances in strategies to correct single-gene defects of rare monogenic disorders, beginning with cells in vitro and in several cases advancing to in vivo and clinical trials. In contrast, genetic correction of the over-dose of genes across a whole extra chromosome in trisomic cells has remained outside the realm of possibility.

SUMMARY

At least in part, the present invention is based on the discovery that the imbalanced expression of hundreds of genes across an extra chromosome can be de facto corrected in DS patient stem cells, by the targeted addition of one gene, XIST, into a specified gene, e.g., the Dual specificity tyrosine-phosphorylation-regulated kinase 1A (DYRK1A) locus, or the Regulator of calcineurin 1 (RCAN1) locus, on Chromosome 21 ("Chr 21"). Using genome editing with zinc finger nucleases, addition of a large, inducible XIST transgene to a precise position in the Chr 21 DYRK1A or RCAN1 loci was achieved in DS iPSCs. This resulted in Chr 21 coating by the non-coding XIST RNA, heterochromatin modifications, chromosome-wide transcriptional silencing and DNA methylation to form a "Chr 21 Barr Body". Silencing became irreversible in differentiated cells. By making XIST inducible, a model to study human chromosome silencing that avoids the selection against silencing of a disomic autosome was created. Such inducible correction of the trisomy provides a system to investigate genomic expression changes and the cellular pathology of trisomy 21, free from genetic and epigenetic noise. Remarkably, a proliferative deficit of DS cells in vitro was reversed upon induced silencing of one Chr 21. The present vectors may be useful in "chromosome therapy" for Down syndrome.

Accordingly, the present invention features nucleic acid constructs that include a silencing sequence encoding an XIST RNA or fragment thereof that silences a segment of a chromosome), driven by a regulatory sequence comprising a promoter; first and second sequences that direct insertion of the silencing sequence into or near the DYRK1A or RCAN1 genes on chromosome 21; and, optionally, a selectable marker. The first and second sequences that direct insertion of the silencing sequence into DYRK1A or RCAN1 may also be referred to herein as "first and second targeting elements." These sequences or elements can be readily selected and inserted into the nucleic acid constructs using methods well known in the art.

Thus, in one aspect, the invention provides silencing vectors comprising: a silencing element comprising a silencing sequence flanked by first and second targeting sequences, wherein each of the first and second targeting sequences are homologous to at least 50 bp (e.g., 50, 100, 200, or 500) of sequence in or near (e.g., within 1 MB, 0.5 MB, 0.1 MB, 0.05 MB, 10000 MB, 5000 MB, 1000 KB, 500 KB, 100 KB, 50 KB, 10 KB, 5 KB, or 1 KB) the dual specificity tyrosine-phosphorylation-regulated kinase 1A (DYRK1A) gene, e.g., in the DYRK1A gene, e.g., in intron 1 of DYRK1A, or in or near the Regulator of calcineurin 1 (RCAN1) gene, e.g., in the RCAN1 gene, e.g., in intron 3 of RCAN1; and a promoter operably linked to the silencing element.

In some embodiments, the vector is a plasmid or a viral vector. In some embodiments, the viral vector is vaccinia virus, adeno-associated virus (MV), or herpes virus.

In some embodiments, the silencing vector targets intron 1 of human DYRK1A and the first targeting sequence comprises a sequence obtained by performing PCR with a primer pair of: Human Chr 21 DYRK1A left arm primers: forward 5'-GCCGTATACCATTAACTCTTTACTGTTC-3' (SEQ ID NO: 3), reverse 5'-TCTGTATACGTAAACTG-GCAAAGGGGTGG-3' (SEQ ID NO: 4); and the second targeting sequence comprises a sequence obtained by performing PCR with a primer pair of: Human Chr 21 DYRK1A right arm primers: forward 5'-ATTTCGC-GAACGGGTGATGAGCAGGCTGT-3' (SEQ ID NO: 5), reverse 5'-CCGTCGCGAAAACCAGAAAGTAT-TCTCAG-3' (SEQ ID NO: 6).

In some embodiments, the silencing vector targets intron 3 of human RCAN1 and the first targeting sequence comprises a sequence obtained by performing PCR with a primer pair of: Human Chr 21 RCAN1 left arm primers: forward 5'-ATT GTATAC CCAAGAGCCC TCCTGACCTC-3' (SEQ ID NO: 7), reverse 5'-AATGTATACGGGTG-GAGGGGCGTGATGCA-3' (SEQ ID NO: 8); and the second targeting sequence comprises a sequence obtained by performing PCR with a primer pair of: RCAN1 right arm primers: forward 5'-TAT TCGCGA CC CGCAGTGTCC CAGGAAT-3' (SEQ ID NO: 9), reverse 5'-CGCTCGCGA-CAATGTTTTCAGAAATGTAA-3' (SEQ ID NO: 10).

In some embodiments, the silencing element comprises a human XIST cDNA or functional fragment thereof.

In some embodiments, the silencing vector includes a selectable marker sequence, e.g., a selectable marker sequence is operably linked to a promoter.

In another aspect, provided herein are the silencing vectors comprising the sequences shown in FIG. 10a-10h.

In another aspect, the invention provides methods for reducing levels of expression of genes on Chromosome 21 in a cell, the method comprising contacting the cell with a silencing vector described herein, under conditions sufficient for the silencing vector to undergo homologous recombination with the genomic DNA of the cell, wherein the silencing element is inserted into intron 1 of DYRK1A or intron 3 of RCAN1.

In some embodiments, the cell is trisomic for chromosome 21.

In some embodiments, the cell is a human cell.

In some embodiments, the cell is a stem cell or a fibroblast.

In some embodiments, the stem cell is an induced pluripotent stem cell (iPSC), a hematopoietic stem cell, or a neural stem cell.

In another aspect, the invention provides cells produced by a method described herein.

In another aspect, the invention provides methods for reducing the risk of transient myeloproliferative disorder (TMD) in a subject who has Down Syndrome (Trisomy 21). The methods include obtaining a hematopoietic stem cell from the subject; contacting the cell with a silencing vector described herein, under conditions sufficient for the silencing vector to undergo homologous recombination with the genomic DNA of the cell, wherein the silencing element is inserted into intron 1 of DYRK1A or intron 3 of RCAN1, to produce a modified cell having reduced levels of expression of genes on Chromosome 21; and administering the modified cell to the subject.

In some embodiments, the methods include contacting the cell with a cleavage vector comprising a sequence that enhances or facilitates homologous recombination.

In some embodiments, the cleavage vector comprises a zinc finger nuclease (ZFN) or a transcription activator-like effector nuclease (TALEN).

In some embodiments, the cleavage vector targets a sequence in intron 1 of DYRK1A comprising GCCAC-CCCTTTGCCAGTTTACACGGGTGATGAGCA GGCT-GTT (SEQ ID NO: 11).

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A-F. Genome-editing integrates XIST into Chr 21 in trisomic iPS cells derived from DS patient cells. Both constructs in a and b were introduced simultaneously, to achieve dual-targeted-addition to two loci, in one step. a, XIST transgene construct (19 kb) with two homologous Chr 21 arms and 14 kb XIST cDNA driven by inducible pTRE3G promoter. The ZFNs cleave intron 1 of DYRK1A locus on Chr 21. FIG. 2A discloses SEQ ID NO: 42. b, Construct designed to target a puromycin selection gene and rtTA cassette into the AAVS1 safe harbor locus on Chr 19 by ZFN. c. A high resolution G-band karyotype was performed to further verify genome integrity of these subclones. Only Chr21 trisomy was observed, and karyotype is consistent with a male chromosome complement. d. Genomic Microarray analysis using the UMass Genomic Microarray platform (Human Genome Build hg19) demonstrated a gain of one chromosome 21(red arrow) (and detected addition of the XIST transgene in these male cells). All other peaks are known human polymorphic variants and are not clinically significant. Note: Chr21 is increased 1.5 fold (from 2 to 3 chromosomes) while the XIST gene is increased 2 fold (from 1 to 2 copies). e. Close-up of Chr21 CGH shows full chromosome 21 trisomy with no deletions or duplications. This analysis was done on transgenic clone 3. f. Percent of cells showing an XIST "paint" (a large, well-localized nuclear RNA territory), in six independent clones. Mean±SE from 500 nuclei.

Figure 1:
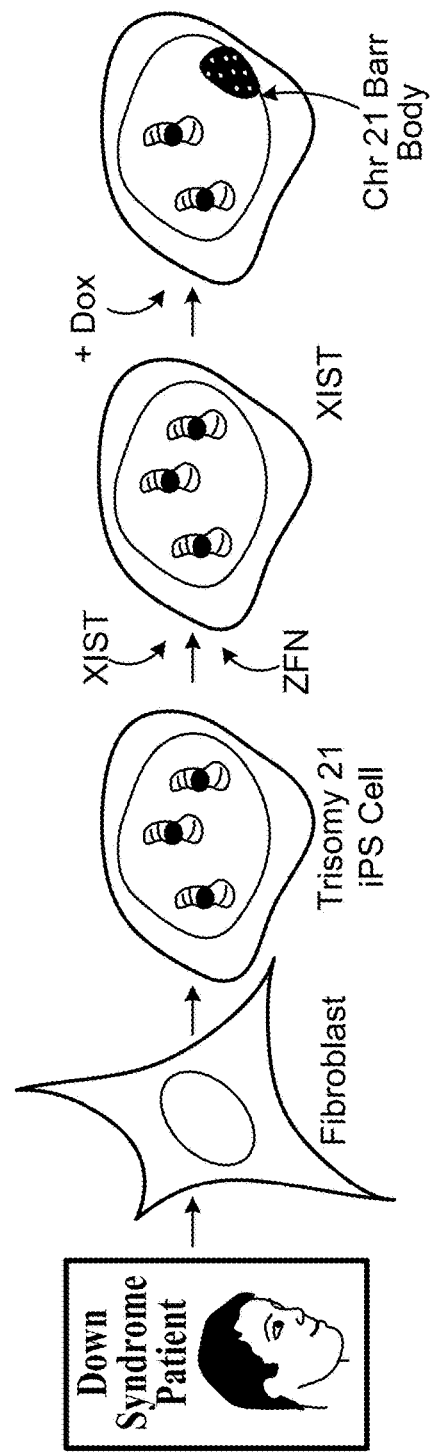
FIG. 1. Schematic outline of the trisomy 21 dosage compensation concept. The natural dosage compensation mechanism (XIST non-coding RNA) is redirected, using ZFN technology, to one trisomic chromosome in iPS cells derived from Down syndrome patient fibroblasts. Subsequent expression of XIST RNA initiates chromosome-wide silencing of the targeted Chr21, producing a stable heterochromatic Chr21-Barr body, and correcting trisomy 21 to functional disomy.

9a: 3G/FL/hXIST/DYRK1A. The plasmid map show the 18.5 kb inducible human XIST construct consists of two homologous arms (left arm, 690 bp; right arm, 508 bp), and a large XIST cDNA driven by an inducible pTRE3G promoter. The 14 kb XIST cDNA contains exons 1-5 and two fragments of exon 6 of XIST gene. The insert is 15.4 kb. The specifically designed ZFN cleaves the intron 1 of DYRK1A locus on Chr 21.

9b: puro/rtTA/AAVS1. The plasmid map shows the puro/rtTA construct contains both puromycin (puro) and tetracycline transactivator (rtTA) cassettes with opposite direction. rtTA is driven by a 3G EF1α promoter that is not inactivated in hESCs and hiPSCs. The puro and rtTA plasmid is targeted the AAVS1 locus on Chr 19 by ZFN.

9c: FL/hXIST/DYRK1A. The plasmid map shows that the 20.7 kb selectable and inducible human XIST construct contains two homologous arms (left arm, 690 bp; right arm, 508 bp), a hygromycin selection gene, and a 14 kb full length XIST cDNA driven by a tetracycline operator inducible promoter. The large XIST transgene is targeted the DYRK1A gene on Chr 21 by ZFNs (as shown in schematic of CONSTRUCT 1).

9d: 6.8 kb/hXIST/DYRK1A. The plasmid map shows that the 13.7 kb selectable and inducible human XIST construct contains two homologous arms (left arm, 690 bp; right arm, 508 bp), a hygromycin selection gene, and a 6.8 kb exon 1 of human XIST cDNA driven by a tetracycline operator inducible promoter. The 6.8 kb XIST transgene is targeted the DYRK1A gene on Chr 21 by ZFNs (as shown in schematic of CONSTRUCT 1).

9e. 6.8 kb/hXIST/AAVS1. The plasmid map shows the 15.7 kb selectable and inducible human XIST construct contains two homologous arms (800 bp each arm), a hygromycin selection gene, and a 6.8 kb exon 1 of human XIST cDNA driven by a tetracycline operator inducible promoter. The 6.8 kb XIST transgene is targeted the AAVS1 locus on Chr 19 by ZFNs.

9f: 6.3 kb/mXist/Runx1. The plasmid map shows that the 20.6 kb selectable and inducible mouse Xist construct contains two homologous arms (4 kb each arm), a hygromycin selection gene, and a 6.3 kb exon 1 of mouse Xist cDNA driven by a tetracycline operator inducible promoter. This 6.3 kb mouse Xist transgene is targeted the Runx1 gene on Chr 16 (synteny to human Chr 21) by conventional homologous recombination.

FIGS. 10a-h are the sequences of constructs 1-8, respectively, which are described more fully below. FIGS. 10a-h disclose SEQ ID NOS 44-49, 44, 50-52, 44, 53, 51-52, 44, 54, 51-52, 44, 55, 51-52, 44, 56, 52, 51, 49, 44, 57, 52, 51, 58, 44 and 59, respectively, in order of appearance.

DETAILED DESCRIPTION

Nature has evolved a mechanism to dosage compensate the difference in X-linked gene copies between mammalian females (XX) and males (XY)[8]. This process is driven by a large (~17 kb in human) non-coding RNA, XIST, which during early development is produced exclusively from the inactive X (Xi)[9], and "paints" (accumulates across) the interphase chromosome structure[10]. The RNA induces a cascade of heterochromatin modifications and architectural changes which transcriptionally silence the Xi and manifest cytologically as a condensed Barr Body (reviewed in[11-14]). There is some DNA sequence specificity to XIST function, since many human genes escape X-inactivation[15-18]; however, autosomal chromatin has substantial capacity to be silenced[19-22]. The full potential of an autosome to be silenced, however, needs to be examined under conditions that avoid creation of a deleterious functional monosomy. The strategy pursued here meets that requirement and creates a tractable model to study the distinct biology of human chromosome inactivation[21].

As demonstrated herein (see FIG. 1), the present constructs and methods can be used to reroute the human X-chromosome inactivation machinery to a supernumerary Chr 21 in DS cells, and thereby enact its epigenetic transformation, in an controlled fashion. The approach directs, e.g., via zinc finger nuclease-driven targeted gene addition[23], a functional, inducible XIST transgene precisely to the gene-rich core of a trisomic chromosome 21 in induced pluripotent stem cells (iPSCs) derived from a subject with DS. The present results demonstrate (i) an unprecedented efficiency and precision of this addition using the largest transgene used for such an effort to date; (ii) the on-demand heterochromatinization of the extra Chr 21 by numerous histone modifications and DNA condensation; (iii) long-range essentially uniform transcriptional repression as gauged by in situ analyses, genome-wide expression profiling, and CpG promoter methylation status; and finally, (iv) inducible trisomy silencing in vitro can also correct a deficit in proliferation of DS stem cells as revealed in this study. Thus, these findings establish a unique system to study DS-related cellular pathologies in a developmental cell context, as well as investigate the initiation of epigenetic chromosome silencing and its relationship to genomic sequence context. In addition, as the present methods result in at least partial correction of the chromosomal imbalance in DS, the methods enable a combined genetic/epigenetic approach to "chromosome therapy" for DS as well as cell therapies using autologous cells.

Unlike random integration into a diploid cell, silencing a trisomic autosome avoids selection against full autosomal silencing and monosomy. Thus, comprehensive analysis demonstrates highly robust competence of Chr21 to be silenced, allowing dosage compensation of trisomy 21 to very near normal disomic levels. This suggests that an RNA evolved for the X-chromosome utilizes epigenome-wide mechanisms. The ability to insert a single XIST transgene in any locus, in multiple isogenic sub-clones, now provides a powerful tool to further study XIST function. The present effort also has almost tripled the size of transgenes compatible with nuclease-driven targeted gene addition, important for a host of other compelling applications that require large sequence insertions.

From a translational perspective, trisomy silencing has immediate impact as a means to define the poorly understood cellular pathways deregulated in DS. Accomplishing this in DS iPSCs provides a means to derive and study various patient-compatible cell-types potentially relevant to DS therapeutics (e.g., hematopoietic, cardiac, neuronal, endocrine, and immune). Inducible "trisomy silencing in a dish" allows discrimination of differences directly due to Chr21 over-expression apart from genetic and epigenetic differences between transgenic sub-clones or rare disomic sub-clones isolated from a trisomic population ([48,49] and this study). Induced XIST expression triggers not only global Chr21 repression, but a defined effect on the genomic expression profile, and, importantly, impacts two major aspects of cell phenotype. This can illuminate the cohort of genes and cognate pathways most consistently impacted in DS, and thus define targets for translational efforts. Our discovery that Chr21 over-expression is linked to a reversible deficit in cell proliferation, and also neural rosette formation, is significant, particularly given that DS individuals show accelerated aging and hypocellularity in certain regions of the brain[42,43]. Understanding the pathways and pathologies of DS will also inform the search for drugs that may rebalance those pathways, and the impact of whole chromosome silencing can be a benchmark to compare the impact of correcting individual genes (e.g. DYRK1A) to disomy. This general strategy can similarly be extended to study other chromosomal disorders, such as trisomy 13 and 18, so often fatal in the first 1-2 years.

Finally, the present methods and compositions can be used for gene therapy to address whole chromosome imbalance.

Nucleic Acid Constructs—Silencing Vectors

Described herein are silencing vectors, nucleic acid constructs that include a silencing sequence driven by a regulatory region comprising a promoter, and one or more targeting sequences (e.g., first and second sequences that flank the silencing sequence and direct insertion of the silencing sequence into a targeted chromosome). The silencing vectors can also include a selectable marker, driven by the same or, more preferably, a different regulatory region.

XIST Silencing Sequences

In the present application, the term "Xist" refers to an Xist gene or the encoded Xist RNA regardless of the origin of the sequence. For example, the present compositions can include, and the present methods can be carried out with, an Xist gene encoding an Xist RNA from humans or another mammal (e.g., a rodent such as a mouse, dog, cat, cow, horse, sheep, goat, or another mammalian or non-mammalian animal). The scientific literature has adopted a loose convention whereby the term is fully capitalized (XIST) when referring to a human sequence but not fully capitalized (Xist) when referring to the murine sequence. That convention is not used here, and either human or non-human sequences may be used as described herein.

The silencing sequence can be a full-length Xist gene sequence, a full-length Xist cDNA, or any biologically active fragment or other biologically active variant thereof. The sequence is "biologically active" where its activity is sufficient to silence the expression of one or more genes in cis when integrated into chromosome 21. The level of activity of a biologically active fragment or other variant may vary so long as a useful chromosomal silencing RNA is produced. Xist RNA is referred to as a chromosomal silencing RNA because it silences by binding across the chromosome or chromosome segment, and therefore silences at the level of transcription, by inducing repressive changes to chromatin. While Xist RNA is a well-studied example of a chromosomal silencing RNA, other non-coding RNAs can silence specific clusters of imprinted genes or segments of a chromosome, and in some embodiments a sequence encoding another full-length silencing RNA (examples of which are provided below) or biologically active fragment can be used in place of XIST. These other chromosomal silencing RNAs include Air RNA, HOTAIR RNA, and Kcnqlotl RNA (see Goodrich and Kugel, Crit. Rev. Biochem. and Mol. Biol. 44:3-15, 2009), any of which can be formulated and used as described herein for Xist. Other intergenic noncoding RNAs, which may be useful in the present nucleic acid constructs and the silencing methods described herein are described by Khalil et al. (Proc. Natl. Acad. Sci. USA 106:11675-11680, 2009).

The silencing vector further includes at least one regulatory sequence (i.e., a regulatory sequence that promotes expression of the Xist RNA, and a regulatory sequence that promotes expression of a selectable marker, if any). More specifically, the regulatory sequence can include a promoter, which may be constitutively active, inducible, tissue-specific, or a developmental stage-specific promoter. Enhancers and polyadenylation sequences can also be included. For example, the Xist transgene may carry one or more regulatory elements found in the Xic region that are not a part of the Xist coding sequence. For example, deletion of the DXPas34 locus found 3' to the Xist coding sequence eliminates Xist expression in mammalian embryonic stem cells as described in Debrand et al. (Mol. Cell. Bio., 19:8513-8525, 1999) herein incorporated by reference. As a further example, silencing by mouse Xist transgenes have been shown to require a conserved repeat sequence located at the 5' end of Xist (Wutz et al., Nat. Genetics, 30:167-174, 2002).

The silencing sequence can exclude one or more introns (wholly or partially) or one or more exons (wholly or partially). However, the silencing sequence cannot exclude all exons. For example, the silencing sequence can be an Xist gene sequence exclusive of one or more introns or one or more exons (but not all exons). For example, the silencing sequence can include about 6 kb to about 10 kb of exon 1 of an Xist gene sequence (e.g., about 6-7 kb, 7-8 kb, 8-9 kb, 6.5-8.5 kb, or about 7.5 kb). More specifically, the silencing sequence can be or can include the full length human Xist cDNA sequence having accession number M97168.1 or a biologically active fragment or other variant thereof, e.g., the full length XIST shown in SEQ ID NO:1, or the variant shown in SEQ ID NO:2.

The Xist transgene need not include the whole of the Xist gene sequence, although it may. For example, the Xist transgene may be derived from an Xist cDNA cloned from one of multiple naturally occurring splice variants. This cDNA may lack sequences corresponding to one or more introns or exons or portions thereof. Additionally, the Xist transgene may include non-naturally occurring Xist coding sequences. For example, the Xist coding sequence may be mutated (e.g., truncated) or otherwise variant with respect to naturally occurring Xist coding sequences so long as it includes sequences that are required for transgene function. For example, deletion analysis demonstrates that the first exon of human Xist is sufficient for both transcript localization and the induction of silencing (Chow et al., Proc. Natl. Acad. Sci. USA 104:10104-10109, 2007). Thus, smaller Xist constructs can be generated that are more easily manipulated but still biologically active.

Non-limiting examples of Xist transgenes (derived from mouse and human sequences) that are useful in this invention are described in the following references which are herein incorporated by reference: Chow et al. (Proc. Natl. Acad. Sci. USA 104:10104-10109, 2007); Hall et al. (Proc. Natl. Acad. Sci. USA 99:8677-8682, 2002); Chow et al. (Genomics, 82:309-322, 2003); and Wutz et al. (Nat. Genet., 2002, 30:167-174, 2002).

Integrated Mouse Xist or human Xist transgenes can silence an autosome, as shown by studies in mouse embryonic stem cells (Wutz and Jaenisch, Mol. Cell, 5:695-705, 2000; Savarese et al., Mol. Cell. Biol. 26:7167-7177, 2006) and in human somatic (fibrosarcoma) cells (FIG. 3; Hall et al., Hum. Mol. Genet. 11:3157-3165, 2002; Chow et al., Proc. Natl. Acad. Sci. USA 104:10104-10109, 2007). Natural autosomal silencing by Xist was also shown in patient cells, with an autosomal trisomy due to X; autosome translocations (Hall et al., Proc. Natl. Acad. Sci. USA 99:8677-8682, 2002; (FIG. 4)). Although the silencing of autosomal material may not be quite as complete or may vary somewhat between autosomal regions, autosomes studied to date are largely if not entirely silenced in response to Xist RNA.

The silencing sequence can be or can include the sequence of an XIC (X inactivation complex) locus or any portion thereof that encodes an RNA capable of silencing the chromosome into which it has been inserted. For example, the constructs can include an XIC locus lacking the sequences 3' to Xist that trigger the "counting" mechanism. Other constructs can include the Xist gene, with or without some or all of the intronic sequences, or a biologically active variant of the Xist gene (e.g., a fragment or other mutant). For information regarding the structure of XIC, one can consult Wutz and Gribnau (Curr. Opin. Genetics Dev. 17:387-393, 2007).

In some embodiments, the silencing sequence comprises one of the following:

```
Full length human XIST sequence-SEQ ID NO: 1
                                                     (SEQ ID NO: 1)
CTAGAACATTTTCTAGTCCCCCAACACCCTTTATGGCGTATTTCTTTAAAAAAATCACCTAAATT

CCATAAAATATTTTTTAAATTCTATACTTTCTCCTAGTGTCTTCTTGACACGTCCTCCATATTT

TTTTAAAGAAAGTATTTGGAATATTTTGAGGCAATTTTTAATATTTAAGGAATTTTTCTTTGGAA

TCATTTTTGGTGACATCTCTGTTTTTTGTGGATCAGTTTTTTACTCTTCCACTCTCTTTTCTATA

TTTTGCCCATCGGGGCTGCGGATACCTGGTTTTATTATTTTTTCTTTGCCCAACGGGGCCGTGGA

TACCTGCCTTTTAATTCTTTTTTATTCGCCCATCGGGGCCGCGGATACCTGCTTTTTATTTTTTT

TTCCTTAGCCCATCGGGGTATCGGATACCTGCTGATTCCCTTCCCCTCTGAACCCCCAACACTCT

GGCCCATCGGGGTGACGGATATCTGCTTTTTAAAAATTTTCTTTTTTTGGCCCATCGGGGCTTCG
```

-continued

```
GATACCTGCTTTTTTTTTTTATTTTCCTTGCCCATCGGGGCCTCGGATACCTGCTTTAATTTT

TGTTTTTCTGCCCATCGGGGCCGCGGATACCTGCTTTGATTTTTTTTTTCATCGCCCATCGGTG

CTTTTTATGGATGAAAAAATGTTGGTTTTGTGGGTTGTTGCACTCTCTGGAATATCTACACTTTT

TTTTGCTGCTGATCATTTGGTGGTGTGTGAGTGTACCTACCGCTTTGGCAGAGAATGACTCTGCA

GTTAAGCTAAGGGCGTGTTCAGATTGTGGAGGAAAAGTGGCCGCCATTTTAGACTTGCCGCATAA

CTCGGCTTAGGGCTAGTCGTTTGTGCTAAGTTAAACTAGGGAGGCAAGATGGATGATAGCAGGTC

AGGCAGAGGAAGTCATGTGCATTGCATGAGCTAAACCTATCTGAATGAATTGATTTGGGGCTTGT

TAGGAGCTTTGCGTGATTGTTGTATCGGGAGGCAGTAAGAATCATCTTTTATCAGTACAAGGGAC

TAGTTAAAAATGGAAGGTTAGGAAAGACTAAGGTGCAGGGCTTAAAATGGCGATTTTGACATTGC

GGCATTGCTCAGCATGGCGGGCTGTGCTTTGTTAGGTTGTCCAAAATGGCGGATCCAGTTCTGTC

GCAGTGTTCAAGTGGCGGGAAGGCCACATCATGATGGGCGAGGCTTTGTTAAGTGGTTAGCATGG

TGGTGGACATGTGCGGTCACACAGGAAAAGATGGCGGCTGAAGGTCTTGCCGCAGTGTAAAACAT

GGCGGGCCTCTTTGTCTTTGCTGTGTGCTTTTCGTGTTGGGTTTTGCCGCAGGGACAATATGGCA

GGCGTTGTCATATGTATATCATGGCTTTTGTCACGTGGACATCATGGCGGGCTTGCCGCATTGTT

AAAGATGGCGGGTTTTGCCGCCTAGTGCCACGCAGAGCGGGAGAAAAGGTGGGATGGACAGTGCT

GGATTGCTGCATAACCCAACCAATTAGAAATGGGGGTGGAATTGATCACAGCCAATTAGAGCAGA

AGATGGAATTAGACTGATGACACACTGTCCAGCTACTCAGCGAAGACCTGGGTGAATTAGCATGG

CACTTCGCAGCTGTCTTTAGCCAGTCAGGAGAAAGAAGTGGAGGGGCCACGTGTATGTCTCCCAG

TGGGCGGTACACCAGGTGTTTTCAAGGTCTTTTCAAGGACATTTAGCCTTTCCACCTCTGTCCCC

TCTTATTTGTCCCCTCCTGTCCAGTGCTGCCTCTTGCAGTGCTGGATATCTGGCTGTGTGGTCTG

AACCTCCCTCCATTCCTCTGTATTGGTGCCTCACCTAAGGCTAAGTATACCTCCCCCCCCACCCC

CCAACCCCCCAACTCCCCACCCCCACCCCCCACCCCCCACCTCCCCACCCCCCTACCCCCCTAC

CCCCCTACCCCCCTCTGGTCTGCCCTGCACTGCACTGTTGCCATGGGCAGTGCTCCAGGCCTGCT

TGGTGTGGACATGGTGGTGAGCCGTGGCAAGGACCAGAATGGATCACAGATGATCGTTGGCCAAC

AGGTGGCAGAAGAGGAATTCCTGCCTTCCTCAAGAGGAACACCTACCCCTTGGCTAATGCTGGGG

TCGGATTTTGATTTATATTTATCTTTTGGATGTCAGTCATACAGTCTGATTTTGTGGTTTGCTAG

TGTTTGAATTTAAGTCTTAAGTGACTATTATAGAAATGTATTAAGAGGCTTTATTTGTAGAATTC

ACTTTAATTACATTTAATGAGTTTTTGTTTGAGTTCCTTAAAATTCCTTAAAGTTTTTAGCTTC

TCATTACAAATTCCTTAACCTTTTTTTGGCAGTAGATAGTCAAAGTCAAATCATTTCTAATGTTT

TAAAAATGTGCTGGTCATTTTCTTTGAAATTGACTTAACTATTTTCCTTTGAAGAGTCTGTAGCA

CAGAAACAGTAAAAAATTTAACTTCATGACCTAATGTAAAAAAGAGTGTTTGAAGGTTTACACAG

GTCCAGGCCTTGCTTTGTTCCCATCCTTGATGCTGCACTAATTGACTAATCACCTACTTATCAGA

CAGGAAACTTGAATTGCTGTGGTCTGGTGTCCTCTATTCAGACTTATTATATTGGAGTATTTCAA

TTTTTCGTTGTATCCTGCCTGCCTAGCATCCAGTTCCTCCCCAGCCCTGCTCCCAGCAAACCCCT

AGTCTAGCCCCAGCCCTACTCCCACCCGGCCCCAGCCCTGCCCCAGGCCCAGTCCCCTAACCCCC

CAGCCCTAGGCCCAGTCCCAGTCCTAGTTCCTCAGTCTGTCCAGCTTCTCTCGAAAGTCACTCTA

ATTTTCATTGATTCAGTGCTCAAAATAAGTTGTCCATTGGTATCCTATTATACTGGGATATTCCG

TTTACCCTTGGCATTGCTGATCTTCAGTACTGACTCCTTGACCATTTTCAGTTAAGCATACAATC

CCATTTGTCTGTGATCTCAGGACAAAGAATTTCCTTACTCGGTACGTTGAAGTTAGGGAATGTCA

ATTGAGAGCTTTCTATCAGAGCATTATTGCCCACAATTTGAGTTACTTATCATTTTCTCGATCCC

CTGCCCTTAAAGGAGAAACCATTTCTCTGTCATTGCTTCTGTAGTCACAGTCCCAATTTTGAGTA
```

-continued

```
GTGATCTTTTCTTGTGTACTGTGTTGGCCACCTAAAACTCTTTGCATTGAGTAAAATTCTAATTG

CCAATAATCCTACCCATTGGATTAGACAGCACTCTGAACCCCATTTGCATTCAGCAGGGGGTCGC

AGACAACCCGTCTTTTGTTGGACAGTTAAAATGCTCAGTCCCAATTGTCATAGCTTTGCCTATTA

AACAAAGGCACCCTACTGCGCTTTTTGCTGTGCTTCTGGAGAATCCTGCTGTTCTTGGACAATTA

AAGAACAAAGTAGTAATTGCTAATTGTCTCACCCATTAATCATGAAGACTACCAGTCGCCCTTGC

ATTTGCCTTGAGGCAGCGCTGACTACCTGAGATTTAAGAGTTTCTTAAATTATTGAGTAAAATCC

CAATTATCCATAGTTCTGTTAGTTACACTATGGCCTTTGCAAACATCTTTGCATAACAGCAGTGG

GACTGACTCATTCTTAGAGCCCCTTCCCTTGGAATATTAATGGATACAATAGTAATTATTCATGG

TTCTGCGTAACAGAGAAGACCCACTTATGTGTATGCCTTTATCATTGCTCCTAGATAGTGTGAAC

TACCTACCACCTTGCATTAATATGTAAAACACTAATTGCCCATAGTCCCACTCATTAGTCTAGGA

TGTCCTCTTTGCCATTGCTGCTGAGTTCTGACTACCCAAGTTTCCTTCTCTTAAACAGTTGATAT

GCATAATTGCATATATTCATGGTTCTGTGCAATAAAAATGGATTCTCACCCCATCCCACCTTCTG

TGGGATGTTGCTAACGAGTGCAGATTATTCAATAACAGCTCTTGAACAGTTAATTTGCACAGTTG

CAATTGTCCAGAGTCCTGTCCATTAGAAAGGGACTCTGTATCCTATTTGCACGCTACAATGTGGG

CTGATCACCCAAGGACTCTTCTTGTGCATTGATGTTCATAATTGTATTTGTCCACGATCTTGTGC

ACTAACCCTTCCACTCCCTTTGTATTCCAGCAGGGGACCCTTACTACTCAAGACCTCTGTACTAG

GACAGTTTATGTGCACAATCCTAATTGATTAGAACTGAGTCTTTTATATCAAGGTCCCTGCATCA

TCTTTGCTTTACATCAAGAGGGTGCTGGTTACCTAATGCCCCTCCTCCAGAAATTATTGATGTGC

AAAATGCAATTTCCCTATCTGCTGTTAGTCTGGGGTCTCATCCCCTCATATTCCTTTTGTCTTAC

AGCAGGGGGTACTTGGGACTGTTAATGCGCATAATTGCAATTATGGTCTTTTCCATTAAATTAAG

ATCCCAACTGCTCACACCCTCTTAGCATTACAGTAGAGGGTGCTAATCACAAGGACATTTCTTTT

GTACTGTTAATGTGCTACTTGCATTTGTCCCTCTTCCTGTGCACTAAAGACCCCACTCACTTCCC

TAGTGTTCAGCAGTGGATGACCTCTAGTCAAGACCTTTGCACTAGGATAGTTAATGTGAACCATG

GCAACTGATCACAACAATGTCTTTCAGATCAGATCCATTTTATCCTCCTTGTTTTACAGCAAGGG

ATATTAATTACCTATGTTACCTTTCCCTGGGACTATGAATGTGCAAAATTCCAATGTTCATGGTC

TCTCCCTTTAAACCTATATTCTACCCCTTTTACATTATAGAAAGGGATGCTGGAAACCCAGAGTC

CTTCTCTTGGGACTCTTAATGTGTATTTCTAATTATCCATGACTCTTAATGTGCATATTTTCAAT

TGCCTAATTGATTTCAATTGTCTAAGACATTTCAAATGTCTAATTGATTAGAACTGAGTCTTTTA

TATCAAGCTAATATCTAGCTTTTATATCAAGCTAATATCTTGACTTCTCAGCATCATAGAAGGGG

GTACTGATTTCCTAAAGTCTTTCTTGAATTTCTATTATGCAAAATTGCCCTGAGGCCGGGTGTGG

TGGCTCACACCTGTAATCCCAGCACTTTGGGAGGCTGAGGTGGGAAGATCCCTTACTGCCAGGAG

TTTGAGACCAGCCTGGCCAACATTAAAAAAAAAAAAAAAAGTAAGACAATTGCCCTGGAATCCCA

TCCCCCTCACACCTCCTTGGCAAAGCAGCAGGAGTGCTAACTAGCTAGTGCTTCTTCTCTTATAC

TGCTTAAATGCGCATAATTAGCAGTAGTTGATGTGCCCCTATGTTAGAGTAGAATCCCGCTTCCT

TGCTCCATTTGCATTACTGCAGGAGCTTCTAACTAGCCTGAATTCACTCTCTTGGACTGTTAATG

TGCATACTTATATTTGCTGCTGTACTTTTTTACCATGTAAGGACCCCACCCACTGTATTTACATC

CCAGCTGGAAGTACCTACTACTTAAGACCCTTAGACTAGTAAAGTTAGCGTGCATAATCTTAGGT

GTTATATACACATTTTCAGTTGCATACAGTTGTGCCTTTTATCAGGACTCCTGTACTTATCAAAG

CAGAGAGTGCTAATCAATATTAAGCCCTTCTCTTCGAACTGTAGATGGCATGTAATTGCAGTTGT

CAATGGTCCTTCAATTAGACTTGGGTTTCTGACCTATCACACCCTCTTTGCTTTATTGCATGGGG
```

-continued

```
TACTATTCACTTAAGGCCCCTTTCTCAAACTGTTAATGTGCCTAATGACAATTACATCAGTATCC

TTCCTTTTGAAGGACAGCATGGTTGGTGACACCTAAGGCCCCATTTCTTGGCCTCCCAATATGTG

TGATTGTATTTGTCGAGGTTGCTATGCACTAGAGAAGGAAAGTGCTCCCCTCATCCCCACTTTTC

CCTTCCAGCAGGAAGTGCCCACCCCATAAGACCCTTTTATTTGGAGAGTCTAGGTGCACAATTGT

AAGTGACCACAAGCATGCATCTTGGACATTTATGTGCGTAATCGCACACTGCTCATTCCATGTGA

ATAAGGTCCTACTCTCCGACCCCTTTTGCAATACAGAAGGGTTGCTGATAACGCAGTCCCCTTTT

CTTGGCATGTTGTGTGTGATTATAATCGTCTGGGATCCTATGCACTAGAAAAGGAGGGTCCTCTC

CACATACCTCAGTCTCACCTTTCCCTTCCAGCAGGGAGTGCCCACTCCATAAGACTCTCACATTT

GGACAGTCAAGGTGCGTAATTGTTAAGTGAACACAACCATGCACCTTAGACATGGATTTGCATAA

CTACACACAGCTCAACCTATCTGAATAAAATCCTACTCTCAGACCCCTTTTGCAGTACAGCAGGG

GTGCTGATCACCAAGGCCCTTTTTCCTGGCCTGGTATGCGTGTGATTATGTTTGTCCCGGTTCCT

GTGTATTAGACATGGAAGCCTCCCCTGCCACACTCCACCCCCAATCTTCCTTTCCCTTCCGGCAG

GAGTGCCCTCTCCATAAGACGCTTACGTTTGGACAATCAAGGTGCACAGTTGTAAGTGACCACAG

GCATACACCTTGGACATTAATGTGCATAACCACTTTGCCCATTCCATCTGAATAAGGTCCTACTC

TCAGACCCCTTTTGCAGTACAGCAGGGGTGCTGATCACCAAGGCCCCTTTTCTTGGCCTGTTATG

TGCGTGATTATATTTGTCTGGGTTCCTGTGTATTAGACAAGGAAGCCTTCCCCCCGCCCCCACCC

CCACTCCCAGTCTTCCTTTCCCTTCCAGCAGGGAGTGCCCCCTCCATAAGATCATTACATTTGGA

CAATCAAGGTGCACAATTATAAGTGACCACAGCCATGCACCTTGGACATTATTGGACATTAATGT

GCGTAACTGCACATGGCCCATCCCATCTGAATAAGGACCTACTCTCAGATGCCTTTGCAGTACAG

CAGGGGTACTGAATCACCAAGGCCCTTTTTCTTGGCCTGTTATGTGTGTGATTATATTTATCCCA

GTTTCTGTGTAATAGACATGAAAGCCTCCCCTGCCACACCCCACCTCCAATCTTCCTTTCCCTTC

CACCAGGGAGTGTCCACTCCATATACCCTTACATTTGGACAATCAAGGTGCACAATTGTAAGTGA

GCATAGGCACTCACCTTGGACATGAATGTGCATAACTGCACATGGCCCATCCCATCTGAATAAGG

TCCTACTCTCAGACCCTTTTTGCAGTACAGCAGGGGTGCTGATCACCAAGGCCCCTTTTCCTGGC

CTGTTATGTGTGTGATTATATTTGTTCCAGTTCCTGTGTAATAGACATGGAAGCCTCCCCTGCCA

CACTCCACCCCCAATCTTCCTTTCCTTCTGGCAGGAAGTACCCGCTCCATAAGACCCTTACATTT

GGACAGTCAAGGTGCACAATTGTATGTGACCACAACCATGCACCTTGGACATAAATGTGTGTAAC

TGCACATGGCCCATCCCATCTGAATAAGGTCCTACTCTCAGACCCCTTTTGCAGTACAGTAGGTG

TGCTGATAACCAAGGCCCCTCTTCCTGGCCTGTTAACGTATGTGATTATATTTGTCTGGGTTCCA

GTGTATAAGACATGGAAGCCTCCCCTGCCCCACCCCACCCTCAATCTTCCTTTCCCTTCTGGCAG

GGAGTGCCAGCTCCATAAGAACCTTACATTTGGACAGTCAAGGTGCACAATTCTAAGTGACCGCA

GCCATGCACCTTGGTCAATAATGTGTGTAACTGCACACGGCCTATCTCATCTGAATAAGGCCTTA

CTCTCAGACCCCTTTTGCAGTACAGCAGGGGTGCTGATAACCAAGGCCCATTTTCCTGGCCTGTT

ATGTGTGTGATTATATTTGTCCAGGTTTCTGTGTACTAGACAAGGAAGCCTCCTCTGCCCCATCC

CATCTACGCATAATCTTTCTTTTCCTCCCAGCAGGGAGTGCTCACTCCATAAGACCCTTACATTT

GGACAATCAAGGTGCACAATTGTAAGTGACCACAACCATGCATCTTGGAAATTTATGTGCATAAC

TGCACATGGCTTATCCTATTTGAATAAAGTCCTACTCTCAGACCCCCTTTGCAGTATAGCTGGGG

TGCTGATCACTGAGGCCTCTTTGCTTGGCTTGTCTATATTCTTGTGTACTAGATAAGGGCACCTT

CTCATGGACTCCCTTTGCTTTTCAACAAGGAGTACCCACTACTTTTTAAGATTCTTATATTTGTC

CAAAGTACATGGTTTTAATTGACCACAACAATGTCCCTTGGACATTAATGTATGTAATCACCACA

TGGTTCATCCTAATTAAACAAAGTTCTACCTTCTCACCCTCCATTTGCAGTATACCAGGGTTGCT
```

-continued

```
GACCCCCTAAGTCCCCTTTTCTTGGCTTGTTGACATGCATAATTGCATTTATGTTGGTTCTTGTG

CCCTAGACAAGGATGCCCCACCTCTTTTCAATAGTGGGTGCCCACTCCTTATGATCTTTACATTT

GAACAGTTAATGTGAATAATTGCAGTTGTCCACAACCCTATCACTTCTAGGACCATTATACCTCT

TTTGCATTACTGTGGGGTATACTGTTTCCCTCCAAGGCCCCTTCTGGTGGACTATCAACATATAA

TTGAAATTTTCTTTTGTCTTTGTCAGTAGATTAAGGTCATACCCCATCACCTTTCCTTTGTAGTA

CAACAGGGTGTCCTGATCAACCAAAGTCCTGTTGTTTTGGACTGTTAATATGTGCAATTACATTT

GCTCCTGATCTGTGCACTAGATAAGGATCCTACCTACTTTCTTAGTGTTTTTAGCAGGTAGTGCC

CACTACTCAAGACTGTCACTTGGAATGTTCATGTGCACAAACTCAATTCTCTAAGCATGTTCCTG

TACCACCTTTGCTTTAGAGCAGGGGGATGATATTCACTAAGTGCCCCTTCTTTTGGACTTAATAT

GCATTAATGCAATTGTCCACCTCTTCTTTTAGACTAAGAGTTGATCTCCACATATTCCCCTTGCA

TCAGGGGCATGTTAATTATGAATGAACCCTTTTCTTTTAATATTAATGTCATAATTGTATTTGTG

GACCTGTGTAGGAGAAAAAGACCCTATGTTCCTCCCATTACCCTTTGGATTGCTGCTGAGAAGTG

TTAACTACTCATAATCTCAGCTCTTGGACAATTAATAGCATTAATAACAATTATCAAGGGCACTG

ATCATTAGATAAGACTCCTGCTTCCTCGTTGCTTACATCGGGGGTACTGACCCACTAAGGCCCCT

TGTACTGTTAATGTGAATATTTGCAATTATATATGTCTCCTTCTGGTAGAGTGGGATATTATGCC

CTAGTATCCCCTTTGCATTACTGCAGGGGCTGCTGACTACTCAAAACTTCTCCTGGGACTGTTAA

TAGGCACAATGGCAGTTATCAATGGTTTTCTCCCTCCCTGACCTTGTTAAGCAAGCGCCCCACCC

CACCCTTAGTTTCCCATGGCATAATAAAGTATAAGCATTGGAGTATTCCATGCACTTGTCTATCA

AACAGTGGTCCATACTCCCAACCCTTTTGCATTGCGCCAGTGTGTAAAATCACAGGTAGCCATGG

TGTCATGCTTTATATACGAAGTCTTCCCTCTCTCTGCCCCTTGTGTGCCCTTGGCCCCTTTTTAC

AGACTATTGCTCACAATCTCAGGTGTCCATATTTGCAGCTATTAGGTAAGATTGTGCTGTCTCCC

TCTTCCCTTCCCTCTGCCCTGCCCCTTTTGCCTCTTTGCTGGGTAATGTTGACCAGACAAGGCCC

TTTCTCTTGGACTTAAACAATTCTCAGTTGCACTTTCCTTGGTCCACCCATTATACATGAACCCC

TCTACTTCCTTTCGCATTGCTTCTGAGTATGCTGACTACCCAAAGCCCCTTCTGTGTTATTAATA

AACACAGTACTGATTGTCCCATTTTTCAGCCCATCAGTCCAAGATCTCCCTACCACTTTGGTGTG

TTGGTGCAGTGTTGACTATGAAAAGCAGGCCTGAACTAGGTGGATAAGCCTTCACTCATTTTCTT

TCATTTATTAATGATCCTAGTTTCAATTATTGTCAGATTCTGGGACAAGAACCATTCTTGCCCA

CCTGTGTTACTGCTTTACTGTGCAAAATACTGAAGGCAAGTCAGACCCAGGGAGCTGGATTGCCA

TCCTTTATTTTGTGTTTCCAGTGTACACTATAAAATTGTCTCCCCAGGAAGGAAGGTTGGCACTT

TCTCTGCATTCTTCTTTCCAGAGCAGATTGCCTGGTTAAGAATCTCTTGTTGTCCCTTCTGTATA

TTGTTATTGTAAAGTGCCAAATGCCAGGATACAGCCAGAAAAATTGCTTATTATTATTAAAAAAA

TTTTTTTAAGAAAGACATCTGGATTGTAGGGTGGACTCGATAACCTGGTCATTATTTTTTTGAAG

CCAAAATATCCATTTATACTATGTACCTGGTGACCAGTGTCTCTCATTTTAACTGAGGGTGGTGG

GTCTGTGGATAGAACACTGACTCTTGCTATTTTAATATCAAAGATATTCTAGATCCAGCACAGTG

GCGGCCGCTCTAGAGTGGAACTCTTAAGACCAGTATCTTTGTGTGGGCTTTACCAGCATTCACTT

TTAGAAAAACTACCTAAATTTTATAATCCTTTAATTTCTTCATCTGGAGCACCTGCCCCTACTTA

TTTCAAGAAGATTGCAGTAAAACGATTAAATGAGGGAACATATGCAGAGGTGCTTTTAAAAAGCA

TATGCCACCTTTTTTATTAATTATTATATAAAATGAAGCATTTAATTATAGTAATAATTTGAAGT

AGTTTGAAGTACCACACTGAGGTGAGGACTTAAAAATGATAAGACGAGTTCCCTATTTTATAAGA

AAAATAAGCCAAAATTAAATATTCTTTTGGATATAAATTTCAACAGTGAGATAGCTGCCTAGTGG
```

-continued

```
AAATGAATAATATCCCAGCCACTAGTGTACAGGGTGTTTTGTGGCACAGGATTATGTAATATGGA

ACTGCTCAAGCAAATAACTAGTCATCACAACAGCAGTTCTTTGTAATAACTGAAAAAGAATATTG

TTTCTCGGAGAAGGATGTCAAAAGATCGGCCCAGCTCAGGGAGCAGTTTGCCCTACTAGCTCCTC

GGACAGCTGTAAAGAAGAGTCTCTGGCTCTTTAGAATACTGATCCCATTGAAGATACCACGCTGC

ATGTGTCCTTAGTAGTCATGTCTCCTTAGGCTCCTCTTGGACATTCTGAGCATGTGAGACCTGAG

GACTGCAAACAGCTATAAGAGGCTCCAAATTAATCATATCTTTCCCTTTGAGAATCTGGCCAAGC

TCCAGCTAATCTACTTGGATGGGTTGCCAGCTATCTGGAGAAAAGATCTTCCTCAGAAGAATAG

GCTTGTTGTTTTACAGTGTTAGTGATCCATTCCCTTTGACGATCCCTAGGTGGAGATGGGGCATG

AGGATCCTCCAGGGGAAAAGCTCACTACCACTGGGCAACAACCCTAGGTCAGGAGGTTCTGTCAA

GATACTTTCCTGGTCCCAGATAGGAAGATAAAGTCTCAAAAACAACCACCACACGTCAAGCTCTT

CATTGTTCCTATCTGCCAAATCATTATACTTCCTACAAGCAGTGCAGAGAGCTGAGTCTTCAGCA

GGTCCAAGAAATTTGAACACACTGAAGGAAGTCAGCCTTCCCACCTGAAGATCAACATGCCTGGC

ACTCTAGCACTTGAGGATAGCTGAATGAATGTGTATTTCTTTGTCTCTTTCTTTCTTGTCTTTGC

TCTTTGTTCTCTATCTAAAGTGTGTCTTACCCATTTCCATGTTTCTCTTGCTAATTTCTTTCGTG

TGTGCCTTTGCCTCATTTTCTCTTTTTGTTCACAAGAGTGGTCTGTGTCTTGTCTTAGACATATC

TCTCATTTTTCATTTTGTTGCTATTTCTCTTTGCTCTCCTAGATGTGGCTCTTCTTTCACGCTTT

ATTTCATGTCTCCTTTTTGGGTCACATGCTGTGTGCTTTTTGTCCTTTTCTTGTTCTGTCTACCT

CTCCTTTCTCTGCCTACCTCTCTTTTCTCTTTGTGAACTGTGATTATTTGTTACCCCTTCCCCTT

CTCGTTCGTTTTAAATTTCACCTTTTTTCTGAGTCTGGCCTCCTTTCTGCTGTTTCTACTTTTTA

TCTCACATTTCTCATTTCTGCATTTCCTTTCTGCCTCTCTTGGGCTATTCTCTCTCTCCTCCCCT

GCGTGCCTCAGCATCTCTTGCTGTTTGTGATTTTCTATTTCAGTATTAATCTCTGTTGGCTTGTA

TTTGTTCTCTGCTTCTTCCCTTTCTACTCACCTTTGAGTATTTCAGCCTCTTCATGAATCTATCT

CCCTCTCTTTGATTTCATGTAATCTCTCCTTAAATATTTCTTTGCATATGTGGGCAAGTGTACGT

GTGTGTGTCATGTGTGGCAGAGGGGCTTCCTAACCCCTGCCTGATAGGTGCAGAACGTCGGCT

ATCAGAGCAAGCATTGTGGAGCGGTTCCTTATGCCAGGCTGCCATGTGAGATGATCCAAGACCAA

AACAAGGCCCTAGACTGCAGTAAAACCCAGAACTCAAGTAGGGCAGAAGGTGGAAGGCTCATATG

GATAGAAGGCCCAAAGTATAAGACAGATGGTTTGAGACTTGAGACCCGAGGACTAAGATGGAAAG

CCCATGTTCCAAGATAGATAGAAGCCTCAGGCCTGAAACCAACAAAAGCCTCAAGAGCCAAGAAA

ACAGAGGGTGGCCTGAATTGGACCGAAGGCCTGAGTTGGATGGAAGTCTCAAGGCTTGAGTTAGA

AGTCTTAAGACCTGGGACAGGACACATGGAAGGCCTAAGAACTGAGACTTGTGACACAAGGCCAA

CGACCTAAGATTAGCCCAGGGTTGTAGCTGGAAGACCTACAACCCAAGGATGGAAGGCCCCTGTC

ACAAAGCCTACCTAGATGGATAGAGGACCCAAGCGAAAAGGTATCTCAAGACTAACGGCCGGAA

TCTGGAGGCCCATGACCCAGAACCCAGGAAGGATAGAAGCTTGAAGACCTGGGGAAATCCCAAGA

TGAGAACCCTAAACCCTACCTCTTTTCTATTGTTTACACTTCTTACTCTTAGATATTTCCAGTTC

TCCTGTTTATCTTTAAGCCTGATTCTTTTGAGATGTACTTTTTGATGTTGCCGGTTACCTTTAGA

TTGACAGTATTATGCCTGGGCCAGTCTTGAGCCAGCTTTAAATCACAGCTTTTACCTATTTGTTA

GGCTATAGTGTTTTGTAAACTTCTGTTTCTATTCACATCTTCTCCACTTGAGAGAGACACCAAAA

TCCAGTCAGTATCTAATCTGGCTTTTGTTAACTTCCCTCAGGAGCAGACATTCATATAGGTGATA

CTGTATTTCAGTCCTTTCTTTTGACCCCAGAAGCCCTAGACTGAGAAGATAAAATGGTCAGGTTG

TTGGGGAAAAAAAAGTGCCAGGCTCTCTAGAGAAAAATGTGAAGAGATGCTCCAGGCCAATGAG

AAGAATTAGACAAGAAATACACAGATGTGCCAGACTTCTGAGAAGCACCTGCCAGCAACAGCTTC
```

CTTCTTTGAGCTTAG 6.8 kb human XIST sequence-SEQ ID NO: 2
tctagaacatttttctagtcccccaacacccttttatggcgtatttctttaaaaaaatcacc taaattccataaaatatttttttaaattctatactttctcctagtgtcttcttgacacgt cctccatatttttttaaagaaagtatttggaatattttgaggcaattttttaatatttaag gaattttctttggaatcatttttggtgacatctctgttttttgtggatcagttttttac tcttccactctcttttctatattttgcccatcggggctgcggatacctggttttattatt ttttctttgcccaacggggccgtggatacctgccttttaattctttttttattcgcccatc ggggccgcggatacctgcttttttattttttttttccttagcccatcggggtatcggatacc tgctgattcccttccctctgaaccccaacactctggcccatcggggtgacggatatct gcttttaaaaatttttcttttttggcccatcggggcttcggatacctgcttttttttttt tttattttccttgcccatcggggcctcggatacctgctttaattttttgttttttctgccca tcggggccgcggatacctgctttgattttttttttttcatcgcccatcggtgcttttatg gatgaaaaatgttggttttgtgggttgttgcactctctggaatatctacactttttttt gctgctgatcatttggtggtgtgtgagtgtacctaccgctttggcagagaatgactctgc agttaagctaagggcgtgttcagattgtggaggaaaagtggccgccatttttagacttgcc gcataactcggcttagggctagtcgtttgtgctaagttaaactagggaggcaagatggat gatagcaggtcaggcagaggaagtcatgtgcattgcatgagctaaacctatctgaatgaa ttgatttggggcttgttaggagcttttgcgtgattgttgtatcgggaggcagtaagaatca tcttttatcagtacaagggactagttaaaaatggaaggttaggaaagactaaggtgcagg gcttaaaatggcgattttgacattgcggcattgctcagcatggcgggctgtgctttgtta ggttgtccaaaatggcggatccagttctgtcgcagtgttcaagtggcgggaaggccacat catgatgggcgaggctttgttaagtggttagcatggtggtggacatgtgcggtcacacag gaaaagatggcggctgaaggtcttgccgcagtgtaaaacatggcgggcctctttgtcttt gctgtgtgcttttcgtgtgggttttgccgcagggacaatatggcaggcgttgtcatatg tatatcatggcttttgtcacgtggacatcatggcgggcttgccgcattgttaaagatggc gggttttgccgcctagtgccacgcagagcgggagaaaaggtgggatggacagtgctggat tgctgcataacccaaccaattagaaatgggggtggaattgatcacagccaattagagcag aagatggaattagactgatgacacactgtccagctactcagcgaagacctgggtgaatta gcatggcacttcgcagctgtctttagccagtcaggagaaagaagtggaggggccacgtgt atgtctcccagtgggcggtacaccaggtgttttcaaggtcttttcaaggacatttagcct ttccacctctgtcccctcttatttgtcccctcctgtccagtgctgcctcttgcagtgctg gatatctggctgtgtggtctgaacctccctccattcctctgtattggtgcctcacctaag gctaagtatacctcccccccacccccaaccccccaactcccaccccaccccac ccccacctccccaccccctaccccctaccccctaccccctctggtctgccctgca ctgcactgttgccatgggcagtgctccaggcctgcttggtgtggacatggtggtgagccg tggcaaggaccagaatggatcacagatgatcgttggccaattggcctcccaatatgtgtg attgtatttgtcgaggttgctatgcactagagaaggaaagtgctcccctcatccccactt ttcccttccagcaggaagtgcccaccccataagacccttttatttggagagtctaggtgc acaattgtaagtgaccacaagcatgcatcttggacatttatgtgcgtaatcgcacactgc tcattccatgtgaataaggtcctactctccgaccccttttgcaatacagaagggttgctg -continued ataacgcagtcccctttctcttggcatgttgtgtgtgattataatcgtctgggatcctatg cactagaaaaggagggtcctctccacatacctcagtctcacctttcccttccagcaggga gtgcccactccataagactctcacatttggacagtcaaggtgcgtaattgttaagtgaac acaaccatgcaccttagacatggatttgcataactacacacagctcaacctatctgaata aaatcctactctcagaccccttttgcagtacagcaggggtgctgatcaccaaggccttt ttcctggcctggtatgcgtgtgattatgtttgtcccggttcctgtgtattagacatggaa gcctcccctgccacactccaccccaatcttcctttcccttccggcaggagtgccctctc cataagacgcttacgtttggacaatcaaggtgcacagttgtaagtgaccacaggcataca ccttggacattaatgtgcataaccactttgcccattccatctgaataaggtcctactctc agacccctttgcagtacagcaggggtgctgatcaccaaggccccttttcttggcctgtt atgtgcgtgattatatttgtctgggttcctgtgtattagacaaggaagccttccccccgc ccccaccccactcccagtcttcctttcccttccagcagggagtgcccctccataagat cattacatttggacaatcaaggtgcacaattataagtgaccacagccatgcaccttggac attattggacattaatgtgcgtaactgcacatggcccatcccatctgaataaggacctac tctcagatgcctttgcagtacagcaggggtactgaatcaccaaggccccttttcttggcc tgttatgtgtgtgattatatttatcccagtttctgtgtaatagacatgaaagcctcccct gccacaccccacctccaatcttcctttcccttccaccagggagtgtccactccatatacc cttacatttggacaatcaaggtgcacaattgtaagtgagcataggcactcaccttggaca tgaatgtgcataactgcacatggcccatcccatctgaataaggtcctactctcagaccct ttttgcagtacagcaggggtgctgatcaccaaggccccttttcctggcctgttatgtgtg tgattatatttgttccagttcctgtgtaatagacatggaagcctcccctgccacactcca ccccaatcttcctttccttctggcaggaagtacccgctccataagacccttacatttgg acagtcaaggtgcacaattgtatgtgaccacaaccatgcaccttggacataaatgtgtgt aactgcacatggcccatcccatctgaataaggtcctactctcagaccccttttgcagtac agtaggtgtgctgataaccaaggcccctcttcctggcctgttaacgtatgtgattatatt tgtctgggttccagtgtataagacatggaagcctcccctgccccacccaccctcaatct tcctttcccttctggcagggagtgccagctccataagaaccttacatttggacagtcaag gtgcacaattctaagtgaccgcagccatgcaccttggtcaataatgtgtgtaactgcaca cggcctatctcatctgaataaggccttactctcagaccccttttgcagtacagcaggggt gctgataaccaaggcccattttcctggcctgttatgtgtgtgattatatttgtccaggtt tctgtgtactagacaaggaagcctcctctgccccatcccatctacgcataatctttcttt tcctcccagcagggagtgctcactccataagacccttacatttggacaatcaaggtgcac aattgtaagtgaccacaaccatgcatcttggaaatttatgtgcataactgcacatggctt atcctatttgaataaagtcctactctcagaccccctttgcagtatagctggggtgctgat cactgaggcctctttgcttggcttgtctatattcttgtgtactagataagggcaccttct catggactccctttgcttttcaacaaggagtacccactacttttttaagattcttatattt gtccaaagtacatggttttaattgaccacaacaatgtcccttggacattaatgtatgtaa tcaccacatggttcatcctaattaaacaaagttctaccttctcaccctccatttgcagta taccaggggttgctgaccccctaagtccccttttcttggcttgttgacatgcataattgca tttatgttggttcttgtgccctagacaaggatgccccacctctttttcaatagtgggtgcc -continued

```
cactccttatgatctttacatttgaacagttaatgtgaataattgcagttgtccacaacc ctatcacttctaggaccattatacctcttttgcattactgtggggtatactgtttccctc caaggccccttctggtggactatcaacatataattgaaattttcttttgtctttgtcagt agattaaggtcatacoccatcacctttccttttgtagtacaacagggtgtcctgatcaacc aaagtcctgttgttttggactgttaatatgtgcaattacatttgctcctgatctgtgcac tagataaggatcctacctactttcttagtgtttttagcaggtagtgcccactactcaaga ctgtcacttggaatgttcatgtgcacaaactcaattctctaagcatgttcctgtaccacc tttgctttagagcaggggatgatattcactaagtgcccttcttttggacttaatatgc attaatgcaattgtccacctcttcttttagactaagagttgatctccacatattcccctt gcatcagggcatgttaattatgaatgaaccctttcttttaatattaatgtcataattg tatttgtggacctgtgtaggagaaaaagacctatgttcctcccattaccctttggattg ctgctgagaagtgttaactactcataatctcagctcttggacaattaatagcattaataa caattatcaagggcactgatcattagataagactcctgcttcctcgttgcttacatcggg ggtactgacccactaaggcccttgtactgttaatgtgaatatttgcaattatatatgtc tccttctggtagagtgggatattatgccctagtatccccctttgcattactgcagggggctg ctgactactcaaaacttctcctgggactgttaataggcacaatggcagttatcaatggtt ttctccctccctgaccttgttaagcaagcgccccaccccaccctttagtttcccatggcat aataaagtataagcattggagtattccatgcacttgtctatcaaacagtggtccatactc ccaacccttttgcattgcgccagtgtgtaaaatcacaggtagccatggtgtcatgcttta tatacgaagtcttccctctctctgcccttgtgtgcccttggccctttttacagactat tgctcacaatctcaggtgtccatatttgcagctattaggtaagattgtgctgtctccctc ttcccttccctctgccctgcccttttgcctctttgctgggtaatgttgaccGgacaagg cccttttctcttggacttaaacaattctcagttgcactttccttggtccCacccattatac atgaaccctctacttcctttcgcattgcttctgagtatgctgactacccaaagcccctt ctgtgttattaataaacacagtactgattgtcccattttcagcccatcagtccaagatc tccctaccactttggtgtgttggtgcagtgttgactatgaaaagcaggcctgaactaggt ggataagccttcactcattttctttcatttattaatgatcctagtttcaattattgtcag attctggggacaagaaccattcttgcccacctgtgttactgctttactgtgcaaaatact gaaggcaagtcagacccagggagctggattgccatcctttattttgtgtttccagtgtac actataaaattgtctccccaggaaggaaggttggcactttctctgcattcttctttccag agcagattgcctggttaagaatctcttgttgtcccCtTgtatattgttattgtaaagtg ccaaatgccaggatacagccagaaaaattgcttattattattaaaaaattttttaaga aagacatctggattgtagggtggactcgataacctggtcattattttttttgaagccaaaa tatccatttatactatgtacctggtgaccagtgtctctcattttaactgagggtggtggg tctgtggatagaacactgactcttgctattttaatatcaaagatattctagATCCAGCAC AGTGGCggcccgataccgtcgacc
```

Targeting Sequences

The nucleic acid constructs described herein include targeting sequences or elements (the terms are used interchangeably herein) that promote sequence specific integration of an Xist transgene into the DYRK1A or RCAN1 gene (e.g., by homologous recombination). Methods for achieving site-specific integration by ends-in or ends-out targeting are known in the art and in the nucleic acid constructs of this invention, the targeting elements are selected and oriented with respect to the Xist transgene according to whether ends-in or ends-out targeting is desired. In certain embodiments, two targeting elements flank the Xist transgene.

A targeting sequence or element may vary in size. In certain embodiments, a targeting element may be at least or about 50, 100, 200, 300, 400, 500, 600, 700, 800, 900, 1000, 2000, 3000, 4000, 5000, 6000, 7000, 8000, 9000, 10000 bp in length (or any integer value in between). In certain embodiments, a targeting element is homologous to a sequence that occurs naturally in a trisomic and/or translocated chromosomal region, including a polymorphic sequence which may be present on just one of the homologous chromosomes.

The construct elements as described here may be variants of naturally occurring DYRK1A or RCAN1 sequences. Preferably, any construct element (e.g., an Xist transgene, other non-coding, silencing RNA, or a targeting element) includes a nucleotide sequence that is at least 80% identical to its corresponding naturally occurring sequence (its reference sequence, e.g., an Xist coding region, a human Chr 21 sequence, or any duplicated or translocated genomic sequence). More preferably, the silencing sequence or the sequence of a targeting element is at least 85%, 90%, 91%, 92%, 93%, 94%, 95%, 96%, 97%, 98%, 99% identical to its reference sequence (e.g., NG_009366.1, the human refGene Sequence of DYRK1A, or NG_007071.1, the human refGene Sequence of RCAN1).

As used herein, "% identity" of two nucleic acid sequences is determined using the algorithm of Karlin and Altschul (Proc. Natl. Acad. Sci. USA, 87:2264-2268, 1990), modified as in Karlin and Altschul, Proc. Natl. Acad. Sci. USA, 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucl. Acids Res., 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

In preferred embodiments, the targeting elements comprise all or part of the following sequences, with the DYRK1A target sequences shown in bold and underlined:

```
DYRK1A LEFT ARM:
                                                    (SEQ ID NO: 12)
ATGGTAATTGAGAAATGACAAGAATCATGGAACTCCAAATTCATGACAATATTTGGGTAAGACGT

CTACCTTTCCCTCCATACCTAAATTAACTAAACGGGTTTCGCTGTGTCTTCAACCATCGATCGAT

CATTTACCGTTTTAACTTAGGTCTGAGGAATACCACAATTAACGATATCGATTTCTACTTTGACC

TCAACACGGTGAGGAACGTGTGAAAATAGACAGTGGGAGAATCCGACAAAATCTTTTAGGGTACA

AAATCGAACGGTAAGACAACTGGGTCGGACGGAAAGATCGGAATTGAATGGGGAGACAGATATAA

GATAAAGGTCGGTTTATACTCCACTGCAAATTCGACGATGAACTTTCTCTTCACCCTCAATCCG

TCTCGTCATCCCCTTAGTACAAACCCCTTCTCACTTCTCACATGAACTCTCTCACACCTCCACGG

AACCTCCTCGACCTCGGGTCTCCACGGGGTACTCTTGTTGTGTCCTCCGACGTCCACCTCCACCC

ACGGACTAACATCTTACGAAAGATCAACAGAAGGTGTCCTGTAAAAACCCTCGATAAGTGTTCTA

AGTACCGATGGCACGAGATTTTAAACTACACTTCAAGTAAAAAGGACCTGAAGAATGAATTAAGG

AGACAGAAAACCGGGTCGGTGGGGAAACGGTCAAA
```

```
DYRK1A RIGHT ARM:
                                                    (SEQ ID NO: 13)
CCACTACTCGTCCGACAAACCTTTCTTGCAGGAGCTCGTCCCACGACAAAGGATTGGGACGCAGA

AAAAGGGGAGACTCTAGTCAAATAGAAATAAGTGAACGTCCACAAGTTGTTAGAACAGAAAATAC

CCCTTAAAGATTACACAGAACTCGTGAAAGGGTGGGAGGATAGAACCTCCGTACCAAGTCTCACC

TTTTCCCGCGCCCGGGTGGATGGAGACCGGAAGGGTGGAGTCGGTGGTACGAATCCCGGCACCAC

CTCACGAACTGGAGAAACACACATGTTACGTTATGTACGACCTTATTACGGTGGAATACGTATCC

CGAAAACACCCACATTCCCGTATGGCCTTGTTCAACCGTATCTTATTCTCAAGTCACTTACAACA

GTGATGAAAAATAATGAAAAATTAACACTTTTTGAGTGTCTAAGACATTATTTCCCAGTATCTTT

GGACGAAATAGGTATGATAGTAATGACTCTTATGAAAGACCAAAAGC
```

In some embodiments, the XIST cDNA is inserted into the silencing vector in the opposite direction in order to avoid generating a fused RNA with DYRK1A exon1. In these embodiments, exemplary targeting arms comprise the sequences of SEQ ID NO: 14 and SEQ ID NO: 15, set forth below.

Selection Markers

In addition, the nucleic acids may contain a marker for the selection of transfected cells (for instance, a drug resistance gene for selection by a drug such as neomycin, hygromycin, and G418). Such vectors include pMAM, pDR2, pBK-RSV, pBK-CMV, pOPRSV, pOP13, and so on. More generally, the term "marker" refers to a gene or sequence whose presence or absence conveys a detectable phenotype to the host cell or organism. Various types of markers include, but are not limited to, selection markers, screening markers, and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as green fluorescent protein (GFP), GUS or β-galactosidase. Molecular markers are, for example, sequence features that can be uniquely identified by oligonucleotide probing, for example RFLP (restriction fragment length polymorphism), or SSR markers (simple sequence repeat). To amplify the gene copies in host cell lines, the expression vector may include an aminoglycoside transferase (APH) gene, thymidine kinase (TK) gene, E. coli xanthine guanine phosphoribosyl transferase (Ecogpt) gene, dihydrofolate reductase (dhfr) gene, and such as a selective marker.

Expression of the selection marker can be driven by the same regulatory elements (e.g., promoters) as the silencing sequence, or can be driven by a separate regulatory element.

Recombination Facilitating Elements—Cleavage Vectors

In some embodiments, the present methods include the use of cleavage vectors, i.e., nucleic acid constructs include a sequence that enhances or facilitates homologous recombination (e.g., a zinc finger nuclease or TALEN). Zinc finger domains and TALENs can recognize and target highly specific chromosomal sequences to facilitate targeted integration of the transgene into the DYRK1A or RCAN1 gene. As would be understood in the art, the term "recombination" is used to indicate the process by which genetic material at a given locus is modified as a consequence of an interaction with other genetic material. Homologous recombination indicates that recombination has occurred as a consequence of interaction between segments of genetic material that are homologous or identical. In contrast, "non-homologous" recombination indicates a recombination occurring as a consequence of the interaction between segments of genetic material that are not homologous (and therefore not identical). Non-homologous end joining (NHEJ) is an example of non-homologous recombination.

In some embodiments, targeting the present silencing constructs to DYRK1A or RCAN1 can be facilitated by introducing a chimeric zinc finger nuclease (ZFN), i.e., a DNA-cleavage domain (nuclease) operatively linked to a DNA-binding domain including at least one zinc finger, into a cell. Typically the DNA-binding domain is at the N-terminus of the chimeric protein molecule, and the DNA-cleavage domain is located at the C-terminus of the molecule. These nucleases exploit endogenous cellular mechanisms for homologous recombination and repair of double stranded breaks in genetic material. ZFNs can be used to target a wide variety of endogenous nucleic acid sequences in a cell or organism. The present compositions can include cleavage vectors that target a ZFN to a region within DYRK1A or RCAN1, and the methods include transfection or transformation of a host cell or organism by introducing a cleavage vector encoding a ZFN (e.g., a chimeric ZFN), or by introducing directly into the cell the mRNA that encodes the recombinant zinc finger nuclease, or the protein for the ZFN itself. One can then identify a resulting cell or organism in which a selected endogenous DNA sequence is cleaved and exhibits a mutation or DNA break at a specific site, into which the transgene will become integrated.

The ZFN can include multiple (e.g., at least three (e.g., 3, 4, 5, 6, 7, 8, 9 or more)) zinc fingers in order to improve its target specificity. The zinc finger domain can be derived from any class or type of zinc finger. For example, the zinc finger domain can include the Cys2His2 type of zinc finger that is very generally represented, for example, by the zinc finger transcription factors TFIIIA or Sp1. In a preferred embodiment, the zinc finger domain comprises three Cys2His2 type zinc fingers.

The ZFN DNA-cleavage domain can be derived from a class of non-specific DNA cleavage domains, for example the DNA-cleavage domain of a Type II restriction enzyme such as FokI. Thus, a chimeric ZFN useful in the present methods can include three Cys2His2 type zinc fingers and a DNA-cleavage domain derived from the Type II restriction enzyme FokI. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer."

A linker, if present, between the cleavage and recognition domains of the ZFN can be a sequence of amino acid residues that result in a flexible linker is flexible, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

A silencing sequence flanked by sequences (typically 400 bp-5 kb in length) homologous to the desired site of integration can be inserted (e.g., by homologous recombination) into the site cleaved by the endonuclease, thereby achieving a targeted insertion. When used in combination with a ZFN construct, the silencing sequence may be referred to as "donor" nucleic acid or DNA.

In some embodiments, the cleavage vector includes a transcription activator-like effector nuclease (TALEN). TALENs function in a manner somewhat similar to ZFNs, in that they can be used to induce sequence-specific cleavage; see, e.g., Hockemeyer et al., Nat. Biotechnol. 29(8):731-4 (2011); Moscou et al., 2009, Science 326:1501; Boch et al., 2009, Science 326:1509-1512. Methods are known in the art for designing TALENs, see, e.g., Rayon et al., Nature Biotechnology 30:460-465 (2012).

Vectors and Transformation

The various active sequences, including the silencing sequence and the sequence encoding a chimeric ZFN can be introduced into a host cell on the same vector or separately (e.g., on separate vectors or separate types of vectors at the same time or sequentially). Methods for introducing the various nucleic acids, constructs, and vectors are discussed further below and are well known in the art.

Transformation can be carried out by a variety of known techniques which depend on the particular requirements of each cell or organism. Such techniques have been worked out for a number of organisms and cells and are readily adaptable. Stable transformation involves DNA entry into cells and into the cell nucleus. For example, transformation can be carried out in culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors.

Liposomal formulations: In certain embodiments of the invention, the oligo- or polynucleotides and/or expression vectors containing silencing sequences and/or ZFNs may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids and liposomes suitable for use in delivering the present constructs and vectors can be obtained from commercial sources or made by methods known in the art.

Microinjection: Direct microinjection of DNA into various cells, including egg or embryo cells, has also been employed effectively for transforming many species. In the mouse, the existence of pluripotent embryonic stem (ES) cells that can be cultured in vitro has been exploited to generate transformed mice. The ES cells can be transformed in culture, then micro-injected into mouse blastocysts, where they integrate into the developing embryo and ultimately generate germline chimeras. By interbreeding heterozygous siblings, homozygous animals carrying the desired gene can be obtained.

Viral Vectors as Expression Constructs: Other viral vectors may be employed as expression constructs in the present invention. Vectors derived from, for example, vaccinia virus, adeno-associated virus (AAV, e.g., MV), or herpes virus may be employed. Extensive literature is available regarding the construction and use of viral vectors. For example, see Miller et al. (Nature Biotechnol. 24:1022-1026, 2006) for information regarding adeno associated viruses. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was subsequently detected.

Non-viral Methods: Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression constructs may simply consist of naked recombinant DNA, or in some cases mRNA for the recombinant ZFN. Transfer of the construct may be performed by any of the nuclei acid transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

Pharmaceutical Compositions, RNAs, and Cells

In another embodiment, the invention features compositions (e.g., pharmaceutically acceptable compositions) that include the nucleic acid constructs or vectors described herein. Various combinations of the constructs and vectors described herein can be formulated as pharmaceutical compositions.

Also within the scope of the invention are RNAs and proteins encoded by the cleavage vector and compositions that include them (e.g., lyophilized preparations or solutions, including pharmaceutically acceptable solutions or other pharmaceutical formulations).

In another embodiment, the invention features cells that include the nucleic acid constructs, vectors (e.g., an adeno associated vector), and compositions described herein. The cell can be isolated in the sense that it can be a cell within an environment other than that in which it normally resides (e.g., the cell can be one that is removed from the organism in which it originated). The cell can be a germ cell, a stem cell (e.g., an embryonic stem cell, an adult stem cell, or an induced pluripotent stem cell (iPS cell or IPSC)), or a precursor cell. Where adult stem cells are used, the cell can be a hematopoietic stem cell, a cardiac muscle stem cell, a mesenchymal stem cell, or a neural stem cell (e.g., a neural progenitor cell). The cell can also be a differentiated cell (e.g., a fibroblast or neuron).

Methods of Treatment

The methods of the invention can be used to treat patients who have trisomy 21. Any of the methods can include the step of identifying a patient in need of treatment; any of the patients can be human; and any of the methods can be carried out by either administering the present compositions to the patient, or removing cells from the patient, treating the cells, and "readministering" those cells. For example, the invention features methods of treating a genetic disorder associated with a trisomic chromosome 21 by identifying a patient in need of treatment; and administering to the patient a nucleic acid construct, vector, and/or cleavage vector as described herein. The amount of the construct or vector administered will be an amount sufficient to improve a condition associated with the disorder. Where cells are harvested from a patient to treat a condition or disorder described herein (or an associated symptom), the methods can include the steps of identifying a patient in need of treatment; harvesting cells from the patient; transfecting the cells with one or more of the types of constructs and/or vectors described herein; and administering to the patient a sufficient number of the transfected cells to treat the condition or improve a condition or symptom associated with the disorder. The symptoms associated with many birth defects and other conditions are well known. For example, individuals having Down Syndrome often experience mental retardation, hypotonia, cardiac defects, Alzheimer's Disease, hematological abnormalities and leukemia (see Antonarakis and Epstein, *Trends Mol. Med.* 12:473-479, 2006). As noted above, treatment can also be carried out in vivo by administering present compositions to the patient via pharmaceutically acceptable compositions.

The cells can include differentiated cells (e.g., white blood cells or fibroblasts) and/or undifferentiated cells (e.g., stem cells or precursor cells). The cells can also be differentiated cells that are induced, ex vivo, into iPS cells, or multi-potent stem cells or stem cells of particular lineage, such as neural stem cells. Neural stem cells (also called neural progenitors), are characterized by the ability to form neural rosettes, a neural tube-like structure (see, e.g., FIG. 6). The condition can be a neurological or blood disorder such as Alzheimer's Disease and leukemia, respectively, or a muscular defect, including defects of the heart.

To illustrate a particular application, Xist mediated chromosomal therapy could be used to ameliorate transient myeloproliferative disorder (TMD) in Down Syndrome children and possibly prevent the later development of acute leukemia. Successful bone marrow transplants for diseases like leukemia depend upon immune compatibility, to avoid Graft versus Host Disease (GVHD). To avoid graft rejection, the patient's own cells can be used and transgenically modified prior to transplant. There are two scenarios to acquire and modify stem cells for bone marrow transplant. In the first, the patient's own bone marrow stem cells can be obtained and an Xist transgene as described herein can be introduced and targeted to chromosome 21. When Xist expression silences the trisomic chromosome, these cells can then be transplanted back into the patient following standard bone marrow transplant procedures following the destruction of the patient's bone marrow using irritation. Modified autologous (from the patient) bone marrow cells can be transplanted without first irradiating the patient to destroy the unmodified bone marrow. This would produce a situation where the patient's bone marrow would be mosaic for trisomy 21 (a mixture of modified and unmodified cells). The data presented herein indicate that the modified cells would have a growth advantage over the non-modified fully trisomic cells, and the modified cells would eventually outgrow the non-modified disease-inducing cells (see Douillard-Guilloux et al., *J. Gene Med.* 11:279-287, 2009). In the second approach, the patient's fibroblast (skin) cells can be used to produce iPS cells, into which a transgenic Xist gene is inserted and targeted to chromosome 21. IPS cells that silence one of the three trisomic chromosomes will then be differentiated into adult hemopoietic stem cells and introduced back into the patient as described herein.

EXAMPLES

The invention is further described in the following examples, which do not limit the scope of the invention described in the claims.

Materials & Methods

The following materials and methods were used in the Examples set forth below.

Cell Culture.

HT1080 TetR cells (Invitrogen) and Female DS human primary fibroblast line (Coriell) (AG13902) were cultured as recommended by supplier. DS iPSC parent line (DS1-iPS4) was provided by George Q. Daley (Children's Hospital Boston, USA) and maintained on irradiated mouse embryonic fibroblasts (iMEFs) (R & D Systems, PSC001) in hiPSC medium containing DNEM/F12 supplemented with 20% knockout Serum Replacement (Invitrogen), 1 mM glutamine (Invitrogen), 100 µM non-essential amino acids (Invitrogen), 100 µM β-mercaptoethanol (Sigma) and 10 ng/ml FGF-β (Invitrogen, PHG0024). Cultures were passaged every 5-7 days with 1 mg/ml of collagenase type IV (Invitrogen).

ZFN Design.

ZFNs against the human AAVS1 locus (PPP1R12C) on Chr19 have been previously described[25]. ZFNs against the DYRK1A locus were designed using an archive of pre-validated zinc finger modules[24,53,54], and validated for genome editing activity by transfection into K562 cells and Surveyor endonuclease-based measurement of endogenous locus disruption ("Cell"[55,56]) exactly as described[54]. Southern blotting for targeted gene addition was performed exactly as described[23,57] on SphI-digested genomic DNA probed with a fragment corresponding to positions Chr 21:38825803+38826056 (hg19).

iPSC reprogramming of DS fibroblasts.

Three primary DS fibroblast cultures (Coriell: GM02504, AG13902, GM02067) were obtained and cultured. Two of these cultures (GM02504, AG13902) were used for reprogramming with assistance of the UConn Stem Cell Core Laboratory, using retroviral transduction with five reprogramming factors (OSKML).

It was initially noted that two of the three human primary DS fibroblast samples showed very limited proliferation even though age of donor and passage number would not predict this. In addition, a marked deficit in DS mouse tail tip fibroblast proliferation was seen. Additionally, in two attempts at reprogramming human DS fibroblasts, only the AG13902 sample was modestly successful, suggesting DS fibroblasts were more difficult to reprogram than control fibroblasts. Fewer subclones were obtained and most of these showed poor morphology and slower growth than controls.

XIST and rtTA/Puro Plasmid Construction.

14 kb human XIST cDNA, a splicing isoform of full length XIST cDNA was subcloned into pTRE3G (Clontech, Cat#: 631167). Two homologous arms (left arm, 690 bp; right arm, 508 bp) of DYRK1A gene on Chr 21 were amplified by PCR from primary DS fibroblasts (AG13902) (Coriell) and cloned into the pTRE3G vector (Human Chr 21 DYRK1A left arm primers: forward 5'-GCCGTATAC-CATTAACTCTTTACTGTTC-3' (SEQ ID NO: 3), reverse 5'-TCTGTATACGTAAACTGGCAAAGGGGTGG-3' (SEQ ID NO: 4); Human Chr 21 DYRK1A right arm primers: forward 5'-ATTTCGCGAACGGGTGATGAGCA-GGCTGT-3' (SEQ ID NO: 5), reverse 5'-CCGTCGC-GAAAACCAGAAAGTATTCTCAG-3' (SEQ ID NO: 6)).

DYRK1A left arm, reverse:
(SEQ ID NO: 14)
AAACTGGCAAAGGGGTGGCTGGGCCAAAAGACAGAGGAATTAAGTAAGAAGTCCAGGAAAAATGA

ACTTCACATCAAATTTTAGAGCACGGTAGCCATGAATCTTGTGAATAGCTCCCAAAAATGTCCTG

TGGAAGACAACTAGAAAGCATTCTACAATCAGGCACCCACCTCCACCTGCAGCCTCCTGTGTTGT

TCTCATGGGGCACCTCTGGGCTCCAGCTCCTCCAAGGCACCTCCACACTCTCTCAAGTACACTCT

TCACTCTTCCCCAAACATGATTCCCCTACTGCTCTGCCTAACTCCCACTTCTCTTTCAAGTAGCA

GCTTAAACGTCACCTCATATTTGGCTGGAAAATAGAATATAGACAGAGGGGTAAGTTAAGGCTAG

AAAGGCAGGCTGGGTCAACAGAATGGCAAGCTAAAACATGGGATTTTCTAAAACAGCCTAAGAGG

GTGACAGATAAAAGTGTGCAAGGAGTGGCACAACTCCAGTTTCATCTTTAGCTATAGCAATTAAC

ACCATAAGGAGTCTGGATTCAATTTTGCCATTTACTAGCTAGCTACCAACTTCTGTGTCGCTTTG

GGCAAATCAATTAAATCCATACCTCCCTTTCCATCTGCAGAATGGGTTTATAACAGTACTTAAAC

CTCAAGGTACTAAGAACAGTAAAGAGTTAATGGTA

DYRK1A right arm, reverse:
(SEQ ID NO: 15)
CGAAAACCAGAAAGTATTCTCAGTAATGATAGTATGGATAAAGCAGGTTTCTATGACCCTTTATT

ACAGAATCTGTGAGTTTTTCACAATTAAAAAGTAATAAAAAGTAGTGACAACATTCACTGAACTC

TTATTCTATGCCAACTTGTTCCGGTATGCCCTTACACCCACAAAAGCCCTATGCATAAGGTGGCA

TTATTCCAGCATGTATTGCATTGTACACACAAAGAGGTCAAGCACTCCACCACGGCCCTAAGCAT

GGTGGCTGAGGTGGGAAGGCCAGAGGTAGGTGGGCCCGCGCCCTTTTCCACTCTGAACCATGCCT

CCAAGATAGGAGGGTGGGAAAGTGCTCAAGACACATTAGAAATTCCCCATAAAAGACAAGATTGT

TGAACACCTGCAAGTGAATAAAGATAAACTGATCTCAGAGGGGAAAAAGACGCAGGGTTAGGAAA

CAGCACCCTGCTCGAGGACGTTCTTTCCAAACAGCCTGCTCATCACC

The pEF1α-3G rtTA-pA cassette from pEF1α-Tet3G vector (Clontech) was subcloned into a plasmid for targeted gene addition to the PPP1R12C/AAVS1 locus 25, which contains a unique HindIII site flanked by two 800 bp stretches of homology to the ZFN-specified position in the genome.

See FIGS. 2a & 9a, and 2b & 9b.

Constructs for Targeting DYRK1 or RCAN1:

The following constructs were made and tested. Two constructs for a dual-targeting strategy in human Down Syndrome iPSCs were made as follows:

CONSTRUCT 1 (3G/FL/hXIST/DYRK1A): The 18.5 kb inducible human XIST construct that contains 14 kb full length human XIST cDNA is targeted the DYRK1A gene on Chr 21 by a dual-targeting strategy in human Down syndrome iPSCs. See FIGS. 2a, 9a, and 10a for the sequence.

CONSTRUCT 2 (puro/rtTA/AAVS1): The puro/rtTA construct is targeted the AAVS1 locus on Chr 19 for the dual-targeting strategy. See FIGS. 2b, 9B and 10b for the sequence.

The dual-targeting strategy was specifically designed for Down Syndrome iPSCs. The 18.5 kb inducible human XIST transgene (3G/FL/hXIST/DYRK1A) is targeted the DYRK1A gene on Chr 21, and the puro/rtTA plasmid (puro/rtTA/AAVS1) is targeted a safe harbor of human genome (AAVS1 locus) on Chr 19. Puromycin on the puro/rtTA construct is for selection of XIST-targeted clones (by 3G/FL/hXIST/DYRK1A) and tetracycline transactivator (rtTA) is for induction of XIST transgene expression on Chr 21.

Four selectable and inducible XIST constructs targeted the RCAN1 and DYRK1A loci on Chr 21 in human somatic cells were made as follows:

CONSTRUCT 3 (FL/hXIST/RCAN1): The 21.1 kb selectable and inducible human XIST construct that contains 14 kb full length human XIST cDNA is targeted the RCAN1 gene on Chr 21 by ZFNs in human somatic cells. See FIGS. 7A-B and 10c for the sequence.

CONSTRUCT 4 (FL/hXIST/DYRK1A): The 20.7 kb selectable and inducible human XIST construct that contains 14 kb full length human XIST cDNA is targeted the DYRK1A gene on Chr 21 by ZFNs in human somatic cells. See FIGS. 9c and 10d for the sequence.

CONSTRUCT 5 (6.8 kb/hXIST/RCAN1): The 14.0 kb selectable and inducible human XIST construct that contains 6.8 kb exon 1 of human XIST cDNA (SEQ ID NO:2, obtained from C. Brown, University of British Columbia) is targeted the RCAN1 gene on Chr 21 by ZFNs in human somatic cells. See FIGS. 7c and 10e for the sequence.

Figure 9A:
FIGS. 9a-f show schematic illustrations of some of the constructs used in the present application.
Figure 9B:
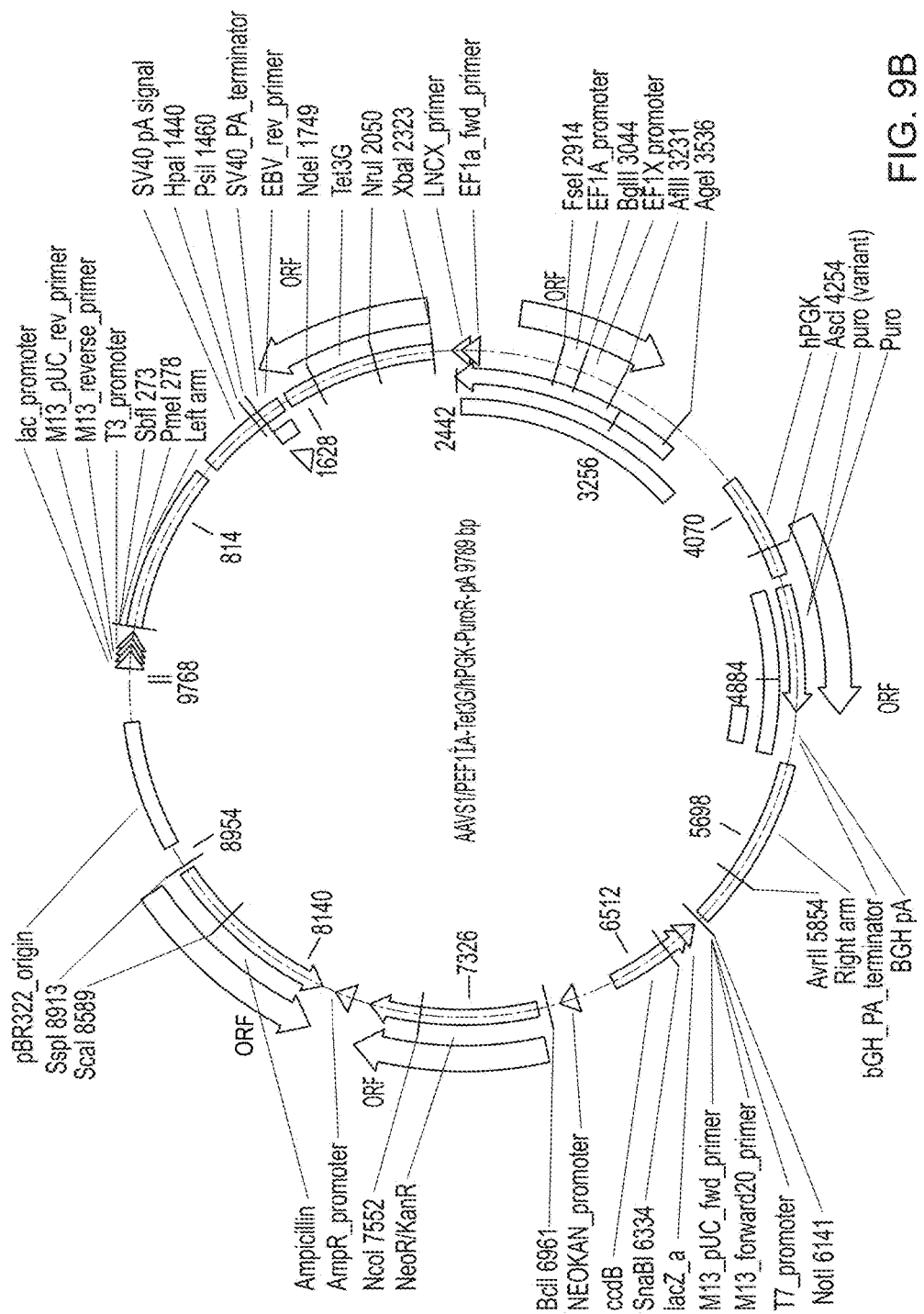

CONSTRUCT 6 (6.8 kb/hXIST/DYRK1A): The 13.7 kb selectable and inducible human XIST construct that contains 6.8 kb exon 1 of human XIST cDNA (SEQ ID NO:2, obtained from C. Brown, University of British Columbia) is targeted the DYRK1A gene on Chr 21 by ZFNs in human somatic cells. See FIGS. 9d and 10f for the sequence.

One selectable and inducible XIST construct targeted AAVS1 locus on Chr 19 in human somatic cells was made as follows:

CONSTRUCT 7 (6.8 kb/hXIST/AAVS1): The 15.7 kb selectable and inducible human XIST construct that contains 6.8 kb exon 1 of human XIST cDNA (SEQ ID NO:2, obtained from C. Brown, University of British Columbia) is targeted the AAVS1 locus on Chr 19 by ZFNs in human somatic cells. See FIGS. 9e and 10g for the sequence.

One selectable and inducible mouse Xist construct targeted the Runx1 gene on mouse Chr 16 was made as follows:

CONSTRUCT 8 (6.3 kb/mXist/Runx1): The 20.6 kb selectable and inducible mouse Xist construct that contains a 6.3 kb exon 1 of mouse Xist cDNA is targeted the Runx1 gene on Chr 16 (synteny to human Chr 21) by conventional homologous recombination. See FIGS. 9f and 10h for the sequence.

The constructs described above targeting human Chr 21 or mouse Chr 16 constitute the first "dosage compensating transgenes" designed to silence chromosome imbalance involving duplication of chromosomal material, particular trisomy with much clinical import.

Dual-Targeted-Addition of Human DS iPSCs and Generation of Stable Targeted Clones.

The DS iPSC line was cultured in 10 µM of Rho-associated protein kinases (ROCK) inhibitor (Calbiochem; Y27632) 24 h before electroporation. Single cells ($1\times10^7$) were harvested using TryPLE select (Invitrogen), resuspended in 1×PBS and electroporated with a total of 55 µg DNA including five plasmids (XIST, DYRK1A ZFN1, DYRK1A ZFN2, rtTA/puro, and AAVS1 ZFN) with both 3:1 and 5:1 ratios of XIST: rtTA/puro. The electroporation conditions were 220 v, and 750 µF (BioRad Gene Pulser II System)[53]. Cells were subsequently plated on puromycin-resistant DR4 MEF feeders (Open Biosystems, Cat#: MES3948) in hiPSC medium supplemented with ROCK inhibitor for the first 24 h. Over 300 colonies remained after 12 days of 0.4 µg/ml puromycin selection and 245 randomly chosen individual colonies across 36 pooled wells were examined by interphase DNA/RNA FISH for the presence and expression of XIST, correct targeting and retention of trisomy (since some subclones lacked XIST or showed just two DYRK1A DNA signals). Over 100 individual clones were isolated and characterized, and those of interest, containing targeted XIST on one of three DYRK1A loci, were frozen. Six single target clones with good pluripotent morphology, OCT4 positive staining, correct targeting to one trisomic chromosome, and good XIST RNA paint were expanded for further characterization. One double and one triple target line, two non-target clones, and one disomic clone were also isolated and frozen. Targeting and correct chromosome number (47) was confirmed by interphase and metaphase FISH and genome integrity by high resolution G-band karyotype and CGH array.

Chromosome Preparation.

iPSCs were treated with 100 ng/ml KaryoMAX colcemid (Invitrogen) for 2-4 h at 37° C. in a 5% $CO_2$ incubator. Cells were trypsinized, treated with hypotonic solution, and fixed with methanol:acetic acid (3:1). Metaphases were spread on microscope slides, and at least 20 analyzed per clone. Karyotype analysis was done on pro-metaphase chromosomes using Standard Giemsa-trypsin G band methods.

CGH Array.

CGH was performed in the Cytogenetics Laboratory at UMASS Medical School. 1 ug of DNA was used for Genomic Microarray analysis using UMass Genomic Microarray platform (Human Genome Build hg19). The array contains approximately 180,000 oligonucleotides (60 mers) that represent coding and noncoding human sequences and high density coverage for clinically relevant deletion/duplication syndromes and the telomeric and pericentromeric regions of the genome. Data was analyzed by Blue-Fuse Multi, v3.1 (BlueGnome, Ltd).

DNA/RNA FISH, and Immunostaining.

DNA and RNA FISH were carried out as previously described[10,19,21,58]. The XIST probe is a cloned 14 kb XIST cDNA (the same sequence as XIST transgene in FIG. 2a) in pGEM-7Zf(+) (Promega). Six Chr 21 gene probes are BACs from BACPAC Resources (DYRK1A: Rp11-105024, APP: RP11-910G8, USP25: RP11-840D8, CXADR: RP11-1150114, ITSN1: RP11-1033C16, COL18A1: RP11-867018). DNA probes were labeled by nick translation with either biotin-11-dUTP or digoxigenin-16-dUTP (Roche). In simultaneous DNA/RNA FISH (interphase targeting assay), cellular DNA was denatured and hybridization performed without eliminating RNA and also treated with 2 U/µl of RNasin Plus RNase inhibitor (Promega). For immunostaining with RNA FISH, cells were immunostained first with RNasin Plus and fixed in 4% paraformaldehyde before RNA FISH. Antibodies: H3K27me3 (Millipore, 07-449), UbH2A (Cell Signaling, 8240), H4K20Me (ABcam, ab9051), MacroH2A (Millipore, 07-219), OCT4 (Santa Cruz, sc-9081), PAX6 (Stemgent, 09-0075), SOX1 (R & D Systems, AF3369).

Allele-Specific SNP Analysis:

Primers were designed to amplify 3' UTR regions of chromosome 21 genes reported to contain SNPs (Table 1). Total cDNA was used from three transgenic clones with and without XIST induction for 22 days. RT-PCR products were sequenced by GENEWIZ. Of ~10 genes examined, four were heterozygous and informative in the patient DS iPS cell line used here.

TABLE 1

Primers for Chr21 gene amplification (allele-specific SNP silencing analysis)

| Genes | Forward primer 5'-xxx-3' | SEQ ID NO: | reverse primer 5'-xxx-3' | SEQ ID NO: |
|---|---|---|---|---|
| ADAMTS1 | TCTCTGAAACCATAGCAGCCA | 16 | CTTGTGCAGACCATCCCTGC | 17 |
| ETS2 | GCCTTTTGCAACCAGGAACAGC | 18 | ATCACACAGAAGAACGTGGAGC | 19 |
| SPA13 | AACTCTGCTCCAAATGCCGA | 20 | CCTGTACATCATTCTCTGCTTGG | 21 |
| TIAM1 | TGGGGTGATTTGCTTTCCAGTGC | 22 | GTGCAGTGTCTGCCCCAAGC | 23 |

Microarray Analysis.

Three independently targeted subclones plus the parental Chr21 trisomic (non-targeted) iPS cell line were grown±doxycycline (2 µg/ml) for 22 d. Normal male iPS and disomic isogenic lines were also cultured for 22 d and total RNA was extracted with a High Pure RNA extraction kit (Roche) in triplicate for each, processed with a Gene Chip 3' IVT Express Kit (Affymetrix), and hybridized to Affymetrix human gene expression PrimeView arrays. Array normalization was performed with Affymetrix Expression Console Software with Robust Multichip Analysis (RMA)[59]. Probesets with the top 60% of signal values were considered present and "expressed" and were used for all further analysis. Data in FIG. 5 has no other threshold applied. When designated, a gene expression change significance threshold was applied using a two-tailed T-test comparing samples±doxycycline in triplicate (N=3) (FIG. 5d, $p<0.01$). For the ~200 genes found to significantly change in all three clones (in text), a T-test with $p<0.001$ was applied.

Microarray Data Interpretation:

Using extraction-based methods, changes on just one of three alleles (from the XIST-bearing chromosome) will be diluted by the other two. If all three chromosomes are fully expressed, this would predict a 33% reduction in Chr21 expression levels per cell when one Chr21 is fully silenced. However, 33% would apply only if Chr 21 genes are fully over-expressed to start, and prior evidence and results in this study shows this is not the case for many genes. Previous microarray studies have analyzed expression levels of Chr 21 in DS patient cells, although such analyses are hampered by the extensive genetic and epigenetic differences between any two individuals[60-62]. The fraction of Chr 21 genes detected as over-expressed varies with the study and tissue, but generally is in the 19-36% range[3,34,35,63], with individual gene increases often in the ~1.2-1.4 range (less than the theoretical 1.5). For example, one study of DS embryoid bodies showed only 6-15% of genes appeared significantly up-regulated, but this was comparing non-isogenic samples of different ES cell isolates.

Our trisomy correction system allows direct comparison of the same cells grown in identical parallel cultures, with and without XIST-mediated chromosome silencing. Our data shows a ~20% reduction in Chr 21 expression overall; importantly this level of reduction is seen either when the third chromosome is silenced in trisomic cells, or when disomic and trisomic cells are compared. This 20% reduction represents an average per cell for all three chromosomes, but corresponds to a 60% reduction in expression for just one Chr21 (the one silenced by XIST RNA, as shown here).

Apart from our goal here of trisomy dosage compensation, these results add significantly to understanding the extent of Chr 21 over-expression in Down Syndrome, by providing a more comprehensive analysis which shows expression of most genes is increased, but less than the theoretical 1.5 fold.

qRT-PCR.

qRT-PCR was performed for eight down-regulated Chr 21 genes determined by microarray on an BIO-RAD MyiQ™ Real-Time PCR Detection System in triplicate for clone 3 with/without doxycycline treatment for 22 d. The β-actin gene was used as an internal standard for calculation of expression levels. Primers for eight Chr 21 genes and β-actin were described in Table 2.

TABLE 2

Primers for qRT-PCR

| genes | Forward primer 5'-xxx-3' | SEQ ID NO: | reverse primer 5'-xxx-3' | SEQ ID NO: |
|---|---|---|---|---|
| CXADR | TGCGTCTAAACGTT GTCCCT | 24 | AGTGGACGTACGGC TCTTTG | 25 |
| COL6A1 | ATCAGCCAGACCAT CGACAC | 26 | GCCCTTCTCTCCCT TGTAGC | 27 |
| PTTG1IP | GTTGGGTGAACTTT GAGGCG | 28 | GTGCTGGAGCGCTT TAGTTG | 29 |
| ADAMTS1 | CCCTCACTCTGCGG AACTTTT | 30 | ATTAAGGCTGGCAC ACTGCTT | 31 |
| BTG3 | CCCATGTGAGGTGT GCTGT | 32 | AGGGCCCTGGTAAC TTTCCT | 33 |

TABLE 2 -continued

Primers for qRT-PCR

| genes | Forward primer 5'-xxx-3' | SEQ ID NO: | reverse primer 5'-xxx-3' | SEQ ID NO: |
|---|---|---|---|---|
| TIAM1 | TCAAAACCGAGAGC CTTCCC | 34 | CGGAGACGGCATCA GAATCA | 35 |
| USP16 | AGCCTTCAGTTTGG CTGTGT | 36 | GGCTTTGGAGTTGT AATGCTGG | 37 |
| APP | GGAGCGCTCTCGAC TTTTCT | 38 | TGTGCATGTTCAGT CTGCCA | 39 |
| β-ACTIN | TTGCCGACAGGATG CAGAAGGA | 40 | AGGTGGACAGCGAG GCCAGGAT | 41 |

DNA Methylation Analysis.

The parent line, and two independent targeted lines were grown with and without doxycycline for 22 d, in duplicate cultures. Genomic DNA was extracted using PureLink Genomic DNA Mini Kit (Invitrogen) and 750 ng bisulfite modified with the Alternative Incubation Conditions from the EZ DNA Methylation Kit (Zymo Research). 160 ng of bisulfite DNA was amplified, fragmented and hybridized to Illumina Infinium HumanMethylation450 array following standard protocol as outlined in the user guide. CpG islands were defined as high and intermediate CpG densities using the CpG density classifications based on those used by[64]. The program CpGIE[65] was used to locate HC and IC islands on the X chromosome and chromosomes 21 and 22. When multiple probes in CpG islands were associated with the same TSS, an average genic methylation value calculated. These average genic values were compared pre and post doxycycline induction using the Mann-Whitney test. Analysis was based on CpG islands within promoters of 143 Chr 21 genes.

The average methylation value was 6% on Chr 21 before XIST induction, and increased to 20-21% in both subclones after induction. Since any methylation increase on the transgenic chromosome would be diluted by the presence of three Chr 21s, this suggests the range of 60% methylation on the one XIST-coated chromosome, which is within the range seen for the inactive X chromosome[37].

Cell Proliferation Analysis.

Eight different iPSC lines (parent line, one non-targeted subclone, and six independent targeted subclones) were passaged onto 6-well plates at equal cell densities per well of each line and grown±doxycycline for 7 d. At least four replicates of each line were analyzed in two independent experiments. Rigorous measures were taken to minimize and control for any minor variations in seeding densities of iPS cells, which cannot be plated as single cell suspensions. First the analysis was done twice for six different transgenic clones, in each case comparing triplicate plates of corrected vs not corrected (Dox vs no Dox). To avoid differences in plating efficiencies of Dox and no Dox cells, we performed the experiments over a time course that did not require passage. For each of the six transgenic clones, the parental line and one negative control (non-targeted) sublcone, a single well of DS iPS cells (without Dox) was used to generate a cell suspension (cells and small disaggregated clumps). Next, equal aliquots of the cell suspension were plated into each of six wells once, then again, then a third time and then a fourth time (not relying on one measurement but the average of four for seeding each well). After plating, Dox was added to three of the six wells, and the cultures were maintained for 7 days. For images, plates were fixed, stained with 1 mg/ml crystal violet (Sigma) in 70% ethanol for 30 min and scanned to generate TIFF images. For cell counts, single cells were harvested by TryPLE select and counted using Beckman Coulter Z1 Particle Counter.

Differentiation of Neural Progenitors and Irreversibility in Cortical Neurons.

Differentiation: Independent XIST-transgenic iPSC clones, and the parental DS iPS line, were dissociated with Accutase (Innovative Cell Technologies) and $4\times10^5$ single cells were plated on Matrigel-coated 6-well plates in mTeSR1 medium (Stemcell technologies). Once the cell culture reached 90%-100% confluence, neural induction was initiated by changing the culture medium to neural induction medium, a 1:1 mixture of N2- and B27-containing media supplemented with 500 ng/ml Noggin (R&D Systems), 10 µM SB431542 (Tocris Bioscience), and 1 µM retinoic acid (Sigma, cat#: R2625), with/without treatment of doxycycline for the specified times. The neural rosettes were counted and their diameter measured, for at least 300 rosettes (sampled in random areas from triplicate dishes). At Day 14, the dox-induced culture had an average rosette diameter of 142 µm±0.55 µm in Clone 1 and 141 µm±3.49 µm in Clone 3. Rosettes could not be measured at the same time point in the uncorrected culture, since they had not formed. At day 17, the uncorrected culture had neural rosettes of similar number and size for both Clones 1 (140 µm±0.87 µm) and 3 (140 µm±1.09 µm). The corrected culture could not be accurately compared for Day 17 because the rosettes had become so mature and often had merged. After 17 d, neural rosettes were collected by dissociation with Dispase and replated on poly-ornithine and laminin-coated plastic dishes in N2- and B27-containing media including 20 ng/ml FGF2. After a further 2 d, FGF2 was withdrawn to promote differentiation of cortical neurons. Test of the irreversibility of silencing: Two independent clones were differentiated to cortical neurons in the presence of Dox for 70 days to initiate silencing. They were then split into parallel cultures grown with and without Dox for another 30 days, and XIST and APP expression analyzed by RNA FISH.

Targeted Addition to Primary Fibroblasts.

Here we used non-immortalized primary human female DS fibroblasts, which like all primary fibroblasts have a limited lifespan in culture (potentially more limited for DS fibroblasts). We reasoned that the robustness of ZFN-driven editing, combined with reduction to disomy for the DRYK1A gene, may make it possible to observe some edited cells before they senesce. We used a transgene carrying an near full length (~14 kb) XIST cDNA under a TetO$_2$ inducible promoter, and a selectable marker on the same construct, with ~600 bp homology arms to the DYRK1A gene (vector is ~21 kb total size, with a total insert size of ~17 kb) (data not shown). When introduced without the Tet-repressor construct, the TetO$_2$ CMV promoter is constitutively active. Two ZFN containing vectors as well as the 21 kb XIST transgene were transfected into the primary DS fibroblasts (ATCC) using Stemfect polymer (Stemgent) (10:1 ratio of XIST to ZFN, and 13 ug DNA to 1.3 ul Stemfect per well of 6 well plate). Surprisingly, the frequency of stable integrants was such that a sparse monolayer of transgenic fibroblasts emerged, rather than a few individual colonies following selection with hygromycin (75 ug/ml). The pooled population of selected cells was analyzed by FISH and IF for targeting, XIST expression and heterochromatin marks. XIST RNA was observed over the DYRK1A locus in ~74% of cells, indicating accurate transgene targeting, which was also verified by metaphase FISH. In many cells there was notable enrichment of H3K27me, H3K20me & UbH2A heterochromatic marks. Due to the limited lifespan of primary cells and the progressive silencing of the CMV promoter used in this construct, these cells were not more fully characterized.

Example 1

Figure 9C:
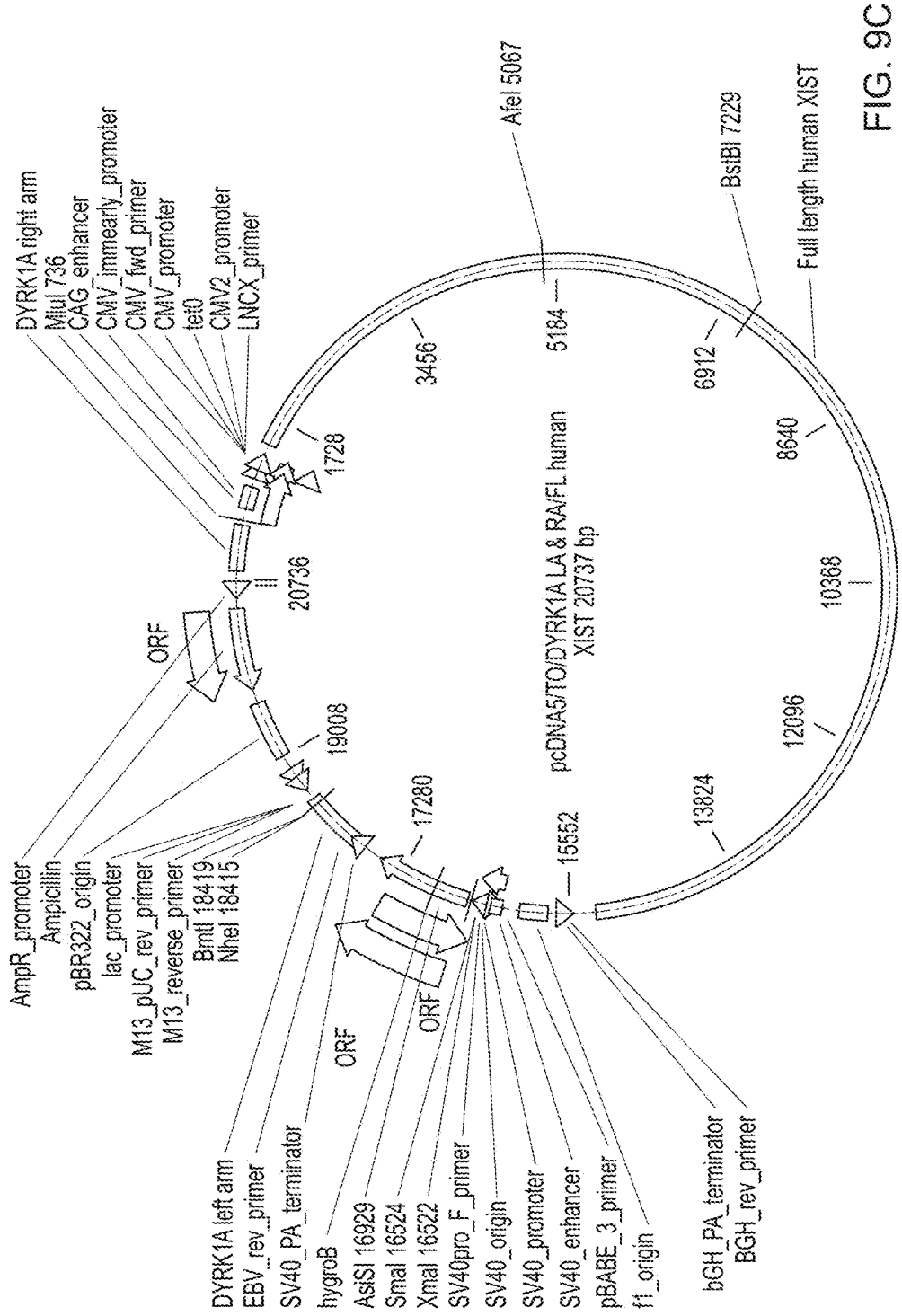
Figure 9D:
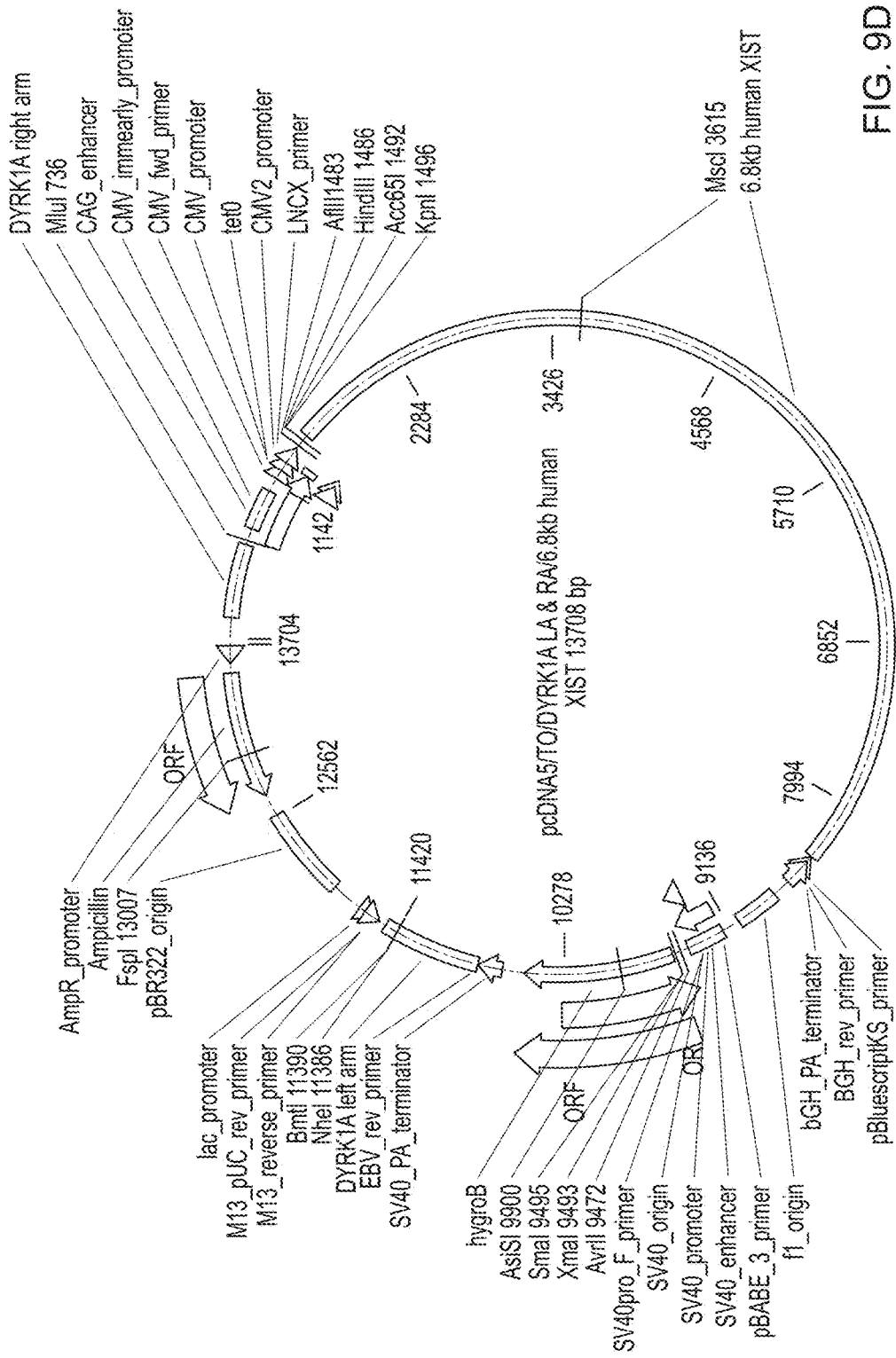
Figure 9E:
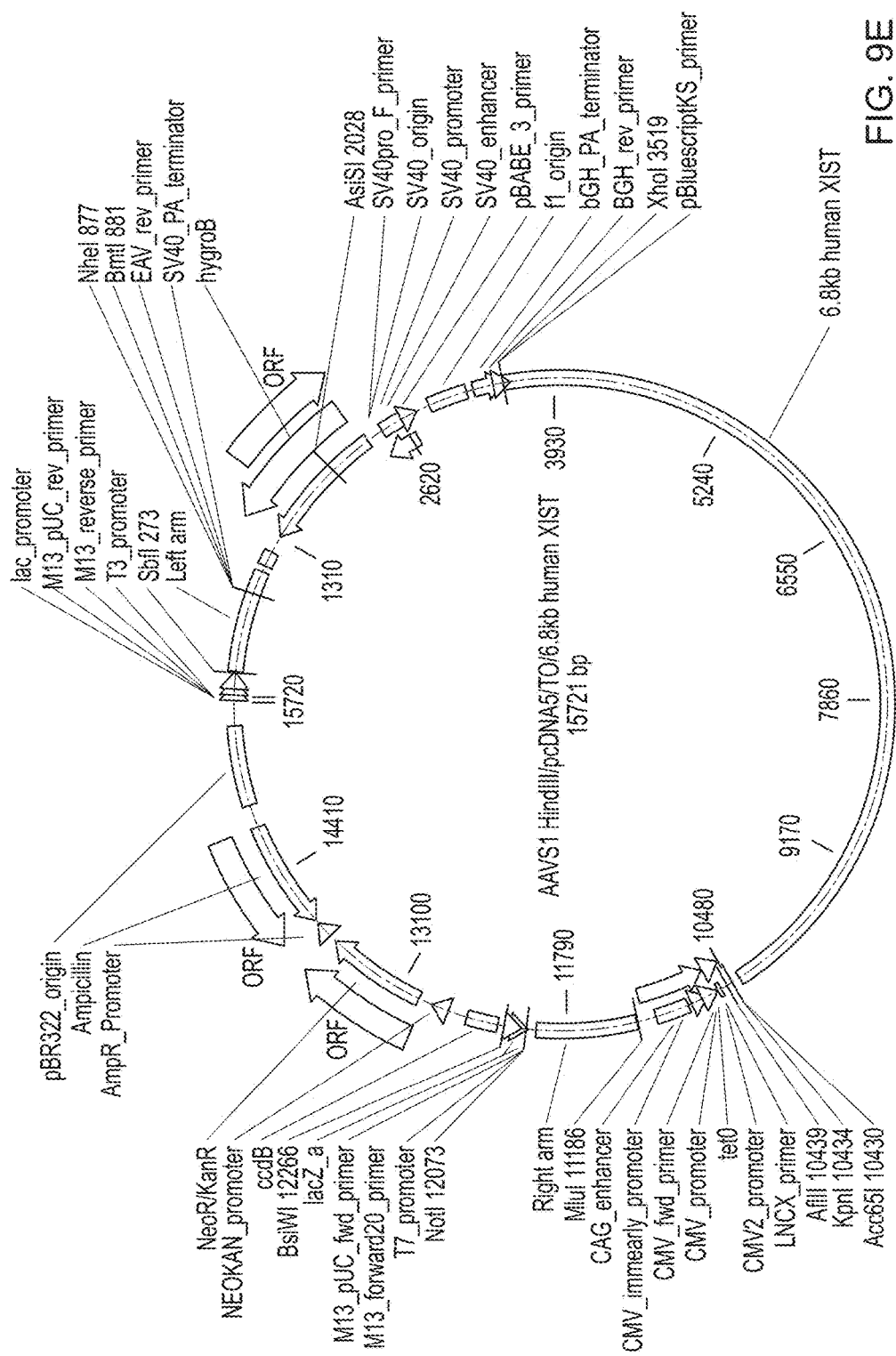
Figure 9F:
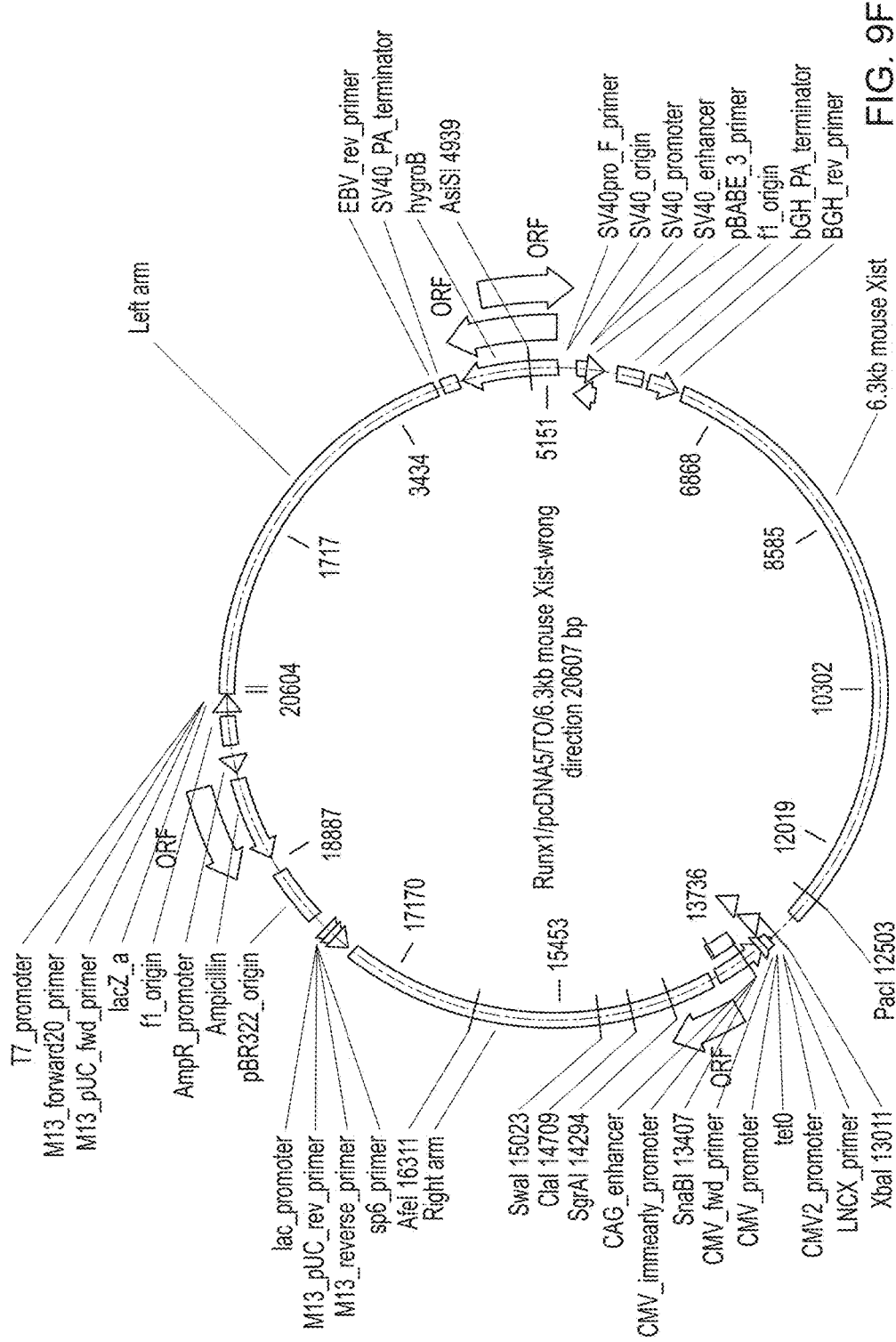

Accurate Targeted Addition of a Very Large XIST Transgene to a Trisomic Chr21 in Down Syndrome iPSCs Given its large size, neither the XIST gene nor its cDNA has previously been integrated in a targeted fashion. Thus our first goal was to demonstrate feasibility of targeted addition of by far the largest transgene targeted to date by nuclease-driven genome editing, orders of magnitude larger than sequences commonly used as templates for homology-directed double-strand break repair[24]. Therefore we first attempted targeted addition of a ~16 kb XIST transgene in an easily manipulated cell line (HT1080 fibrosarcoma cells), using established ZFNs to the AAVS1 locus on Chr19[25]; see FIG. 9e. This proved highly successful. To extend this to Chr21, we chose the DYRK1A locus at Chr21q22 for its interest in DS (reviewed in [26]) and its potential role in pluripotency and senescence[27,28]. From this we reasoned that disrupting one of three DYRK1A alleles may enhance the likelihood of obtaining targeted trisomic pluripotent sub-clones. We engineered a ZFN heterodimer that binds a 36 bp target sequence in intron 1 of DYRK1A and validated robust activity. Next, an even larger (~21 kb) construct was built containing near full-length XIST cDNA (17 kb), flanked by ~600 bp homology arms (FIG. 9c). Testing in the HT1080 cells demonstrated efficient, accurate addition of the entire 21 kb transgene to the "DS critical region" of Chr21.

We next determined whether this would be achievable in the technically challenging but translationally relevant iPSCs derived from reprogramming DS patient fibroblasts. These cells have unique therapeutic and developmental potential[29] due to their ability to form a variety of cell types, and thus would represent an important target of any future ex vivo cellular therapy efforts. We used a male DS iPSC line from the Daley lab[30], which we confirmed maintains pluripotency markers and trisomy 21. Although a single constitutively transcribed XIST transgene could be used, we engineered an inducible system to maximize utility for investigating the biology of DS. In one step, we targeted a doxycycline-based transgene control component (rtTA) to the AAVS1 safe harbor locus on Chr19[25] (FIGS. 2b & 9b), and the Dox-controlled XIST transgene to Chr21 (FIGS. 2a & 9a).

Figure 2C:
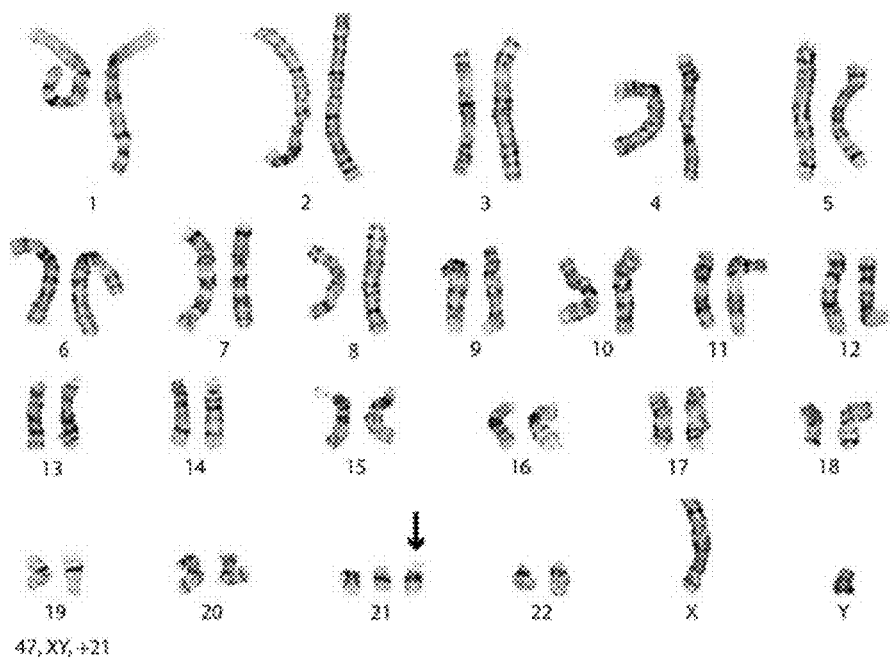
Figure 2D:
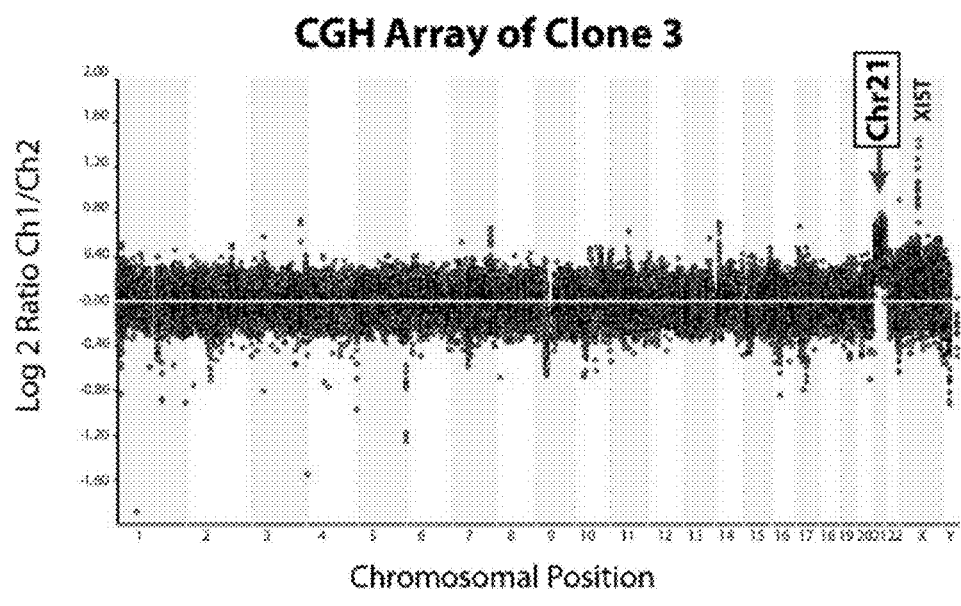
Figure 2E:
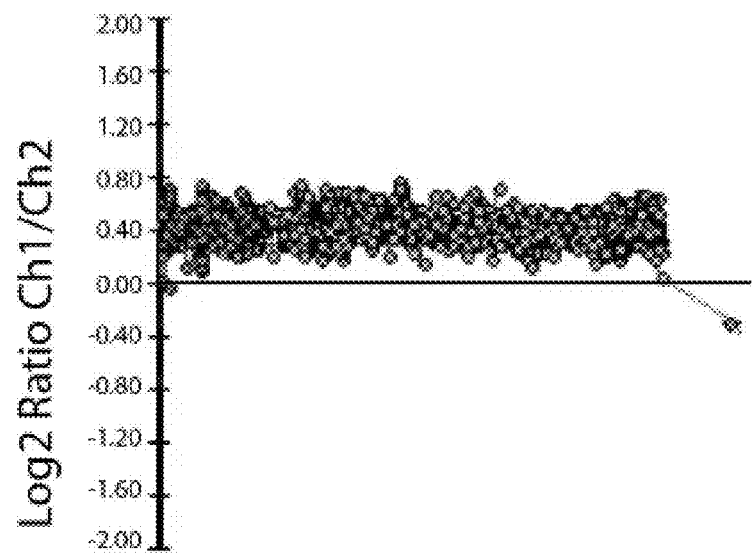
Figure 2E:
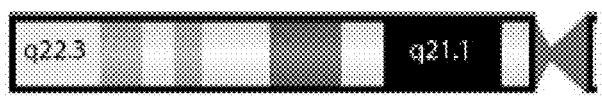

We analyzed 245 colonies from the first passage of pooled transformants by dual-color interphase in situ RNA/DNA FISH to determine if XIST was present and overlapped one of three DYRK1A alleles. Remarkably, 99% of XIST RNA-positive colonies carried the XIST transgene at this location on Chr21, and also contained rtTA/selection transgene. Efficiency was sufficiently high that, through modifications to editing conditions, we also obtained a few sub-clones with XIST integrated into two or even all three alleles of DYRK1A (see Table 3). Six independent sub-clones were chosen for further study based on: the presence of an XIST transgene on one of three copies of Chr21; pluripotent colony morphology; robust Oct4 staining; and the ability to form embryoid bodies. Southern blotting and FISH to metaphase chromosomes confirmed the interphase FISH analysis and gene addition accuracy, and all six clones retained 47 chromosomes. Selected clones were also examined by high-resolution cytogenetic banding and/or array CGH, which showed no significant abnormalities other than full trisomy for all of Chr21 (FIGS. 2c-e).

TABLE 3

Accuracy of targeted addition for XIST transgene on Chr 21 in Down Syndrome iPCSs

| Ratio of XIST to Puro | XIST+ clones (Puro+) | Random Integration | Targeted Integration | Single Target | Double Target | Triple Target |
|---|---|---|---|---|---|---|
| 3:1 | 65 | 1 (1.5%) | 64 (98.5%) | 57 (87.7%) | 7 (10.8%) | 0 (0.0%) |
| 5:1 | 16 | 1 (6.3%) | 15 (93.8%) | 8 (50.0%) | 5 (31.3%) | 2 (12.5%) |

Example 2

Figure 2F:
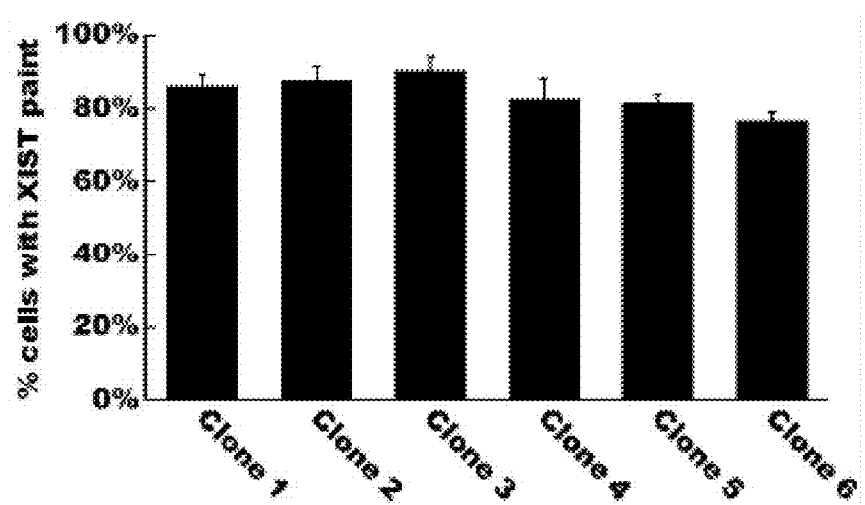

XIST RNA Coats the Chromosome in Cis and Induces a Heterochromatic Chr21 Barr Body In the panel of six independent genome-edited clones, we induced transgene expression and detected XIST RNA by FISH three days later. XIST RNA expression was consistently robust and localized in a nuclear "territory" over one Chr21, in over 85% of cells in the six clones (FIG. 2f). This mirrored the unique behavior of endogenous XIST RNA which "paints" the inactive X nuclear territory[10].

Figure 3:
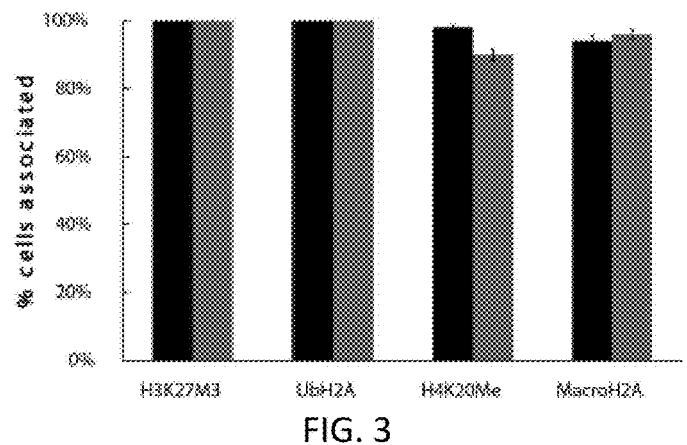
FIG. 3. XIST expression induces a cascade of heterochromatin modifications, and a condensed Chr21 Barr Body in transgenic, pluripotent sub-clones. Percentage of XIST territories with associated hallmarks H3K27me3, UbH2A, H4K20me, and MacroH2A. Mean±SE from 100 nuclei in five or more colonies.

The Xi in female cells forms a visibly condensed "Barr Body" that carries an epigenetic signature of repressive histone modifications and CpG DNA methylation (reviewed in[13]). Five days after XIST induction, the edited Chr21 became markedly enriched in all heterochromatin marks examined, including H3K27Me3, UbH2A, and H4K20Me in 90%-100% of cells and, later, with macroH2A (FIG. 3). H3K27me could be seen across the metaphase Chr21. Moreover, the chromosomal DNA in many nuclei became notably condensed, further evidence that we successfully generated a heterochromatic "Chr21 Barr Body," which appeared, by multiple criteria, indistinguishable from the Xi in female cells.

Example 3

XIST RNA Drives Long-Range, Allele-Specific Gene Silencing Across the Targeted Chr21

We examined the overall transcriptional impact of XIST RNA "painting" on Chr21 using an approach we developed to broadly assay hnRNA by detecting CoT-1 repeat containing RNAs, which clearly distinguishes Xi from Xa[21]. The Chr21 XIST RNA territory is depleted for CoT-1 RNA, suggesting heterochromatic silencing, as on Xi.

We next used multi-color RNA FISH to determine the presence of transcription foci at each allele for six specific Chr21 genes, an established approach we developed to discriminate active versus silenced genes on Xi[31]. Although XIST addition disrupts the large DYRK1A gene (FIG. 2a), without XIST expression, three bright transcription foci remained. However, when XIST RNA was induced, the targeted allele became weaker or undetectable, indicating significant repression of DYRK1A.

Figure 4A:
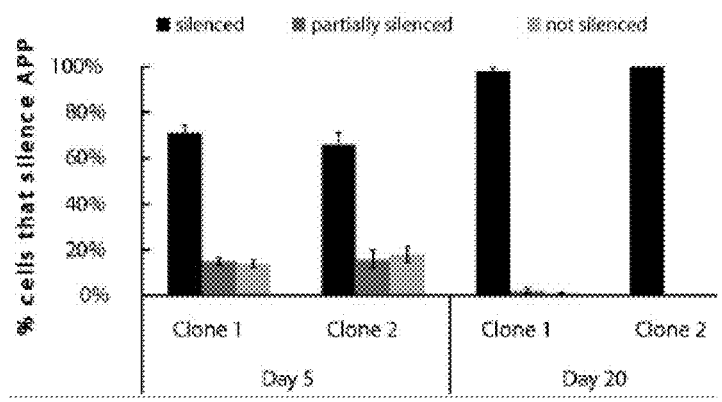
FIGS. 4A-F. XIST expression induces long-range transcriptional silencing in transgenic, pluripotent sub-clones. a. Quantification of APP silencing after 5 d and 20 d Dox induction in two independent sub-clones. Mean±SE from 100 nuclei. b. Four more Chr21-linked genes were also shown to be effectively silenced by RNA FISH, and scored before and after XIST induction. c. The silenced genes assessed by RNA FISH spanned the entire length of Chr21 (USP25 gene is ~21 Mb from XIST integration site at DYRK1A; black arrow), suggesting long range silencing of Chr21 by XIST RNA. Mean±SE from 100 nuclei. d. Sequencing analysis of gene transcripts informative for SNPs indicates one of three alleles are silenced by XIST expression. Primer pairs were used that amplified SNP-containing regions of four Chr21 genes to assess allele-specific silencing after sequencing. RNA was amplified from Dox treated and untreated samples of three different clones. Eight of 12 SNPs tested were informative in these cells, and all eight SNPs (in four genes) show reduction in one of the three alleles upon XIST induction. For example, in Clone 3 ADAMTS1 goes from TTC to TT, ETS2 from CCA to CA, TIAM1 from TTC to TC, and HSPA13 from TTC to TT. e. In two of the three transgenic clones, the same eight SNP alleles were repressed, consistent with a chromosome-wide mechanism and allows us to extrapolate the haplotype of each chromosome and surmise which carried XIST in each clone. Both clones 2 and 3 silence the far right chromosome and the center chromosome is silenced in Clone 1. f. Although XIST RNA is robustly expressed in early time points (3 days) in the double and triple targeted clones, XIST becomes almost entirely silenced in later time points (20 days). Mean±SE from 100 nuclei.
Figure 4B:
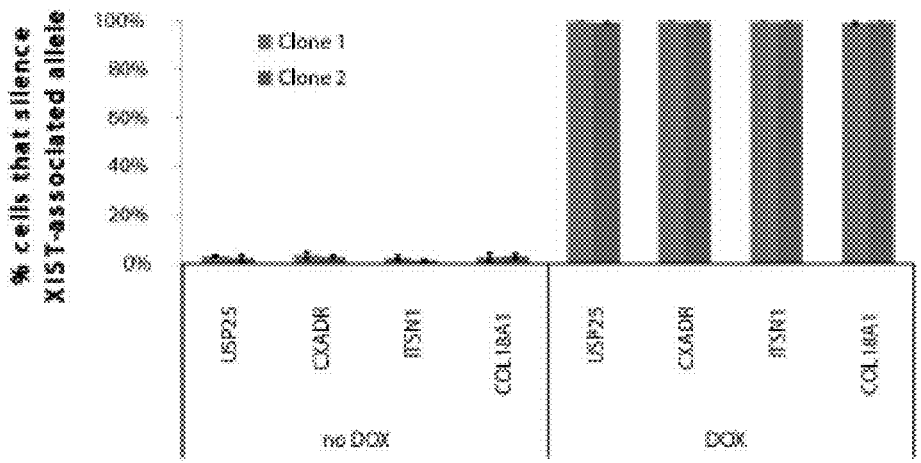
Figure 4C:
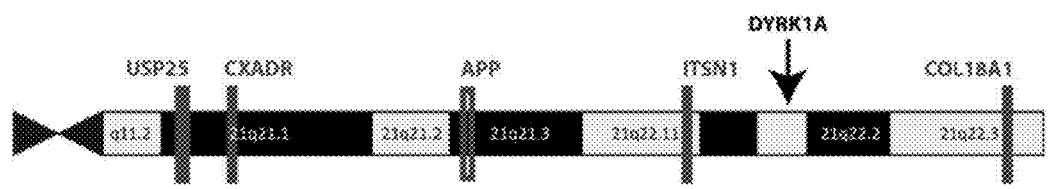

Next we examined the APP gene, which encodes amyloid beta precursor protein. Mutations in APP (causing accumulation of β-amyloid) lead to early onset familial Alzheimer disease (EOFAD)[32], and APP over-expression is linked to AD in DS as well[33]. RNA FISH data for APP are quantified in FIG. 4a. Without XIST induction, three bright RNA transcription foci for each allele were readily visualized. Brief XIST expression often resulted in incomplete repression of the targeted allele, which after 20 days was completely silenced in both independent clones (FIG. 4a).

Figure 4D:
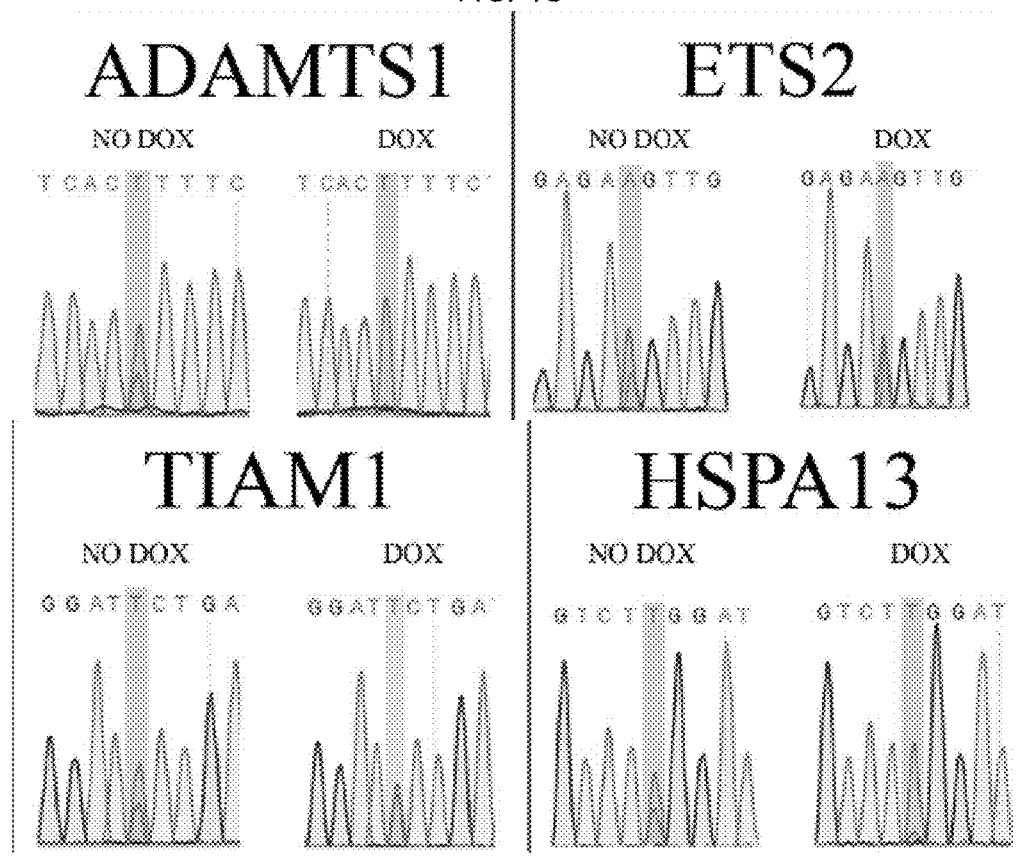
Figure 4E:
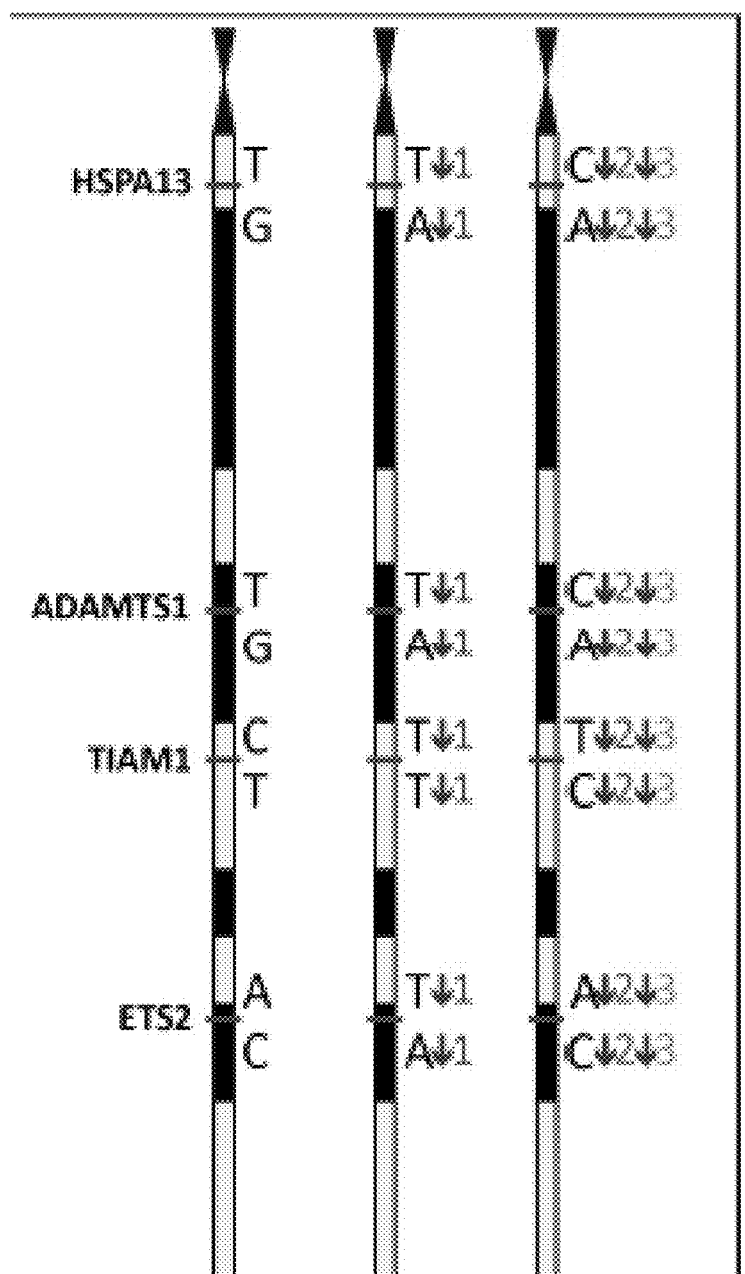

We extended this analysis to four more genes that ranged from 3 to 21 Mb from the XIST integration site (FIGS. 4b-c): ITSN1 (Intersectin-1), USP25, CXADR, and COL18A1. Complete silencing of the allele on the edited Chr21 was seen in ~100% of cells accumulating XIST RNA (FIG. 4b), demonstrating silencing of the XIST-associated allele. Allele-specific silencing was also validated using SNP analysis. RT-PCR products for eight known polymorphic sites (in four genes) were sequenced (ADAMTS1, ETS2, TIAM1, and HSPA13) (FIGS. 4d-e). Interestingly, clones 2 and 3 showed the identical pattern of eight SNP alleles repressed, whereas clone 1 showed an alternate pattern. As summarized in FIG. 4e, this chromosome-wide pattern allows extrapolation of the haplotype for each of the three Chr21s, and indirectly identifies for each clone which Chr21 homolog integrated XIST.

Figure 4F:
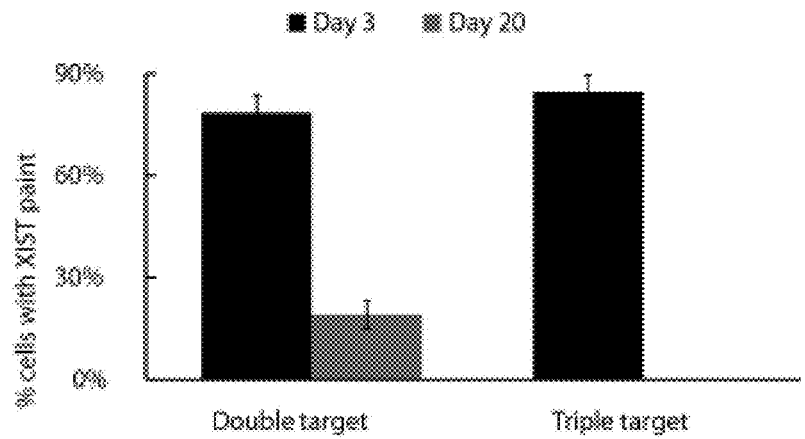

We also examined APP silencing in clones carrying XIST on two or all three copies of Chr21. After 20 days of dox, most or all cells carrying XIST on two or three Chr21s, respectively, no longer accumulated XIST RNA across the chromosome, and thus failed to silence the APP gene (FIG. 4f). These data argue there is in vitro selection against creating a functional monosomy or nullisomy, consistent with the lethality of any monosomy in vivo, and clinical observations that cells monosomic for Chr21 do not persist in mosaic patients.

Example 4

Genome-Wide Expression Analysis Demonstrates Transcriptional Repression Across the Edited Chr21

The above approaches demonstrate XIST RNA induces a heterochromatic Chr21 Barr Body and allele-specific repression for the nine genes examined, yet we extended this to include genome-wide expression profiling. Three independent transgenic clones and the parent line were treated with Dox for three weeks, and their transcriptome compared to parallel cultures without XIST-transcription, all in triplicate. Strikingly, only on Chr21 is there overwhelming change, in all three clones (FIG. 5a), with ~95% of genes significantly expressed showing repression (FIG. 5d).

Figure 5A:
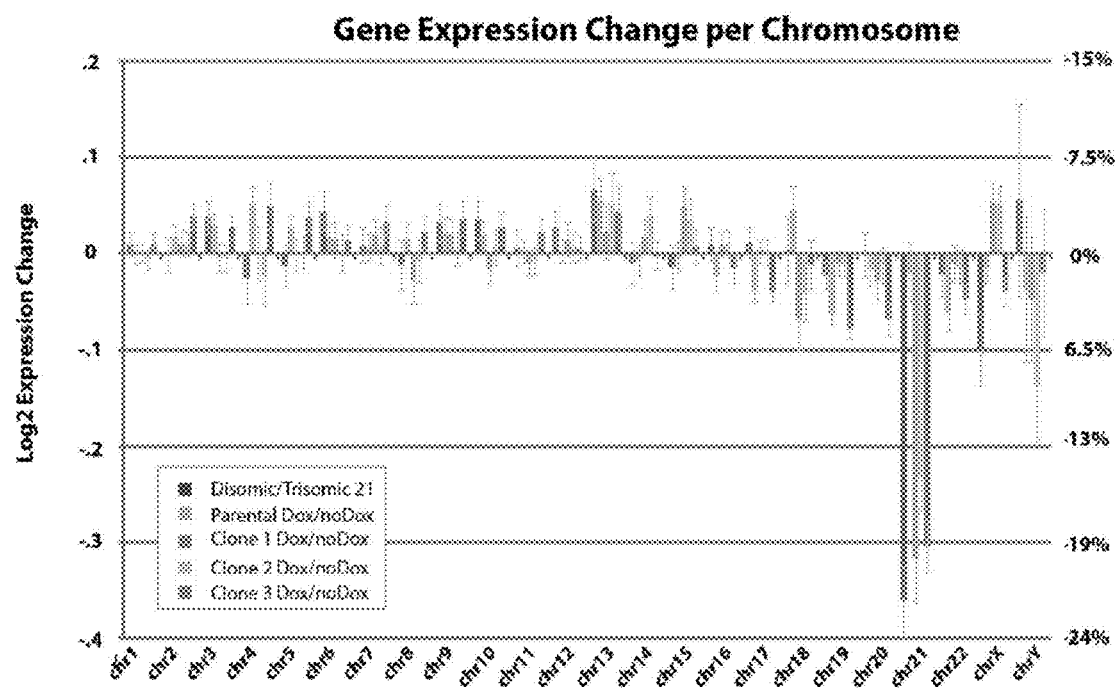
FIGS. 5A-D. Genomic expression profiling with RNA microarray and methylation levels shows widespread silencing of genes across Chr21. a. Microarray: Gene expression of parallel cultures grown with and without Dox treatment (Dox/no Dox) in clones 1, 2 &3 was compared to normal male iPS (euploid) and trisomy 21 (untargeted parent line) iPS cells (disomic/trisomic above). Total change in gene expression (N=3) per chromosome shows correction to disomic levels for XIST-expressing sub-clones on Chr21 with only limited changes on other chromosomes. Right Y-axis is scaled to reflect percent of gene expression change b. Distribution of individual repressed genes across Chr21 and corresponding level of repression for Clone 3 (Dox/no Dox) and Disomic/Trisomic. c. Methylation analysis: Genes with CpG island promoters are colored based on the levels of methylation after 22 days of Dox induction. Grey: decrease in methylation, green: no change in methylation, and red: increase in methylation. Ideograms (shown to the left of each heatmap) denote the location of genes (note: no gene probes unique to short arm of Chrs 21 and 22). Length of each chromosome is proportional to the number of gene promoters with CpG islands. Of the 143 individual Chr21 genes that had CpG islands in their promoters, 97-98% in both clones increased methylation by at least 5% (approximately two-fold increase over the average), compared to none in the parent line. d. Relative expression levels of eight genes on Chr21 by qRT-PCR for Clone 3. All 8 genes showed repression. Mean±SE from triplicate samples.
Figure 5B:
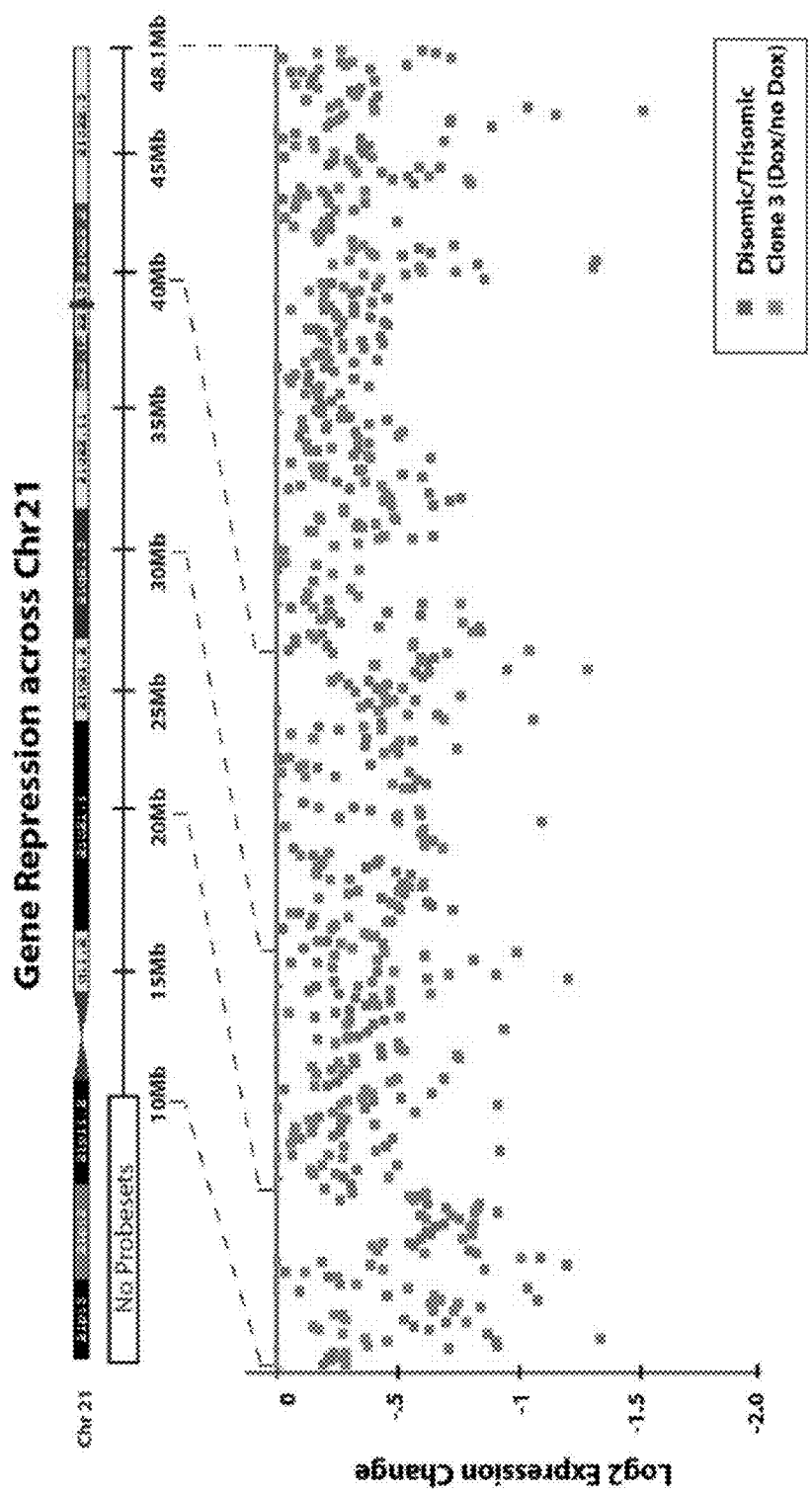
Figure 5C:
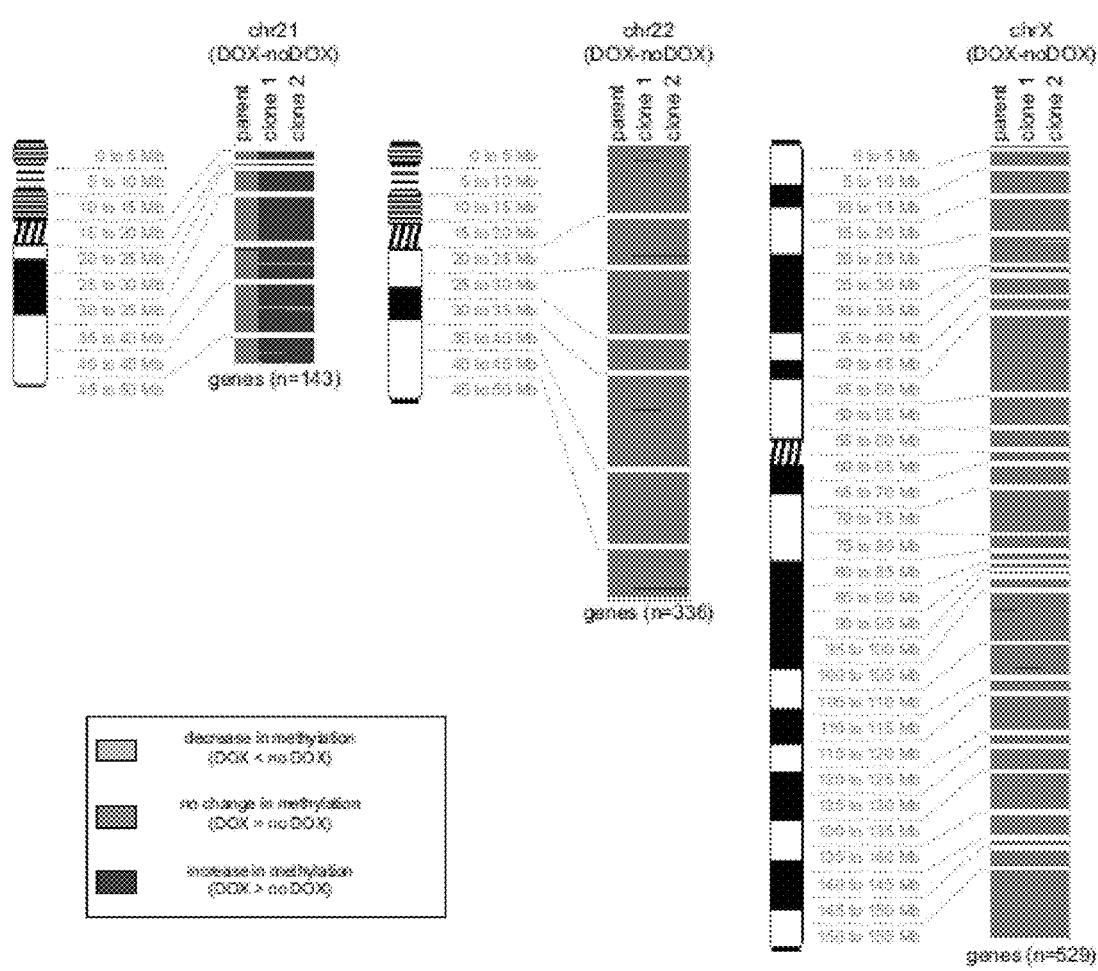
Figure 5D:
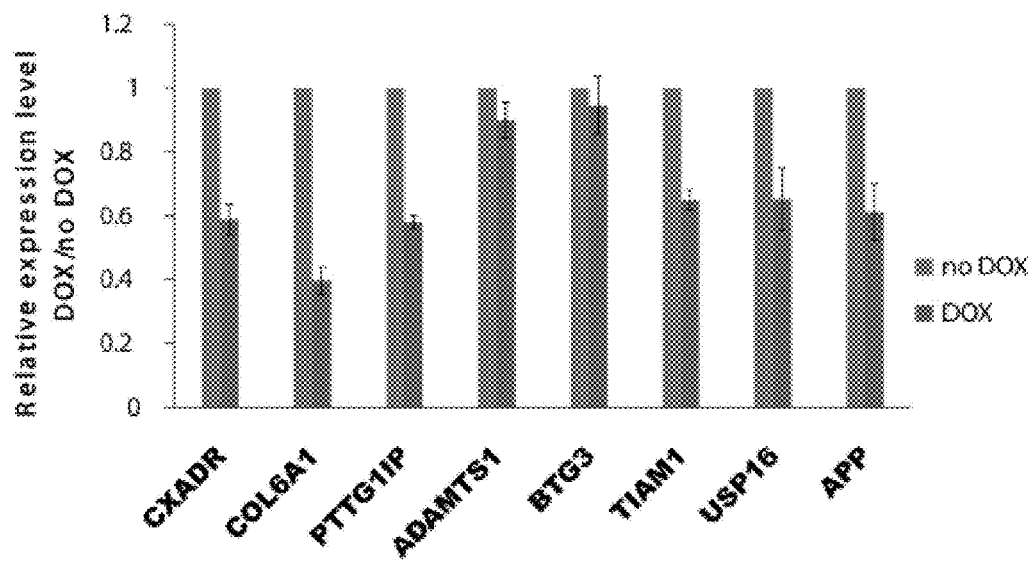

FIG. 5a summarizes the key finding that dosage compensation of trisomy corrects Chr21 expression to near normal disomic levels. This is based on calculation of the change in total output of expressed genes per chromosome after XIST is induced. Since evidence indicates that many Chr21 genes are not increased to the theoretical maximum of 1.5 fold in trisomic cells ([34-36] and further explained above), we included a direct comparison to trisomic versus disomic cells; this provides a baseline to evaluate the degree to which Chr21 over-expression is corrected by XIST-mediated silencing. After XIST induction, overall Chr21 expression is reduced by 20%, 15%, and 19% for clones 1, 2, and 3, respectively; this mirrors very well the 22% reduction for disomic iPS cells that lack the third Chr21 altogether (FIG. 5a). This disomic iPS line is representative, as a similar (21%) Chr21 difference was seen for another isogenic disomic sub-clone recently isolated from the parental DS iPS cells. FIG. 5b shows that individual genes repressed by XIST distribute across Chr21, as do genes over-expressed in trisomic versus disomic cells. In addition, qRT-PCR confirmed repression for all eight Chr21 genes examined (FIG. 5d). Taken together, these results clearly demonstrate that XIST induces robust dosage compensation of most over-expressed genes throughout the length of Chr21.

Trisomy 21 likely has broader impact on genomic expression pathways (e.g., [36]), but the differences attributable to trisomy 21 are confounded by genetic and epigenetic variability. This inducible trisomy correction system provides a new foothold into that important question. For example, microarray profiles of our three independent transgenic sub-clones reveal that even these isogenic sub-clones show many expression differences (>1000) throughout the genome, but upon XIST induction, a smaller cohort of genes (~200) change in common in all three clones (but not the dox-treated parental line); this cohort is more likely due to Chr21 over-expression. While not our focus here, these findings support the promise for "trisomy correction in a dish" as a means to identify genome-wide pathways perturbed by trisomy of Chr21.

Example 5

Chromosome-Wide Methylation of Genes on the XIST-Carrying Chr21

X-inactivation in female cells is further stabilized by hypermethylation of DNA in promoter CpG islands[37-39], which occurs late in the silencing process. Therefore, we examined the promoter methylome in two independent genome-edited clones three weeks after XIST induction. The global promoter methylome remained largely unaltered, with one striking exception (P-value<2.2e-16): the genes on Chr21 (FIG. 5c). Here, 97% of CpG-island-containing genes exhibited a robust increase in promoter DNA methylation on Chr21, within the range of that seen for Xi[37] (when adjusted for the number of active versus silenced chromosomes: see Methods). This change swept across the entire chromosome (FIG. 5c), strongly reinforcing above analyses on gene expression. Interestingly, the fact that a small subset of specific genes "escape" methylation on Chr21 in both clones demonstrates the impact of DNA sequence on XIST-mediated silencing (as long suggested[15,18,40] and reviewed in[41]).

The sum total of data, from eight different approaches, demonstrates an impressive competence of most sequences across Chr21 to undergo epigenetic modification and silencing in response to XIST RNA, an RNA evolved to silence the X-chromosome.

Example 6

Chr21 Dosage Compensation Impacts Cell Phenotype to Enhance Cell Proliferation and Neural Rosette Formation Correction of whole chromosome imbalance by manipulating just one gene presents a new paradigm, with opportunities to advance DS research in multiple directions. Currently, the specific cellular processes perturbed by trisomy 21 which generate patient pathology are largely unknown. Inducing trisomy silencing in parallel cultures of otherwise identical cells may reveal cellular pathologies due to trisomy 21, which could be obscured by differences between cell isolates. To address whether an impact in cell phenotype could be discerned, we examined two properties—cell proliferation and neural rosette formation.

Figure 6A:
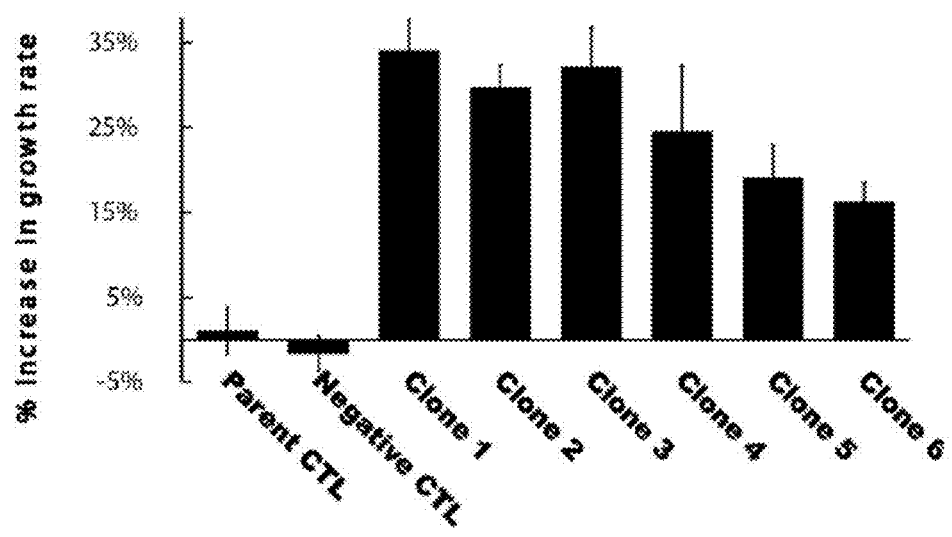
FIGS. 6A-C. "Trisomy correction" in vitro has marked effects on cell proliferation and neurogenesis, and is stable upon removal of XIST RNA. a. Changes in cell number for parent line, non-transgenic DS subclone (negative control), and six transgenic lines after 1 week of +/−Dox treatment. Mean±SE. (n=4-6). b. Quantification of number of neural rosettes at days 14 and 17 for two clones. Mean±SE from 10-12 random fields in triplicate. c. Gene silencing is stable following withdrawal of XIST RNA in cortical neurons. Transgenic cells were treated with Dox for 70 days and then Dox was removed for 30 days. Only two APP RNA transcription foci are present, as seen, with or without Dox. Mean±SE from 100 nuclei.

There is some evidence of proliferative impairment in DS[42,43], however we found this was variable between DS fibroblast cell samples, and highly sensitive to culture history and population doublings. However, a clear answer emerged from comparing multiple transgenic clones, grown in the presence or absence of doxycycline for one week. Initial analysis of clones 1 and 2 in triplicate indicated that XIST-induction rapidly resulted in larger, more numerous and more tightly packed cell colonies. This analysis was repeated for six independent transgenic sub-clones, the parental line, and a trisomic sub-clone, each replicated 4-6 times, minimizing technical variations in plating and counting iPS cells (Methods). All transgenic clones showed larger, more tightly packed colonies after just seven days of XIST induction, which contained 18-34% (average 26%) more cells than uninduced cultures (FIG. 6a). In contrast, Dox did not enhance growth of the parental DS cells or sub-clone (FIG. 6a). Thus, a proliferative impairment linked to Chr21 over-expression can be rapidly ameliorated by dosage compensation. Interestingly, this effect is not dependent on DYRK1A silencing[27,28], since the DYRK1A locus is disrupted irrespective of XIST expression.

Figure 6B:
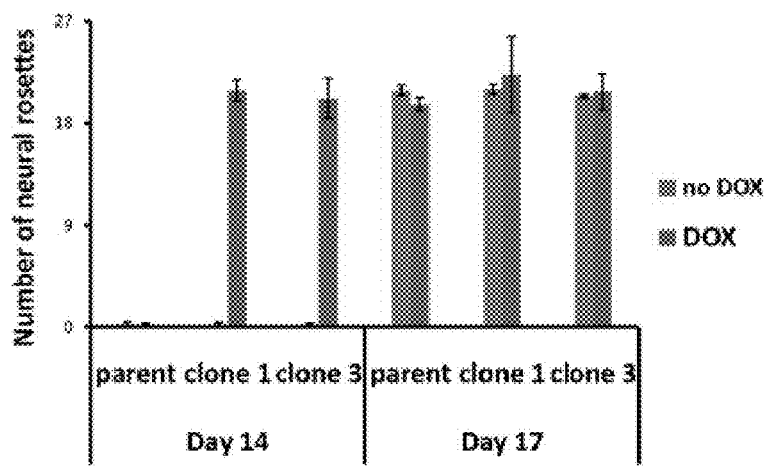
Figure 6C:
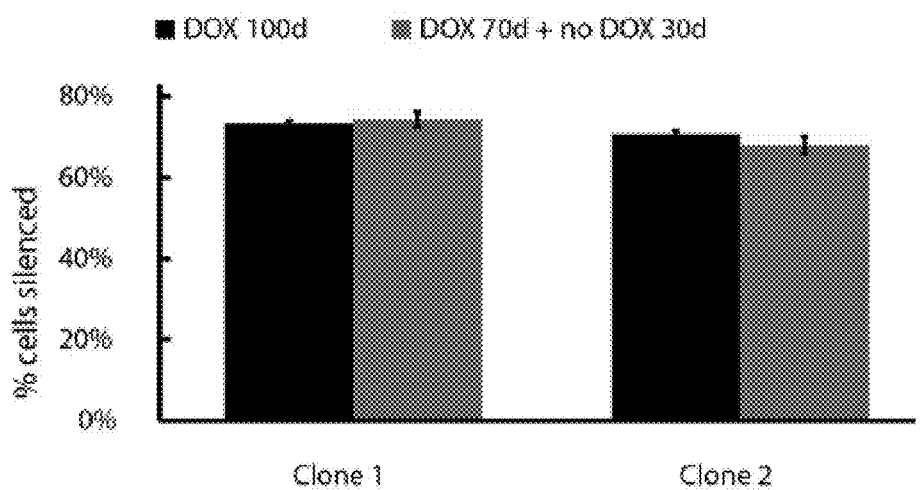

We next examined differentiation into neural progenitor cells, using a protocol to derive cortical neurons[44]. Six replicate cultures for the parental DS iPSC line and clones 1 and 3 were grown to confluency, placed in neural differentiation medium, and half of the identical samples induced to express XIST. Just 11-12 days after neural induction, all XIST-expressing cultures (in triplicate for both clones) began to form neural rosettes, and in 1-2 days were replete with neural rosettes. These cell structures are a signature of neural progenitors, and were confirmed by expression of Pax6 and Sox1. Remarkably, even at day 14, parallel uninduced cultures were still devoid of any neural rosettes (FIG. 6b). Thus uncorrected cultures required 4-5 more days in neural-induction media to fill with neural rosettes of similar size and number, as they did on day 17 (FIG. 6b). This difference is due to XIST, as there was no effect of Dox on neurogenesis in the parental DS line. This marked delay in neural differentiation appears primarily independent of cell proliferation (Methods). A similar difference occurred in repeat experiments with clones 1 and 2. Variability in the kinetics of neural differentiation that exists between various iPS cell lines[45] would likely obscure differences due to trisomy 21. We circumvented this using parallel cultures and on-demand Chr21 silencing, which made clear these important phenotypic differences.

These data highlight the potential of this new experimental model to identify and study cellular pathologies directly attributable to over-expression of Chr21 in iPSCs and their differentiated progeny.

Example 7

Stable Chr21 Silencing and Successful Targeting of XIST in DS Primary Fibroblasts Finally, we briefly consider two points relevant to any future potential for ex vivo or in vivo therapeutic strategies. While a constitutively expressed XIST transgene could be used, it is advantageous if the heterochromatic state induced by XIST RNA is stably maintained, even if XIST is no longer expressed (as reported in mouse[46]). We tested this in our human Chr21 system by removing dox and XIST expression for 30 days, after iPS cells had silenced Chr21 and differentiated to neurons. As shown (FIG. 6c), APP gene silencing remained indistinguishable between cultures with and without continued XIST expression, supporting other evidence that in somatic cells multi-layered chromatin modifications triggered by XIST maintain a largely irreversible silent state [39,47].

Finally, we considered the forward-looking question of whether targeted XIST addition could be achieved in primary human cells, as tested in non-immortalized female DS fibroblasts. Surprisingly, in our first attempt we generated not a few sub-clones but a sparse monolayer of edited fibroblasts, most of which carried XIST on Chr21. Due to limited lifespan, these cells were not examined in depth, but notably many showed enrichment of H3K27me3, H3K20me, and UbH2A at the transgene site. This is consistent with evidence that chromosome silencing does not necessarily require the optimal pluripotent cell context. Although pluripotent cells clearly have the optimal capacity to rapidly and fully silence chromatin in response to XIST RNA (Wutz et al., Mol Cell 5, 695-705 (2000)), several observations indicate the pluripotent cell context is not necessarily required. For example, random integration of an XIST transgene into human HT1080 cells (a transformed cell line) produced a robust Barr Body (on a Chr4 autosome), although this took longer than in pluripotent cells (Hall et al., Proc Natl Acad Sci USA 99, 8677-8682. (2002)). Similarly, gene silencing has been seen in other somatic cell lines (Chow et al., Cytogene Genome Research 99, 92-98 (2002); Chow et al., Genomics 82, 309-322 (2003)). Savarese et al. (Mol Cell Biol 26, 7167-7177 (2006)) reported that hematopoietic cells in mouse bone marrow are still capable of Xist-mediated chromosomal inactivation. The Wutz lab also reported that addition of SATB1 to mouse fibroblasts can enhance their ability to silence chromatin in response to XIST RNA (Dev Cell 16, 507-516 (2009)). Data herein suggests that primary human fibroblasts still exhibit significant capacity to induce heterochromatin modifications in response to XIST. In addition, we have data in differentiated mouse and human ES/iPS cells that demonstrate cells in the neuronal pathway can silence chromatin in response to XIST RNA. Finally, our XIST transgene lacks X-chromosome "counting" sequences, and thus is compatible with natural X-inactivation in female cells.

Example 8

Targeting XIST to Alternative Locations on Chr.21: Targeting RCAN1

Figure 7A:
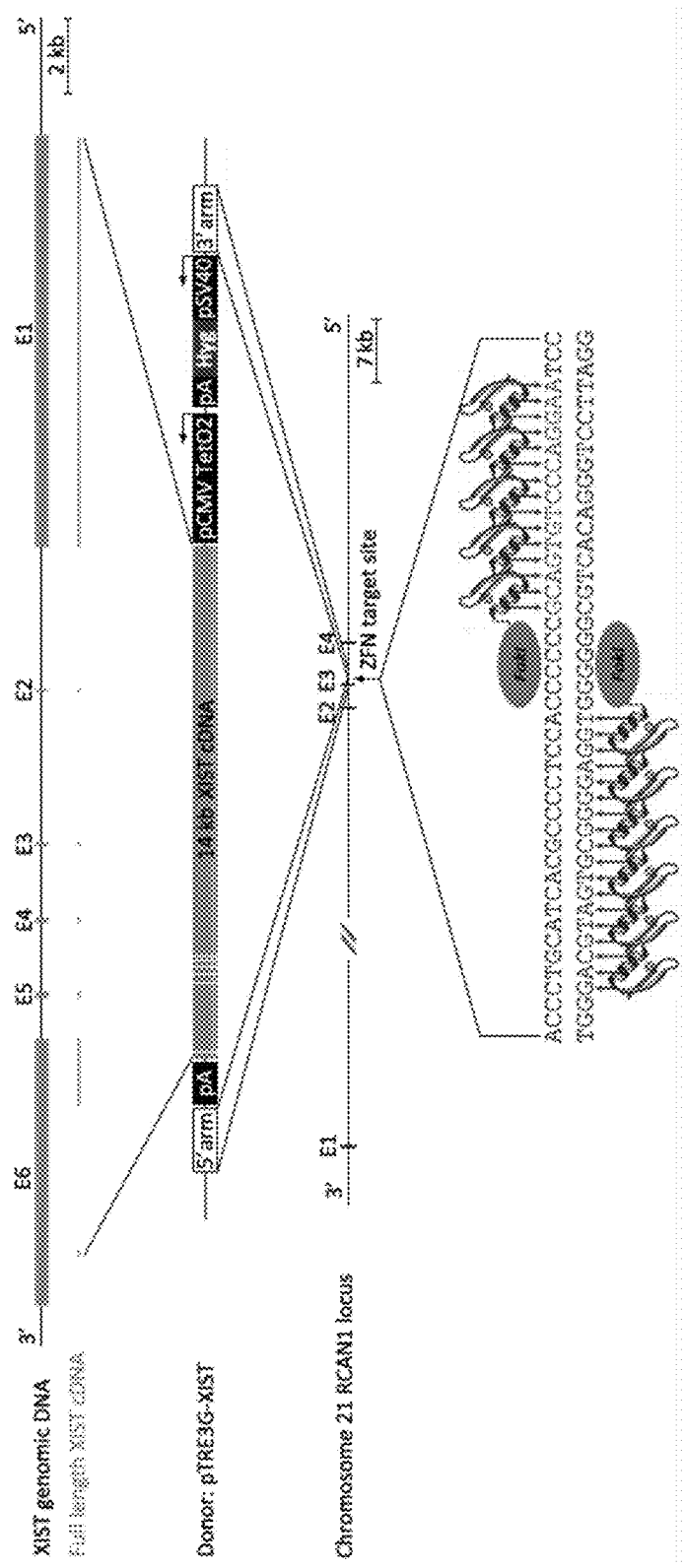
FIGS. 7a-c. RCAN1 targeting constructs. a. Schematic and (FIG. 7A discloses SEQ ID NO: 43) b. plasmid map show that the 21.1 kb selectable and inducible human XIST construct contains two homologous arms (left arm, 759 bp; right arm, 758 bp), a hygromycin selection gene, and a 14 kb full length XIST cDNA driven by a tetracycline operator inducible promoter. The specifically designed ZFN cuts the intron 3 of RCAN1 gene on Chr 21. c. Plasmid map showing the 14.0 kb selectable and inducible human XIST construct contains two homologous arms (left arm, 759 bp; right arm, 758 bp), a hygromycin selection gene, and a 6.8 kb exon 1 of human XIST cDNA driven by a tetracycline operator inducible promoter. The 6.8 kb XIST transgene is targeted the RCAN1 gene on Chr 21 by ZFNs (as shown in schematic of FIG. 7b).
Figure 7B:
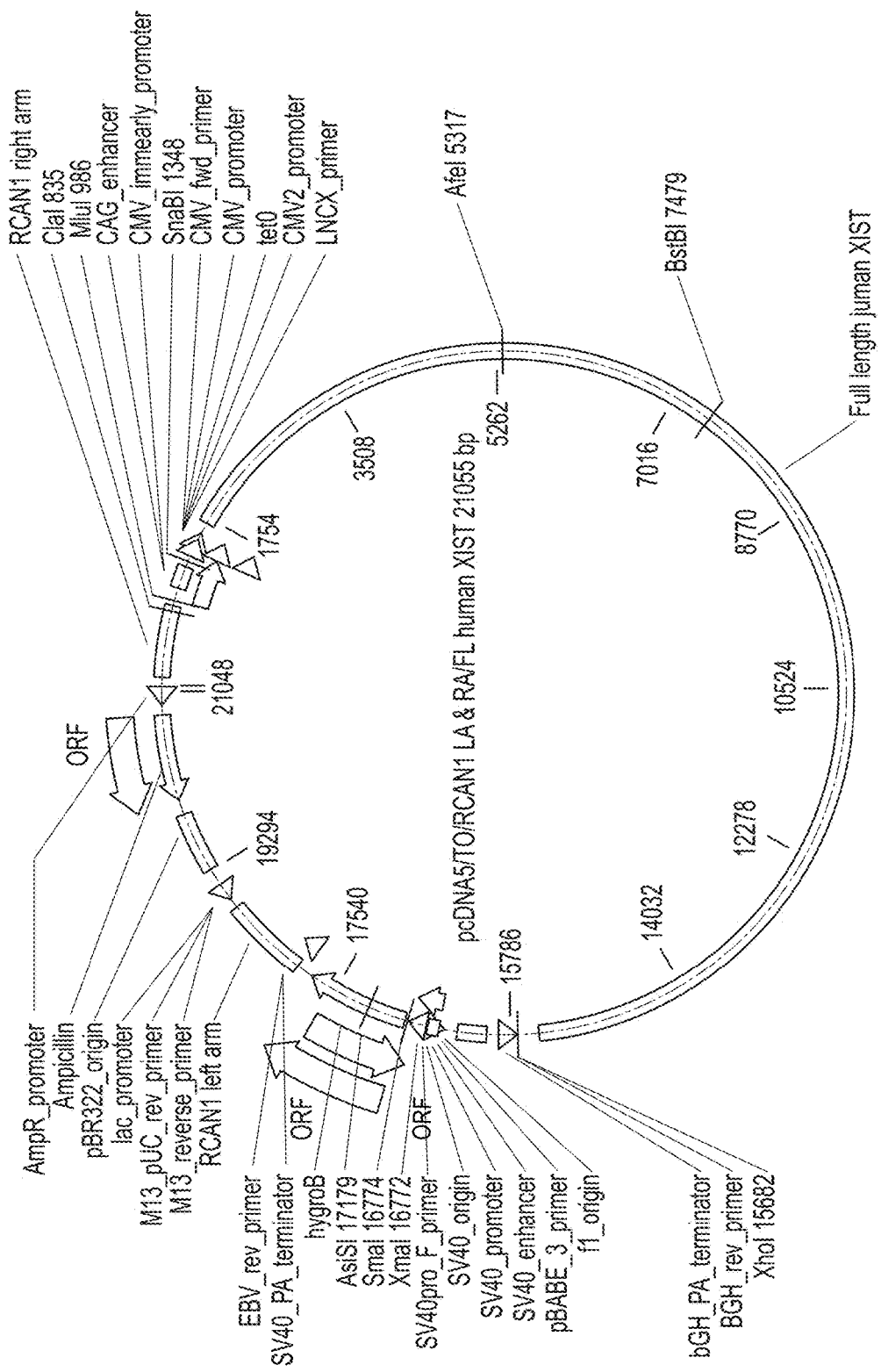
Figure 7C:
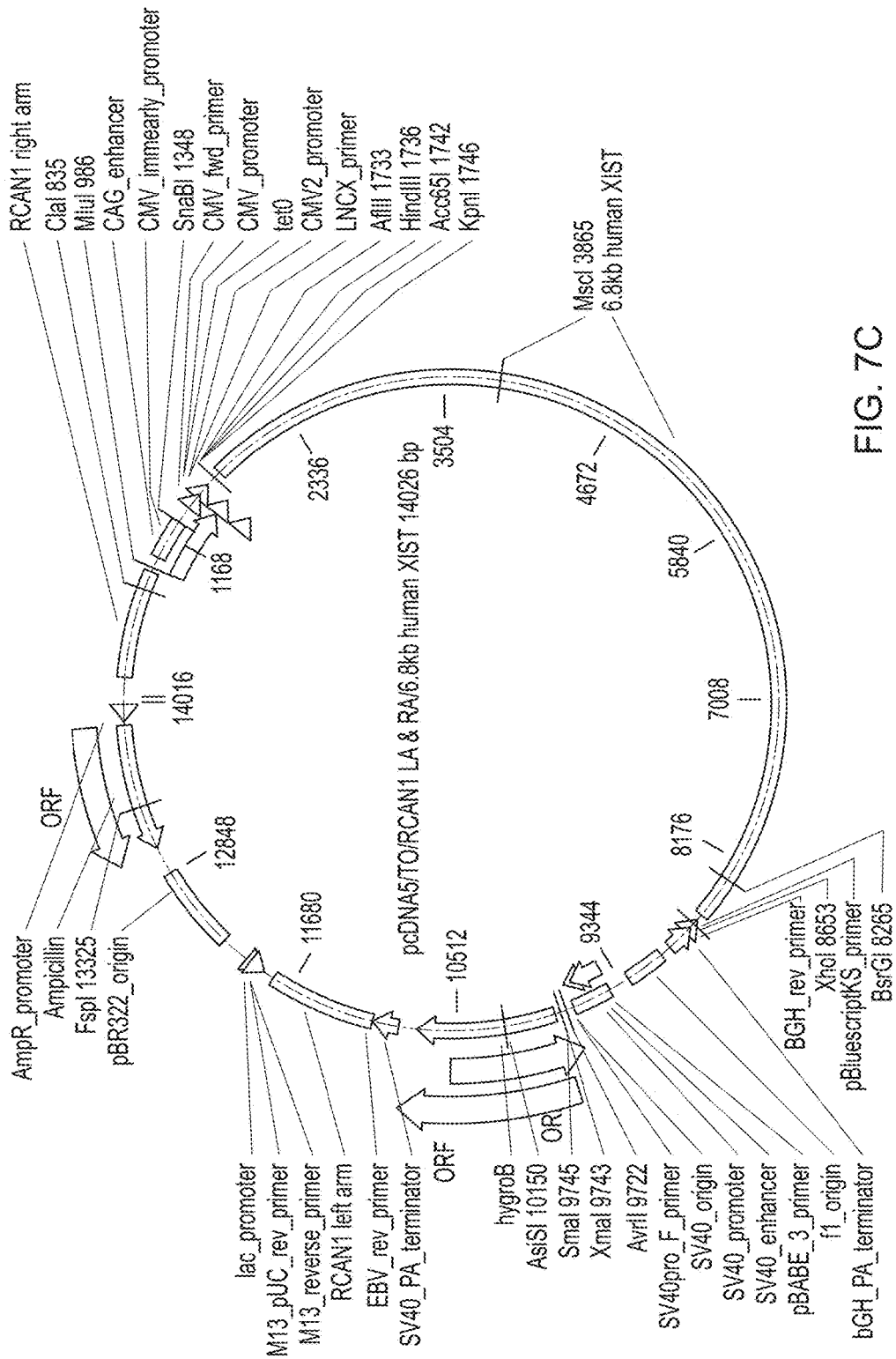
Figure 8A:
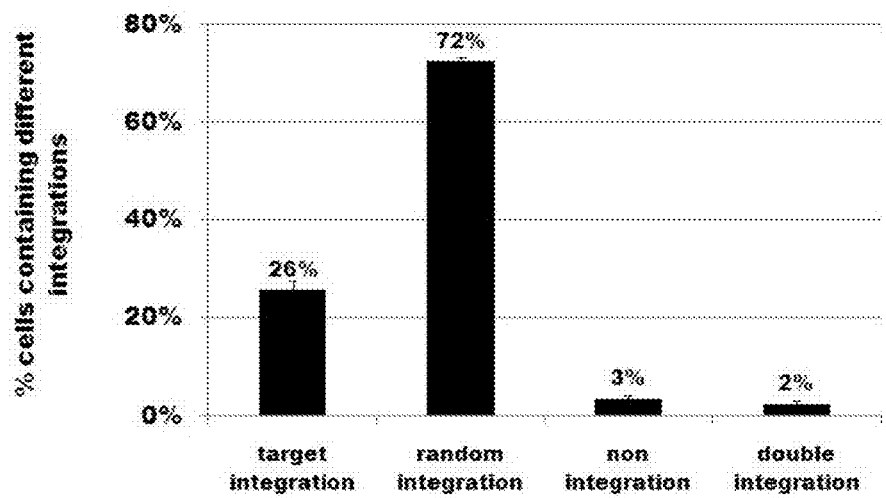
FIGS. 8a-f. ZFN Targeting XIST to RCAN1 a. Cells containing the FL XIST transgene construct shown in FIGS. 7a-b targeted to RCAN1 locus on chr. 21 at metaphase. Graph shows quantification of cells containing different integrations. N=145 cells. b-c, Cells containing the FL XIST transgene targeted to RCAN1 locus on chr. 21 at interphase. b, Graph shows quantification of cells containing different integrations. c, Graph shows quantification of cells containing different localizations of XIST RNA. d-f. Cells containing the RCAN1 6.8 kb XIST transgene at interphase. d, Graph shows quantification of cells containing different integrations. e, Graph shows quantification of cells containing different integrations in the cells expressing XIST RNA. f, Graph shows quantification of cells containing different localizations of XIST RNA. The Distance between chr.21 BAC and RCAN1 gene is 2.3 M b.
Figure 8B:
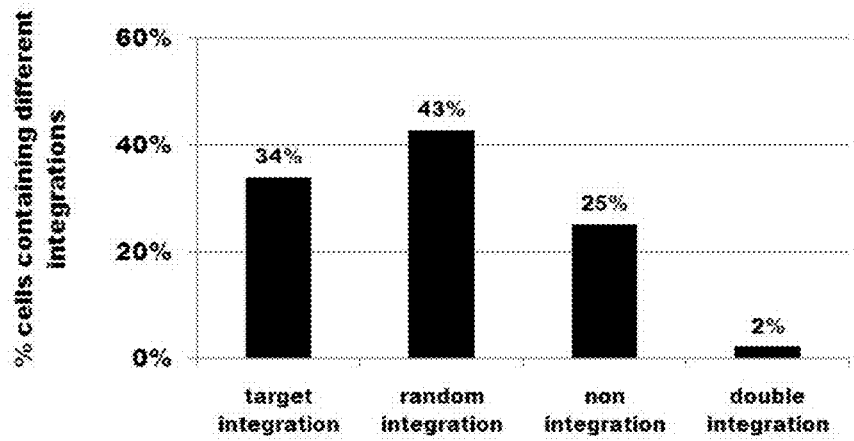
Figure 8C:
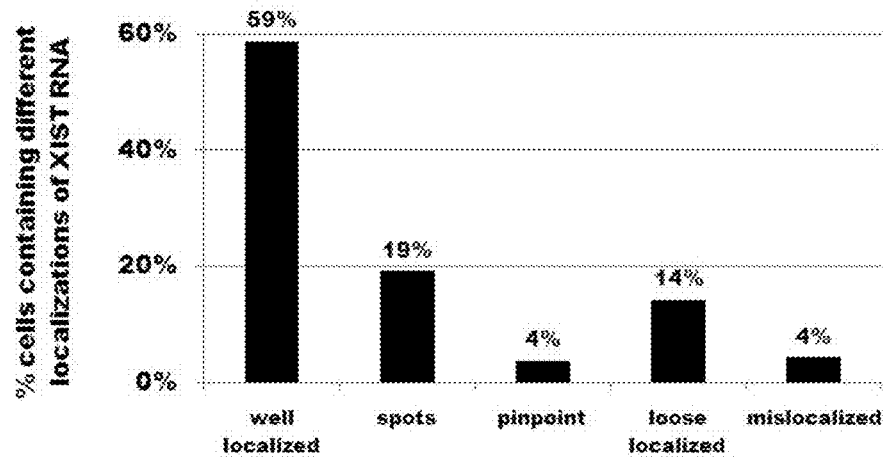
Figure 8D:
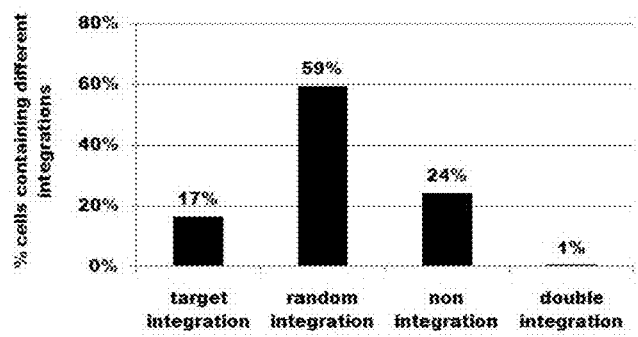
Figure 8E:
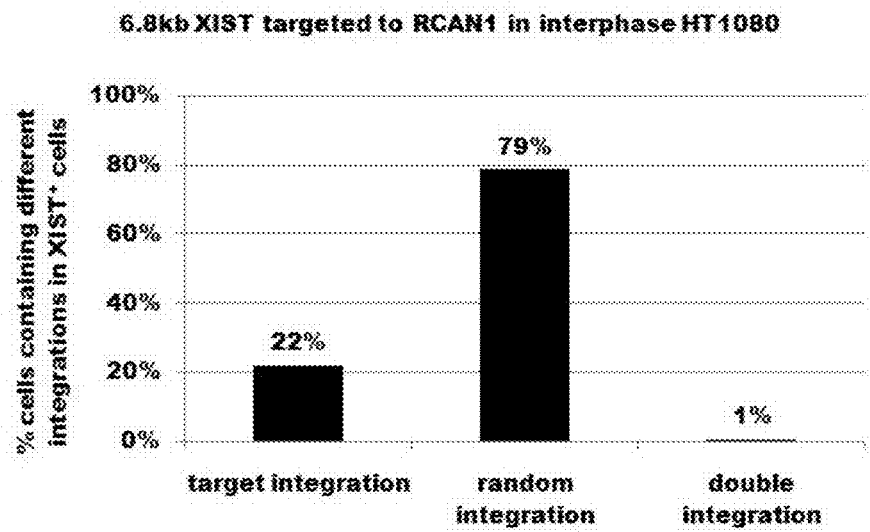
Figure 8F:
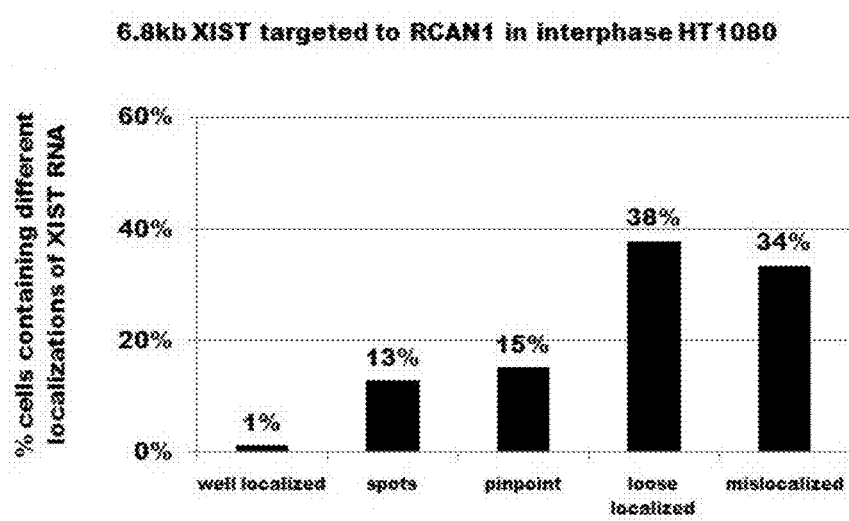

Methods as described above were used to create targeting constructs including the 6.8 kb inducible/selectable XIST transgene or the 14 kb full length XIST transgene as shown in FIGS. 7a-c. The lengths are shown in Table 4.

TABLE 4

| chr.21 RCAN1 targeting constructs | | | | |
|---|---|---|---|---|
| | Left arm | Right arm | Total construct length | Insert length between two arms |
| RCAN1 | 759 bp | 758 bp | 6.8 kb 14026 bp | 10108 bp |
| | | | FL 21055 bp | 17137 bp |

The constructs were introduced into cells as described above. Integration of the transgene and localization of XIST RNA were confirmed by interphase and metaphase FISH; the results are shown in FIGS. 8a-f. These data demonstrate the feasibility of using ZFN-driven genome editing to direct an entire or active XIST cassette to different loci of the "DS critical region" of Chr21.

REFERENCES

1 Antonarakis, S. E. & Epstein, C. J. The challenge of Down syndrome. Trends in molecular medicine 12, 473-479 (2006).
2 Megarbane, A. et al. The 50th anniversary of the discovery of trisomy 21: the past, present, and future of research and treatment of Down syndrome. Genetics in medicine: official journal of the American College of Medical Genetics 11, 611-616 (2009).
3 Prandini, P. et al. Natural gene-expression variation in Down syndrome modulates the outcome of gene-dosage imbalance. Am J Hum Genet. 81, 252-263 (2007).
4 O'Doherty, A. et al. An aneuploid mouse strain carrying human chromosome 21 with Down syndrome phenotypes. Science 309, 2033-2037 (2005).
5 Reeves, R. H. Down syndrome mouse models are looking up. Trends Mol Med 12, 237-240 (2006).
6 Liu, C. et al. Mouse models for Down syndrome-associated developmental cognitive disabilities. Dev Neurosci 33, 404-413 (2011).
7 Gardiner, K. J. Molecular basis of pharmacotherapies for cognition in Down syndrome. Trends Pharmacol Sci 31, 66-73 (2010).
8 Lyon, M. Gene Action in the X-chromosome of the Mouse (*Mus musculus* L.). Nature 190, 372-373 (1961).
9 Brown, C. J. et al. The human XIST gene: analysis of a 17 kb inactive X-specific RNA that contains conserved repeats and is highly localized within the nucleus. Cell 71, 527-542 (1992).
10 Clemson, C. M., McNeil, J. A., Willard, H. F. & Lawrence, J. B. XIST RNA paints the inactive X chromosome at interphase: Evidence for a novel RNA involved in nuclear/chromosome structure. J. Cell Biol. 132, 259-275 (1996).
11 Hall, L. L. & Lawrence, J. B. The cell biology of a novel chromosomal RNA: chromosome painting by XIST/Xist RNA initiates a remodeling cascade. Semin Cell Dev Biol 14, 369-378 (2003).
12 Heard, E. Delving into the diversity of facultative heterochromatin: the epigenetics of the inactive X chromosome. Curr Opin Genet Dev 15, 482-489 (2005).
13 Wutz, A. Gene silencing in X-chromosome inactivation: advances in understanding facultative heterochromatin formation. Nat Rev Genet. 12, 542-553 (2011).

14. Lee, J. T. Gracefully ageing at 50, X-chromosome inactivation becomes a paradigm for RNA and chromatin control. Nat Rev Mol Cell Biol 12, 815-826 (2011).
15. Bailey, J. A., Carrel, L., Chakravarti, A. & Eichler, E. E. Molecular evidence for a relationship between LINE-1 elements and X chromosome inactivation: the Lyon repeat hypothesis. Proc Natl Acad Sci USA 97, 6634-6639. (2000).
16. Brown, C. J., Carrel, L. & Willard, H. F. Expression of genes from the human active and inactive X chromosomes. Am J Hum Genet. 60, 1333-1343 (1997).
17. Carrel, L. & Willard, H. F. X-inactivation profile reveals extensive variability in X-linked gene expression in females. Nature 434, 400-404 (2005).
18. McNeil, J. A., Smith, K. P., Hall, L. L. & Lawrence, J. B. Word frequency analysis reveals enrichment of dinucleotide repeats on the human X chromosome and [GATA]n in the X escape region. Genome Res 16, 477-484 (2006).
19. Hall, L. L., Clemson, C. M., Byron, M., Wydner, K. & Lawrence, J. B. Unbalanced X; autosome translocations provide evidence for sequence specificity in the association of XIST RNA with chromatin. Hum Mol Genet. 11, 3157-3165. (2002).
20. Wutz, A. & Jaenisch, R. A shift from reversible to irreversible X inactivation is triggered during ES cell differentiation. Mol Cell 5, 695-705 (2000).
21. Hall, L. L. et al. An ectopic human XIST gene can induce chromosome inactivation in post differentiation human HT-1080 cells. Proc Natl Acad Sci USA 99, 8677-8682. (2002).
22. Lee, J. T., Strauss, W. M., Dausman, J. A. & Jaenisch, R. A 450 kb transgene displays properties of the mammalian X-inactivation center. Cell 86, 83-94 (1996).
23. Moehle, E. A. et al. Targeted gene addition into a specified location in the human genome using designed zinc finger nucleases. Proc Natl Acad Sci USA 104, 3055-3060 (2007).
24. Urnov, F. D., Rebar, E. J., Holmes, M. C., Zhang, H. S. & Gregory, P. D. Genome editing with engineered zinc finger nucleases. Nat Rev Genet. 11, 636-646 (2010).
25. DeKelver, R. C. et al. Functional genomics, proteomics, and regulatory DNA analysis in isogenic settings using zinc finger nuclease-driven transgenesis into a safe harbor locus in the human genome. Genome Research 20, 1133-1142 (2010).
26. Park, J., Song, W. J. & Chung, K. C. Function and regulation of Dyrk1A: towards understanding Down syndrome. Cellular and molecular life sciences: CMLS 66, 3235-3240 (2009).
27. Yabut, O., Domogauer, J. & D'Arcangelo, G. Dyrk1A overexpression inhibits proliferation and induces premature neuronal differentiation of neural progenitor cells. J Neurosci 30, 4004-4014 (2010).
28. Litovchick, L., Florens, L. A., Swanson, S. K., Washburn, M. P. & DeCaprio, J. A. DYRK1A protein kinase promotes quiescence and senescence through DREAM complex assembly. Genes & development 25, 801-813 (2011).
Gurdon, J. B. & Yamanaka, S. The Nobel Prize in Physiology or Medicine 2012, Available on the world wide web at nobelprize.org/nobel_prizes/medicine/laureates/2012/press.html (2012).
30. Park, I. H. et al. Disease-specific induced pluripotent stem cells. Cell 134, 877-886 (2008).
31. Clemson, C. M., Hall, L. L., Byron, M., McNeil, J. & Lawrence, J. B. The X chromosome is organized into a gene-rich outer rim and an internal core containing silenced nongenic sequences. Proc Natl Acad Sci USA 103, 7688-7693 (2006).
32. Tanzi, R. E. & Bertram, L. Twenty years of the Alzheimer's disease amyloid hypothesis: a genetic perspective. Cell 120, 545-555 (2005).
33. Webb, R. L. & Murphy, M. P. beta-Secretases, Alzheimer's Disease, and Down Syndrome. Curr Gerontol Geriatr Res 2012, 362839 (2012).
34. Biancotti, J. C. et al. Human embryonic stem cells as models for aneuploid chromosomal syndromes. Stem Cells 28, 1530-1540 (2010).
35. Lockstone, H. E. et al. Gene expression profiling in the adult Down syndrome brain. Genomics 90, 647-660 (2007).
36. Ait Yahya-Graison, E. et al. Classification of human chromosome 21 gene-expression variations in Down syndrome: impact on disease phenotypes. Am J Hum Genet. 81, 475-491 (2007).
37. Cotton, A. M. et al. Chromosome-wide DNA methylation analysis predicts human tissue-specific X inactivation. Human genetics 130, 187-201 (2011).
38. Sharp, A. J. et al. DNA methylation profiles of human active and inactive X chromosomes. Genome research 21, 1592-1600 (2011).
39. Csankovszki, G., Nagy, A. & Jaenisch, R. Synergism of Xist RNA, DNA methylation, and histone hypoacetylation in maintaining X chromosome inactivation. J. of Cell Biol. 153, p. 773-783 (2001).
40. Carrel, L. et al. Genomic environment predicts expression patterns on the human inactive X chromosome. PLoS Genet. 2, e151 (2006).
41. Hall, L. L. & Lawrence, J. B. XIST RNA and architecture of the inactive X chromosome: implications for the repeat genome. Cold Spring Harb Symp Quant Biol 75, 345-356 (2010).
42. Guidi, S., Ciani, E., Bonasoni, P., Santini, D. & Bartesaghi, R. Widespread proliferation impairment and hypocellularity in the cerebellum of fetuses with down syndrome. Brain Pathol 21, 361-373 (2011).
43. Haydar, T. F. & Reeves, R. H. Trisomy 21 and early brain development. Trends Neurosci 35, 81-91 (2012).
44. Shi, Y., Kirwan, P., Smith, J., Robinson, H. P. & Livesey, F. J. Human cerebral cortex development from pluripotent stem cells to functional excitatory synapses. Nat Neurosci 15, 477-486, S471 (2012).
45. Shi, Y. et al. A human stem cell model of early Alzheimer's disease pathology in Down syndrome. Sci Transl Med 4, 124ra129 (2012).
46. Csankovszki, G., Panning, B., Bates, B., Pehrson, J. R. & Jaenisch, R. Conditional deletion of Xist disrupts histone macroH2A localization but not maintenance of X inactivation [letter]. Nat Genet. 22, 323-324 (1999).
47. Ohhata, T. & Wutz, A. Reactivation of the inactive X chromosome in development and reprogramming. Cellular and molecular life sciences: CMLS (2012).
48. Li, L. B. et al. Trisomy correction in down syndrome induced pluripotent stem cells. Cell Stem Cell 11, 615-619 (2012).
49. Lavon, N. et al. Derivation of euploid human embryonic stem cells from aneuploid embryos. Stem cells 26, 1874-1882 (2008).
50. Morey, C. & Avner, P. The demoiselle of X-inactivation: 50 years old and as trendy and mesmerising as ever. PLoS genetics 7, e1002212 (2011).

51 Brockdorff, N. Chromosome silencing mechanisms in X-chromosome inactivation: unknown unknowns. Development 138, 5057-5065 (2011).

52 Minkovsky, A., Patel, S. & Plath, K. Concise review: Pluripotency and the transcriptional inactivation of the female Mammalian X chromosome. Stem cells 30, 48-54 (2012).

53 Hockemeyer, D. et al. Efficient targeting of expressed and silent genes in human ESCs and iPSCs using zinc-finger nucleases. Nat Biotechnol 27, 851-857 (2009).

54 Doyon, J. B. et al. Rapid and efficient clathrin-mediated endocytosis revealed in genome-edited mammalian cells. Nat Cell Biol (2011).

55 Miller, J. C. et al. An improved zinc-finger nuclease architecture for highly specific genome editing. Nat Biotechnol 25, 778-785 (2007).

56 Guschin, D. Y. et al. A rapid and general assay for monitoring endogenous gene modification. Methods in molecular biology 649, 247-256 (2010).

57 Urnov, F. D. et al. Highly efficient endogenous human gene correction using designed zinc-finger nucleases. Nature 435, 646-651 (2005).

58 Tam, R., Smith, K. P., and Lawrence, J. B. The 4q subtelomere harboring the FSHD locus is specifically anchored with peripheral heterochromatic unlike most human telomeres. Journal of Cell Biology 167, 269-279 (2004).

59 Irizarry, R. A. et al. Summaries of Affymetrix GeneChip probe level data. Nucleic acids research 31, e15 (2003).

60 Gardiner, K. Gene-dosage effects in Down syndrome and trisomic mouse models. Genome Biol 5, 244 (2004).

61 Antonarakis, S. E. & Epstein, C. J. The challenge of Down syndrome. Trends Mol Med 12, 473-479 (2006).

62 Antonarakis, S. E., Lyle, R., Chrast, R. & Scott, H. S. Differential gene expression studies to explore the molecular pathophysiology of Down syndrome. Brain Res Brain Res Rev 36, 265-274 (2001).

63 Tang, Y. et al. Blood expression profiles for tuberous sclerosis complex 2, neurofibromatosis type 1, and Down's syndrome. Ann Neurol 56, 808-814 (2004).

64 Weber, M. et al. Distribution, silencing potential and evolutionary impact of promoter DNA methylation in the human genome. Nat Genet. 39, 457-466 (2007).

65 Wang, Y. & Leung, F. C. An evaluation of new criteria for CpG islands in the human genome as gene markers. Bioinformatics 20, 1170-1177 (2004).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A silencing vector comprising:

a silencing element comprising a silencing sequence flanked by first and second targeting sequences, wherein the first and second targeting sequences target a sequence within intron 1 of the dual specificity tyrosine-phosphorylation-regulated kinase 1A (DYRK1A) gene comprising GCCACCCCTTTGC-CAGTTTACACGGGTGATGAGCAGGCTGTT (SEQ ID NO: 11), wherein the first targeting sequence consists of SEQ ID NO:12 or 14, and/or the second targeting sequence consists of SEQ ID NO:13 or 15; and a promoter operably linked to the silencing element.

2. The silencing vector of claim 1, wherein the vector is a plasmid or a viral vector.

3. The silencing vector of claim 2, wherein the viral vector is vaccinia virus, adeno-associated virus (MV), or herpes virus.

4. The silencing vector of claim 1, wherein the silencing element comprises a human X inactive specific transcript (XIST) cDNA or functional fragment thereof.

5. The silencing vector of claim 4, further comprising a selectable marker sequence.

6. The silencing vector of claim 5, wherein the selectable marker sequence is operably linked to a promoter.

7. A silencing vector comprising SEQ ID NO: 45, 54, or 56.

8. A method of reducing levels of expression of genes on Chromosome 21 in a cell, the method comprising contacting the cell with the silencing vector of claim 1, under conditions sufficient for the silencing vector to undergo homologous recombination with the genomic DNA of the cell, wherein the silencing element is inserted into intron 1 of DYRK1A.

9. The method of claim 8, wherein the cell is trisomic for chromosome 21.

10. The method of claim 8, wherein the cell is a human cell.

11. The method of claim 10, wherein the cell is a stem cell or a fibroblast.

12. The method of claim 11, wherein the stem cell is an induced pluripotent stem cell (iPSC), a hematopoietic stem cell, or a neural stem cell.

13. An isolated cell produced by the method of claim 8.

14. A method of reducing the risk of transient myeloproliferative disorder (TMD) in a subject who has Down Syndrome (Trisomy 21), the method comprising:

obtaining a hematopoietic stem cell from the subject;

contacting the cell with the silencing vector of claim 1, under conditions sufficient for the silencing vector to undergo homologous recombination with the genomic DNA of the cell, wherein the silencing element is inserted into DYRK1A, to produce a modified cell having reduced levels of expression of genes on Chromosome 21; and administering the modified cell to the subject.

15. The method of claim 8, further comprising contacting the cell with a cleavage vector comprising a sequence that enhances or facilitates homologous recombination.

16. The method of claim 15, wherein the cleavage vector comprises a zinc finger nuclease (ZFN) or a transcription activator-like effector nuclease (TALEN).

17. The method of claim 15, wherein the cleavage vector comprises SEQ ID NO: 45, 54, or 56.

* * * * *

SEQUENCE LISTING

```
<160> NUMBER OF SEQ ID NOS: 59

<210> SEQ ID NO 1
<211> LENGTH: 13730
<212> TYPE: DNA
<213> ORGANISM: Homo sapiens

<400> SEQUENCE: 1
ctagaacatt ttctagtccc ccaacaccct ttatggcgta tttctttaaa aaaatcacct      60
aaattccata aaatatttt ttaaattcta tactttctcc tagtgtcttc ttgacacgtc     120
ctccatattt ttttaaagaa agtatttgga atattttgag gcaattttta atatttaagg    180 aattttctt tggaatcatt tttggtgaca tctctgtttt ttgtggatca gttttttact     240
cttccactct cttttctata ttttgcccat cggggctgcg gatacctggt tttattattt    300
tttctttgcc caacggggcc gtggatacct gccttttaat tcttttttat tcgcccatcg    360
gggccgcgga tacctgcttt ttattttttt ttccttagcc catcggggta tcggatacct    420
gctgattccc ttcccctctg aaccccaac actctggccc atcgggtga cggatatctg     480 ctttttaaaa attttcttt tttggcccat cgggcttcg gatacctgct ttttttttt      540 ttattttcct tgcccatcgg ggcctcggat acctgcttta attttgttt ttctgcccat     600 cggggccgcg gatacctgct ttgattttt tttttcatcg cccatcggtg cttttatgg     660 atgaaaaaat gttggttttg tgggttgttg cactctctgg aatatctaca ctttttttg    720 ctgctgatca tttggtggtg tgtgagtgta cctaccgctt tggcagagaa tgactctgca    780
gttaagctaa gggcgtgttc agattgtgga ggaaaagtgg ccgccatttt agacttgccg    840
cataactcgg cttagggcta gtcgtttgtg ctaagttaaa ctagggaggc aagatggatg    900
atagcaggtc aggcagagga agtcatgtgc attgcatgag ctaaacctat ctgaatgaat    960
tgatttgggg cttgttagga gctttgcgtg attgttgtat cgggaggcag taagaatcat   1020
```

```
cttttatcag tacaagggac tagttaaaaa tggaaggtta ggaaagacta aggtgcaggg    1080
cttaaaatgg cgattttgac attgcggcat tgctcagcat ggcgggctgt gctttgttag    1140
gttgtccaaa atggcggatc cagttctgtc gcagtgttca agtggcggga aggccacatc    1200
atgatgggcg aggctttgtt aagtggttag catggtggtg gacatgtgcg gtcacacagg    1260
aaaagatggc ggctgaaggt cttgccgcag tgtaaaacat ggcgggcctc tttgtctttg    1320
ctgtgtgctt ttcgtgttgg gttttgccgc agggacaata tggcaggcgt tgtcatatgt    1380
atatcatggc ttttgtcacg tggacatcat ggcgggcttg ccgcattgtt aaagatggcg    1440
ggttttgccg cctagtgcca cgcagagcgg gagaaaggt gggatggaca gtgctggatt    1500
gctgcataac ccaaccaatt agaaatgggg gtggaattga tcacagccaa ttagagcaga    1560
agatggaatt agactgatga cacactgtcc agctactcag cgaagacctg ggtgaattag    1620
catggcactt cgcagctgtc tttagccagt caggagaaag aagtggaggg gccacgtgta    1680
tgtctcccag tgggcggtac accaggtgtt ttcaaggtct tttcaaggac atttagcctt    1740
tccacctctg tcccctctta tttgtcccct cctgtccagt gctgcctctt gcagtgctgg    1800
atatctggct gtgtggtctg aacctccctc cattcctctg tattggtgcc tcacctaagg    1860
ctaagtatac ctcccccccc accccccaac cccccaact cccacccccc acccccacc    1920 ccccacctcc ccaccccct acccccctac cccctaccc ccctctggtc tgccctgcac    1980
tgcactgttg ccatgggcag tgctccaggc ctgcttggtg tggacatggt ggtgagccgt    2040
ggcaaggacc agaatggatc acagatgatc gttggccaac aggtggcaga agaggaattc    2100
ctgccttcct caagaggaac acctacccct tggctaatgc tggggtcgga ttttgattta    2160
tatttatctt ttggatgtca gtcatacagt ctgattttgt ggtttgctag tgtttgaatt    2220
taagtcttaa gtgactatta tagaaatgta ttaagaggct ttatttgtag aattcacttt    2280
aattacattt aatgagtttt tgttttgagt tccttaaaat tccttaaagt ttttagcttc    2340
tcattacaaa ttccttaacc ttttttggc agtagatagt caaagtcaaa tcatttctaa    2400
tgttttaaaa atgtgctggt catttttcttt gaaattgact taactatttt cctttgaaga    2460
gtctgtagca cagaaacagt aaaaaattta acttcatgac ctaatgtaaa aaagagtgtt    2520
tgaaggttta cacaggtcca ggccttgctt tgttcccatc cttgatgctg cactaattga    2580
ctaatcacct acttatcaga caggaaactt gaattgctgt ggtctggtgt cctctattca    2640
gacttattat attggagtat ttcaattttt cgttgtatcc tgcctgccta gcatccagtt    2700
cctccccagc cctgctccca gcaaacccct agtctagccc cagccctact cccacccggc    2760
cccagccctg ccccaggccc agtccctaa ccccccagcc ctaggccag tcccagtcct    2820 agttcctcag tctgtccagc ttctctcgaa agtcactcta attttcattg attcagtgct    2880
caaaataagt tgtccattgg tatcctatta tactgggata ttccgtttac ccttggcatt    2940
gctgatcttc agtactgact ccttgaccat tttcagttaa gcatacaatc ccatttgtct    3000
gtgatctcag gacaaagaat ttccttactc ggtacgttga agttagggaa tgtcaattga    3060
gagctttcta tcagagcatt attgcccaca atttgagtta cttatcattt tctcgatccc    3120
ctgcccttaa aggagaaacc atttctctgt cattgcttct gtagtcacag tcccaatttt    3180
gagtagtgat cttttcttgt gtactgtgtt ggccacctaa aactctttgc attgagtaaa    3240
attctaattg ccaataatcc tacccattgg attagacagc actctgaacc ccatttgcat    3300
tcagcagggg gtcgcagaca acccgtcttt tgttggacag ttaaaatgct cagtcccaat    3360
```

```
tgtcatagct ttgcctatta aacaaaggca ccctactgcg cttttttgctg tgcttctgga    3420 gaatcctgct gttcttggac aattaaagaa caaagtagta attgctaatt gtctcaccca    3480
ttaatcatga agactaccag tcgcccttgc atttgccttg aggcagcgct gactacctga    3540
gatttaagag tttcttaaat tattgagtaa aatcccaatt atccatagtt ctgttagtta    3600
cactatggcc tttgcaaaca tctttgcata acagcagtgg gactgactca ttcttagagc    3660
cccttccctt ggaatattaa tggatacaat agtaattatt catggttctg cgtaacagag    3720
aagacccact tatgtgtatg cctttatcat tgctcctaga tagtgtgaac tacctaccac    3780
cttgcattaa tatgtaaaac actaattgcc catagtccca ctcattagtc taggatgtcc    3840
tctttgccat tgctgctgag ttctgactac ccaagtttcc ttctcttaaa cagttgatat    3900
gcataattgc atatattcat ggttctgtgc aataaaaatg gattctcacc ccatcccacc    3960
ttctgtggga tgttgctaac gagtgcagat tattcaataa cagctcttga acagttaatt    4020
tgcacagttg caattgtcca gagtcctgtc cattagaaag ggactctgta tcctatttgc    4080
acgctacaat gtgggctgat cacccaagga ctcttcttgt gcattgatgt tcataattgt    4140
atttgtccac gatcttgtgc actaacccct ccactccctt tgtattccag caggggaccc    4200
ttactactca agacctctgt actaggacag tttatgtgca caatcctaat tgattagaac    4260
tgagtctttt atatcaaggt ccctgcatca tctttgcttt acatcaagag ggtgctggtt    4320
acctaatgcc cctcctccag aaattattga tgtgcaaaat gcaatttccc tatctgctgt    4380
tagtctgggg tctcatcccc tcatattcct tttgtcttac agcagggggt acttgggact    4440
gttaatgcgc ataattgcaa ttatggtctt ttccattaaa ttaagatccc aactgctcac    4500
accctcttag cattacagta gagggtgcta atcacaagga catttctttt gtactgttaa    4560
tgtgctactt gcatttgtcc ctcttcctgt gcactaaaga ccccactcac ttccctagtg    4620
ttcagcagtg gatgacctct agtcaagacc tttgcactag gatagttaat gtgaaccatg    4680
gcaactgatc acaacaatgt cttcagatc agatccattt tatcctcctt gttttacagc    4740
aagggatatt aattacctat gttacctttc cctgggacta tgaatgtgca aaattccaat    4800
gttcatggtc tctcccttta aacctatatt ctacccctt tacattatag aaagggatgc    4860
tggaaaccca gagtccttct cttgggactc ttaatgtgta tttctaatta tccatgactc    4920
ttaatgtgca tattttcaat tgcctaattg atttcaattg tctaagacat ttcaaatgtc    4980
taattgatta gaactgagtc ttttatatca agctaatatc tagcttttat atcaagctaa    5040
tatcttgact tctcagcatc atagaagggg gtactgattt cctaaagtct ttcttgaatt    5100
tctattatgc aaaattgccc tgaggccggg tgtggtggct cacacctgta atcccagcac    5160
tttgggaggc tgaggtggga agatccctta ctgccaggag tttgagacca gcctggccaa    5220
cattaaaaaa aaaaaaaaa gtaagacaat tgccctggaa tcccatcccc ctcacacctc    5280
cttggcaaag cagcaggagt gctaactagc tagtgcttct tctcttatac tgcttaaatg    5340
cgcataatta gcagtagttg atgtgcccct atgttagagt agaatcccgc ttccttgctc    5400
catttgcatt actgcaggag cttctaacta gcctgaattc actctcttgg actgttaatg    5460
tgcatactta tatttgctgc tgtactttt taccatgtaa ggaccccacc cactgtattt    5520
acatcccagc tggaagtacc tactacttaa gacccttaga ctagtaaagt tagcgtgcat    5580
aatcttaggt gttatataca cattttcagt tgcatacagt tgtgccttt atcaggactc    5640 ctgtacttat caaagcagag agtgctaatc aatattaagc ccttctcttc gaactgtaga    5700
tggcatgtaa ttgcagttgt caatggtcct tcaattagac ttgggtttct gacctatcac    5760
```

```
accctctttg ctttattgca tggggtacta ttcacttaag gccccttcct caaactgtta    5820
atgtgcctaa tgacaattac atcagtatcc ttccttttga aggacagcat ggttggtgac    5880
acctaaggcc ccatttcttg gcctcccaat atgtgtgatt gtatttgtcg aggttgctat    5940
gcactagaga aggaaagtgc tcccctcatc cccacttttc ccttccagca ggaagtgccc    6000
accccataag acccttttat ttggagagtc taggtgcaca attgtaagtg accacaagca    6060
tgcatcttgg acatttatgt gcgtaatcgc acactgctca ttccatgtga ataaggtcct    6120
actctccgac cccttttgca atacagaagg gttgctgata acgcagtccc cttttcttgg    6180
catgttgtgt gtgattataa tcgtctggga tcctatgcac tagaaaagga gggtcctctc    6240
cacataccct agtctcacct ttcccttcca gcagggagtg cccactccat aagactctca    6300
catttggaca gtcaaggtgc gtaattgtta agtgaacaca accatgcacc ttagacatgg    6360
atttgcataa ctacacacag ctcaacctat ctgaataaaa tcctactctc agacccctt    6420
tgcagtacag caggggtgct gatcaccaag gccctttttc ctggcctggt atgcgtgtga    6480
ttatgtttgt cccggttcct gtgtattaga catggaagcc tcccctgcca cactccaccc    6540
ccaatcttcc tttcccttcc ggcaggagtg ccctctccat aagacgctta cgtttggaca    6600
atcaaggtgc acagttgtaa gtgaccacag gcatacacct tggacattaa tgtgcataac    6660
cactttgccc attccatctg aataaggtcc tactctcaga ccccttttgc agtacagcag    6720
gggtgctgat caccaaggcc ccttttcttg gcctgttatg tgcgtgatta tatttgtctg    6780
ggttcctgtg tattagacaa ggaagccttc ccccgcccc cacccccact cccagtcttc    6840
ctttcccttc cagcagggag tgccccctcc ataagatcat tacatttgga caatcaaggt    6900
gcacaattat aagtgaccac agccatgcac cttggacatt attggacatt aatgtgcgta    6960
actgcacatg gcccatccca tctgaataag gacctactct cagatgcctt tgcagtacag    7020
cagggggtact gaatcaccaa ggcccttttt cttggcctgt tatgtgtgtg attatatttta    7080
tcccagttc tgtgtaatag acatgaaagc ctcccctgcc acccccacc tccaatcttc    7140
ctttcccttc caccagggag tgtccactcc atatacccctt acatttggac aatcaaggtg    7200
cacaattgta agtgagcata ggcactcacc ttggacatga atgtgcataa ctgcacatgg    7260
cccatcccat ctgaataagg tcctactctc agaccctttt tgcagtacag caggggtgct    7320
gatcaccaag gccccttttc ctggcctgtt atgtgtgtga ttatatttgt tccagttcct    7380
gtgtaataga catggaagcc tcccctgcca cactccaccc ccaatcttcc tttccttctg    7440
gcaggaagta cccgctccat aagacccttta catttggaca gtcaaggtgc acaattgtat    7500
gtgaccacaa ccatgcacct tggacataaa tgtgtgtaac tgcacatggc ccatcccatc    7560
tgaataaggt cctactctca gacccctttt gcagtacagt aggtgtgctg ataaccaagg    7620
cccctcttcc tggcctgtta acgtatgtga ttatatttgt ctgggttcca gtgtataaga    7680
catgaagcc tcccctgccc caccccaccc tcaatcttcc tttcccttct ggcagggagt    7740
gccagctcca taagaaccctt acatttggac agtcaaggtg cacaattcta agtgaccgca    7800
gccatgcacc ttggtcaata atgtgtgtaa ctgcacacgg cctatctcat ctgaataagg    7860
ccttactctc agaccccttt tgcagtacag caggggtgct gataaccaag gcccattttc    7920
ctggcctgtt atgtgtgtga ttatatttgt ccaggtttct gtgtactaga caaggaagcc    7980
tcctctgccc catcccatct acgcataatc tttcttttcc tcccagcagg gagtgctcac    8040
tccataagac ccttacattt ggacaatcaa ggtgcacaat tgtaagtgac cacaaccatg    8100
```

```
catcttggaa atttatgtgc ataactgcac atggcttatc ctatttgaat aaagtcctac   8160
tctcagaccc cctttgcagt atagctgggg tgctgatcac tgaggcctct ttgcttggct   8220
tgtctatatt cttgtgtact agataagggc accttctcat ggactccctt tgcttttcaa   8280
caaggagtac ccactacttt ttaagattct tatatttgtc caaagtacat ggttttaatt   8340
gaccacaaca atgtcccttg acattaatg tatgtaatca ccacatggtt catcctaatt    8400
aaacaaagtt ctaccttctc accctccatt tgcagtatac cagggttgct gaccccctaa   8460 gtccccttt cttggcttgt tgacatgcat aattgcattt atgttggttc ttgtgcccta    8520
gacaaggatg ccccacctct tttcaatagt gggtgcccac tccttatgat ctttacattt   8580
gaacagttaa tgtgaataat tgcagttgtc cacaaccctc tcacttctag gaccattata   8640
cctcttttgc attactgtgg ggtatactgt ttccctccaa ggccccttct ggtggactat   8700
caacatataa ttgaaatttt cttttgtctt tgtcagtaga ttaaggtcat accccatcac   8760
ctttcctttg tagtacaaca gggtgtcctg atcaaccaaa gtcctgttgt tttggactgt   8820
taatatgtgc aattacattt gctcctgatc tgtgcactag ataaggatcc tacctacttt   8880
cttagtgttt ttagcaggta gtgcccacta ctcaagactg tcacttggaa tgttcatgtg   8940
cacaaactca attctctaag catgttcctg taccaccttt gctttagagc aggggggatga  9000 tattcactaa gtgcccccttc ttttggactt aatatgcatt aatgcaattg tccacctctt  9060
cttttagact aagagttgat ctccacatat tcccccttgca tcaggggcat gttaattatg  9120
aatgaaccct tttctttttaa tattaatgtc ataattgtat tgtggaccct gtgtaggaga  9180
aaaagaccct atgttcctcc cattacccctt tggattgctg ctgagaagtg ttaactactc   9240
ataatctcag ctcttggaca attaatagca ttaataacaa ttatcaaggg cactgatcat   9300
tagataagac tcctgcttcc tcgttgctta catcgggggt actgacccac taaggcccct   9360
tgtactgtta atgtgaatat ttgcaattat atatgtctcc ttctggtaga gtgggatatt   9420 atgcccctagt atcccccttttg cattactgca ggggctgctg actactcaaa acttctcctg  9480
ggactgttaa taggcacaat ggcagttatc aatggttttc tccctccctg accttgttaa   9540
gcaagcgccc caccccaccc ttagttttccc atggcataat aaagtataag cattggagta   9600
ttccatgcac ttgtctatca aacagtggtc catactccca acccttttgc attgcgccag   9660
tgtgtaaaat cacaggtagc catggtgtca tgctttatat acgaagtctt ccctctctct   9720
gccccttgtg tgcccttggc cccttttttac agactattgc tcacaatctc aggtgtccat   9780
atttgcagct attaggtaag attgtgctgt ctccctcttc ccttccctct gccctgcccc   9840
ttttgcctct tgctgggta atgttgacca gacaaggccc tttctcttgg acttaaacaa   9900
ttctcagttg cactttcctt ggtccaccca ttatacatga acccctctac ttcctttcgc   9960
attgcttctg agtatgctga ctacccaaag ccccttctgt gttattaata aacacagtac  10020
tgattgtccc atttttcagc ccatcagtcc aagatctccc taccactttg gtgtgttggt  10080
gcagtgttga ctatgaaaag caggcctgaa ctaggtggat aagccttcac tcatttttctt 10140 tcatttatta atgatcctag tttcaattat tgtcagattc tggggacaag aaccattctt  10200
gcccacctgt gttactgctt tactgtgcaa aatactgaag gcaagtcaga cccagggagc  10260
tggattgcca tcctttattt tgtgtttcca gtgtacacta taaaattgtc tccccaggaa   10320
ggaaggttgg cactttctct gcattcttct ttccagagca gattgcctgg ttaagaatct  10380
cttgttgtcc cttctgtata ttgttattgt aaagtgccaa atgccaggat acagccagaa  10440
aaattgctta ttattattaa aaaaattttt ttaagaaaga catctggatt gtagggtgga  10500
```

```
ctcgataacc tggtcattat tttttgaag ccaaaatatc catttatact atgtacctgg   10560
tgaccagtgt ctctcatttt aactgagggt ggtgggtctg tggatagaac actgactctt   10620
gctattttaa tatcaaagat attctagatc cagcacagtg gcggccgctc tagagtggaa   10680
ctcttaagac cagtatcttt gtgtgggctt taccagcatt cacttttaga aaaactacct   10740
aaatttata  tccttaat   ttcttcatct ggagcacctg ccctactta  tttcaagaag   10800
attgcagtaa aacgattaaa tgagggaaca tatgcagagg tgcttttaaa aagcatatgc   10860
cacctttttt attaattatt atataaaatg aagcatttaa ttatagtaat aatttgaagt   10920
agtttgaagt accacactga ggtgaggact taaaaatgat aagacgagtt ccctatttta   10980
taagaaaaat aagccaaaat taaatattct tttggatata aatttcaaca gtgagatagc   11040
tgcctagtgg aaatgaataa tatcccagcc actagtgtac agggtgtttt gtggcacagg   11100
attatgtaat atggaactgc tcaagcaaat aactagtcat cacaacagca gttctttgta   11160
ataactgaaa aagaatattg tttctcggag aaggatgtca aaagatcggc ccagctcagg   11220
gagcagtttg ccctactagc tcctcggaca gctgtaaaga agagtctctg gctctttaga   11280
atactgatcc cattgaagat accacgctgc atgtgtcctt agtagtcatg tctccttagg   11340
ctcctcttgg acattctgag catgtgagac ctgaggactg caaacagcta taagaggctc   11400
caaattaatc atatctttcc ctttgagaat ctggccaagc tccagctaat ctacttggat   11460
gggttgccag ctatctggag aaaaagatct tcctcagaag aataggcttg ttgttttaca   11520
gtgttagtga tccattccct ttgacgatcc ctaggtggag atggggcatg aggatcctcc   11580
agggaaaag  ctcactacca ctgggcaaca accctaggtc aggaggttct gtcaagatac   11640
tttcctggtc ccagatagga agataaagtc tcaaaaacaa ccaccacacg tcaagctctt   11700
cattgttcct atctgccaaa tcattatact tcctacaagc agtgcagaga gctgagtctt   11760
cagcaggtcc aagaaatttg aacacactga aggaagtcag ccttcccacc tgaagatcaa   11820
catgcctggc actctagcac ttgaggatag ctgaatgaat gtgtatttct ttgtctcttt   11880
cttcttgtc  tttgctcttt gttctctatc taaagtgtgt cttacccatt tccatgtttc   11940
tcttgctaat ttcttcgtg  tgtgcctttg cctcatttc  tcttttgtt  cacaagagtg   12000
gtctgtgtct tgtcttagac atatctctca tttttcattt tgttgctatt tctctttgct   12060
ctcctagatg tggctcttct ttcacgcttt atttcatgtc tcctttttgg gtcacatgct   12120
gtgtgctttt tgtccttttc ttgttctgtc tacctctcct ttctctgcct acctctcttt   12180
tctctttgtg aactgtgatt atttgttacc cctcccctt  ctcgttcgtt ttaaatttca   12240
cctttttct  gagtctggcc tcctttctgc tgttctact  ttttatctca catttctcat   12300
ttctgcattt cctttctgcc tctccttggc tattctctct ctcctcccct gcgtgcctca   12360
gcatctcttg ctgtttgtga ttttctattt cagtattaat ctctgttggc ttgtatttgt   12420
tctctgcttc ttccctttct actcaccttt gagtatttca gcctcttcat gaatctatct   12480
ccctctcttt gatttcatgt aatctctcct taaatatttc tttgcatatg tgggcaagtg   12540
tacgtgtgtg tgtgtcatgt gtggcagagg ggcttcctaa cccctgcctg ataggtgcag   12600
aacgtcggct atcagagcaa gcattgtgga gcggttcctt atgccaggct gccatgtgag   12660
atgatccaag accaaaacaa ggccctagac tgcagtaaaa cccagaactc aagtagggca   12720
gaaggtggaa ggctcatatg gatagaaggc ccaaagtata agacagatgg tttgagactt   12780
gagacccgag gactaagatg gaaagcccat gttccaagat agatagaagc ctcaggcctg   12840
```

```
aaaccaacaa aagcctcaag agccaagaaa acagagggtg gcctgaattg gaccgaaggc    12900
ctgagttgga tggaagtctc aaggcttgag ttagaagtct taagacctgg gacaggacac    12960
atggaaggcc taagaactga gacttgtgac acaaggccaa cgacctaaga ttagcccagg    13020
gttgtagctg gaagacctac aacccaagga tggaaggccc ctgtcacaaa gcctacctag    13080
atggatagag gacccaagcg aaaaaggtat ctcaagacta acggccggaa tctggaggcc    13140
catgacccag aacccaggaa ggatagaagc ttgaagacct ggggaaatcc caagatgaga    13200
accctaaacc ctacctcttt tctattgttt acacttctta ctcttagata tttccagttc    13260
tcctgtttat ctttaagcct gattcttttg agatgtactt tttgatgttg ccggttacct    13320
ttagattgac agtattatgc ctgggccagt cttgagccag ctttaaatca cagcttttac    13380
ctatttgtta ggctatagtg tttttgtaaac ttctgtttct attcacatct tctccacttg    13440
agagagacac caaaatccag tcagtatcta atctggcttt tgttaacttc cctcaggagc    13500
agacattcat ataggtgata ctgtatttca gtcctttctt ttgacccccag aagccctaga    13560 ctgagaagat aaaatggtca ggttgttggg gaaaaaaaaa gtgccaggct ctctagaaa     13620 aaatgtgaag agatgctcca ggccaatgag aagaattaga caagaaatac acagatgtgc    13680
cagacttctg agaagcacct gccagcaaca gcttccttct ttgagcttag                13730

<210> SEQ ID NO 2
<211> LENGTH: 6864
<212> TYPE: DNA
<213> ORGANISM: Homo sapiens

<400> SEQUENCE: 2
tctagaacat tttctagtcc cccaacaccc tttatggcgt atttctttaa aaaaatcacc       60
taaattccat aaaatatttt tttaaattct atactttctc ctagtgtctt cttgacacgt      120
cctccatatt ttttaaaga aagtatttgg aatattttga ggcaattttt aatatttaag       180 gaattttttct ttggaatcat ttttggtgac atctctgttt tttgtggatc agttttttac    240
tcttccactc tcttttctat attttgccca tcggggctgc ggataccctgg ttttattatt    300 ttttctttgc ccaacggggc cgtggatacc tgccttttaa ttcttttttta ttcgcccatc    360 ggggccgcgg atacctgctt tttatttttt tttccttagc ccatcggggt atcggatacc    420
tgctgattcc cttcccctct gaaccccaa cactctggcc catcggggtg acggatatct    480 gcttttttaaa aattttctttt tttggcccca tcggggcttc ggatacctgc tttttttttt    540 tttatttttcc ttgcccatcg gggctcgga tacctgcttt aattttttgtt tttctgccca    600 tcggggccgc ggatacctgc tttgattttt ttttttcatc gcccatcggt gcttttatg     660 gatgaaaaaa tgttggtttt gtgggttgtt gcactctctg gaatatctac acttttttttt   720 gctgctgatc atttggtggt gtgtgagtgt acctaccgct ttggcagaga atgactctgc    780
agttaagcta agggcgtgtt cagattgtgg aggaaaagtg gccgccatttt tagacttgcc    840 gcataactcg gcttagggct agtcgttgt gctaagttaa actagggagg caagatggat    900
gatagcaggt caggcagagg aagtcatgtg cattgcatga gctaaaccta tctgaatgaa    960
ttgatttggg gcttgttagg agctttgcgt gattgttgta tcgggaggca gtaagaatca   1020
tcttttatca gtacaaggga ctagttaaaa atggaaggtt aggaaagact aaggtgcagg   1080
gcttaaaatg gcgattttga cattgcggca ttgctcagca tggcgggctg tgctttgtta   1140
ggttgtccaa aatggcggat ccagttcgt cgcagtgttc aagtggcggg aaggccacat   1200
catgatgggc gaggctttgt taagtggtta gcatggtggt ggacatgtgc ggtcacacag   1260
```

```
gaaaagatgg cggctgaagg tcttgccgca gtgtaaaaca tggcgggcct ctttgtcttt    1320
gctgtgtgct tttcgtgttg ggttttgccg cagggacaat atggcaggcg ttgtcatatg    1380
tatatcatgg cttttgtcac gtggacatca tggcgggctt gccgcattgt taaagatggc    1440
gggttttgcc gcctagtgcc acgcagagcg ggagaaaagg tgggatggac agtgctggat    1500
tgctgcataa cccaaccaat tagaaatggg ggtggaattg atcacagcca attagagcag    1560
aagatggaat tagactgatg acacactgtc cagctactca gcgaagacct gggtgaatta    1620
gcatggcact tcgcagctgt ctttagccag tcaggagaaa gaagtggagg ggccacgtgt    1680
atgtctccca gtgggcggta caccaggtgt tttcaaggtc ttttcaagga catttagcct    1740
ttccacctct gtcccctctt atttgtcccc tcctgtccag tgctgcctct tgcagtgctg    1800
gatatctggc tgtgtggtct gaacctccct ccattcctct gtattggtgc ctcacctaag    1860
gctaagtata cctccccccc cacccccaa cccccccaac tccccacccc cacccccac     1920 cccccacctc cccaccccc tacccccta cccccctacc cccctctggt ctgccctgca      1980
ctgcactgtt gccatgggca gtgctccagg cctgcttggt gtggacatgg tggtgagccg    2040
tggcaaggac cagaatggat cacagatgat cgttggccaa ttggcctccc aatatgtgtg    2100
attgtatttg tcgaggttgc tatgcactag agaaggaaag tgctcccctc atccccactt    2160
ttcccttcca gcaggaagtg cccacccat aagacccttt tatttggaga gtctaggtgc     2220
acaattgtaa gtgaccacaa gcatgcatct tggacattta tgtgcgtaat cgcacactgc    2280
tcattccatg tgaataaggt cctactctcc gacccctttt gcaatacaga agggttgctg    2340
ataacgcagt cccctttct tggcatgttg tgtgtgatta taatcgtctg ggatcctatg     2400
cactagaaaa ggagggtcct ctccacatac ctcagtctca cctttccctt ccagcaggga    2460
gtgcccactc cataagactc tcacatttgg acagtcaagg tgcgtaattg ttaagtgaac    2520
acaaccatgc accttagaca tggatttgca taactacaca cagctcaacc tatctgaata    2580
aaatcctact ctcagacccc ttttgcagta cagcaggggt gctgatcacc aaggcccttt    2640
ttcctggcct ggtatgcgtg tgattatgtt tgtcccggtt cctgtgtatt agacatggaa    2700
gcctcccctg ccacactcca ccccaatct tcctttccct tccggcagga gtgccctctc     2760
cataagacgc ttacgtttgg acaatcaagg tgcacagttg taagtgacca caggcataca    2820
ccttggacat taatgtgcat aaccactttg cccattccat ctgaataagg tcctactctc    2880 agacccettt tgcagtacag caggggtgct gatcaccaag gccctttttc ttggcctgtt    2940
atgtgcgtga ttatatttgt ctgggttcct gtgtattaga caaggaagcc ttccccccgc    3000
cccccacccc actcccagtc ttccttccc ttccagcagg gagtgcccc tccataagat       3060 cattacattt ggacaatcaa ggtgcacaat tataagtgac cacagccatg caccttggac    3120
attattggac attaatgtgc gtaactgcac atggcccatc ccatctgaat aaggacctac    3180
tctcagatgc ctttgcagta cagcagggg actgaatcac caaggccctt tttcttggcc     3240
tgttatgtgt gtgattatat ttatcccagt ttctgtgtaa tagacatgaa agcctccct    3300 gccacacccc acctccaatc ttcctttccc ttccaccagg gagtgtccac tccatatacc    3360
cttacatttg gacaatcaag gtgcacaatt gtaagtgagc ataggcactc accttggaca    3420
tgaatgtgca taactgcaca tggcccatcc catctgaata aggtcctact ctcagaccct    3480
ttttgcagta cagcaggggt gctgatcacc aaggcccctt ttcctggcct gttatgtgtg    3540
tgattatatt tgttccagtt cctgtgtaat agacatggaa gcctcccctg ccacactcca    3600
```

```
cccccaatct tcctttcctt ctggcaggaa gtacccgctc cataagaccc ttacatttgg    3660
acagtcaagg tgcacaattg tatgtgacca caaccatgca ccttggacat aaatgtgtgt    3720
aactgcacat ggcccatccc atctgaataa ggtcctactc tcagacccct tttgcagtac    3780
agtaggtgtg ctgataacca aggcccctct tcctggcctg ttaacgtatg tgattatatt    3840
tgtctgggtt ccagtgtata agacatggaa gcctcccctg ccccacccca ccctcaatct    3900
tcctttccct tctggcaggg agtgccagct ccataagaac cttacatttg gacagtcaag    3960
gtgcacaatt ctaagtgacc gcagccatgc accttggtca ataatgtgtg taactgcaca    4020
cggcctatct catctgaata aggccttact ctcagacccc ttttgcagta cagcaggggt    4080
gctgataacc aaggcccatt ttcctggcct gttatgtgtg tgattatatt tgtccaggtt    4140
tctgtgtact agacaaggaa gcctcctctg ccccatccca tctacgcata atctttcttt    4200
tcctcccagc agggagtgct cactccataa gaccttaca  tttggacaat caaggtgcac    4260
aattgtaagt gaccacaacc atgcatcttg gaaatttatg tgcataactg cacatggctt    4320
atcctatttg aataaagtcc tactctcaga ccccctttgc agtatagctg gggtgctgat    4380
cactgaggcc tctttgcttg gcttgtctat attcttgtgt actagataag gcaccttct     4440
catggactcc ctttgctttt caacaaggag tacccactac tttttaagat tcttatattt    4500
gtccaaagta catggtttta attgaccaca acaatgtccc ttggacatta atgtatgtaa    4560
tcaccacatg gttcatccta attaaacaaa gttctacctt ctcaccctcc atttgcagta    4620
taccagggtt gctgaccccc taagtcccct tttcttggct tgttgacatg cataattgca    4680
tttatgttgg ttcttgtgcc ctagacaagg atgccccacc tcttttcaat agtgggtgcc    4740
cactccttat gatctttaca tttgaacagt taatgtgaat aattgcagtt gtccacaacc    4800
ctatcacttc taggaccatt atacctcttt tgcattactg tggggtatac tgtttccctc    4860
caaggcccct tctggtggac tatcaacata taattgaaat tttcttttgt ctttgtcagt    4920
agattaaggt catacccca  caccttttcct ttgtagtaca acagggtgtc ctgatcaacc    4980
aaagtcctgt tgttttggac tgttaatatg tgcaattaca tttgctcctg atctgtgcac    5040
tagataagga tcctacctac tttcttagtg ttttttagcag gtagtgccca ctactcaaga    5100
ctgtcacttg gaatgttcat gtgcacaaac tcaattctct aagcatgttc ctgtaccacc    5160
tttgctttag agcaggggga tgatattcac taagtgcccc ttcttttgga cttaatatgc    5220
attaatgcaa ttgtccacct cttcttttag actaagagtt gatctccaca tattcccctt    5280
gcatcagggg catgttaatt atgaatgaac ccttttcttt taatattaat gtcataattg    5340
tatttgtgga cctgtgtagg agaaaaagac cctatgttcc tcccattacc ctttggattg    5400
ctgctgagaa gtgttaacta ctcataatct cagctcttgg acaattaata gcattaataa    5460
caattatcaa gggcactgat cattagataa gactcctgct tcctcgttgc ttacatcggg    5520
ggtactgacc cactaaggcc ccttgtactg ttaatgtgaa tatttgcaat tatatatgtc    5580
tccttctggt agagtgggat attatgccct agtatcccct ttgcattact gcaggggctg    5640
ctgactactc aaaacttctc ctgggactgt taataggcac aatggcagtt atcaatggtt    5700
ttctccctcc ctgaccttgt taagcaagcg ccccacccca cccttagttt cccatggcat    5760
aataaagtat aagcattgga gtattccatg cacttgtcta tcaaacagtg gtccatactc    5820
ccaacccttt tgcattgcgc cagtgtgtaa aatcacaggt agccatggtg tcatgcttta    5880
tatacgaagt cttccctctc tctgcccctt gtgtgccctt ggccccttt  tacagactat    5940
tgctcacaat ctcaggtgtc catatttgca gctattaggt aagattgtgc tgtctccctc    6000
```

```
ttcccttccc tctgccctgc ccctttttgcc tctttgctgg gtaatgttga ccggacaagg    6060 cccttctct  tggacttaaa caattctcag ttgcactttc cttggtccca cccattatac    6120
atgaacccct ctacttcctt tcgcattgct tctgagtatg ctgactaccc aaagccccctt   6180 ctgtgttatt aataaacaca gtactgattg tcccattttt cagcccatca gtccaagatc    6240
tccctaccac tttggtgtgt tggtgcagtg ttgactatga aaagcaggcc tgaactaggt    6300
ggataagcct tcactcattt tctttcattt attaatgatc ctagtttcaa ttattgtcag    6360
attctgggga caagaaccat tcttgcccac ctgtgttact gctttactgt gcaaaatact    6420
gaaggcaagt cagacccagg gagctggatt gccatccttt attttgtgtt tccagtgtac    6480
actataaaat tgtctcccca ggaaggaagg ttggcactttt ctctgcattc ttctttccag   6540
agcagattgc ctggttaaga atctcttgtt gtccccttttg tatattgtta ttgtaaagtg   6600
ccaaatgcca ggatacagcc agaaaaattg cttattatta ttaaaaaaat tttttttaaga  6660 aagacatctg gattgtaggg tggactcgat aacctggtca ttattttttt gaagccaaaa    6720
tatccattta tactatgtac ctggtgacca gtgtctctca ttttaactga gggtggtggg    6780
tctgtggata gaacactgac tcttgctatt ttaatatcaa agatattcta gatccagcac    6840
agtggcggcc cgataccgtc gacc                                            6864

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccgtatacc attaactctt tactgttc                                        28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctgtatacg taaactggca aagggggtgg                                      29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atttcgcgaa cgggtgatga gcaggctgt                                       29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
ccgtcgcgaa aaccagaaag tattctcag                                         29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attgtatacc caagagccct cctgacctc                                         29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatgtatacg ggtggagggg cgtgatgca                                         29

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattcgcgac ccgcagtgtc ccaggaat                                          28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgctcgcgac aatgttttca gaaatgtaa                                         29

<210> SEQ ID NO 11
<211> LENGTH: 42
<212> TYPE: DNA
<213> ORGANISM: Homo sapiens

<400> SEQUENCE: 11 gccaccccatt tgccagttta cacgggtgat gagcaggctg tt                         42

<210> SEQ ID NO 12
<211> LENGTH: 685
<212> TYPE: DNA
<213> ORGANISM: Homo sapiens

<400> SEQUENCE: 12
atggtaattg agaaatgaca agaatcatgg aactccaaat tcatgacaat atttgggtaa       60
gacgtctacc tttccctcca tacctaaatt aactaaacgg gtttcgctgt gtcttcaacc      120
atcgatcgat catttaccgt tttaacttag gtctgaggaa taccacaatt aacgatatcg      180
```

```
atttctactt tgacctcaac acggtgagga acgtgtgaaa atagacagtg ggagaatccg    240
acaaaatctt ttagggtaca aaatcgaacg gtaagacaac tgggtcggac ggaaagatcg    300
gaattgaatg gggagacaga tataagataa aaggtcggtt tatactccac tgcaaattcg    360
acgatgaact ttctcttcac cctcaatccg tctcgtcatc cccttagtac aaacccttc     420 tcacttctca catgaactct ctcacacctc cacggaacct cctcgacctc gggtctccac    480
ggggtactct tgttgtgtcc tccgacgtcc acctccaccc acggactaac atcttacgaa    540
agatcaacag aaggtgtcct gtaaaaaccc tcgataagtg ttctaagtac cgatggcacg    600
agattttaaa ctacacttca gtaaaaaagg acctgaagaa tgaattaagg agacagaaaa    660
ccgggtcggt ggggaaacgg tcaaa                                          685

<210> SEQ ID NO 13
<211> LENGTH: 502
<212> TYPE: DNA
<213> ORGANISM: Homo sapiens

<400> SEQUENCE: 13
ccactactcg tccgacaaac ctttcttgca ggagctcgtc ccacgacaaa ggattgggac     60
gcagaaaaag gggagactct agtcaaatag aaataagtga acgtccacaa gttgttagaa    120
cagaaaatac cccttaaaga ttacacagaa ctcgtgaaag ggtgggagga tagaaccctcc   180 gtaccaagtc tcacctttc ccgcgcccgg gtggatggag accggaaggg tggagtcggt    240
ggtacgaatc ccggcaccac ctcacgaact ggagaaacac acatgttacg ttatgtacga    300
ccttattacg gtggaatacg tatcccgaaa acacccacat tcccgtatgg ccttgttcaa    360
ccgtatctta ttctcaagtc acttacaaca gtgatgaaaa ataatgaaaa attaacactt    420
tttgagtgtc taagacatta tttcccagta tctttggacg aaataggtat gatagtaatg    480
actcttatga aagaccaaaa gc                                             502

<210> SEQ ID NO 14
<211> LENGTH: 685
<212> TYPE: DNA
<213> ORGANISM: Homo sapiens

<400> SEQUENCE: 14
aaactggcaa aggggtggct gggccaaaag acagaggaat taagtaagaa gtccaggaaa     60
aatgaacttc acatcaaatt ttagagcacg gtagccatga atcttgtgaa tagctcccaa    120
aaatgtcctg tggaagacaa ctagaaagca ttctacaatc aggcacccac ctccacctgc    180
agcctcctgt gttgttctca tggggcacct ctgggctcca gctcctccaa ggcacctcca    240
cactctctca gtacactct tcactcttcc ccaaacatga ttccctact gctctgccta     300 actcccactt ctctttcaag tagcagctta aacgtcacct catatttggc tggaaaatag    360
aatatagaca gaggggtaag ttaaggctag aaaggcaggc tgggtcaaca gaatggcaag    420
ctaaaacatg ggattttcta aaacagccta agagggtgac agataaaagt gtgcaaggag    480
tggcacaact ccagtttcat ctttagctat agcaattaac accataagga gtctggattc    540
aattttgcca tttactagct agctaccaac ttctgtgtcg ctttgggcaa atcaattaaa    600 tccataccctc cctttccatc tgcagaatgg gtttataaca gtacttaaac ctcaaggtac    660
taagaacagt aaagagttaa tggta                                          685

<210> SEQ ID NO 15
```

<211> LENGTH: 502
<212> TYPE: DNA
<213> ORGANISM: Homo sapiens

<400> SEQUENCE: 15

```
cgaaaaccag aaagtattct cagtaatgat agtatggata aagcaggttt ctatgaccct      60
ttattacaga atctgtgagt ttttcacaat taaaaagtaa taaaaagtag tgacaacatt     120
cactgaactc ttattctatg ccaacttgtt ccggtatgcc cttacaccca caaaagccct     180
atgcataagg tggcattatt ccagcatgta ttgcattgta cacacaaaga ggtcaagcac     240
tccaccacgg ccctaagcat ggtggctgag gtgggaaggc cagaggtagg tgggcccgcg     300
cccttttcca ctctgaacca tgcctccaag ataggagggt gggaaagtgc tcaagacaca     360
ttagaaattc cccataaaag acaagattgt tgaacacctg caagtgaata aagataaact     420
gatctcagag gggaaaaaga cgcagggtta ggaaacagca ccctgctcga ggacgttctt     480
tccaaacagc ctgctcatca cc                                              502
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
tctctgaaac catagcagcc a                                                21
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cttgtgcaga ccatccctgc                                                  20
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
gccttttgca accaggaaca gc                                               22
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
atcacacaga agaacgtgga gc                                               22
```

<210> SEQ ID NO 20
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aactctgctc caaatgccga                                                    20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctgtacatc attctctgct tgg                                                23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggggtgatt tgctttccag tgc                                                23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgcagtgtc tgccccaagc                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcgtctaaa cgttgtccct                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtggacgta cggctctttg                                                    20

<210> SEQ ID NO 26
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 26
atcagccaga ccatcgacac                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcccttctct cccttgtagc                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttgggtgaa ctttgaggcg                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtgctggagc gctttagttg                                                 20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccctcactct gcggaacttt t                                               21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
attaaggctg gcacactgct t                                               21

<210> SEQ ID NO 32
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 32
cccatgtgag gtgtgctgt                                                      19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agggccctgg taactttcct                                                     20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcaaaaccga gagccttccc                                                     20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cggagacggc atcagaatca                                                     20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agccttcagt ttggctgtgt                                                     20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggctttggag ttgtaatgct gg                                                  22

<210> SEQ ID NO 38
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 38
ggagcgctct cgactttttct                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtgcatgtt cagtctgcca                                                     20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttgccgacag gatgcagaag ga                                                  22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aggtggacag cgaggccagg at                                                  22

<210> SEQ ID NO 42
<211> LENGTH: 48
<212> TYPE: DNA
<213> ORGANISM: Homo sapiens

<400> SEQUENCE: 42
ggtcggtggg gaaacggtca aatgtgccca ctactcgtcc gacaaacc                      48

<210> SEQ ID NO 43
<211> LENGTH: 45
<212> TYPE: DNA
<213> ORGANISM: Homo sapiens

<400> SEQUENCE: 43
tgggacgtag tgcggggagg tgggggcgt cacagggtcc ttagg                          45

<210> SEQ ID NO 44
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ser Ile Gln His Phe Arg Val Ala Leu Ile Pro Phe Phe Ala Ala
1               5                   10                  15
```

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
            130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
            275                 280                 285

<210> SEQ ID NO 45
<211> LENGTH: 18515
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
ctcgagttta ctccctatca gtgatagaga acgtatgaag agtttactcc ctatcagtga     60
tagagaacgt atgcagactt tactccctat cagtgataga gaacgtataa ggagtttact    120
ccctatcagt gatagagaac gtatgaccag tttactccct atcagtgata gagaacgtat    180
ctacagttta ctccctatca gtgatagaga acgtatatcc agtttactcc ctatcagtga    240
tagagaacgt ataagcttta ggcgtgtacg gtgggcgcct ataaaagcag agctcgttta    300
gtgaaccgtc agatcgcctg gagcaattcc acaacacttt tgtcttatac caactttccg    360
taccacttcc tacccgtcgta aagtcgacac cggggcccag atctggtacc gagctcggat    420
ccactagtcc agtgtggtgg aattctgcag attctagaac attttctagt cccccaacac    480

```
cctttatggc gtatttcttt aaaaaaatca cctaaattcc ataaatatt tttttaaatt      540 ctatactttc tcctagtgtc ttcttgacac gtcctccata ttttttttaaa gaaagtattt    600 ggaatatttt gaggcaattt ttaatatta aggaattttt ctttggaatc attttggtg      660 acatctctgt ttttgtgga tcagtttttt actcttccac tctctttct atattttgcc      720 catcggggct gcggatacct ggttttatta ttttttcttt gcccaacggg gccgtggata    780
cctgcctttt aattctttt tattcgccca tcggggccgc ggatacctgc ttttttattt    840 ttttcctta gcccatcggg gtatcggata cctgctgatt cccttcccct ctgaaccccc     900
aacactctgg cccatcgggg tgacggatat ctgcttttta aaattttct tttttggcc    960 catcggggct tcggatacct gcttttttt tttttatttt ccttgcccat cggggcctcg    1020
gatacctgct ttaattttg tttttctgcc catcggggcc gcggatacct gctttgattt    1080 tttttttca tcgcccatcg gtgcttttta tggatgaaaa aatgttggtt ttgtgggttg     1140
ttgcactctc tggaatatct acactttttt ttgctgctga tcatttggtg gtgtgtgagt    1200
gtacctaccg ctttggcaga gaatgactct gcagttaagc taagggcgtg ttcagattgt    1260
ggaggaaaag tggccgccat tttagacttg ccgcataact cggcttaggg ctagtcgttt    1320
gtgctaagtt aaactaggga ggcaagatgg atgatagcag gtcaggcaga ggaagtcatg    1380
tgcattgcat gagctaaacc tatctgaatg aattgatttg gggcttgtta ggagctttgc    1440
gtgattgttg tatcgggagg cagtaagaat catcttttat cagtacaagg gactagttaa    1500
aaatggaagg ttaggaaaga ctaaggtgca gggcttaaaa tggcgatttt gacattgcgg    1560
cattgctcag catggcgggc tgtgcttttgt taggttgtcc aaaatggcgg atccagttct    1620
gtcgcagtgt tcaagtggcg ggaaggccac atcatgatgg gcgaggcttt gttaagtggt    1680
tagcatggtg gtggacatgt gcggtcacac aggaaaagat ggcggctgaa ggtcttgccg    1740
cagtgtaaaa catggcgggc ctctttgtct ttgctgtgtg cttttcgtgt tgggttttgc    1800
cgcagggaca atatgcagg cgttgtcata tgtatatcat ggcttttgtc acgtggacat    1860
catggcgggc ttgccgcatt gttaaagatg gcgggttttg ccgcctagtg ccacgcagag    1920
cgggagaaaa ggtgggatgg acagtgctgg attgctgcat aacccaacca attagaaatg    1980
ggggtggaat tgatcacagc caattagagc agaagatgga attagactga tgacacactg    2040
tccagctact cagcgaagac ctgggtgaat tagcatggca cttcgcagct gtctttagcc    2100
agtcaggaga aagaagtgga ggggccacgt gtatgtctcc cagtgggcgg tacaccaggt    2160
gttttcaagg tcttttcaag gacatttagc ctttccacct ctgtccctc ttatttgtcc    2220 cctcctgtcc agtgctgcct cttgcagtgc tggatatctg gctgtgtggt ctgaacctcc    2280
ctccattcct ctgtattggt gcctcaccta aggctaagta tacctccccc cccacccccc    2340
aaccccccca actccccacc cccacccccc acccccacc tccccacccc cctaccccccc    2400 tacccccta ccccctctg gtctgccctg cactgcactg ttgccatggg cagtgctcca    2460
ggcctgcttg gtgtggacat ggtggtgagc cgtggcaagg accagaatgg atcacagatg    2520
atcgttggcc aacaggtggc agaagaggaa ttcctgcctt cctcaagagg aacacctacc    2580
ccttggctaa tgctggggtc ggattttgat ttatatttat cttttggatg tcagtcatac    2640
agtctgattt tgtggtttgc tagtgtttga atttaagtct taagtgacta ttatagaaat    2700
gtattaagag gctttatttg tagaattcac tttaattaca tttaatgagt ttttgttttg    2760
agttccttaa aattccttaa agtttttagc ttctcattac aaattcctta acctttttt    2820 ggcagtagat agtcaaagtc aaatcatttc taatgtttta aaaatgtgct ggtcattttc    2880
```

```
tttgaaattg acttaactat tttcctttga agagtctgta gcacagaaac agtaaaaaat    2940
ttaacttcat gacctaatgt aaaaaagagt gtttgaaggt ttacacaggt ccaggccttg    3000
ctttgttccc atccttgatg ctgcactaat tgactaatca cctacttatc agacaggaaa    3060
cttgaattgc tgtggtctgg tgtcctctat tcagacttat tatattggag tatttcaatt    3120
tttcgttgta tcctgcctgc ctagcatcca gttcctcccc agccctgctc ccagcaaacc    3180
cctagtctag ccccagccct actcccaccc ggccccagcc ctgccccagg cccagtcccc    3240
taacccccca gccctaggcc cagtcccagt cctagttcct cagtctgtcc agcttctctc    3300
gaaagtcact ctaattttca ttgattcagt gctcaaaata agttgtccat ggtatcctaa    3360
ttatactggg atattccgtt tacccttggc attgctgatc ttcagtactg actccttgac    3420
cattttcagt taagcataca atcccatttg tctgtgatct caggacaaag aatttcctta    3480
ctcggtacgt tgaagttagg gaatgtcaat tgagagcttt ctatcagagc attattgccc    3540
acaatttgag ttacttatca ttttctcgat cccctgccct aaaggagaa accatttctc     3600 tgtcattgct tctgtagtca cagtcccaat tttgagtagt gatcttttct tgtgtactgt    3660
gttggccacc taaaactctt tgcattgagt aaaattctaa ttgccaataa tcctacccat    3720
tggattagac agcactctga accccatttg cattcagcag ggggtcgcag acaacccgtc    3780
ttttgttgga cagttaaaat gctcagtccc aattgtcata gctttgccta ttaaacaaag    3840
gcaccctact gcgcttttg ctgtgcttct ggagaatcct gctgttcttg acaattaaa     3900 gaacaaagta gtaattgcta attgtctcac ccattaatca tgaagactac cagtcgccct    3960
tgcatttgcc ttgaggcagc gctgactacc tgagatttaa gagtttctta aattattgag    4020
taaaatccca attatccata gttctgttag ttacactatg gcctttgcaa acatctttgc    4080
ataacagcag tgggactgac tcattcttag agccccttcc cttggaatat taatggatac    4140
aatagtaatt attcatggtt ctgcgtaaca gagaagaccc acttatgtgt atgcctttat    4200
cattgctcct agatagtgtg aactacctac caccttgcat taatatgtaa aacactaatt    4260
gcccatagtc ccactcatta gtctaggatg tcctctttgc cattgctgct gagttctgac    4320
tacccaagtt tccttctctt aaacagttga tatgcataat tgcatatatt catggttctg    4380
tgcaataaaa atggattctc accccatccc accttctgtg ggatgttgct aacgagtgca    4440
gattattcaa taacagctct tgaacagtta atttgcacag ttgcaattgt ccagagtcct    4500
gtccattaga aagggactct gtatcctatt tgcacgctac aatgtgggct gatcacccaa    4560
ggactcttct tgtgcattga tgttcataat tgtatttgtc cacgatcttg tgcactaacc    4620
cttccactcc ctttgtattc cagcagggga cccttactac tcaagacctc tgtactagga    4680
cagtttatgt gcacaatcct aattgattag aactgagtct tttatatcaa ggtccctgca    4740
tcatctttgc tttacatcaa gagggtgctg gttacctaat gcccctcctc cagaaattat    4800
tgatgtgcaa aatgcaattt ccctatctgc tgttagtctg gggtctcatc ccctcatatt    4860
ccttttgtct tacagcaggg ggtacttggg actgttaatg cgcataattg caattatggt    4920
cttttccatt aaattaagat cccaactgct cacaccctct tagcattaca gtagagggtg    4980
ctaatcacaa ggacatttct tttgtactgt taatgtgcta cttgcatttg tccctcttcc    5040
tgtgcactaa agaccccact cacttcccta gtgttcagca gtggatgacc tctagtcaag    5100
acctttgcac taggatagtt aatgtgaacc atggcaactg atcacaacaa tgtctttcag    5160
atcagatcca ttttatcctc cttgttttac agcaagggat attaattacc tatgttacct    5220
```

```
ttccctggga ctatgaatgt gcaaaattcc aatgttcatg gtctctccct ttaaacctat   5280
attctacccc ttttacatta tagaaaggga tgctggaaac ccagagtcct tctcttggga   5340
ctcttaatgt gtatttctaa ttatccatga ctcttaatgt gcatattttc aattgcctaa   5400
ttgatttcaa ttgtctaaga catttcaaat gtctaattga ttagaactga gtcttttata   5460
tcaagctaat atctagcttt tatatcaagc taatatcttg acttctcagc atcatagaag   5520
ggggtactga tttcctaaag tctttcttga atttctatta tgcaaaattg ccctgaggcc   5580
gggtgtggtg gctcacacct gtaatcccag cactttggga ggctgaggtg ggaagatccc   5640
ttactgccag gagtttgaga ccagcctggc aacattaaaa aaaaaaaaaa aaagtaagac   5700
aattgccctg gaatcccatc cccctcacac ctccttggca aagcagcagg agtgctaact   5760
agctagtgct tcttctctta tactgcttaa atgcgcataa ttagcagtag ttgatgtgcc   5820
cctatgttag agtagaatcc cgcttccttg ctccatttgc attactgcag gagcttctaa   5880
ctagcctgaa ttcactctct tggactgtta atgtgcatac ttatatttgc tgctgtactt   5940
ttttaccatg taaggacccc acccactgta tttacatccc agctggaagt acctactact   6000 taagacccctt agactagtaa agttagcgtg cataatctta ggtgttatat acacattttc   6060
agttgcatac agttgtgcct tttatcagga ctcctgtact tatcaaagca gagagtgcta   6120
atcaatatta agcccttctc ttcgaactgt agatggcatg taattgcagt tgtcaatggt   6180
ccttcaatta gacttgggtt tctgacctat cacaccctct ttgctttatt gcatggggta   6240
ctattcactt aaggccccttt tctcaaactg ttaatgtgcc taatgacaat tacatcagta   6300
tccttccttt tgaaggacag catggttggt gacacctaag gccccatttc ttggcctccc   6360
aatatgtgtg attgtatttg tcgaggttgc tatgcactag agaaggaaag tgctcccctc   6420
atccccactt ttcccttcca gcaggaagtg cccaccccat aagacccttt tatttggaga   6480
gtctaggtgc acaattgtaa gtgaccacaa gcatgcatct tggacattta tgtgcgtaat   6540
cgcacactgc tcattccatg tgaataaggt cctactctcc gaccccttttt gcaatacaga   6600 agggttgctg ataacgcagt cccctttttct tggcatgttg tgtgtgatta taatcgtctg   6660
ggatcctatg cactagaaaa ggagggtcct ctccacatac ctcagtctca cctttccctt   6720
ccagcaggga gtgcccactc cataagactc tcacatttgg acagtcaagg tgcgtaattg   6780
ttaagtgaac acaaccatgc accttagaca tggatttgca taactacaca cagctcaacc   6840
tatctgaata aaatcctact ctcagacccc ttttgcagta cagcagggggt gctgatcacc   6900 aaggcccttt ttcctggcct ggtatgcgtg tgattatgtt tgtcccggtt cctgtgtatt   6960
agacatggaa gcctccctg ccacactcca cccccaatct tccttttccct tccggcagga   7020 gtgccctctc cataagacgc ttacgtttgg acaatcaagg tgcacagttg taagtgacca   7080
caggcataca ccttggacat taatgtgcat aaccactttg cccattccat ctgaataagg   7140
tcctactctc agacccctttt tgcagtacag caggggtgct gatcaccaag gccccttttc   7200
ttggcctgtt atgtgcgtga ttatatttgt ctgggttcct gtgtattaga caaggaagcc   7260
ttccccccgc ccccaccccc actcccagtc ttccttcccc ttccagcagg gagtgcccc   7320 tccataagat cattacattt ggacaatcaa ggtgcacaat tataagtgac cacagccatg   7380
caccttggac attattggac attaatgtgc gtaactgcac atggcccatc ccatctgaat   7440
aaggacctac tctcagatgc ctttgcagta cagcagggggt actgaatcac caaggcccttt   7500 tttcttggcc tgttatgtgt gtgattatat ttatcccagt ttctgtgtaa tagacatgaa   7560
agcctcccct gccacacccc acctccaatc ttccttttccc ttccaccagg gagtgtccac   7620
```

```
tccatatacc cttacatttg gacaatcaag gtgcacaatt gtaagtgagc ataggcactc    7680
accttggaca tgaatgtgca taactgcaca tggcccatcc catctgaata aggtcctact    7740
ctcagaccct ttttgcagta cagcaggggt gctgatcacc aaggcccctt ttcctggcct    7800
gttatgtgtg tgattatatt tgttccagtt cctgtgtaat agacatggaa gcctcccctg    7860
ccacactcca cccccaatct tcctttcctt ctggcaggaa gtacccgctc cataagaccc    7920
ttacatttgg acagtcaagg tgcacaattg tatgtgacca caaccatgca ccttggacat    7980
aaatgtgtgt aactgcacat ggcccatccc atctgaataa ggtcctactc tcagacccct    8040
tttgcagtac agtaggtgtg ctgataacca aggcccctct tcctggcctg ttaacgtatg    8100
tgattatatt tgtctgggtt ccagtgtata agacatggaa gcctcccctg ccccacccca    8160
ccctcaatct tcctttccct tctggcaggg agtgccagct ccataagaac cttacatttg    8220
gacagtcaag gtgcacaatt ctaagtgacc gcagccatgc accttggtca ataatgtgtg    8280
taactgcaca cggcctatct catctgaata aggccttact ctcagacccc ttttgcagta    8340
cagcaggggt gctgataacc aaggcccatt ttcctggcct gttatgtgtg tgattatatt    8400
tgtccaggtt tctgtgtact agacaaggaa gcctcctctg ccccatccca tctacgcata    8460
atctttcttt tcctcccagc agggagtgct cactccataa gacccttaca tttggacaat    8520
caaggtgcac aattgtaagt gaccacaacc atgcatcttg gaaatttatg tgcataactg    8580
cacatggctt atcctatttg aataaagtcc tactctcaga ccccctttgc agtatagctg    8640
gggtgctgat cactgaggcc tctttgcttg gcttgtctat attcttgtgt actagataag    8700
ggcaccttct catggactcc ctttgctttt caacaaggag tacccactac tttttaagat    8760
tcttatattt gtccaaagta catggtttta attgaccaca acaatgtccc ttggacatta    8820
atgtatgtaa tcaccacatg gttcatccta attaaacaaa gttctacctt ctcaccctcc    8880
atttgcagta taccagggtt gctgaccccc taagtcccct tttcttggct tgttgacatg    8940
cataattgca tttatgttgg ttcttgtgcc ctagacaagg atgccccacc tcttttcaat    9000
agtgggtgcc cactccttat gatctttaca tttgaacagt taatgtgaat aattgcagtt    9060
gtccacaacc ctatcacttc taggaccatt atacctcttt tgcattactg tggggtatac    9120
tgtttccctc caaggcccct tctggtggac tatcaacata taattgaaat tttcttttgt    9180 cttttgtcagt agattaaggt cataccccat cacctttcct tgtagtaca acagggtgtc    9240 ctgatcaacc aaagtcctgt tgttttggac tgttaatatg tgcaattaca tttgctcctg    9300
atctgtgcac tagataagga tcctacctac tttcttagtg tttttagcag gtagtgccca    9360
ctactcaaga ctgtcacttg gaatgttcat gtgcacaaac tcaattctct aagcatgttc    9420
ctgtaccacc tttgctttag agcaggggga tgatattcac taagtgcccc ttcttttgga    9480
cttaatatgc attaatgcaa ttgtccacct cttctttag actaagagtt gatctccaca    9540
tattcccctt gcatcagggg catgttaatt atgaatgaac ccttttcttt taatattaat    9600
gtcataattg tatttgtgga cctgtgtagg agaaaaagac cctatgttcc tcccattacc    9660
ctttggattg ctgctgagaa gtgttaacta ctcataatct cagctcttgg acaattaata    9720
gcattaataa caattatcaa gggcactgat cattagataa gactcctgct tcctcgttgc    9780
ttacatcggg ggtactgacc cactaaggcc ccttgtactg ttaatgtgaa tatttgcaat    9840
tatatatgtc tccttctggt agagtgggat attatgccct agtatcccct ttgcattact    9900 gcagggggctg ctgactactc aaaacttctc ctgggactgt taataggcac aatggcagtt    9960
```

```
atcaatggtt ttctccctcc ctgaccttgt taagcaagcg ccccacccca cccttagttt   10020
cccatggcat aataaagtat aagcattgga gtattccatg cacttgtcta tcaaacagtg   10080
gtccatactc ccaaccctt tgcattgcgc cagtgtgtaa aatcacaggt agccatggtg   10140
tcatgcttta tatacgaagt cttccctctc tctgcccctt gtgtgcccct tggcccctttt   10200 tacagactat tgctcacaat ctcaggtgtc catatttgca gctattaggt aagattgtgc   10260
tgtctccctc ttcccttccc tctgccctgc ccttttgcc tctttgctgg gtaatgttga   10320
ccagacaagg ccctttctct tggacttaaa caattctcag ttgcactttc cttggtccac   10380
ccattataca tgaacccctc tacttccttt cgcattgctt ctgagtatgc tgactaccca   10440
aagcccctcc tgtgttatta ataaacacag tactgattgt cccatttttc agcccatcag   10500
tccaagatct ccctaccact ttggtgtgtt ggtgcagtgt tgactatgaa aagcaggcct   10560
gaactaggtg gataagcctt cactcatttt ctttcattta ttaatgatcc tagtttcaat   10620
tattgtcaga ttctggggac aagaaccatt cttgcccacc tgtgttactg ctttactgtg   10680
caaaatactg aaggcaagtc agacccaggg agctggattc catccttta ttttgtgttt   10740 ccagtgtaca ctataaaatt gtctccccag gaaggaaggt tggcactttc tctgcattct   10800 tcttccccaga gcagattgcc tggttaagaa tctcttgttg tcccttctgt atattgttat   10860
tgtaaagtgc caaatgccag gatacagcca gaaaaattgc ttattattat taaaaaaatt   10920
tttttaagaa agacatctgg attgtagggt ggactcgata acctggtcat tatttttttg   10980
aagccaaaat atccatttat actatgtacc tggtgaccag tgtctctcat tttaactgag   11040
ggtggtgggt ctgtggatag aacactgact cttgctattt taatatcaaa gatattctag   11100
atccagcaca gtggcggccg ctctagagtg gaactcttaa gaccagtatc tttgtgtggg   11160
ctttaccagc attcactttt agaaaaacta cctaaattt ataatccttt aatttcttca   11220
tctggagcac ctgcccctac ttatttcaag aagattgcag taaaacgatt aaatgaggga   11280
acatatgcag aggtgctttt aaaaagcata tgccacctt tttattaatt attatataaa   11340
atgaagcatt taattatagt aataatttga agtagtttga agtaccacac tgaggtgagg   11400
acttaaaaat gataagacga gttccctatt ttataagaaa aataagccaa aattaaatat   11460
tcttttggat ataaatttca acagtgagat agctgcctag tggaaatgaa taatatccca   11520
gccactagtg tacagggtgt tttgtggcac aggattatgt aatatggaac tgctcaagca   11580
aataactagt catcacaaca gcagttcttt gtaataactg aaaagaata ttgtttctcg   11640 gagaaggatg tcaaaagatc ggcccagctc agggagcagt ttgccctact agctcctcgg   11700
acagctgtaa agaagagtct ctggctcttt agaatactga tcccattgaa gataccacgc   11760
tgcatgtgtc cttagtagtc atgtctcctt aggctcctct tggacattct gagcatgtga   11820
gacctgagga ctgcaaacag ctataagagg ctccaaatta atcatatctt tcccttgag   11880 aatctggcca agctccagct aatctacttg gatgggttgc cagctatctg gagaaaaaga   11940
tcttcctcag aagaataggc ttgttgttt acagtgttag tgatccattc cctttgacga   12000
tccctaggtg gagatggggc atgaggatcc tcaggggaa aagctcacta ccactgggca   12060
acaaccctag gtcaggaggt tctgtcaaga tactttcctg gtcccagata ggaagataaa   12120
gtctcaaaaa caaccaccac acgtcaagct cttcattgtt cctatctgcc aaatcattat   12180
acttcctaca agcagtgcag agagctgagt cttcagcagg tccaagaaat ttgaacacac   12240
tgaaggaagt cagccttccc acctgaagat caacatgcct ggcactctag cacttgagga   12300
tagctgaatg aatgtgtatt tctttgtctc tttctttctt gtctttgctc tttgttctct   12360
```

```
atctaaagtg tgtcttaccc atttccatgt ttctcttgct aatttctttc gtgtgtgcct   12420
ttgcctcatt ttctcttttt gttcacaaga gtggtctgtg tcttgtctta gacatatctc   12480 tcattttca ttttgttgct atttctcttt gctctcctag atgtggctct tctttcacgc    12540
tttatttcat gtctccttt tgggtcacat gctgtgtgct ttttgtcctt ttcttgttct    12600
gtctacctct cctttctctg cctacctctc ttttctcttt gtgaactgtg attatttgtt   12660
accccttccc cttctcgttc gttttaaatt tcaccttttt tctgagtctg gcctcctttc   12720
tgctgtttct acttttatc tcacatttct catttctgca tttcctttct gcctctcttg   12780
ggctattctc tctctcctcc cctgcgtgcc tcagcatctc ttgctgtttg tgattttcta   12840
tttcagtatt aatctctgtt ggcttgtatt tgttctctgc ttcttcccct tctactcacc   12900
tttgagtatt tcagcctctt catgaatcta tctccctctc tttgatttca tgtaatctct   12960
ccttaaatat ttctttgcat atgtgggcaa gtgtacgtgt gtgtgtgtca tgtgtggcag   13020
aggggcttcc taaccctgc ctgataggtg cagaacgtcg gctatcagag caagcattgt    13080
ggagcggttc cttatgccag gctgccatgt gagatgatcc aagaccaaaa caaggcccta   13140
gactgcagta aaacccagaa ctcaagtagg gcagaaggtg gaaggctcat atggatagaa   13200
ggcccaaagt ataagacaga tggtttgaga cttgagaccc gaggactaag atggaaagcc   13260
catgttccaa gatagataga agcctcaggc ctgaaaccaa caaaagcctc aagagccaag   13320
aaaacagagg gtggcctgaa ttggaccgaa ggcctgagtt ggatggaagt ctcaaggctt   13380
gagttagaag tcttaagacc tgggacagga cacatggaag gcctaagaac tgagacttgt   13440
gacacaaggc caacgaccta agattagccc agggttgtag ctggaagacc tacaacccaa   13500
ggatggaagg cccctgtcac aaagcctacc tagatggata gaggacccaa gcgaaaaagg   13560
tatctcaaga ctaacggccg gaatctggag gcccatgacc cagaacccag gaaggataga   13620
agcttgaaga cctggggaaa tcccaagatg agaaccctaa accctacctc ttttctattg   13680
tttacacttc ttactcttag atatttccag ttctcctgtt tatctttaag cctgattctt    13740
ttgagatgta cttttttgatg ttgccggtta cctttagatt gacagtatta tgcctgggcc   13800
agtcttgagc cagctttaaa tcacagcttt tacctatttg ttaggctata gtgttttgta   13860
aacttctgtt tctattcaca tcttctccac ttgagagaga caccaaaatc cagtcagtat   13920
ctaatctggc ttttgttaac ttccctcagg agcagacatt catataggtg atactgtatt   13980
tcagtccttt ctttttgaccc cagaagccct agactgagaa gataaaatgg tcaggttgtt   14040
ggggaaaaaa aaagtgccag gctctctaga gaaaaatgtg aagagatgct ccaggccaat   14100
gagaagaatt agacaagaaa tacacagatg tgccagactt ctgagaagca cctgccagca   14160
acagcttcct tctttgagct tagattttcc tagtccatcc ctcatgaaaa atgactgacc   14220
actgctgggc agcaggaggg atgatgacca actaattccc aaaccccagt ctcattggta   14280
ccatcgatcg gccggatatc acgcgtcata tggctagcct gcaggatcc aatgtaactg    14340 tattcagcga tgacgaaatt cttagctatt gtaatactct agaggatctt tgtgaaggaa   14400
ccttacttct gtggtgtgac ataattggac aaactaccta cagagattta aagctctaag   14460
gtaaatataa aattttttaag tgtataatgt gttaaactac tgattctaat tgtttgtgta   14520
ttttagattc caacctatgg aactgatgaa tgggagcagt ggtggaatgc ctttaatgag   14580
gaaaacctgt tttgctcaga agaaatgcca tctagtgatg atgaggctac tgctgactct   14640
caacattcta ctcctccaaa aaagaagaga aaggtagaag accccaagga ctttccttca   14700
```

```
gaattgctaa gttttttgag tcatgctgtg tttagtaata gaactcttgc ttgctttgct   14760
atttacacca caaaggaaaa agctgcactg ctatacaaga aaattatgga aaaatattct   14820
gtaaccttta taagtaggca taacagttat aatcataaca tactgttttt tcttactcca   14880
cacaggcata gagtgtctgc tattaataac tatgctcaaa aattgtgtac ctttagcttt   14940
ttaatttgta aaggggttaa taaggaatat ttgatgtata gtgccttgac tagagatcat   15000
aatcagccat accacatttg tagaggtttt acttgcttta aaaaacctcc cacacctccc   15060
cctgaacctg aaacataaaa tgaatgcaat tgttgttgtt aacttgttta ttgcagctta   15120
taatggttac aaataaagca atagcatcac aaatttcaca ataaagcat tttttttcact   15180 gcattctagt tgtggtttgt ccaaactcat caatgtatct tatcatgtct gcggctctag   15240
agctgcatta atgaatcggc caacgcgcgg ggagaggcgg tttgcgtatt gggcgctctt   15300
ccgcttcctc gctcactgac tcgctgcgct cggtcgttcg gctgcggcga gcggtatcag   15360
ctcactcaaa ggcggtaata cggttatcca cagaatcagg ggataacgca ggaaagaaca   15420
tgtacgtaaa ctggcaaagg ggtggctggg ccaaaagaca gaggaattaa gtaagaagtc   15480
caggaaaaat gaacttcaca tcaaatttta gagcacggta gccatgaatc ttgtgaatag   15540
ctcccaaaaa tgtcctgtgg aagacaacta gaaagcattc tacaatcagg cacccacctc   15600
cacctgcagc ctcctgtgtt gttctcatgg ggcacctctg ggctccagct cctccaaggc   15660
acctccacac tctctcaagt acactcttca ctcttcccca aacatgattc ccctactgct   15720
ctgcctaact cccacttctc tttcaagtag cagcttaaac gtcacctcat atttggctgg   15780
aaaatagaat atagacagag gggtaagtta aggctagaaa ggcaggctgg gtcaacagaa   15840
tggcaagcta aaacatggga ttttctaaaa cagcctaaga gggtgacaga taaaagtgtg   15900
caaggagtgg cacaactcca gtttcatctt tagctatagc aattaacacc ataaggagtc   15960
tggattcaat tttgccattt actagctagc taccaacttc tgtgtcgctt tgggcaaatc   16020
aattaaatcc atacctccct ttccatctgc agaatgggtt tataacagta cttaaacctc   16080
aaggtactaa gaacagtaaa gagttaatgg tacatgtgag caaaaggcca gcaaaaggcc   16140
aggaaccgta aaaaggccgc gttgctggcg tttttccata ggctccgccc ccctgacgag   16200
catcacaaaa atcgacgctc aagtcagagg tggcgaaacc cgacaggact ataaagatac   16260
caggcgtttc cccctggaag ctccctcgtg cgctctcctg ttccgaccct gccgcttacc   16320
ggatacctgt ccgcctttct cccttcggga agcgtggcgc tttctcatag ctcacgctgt   16380
aggtatctca gttcggtgta ggtcgttcgc tccaagctgg gctgtgtgca cgaaccccc   16440 gttcagcccg accgctgcgc cttatccggt aactatcgtc ttgagtccaa cccggtaaga   16500
cacgacttat cgccactggc agcagccact ggtaacagga ttagcagagc gaggtatgta   16560
ggcggtgcta cagagttctt gaagtggtgg cctaactacg gctacactag aagaacagta   16620
tttggtatct gcgctctgct gaagccagtt accttcggaa aaagagttgg tagctcttga   16680
tccggcaaac aaaccaccgc tggtagcggt ggtttttttg tttgcaagca gcagattacg   16740
cgcagaaaaa aaggatctca agaagatcct ttgatctttt ctacggggtc tgacgctcag   16800
tggaacgaaa actcacgtta agggattttg gtcatgagat tatcaaaaag gatcttcacc   16860
tagatccttt taaattaaaa atgaagtttt aaatcaatct aaagtatata tgagtaaact   16920
tggtctgaca gttaccaatg cttaatcagt gaggcaccta tctcagcgat ctgtctattt   16980
cgttcatcca tagttgcctg actccccgtc gtgtagataa ctacgatacg ggagggctta   17040
ccatctggcc ccagtgctgc aatgataccg cgagacccac gctcaccggc tccagattta   17100
```

-continued

```
tcagcaataa accagccagc cggaagggcc gagcgcagaa gtggtcctgc aactttatcc   17160
gcctccatcc agtctattaa ttgttgccgg gaagctagag taagtagttc gccagttaat   17220
agtttgcgca acgttgttgc cattgctaca ggcatcgtgg tgtcacgctc gtcgtttggt   17280
atggcttcat tcagctccgg ttcccaacga tcaaggcgag ttacatgatc ccccatgttg   17340
tgcaaaaaag cggttagctc cttcggtcct ccgatcgttg tcagaagtaa gttggccgca   17400
gtgttatcac tcatggttat ggcagcactg cataattctc ttactgtcat gccatccgta   17460
agatgctttt ctgtgactgg tgagtactca accaagtcat tctgagaata gtgtatgcgg   17520
cgaccgagtt gctcttgccc ggcgtcaata cgggataata ccgcgccaca tagcagaact   17580
ttaaaagtgc tcatcattgg aaaacgttct cggggcgaaa actctcaag gatcttaccg   17640
ctgttgagat ccagttcgat gtaacccact cgtgcaccca actgatcttc agcatctttt   17700
actttcacca gcgtttctgg gtgagcaaaa acaggaaggc aaaatgccgc aaaaaaggga   17760
ataagggcga cacggaaatg ttgaatactc atactcttcc ttttcaata ttattgaagc   17820
atttatcagg gttattgtct catgagcgga tacatatttg aatgtattta gaaaaataaa   17880
caaatagggg ttccgcgcac atttccccga aaagtgccac ctgacgtcta agaaaccatt   17940
attatcatga cattaaccta taaaaatagg cgtatcacga ggcccttcg tcttcaagaa   18000
ttcgaaaacc agaaagtatt ctcagtaatg atagtatgga taaagcaggt ttctatgacc   18060
ctttattaca gaatctgtga gttttcaca attaaaagt aataaaaagt agtgacaaca   18120
ttcactgaac tcttattcta tgccaacttg ttccggtatg cccttacacc cacaaaagcc   18180
ctatgcataa ggtggcatta ttccagcatg tattgcatta tacacacaaa gaggtcaagc   18240
actccaccac ggccctaagc atggtggctg aggtgggaag gccagaggta ggtgggcccg   18300
cgcccttttc cactctgaac catgcctcca agataggagg gtgggaaagt gctcaagaca   18360
cattagaaat tccccataaa agacaagatt gttgaacacc tgcaagtgaa taaagataaa   18420
ctgatctcag aggggaaaaa gacgcagggt taggaaacag cacccctgctc gaggacgttc   18480
tttccaaaca gcctgctcat cacccgttcg aattc                              18515
```

<210> SEQ ID NO 46
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Pro Ile Glu Met Leu Asp Arg His His
        50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
```

```
                    100                 105                 110
Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
                210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245

<210> SEQ ID NO 47
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Lys Arg Arg Leu Arg Thr Glu Arg Pro Phe Ser Phe Val Trp Val
1               5                   10                  15

Thr His Pro Pro Ala Leu Pro Ser Ala Ala Ser Ser Ile Leu Ser Ser
                20                  25                  30

Leu Gln Gln Gly Arg Glu Ala Ala Ile Phe Pro Leu Thr Gln Leu Val
            35                  40                  45

Pro Thr Gly Pro Ala Leu Pro Pro Arg Ala Gly Arg Tyr Thr Ala Ala
        50                  55                  60

Arg Gly Gln Ala Pro Glu Gln Ala Gly Gln Leu Glu Thr Thr Pro Val
65                  70                  75                  80

Arg Phe Ser Val Ala Ala Leu Ala Gly Pro Ala Ser Pro Asn Met Cys
                85                  90                  95

Ala Gly Thr His Gly Pro Arg Arg Pro Arg Pro Gln Lys Pro Lys
                100                 105                 110

Tyr Gln Cys Ala Asp Leu Gly Pro His Leu Gln Asp Tyr Leu Ala Arg
            115                 120                 125

Lys Lys Ala Ser Gln Gln Val Ile Lys Asn Phe Lys Trp Leu Glu Thr
        130                 135                 140

Tyr Arg Lys Gln Arg Asp Arg Arg Glu Gly Ala Thr Arg Phe Ala Arg
145                 150                 155                 160

Gly Gly Pro Ser Ala Gln Ala Arg Pro Gln Leu Lys His Glu Ala Lys
                165                 170                 175

Gly Leu Leu Lys Arg Lys Ala Ser Asn Ser Pro Thr His Phe Gln Pro
            180                 185                 190

Glu Ala Arg Asp Gln Glu Ser Arg Thr Ala Ala Arg Gly Val Glu Val
        195                 200                 205
```

```
Ile Gln Gly Thr Gln Gly Pro
    210             215
```

<210> SEQ ID NO 48
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Ala Ala Arg Arg Pro Arg Trp Ala Val Ala Asn Ser Gly Cys Ser
1               5                   10                  15

Ala Gly Arg Ala Glu Ser Ser Gly Arg Glu Gly Ala Val Arg Glu Ala
            20                  25                  30

Gly Cys Gly Ala Val Val Trp Ala Leu Phe Leu Pro Ala Arg Cys Ser
        35                  40                  45

Ala Phe Cys Lys Pro Pro Glu Arg Thr Ser Ala Val Gly Ser Leu Val
    50                  55                  60

Asp Arg Ile Thr Asp Leu Ser Pro Gln Gly Asp Pro Pro Glu Leu Thr
65                  70                  75                  80

Met Thr Glu Tyr Lys Pro Thr Val Arg Leu Ala Thr Arg Asp Asp Val
                85                  90                  95

Pro Arg Ala Val Arg Thr Leu Ala Ala Ala Phe Ala Asp Tyr Pro Ala
            100                 105                 110

Thr Arg His Thr Val Asp Pro Asp Arg His Ile Glu Arg Val Thr Glu
        115                 120                 125

Leu Gln Glu Leu Phe Leu Thr Arg Val Gly Leu Asp Ile Gly Lys Val
    130                 135                 140

Trp Val Ala Asp Asp Gly Ala Val Ala Val Trp Thr Thr Pro Glu
145                 150                 155                 160

Ser Val Glu Ala Gly Ala Val Phe Ala Glu Ile Gly Pro Arg Met Ala
                165                 170                 175

Glu Leu Ser Gly Ser Arg Leu Ala Ala Gln Gln Gln Met Glu Gly Leu
            180                 185                 190

Leu Ala Pro His Arg Pro Lys Glu Pro Ala Trp Phe Leu Ala Thr Val
        195                 200                 205

Gly Val Ser Pro Asp His Gln Gly Lys Gly Leu Gly Ser Ala Val Val
    210                 215                 220

Leu Pro Gly Val Glu Ala Ala Glu Arg Ala Gly Val Pro Ala Phe Leu
225                 230                 235                 240

Glu Thr Ser Ala Pro Arg Asn Leu Pro Phe Tyr Glu Arg Leu Gly Phe
                245                 250                 255

Thr Val Thr Ala Asp Val Glu Val Pro Glu Gly Pro Arg Thr Trp Cys
            260                 265                 270

Met Thr Arg Lys Pro Gly Ala
        275
```

<210> SEQ ID NO 49
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 50
<211> LENGTH: 9789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc cctttgcttt     300
ctctgaccag cattctctcc cctgggcctg tgccgctttc tgtctgcagc ttgtggcctg     360
ggtcacctct acggctggcc cagatccttc cctgccgcct ccttcaggtt ccgtcttcct     420
ccactccctc ttcccctggc tctctgctgt gttgctgccc aaggatgctc tttccggagc     480
acttccttct cggcgctgca ccacgtgatg tcctctgagc ggatcctccc cgtgtctggg     540
```

| | |
|---|---|
| tcctctccgg gcatctctcc tccctcaccc aacccatgc cgtcttcact cgctgggttc | 600 |
| ccttttcctt ctccttctgg ggcctgtgcc atctctcgtt tcttaggatg gccttctccg | 660 |
| acggatgtct cccttgcgtc ccgcctcccc ttcttgtagg cctgcatcat caccgttttt | 720 |
| ctggacaacc ccaaagtacc ccgtctccct ggctttagcc acctctccat cctcttgctt | 780 |
| tctttgcctg gacaccccgt tctcctgtgg attcgggtca cctctcactc ctttcatttg | 840 |
| ggcagctccc ctaccccct tacctctcta gtctgtgcta gctcttccag cccctgtca | 900 |
| tggcatcttc caggggtccg agagctcagc tagtcttctt cctccaaccc gggcccctat | 960 |
| gtccacttca ggacagcatg tttgctgcct ccagggatcc tgtgtccccg agctgggacc | 1020 |
| accttatatt cccagggccg gttaatgtgg ctctggttct gggtactttt atctgtcccc | 1080 |
| tccaccccac agtggggcaa gctagcttgg tcgagctgga tacttcccgt ccgcagggg | 1140 |
| gacatgccgg cgatgctgaa ggtcgcgcgc attcccgatg aagaggccgg ttaccgcctg | 1200 |
| ttgacctggt gggacgggca gggcgccgcc cgagtcttcg cctcggcggc gggcgctctg | 1260 |
| ctcatggagc gcgcgtccgg ggccggggac cttgcacaga tagcgtggtc cggccaggac | 1320 |
| gacgaggctt gcaggatcat aatcagccat accacatttg tagaggtttt acttgcttta | 1380 |
| aaaaacctcc cacacctccc cctgaacctg aaacataaaa tgaatgcaat tgttgttgtt | 1440 |
| aacttgttta ttgcagctta taatggttac aaataaagca atagcatcac aaatttcaca | 1500 |
| aataaagcat ttttttcact gcattctagt tgtggtttgt ccaaactcat caatgtatct | 1560 |
| tatcatgtct ggatccttac ttagttaccc ggggagcatg tcaaggtcaa aatcgtcaag | 1620 |
| agcgtcagca ggcagcatat caaggtcaaa gtcgtcaagg gcatcggctg ggagcatgtc | 1680 |
| taagtcaaaa tcgtcaaggg cgtcggtcgg cccgccgctt tcgcacttta gctgtttctc | 1740 |
| caggccacat atgattagtt ccaggccgaa aaggaaggca ggttcggctc cctgccggtc | 1800 |
| gaacagctca attgcttgtt tcagaagtgg gggcatagaa tcggtggtag gtgtctctct | 1860 |
| ttcctctttt gctacttgat gctcctgttc ctccaatacg cagcccagtg taaagtggcc | 1920 |
| cacggcggac agagcgtaca gtgcgttctc caggagaaag ccttgctgac acaggaacgc | 1980 |
| gagctgattt tccagggttt cgtactgttt ctctgttggg cgggtgccga gatgcacttt | 2040 |
| agccccgtcg cgatgtgaga ggagagcaca gcggtatgac ttggcgttgt ccgcagaaa | 2100 |
| gtcttgccat gactcgcctt ccaggggca ggagtgggta tgatgcctgt ccagcatctc | 2160 |
| gattggcagg gcatcgagca gggcccgctt gttcttcacg tgccagtaca gggtaggctg | 2220 |
| ctcaactccc agcttttgag cgagtttcct tgtcgtcagg cctcgatac cgactccatt | 2280 |
| gagtaattcc agagcagagt ttatgacttt gctcttgtcc agtctagaca tggtgaattc | 2340 |
| ggggccgcg aggctggatc ggtcccgtg tcttctatgg aggtcaaaac agcgtggatg | 2400 |
| gcgtctccag gcgatctgac ggttcactaa acgagctcac gacacctgaa atggaagaaa | 2460 |
| aaaactttga accactgtct gaggcttgag aatgaaccaa gatccaaact caaaagggc | 2520 |
| aaattccaag gagaattaca tcaagtgcca agctggccta acttcagtct ccacccactc | 2580 |
| agtgtgggga aactccatcg cataaaaccc ctccccccaa cctaaagacg acgtactcca | 2640 |
| aaagctcgag aactaatcga ggtgcctgga cggcgcccgg tactccgtgg agtcacatga | 2700 |
| agcgacggct gaggacggaa aggccttttt cctttgtgtg ggtgactcac ccgcccgctc | 2760 |
| tcccgagcgc cgcgtcctcc attttgagct ccctgcagca gggccgggaa gcggccatct | 2820 |
| ttccgctcac gcaactggtg ccgaccgggc cagccttgcc gcccagggcg gggcgataca | 2880 |

```
cggcggcgcg aggccaggca ccagagcagg ccggccagct tgagactacc cccgtccgat    2940
tctcggtggc cgcgctcgca ggccccgcct cgccgaacat gtgcgctggg acgcacgggc    3000
cccgtcgccg cccgcggccc caaaaaccga ataccagtg tgcagatctt ggcccgcatt     3060
tacaagacta tcttgccaga aaaaagcgt cgcagcaggt catcaaaaat tttaaatggc     3120
tagagactta tcgaaagcag cgagacaggc gcgaaggtgc caccagattc gcacgcggcg    3180
gccccagcgc ccaagccagg cctcaactca agcacgaggc gaaggggctc cttaagcgca    3240
aggcctcgaa ctctcccacc cacttccaac ccgaagctcg ggatcaagaa tcacgtactg    3300
cagccagggg cgtggaagta attcaaggca cgcaagggcc ataacccgta aagaggccag    3360
gcccgcggga accacacacg gcacttacct gtgttctggc ggcaaacccg ttgcgaaaaa    3420
gaacgttcac ggcgactact gcacttatat acggttctcc cccacccctcg gaaaaaggc    3480 ggagccagta cacgacatca ctttcccagt ttaccccgcg ccaccttctc taggcaccgg    3540
ttcaattgcc gacccctccc cccaacttct cggggactgt gggcgatgtg cgctctgccc    3600
actgacgggc accggagcct cacgcatgct cttctccacc tcagtgatga cgagagcggg    3660
cgggtgaggg ggcgggaacg cagcgatctc tgggttctac gttagtggga gtttaacgac    3720
ggtccctggg attccccaag gcaggggcga gtccttttgt atgaattact catggcggta    3780
atgttggaca tgagccaata taaatgtaca tattatgata tggatacaac gtatgcaatg    3840
ggccaagctc ctcgaggtgg tgcactctca gtacaatctg ctctgatgcc gcatagttaa    3900
gccagtaagc ttttggggtt gcgccttttc caaggcagcc ctgggtttgc gcaggacgc     3960 ggctgctctg ggcgtggttc cgggaaacgc agcggcgccg accctgggtc tcgcacattc    4020
ttcacgtccg ttcgcagcgt caccccggatc ttcgccgcta cccttgtggg ccccccggcg   4080
acgcttcctg ctccgcccct aagtcgggaa ggttccttgc ggttcgcggc gtgccggacg    4140
tgacaaacgg aagccgcacg tctcactagt accctcgcag acggacagcg ccagggagca    4200
atggcagcgc gccgaccgcg atgggctgtg gccaatagcg gctgctcagc agggcgcgcc    4260
gagagcagcg gccgggaagg ggcggtgcgg gaggcggggt gtgggcggt agtgtgggcc     4320 ctgttcctgc ccgcgcggtg ttccgcattc tgcaagcctc cggagcgcac gtcggcagtc    4380
ggctccctcg ttgaccgaat caccgacctc tctccccagg gggatccacc ggagcttacc    4440
atgaccgagt acaagcccac ggtgcgcctc gccaccccgcg acgacgtccc cagggccgta   4500
cgcaccctcg ccgccgcgtt cgccgactac cccgccacgc gccacaccgt cgatccggac    4560
cgccacatcg agcgggtcac cgagctgcaa gaactcttcc tcacgcgcgt cgggctcgac    4620
atcggcaagg tgtgggtcgc ggacgacggc gccgcggtgg cggtctggac cacgccggag    4680
agcgtcgaag cggggcggt gttcgccgag atcggcccgc gcatggccga gttgagcggt     4740
tcccggctgg ccgcgcagca acagatggaa ggcctcctgg cgccgcaccg gcccaaggag    4800
cccgcgtggt tcctggccac cgtcggcgtc tcgcccgacc accaggggcaa gggtctgggc    4860 agcgccgtcg tgctccccgg agtggaggcg gccgagcgcg ccggggtgcc cgccttcctg    4920
gagacctccg cgccccgcaa cctccccttc tacgagcggc tcggcttcac cgtcaccgcc    4980
gacgtcgagg tgcccgaagg accgcgcacc tggtgcatga cccgcaagcc cggtgcctga    5040
ggtaccctgt gccttctagt tgccagccat ctgttgtttg ccctcccccc gtgccttcct    5100
tgaccctgga aggtgccact cccactgtcc tttcctaata aaatgaggaa attgcatcgc    5160
attgtctgag taggtgtcat tctattctgg ggggtgggggt ggggcaggac agcaagggggg  5220 aggattggga agacaatagc aggcatgctg gggatgcggt gggctctatg gggtaccaag    5280
```

```
ctttactagg gacaggattg gtgacagaaa agccccatcc ttaggcctcc tccttcctag   5340
tctcctgata ttgggtctaa cccccacctc ctgttaggca gattccttat ctggtgacac   5400 accccccattt cctggagcca tctctctcct tgccagaacc tctaaggttt gcttacgatg   5460
gagccagaga ggatcctggg agggagagct tggcaggggg tgggagggaa ggggggggatg   5520 cgtgacctgc ccggttctca gtggccaccc tgcgctaccc tctcccagaa cctgagctgc   5580
tctgacgcgg ctgtctggtg cgtttcactg atcctggtgc tgcagcttcc ttacacttcc   5640
caagaggaga agcagtttgg aaaaacaaaa tcagaataag ttggtcctga gttctaactt   5700
tggctcttca cctttctagt ccccaattta tattgttcct ccgtgcgtca gttttacctg   5760
tgagataagg ccagtagcca gccccgtcct ggcagggctg tggtgaggag ggggggtgtcc  5820 gtgtggaaaa ctcccctttgt gagaatggtg cgtcctaggt gttcaccagg tcgtggccgc   5880
ctctactccc tttctctttc tccatccttc tttccttaaa gagtccccag tgctatctgg   5940
gacatattcc tccgcccaga gcagggtccc gcttccctaa ggccctgctc tgggcttctg   6000
ggtttgagtc cttggcaagc ccaggagagg cgctcaggct tccctgtccc ccttcctcgt   6060
ccaccatctc atgcccctgg ctctcctgcc ccttccctac aggggttcct ggctctgctc   6120
taagggcaag ggcgaattcg cggccgctaa attcaattcg ccctatagtg agtcgtatta   6180
caattcactg gccgtcgttt tacaacgtcg tgactgggaa aaccctggcg ttacccaact   6240
taatcgcctt gcagcacatc ccctttcgc cagctggcgt aatagcgaag aggcccgcac   6300
cgatcgccct tcccaacagt tgcgcagcct atacgtacgg cagtttaagg tttacaccta   6360
taaaagagag agccgttatc gtctgtttgt ggatgtacag agtgatatta ttgacacgcc   6420
ggggcgacgg atggtgatcc ccctggccag tgcacgtctg ctgtcagata aagtctcccg   6480
tgaactttac ccggtggtgc atatcgggga tgaaagctgg cgcatgatga ccaccgatat   6540
ggccagtgtg ccggtctccg ttatcgggga agaagtggct gatctcagcc accgcgaaaa   6600
tgacatcaaa aacgccatta acctgatgtt ctggggaata taaatgtcag gcatgagatt   6660
atcaaaaagg atcttcacct agatcctttt cacgtagaaa gccagtccgc agaaacggtg   6720
ctgaccccgg atgaatgtca gctactgggc tatctggaca agggaaaacg caagcgcaaa   6780
gagaaagcag gtagcttgca gtgggcttac atggcgatag ctagactggg cggttttatg   6840
gacagcaagc gaaccggaat tgccagctgg ggcgccctct ggtaaggttg gaagccctg    6900 caaagtaaac tggatggctt tcttgccgcc aaggatctga tggcgcaggg gatcaagctc   6960
tgatcaagag acaggatgag gatcgtttcg catgattgaa caagatggat tgcacgcagg   7020
ttctccggcc gcttgggtgg agaggctatt cggctatgac tgggcacaac agacaatcgg   7080
ctgctctgat gccgccgtgt tccggctgtc agcgcagggg cgcccggttc tttttgtcaa   7140
gaccgacctg tccggtgccc tgaatgaact gcaagacgag gcagcgcggc tatcgtggct   7200
ggccacgacg ggcgttcctt gcgcagctgt gctcgacgtt gtcactgaag cgggaaggga   7260
ctggctgcta ttgggcgaag tgccggggca ggatctcctg tcatctcacc ttgctcctgc   7320
cgagaaagta tccatcatgg ctgatgcaat gcggcggctg catacgcttg atccggctac   7380
ctgcccattc gaccaccaag cgaaacatcg catcgagcga gcacgtactc ggatggaagc   7440
cggtcttgtc gatcaggatg atctggacga agagcatcag gggctcgcgc cagccgaact   7500
gttcgccagg ctcaaggcga gcatgcccga cggcgaggat ctcgtcgtga cccatggcga   7560
tgcctgcttg ccgaatatca tggtggaaaa tggccgcttt tctggattca tcgactgtgg   7620
```

-continued

```
ccggctgggt gtggcggacc gctatcagga catagcgttg gctacccgtg atattgctga   7680
agagcttggc ggcgaatggg ctgaccgctt cctcgtgctt tacggtatcg ccgctcccga   7740
ttcgcagcgc atcgccttct atcgccttct tgacgagttc ttctgaatta ttaacgctta   7800
caatttcctg atgcggtatt ttctccttac gcatctgtgc ggtatttcac accgcatcag   7860
gtggcacttt tcggggaaat gtgcgcggaa cccctatttg tttatttttc taaatacatt   7920
caaatatgta tccgctcatg agattatcaa aaaggatctt cacctagatc cttttaaatt   7980
aaaaatgaag ttttaaatca atctaaagta tatatgagta aacttggtct gacagttacc   8040
aatgcttaat cagtgaggca cctatctcag cgatctgtct atttcgttca tccatagttg   8100
cctgactccc cgtcgtgtag ataactacga tacgggaggg cttaccatct ggccccagtg   8160
ctgcaatgat accgcgagac ccacgctcac cggctccaga tttatcagca ataaaccagc   8220
cagccggaag ggccgagcgc agaagtggtc ctgcaacttt atccgcctcc atccagtcta   8280
ttaattgttg ccgggaagct agagtaagta gttcgccagt taatagtttg cgcaacgttg   8340
ttgccattgc tacaggcatc gtggtgtcac gctcgtcgtt tggtatggct tcattcagct   8400
ccggttccca acgatcaagg cgagttacat gatcccccat gttgtgcaaa aaagcggtta   8460
gctccttcgg tcctccgatc gttgtcagaa gtaagttggc cgcagtgtta tcactcatgg   8520
ttatggcagc actgcataat tctcttactg tcatgccatc cgtaagatgc ttttctgtga   8580
ctggtgagta ctcaaccaag tcattctgag aatagtgtat gcggcgaccg agttgctctt   8640
gcccggcgtc aatacgggat aataccgcgc cacatagcag aactttaaaa gtgctcatca   8700
ttggaaaacg ttcttcgggg cgaaaactct caaggatctt accgctgttg agatccagtt   8760
cgatgtaacc cactcgtgca cccaactgat cttcagcatc ttttactttc accagcgttt   8820
ctgggtgagc aaaaacagga aggcaaaatg ccgcaaaaaa gggaataagg gcgacacgga   8880
aatgttgaat actcatactc ttcctttttc aatattattg aagcatttat cagggttatt   8940
gtctcatgac caaaatccct taacgtgagt tttcgttcca ctgagcgtca ccccgtag   9000 aaaagatcaa aggatcttct tgagatcctt ttttttctgcg cgtaatctgc tgcttgcaaa   9060
caaaaaaacc accgctacca gcggtggttt gtttgccgga tcaagagcta ccaactcttt   9120
ttccgaaggt aactggcttc agcagagcgc agataccaaa tactgttctt ctagtgtagc   9180
cgtagttagg ccaccacttc aagaactctg tagcaccgcc tacatacctc gctctgctaa   9240
tcctgttacc agtggctgct gccagtggcg ataagtcgtg tcttaccggg ttggactcaa   9300
gacgatagtt accggataag gcgcagcggt cgggctgaac ggggggttcg tgcacacagc   9360
ccagcttgga gcgaacgacc tacaccgaac tgagatacct acagcgtgag ctatgagaaa   9420
gcgccacgct tcccgaaggg agaaaggcgg acaggtatcc ggtaagcggc agggtcggaa   9480
caggagagcg cacgagggag cttccagggg gaaacgcctg gtatctttat agtcctgtcg   9540
ggtttcgcca cctctgactt gagcgtcgat ttttgtgatg ctcgtcaggg ggcggagcc   9600 tatgaaaaaa cgccagcaac gcggcctttt tacggttcct ggccttttgc tggccttttg   9660
ctcacatgtt ctttcctgcg ttatcccctg attctgtgga taaccgtatt accgcctttg   9720
agtgagctga taccgctcgc cgcagccgaa cgaccgagcg cagcgagtca gtgagcgagg   9780
aagcggaag                                                         9789
```

<210> SEQ ID NO 51
<211> LENGTH: 273
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 51

Met Pro Pro Leu Glu Val Ala Arg Leu Leu His Thr Ser Gln Pro
1               5                   10                  15

Arg Pro Pro Glu Glu Asp Val Gly Asp Leu Val Leu Gly Ile Pro Glu
                20                  25                  30

His Arg Leu Ala Pro Val Asn Asp Arg Cys Tyr Ala Ala Ile Val Arg
            35                  40                  45

Gln Asp Ile Val Gly Ala Glu Ile Arg Val His Glu Val Pro Asp Phe
    50                  55                  60

Gly Ala Val Leu Gly Pro Lys His Gln Leu Ile Glu Ser Leu Arg Asp
65                  70                  75                  80

Gly Arg Thr Asp Gly Val Val His Ser Leu Pro Val Ile His Met
                85                  90                  95

Gly Ile Ser Asn Arg Ala Tyr Glu Ile Thr Pro Cys Ser Val Leu Thr
                100                 105                 110

Asp Ser Leu Arg Ser Glu Trp Ala Glu Pro Ala Arg Leu Ala Lys Ile
            115                 120                 125

Gly Arg Ser Asp Arg Ile His Gly Leu Arg Asp Arg Leu Gln Asn Ser
    130                 135                 140

Gly Gln Phe Gly Phe Arg Gln Val Leu Gln Arg Asp Thr Leu Cys Thr
145                 150                 155                 160

Ala Gly Asp Ala Ile Gly Gln Ala Leu Ala Glu Phe Pro Asn Val Lys
                165                 170                 175

His Phe Arg Asn Arg Glu Arg Gly Arg Cys Lys Val Pro Ile Asn Ile
            180                 185                 190

Thr Ile Phe Val Glu Thr Ile Gly Ala Ala Ile Tyr Pro Gln Asp Ile
    195                 200                 205

Ser Thr Pro Ser Tyr Ile Glu Ala Glu Ser Thr Arg Phe Phe Ala Leu
210                 215                 220

Arg Glu Leu His Gln Val Gly Asp Ala Val Glu Leu Phe Asp Gln Lys
225                 230                 235                 240

Leu Leu Asp Arg Arg Gly Glu Phe Arg Leu Phe His His Val Leu
                245                 250                 255

Ile Arg Ser Glu Asn Gly Tyr Thr Ser Ser Arg Glu Leu Phe Ala Lys
            260                 265                 270

Ala

<210> SEQ ID NO 52
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45
```

```
Arg Val Asn Ser Cys Ala Asp Gly Phe Tyr Lys Asp Arg Tyr Val Tyr
    50                  55                  60
Arg His Phe Ala Ser Ala Ala Leu Pro Ile Pro Glu Val Leu Asp Ile
65                  70                  75                  80
Gly Glu Phe Ser Glu Ser Leu Thr Tyr Cys Ile Ser Arg Arg Ala Gln
                85                  90                  95
Gly Val Thr Leu Gln Asp Leu Pro Glu Thr Glu Leu Pro Ala Val Leu
            100                 105                 110
Gln Pro Val Ala Glu Ala Met Asp Ala Ile Ala Ala Asp Leu Ser
            115                 120                 125
Gln Thr Ser Gly Phe Gly Pro Phe Gly Pro Gln Gly Ile Gly Gln Tyr
        130                 135                 140
Thr Thr Trp Arg Asp Phe Ile Cys Ala Ile Ala Asp Pro His Val Tyr
145                 150                 155                 160
His Trp Gln Thr Val Met Asp Asp Thr Val Ser Ala Ser Val Ala Gln
                165                 170                 175
Ala Leu Asp Glu Leu Met Leu Trp Ala Glu Asp Cys Pro Glu Val Arg
            180                 185                 190
His Leu Val His Ala Asp Phe Gly Ser Asn Asn Val Leu Thr Asp Asn
        195                 200                 205
Gly Arg Ile Thr Ala Val Ile Asp Trp Ser Glu Ala Met Phe Gly Asp
    210                 215                 220
Ser Gln Tyr Glu Val Ala Asn Ile Phe Phe Trp Arg Pro Trp Leu Ala
225                 230                 235                 240
Cys Met Glu Gln Gln Thr Arg Tyr Phe Glu Arg Arg His Pro Glu Leu
                245                 250                 255
Ala Gly Ser Pro Arg Leu Arg Ala Tyr Met Leu Arg Ile Gly Leu Asp
            260                 265                 270
Gln Leu Tyr Gln Ser Leu Val Asp Gly Asn Phe Asp Asp Ala Ala Trp
        275                 280                 285
Ala Gln Gly Arg Cys Asp Ala Ile Val Arg Ser Gly Ala Gly Thr Val
    290                 295                 300
Gly Arg Thr Gln Ile Ala Arg Arg Ser Ala Ala Val Trp Thr Asp Gly
305                 310                 315                 320
Cys Val Glu Val Leu Ala Asp Ser Gly Asn Arg Arg Pro Ser Thr Arg
                325                 330                 335
Pro Arg Ala Lys Glu
            340
```

<210> SEQ ID NO 53
<211> LENGTH: 21055
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg acaatgtttt cagaaatgta atcttttcaa   240
tatgaaactg ctgatggacc aagaaaacaa aaccctcaac ccaagggaac atcagattgc   300
tggtcaagga gaaatgagga gctgacggtc tcagcattta tttgacttgc tccacggaca   360
```

```
gagcaggaga aggctcaaac ctcttcaccc caagactctc cctcacacct gcctcctcac    420
ccaaaccctg aggacagga caggaaccac caacatttta tggttttcaa aaatcctgca     480
ttgaacactg actgtgagcc aggtgctgat ggaagtgcct ttcactcgat gatctcatct    540
actgctcaca attccaccag ttaaggccca cattttggac aaagagcctg aggaacctac    600
cccctccccg cagtgctcac acttttgtcc ctccagagga cgggaacttc ctctttcttt    660
agcaagctct gtaggggacc agcccacagg ccctggggta gggcagcccg accgcggccc    720
ttccctcacc atggcctatg ttctccttc ccttttcctt taagaaggcc aggtgagaat     780
cacaggaaag ggagaattta ttttgattaa aaataacatt tcttaaaggg gcatcgatt     840 ttcccttcc aaagtccaat cactcatccc tatccggagc dacagaacct ggggccgggg     900
ctcaggcctc ccacgcaggc tgtgctcagt ggacacagga atggattcct gggacactgc    960
gggtcgcgat gtacgggcca gatatacgcg ttgacattga ttattgacta gttattaata    1020
gtaatcaatt acggggtcat tagttcatag cccatatatg gagttccgcg ttacataact    1080
tacggtaaat ggcccgcctg gctgaccgcc caacgacccc cgcccattga cgtcaataat    1140
gacgtatgtt cccatagtaa cgccaatagg gactttccat tgacgtcaat gggtggagta    1200
tttacggtaa actgcccact tggcagtaca tcaagtgtat catatgccaa gtacgccccc    1260
tattgacgtc aatgacggta aatggcccgc ctggcattat gcccagtaca tgaccttatg    1320
ggactttcct acttggcagt acatctacgt attagtcatc gctattacca tggtgatgcg    1380
gttttggcag tacatcaatg ggcgtggata gcggtttgac tcacgggat ttccaagtct     1440 ccaccccatt gacgtcaatg ggagtttgtt ttggcaccaa aatcaacggg actttccaaa    1500
atgtcgtaac aactccgccc cattgacgca aatgggcggt aggcgtgtac ggtgggaggt    1560
ctatataagc agagctctcc ctatcagtga tagagatctc cctatcagtg atagagatcg    1620
tcgacgagct cgtttagtga accgtcagat cgcctggaga cgccatccac gctgttttga    1680
cctccataga agacaccggg accgatccag cctccggact ctagcgttta aacttaagct    1740
tggtaccgag ctcggatcca ctagtccagt gtggtggaat tctgcagatt ctagaacatt    1800
ttctagtccc ccaacaccct ttatggcgta tttcttaa aaaatcacct aaattccata      1860 aaatatttt ttaaattcta tactttctcc tagtgtcttc ttgacacgtc ctccatattt     1920
ttttaaagaa agtatttgga atattttgag gcaattttta atatttaagg aattttctctt    1980 tggaatcatt tttggtgaca tctctgtttt ttgtggatca gtttttact cttccactct      2040 cttttctata ttttgcccat cggggctgcg gatacctggt tttattattt tttctttgcc    2100
caacggggcc gtggatacct gccttttaat tctttttat tcgcccatcg ggccgcgga      2160 tacctgcttt ttatttttt ttccttagcc catcgggta tcggatacct gctgattccc      2220
ttcccctctg aacccccaac actctggccc atcggggtga cggatatctg cttttttaaaa   2280 attttcttt tttggcccat cggggcttcg gataccgtgct ttttttttt ttatttttcct    2340 tgcccatcgg ggcctcggat acctgcttta attttttgttt tctgccatc cggggccgcg    2400 gatacctgct tgattttttt ttttcatcg cccatcggtg cttttattgg atgaaaaaat    2460
gttggttttg tggttgttg cactctctgg aatatctaca cttttttttg ctgctgatca     2520
tttggtggtg tgtgagtgta cctaccgctt tggcagagaa tgactctgca gttaagctaa    2580
gggcgtgttc agattgtgga ggaaaagtgg ccgccatttt agacttgccg cataactcgg    2640
cttagggcta gtcgtttgtg ctaagttaaa ctagggaggc aagatggatg atagcaggtc    2700
```

```
aggcagagga agtcatgtgc attgcatgag ctaaacctat ctgaatgaat tgatttgggg    2760
cttgttagga gctttgcgtg attgttgtat cgggaggcag taagaatcat cttttatcag    2820
tacaagggac tagttaaaaa tggaaggtta ggaaagacta aggtgcaggg cttaaaatgg    2880
cgattttgac attgcggcat tgctcagcat ggcgggctgt gctttgttag gttgtccaaa    2940
atggcggatc cagttctgtc gcagtgttca agtggcggga aggccacatc atgatgggcg    3000
aggctttgtt aagtggttag catggtggtg gacatgtgcg gtcacacagg aaaagatggc    3060
ggctgaaggt cttgccgcag tgtaaaacat ggcgggcctc tttgtctttg ctgtgtgctt    3120
ttcgtgttgg gttttgccgc agggacaata tggcaggcgt tgtcatatgt atatcatggc    3180
ttttgtcacg tggacatcat ggcgggcttg ccgcattgtt aaagatggcg ggttttgccg    3240
cctagtgcca cgcagagcgg gagaaaaggt gggatggaca gtgctggatt gctgcataac    3300
ccaaccaatt agaaatgggg gtggaattga tcacagccaa ttagagcaga agatggaatt    3360
agactgatga cacactgtcc agctactcag cgaagacctg ggtgaattag catggcactt    3420
cgcagctgtc tttagccagt caggagaaag aagtggaggg gccacgtgta tgtctcccag    3480
tgggcggtac accaggtgtt ttcaaggtct tttcaaggac atttagcctt tccacctctg    3540
tcccctctta tttgtcccct cctgtccagt gctgcctctt gcagtgctgg atatctggct    3600
gtgtggtctg aacctccctc cattcctctg tattggtgcc tcacctaagg ctaagtatac    3660 ctccccccc  accccccaac cccccaact  ccccacccc  acccccacc  cccacctcc    3720 ccaccccct  accccctac  cccctaccc  ccctctggtc tgccctgcac tgcactgttg    3780
ccatgggcag tgctccaggc ctgcttggtg tggacatggt ggtgagccgt ggcaaggacc    3840
agaatggatc acagatgatc gttggccaac aggtggcaga agaggaattc ctgccttcct    3900
caagaggaac acctacccct tggctaatgc tggggtcgga ttttgattta tatttatctt    3960
ttggatgtca gtcatacagt ctgattttgt ggtttgctag tgtttgaatt taagtcttaa    4020
gtgactatta tagaaatgta ttaagaggct ttatttgtag aattcacttt aattacattt    4080
aatgagtttt tgttttgagt tccttaaaat tccttaaagt ttttagcttc tcattacaaa    4140
ttccttaacc ttttttggc agtagatagt caaagtcaaa tcatttctaa tgttttaaaa    4200
atgtgctggt cattttcttt gaaattgact taactatttt cctttgaaga gtctgtagca    4260
cagaaacagt aaaaaattta acttcatgac ctaatgtaaa aaagagtgtt tgaaggttta    4320
cacaggtcca ggccttgctt tgttcccatc cttgatgctg cactaattga ctaatcacct    4380
acttatcaga caggaaactt gaattgctgt ggtctggtgt cctctattca gacttattat    4440
attggagtat ttcaattttt cgttgtatcc tgcctgccta gcatccagtt cctccccagc    4500
cctgctccca gcaaacccct agtctagccc cagccctact cccacccggc ccagccctg    4560 ccccaggccc agtcccctaa ccccccagcc ctaggcccag tccagtcct agttcctcag    4620 tctgtccagc ttctctcgaa agtcactcta attttcattg attcagtgct caaaataagt    4680
tgtccattgg tatcctatta tactgggata ttccgtttac ccttggcatt gctgatcttc    4740
agtactgact ccttgaccat tttcagttaa gcatacaatc ccatttgtct gtgatctcag    4800
gacaaagaat ttccttactc ggtacgttga agttagggaa tgtcaattga gagctttcta    4860
tcagagcatt attgcccaca atttgagtta cttatcattt tctcgatccc ctgcccttaa    4920
aggagaaacc atttctctgt cattgcttct gtagtcacag tcccaatttt gagtagtgat    4980
cttttcttgt gtactgtgtt ggccacctaa aactctttgc attgagtaaa attctaattg    5040
ccaataatcc tacccattgg attagacagc actctgaacc ccatttgcat tcagcagggg    5100
```

```
gtcgcagaca acccgtctttt tgttggacag ttaaaatgct cagtcccaat tgtcatagct    5160
ttgcctatta aacaaaggca ccctactgcg cttttgctg tgcttctgga gaatcctgct      5220
gttcttggac aattaaagaa caaagtagta attgctaatt gtctcaccca ttaatcatga    5280
agactaccag tcgcccttgc atttgccttg aggcagcgct gactacctga gatttaagag    5340
tttcttaaat tattgagtaa aatcccaatt atccatagtt ctgttagtta cactatggcc    5400
tttgcaaaca tctttgcata acagcagtgg gactgactca ttcttagagc cccttccctt    5460
ggaatattaa tggatacaat agtaattatt catggttctg cgtaacagag aagacccact    5520
tatgtgtatg cctttatcat tgctcctaga tagtgtgaac tacctaccac cttgcattaa    5580
tatgtaaaac actaattgcc catagtccca ctcattagtc taggatgtcc tctttgccat    5640
tgctgctgag ttctgactac ccaagtttcc ttctcttaaa cagttgatat gcataattgc    5700
atatattcat ggttctgtgc aataaaaatg gattctcacc ccatcccacc ttctgtggga    5760
tgttgctaac gagtgcagat tattcaataa cagctcttga acagttaatt tgcacagttg    5820
caattgtcca gagtcctgtc cattagaaag ggactctgta tcctatttgc acgctacaat    5880
gtgggctgat cacccaagga ctcttcttgt gcattgatgt tcataattgt atttgtccac    5940
gatcttgtgc actaacccctt ccactccctt tgtattccag caggggaccc ttactactca    6000
agacctctgt actaggacag tttatgtgca caatcctaat tgattagaac tgagtctttt    6060
atatcaaggt ccctgcatca tctttgcttt acatcaagag ggtgctggtt acctaatgcc    6120
cctcctccag aaattattga tgtgcaaaat gcaatttccc tatctgctgt tagtctgggg    6180
tctcatcccc tcatattcct tttgtcttac agcaggggt acttgggact gttaatgcgc    6240
ataattgcaa ttatggtctt ttccattaaa ttaagatccc aactgctcac accctcttag    6300
cattacagta gagggtgcta atcacaagga catttctttt gtactgttaa tgtgctactt    6360
gcatttgtcc ctcttcctgt gcactaaaga ccccactcac ttccctagtg ttcagcagtg    6420
gatgacctct agtcaagacc tttgcactag gatagttaat gtgaaccatg caactgatc    6480 acaacaatgt ctttcagatc agatccattt tatcctcctt gttttacagc aagggatatt    6540
aattacctat gttacctttc cctgggacta tgaatgtgca aaattccaat gttcatggtc    6600 tctccctttta aacctatatt ctacccctt tacattatag aaagggatgc tggaaaccca    6660
gagtccttct cttgggactc ttaatgtgta tttctaatta ccatgactc ttaatgtgca    6720 tattttcaat tgcctaattg atttcaattg tctaagacat ttcaaatgtc taattgatta    6780
gaactgagtc ttttatatca agctaatatc tagcttttat atcaagctaa tatcttgact    6840
tctcagcatc atagaagggg gtactgattt cctaaagtct ttcttgaatt tctattatgc    6900
aaaattgccc tgaggccggg tgtggtggct cacacctgta atcccagcac tttgggaggc    6960
tgaggtggga agatcccctta ctgccaggag tttgagacca gcctggccaa cattaaaaaa    7020
aaaaaaaaaa gtaagacaat tgccctggaa tccatcccc ctcacacctc cttggcaaag    7080
cagcaggagt gctaactagc tagtgcttct tctcttatac tgcttaaatg cgcataatta    7140
gcagtagttg atgtgcccct atgttagagt agaatcccgc ttccttgctc catttgcatt    7200
actgcaggag cttctaacta gcctgaattc actctcttgg actgttaatg tgcatactta    7260
tatttgctgc tgtactttt taccatgtaa ggaccccacc cactgtattt acatcccagc    7320
tggaagtacc tactacttaa gacccttaga ctagtaaagt tagcgtgcat aatcttaggt    7380
gttatataca cattttcagt tgcatacagt tgtgccttt atcaggactc ctgtacttat    7440
```

-continued

```
caaagcagag agtgctaatc aatattaagc ccttctcttc gaactgtaga tggcatgtaa    7500
ttgcagttgt caatggtcct tcaattagac ttgggtttct gacctatcac accctctttg    7560
ctttattgca tggggtacta ttcacttaag gccccttttct caaactgtta atgtgcctaa    7620
tgacaattac atcagtatcc ttcctttttga aggacagcat ggttggtgac acctaaggcc    7680
ccatttcttg gcctcccaat atgtgtgatt gtatttgtcg aggttgctat gcactagaga    7740
aggaaagtgc tccctcatc cccactttttc ccttccagca ggaagtgccc accccataag    7800
acccttttat ttggagagtc taggtgcaca attgtaagtg accacaagca tgcatcttgg    7860
acatttatgt gcgtaatcgc acactgctca ttccatgtga ataaggtcct actctccgac    7920
ccctttttgca atacagaagg gttgctgata acgcagtccc ctttttcttgg catgttgtgt    7980
gtgattataa tcgtctggga tcctatgcac tagaaaagga gggtcctctc cacataccctc    8040
agtctcacct ttcccttcca gcagggagtg cccactccat aagactctca catttggaca    8100
gtcaaggtgc gtaattgtta agtgaacaca accatgcacc ttagacatgg atttgcataa    8160
ctacacacag ctcaacctat ctgaataaaa tcctactctc agacccctttt tgcagtacag    8220
caggggtgct gatcaccaag gcccttttttc ctggcctggt atgcgtgtga ttatgtttgt    8280
cccggttcct gtgtattaga catggaagcc tccctgcca cactccaccc ccaatcttcc    8340
tttcccttcc ggcaggagtg ccctctccat aagacgctta cgtttggaca atcaaggtgc    8400
acagttgtaa gtgaccacag gcatacacct tggacattaa tgtgcataac cactttgccc    8460
attccatctg aataaggtcc tactctcaga ccccttttgc agtacagcag gggtgctgat    8520
caccaaggcc ccttttcttg gcctgttatg tgcgtgatta tatttgtctg ggttcctgtg    8580
tattagacaa ggaagccttc ccccgcccc accccccact cccagtcttc ctttcccttc    8640
cagcaggag tgcccctcc ataagatcat tacatttgga caatcaaggt gcacaattat    8700
aagtgaccac agccatgcac cttggacatt attggacatt aatgtgcgta actgcacatg    8760
gcccatccca tctgaataag gacctactct cagatgcctt tgcagtacag caggggtact    8820
gaatcaccaa ggcccttttt cttggcctgt tatgtgtgtg attatattta tcccagtttc    8880
tgtgtaatag acatgaaagc ctcccctgcc acacccacc tccaatcttc ctttcccttc    8940
caccagggag tgtccactcc atatacccttt acatttggac aatcaaggtg cacaattgta    9000
agtgagcata gcactcacc ttggacatga atgtgcataa ctgcacatgg cccatcccat    9060
ctgaataagg tcctactctc agacccttttt tgcagtacag caggggtgct gatcaccaag    9120
gccccttttc ctggcctgtt atgtgtgtga ttatatttgt tccagttcct gtgtaataga    9180
catggaagcc tcccctgcca cactccaccc ccaatcttcc tttccttctg gcaggaagta    9240
cccgctccat aagaccctta catttggaca gtcaaggtgc acaattgtat gtgaccacaa    9300
ccatgcacct tggacataaa tgtgtgtaac tgcacatggc ccatcccatc tgaataaggt    9360
cctactctca gaccccttttt gcagtacagt aggtgtgctg ataaccaagg ccctcttcc    9420
tggcctgtta acgtatgtga ttatatttgt ctgggttcca gtgtataaga catggaagcc    9480
tcccctgccc caccccaccc tcaatcttcc tttcccttct ggcagggagt gccagctcca    9540
taagaaccctt acatttggac agtcaaggtg cacaattcta agtgaccgca gccatgcacc    9600
ttggtcaata atgtgtgtaa ctgcacacgg cctatctcat ctgaataagg ccttactctc    9660
agacccctttt tgcagtacag caggggtgct gataaccaag gcccattttc ctggcctgtt    9720
atgtgtgtga ttatatttgt ccaggtttct gtgtactaga caaggaagcc tcctctgccc    9780
catcccatct acgcataatc tttcttttcc tcccagcagg gagtgctcac tccataagac    9840
```

```
ccttacattt ggacaatcaa ggtgcacaat tgtaagtgac cacaaccatg catcttggaa    9900
atttatgtgc ataactgcac atggcttatc ctatttgaat aaagtcctac tctcagaccc    9960
cctttgcagt atagctgggg tgctgatcac tgaggcctct ttgcttggct tgtctatatt   10020
cttgtgtact agataagggc accttctcat ggactccctt tgcttttcaa caaggagtac   10080
ccactacttt ttaagattct tatatttgtc caaagtacat ggttttaatt gaccacaaca   10140
atgtcccttg gacattaatg tatgtaatca ccacatggtt catcctaatt aaacaaagtt   10200
ctaccttctc accctccatt tgcagtatac caggggttgct gaccccctaa gtccccttttt  10260
cttggcttgt tgacatgcat aattgcattt atgttggttc ttgtgcccta gacaaggatg   10320
ccccacctct tttcaatagt gggtgcccac tccttatgat cttttacattt gaacagttaa   10380
tgtgaataat tgcagttgtc cacaaccta tcacttctag gaccattata cctcttttgc    10440
attactgtgg ggtatactgt ttccctccaa ggccccttct ggtggactat caacatataa   10500
ttgaaatttt cttttgtctt tgtcagtaga ttaaggtcat accccatcac ctttcctttg   10560
tagtacaaca gggtgtcctg atcaaccaaa gtcctgttgt tttggactgt taatatgtgc   10620
aattacattt gctcctgatc tgtgcactag ataaggatcc tacctacttt cttagtgttt   10680
ttagcaggta gtgcccacta ctcaagactg tcacttggaa tgttcatgtg cacaaactca   10740
attctctaag catgttcctg taccacctttt gctttagagc aggggatga tattcactaa   10800
gtgcccctc ttttggactt aatatgcatt aatgcaattg tccacctctt cttttagact   10860
aagagttgat ctccacatat tccccttgca tcagggcat gttaattatg aatgaaccct   10920
tttctttta tattaatgtc ataattgtat ttgtggacct gtgtaggaga aaaagacccct  10980
atgttcctcc cattcccttt tggattgctg ctgagaagtg ttaactactc ataatctcag   11040
ctcttggaca attaatagca ttaataacaa ttatcaaggg cactgatcat tagataagac   11100
tcctgcttcc tcgttgctta catcgggggt actgacccac taaggcccct tgtactgtta   11160
atgtgaatat ttgcaattat atatgtctcc ttctggtaga gtgggatatt atgccctagt   11220
atccccttg cattactgca ggggctgctg actactcaaa acttctcctg ggactgttaa   11280
taggcacaat ggcagttatc aatggttttc tccctccctg accttgttaa gcaagcgccc   11340
cacccccaccc ttagttttccc atggcataat aaagtataag cattggagta ttccatgcac  11400
ttgtctatca aacagtggtc catactccca acccttttgc attgcgccag tgtgtaaaat   11460
cacaggtagc catggtgtca tgctttatat acgaagtctt ccctctctct gcccccttgtg   11520
tgcccttggc ccctttttac agactattgc tcacaatctc aggtgtccat atttgcagct   11580
attaggtaag attgtgctgt ctccctcttc ccttccctct gcctgcccc ttttgcctct   11640
ttgctgggta atgttgacca gacaaggcc tttctcttgg acttaaacaa ttctcagttt   11700
cactttcctt ggtccaccca ttatacatga acccctctac ttcctttcgc attgcttctg   11760
agtatgctga ctacccaaag cccccttctgt gttattaata aacacagtac tgattgtccc   11820
attttttcagc ccatcagtcc aagatctccc taccactttg gtgtgttggt gcagtgttga   11880
ctatgaaaag caggcctgaa ctaggtggat aagccttcac tcattttctt tcatttatta   11940
atgatcctag tttcaattat tgtcagattc tggggacaag aaccattctt gcccacctgt   12000
gttactgctt tactgtgcaa aatactgaag gcaagtcaga cccagggagc tggattgcca   12060
tcctttattt tgtgtttcca gtgtacacta taaaattgtc tccccaggaa ggaaggttgg   12120
cactttctct gcattcttct ttccagagca gattgcctgg ttaagaatct cttgttgtcc   12180
```

```
cttctgtata ttgttattgt aaagtgccaa atgccaggat acagccagaa aaattgctta    12240
ttattattaa aaaaattttt ttaagaaaga catctggatt gtagggtgga ctcgataacc    12300
tggtcattat tttttgaag ccaaaatatc catttatact atgtacctgg tgaccagtgt     12360
ctctcatttt aactgagggt ggtgggtctg tggatagaac actgactctt gctattttaa    12420
tatcaaagat attctagatc cagcacagtg gcggccgctc tagagtggaa ctcttaagac    12480
cagtatcttt gtgtgggctt taccagcatt cacttttaga aaaactacct aaattttata    12540
atcctttaat ttcttcatct ggagcacctg ccctactta tttcaagaag attgcagtaa     12600
aacgattaaa tgagggaaca tatgcagagg tgcttttaaa aagcatatgc cacctttttt    12660
attaattatt atataaaatg aagcatttaa ttatagtaat aatttgaagt agtttgaagt    12720
accacactga ggtgaggact taaaaatgat aagacgagtt ccctatttta taagaaaaat    12780
aagccaaaat taaatattct tttggatata aatttcaaca gtgagatagc tgcctagtgg    12840
aaatgaataa tatcccagcc actagtgtac agggtgtttt gtggcacagg attatgtaat    12900
atggaactgc tcaagcaaat aactagtcat cacaacagca gttctttgta ataactgaaa    12960
aagaatattg tttctcggag aaggatgtca aaagatcggc ccagctcagg gagcagtttg    13020
ccctactagc tcctcggaca gctgtaaaga agagtctctg gctctttaga atactgatcc    13080
cattgaagat accacgctgc atgtgtcctt agtagtcatg tctccttagg ctcctcttgg    13140
acattctgag catgtgagac ctgaggactg caaacagcta aagaggctc caaattaatc     13200 atatctttcc ctttgagaat ctggccaagc tccagctaat ctacttggat gggttgccag    13260
ctatctggag aaaaagatct tcctcagaag aataggcttg ttgttttaca gtgttagtga    13320
tccattccct ttgacgatcc ctaggtggag atggggcatg aggatcctcc aggggaaaag    13380
ctcactacca ctgggcaaca acctaggtc aggaggttct gtcaagatac tttcctggtc     13440
ccagatagga agataaagtc tcaaaaacaa ccaccacacg tcaagctctt cattgttcct    13500
atctgccaaa tcattatact tcctacaagc agtgcagaga gctgagtctt cagcaggtcc    13560
aagaaatttg aacacactga aggaagtcag ccttcccacc tgaagatcaa catgcctggc    13620
actctagcac ttgaggatag ctgaatgaat gtgtatttct ttgtctcttt ctttcttgtc    13680
tttgctcttt gttctctatc taaagtgtgt cttacccatt tccatgtttc tcttgctaat    13740
ttctttcgtg tgtgccttg cctcattttc tcttttgtt cacaagagtg gtctgtgtct      13800
tgtcttagac atatctctca ttttcattt tgttgctatt tctctttgct ctcctagatg     13860
tggctcttct ttcacgcttt atttcatgtc tccttttgg gtcacatgct gtgtgctttt     13920
tgtccttttc ttgttctgtc tacctctcct ttctctgcct acctctcttt tctctttgtg    13980
aactgtgatt atttgttacc ccttcccctt ctcgttcgtt ttaaatttca cttttttct    14040 gagtctggcc tcctttctgc tgtttctact ttttatctca catttctcat ttctgcattt    14100
cctttctgcc tctcttgggc tattctctct ctcctcccct gcgtgcctca gcatctcttg    14160
ctgtttgtga ttttctattt cagtattaat ctctgttggc ttgtatttgt tctctgcttc    14220 ttcccttttct actcaccttt gagtatttca gcctcttcat gaatctatct ccctctcttt   14280
gatttcatgt aatctctcct taaatatttc tttgcatatg tgggcaagtg tacgtgtgtg    14340
tgtgtcatgt gtggcagagg ggcttcctaa cccctgcctg ataggtgcag aacgtcggct    14400
atcagagcaa gcattgtgga gcggttcctt atgccaggct gccatgtgag atgatccaag    14460
accaaaacaa ggccctagac tgcagtaaaa cccagaactc aagtagggca gaaggtggaa    14520
ggctcatatg gatagaaggc ccaaagtata agacagatgg tttgagactt gagacccgag    14580
```

```
gactaagatg gaaagcccat gttccaagat agatagaagc ctcaggcctg aaaccaacaa    14640
aagcctcaag agccaagaaa acagagggtg gcctgaattg gaccgaaggc ctgagttgga    14700
tggaagtctc aaggcttgag ttagaagtct taagacctgg gacaggacac atggaaggcc    14760
taagaactga gacttgtgac acaaggccaa cgacctaaga ttagcccagg gttgtagctg    14820
gaagacctac aacccaagga tggaaggccc ctgtcacaaa gcctacctag atggatagag    14880
gacccaagcg aaaaaggtat ctcaagacta acggccggaa tctggaggcc catgacccag    14940
aacccaggaa ggatagaagc ttgaagacct ggggaaatcc caagatgaga accctaaacc    15000
ctacctcttt tctattgttt acacttctta ctcttagata tttccagttc tcctgtttat    15060
ctttaagcct gattcttttg agatgtactt tttgatgttg ccggttacct ttagattgac    15120
agtattatgc ctgggccagt cttgagccag ctttaaatca cagcttttac ctatttgtta    15180
ggctatagtg ttttgtaaac ttctgtttct attcacatct tctccacttg agagagacac    15240
caaaatccag tcagtatcta atctggcttt tgttaacttc cctcaggagc agacattcat    15300
ataggtgata ctgtatttca gtcctttctt ttgaccccag aagccctaga ctgagaagat    15360
aaaatggtca ggttgttggg gaaaaaaaaa gtgccaggct ctctagagaa aaatgtgaag    15420
agatgctcca ggccaatgag aagaattaga caagaaatac acagatgtgc cagacttctg    15480
agaagcacct gccagcaaca gcttccttct ttgagcttag attttcctag tccatccctc    15540
atgaaaaatg actgaccact gctgggcagc aggagggatg atgaccaact aattcccaaa    15600
ccccagtctc attggtaccg agctcggatc cactagtcca gtgtggtgga attctgcaga    15660
tatccagcac agtggcggcc gctcgagtct agagggcccg tttaaacccg ctgatcagcc    15720
tcgactgtgc cttctagttg ccagccatct gttgtttgcc cctcccccgt gccttccttg    15780
accctggaag gtgccactcc cactgtcctt tcctaataaa atgaggaaat tgcatcgcat    15840
tgtctgagta ggtgtcattc tattctgggg ggtggggtgg ggcaggacag caaggggag    15900 gattgggaag acaatagcag gcatgctggg gatgcggtgg gctctatggc ttctgaggcg    15960
gaaagaacca gctggggctc tagggggtat ccccacgcgc cctgtagcgg cgcattaagc    16020
gcggcgggtg tggtggttac gcgcagcgtg accgctacac ttgccagcgc cctagcgccc    16080
gctcctttcg ctttcttccc ttcctttctc gccacgttcg ccggctttcc ccgtcaagct    16140
ctaaatcggg ggctcccttt agggttccga tttagtgctt tacggcacct cgaccccaaa    16200
aaacttgatt agggtgatgg ttcacgtagt gggccatcgc cctgatagac ggttttcgc    16260 cctttgacgt tggagtccac gttctttaat agtggactct tgttccaaac tggaacaaca    16320
ctcaacccta tctcggtcta ttcttttgat ttataaggga ttttgccgat ttcggcctat    16380
tggttaaaaa atgagctgat ttaacaaaaa tttaacgcga attaattctg tggaatgtgt    16440
gtcagttagg gtgtggaaag tccccaggct ccccagcagg cagaagtatg caaagcatgc    16500
atctcaatta gtcagcaacc aggtgtggaa agtcccagg ctccccagca ggcagaagta    16560
tgcaaagcat gcatctcaat tagtcagcaa ccatagtccc gcccctaact ccgcccatcc    16620
cgcccctaac tccgcccagt tccgcccatt ctccgcccca tggctgacta attttttta    16680 tttatgcaga ggccgaggcc gcctctgcct ctgagctatt ccagaagtag tgaggaggct    16740
tttttggagg cctaggcttt tgcaaaaagc tcccgggagc ttgtatatcc attttcggat    16800
ctgatcagca cgtgatgaaa aagcctgaac tcaccgcgac gtctgtcgag aagtttctga    16860
tcgaaaagtt cgacagcgtc tccgacctga tgcagctctc ggagggcgaa gaatctcgtg    16920
```

-continued

```
ctttcagctt cgatgtagga gggcgtggat atgtcctgcg ggtaaatagc tgcgccgatg    16980
gtttctacaa agatcgttat gtttatcggc actttgcatc ggccgcgctc ccgattccgg    17040
aagtgcttga cattggggaa ttcagcgaga gcctgaccta ttgcatctcc cgccgtgcac    17100
agggtgtcac gttgcaagac ctgcctgaaa ccgaactgcc cgctgttctg cagccggtcg    17160
cggaggccat ggatgcgatc gctgcggccg atcttagcca gacgagcggg ttcggcccat    17220
tcggaccgca aggaatcggt caatacacta catggcgtga tttcatatgc gcgattgctg    17280
atccccatgt gtatcactgg caaactgtga tggacgacac cgtcagtgcg tccgtcgcgc    17340
aggctctcga tgagctgatg ctttgggccg aggactgccc cgaagtccgg cacctcgtgc    17400
acgcggattt cggctccaac aatgtcctga cggacaatgg ccgcataaca gcggtcattg    17460
actggagcga ggcgatgttc ggggattccc aatacgaggt cgccaacatc ttcttctgga    17520
ggccgtggtt ggcttgtatg gagcagcaga cgcgctactt cgagcggagg catccggagc    17580
ttgcaggatc gccgcggctc cgggcgtata tgctccgcat tggtcttgac caactctatc    17640
agagcttggt tgacggcaat ttcgatgatg cagcttgggc gcagggtcga tgcgacgcaa    17700
tcgtccgatc cggagccggg actgtcgggc gtacacaaat cgcccgcaga agcgcggccg    17760
tctgaccgga tggctgtgta gaagtactcg ccgatagtgg aaaccgacgc cccagcactc    17820
gtccgagggc aaaggaatag cacgtgctac gagatttcga ttccaccgcc gccttctatg    17880
aaaggttggg cttcggaatc gttttccggg acgccggctg gatgatcctc cagcgcgggg    17940
atctcatgct ggagttcttc gcccacccca acttgtttat tgcagcttat aatggttaca    18000
aataaagcaa tagcatcaca aatttcacaa ataaagcatt ttttttcactg cattctagtt    18060 gtggtttgtc caaactcatc aatgtatctt atcatgtctg tatacgggtg gaggggcgtg    18120
atgcagggtc cccacgatca gccgcagtct ctctaacact gcaggtggtg ccaagaggca    18180
ggcatgctcc cagcacaagg gacggtggcg cagaagaata cagagaagct cacaaaacat    18240
gccggcatgg gctcaggaga gctacggggg tagtggtggt actgctccct ggtgcagggc    18300
agcagctgtg tctcccccctg cctccctccc acccgagggc cctgctcacc tggccccagc    18360
ttggagatgg catataagag atcatagttt atgactgggg tcgcatcttc cacttgtttc    18420
catcccactg gcggagaggc gggaggggag atcagaaact gcttgtctgg atttggcgga    18480
gccaggtgtg agcttcctat gtgtaaggtc tgaggagaga aaataagcac aggtcagttg    18540
ttgccaggga agaactgcag tgaggcaaca gcacctaacg ccagttccgg gagatgggca    18600
ggtcaatgtc caggcgtcag gacaggtgtg attccaggac caattgtaag atggtctgta    18660
atggggaggg caaaaggaca tatgaactct ggttgtggca cagataggat gacagccccc    18720
tcccagggct atgggagtca caggcacagg gactgcaaat aattacgctt gacctagatg    18780
gacagaaaat cagcagaggt gactttagta tatatggaaa tttaagtcac tgtcattgag    18840
gtcaggaggg ctcttgggta taccgtcgac ctctagctag agcttggcgt aatcatggtc    18900
atagctgttt cctgtgtgaa attgttatcc gctcacaatt ccacacaaca tacgagccgg    18960
aagcataaag tgtaaagcct ggggtgccta atgagtgagc taactcacat taattgcgtt    19020
gcgctcactg cccgctttcc agtcgggaaa cctgtcgtgc cagctgcatt aatgaatcgg    19080
ccaacgcgcg gggagaggcg gtttgcgtat tgggcgctct tccgcttcct cgctcactga    19140
ctcgctgcgc tcggtcgttc ggctgcggcg agcggtatca gctcactcaa aggcggtaat    19200
acggttatcc acagaatcag gggataacgc aggaaagaac atgtgagcaa aaggccagca    19260
aaaggccagg aaccgtaaaa aggccgcgtt gctggcgttt ttccataggc tccgcccccc    19320
```

```
tgacgagcat cacaaaaatc gacgctcaag tcagaggtgg cgaaacccga caggactata    19380
aagataccag gcgtttcccc ctggaagctc cctcgtgcgc tctcctgttc cgaccctgcc    19440
gcttaccgga tacctgtccg cctttctccc ttcgggaagc gtggcgcttt ctcatagctc    19500
acgctgtagg tatctcagtt cggtgtaggt cgttcgctcc aagctgggct gtgtgcacga    19560
accccccgtt cagcccgacc gctgcgcctt atccggtaac tatcgtcttg agtccaaccc    19620
ggtaagacac gacttatcgc cactggcagc agccactggt aacaggatta gcagagcgag    19680
gtatgtaggc ggtgctacag agttcttgaa gtggtggcct aactacggct acactagaag    19740
aacagtattt ggtatctgcg ctctgctgaa gccagttacc ttcggaaaaa gagttggtag    19800
ctcttgatcc ggcaaacaaa ccaccgctgg tagcggttgg ttttttgttt gcaagcagca    19860
gattacgcgc agaaaaaaag gatctcaaga agatcctttg atcttttcta cggggtctga    19920
cgctcagtgg aacgaaaact cacgttaagg gattttggtc atgagattat caaaaaggat    19980
cttcacctag atccttttaa attaaaaatg aagttttaaa tcaatctaaa gtatatatga    20040
gtaaacttgg tctgacagtt accaatgctt aatcagtgag gcacctatct cagcgatctg    20100
tctatttcgt tcatccatag ttgcctgact ccccgtcgtg tagataacta cgatacggga    20160
gggcttacca tctggcccca gtgctgcaat gataccgcga gacccacgct caccggctcc    20220
agatttatca gcaataaacc agccagccgg aagggccgag cgcagaagtg gtcctgcaac    20280
tttatccgcc tccatccagt ctattaattg ttgccgggaa gctagagtaa gtagttcgcc    20340
agttaatagt ttgcgcaacg ttgttgccat tgctacaggc atcgtggtgt cacgctcgtc    20400
gtttggtatg gcttcattca gctccggttc ccaacgatca aggcgagtta catgatcccc    20460
catgttgtgc aaaaaagcgg ttagctcctt cggtcctccg atcgttgtca gaagtaagtt    20520
ggccgcagtg ttatcactca tggttatggc agcactgcat aattctctta ctgtcatgcc    20580
atccgtaaga tgcttttctg tgactggtga gtactcaacc aagtcattct gagaatagtg    20640
tatgcggcga ccgagttgct cttgcccggc gtcaatacgg gataataccg cgccacatag    20700
cagaacttta aaagtgctca tcattggaaa acgttcttcg gggcgaaaac tctcaaggat    20760
cttaccgctg ttgagatcca gttcgatgta acccactcgt gcacccaact gatcttcagc    20820
atcttttact ttcaccagcg tttctgggtg agcaaaaaca ggaaggcaaa atgccgcaaa    20880
aaagggaata agggcgacac ggaaatgttg aatactcata ctcttccttt ttcaatatta    20940
ttgaagcatt tatcagggtt attgtctcat gagcggatac atatttgaat gtatttagaa    21000
aaataaacaa atagggggttc cgcgcacatt tccccgaaaa gtgccacctg acgtc         21055
```

<210> SEQ ID NO 54
<211> LENGTH: 20737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg aaaaccagaa agtattctca gtaatgatag      240
tatggataaa gcaggtttct atgaccctt attacagaat ctgtgagttt ttcacaatta       300
```

```
aaaagtaata aaaagtagtg acaacattca ctgaactctt attctatgcc aacttgttcc      360
ggtatgccct tacacccaca aaagccctat gcataaggtg gcattattcc agcatgtatt      420
gcattgtaca cacaaagagg tcaagcactc caccacggcc ctaagcatgg tggctgaggt      480
gggaaggcca gaggtaggtg ggcccgcgcc cttttccact ctgaaccatg cctccaagat      540
aggagggtgg gaaagtgctc aagacacatt agaaattccc cataaaagac aagattgttg      600
aacacctgca agtgaataaa gataaactga tctcagaggg gaaaaagacg cagggttagg      660
aaacagcacc ctgctcgagg acgttctttc caaacagcct gctcatcacc cgttcgcgat      720
gtacgggcca gatatacgcg ttgacattga ttattgacta gttattaata gtaatcaatt      780
acggggtcat tagttcatag cccatatatg gagttccgcg ttacataact tacggtaaat      840
ggcccgcctg gctgaccgcc caacgacccc cgcccattga cgtcaataat gacgtatgtt      900
cccatagtaa cgccaatagg gactttccat tgacgtcaat gggtggagta tttacggtaa      960
actgcccact tggcagtaca tcaagtgtat catatgccaa gtacgccccc tattgacgtc     1020
aatgacggta aatggcccgc ctggcattat gcccagtaca tgaccttatg ggactttcct     1080
acttggcagt acatctacgt attagtcatc gctattacca tggtgatgcg gttttggcag     1140
tacatcaatg ggcgtggata gcggtttgac tcacggggat ttccaagtct ccaccccatt     1200
gacgtcaatg ggagtttgtt ttggcaccaa aatcaacggg actttccaaa atgtcgtaac     1260
aactccgccc cattgacgca aatgggcggt aggcgtgtac ggtgggaggt ctatataagc     1320
agagctctcc ctatcagtga tagagatctc cctatcagtg atagagatcg tcgacgagct     1380
cgtttagtga accgtcagat cgcctggaga cgccatccac gctgttttga cctccataga     1440
agacaccggg accgatccag cctccggact ctagcgttta aacttaagct tggtaccgag     1500
ctcggatcca ctagtccagt gtggtggaat tctgcagatt ctagaacatt ttctagtccc     1560
ccaacaccct ttatggcgta tttctttaaa aaaatcacct aaattccata aaatattttt     1620
ttaaattcta tactttctcc tagtgtcttc ttgacacgtc ctccatattt tttttaaagaa    1680
agtatttgga atattttgag gcaattttta atatttaagg aatttttctt tggaatcatt     1740
tttggtgaca tctctgtttt ttgtggatca gtttttttact cttccactct cttttctata    1800
ttttgcccat cggggctgcg gatacctggt tttattattt tttctttgcc caacggggcc     1860
gtggatacct gccttttaat tcttttttat tcgcccatcg gggccgcgga tacctgcttt     1920
ttattttttt ttccttagcc catcgggggta tcggatacct gctgattccc ttcccctctg    1980
aaccccaac actctggccc atcggggtga cggatatctg cttttttaaaa atttttcttt     2040
tttggcccat cggggcttcg gatacctgct tttttttttt ttattttcct tgcccatcgg     2100
ggcctcggat acctgcttta atttttgttt ttctgcccat cggggccgcg gatacctgct     2160
ttgatttttt ttttttcatcg cccatcggtg cttttttatgg atgaaaaaat gttggttttg    2220
tgggttgttg cactctctgg aatatctaca ctttttttg ctgctgatca tttggtggtg      2280
tgtgagtgta cctaccgctt tggcagagaa tgactctgca gttaagctaa gggcgtgttc     2340
agattgtgga ggaaaagtgg ccgccatttt agacttgccg cataactcgg cttagggcta     2400
gtcgtttgtg ctaagttaaa ctagggaggc aagatggatg atagcaggtc aggcagagga     2460
agtcatgtgc attgcatgag ctaaaccctat ctgaatgaat tgatttgggg cttgttagga    2520
gctttgcgtg attgttgtat cgggaggcag taagaatcat cttttatcag tacaagggac     2580
tagttaaaaa tggaaggtta ggaaagacta aggtgcaggg cttaaaatgg cgattttgac     2640
```

```
attgcggcat tgctcagcat ggcgggctgt gctttgttag gttgtccaaa atggcggatc      2700
cagttctgtc gcagtgttca agtggcggga aggccacatc atgatgggcg aggctttgtt      2760
aagtggttag catggtggtg gacatgtgcg gtcacacagg aaaagatggc ggctgaaggt      2820
cttgccgcag tgtaaaacat ggcgggcctc tttgtctttg ctgtgtgctt ttcgtgttgg      2880
gttttgccgc agggacaata tggcaggcgt tgtcatatgt atatcatggc ttttgtcacg      2940
tggacatcat ggcgggcttg ccgcattgtt aaagatggcg ggttttgccg cctagtgcca      3000
cgcagagcgg gagaaaaggt gggatggaca gtgctggatt gctgcataac ccaaccaatt      3060
agaaatgggg gtggaattga tcacagccaa ttagagcaga agatggaatt agactgatga      3120
cacactgtcc agctactcag cgaagacctg ggtgaattag catggcactt cgcagctgtc      3180
tttagccagt caggagaaag aagtggaggg gccacgtgta tgtctcccag tgggcggtac      3240
accaggtgtt ttcaaggtct tttcaaggac atttagcctt ccacctctg tccctctta      3300 tttgtcccct cctgtccagt gctgcctctt gcagtgctgg atatctggct gtgtggtctg      3360
aacctccctc cattcctctg tattggtgcc tcacctaagg ctaagtatac ctcccccccc      3420
accccccaac ccccccaact ccccaccccc accccccacc cccacctcc ccacccccct      3480 acccccctac cccctaccc ccctctggtc tgccctgcac tgcactgttg ccatgggcag      3540
tgctccaggc ctgcttggtg tggacatggt ggtgagccgt ggcaaggacc agaatggatc      3600
acagatgatc gttggccaac aggtggcaga agaggaattc ctgccttcct caagaggaac      3660 acctaccct tggctaatgc tggggtcgga ttttgattta tatttatctt ttggatgtca      3720
gtcatacagt ctgattttgt ggtttgctag tgtttgaatt taagtcttaa gtgactatta      3780
tagaaatgta ttaagaggct ttatttgtag aattcactt aattacattt aatgagtttt      3840
tgttttgagt tccttaaaat tccttaaagt ttttagcttc tcattacaaa ttccttaacc      3900 ttttttttggc agtagatagt caaagtcaaa tcatttctaa tgttttaaaa atgtgctggt      3960 catttttcttt gaaattgact taactatttt cctttgaaga gtctgtagca cagaaacagt      4020
aaaaaattta acttcatgac ctaatgtaaa aaagagtgtt tgaaggttta cacaggtcca      4080
ggccttgctt tgttcccatc cttgatgctg cactaattga ctaatcacct acttatcaga      4140
caggaaactt gaattgctgt ggtctggtgt cctctattca gacttattat attggagtat      4200
ttcaattttt cgttgtatcc tgcctgccta gcatccagtt cctccccagc cctgctccca      4260
gcaaacccct agtctagccc cagccctact cccacccggc cccagccctg ccccaggccc      4320
agtcccctaa ccccccagcc ctaggcccag tcccagtcct agttcctcag tctgtccagc      4380
ttctctcgaa agtcactcta attttcattg attcagtgct caaaataagt tgtccattgg      4440
tatcctatta tactgggata ttccgtttac ccttggcatt gctgatcttc agtactgact      4500
ccttgaccat tttcagttaa gcatacaatc ccatttgtct gtgatctcag gacaaagaat      4560
ttccttactc ggtacgttga agttagggaa tgtcaattga gagcttcta tcagagcatt      4620 attgcccaca atttgagtta cttatcattt tctcgatccc ctgcccttaa aggagaaacc      4680
atttctctgt cattgcttct gtagtcacag tcccaatttt gagtagtgat ctttctcttgt      4740 gtactgtgtt ggccacctaa aactctttgc attgagtaaa attctaattg ccaataatcc      4800
tacccattgg attagacagc actctgaacc ccatttgcat tcagcagggg gtcgcagaca      4860
acccgtcttt tgttggacag ttaaaatgct cagtcccaat tgtcatagct ttgcctatta      4920
aacaaaggca ccctactgcg cttttttgctg tgcttctgga gaatcctgct gttcttggac      4980
aattaaagaa caaagtagta attgctaatt gtctcaccca ttaatcatga agactaccag      5040
```

```
tcgcccttgc atttgccttg aggcagcgct gactacctga gatttaagag tttcttaaat    5100
tattgagtaa aatcccaatt atccatagtt ctgttagtta cactatggcc tttgcaaaca    5160
tctttgcata acagcagtgg gactgactca ttcttagagc ccttcccctt ggaatattaa    5220
tggatacaat agtaattatt catggttctg cgtaacagag aagacccact tatgtgtatg    5280
cctttatcat tgctcctaga tagtgtgaac tacctaccac cttgcattaa tatgtaaaac    5340
actaattgcc catagtccca ctcattagtc taggatgtcc tctttgccat tgctgctgag    5400
ttctgactac ccaagtttcc ttctcttaaa cagttgatat gcataattgc atatattcat    5460
ggttctgtga aataaaaatg gattctcacc ccatcccacc ttctgtggga tgttgctaac    5520
gagtgcagat tattcaataa cagctcttga acagttaatt tgcacagttg caattgtcca    5580
gagtcctgtc cattagaaag ggactctgta tcctatttgc acgctacaat gtgggctgat    5640
cacccaagga ctcttcttgt gcattgatgt tcataattgt atttgtccac gatcttgtgc    5700
actaacccct ccactccctt tgtattccag caggggaccc ttactactca agacctctgt    5760
actaggacag tttatgtgca caatcctaat tgattagaac tgagtctttt atatcaaggt    5820
ccctgcatca tctttgcttt acatcaagag ggtgctggtt acctaatgcc cctcctccag    5880
aaattattga tgtgcaaaat gcaatttccc tatctgctgt tagtctgggg tctcatcccc    5940
tcatattcct tttgtcttac agcagggggt acttgggact gttaatgcgc ataattgcaa    6000
ttatggtctt ttccattaaa ttaagatccc aactgctcac accctcttag cattacagta    6060
gagggtgcta atcacaagga catttctttt gtactgttaa tgtgctactt gcatttgtcc    6120
ctcttcctgt gcactaaaga ccccactcac ttccctagtg ttcagcagtg gatgacctct    6180
agtcaagacc tttgcactag gatagttaat gtgaaccatg gcaactgatc acaacaatgt    6240
ctttcagatc agatccattt tatcctcctt gttttacagc aagggatatt aattacctat    6300
gttacctttc cctgggacta tgaatgtgca aaattccaat gttcatggtc tctccctta    6360 aacctatatt ctacccctttt tacattatag aaagggatgc tggaaaccca gagtccttct    6420
cttgggactc ttaatgtgta tttctaatta tccatgactc ttaatgtgca tattttcaat    6480
tgcctaattg atttcaattg tctaagacat ttcaaatgtc taattgatta gaactgagtc    6540
ttttatatca agctaatatc tagctttat atcaagctaa tatcttgact tctcagcatc    6600
atagaagggg gtactgattt cctaaagtct ttcttgaatt tctattatgc aaaattgccc    6660
tgaggccggg tgtggtggct cacacctgta atcccagcac tttgggaggc tgaggtggga    6720 agatcccctta ctgccaggag tttgagacca gcctggccaa cattaaaaaa aaaaaaaaa    6780 gtaagacaat tgccctggaa tcccatcccc ctcacacctc cttggcaaag cagcaggagt    6840
gctaactagc tagtgcttct tctcttatac tgcttaaatg cgcataatta gcagtagttg    6900
atgtgcccct atgttagagt agaatcccgc ttccttgctc catttgcatt actgcaggag    6960
cttctaacta gcctgaattc actctcttgg actgttaatg tgcatactta tatttgctgc    7020
tgtacttttt taccatgtaa ggaccccacc cactgtattt acatcccagc tggaagtacc    7080
tactacttaa gacccttaga ctagtaaagt tagcgtgcat aatcttaggt gttatataca    7140 catttttcagt tgcatacagt tgtgcctttt atcaggactc ctgtacttat caaagcagag    7200
agtgctaatc aatattaagc ccttctcttc gaactgtaga tggcatgtaa ttgcagttgt    7260
caatggtcct tcaattagac ttgggtttct gacctatcac accctctttg ctttattgca    7320
tggggtacta ttcacttaag gccccttttct caaactgtta atgtgcctaa tgacaattac    7380
```

```
atcagtatcc ttccttttga aggacagcat ggttggtgac acctaaggcc ccatttcttg    7440
gcctcccaat atgtgtgatt gtatttgtcg aggttgctat gcactagaga aggaaagtgc    7500
tcccctcatc cccactttc ccttccagca ggaagtgccc accccataag acccttttat    7560
ttggagagtc taggtgcaca attgtaagtg accacaagca tgcatcttgg acatttatgt    7620
gcgtaatcgc acactgctca ttccatgtga ataaggtcct actctccgac cccttttgca    7680
atacagaagg gttgctgata acgcagtccc cttttcttgg catgttgtgt gtgattataa    7740
tcgtctggga tcctatgcac tagaaaagga gggtcctctc acatacctc agtctcacct     7800
ttcccttcca gcagggagtg cccactccat aagactctca catttggaca gtcaaggtgc    7860
gtaattgtta agtgaacaca accatgcacc ttagacatgg atttgcataa ctacacacag    7920
ctcaacctat ctgaataaaa tcctactctc agaccccttt tgcagtacag caggggtgct    7980
gatcaccaag gccctttttc ctggcctggt atgcgtgtga ttatgtttgt cccggttcct    8040
gtgtattaga catggaagcc tcccctgcca cactccaccc ccaatcttcc tttcccttcc    8100
ggcaggagtg ccctctccat aagacgctta cgtttggaca atcaaggtgc acagttgtaa    8160
gtgaccacag gcatacacct tggacattaa tgtgcataac cactttgccc attccatctg    8220
aataaggtcc tactctcaga ccccttttgc agtacagcag gggtgctgat caccaaggcc    8280
ccttttcttg gcctgttatg tgcgtgatta tatttgtctg ggttcctgtg tattagacaa    8340
ggaagccttc ccccgcccc caccccact cccagtcttc ctttccttc cagcagggag       8400
tgccccctcc ataagatcat tacatttgga caatcaaggt gcacaattat aagtgaccac    8460
agccatgcac cttggacatt attggacatt aatgtgcgta actgcacatg gcccatccca    8520
tctgaataag gacctactct cagatgcctt tgcagtacag caggggtact gaatcaccaa    8580
ggccctttt cttggcctgt tatgtgtgtg attatattta tcccagtttc tgtgtaatag     8640
acatgaaagc ctcccctgcc acaccccacc tccaatcttc cttccttc caccagggag      8700
tgtccactcc atatacccctt acatttggac aatcaaggtg cacaattgta agtgagcata   8760
ggcactcacc ttggacatga atgtgcataa ctgcacatgg cccatcccat ctgaataagg    8820
tcctactctc agacccttt tgcagtacag caggggtgct gatcaccaag gcccctttc     8880
ctggcctgtt atgtgtgtga ttatatttgt tccagttcct gtgtaataga catggaagcc    8940
tcccctgcca cactccaccc ccaatcttcc tttccttctg gcaggaagta cccgctccat    9000
aagaccctta catttggaca gtcaaggtgc acaattgtat gtgaccacaa ccatgcacct    9060
tggacataaa tgtgtgtaac tgcacatggc ccatcccatc tgaataaggt cctactctca    9120
gaccccttt gcagtacagt aggtgtgctg ataaccaagg cccctcttcc tggcctgtta    9180
acgtatgtga ttatatttgt ctgggttcca gtgtataaga catggaagcc tcccctgccc    9240
caccccaccc tcaatcttcc tttcccttct ggcagggagt gccagctcca taagaacctt    9300
acatttggac agtcaaggtg cacaattcta agtaccgca gccatgcacc ttggtcaata    9360
atgtgtgtaa ctgcacacgg cctatctcat ctgaataagg ccttactctc agaccccttt    9420
tgcagtacag caggggtgct gataaccaag gcccattttc ctggcctgtt atgtgtgtga    9480
ttatatttgt ccaggtttct gtgtactaga caaggaagcc tcctctgccc catcccatct    9540
acgcataatc tttcttttcc tcccagcagg gagtgctcac tccataagac ccttacattt    9600
ggacaatcaa ggtgcacaat tgtaagtgac cacaaccatg catcttggaa atttatgtgc    9660
ataactgcac atggcttatc ctatttgaat aaagtcctac tctcagaccc ccttgcagt    9720
atagctgggg tgctgatcac tgaggcctct ttgcttggct tgtctatatt cttgtgtact    9780
```

```
agataagggc accttctcat ggactcccct tgcttttcaa caaggagtac ccactacttt    9840
ttaagattct tatatttgtc caaagtacat ggttttaatt gaccacaaca atgtcccttg    9900
gacattaatg tatgtaatca ccacatggtt catcctaatt aaacaaagtt ctaccttctc    9960
accctccatt tgcagtatac cagggttgct gaccccctaa gtccccttt cttggcttgt   10020 tgacatgcat aattgcattt atgttggttc ttgtgcccta gacaaggatg ccccacctct   10080
tttcaatagt gggtgcccac tcctt atgat ctttacattt gaacagttaa tgtgaataat   10140
tgcagttgtc cacaaccca tcacttctag gaccattata cctcttttgc attactgtgg   10200
ggtatactgt ttccctccaa ggccccttct ggtggactat caacatataa ttgaaatttt   10260
cttttgtctt tgtcagtaga ttaaggtcat accccatcac ctttcctttg tagtacaaca   10320
gggtgtcctg atcaaccaaa gtcctgttgt tttggactgt taatatgtgc aattacattt   10380
gctcctgatc tgtgcactag ataaggatcc tacctacttt cttagtgttt ttagcaggta   10440
gtgcccacta ctcaagactg tcacttggaa tgttcatgtg cacaaactca attctctaag   10500
catgttcctg taccaccttt gctttagagc aggggatga tattcactaa gtgccccttc   10560
ttttggactt aatatgcatt aatgcaattg tccacctctt cttttagact aagagttgat   10620
ctccacatat tccccttgca tcaggggcat gttaattatg aatgaaccct tttcttttaa   10680
tattaatgtc ataattgtat ttgtggacct gtgtaggaga aaaagaccct atgttcctcc   10740 cattacccctt tggattgctg ctgagaagtg ttaactactc ataatctcag ctcttggaca   10800
attaatagca ttaataacaa ttatcaaggg cactgatcat tagataagac tcctgcttcc   10860
tcgttgctta catcgggggt actgacccac taaggcccct tgtactgtta atgtgaatat   10920
ttgcaattat atatgtctcc ttctggtaga gtgggatatt atgccctagt atccccttg   10980 cattactgca ggggctgctg actactcaaa acttctcctg ggactgttaa taggcacaat   11040
ggcagttatc aatggttttc tccctccctg accttgttaa gcaagcgccc caccccaccc   11100
ttagtttccc atggcataat aaagtataag cattggagta ttccatgcac ttgtctatca   11160
aacagtggtc catactccca acccttttgc attgcgccag tgtgtaaaat cacaggtagc   11220
catggtgtca tgctttatat acgaagtctt ccctctctct gccccttgtg tgcccttggc   11280 cccttttac agactattgc tcacaatctc aggtgtccat atttgcagct attaggtaag   11340
attgtgctgt ctccctcttc ccttccctct gccctgcccc ttttgcctct ttgctgggta   11400
atgttgacca gacaaggccc tttctcttgg acttaaacaa ttctcagttg cactttcctt   11460
ggtccaccca ttatacatga accctctac ttcctttcgc attgcttctg agtatgctga   11520
ctacccaaag cccttctgt gttattaata aacacagtac tgattgtccc attttcagc    11580 ccatcagtcc aagatctccc taccactttg gtgtgttggt gcagtgttga ctatgaaaag   11640
caggcctgaa ctaggtggat aagccttcac tcattttctt tcatttatta atgatcctag   11700
tttcaattat tgtcagattc tggggacaag aaccattctt gcccacctgt gttactgctt   11760
tactgtgcaa aatactgaag gcaagtcaga cccagggagc tggattgcca tcctttattt   11820
tgtgtttcca gtgtacacta taaaattgtc tccccaggaa ggaaggttgg cacttttctct   11880 gcattcttct ttccagagca gattgcctgg ttaagaatct cttgttgtcc cttctgtata   11940
ttgttattgt aaagtgccaa atgccaggat acagccagaa aaattgctta ttattattaa   12000 aaaaatttt ttaagaaaga catctggatt gtagggtgga ctcgataacc tggtcattat   12060
ttttttgaag ccaaaatatc catttatact atgtacctgg tgaccagtgt ctctcatttt   12120
```

```
aactgagggt ggtgggtctg tggatagaac actgactctt gctattttaa tatcaaagat   12180
attctagatc cagcacagtg gcggccgctc tagagtggaa ctcttaagac cagtatcttt   12240
gtgtgggctt taccagcatt cacttttaga aaaactacct aaattttata atcctttaat   12300
ttcttcatct ggagcacctg cccctactta tttcaagaag attgcagtaa aacgattaaa   12360
tgagggaaca tatgcagagg tgcttttaaa aagcatatgc caccttttt attaattatt    12420 atataaaatg aagcatttaa ttatagtaat aatttgaagt agtttgaagt accacactga   12480
ggtgaggact taaaaatgat aagacgagtt ccctatttta taagaaaaat aagccaaaat   12540
taaatattct tttggatata aatttcaaca gtgagatagc tgcctagtgg aaatgaataa   12600
tatcccagcc actagtgtac agggtgtttt gtggcacagg attatgtaat atggaactgc   12660
tcaagcaaat aactagtcat cacaacagca gttctttgta ataactgaaa aagaatattg   12720
tttctcggag aaggatgtca aaagatcggc ccagctcagg gagcagtttg ccctactagc   12780
tcctcggaca gctgtaaaga agagtctctg gctctttaga atactgatcc cattgaagat   12840
accacgctgc atgtgtcctt agtagtcatg tctcctagg  ctcctcttgg acattctgag   12900
catgtgagac ctgaggactg caaacagcta taagaggctc caaattaatc atatctttcc   12960 cttttgagaat ctggccaagc tccagctaat ctacttggat gggttgccag ctatctggag   13020
aaaaagatct tcctcagaag aataggcttg ttgttttaca gtgttagtga tccattccct   13080
ttgacgatcc ctaggtggag atggggcatg aggatcctcc aggggaaaag ctcactacca   13140
ctgggcaaca accctaggtc aggaggttct gtcaagatac tttcctggtc ccagatagga   13200
agataaagtc tcaaaaacaa ccaccacacg tcaagctctt cattgttcct atctgccaaa   13260
tcattatact tcctacaagc agtgcagaga gctgagtctt cagcaggtcc aagaaatttg   13320
aacacactga aggaagtcag ccttcccacc tgaagatcaa catgcctggc actctagcac   13380
ttgaggatag ctgaatgaat gtgtatttct ttgtctcttt cttccttgtc tttgctcttt    13440
gttctctatc taaagtgtgt cttacccatt tccatgtttc tcttgctaat ttctttcgtg   13500
tgtgcctttg cctcatttc  tcttttttgtt cacaagagtg gtctgtgtct tgtcttagac   13560
atatctctca ttttcattt  tgttgctatt tctctttgct ctcctagatg tggctcttct    13620
ttcacgcttt atttcatgtc tccttttgg  gtcacatgct gtgtgctttt tgtccttttc    13680
ttgttctgtc tacctctcct ttctctgcct acctctcttt tctctttgtg aactgtgatt   13740
atttgttacc ccttcccctt ctcgttcgtt ttaaatttca cctttttttct gagtctggcc  13800 tcctttctgc tgtttctact ttttatctca catttctcat ttctgcattt cctttctgcc   13860
tctcttgggc tattctctct ctcctcccct gcgtgcctca gcatctcttg ctgtttgtga   13920
ttttctattt cagtattaat ctctgttggc ttgtatttgt tctctgcttc ttcccttttct  13980 actcaccttt gagtatttca gcctcttcat gaatctatct ccctctcttt gatttcatgt   14040
aatctctcct taaatatttc tttgcatatg tgggcaagtg tacgtgtgtg tgtgtcatgt   14100
gtggcagagg ggcttcctaa cccctgcctg ataggtgcag aacgtcggct atcagagcaa   14160
gcattgtgga gcggttcctt atgccaggct gccatgtgag atgatccaag accaaaacaa   14220
ggccctagac tgcagtaaaa cccagaactc aagtagggca gaaggtggaa ggctcatatg   14280
gatagaaggc ccaaagtata agacagatgg tttgagactt gagacccgag gactaagatg   14340
gaaagcccat gttccaagat agatagaagc ctcaggcctg aaaccaacaa aagcctcaag   14400
agccaagaaa acagagggtg gcctgaattg gaccgaaggc ctgagttgga tggaagtctc   14460
aaggcttgag ttagaagtct taagacctgg gacaggacac atggaaggcc taagaactga   14520
```

```
gacttgtgac acaaggccaa cgacctaaga ttagcccagg gttgtagctg aagacctac    14580 aacccaagga tggaaggccc ctgtcacaaa gcctacctag atggatagag acccaagcg    14640 aaaaaggtat ctcaagacta acggccggaa tctggaggcc catgacccag aacccaggaa    14700
ggatagaagc ttgaagacct ggggaaatcc caagatgaga accctaaacc ctacctcttt    14760
tctattgttt acacttctta ctcttagata tttccagttc tcctgtttat ctttaagcct    14820
gattcttttg agatgtactt tttgatgttg ccggttacct ttagattgac agtattatgc    14880
ctgggccagt cttgagccag ctttaaatca cagcttttac ctatttgtta ggctatagtg    14940
ttttgtaaac ttctgtttct attcacatct tctccacttg agagagacac caaaatccag    15000
tcagtatcta atctggcttt tgttaacttc cctcaggagc agacattcat ataggtgata    15060
ctgtatttca gtccttcctt ttgacccag aagccctaga ctgagaagat aaaatggtca    15120
ggttgttggg gaaaaaaaaa gtgccaggct ctctagagaa aaatgtgaag agatgctcca    15180
ggccaatgag aagaattaga caagaaatac acagatgtgc cagacttctg agaagcacct    15240
gccagcaaca gcttccttct ttgagcttag attttcctag tccatccctc atgaaaaatg    15300
actgaccact gctgggcagc aggagggatg atgaccaact aattcccaaa ccccagtctc    15360
attggtaccg agctcggatc cactagtcca gtgtggtgga attctgcaga tatccagcac    15420
agtggcggcc gctcgagtct agagggcccg tttaaacccg ctgatcagcc tcgactgtgc    15480
cttctagttg ccagccatct gttgtttgcc ctcccccgt gccttccttg accctggaag    15540
gtgccactcc cactgtcctt tcctaataaa atgaggaaat tgcatcgcat tgtctgagta    15600
ggtgtcattc tattctgggg gtgggtgg ggcaggacag caaggggag gattgggaag    15660 acaatagcag gcatgctggg gatgcggtgg gctctatggc ttctgaggcg aaagaacca    15720 gctgggctc taggggtat ccccacgcgc cctgtagcgg cgcattaagc gcggcgggtg    15780
tggtggttac gcgcagcgtg accgctacac ttgccagcgc cctagcgccc gctcctttcg    15840
ctttcttccc ttcctttctc gccacgttcg ccggctttcc ccgtcaagct ctaaatcggg    15900 ggctccttt agggttccga tttagtgctt tacggcacct cgaccccaaa aaacttgatt    15960
agggtgatgg ttcacgtagt gggccatcgc cctgatagac ggttttcgc cctttgacgt    16020 tggagtccac gttctttaat agtggactct tgttccaaac tggaacaaca ctcaaccccta    16080 tctcggtcta ttcttttgat ttataaggga ttttgccgat ttcggcctat tggttaaaaa    16140
atgagctgat ttaacaaaaa tttaacgcga attaattctg tggaatgtgt gtcagttagg    16200
gtgtggaaag tccccaggct ccccagcagg cagaagtatg caaagcatgc atctcaatta    16260
gtcagcaacc aggtgtggaa agtccccagg ctccccagca ggcagaagta tgcaaagcat    16320
gcatctcaat tagtcagcaa ccatagtccc gcccctaact ccgcccatcc cgcccctaac    16380
tccgcccagt tccgcccatt ctccgcccca tggctgacta ttttttttta tttatgcaga    16440
ggccgaggcc gcctctgcct ctgagctatt ccagaagtag tgaggaggct ttttttggagg    16500 cctaggcttt tgcaaaaagc tcccgggagc ttgtatatcc attttcggat ctgatcagca    16560
cgtgatgaaa aagcctgaac tcaccgcgac gtctgtcgag aagtttctga tcgaaaagtt    16620
cgacagcgtc tccgacctga tgcagctctc ggagggcgaa gaatctcgtg ctttcagctt    16680
cgatgtagga gggcgtggat atgtcctgcg ggtaaatagc tgcgccgatg gtttctacaa    16740
agatcgttat gtttatcggc actttgcatc ggccgcgctc ccgattccgg aagtgcttga    16800
cattggggaa ttcagcgaga gcctgaccta ttgcatctcc cgccgtgcac agggtgtcac    16860
```

-continued

```
gttgcaagac ctgcctgaaa ccgaactgcc cgctgttctg cagccggtcg cggaggccat   16920
ggatgcgatc gctgcggccg atcttagcca gacgagcggg ttcggcccat tcggaccgca   16980
aggaatcggt caatacacta catggcgtga tttcatatgc gcgattgctg atccccatgt   17040
gtatcactgg caaactgtga tggacgacac cgtcagtgcg tccgtcgcgc aggctctcga   17100
tgagctgatg ctttgggccg aggactgccc cgaagtccgg cacctcgtgc acgcggattt   17160
cggctccaac aatgtcctga cggacaatgg ccgcataaca gcggtcattg actggagcga   17220
ggcgatgttc ggggattccc aatacgaggt cgccaacatc ttcttctgga ggccgtggtt   17280
ggcttgtatg gagcagcaga cgcgctactt cgagcggagg catccggagc ttgcaggatc   17340
gccgcggctc cgggcgtata tgctccgcat tggtcttgac caactctatc agagcttggt   17400
tgacggcaat ttcgatgatg cagcttgggc gcagggtcga tgcgacgcaa tcgtccgatc   17460
cggagccggg actgtcgggc gtacacaaat cgcccgcaga agcgcggccg tctggaccga   17520
tggctgtgta gaagtactcg ccgatagtgg aaaccgacgc cccagcactc gtccgagggc   17580
aaaggaatag cacgtgctac gagatttcga ttccaccgcc gccttctatg aaaggttggg   17640
cttcggaatc gttttccggg acgccggctg gatgatcctc cagcgcgggg atctcatgct   17700
ggagttcttc gcccaccca acttgtttat tgcagcttat aatggttaca aataaagcaa   17760
tagcatcaca aatttcacaa ataaagcatt tttttcactg cattctagtt gtggtttgtc   17820
caaactcatc aatgtatctt atcatgtctg tatacgtaaa ctggcaaagg ggtggctggg   17880
ccaaaagaca gaggaattaa gtaagaagtc caggaaaaat gaacttcaca tcaaattta   17940 gagcacggta gccatgaatc ttgtgaatag ctcccaaaaa tgtcctgtgg aagacaacta   18000
gaaagcattc tacaatcagg cacccacctc cacctgcagc ctcctgtgtt gttctcatgg   18060
ggcacctctg ggctccagct cctccaaggc acctccacac tctctcaagt acactcttca   18120
ctcttcccca aacatgattc ccctactgct ctgcctaact cccacttctc tttcaagtag   18180
cagcttaaac gtcacctcat atttggctgg aaaatagaat atagacagag gggtaagtta   18240
aggctagaaa ggcaggctgg gtcaacagaa tggcaagcta aaacatggga ttttctaaaa   18300
cagcctaaga gggtgacaga taaaagtgtg caaggagtgg cacaactcca gtttcatctt   18360
tagctatagc aattaacacc ataaggagtc tggattcaat tttgccattt actagctagc   18420
taccaacttc tgtgtcgctt tgggcaaatc aattaaatcc atacctccct ttccatctgc   18480
agaatgggtt tataacagta cttaaacctc aaggtactaa gaacagtaaa gagttaatgg   18540
tataccgtcg acctctagct agagcttggc gtaatcatgg tcatagctgt ttcctgtgtg   18600
aaattgttat ccgctcacaa ttccacacaa catacgagcc ggaagcataa agtgtaaagc   18660
ctggggtgcc taatgagtga gctaactcac attaattgcg ttgcgctcac tgcccgcttt   18720
ccagtcggga aacctgtcgt gccagctgca ttaatgaatc ggccaacgcg cggggagagg   18780
cggtttgcgt attgggcgct cttccgcttc ctcgctcact gactcgctgc gctcggtcgt   18840
tcggctgcgg cgagcggtat cagctcactc aaaggcggta atacggttat ccacagaatc   18900
aggggataac gcaggaaaga acatgtgagc aaaaggccag caaaaggcca ggaaccgtaa   18960
aaaggccgcg ttgctggcgt ttttccatag gctccgcccc cctgacgagc atcacaaaaa   19020
tcgacgctca agtcagaggt ggcgaaaccc gacaggacta taaagatacc aggcgtttcc   19080
ccctggaagc tccctcgtgc gctctcctgt tccgaccctg ccgcttaccg gatacctgtc   19140
cgcctttctc ccttcgggaa gcgtggcgct ttctcatagc tcacgctgta ggtatctcag   19200
ttcggtgtag gtcgttcgct ccaagctggg ctgtgtgcac gaaccccccg ttcagcccga   19260
```

```
ccgctgcgcc ttatccggta actatcgtct tgagtccaac ccggtaagac acgacttatc    19320
gccactggca gcagccactg gtaacaggat tagcagagcg aggtatgtag gcggtgctac    19380
agagttcttg aagtggtggc ctaactacgg ctacactaga agaacagtat ttggtatctg    19440
cgctctgctg aagccagtta ccttcggaaa aagagttggt agctcttgat ccggcaaaca    19500
aaccaccgct ggtagcggtt ggttttttgt ttgcaagcag cagattacgc gcagaaaaaa    19560
aggatctcaa aagatccttt gatcttttc tacggggtct gacgctcagt ggaacgaaaa    19620
ctcacgttaa gggattttgg tcatgagatt atcaaaaagg atcttcacct agatcctttt    19680
aaattaaaaa tgaagtttta atcaatcta agtatatat gagtaaactt ggtctgacag      19740
ttaccaatgc ttaatcagtg aggcacctat ctcagcgatc tgtctatttc gttcatccat    19800
agttgcctga ctccccgtcg tgtagataac tacgatacgg gagggcttac catctggccc    19860
cagtgctgca atgataccgc gagacccacg ctcaccggct ccagatttat cagcaataaa    19920
ccagccagcc ggaagggccg agcgcagaag tggtcctgca actttatccg cctccatcca    19980
gtctattaat tgttgccggg aagctagagt aagtagttcg ccagttaata gtttgcgcaa    20040
cgttgttgcc attgctacag gcatcgtggt gtcacgctcg tcgtttggta tggcttcatt    20100
cagctccggt tcccaacgat caaggcgagt tacatgatcc cccatgttgt gcaaaaaagc    20160
ggttagctcc ttcggtcctc cgatcgttgt cagaagtaag ttggccgcag tgttatcact    20220
catggttatg gcagcactgc ataattctct tactgtcatg ccatccgtaa gatgcttttc    20280
tgtgactggt gagtactcaa ccaagtcatt ctgagaatag tgtatgcggc gaccgagttg    20340
ctcttgcccg gcgtcaatac gggataatac cgcgccacat agcagaactt taaaagtgct    20400
catcattgga aaacgttctt cggggcgaaa actctcaagg atcttaccgc tgttgagatc    20460
cagttcgatg taacccactc gtgcacccaa ctgatcttca gcatctttta ctttcaccag    20520
cgtttctggg tgagcaaaaa caggaaggca aaatgccgca aaaaagggaa taagggcgac    20580
acggaaatgt tgaatactca tactcttcct ttttcaatat tattgaagca tttatcaggg    20640
ttattgtctc atgagcggat acatatttga atgtatttag aaaaataaac aaataggggt    20700
tccgcgcaca tttccccgaa aagtgccacc tgacgtc                             20737
```

<210> SEQ ID NO 55
<211> LENGTH: 14026
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg acaatgtttt cagaaatgta atctttcaa     240 tatgaaactg ctgatggacc aagaaaacaa aaccctcaac ccaagggaac atcagattgc    300
tggtcaagga gaaatgagga gctgacggtc tcagcattta tttgacttgc tccacggaca    360
gagcaggaga aggctcaaac ctcttcaccc aagactctc cctcacacct gcctcctcac     420
ccaaacccta gaggacagga caggaaccac caacatttta tggttttcaa aaatcctgca    480
ttgaacactg actgtgagcc aggtgctgat ggaagtgcct ttcactcgat gatctcatct    540
```

```
actgctcaca attccaccag ttaaggccca cattttggac aaagagcctg aggaacctac    600
cccctccccg cagtgctcac acttttgtcc ctccagagga cgggaacttc ctctttcttt    660
agcaagctct gtaggggacc agcccacagg ccctggggta gggcagcccg accgcggccc    720
ttccctcacc atggcctatg gttctccttc ccttttcctt taagaaggcc aggtgagaat    780
cacaggaaag ggagaattta ttttgattaa aaataacatt tcttaaaggg ggcatcgatt    840
ttcccttttcc aaagtccaat cactcatccc tatccgagc acagaacct ggggccgggg    900
ctcaggcctc ccacgcaggc tgtgctcagt ggacacagga atggattcct gggacactgc    960
gggtcgcgat gtacgggcca gatatacgcg ttgacattga ttattgacta gttattaata   1020
gtaatcaatt acggggtcat tagttcatag cccatatatg gagttccgcg ttacataact   1080
tacggtaaat ggcccgcctg gctgaccgcc caacgacccc cgcccattga cgtcaataat   1140
gacgtatgtt cccatagtaa cgccaatagg gactttccat tgacgtcaat gggtggagta   1200
tttacggtaa actgcccact tggcagtaca tcaagtgtat catatgccaa gtacgccccc   1260
tattgacgtc aatgacggta aatggcccgc ctggcattat gcccagtaca tgaccttatg   1320
ggactttcct acttggcagt acatctacgt attagtcatc gctattacca tggtgatgcg   1380
gttttggcag tacatcaatg ggcgtggata gcggtttgac tcacggggat ttccaagtct   1440
ccacccatt gacgtcaatg ggagtttgtt ttggcaccaa aatcaacggg actttccaaa   1500
atgtcgtaac aactccgccc cattgacgca aatgggcggt aggcgtgtac ggtgggaggt   1560
ctatataagc agagctctcc ctatcagtga tagagatctc cctatcagtg atagagatcg   1620
tcgacgagct cgtttagtga accgtcagat cgcctggaga cgccatccac gctgttttga   1680
cctccataga agacaccggg accgatccag cctccggact ctagcgttta aacttaagct   1740
tggtaccgag ctcggatcca ctagtccagt gtggtggaat tctgcagatt ctagaacatt   1800
ttctagtccc ccaacaccct ttatggcgta tttctttaaa aaaatcacct aaattccata   1860
aaatattttt ttaaattcta tactttctcc tagtgtcttc ttgacacgtc ctccatattt   1920
ttttaaagaa agtatttgga atattttgag gcaattttta atatttaagg aattttttctt   1980
tggaatcatt tttggtgaca tctctgtttt ttgtggatca gttttttact cttccactct   2040
cttttctata ttttgcccat cggggctgcg gatacctggt tttattattt tttctttgcc   2100
caacggggcc gtggatacct gccttttaat tctttttttat tcgcccatcg gggccgcgga   2160
tacctgcttt ttatttttt ttccttagcc catcggggta tcggatacct gctgattccc   2220
ttcccctctg aaccccaac actctggccc atcggggtga cggatatctg cttttttaaaa   2280
attttctttt tttggcccat cggggcttcg gatacctgct ttttttttt ttatttttcct   2340
tgcccatcgg ggcctcggat acctgcttta attttgttt ttctgcccat cggggccgcg   2400
gatacctgct ttgatttttt ttttcatcg cccatcggtg cttttatgg atgaaaaat    2460
gttggttttg tgggttgttg cactctctgg aatatctaca ctttttttttg ctgctgatca   2520
tttggtggtg tgtgagtgta cctaccgctt tggcagagaa tgactctgca gttaagctaa   2580
gggcgtgttc agattgtgga ggaaaagtgg ccgccatttt agacttgccg cataactcgg   2640
cttagggcta gtcgtttgtg ctaagttaaa ctagggaggc aagatggatg atagcaggtc   2700
aggcagagga agtcatgtgc attgcatgag ctaaacctat ctgaatgaat tgatttgggg   2760
cttgttagga gctttgcgtg attgttgtat cgggaggcag taagaatcat ctttatcag   2820
tacaagggac tagttaaaaa tggaaggtta ggaaagacta aggtgcaggg cttaaaatgg   2880
```

```
cgattttgac attgcggcat tgctcagcat ggcgggctgt gctttgttag gttgtccaaa    2940
atggcggatc cagttctgtc gcagtgttca agtggcggga aggccacatc atgatgggcg    3000
aggctttgtt aagtggttag catggtggtg gacatgtgcg gtcacacagg aaaagatggc    3060
ggctgaaggt cttgccgcag tgtaaaacat ggcgggcctc tttgtctttg ctgtgtgctt    3120
ttcgtgttgg gttttgccgc agggacaata tggcaggcgt tgtcatatgt atatcatggc    3180
ttttgtcacg tggacatcat ggcgggcttg ccgcattgtt aaagatgcgg ggttttgccg    3240
cctagtgcca cgcagagcgg gagaaaaggt gggatggaca gtgctggatt gctgcataac    3300
ccaaccaatt agaaatgggg gtggaattga tcacagccaa ttagagcaga agatggaatt    3360
agactgatga cacactgtcc agctactcag cgaagacctg ggtgaattag catggcactt    3420
cgcagctgtc tttagccagt caggagaaag aagtggaggg gccacgtgta tgtctcccag    3480
tgggcggtac accaggtgtt ttcaaggtct tttcaaggac atttagcctt tccacctctg    3540 tccctctta tttgtcccct cctgtccagt gctgcctctt gcagtgctgg atatctggct    3600
gtgtggtctg aacctccctc cattcctctg tattggtgcc tcacctaagg ctaagtatac    3660 ctccccccc accccccaac ccccccaact cccacccccc accccccacc cccacctcc    3720 ccaccccct accccccctac ccccctaccc ccctctggtc tgccctgcac tgcactgttg    3780
ccatgggcag tgctccaggc ctgcttggtg tggacatggt ggtgagccgt ggcaaggacc    3840
agaatggatc acagatgatc gttggccaat tggcctccca atatgtgtga ttgtatttgt    3900
cgaggttgct atgcactaga gaaggaaagt gctcccctca tccccacttt tcccttccag    3960
caggaagtgc ccaccccata agacccttt atttggagag tctaggtgca caattgtaag    4020
tgaccacaag catgcatctt ggacatttat gtgcgtaatc gcacactgct cattccatgt    4080
gaataaggtc ctactctccg acccctttg caatacagaa gggttgctga taacgcagtc    4140
cccttttctt ggcatgttgt gtgtgattat aatcgtctgg gatcctatgc actagaaaag    4200
gagggtcctc tccacatacc tcagtctcac ctttcccttc cagcagggag tgcccactcc    4260
ataagactct cacatttgga cagtcaaggt gcgtaattgt taagtgaaca caaccatgca    4320
ccttagacat ggatttgcat aactacacac agctcaacct atctgaataa aatcctactc    4380 tcagaccct tttgcagtac agcaggggtg ctgatcacca aggccctttt tcctggcctg    4440
gtatgcgtgt gattatgttt gtcccggttc ctgtgtatta gacatggaag cctcccctgc    4500
cacactccac ccccaatctt cctttccctt ccggcaggag tgccctctcc ataagacgct    4560
tacgtttgga caatcaaggt gcacagttgt aagtgaccac aggcatacac cttggacatt    4620
aatgtgcata accactttgc ccattccatc tgaataaggt cctactctca gaccccttt    4680 gcagtacagc aggggtgctg atcaccaagg cccttttct tggcctgtta tgtgcgtgat    4740
tatatttgtc tgggttcctg tgtattagac aaggaagcct tcccccgcc cccaccccca    4800 ctcccagtct tcctttccct tccagcaggg agtgccccct cataagatc attcatttg    4860 gacaatcaag gtgcacaatt ataagtgacc acagccatgc accttggaca ttattggaca    4920
ttaatgtgcg taactgcaca tggcccatcc catctgaata aggacctact ctcagatgcc    4980
tttgcagtac agcagggta ctgaatcacc aaggcccttt tcttggcct gttatgtgtg    5040 tgattatatt tatcccagtt tctgtgtaat agacatgaaa gcctcccctg ccacacccca    5100
cctccaatct tcctttccct tccaccaggg agtgtccact ccatatacccc ttacatttgg    5160 acaatcaagg tgcacaattg taagtgagca taggcactca ccttggacat gaatgtgcat    5220
aactgcacat ggcccatccc atctgaataa ggtcctactc tcagaccctt tttgcagtac    5280
```

```
agcagggtg ctgatcacca aggcccctt tcctggcctg ttatgtgtgt gattatattt    5340
gttccagttc ctgtgtaata gacatggaag cctcccctgc cacactccac ccccaatctt    5400
cctttccttc tggcaggaag tacccgctcc ataagaccct tacatttgga cagtcaaggt    5460
gcacaattgt atgtgaccac aaccatgcac cttggacata aatgtgtgta actgcacatg    5520
gcccatccca tctgaataag gtcctactct cagacccctt ttgcagtaca gtaggtgtgc    5580
tgataaccaa ggcccctctt cctggcctgt taacgtatgt gattatattt gtctgggttc    5640
cagtgtataa gacatggaag cctcccctgc cccaccccac cctcaatctt cctttccctt    5700
ctggcaggga gtgccagctc cataagaacc ttacatttgg acagtcaagg tgcacaattc    5760
taagtgaccg cagccatgca ccttggtcaa taatgtgtgt aactgcacac ggcctatctc    5820
atctgaataa ggccttactc tcagacccct tttgcagtac agcaggggtg ctgataacca    5880
aggcccattt tcctggcctg ttatgtgtgt gattatattt gtccaggttt ctgtgtacta    5940
gacaaggaag cctcctctgc cccatcccat ctacgcataa tctttctttt cctcccagca    6000
gggagtgctc actccataag acccttacat ttggacaatc aaggtgcaca attgtaagtg    6060
accacaacca tgcatcttgg aaatttatgt gcataactgc acatggctta tcctatttga    6120
ataaagtcct actctcagac ccctttgca gtatagctgg ggtgctgatc actgaggcct    6180
ctttgcttgg cttgtctata ttcttgtgta ctagataagg gcaccttctc atggactccc    6240
tttgcttttc aacaaggagt acccactact ttttaagatt cttatatttg tccaaagtac    6300
atggttttaa ttgaccacaa caatgtccct tggacattaa tgtatgtaat caccacatgg    6360
ttcatcctaa ttaaacaaag ttctaccttc tcaccctcca tttgcagtat accagggttg    6420 ctgacccct aagtccccctt ttcttggctt gttgacatgc ataattgcat ttatgttggt    6480
tcttgtgccc tagacaagga tgccccacct cttttcaata gtgggtgccc actccttatg    6540
atctttacat ttgaacagtt aatgtgaata attgcagttg ccacaaccc tatcacttct    6600 aggaccatta tacctctttt gcattactgt ggggtatact gtttccctcc aaggcccctt    6660
ctggtggact atcaacatat aattgaaatt ttctttttgtc tttgtcagta gattaaggtc    6720
ataccccatc accttttcctt tgtagtacaa cagggtgtcc tgatcaacca aagtcctgtt    6780
gttttggact gttaatatgt gcaattacat ttgctcctga tctgtgcact agataaggat    6840 cctaccact ttcttagtgt ttttagcagg tagtgcccac tactcaagac tgtcacttgg    6900
aatgttcatg tgcacaaact caattctcta agcatgttcc tgtaccacct ttgctttaga    6960 gcaggggat gatattcact aagtgcccct tcttttggac ttaatatgca ttaatgcaat    7020
tgtccacctc ttctttttaga ctaagagttg atctccacat attccccttg catcaggggc    7080
atgttaatta tgaatgaacc cttttctttt aatattaatg tcataattgt atttgtggac    7140
ctgtgtagga gaaaagacc ctatgttcct cccattaccc tttggattgc tgctgagaag    7200
tgttaactac tcaataatctc agctcttgga caattaatag cattaataac aattatcaag    7260
ggcactgatc attagataag actcctgctt cctcgttgct tacatcgggg gtactgaccc    7320
actaaggccc cttgtactgt taatgtgaat atttgcaatt atatatgtct ccttctggta    7380
gagtgggata ttatgcccta gtatcccctt tgcattactg caggggctgc tgactactca    7440
aaacttctcc tgggactgtt aataggcaca atggcagtta tcaatggttt tctccctccc    7500
tgaccttgtt aagcaagcgc cccacccac cttagtttc ccatggcata ataaagtata    7560
agcattggag tattccatgc acttgtctat caaacagtgg tccatactcc caacccttt    7620
```

```
gcattgcgcc agtgtgtaaa atcacaggta gccatggtgt catgctttat atacgaagtc    7680
ttccctctct ctgcccttg tgtgcccttg gccccttttt acagactatt gctcacaatc    7740
tcaggtgtcc atatttgcag ctattaggta agattgtgct gtctccctct tcccttccct    7800
ctgccctgcc ccttttgcct cttttgctgg gtaatgttgac cggacaaggc cctttctctt   7860
ggacttaaac aattctcagt tgcactttcc ttggtcccac ccattataca tgaacccctc    7920
tacttccttt cgcattgctt ctgagtatgc tgactaccca aagccccttc tgtgttatta    7980
ataaacacag tactgattgt cccattttc agcccatcag tccaagatct ccctaccact     8040
ttggtgtgtt ggtgcagtgt tgactatgaa aagcaggcct gaactaggtg gataagcctt    8100
cactcatttt ctttcattta ttaatgatcc tagtttcaat tattgtcaga ttctggggac    8160
aagaaccatt cttgcccacc tgtgttactg ctttactgtg caaaatactg aaggcaagtc    8220
agacccaggg agctggattg ccatccttta ttttgtgttt ccagtgtaca ctataaaatt    8280
gtctccccag gaaggaaggt tggcactttc tctgcattct tctttccaga gcagattgcc    8340
tggttaagaa tctcttgttg tcccctttgt atattgttat tgtaaagtgc caaatgccag    8400
gatacagcca gaaaaattgc ttattattat taaaaaaatt ttttaagaa agacatctgg      8460
attgtagggt ggactcgata acctggtcat tattttttg aagccaaaat atccatttat     8520
actatgtacc tggtgaccag tgtctctcat tttaactgag ggtggtgggt ctgtggatag     8580
aacactgact cttgctattt taatatcaaa gatattctag atccagcaca gtggcggccc    8640
gataccgtcg acctcgagtc tagagggccc gtttaaaccc gctgatcagc ctcgactgtg   8700
ccttctagtt gccagccatc tgttgtttgc ccctcccccg tgccttcctt gaccctggaa    8760
ggtgccactc ccactgtcct ttcctaataa aatgaggaaa ttgcatcgca ttgtctgagt    8820
aggtgtcatt ctattctggg gggtgggtg gggcaggaca gcaaggggga ggattgggaa     8880
gacaatagca ggcatgctgg ggatgcggtg gctctatgg cttctgaggc ggaaagaacc     8940
agctggggct ctaggggta tccccacgcg ccctgtagcg gcgcattaag cgcggcgggt     9000
gtggtggtta cgcgcagcgt gaccgctaca cttgccagcg ccctagcgcc cgctcctttc    9060
gctttcttcc cttcctttct cgccacgttc gccggctttc cccgtcaagc tctaaatcgg    9120
gggctccctt tagggttccg atttagtgct ttacggcacc tcgaccccaa aaaacttgat    9180
tagggtgatg gttcacgtag tgggccatcg ccctgataga cggttttcg ccctttgacg     9240
ttggagtcca cgttctttaa tagtggactc ttgttccaaa ctggaacaac actcaaccct    9300
atctcggtct attcttttga tttataaggg attttgccga tttcggccta ttggttaaaa    9360
aatgagctga tttaacaaaa atttaacgcg aattaattct gtggaatgtg tgtcagttag    9420
ggtgtggaaa gtccccaggc tccccagcag gcagaagtat gcaaagcatg catctcaatt    9480
agtcagcaac caggtgtgga aagtccccag gctccccagc aggcagaagt atgcaaagca    9540
tgcatctcaa ttagtcagca accatagtcc cgcccctaac tccgcccatc ccgcccctaa   9600
ctccgcccag ttccgcccat tctccgcccc atggctgact aatttttttt atttatgcag    9660
aggccgaggc cgcctctgcc tctgagctat tccagaagta gtgaggaggc ttttttggag   9720
gcctaggctt ttgcaaaaag ctcccgggag cttgtatatc cattttcgga tctgatcagc    9780
acgtgatgaa aaagcctgaa ctcaccgcga cgtctgtcga agtttctg atcgaaaagt      9840
tcgacagcgt ctccgacctg atgcagctct cggagggcga agaatctcgt gctttcagct    9900
tcgatgtagg agggcgtgga tatgtcctgc gggtaaatag ctgcgccgat ggtttctaca    9960
aagatcgtta tgtttatcgg cactttgcat cggccgcgct cccgattccg gaagtgcttg   10020
```

```
acattgggga attcagcgag agcctgacct attgcatctc ccgccgtgca cagggtgtca    10080
cgttgcaaga cctgcctgaa accgaactgc ccgctgttct gcagccggtc gcggaggcca    10140
tggatgcgat cgctgcggcc gatcttagcc agacgagcgg gttcggccca ttcggaccgc    10200
aaggaatcgg tcaatacact acatggcgtg atttcatatg cgcgattgct gatccccatg    10260
tgtatcactg gcaaactgtg atggacgaca ccgtcagtgc gtccgtcgcg caggctctcg    10320
atgagctgat gctttgggcc gaggactgcc ccgaagtccg gcacctcgtg cacgcggatt    10380
tcggctccaa caatgtcctg acggacaatg ccgcataac agcggtcatt gactggagcg     10440
aggcgatgtt cggggattcc caatacgagg tcgccaacat cttcttctgg aggccgtggt    10500
tggcttgtat ggagcagcag acgcgctact cgagcggag gcatccggag cttgcaggat     10560
cgccgcggct ccgggcgtat atgctccgca ttggtcttga ccaactctat cagagcttgg    10620
ttgacggcaa tttcgatgat gcagcttggg cgcagggtcg atgcgacgca atcgtccgat    10680
ccggagccgg gactgtcggg cgtacacaaa tcgcccgcag aagcgcggcc gtctggaccg    10740
atggctgtgt agaagtactc gccgatagtg aaaccgacg ccccagcact cgtccgaggg     10800
caaaggaata gcacgtgcta cgagatttcg attccaccgc cgccttctat gaaaggttgg    10860
gcttcggaat cgttttccgg gacgccggct ggatgatcct ccagcgcggg gatctcatgc    10920
tggagttctt cgcccacccc aacttgttta ttgcagctta taatggttac aaataaagca    10980
atagcatcac aaatttcaca aataaagcat ttttttcact gcattctagt tgtggtttgt    11040
ccaaactcat caatgtatct tatcatgtct gtatacgggt ggaggggcgt gatgcaggt     11100
ccccacgatc agccgcagtc tctctaacac tgcaggtggt gccaagaggc aggcatgctc    11160
ccagcacaag ggacggtggc gcagaagaat acagagaagc tcacaaaaca tgccggcatg    11220
ggctcaggag agctacgggg gtagtggtgg tactgctccc tggtgcaggg cagcagctgt    11280
gtctccccct gcctccctcc cacccgaggg ccctgctcac ctggcccag cttggagatg     11340
gcatataaga gatcatagtt tatgactggg gtcgcatctt ccacttgttt ccatcccact    11400
ggcgagagg cggagggga gatcagaaac tgcttgtctg gatttggcgg agccaggtgt      11460
gagcttccta tgtgtaaggt ctgaggagag aaaataagca caggtcagtt gttgccaggg    11520
aagaactgca gtgaggcaac agcacctaac gccagttccg ggagatgggc aggtcaatgt    11580
ccaggcgtca ggacaggtgt gattccagga ccaattgtaa gatggtctgt aatggggagg    11640
gcaaaaggac atatgaactc tggttgtggc acagatagga tgacagcccc ctcccagggc    11700
tatgggagtc acaggcacag ggactgcaaa taattacgct tgacctagat ggacagaaaa    11760
tcagcagagg tgactttagt atatatggaa atttaagtca ctgtcattga ggtcaggagg    11820
gctcttgggt ataccgtcga cctctagcta gagcttggcg taatcatggt catagctgtt    11880
tcctgtgtga aattgttatc cgctcacaat tccacacaac atacgagccg gaagcataaa    11940
gtgtaaagcc tggggtgcct aatgagtgag ctaactcaca ttaattgcgt tgcgctcact    12000
gcccgctttc cagtcgggaa acctgtcgtg ccagctgcat taatgaatcg gccaacgcgc    12060
ggggagaggc ggtttgcgta ttgggcgctc ttccgcttcc tcgctcactg actcgctgcg    12120
ctcggtcgtt cggctgcggc gagcggtatc agctcactca aaggcggtaa tacggttatc    12180
cacagaatca ggggataacg caggaaagaa catgtgagca aaaggccagc aaaaggccag    12240
gaaccgtaaa aaggccgcgt tgctggcgtt tttccatagg ctccgccccc ctgacgagca    12300
tcacaaaaat cgacgctcaa gtcagaggtg gcgaaacccg acaggactat aaagatacca    12360
```

-continued

```
ggcgtttccc cctggaagct ccctcgtgcg ctctcctgtt ccgaccctgc cgcttaccgg    12420
atacctgtcc gcctttctcc cttcgggaag cgtggcgctt tctcatagct cacgctgtag    12480
gtatctcagt tcggtgtagg tcgttcgctc caagctgggc tgtgtgcacg aaccccccgt    12540
tcagcccgac cgctgcgcct tatccggtaa ctatcgtctt gagtccaacc cggtaagaca    12600
cgacttatcg ccactggcag cagccactgg taacaggatt agcagagcga ggtatgtagg    12660
cggtgctaca gagttcttga agtggtggcc taactacggc tacactagaa gaacagtatt    12720
tggtatctgc gctctgctga agccagttac cttcggaaaa agagttggta gctcttgatc    12780
cggcaaacaa accaccgctg gtagcggttg gttttttgtt tgcaagcagc agattacgcg    12840
cagaaaaaaa ggatctcaag aagatccttt gatcttttct acggggtctg acgctcagtg    12900
gaacgaaaac tcacgttaag ggattttggt catgagatta tcaaaaagga tcttcaccta    12960 gatccttta aattaaaaat gaagttttaa atcaatctaa agtatatatg agtaaacttg    13020
gtctgacagt taccaatgct taatcagtga ggcacctatc tcagcgatct gtctatttcg    13080
ttcatccata gttgcctgac tccccgtcgt gtagataact acgatacggg agggcttacc    13140
atctggcccc agtgctgcaa tgataccgcg agacccacgc tcaccggctc cagatttatc    13200
agcaataaac cagccagccg gaagggccga gcgcagaagt ggtcctgcaa ctttatccgc    13260
ctccatccag tctattaatt gttgccggga agctagagta agtagttcgc cagttaatag    13320
tttgcgcaac gttgttgcca ttgctacagg catcgtggtg tcacgctcgt cgtttggtat    13380
ggcttcattc agctccggtt cccaacgatc aaggcgagtt acatgatccc ccatgttgtg    13440
caaaaaagcg gttagctcct tcggtcctcc gatcgttgtc agaagtaagt tggccgcagt    13500
gttatcactc atggttatgg cagcactgca taattctctt actgtcatgc catccgtaag    13560
atgcttttct gtgactggtg agtactcaac caagtcattc tgagaatagt gtatgcggcg    13620
accgagttgc tcttgcccgg cgtcaatacg ggataatacc gcgccacata gcagaacttt    13680
aaaagtgctc atcattggaa aacgttcttc ggggcgaaaa ctctcaagga tcttaccgct    13740
gttgagatcc agttcgatgt aacccactcg tgcacccaac tgatcttcag catcttttac    13800
tttcaccagc gtttctgggt gagcaaaaac aggaaggcaa aatgccgcaa aaaagggaat    13860
aagggcgaca cggaaatgtt gaatactcat actcttcctt tttcaatatt attgaagcat    13920
ttatcagggt tattgtctca tgagcggata catatttgaa tgtatttaga aaataaaca    13980 aatagggggtt ccgcgcacat ttccccgaaa agtgccacct gacgtc                 14026
```

<210> SEQ ID NO 56
<211> LENGTH: 13708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg aaaaccagaa agtattctca gtaatgatag     240
tatggataaa gcaggtttct atgacccttt attacagaat ctgtgagttt ttcacaatta     300
aaaagtaata aaaagtagtg acaacattca ctgaactctt attctatgcc aacttgttcc     360
```

```
ggtatgccct tacacccaca aaagccctat gcataaggtg gcattattcc agcatgtatt    420
gcattgtaca cacaaagagg tcaagcactc caccacggcc ctaagcatgg tggctgaggt    480
gggaaggcca gaggtaggtg ggcccgcgcc cttttccact ctgaaccatg cctccaagat    540
aggagggtgg gaaagtgctc aagacacatt agaaattccc cataaaagac aagattgttg    600
aacacctgca agtgaataaa gataaactga tctcagaggg gaaaaagacg cagggttagg    660
aaacagcacc ctgctcgagg acgttctttc caaacagcct gctcatcacc cgttcgcgat    720
gtacgggcca gatatacgcg ttgacattga ttattgacta gttattaata gtaatcaatt    780
acggggtcat tagttcatag cccatatatg gagttccgcg ttacataact tacggtaaat    840
ggcccgcctg gctgaccgcc caacgacccc cgcccattga cgtcaataat gacgtatgtt    900
cccatagtaa cgccaatagg gactttccat tgacgtcaat gggtggagta tttacggtaa    960
actgcccact tggcagtaca tcaagtgtat catatgccaa gtacgccccc tattgacgtc   1020
aatgacggta atggcccgc ctggcattat gcccagtaca tgaccttatg ggactttcct    1080
acttggcagt acatctacgt attagtcatc gctattacca tggtgatgcg gttttggcag   1140
tacatcaatg ggcgtggata gcggtttgac tcacggggat ttccaagtct ccaccccatt   1200
gacgtcaatg ggagtttgtt ttggcaccaa aatcaacggg actttccaaa atgtcgtaac   1260
aactccgccc cattgacgca aatgggcggt aggcgtgtac ggtgggaggt ctatataagc   1320
agagctctcc ctatcagtga tagagatctc cctatcagtg atagagatcg tcgacgagct   1380
cgtttagtga accgtcagat cgcctggaga cgccatccac gctgttttga cctccataga   1440
agacaccggg accgatccag cctccggact ctagcgttta aacttaagct tggtaccgag   1500
ctcggatcca ctagtccagt gtggtggaat tctgcagatt ctagaacatt tctagtccc    1560 ccaacaccct ttatggcgta tttctttaaa aaaatcacct aaattccata aaatattttt   1620
ttaaattcta tactttctcc tagtgtcttc ttgacacgtc ctccatattt ttttaaagaa   1680
agtatttgga atattttgag gcaatttta atatttaagg aattttctt tggaatcatt    1740 tttggtgaca tctctgtttt ttgtggatca gttttttact cttccactct cttttctata   1800
ttttgcccat cggggctgcg gatacctggt tttattattt tttctttgcc caacggggcc   1860
gtggatacct gccttttaat tcttttttat tcgcccatcg gggccgcgga tacctgcttt   1920
ttattttttt ttccttagcc catcgggta tcggatacct gctgattccc ttcccctctg   1980 aaccccaac actctggccc atcggggtga cggatatctg cttttttaaa attttctttt   2040
tttggcccat cggggcttcg gatacctgct tttttttttt ttattttcct tgcccatcgg   2100
ggcctcggat acctgcttta attttgttt ttctgcccat cggggccgcg gatacctgct   2160
ttgatttttt tttttcatcg cccatcggtg cttttatgg atgaaaaat gttggttttg   2220 tgggttgttg cactctctgg aatatctaca cttttttttg ctgctgatca tttggtggtg   2280
tgtgagtgta cctaccgctt tggcagagaa tgactctgca gttaagctaa gggcgtgttc   2340
agattgtgga ggaaaagtgg ccgccatttt agacttgccg cataactcgg cttagggcta   2400
gtcgtttgtg ctaagttaaa ctagggaggc aagatggatg atagcaggtc aggcagagga   2460
agtcatgtgc attgcatgag ctaaacctat ctgaatgaat tgatttgggg cttgttagga   2520
gctttgcgtg attgttgtat cgggaggcag taagaatcat cttttatcag tacaagggac   2580
tagttaaaaa tggaaggtta ggaaagacta aggtgcaggg cttaaaatgg cgattttgac   2640
attgcggcat tgctcagcat ggcgggctgt gctttgttag gttgtccaaa atggcggatc   2700
cagttctgtc gcagtgttca agtggcggga aggccacatc atgatgggcg aggctttgtt   2760
```

-continued

| | |
|---|---|
| aagtggttag catggtggtg gacatgtgcg gtcacacagg aaaagatggc ggctgaaggt | 2820 |
| cttgccgcag tgtaaaacat ggcgggcctc tttgtctttg ctgtgtgctt ttcgtgttgg | 2880 |
| gttttgccgc aggacaata tggcaggcgt tgtcatatgt atatcatggc ttttgtcacg | 2940 |
| tggacatcat ggcgggcttg ccgcattgtt aaagatggcg ggttttgccg cctagtgcca | 3000 |
| cgcagagcgg gagaaaggt gggatggaca gtgctggatt gctgcataac ccaaccaatt | 3060 |
| agaaatgggg gtggaattga tcacagccaa ttagagcaga agatggaatt agactgatga | 3120 |
| cacactgtcc agctactcag cgaagacctg ggtgaattag catggcactt cgcagctgtc | 3180 |
| tttagccagt caggagaaag aagtggaggg gccacgtgta tgtctcccag tgggcggtac | 3240 |
| accaggtgtt ttcaaggtct tttcaaggac atttagcctt tccacctctg tccctctta | 3300 |
| tttgtcccct cctgtccagt gctgcctctt gcagtgctgg atatctggct gtgtggtctg | 3360 |
| aacctccctc cattcctctg tattggtgcc tcacctaagg ctaagtatac ctcccccccc | 3420 |
| acccccaac cccccaact cccaccccc accccccacc ccccacctcc caccccct | 3480 |
| accccctac cccctaccc ccctctggtc tgccctgcac tgcactgttg ccatgggcag | 3540 |
| tgctccaggc ctgcttggtg tggacatggt ggtgagccgt ggcaaggacc agaatggatc | 3600 |
| acagatgatc gttggccaat tggcctccca atatgtgtga ttgtatttgt cgaggttgct | 3660 |
| atgcactaga gaaggaaagt gctcccctca tccccacttt tccttccag caggaagtgc | 3720 |
| ccacccata agacccttt atttggagag tctaggtgca caattgtaag tgaccacaag | 3780 |
| catgcatctt ggacattat gtgcgtaatc gcacactgct cattccatgt gaataaggtc | 3840 |
| ctactctccg accccttttg caatacagaa gggttgctga taacgcagtc ccctttttctt | 3900 |
| ggcatgttgt gtgtgattat aatcgtctgg gatcctatgc actagaaaag gagggtcctc | 3960 |
| tccacatacc tcagtctcac cttcccttc cagcagggag tgcccactcc ataagactct | 4020 |
| cacatttgga cagtcaaggt gcgtaattgt taagtgaaca caaccatgca ccttagacat | 4080 |
| ggatttgcat aactacacac agctcaacct atctgaataa aatcctactc tcagacccct | 4140 |
| tttgcagtac agcaggggtg ctgatcacca aggccctttt tcctggcctg gtatgcgtgt | 4200 |
| gattatgttt gtcccggttc ctgtgtatta gacatggaag cctcccctgc cacactccac | 4260 |
| ccccaatctt cctttccctt ccggcaggag tgccctctcc ataagacgct tacgtttgga | 4320 |
| caatcaaggt gcacagttgt aagtgaccac aggcatacac cttggacatt aatgtgcata | 4380 |
| accactttgc ccattccatc tgaataaggt cctactctca gacccctttt gcagtacagc | 4440 |
| aggggtgctg atcaccaagg cccctttct tggcctgtta tgtgcgtgat tatatttgtc | 4500 |
| tgggttcctg tgtattagac aaggaagcct tcccccccgcc cccaccccca ctcccagtct | 4560 |
| tcctttccct tccagcaggg agtgcccct ccataagatc attacatttg gacaatcaag | 4620 |
| gtgcacaatt ataagtgacc acagccatgc accttggaca ttattggaca ttaatgtgcg | 4680 |
| taactgcaca tggcccatcc catctgaata aggacctact ctcagatgcc tttgcagtac | 4740 |
| agcagggta ctgaatcacc aaggcccttt ttcttggcct gttatgtgtg tgattatatt | 4800 |
| tatcccagtt tctgtgtaat agacatgaaa gcctcccctg ccacacccca cctccaatct | 4860 |
| tccttttccct tccaccaggg agtgtccact ccatataccc ttacatttgg acaatcaagg | 4920 |
| tgcacaattg taagtgagca taggcactca ccttggacat gaatgtgcat aactgcacat | 4980 |
| ggcccatccc atctgaataa ggtcctactc tcagaccctt tttgcagtac agcagggtg | 5040 |
| ctgatcacca aggcccttt tcctggcctg ttatgtgtgt gattatattt gttccagttc | 5100 |

```
ctgtgtaata gacatggaag cctcccctgc cacactccac ccccaatctt cctttccttc    5160
tggcaggaag tacccgctcc ataagaccct tacatttgga cagtcaaggt gcacaattgt    5220
atgtgaccac aaccatgcac cttggacata aatgtgtgta actgcacatg gcccatccca    5280
tctgaataag gtcctactct cagaccccct ttgcagtaca gtaggtgtgc tgataaccaa    5340
ggcccctctt cctggcctgt taacgtatgt gattatattt gtctgggttc cagtgtataa    5400
gacatggaag cctcccctgc cccaccccac cctcaatctt cctttcccct ctggcaggga    5460
gtgccagctc cataagaacc ttacatttgg acagtcaagg tgcacaattc taagtgaccg    5520
cagccatgca ccttggtcaa taatgtgtgt aactgcacac ggcctatctc atctgaataa    5580
ggccttactc tcagaccccct tttgcagtac agcaggggtg ctgataacca aggcccattt    5640
tcctggcctg ttatgtgtgt gattatattt gtccaggttt ctgtgtacta gacaaggaag    5700
cctcctctgc cccatcccat ctacgcataa tctttctttt cctcccagca gggagtgctc    5760
actccataag acccttacat ttggacaatc aaggtgcaca attgtaagtg accacaacca    5820
tgcatcttgg aaatttatgt gcataactgc acatggctta tcctatttga ataaagtcct    5880
actctcagac cccctttgca gtatagctgg ggtgctgatc actgaggcct ctttgcttgg    5940
cttgtctata ttcttgtgta ctagataagg caccttctc atggactccc tttgcttttc    6000
aacaaggagt acccactact ttttaagatt cttatatttg tccaaagtac atggttttaa    6060
ttgaccacaa caatgtccct tggacattaa tgtatgtaat caccacatgg ttcatcctaa    6120
ttaaacaaag ttctaccttc tcaccctcca tttgcagtat accagggttg ctgacccct    6180
aagtccccctt ttcttggctt gttgacatgc ataattgcat ttatgttggt tcttgtgccc    6240
tagacaagga tgccccacct ctttttcaata gtgggtgccc actccttatg atctttacat    6300
ttgaacagtt aatgtgaata attgcagttg tccacaaccc tatcacttct aggaccatta    6360
tacctctttt gcattactgt ggggtatact gtttccctcc aaggccccctt ctggtggact    6420
atcaacatat aattgaaatt ttcttttgtc tttgtcagta gattaaggtc ataccccatc    6480
accttccctt tgtagtacaa cagggtgtcc tgatcaacca aagtcctgtt gttttggact    6540
gttaatatgt gcaattacat ttgctcctga tctgtgcact agataaggat cctacctact    6600
ttcttagtgt ttttagcagg tagtgcccac tactcaagac tgtcacttgg aatgttcatg    6660
tgcacaaact caattctcta agcatgttcc tgtaccacct ttgctttaga gcaggggat    6720
gatattcact aagtgccect tcttttggac ttaatatgca ttaatgcaat tgtccacctc    6780
ttcttttaga ctaagagttg atctccacat attcccettg catcaggggc atgttaatta    6840
tgaatgaacc cttttctttt aatattaatg tcataattgt atttgtggac ctgtgtagga    6900
gaaaaagacc ctatgttcct cccattaccc tttggattgc tgctgagaag tgttaactac    6960
tcataatctc agctcttgga caattaatag cattaataac aattatcaag ggcactgatc    7020
attagataag actcctgctt cctcgttgct tacatcgggg gtactgaccc actaaggccc    7080
cttgtactgt taatgtgaat atttgcaatt atatatgtct ccttctggta gagtgggata    7140
ttatgcccta gtatccccctt tgcattactg caggggctgc tgactactca aaacttctcc    7200
tgggactgtt aataggcaca atggcagtta tcaatggttt tctccctccc tgaccttgtt    7260
aagcaagcgc cccacccac ccttagtttc ccatggcata ataaagtata agcattggag    7320
tattccatgc acttgtctat caaacagtgg tccatactcc caacccttt gcattgcgcc    7380
agtgtgtaaa atcacaggta gccatggtgt catgctttat atacgaagtc ttccctctct    7440
ctgccccttg tgtgcccttg gcccctttt acagactatt gctcacaatc tcaggtgtcc    7500
```

-continued

```
atatttgcag ctattaggta agattgtgct gtctccctct tcccttccct ctgccctgcc    7560 cctttttgcct ctttgctggg taatgttgac cggacaaggc cctttctctt ggacttaaac   7620
aattctcagt tgcactttcc ttggtcccac ccattataca tgaaccctc tacttccttt    7680 cgcattgctt ctgagtatgc tgactaccca aagcccttc tgtgttatta ataaacacag    7740
tactgattgt cccattttc agcccatcag tccaagatct ccctaccact ttggtgtgtt    7800
ggtgcagtgt tgactatgaa agcaggcct gaactaggtg ataagcctt cactcatttt    7860 ctttcattta ttaatgatcc tagtttcaat tattgtcaga ttctggggac aagaaccatt   7920
cttgcccacc tgtgttactg ctttactgtg caaaatactg aaggcaagtc agacccaggg   7980
agctggattg ccatccttta ttttgtgttt ccagtgtaca ctataaaatt gtctccccag   8040
gaaggaaggt tggcactttc tctgcattct tctttccaga gcagattgcc tggttaagaa   8100
tctcttgttg tccccttgt atattgttat tgtaaagtgc caaatgccag atacagcca    8160 gaaaaattgc ttattattat taaaaaaatt ttttaagaa agacatctgg attgtagggt   8220
ggactcgata acctggtcat tattttttg aagccaaaat atccatttat actatgtacc   8280
tggtgaccag tgtctctcat tttaactgag ggtggtgggt ctgtggatag aacactgact   8340
cttgctattt taatatcaaa gatattctag atccagcaca gtggcggccc gataccgtcg   8400
acctcgagtc tagagggccc gtttaaaccc gctgatcagc ctcgactgtg ccttctagtt   8460
gccagccatc tgttgtttgc cctccccg tgccttcctt gaccctggaa ggtgccactc    8520
ccactgtcct ttcctaataa aatgaggaaa ttgcatcgca ttgtctgagt aggtgtcatt   8580
ctattctggg gggtgggtg gggcaggaca gcaagggga ggattgggaa gacaatagca    8640
ggcatgctgg ggatgcggtg ggctctatgg cttctgaggc ggaaagaacc agctggggct   8700 ctaggggta tccccacgcg ccctgtagcg gcgcattaag cgcggcgggt gtggtggtta   8760
cgcgcagcgt gaccgctaca cttgccagcg ccctagcgcc cgctcctttc gctttcttcc   8820
cttcctttct cgccacgttc gccggctttc cccgtcaagc tctaaatcgg gggctccctt   8880
tagggttccg atttagtgct ttacggcacc tcgaccccaa aaaacttgat tagggtgatg   8940
gttcacgtag tgggccatcg ccctgataga cggtttttcg ccctttgacg ttggagtcca   9000
cgttctttaa tagtggactc ttgttccaaa ctggaacaac actcaaccct atctcggtct   9060
attcttttga tttataaggg attttgccga tttcggccta ttggttaaaa atgagctga   9120 tttaacaaaa atttaacgcg aattaattct gtggaatgtg tgtcagttag ggtgtggaaa   9180
gtccccaggc tccccagcag gcagaagtat gcaaagcatg catctcaatt agtcagcaac   9240
caggtgtgga aagtccccag gctccccagc aggcagaagt atgcaaagca tgcatctcaa   9300
ttagtcagca accatagtcc cgcccctaac tccgcccatc ccgcccctaa ctccgcccag   9360
ttccgcccat tctccgcccc atggctgact aattttttt atttatgcag aggccgaggc   9420
cgcctctgcc tctgagctat tccagaagta gtgaggaggc ttttttggag gcctaggctt   9480
ttgcaaaaag ctcccgggag cttgtatatc cattttcgga tctgatcagc acgtgatgaa   9540
aaagcctgaa ctcaccgcga cgtctgtcga agtttctg atcgaaaagt tcgacagcgt    9600
ctccgacctg atgcagctct cggagggcga agaatctcgt gctttcagct tcgatgtagg   9660
agggcgtgga tatgtcctgc gggtaaatag ctgcgccgat ggtttctaca agatcgtta   9720 tgtttatcgg cactttgcat cggccgcgct cccgattccg gaagtgcttg acattgggga   9780
attcagcgag agcctgacct attgcatctc ccgccgtgca cagggtgtca cgttgcaaga   9840
```

```
cctgcctgaa accgaactgc ccgctgttct gcagccggtc gcggaggcca tggatgcgat   9900
cgctgcggcc gatcttagcc agacgagcgg gttcggccca ttcggaccgc aaggaatcgg   9960
tcaatacact acatggcgtg atttcatatg cgcgattgct gatccccatg tgtatcactg  10020
gcaaactgtg atggacgaca ccgtcagtgc gtccgtcgcg caggctctcg atgagctgat  10080
gctttgggcc gaggactgcc ccgaagtccg gcacctcgtg cacgcggatt tcggctccaa  10140
caatgtcctg acgacaatg gccgcataac agcggtcatt gactggagcg aggcgatgtt   10200
cggggattcc caatacgagg tcgccaacat cttcttctgg aggccgtggt tggcttgtat  10260
ggagcagcag acgcgctact cgagcggag gcatccggag cttgcaggat cgccgcggct   10320
ccgggcgtat atgctccgca ttggtcttga ccaactctat cagagcttgg ttgacggcaa  10380
tttcgatgat gcagcttggg cgcagggtcg atgcgacgca atcgtccgat ccggagccgg  10440
gactgtcggg cgtacacaaa tcgcccgcag aagcgcggcc gtctggaccg atggctgtgt  10500
agaagtactc gccgatagtg gaaaccgacg ccccagcact cgtccgaggg caaaggaata  10560
gcacgtgcta cgagatttcg attccaccgc cgccttctat gaaaggttgg gcttcggaat  10620
cgttttccgg gacgccggct ggatgatcct ccagcgcggg gatctcatgc tggagttctt  10680
cgcccacccc aacttgttta ttgcagctta taatggttac aaataaagca atagcatcac  10740
aaatttcaca aataaagcat ttttttcact gcattctagt tgtggtttgt ccaaactcat  10800
caatgtatct tatcatgtct gtatacgtaa actggcaaag gggtggctgg gccaaaagac  10860
agaggaatta agtaagaagt ccaggaaaaa tgaacttcac atcaaatttt agagcacggt  10920
agccatgaat cttgtgaata gctcccaaaa atgtcctgtg gaagacaact agaaagcatt  10980
ctacaatcag gcacccacct ccacctgcag cctcctgtgt tgttctcatg gggcacctct  11040
gggctccagc tcctccaagg cacctccaca ctctctcaag tacactcttc actcttcccc  11100
aaacatgatt cccctactgc tctgcctaac tcccacttct ctttcaagta gcagcttaaa  11160
cgtcacctca tatttggctg gaaaatagaa tatagacaga ggggtaagtt aaggctagaa  11220
aggcaggctg ggtcaacaga atggcaagct aaaacatggg attttctaaa acagcctaag  11280
agggtgacag ataaaagtgt gcaaggagtg gcacaactcc agtttcatct ttagctatag  11340
caattaacac cataaggagt ctggattcaa ttttgccatt tactagctag ctaccaactt  11400
ctgtgtcgct ttgggcaaat caattaaatc catacctccc tttccatctg cagaatgggt  11460
ttataacagt acttaaacct caaggtacta agaacagtaa agagttaatg gtataccgtc  11520
gacctctagc tagagcttgg cgtaatcatg gtcatagctg tttcctgtgt gaaattgtta  11580
tccgctcaca attccacaca acatacgagc cggaagcata agtgtaaag cctggggtgc   11640 ctaatgagtg agctaactca cattaattgc gttgcgctca ctgcccgctt tccagtcggg  11700
aaacctgtcg tgccagctgc attaatgaat cggccaacgc gcggggagag gcggtttgcg  11760
tattgggcgc tcttccgctt cctcgctcac tgactcgctg cgctcggtcg ttcggctgcg  11820
gcgagcggta tcagctcact caaaggcggt aatacggtta ccacagaat cagggataa    11880 cgcaggaaag aacatgtgag caaaaggcca gcaaaaggcc aggaaccgta aaaaggccgc  11940
gttgctggcg ttttccata ggctccgccc ccctgacgag catcacaaaa atcgacgctc   12000
aagtcagagg tggcgaaacc cgacaggact ataaagatac caggcgtttc ccctggaag   12060 ctccctcgtg cgctctcctg ttccgaccct gccgcttacc ggatacctgt ccgcctttct  12120
cccttcggga agcgtggcgc tttctcatag ctcacgctgt aggtatctca gttcggtgta  12180
ggtcgttcgc tccaagctgg gctgtgtgca cgaacccccc gttcagcccg accgctgcgc  12240
```

```
cttatccggt aactatcgtc ttgagtccaa cccggtaaga cacgacttat cgccactggc    12300
agcagccact ggtaacagga ttagcagagc gaggtatgta ggcggtgcta cagagttctt    12360
gaagtggtgg cctaactacg gctacactag aagaacagta tttggtatct gcgctctgct    12420
gaagccagtt accttcggaa aaagagttgg tagctcttga tccggcaaac aaaccaccgc    12480
tggtagcggt tggttttttg tttgcaagca gcagattacg cgcagaaaaa aaggatctca    12540
agaagatcct ttgatctttt ctacggggtc tgacgctcag tggaacgaaa actcacgtta    12600
agggattttg gtcatgagat tatcaaaaag gatcttcacc tagatccttt taaattaaaa    12660
atgaagtttt aaatcaatct aaagtatata tgagtaaact tggtctgaca gttaccaatg    12720
cttaatcagt gaggcaccta tctcagcgat ctgtctattt cgttcatcca tagttgcctg    12780
actccccgtc gtgtagataa ctacgatacg ggagggctta ccatctggcc ccagtgctgc    12840
aatgataccg cgagacccac gctcaccggc tccagattta tcagcaataa accagccagc    12900
cggaagggcc gagcgcagaa gtggtcctgc aactttatcc gcctccatcc agtctattaa    12960
ttgttgccgg gaagctagag taagtagttc gccagttaat agtttgcgca acgttgttgc    13020
cattgctaca ggcatcgtgg tgtcacgctc gtcgtttggt atggcttcat tcagctccgg    13080
ttcccaacga tcaaggcgag ttacatgatc ccccatgttg tgcaaaaaag cggttagctc    13140
cttcggtcct ccgatcgttg tcagaagtaa gttggccgca gtgttatcac tcatggttat    13200
ggcagcactg cataattctc ttactgtcat gccatccgta agatgctttt ctgtgactgg    13260
tgagtactca accaagtcat tctgagaata gtgtatgcgg cgaccgagtt gctcttgccc    13320
ggcgtcaata cgggataata ccgcgccaca tagcagaact ttaaaagtgc tcatcattgg    13380
aaaacgttct cggggcgaaa actctcaag gatcttaccg ctgttgagat ccagttcgat    13440
gtaacccact cgtgcaccca actgatcttc agcatctttt actttcacca gcgtttctgg    13500
gtgagcaaaa acaggaaggc aaaatgccgc aaaaaaggga ataagggcga cacggaaatg    13560
ttgaatactc atactcttcc tttttcaata ttattgaagc atttatcagg gttattgtct    13620
catgagcgga tacatatttg aatgtattta gaaaaataaa caaatagggg ttccgcgcac    13680
atttccccga aaagtgccac ctgacgtc                                      13708
```

<210> SEQ ID NO 57
<211> LENGTH: 15721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc ctttgctttc     300 tctgaccag cattctctcc cctgggcctg tgccgctttc tgtctgcagc ttgtggcctg     360 ggtcaccttct acggctggcc cagatccttc cctgccgcct ccttcaggtt ccgtcttcct     420 ccactcccte ttcccttgcc tctctgctgt gttgctgccc aaggatgctc tttccggagc     480
acttccttct cggcgctgca ccacgtgatg tcctctgagc ggatcctccc cgtgtctggg     540
```

| | |
|---|---|
| tcctctccgg gcatctctcc tccctcaccc aacccatgc cgtcttcact cgctgggttc | 600 |
| ccttttcctt ctccttctgg ggcctgtgcc atctctcgtt tcttaggatg gccttctccg | 660 |
| acggatgtct cccttgcgtc ccgcctcccc ttcttgtagg cctgcatcat caccgttttt | 720 |
| ctggacaacc ccaaagtacc ccgtctccct ggctttagcc acctctccat cctcttgctt | 780 |
| tctttgcctg gacaccccgt tctcctgtgg attcgggtca cctctcactc ctttcatttg | 840 |
| ggcagctccc ctaccccct tacctctcta gtctgtgcta gctcttccag ccccctgtca | 900 |
| tggcatcttc caggggtccg agagctcagc tagtcttctt cctccaaccc gggcccctat | 960 |
| gtccacttca ggacagcatg tttgctgcct ccagggatcc tgtgtccccg agctgggacc | 1020 |
| accttatatt cccagggccg gttaatgtgg ctctggttct gggtactttt atctgtcccc | 1080 |
| tccaccccac agtggggcaa gcttacagac atgataagat acattgatga gtttggacaa | 1140 |
| accacaacta gaatgcagtg aaaaaaatgc tttatttgtg aaatttgtga tgctattgct | 1200 |
| ttatttgtaa ccattataag ctgcaataaa caagttgggg tgggcgaaga actccagcat | 1260 |
| gagatccccg cgctggagga tcatccagcc ggcgtcccgg aaaacgattc cgaagcccaa | 1320 |
| cctttcatag aaggcggcgg tggaatcgaa atctcgtagc acgtgctatt cctttgccct | 1380 |
| cggacgagtg ctgggcgtc ggtttccact atcggcgagt acttctacac agccatcggt | 1440 |
| ccagacggcc gcgcttctgc gggcgatttg tgtacgcccg acagtcccgg ctccggatcg | 1500 |
| gacgattgcg tcgcatcgac cctgcgccca agctgcatca tcgaaattgc cgtcaaccaa | 1560 |
| gctctgatag agttggtcaa gaccaatgcg gagcatatac gcccggagcc gcggcgatcc | 1620 |
| tgcaagctcc ggatgcctcc gctcgaagta gcgcgtctgc tgctccatac aagccaacca | 1680 |
| cggcctccag aagaagatgt tggcgacctc gtattgggaa tccccgaaca tcgcctcgct | 1740 |
| ccagtcaatg accgctgtta tgcggccatt gtccgtcagg acattgttgg agccgaaatc | 1800 |
| cgcgtgcacg aggtgccgga cttcggggca gtcctcggcc caaagcatca gctcatcgag | 1860 |
| agcctgcgcg acggacgcac tgacggtgtc gtccatcaca gtttgccagt gatacacatg | 1920 |
| gggatcagca atcgcgcata tgaaatcacg ccatgtagtg tattgaccga ttccttgcgg | 1980 |
| tccgaatggg ccgaacccgc tcgtctggct aagatcggcc gcagcgatcg catccatggc | 2040 |
| ctccgcgacc ggctgcagaa cagcgggcag ttcggtttca ggcaggtctt gcaacgtgac | 2100 |
| accctgtgca cggcgggaga tgcaataggt caggctctcg ctgaattccc caatgtcaag | 2160 |
| cacttccgga atcgggagcg cggccgatgc aaagtgccga taaacataac gatctttgta | 2220 |
| gaaaccatcg cgcagctat ttacccgcag gacatatcca cgccctccta catcgaagct | 2280 |
| gaaagcacga gattcttcgc cctccgagag ctgcatcagg tcggagacgc tgtcgaactt | 2340 |
| ttcgatcaga aacttctcga cagacgtcgc ggtgagttca ggcttttttca tcacgtgctg | 2400 |
| atcagatccg aaaatggata tacaagctcc cgggagcttt ttgcaaaagc ctaggcctcc | 2460 |
| aaaaagcct cctcactact tctggaatag ctcagaggca gaggcggcct cggcctctgc | 2520 |
| ataaataaaa aaaattagtc agccatgggg cggagaatgg gcggaactgg gcggagttag | 2580 |
| gggcgggatg ggcggagtta ggggcgggac tatggttgct gactaattga gatgcatgct | 2640 |
| ttgcatactt ctgcctgctg gggagcctgg ggactttcca cacctggttg ctgactaatt | 2700 |
| gagatgcatg ctttgcatac ttctgcctgc tggggagcct ggggactttc cacaccctaa | 2760 |
| ctgacacaca ttccacagaa ttaattcgcg ttaaattttt gttaaatcag ctcattttttt | 2820 |
| aaccaatagg ccgaaatcgg caaaatccct tataaatcaa agaatagac cgagataggg | 2880 |

-continued

```
ttgagtgttg ttccagtttg aacaagagt ccactattaa agaacgtgga ctccaacgtc    2940
aaagggcgaa aaaccgtcta tcagggcgat ggcccactac gtgaaccatc accctaatca    3000
agttttttgg ggtcgaggtg ccgtaaagca ctaaatcgga accctaaagg gagccccga    3060 tttagagctt gacggggaaa gccggcgaac gtggcgagaa aggaagggaa gaaagcgaaa    3120
ggagcgggcg ctagggcgct ggcaagtgta gcggtcacgc tgcgcgtaac caccacaccc    3180
gccgcgctta atgcgccgct acagggcgcg tggggatacc ccctagagcc ccagctggtt    3240
ctttccgcct cagaagccat agagcccacc gcatcccag catgcctgct attgtcttcc    3300
caatcctccc ccttgctgtc ctgccccacc ccaccccca gaatagaatg acacctactc    3360
agacaatgcg atgcaatttc ctcattttat taggaaagga cagtgggagt ggcaccttcc    3420
agggtcaagg aaggcacggg ggaggggcaa acaacagatg gctggcaact agaaggcaca    3480
gtcgaggctg atcagcgggt ttaaacgggc cctctagact cgaggtcgac ggtatcgggc    3540
cgccactgtg ctggatctag aatatctttg atattaaaat agcaagagtc agtgttctat    3600
ccacagaccc accaccctca gttaaaatga gagacactgg tcaccaggta catagtataa    3660
atggatattt tggcttcaaa aaataatga ccaggttatc gagtccaccc tacaatccag    3720 atgtcttct taaaaaatt ttttaataa taataagcaa ttttctggc tgtatcctgg    3780 catttggcac tttacaataa caatatacaa aggggacaac aagagattct taaccaggca    3840
atctgctctg gaaagaagaa tgcagagaaa gtgccaacct tccttcctgg ggagacaatt    3900
ttatagtgta cactggaaac acaaaataaa ggatggcaat ccagctccct gggtctgact    3960
tgccttcagt attttgcaca gtaaagcagt aacacaggtg ggcaagaatg gttcttgtcc    4020
ccagaatctg acaataattg aaactaggat cattaataaa tgaaagaaaa tgagtgaagg    4080
cttatccacc tagttcaggc ctgcttttca tagtcaacac tgcaccaaca caccaaagtg    4140
gtagggagat cttggactga tgggctgaaa atgggacaa tcagtactgt gtttattaat    4200
aacacagaag gggctttggg tagtcagcat actcagaagc aatgcgaaag gaagtagagg    4260
ggttcatgta taatgggtgg gaccaaggaa agtgcaactg agaattgttt aagtccaaga    4320
gaaagggcct tgtccggtca acattaccca gcaaagaggc aaaaggggca gggcagaggg    4380
aagggaagag ggagacagca caatcttacc taatagctgc aaatatggac acctgagatt    4440
gtgagcaata gtctgtaaaa aggggccaag ggcacacaag gggcagagag agggaagact    4500
tcgtatataa agcatgacac catggctacc tgtgatttta cacactggcg caatgcaaaa    4560
gggttgggag tatggaccac tgtttgatag acaagtgcat ggaatactcc aatgcttata    4620
ctttattatg ccatgggaaa ctaagggtgg ggtggggcgc ttgcttaaca aggtcaggga    4680
gggagaaaac cattgataac tgccattgtg cctattaaca gtcccaggag aagttttgag    4740
tagtcagcag cccctgcagt aatgcaaagg ggatactagg gcataatatc ccactctacc    4800
agaaggagac atatataatt gcaaatattc acattaacag tacaagggc cttagtgggt    4860 cagtaccccc gatgtaagca acgaggaagc aggagtctta tctaatgatc agtgcccttg    4920
ataattgtta ttaatgctat taattgtcca agagctgaga ttatgagtag ttaacacttc    4980
tcagcagcaa tccaaagggt aatgggagga acatagggtc ttttctcct acacaggtcc    5040 acaaatacaa ttatgacatt aatattaaaa gaaagggtt cattcataat taacatgccc    5100
ctgatgcaag gggaatatgt ggagatcaac tcttagtcta aaagaagagg tggacaattg    5160
cattaatgca tattaagtcc aaaagaaggg gcacttagtg aatatcatcc ccctgctcta    5220
aagcaaaggt ggtacaggaa catgcttaga gaattgagtt tgtgcacatg aacattccaa    5280
```

```
gtgacagtct tgagtagtgg gcactacctg ctaaaaacac taagaaagta ggtaggatcc    5340
ttatctagtg cacagatcag gagcaaatgt aattgcacat attaacagtc caaaacaaca    5400
ggactttggt tgatcaggac accctgttgt actacaaagg aaaggtgatg gggtatgacc    5460
ttaatctact gacaaagaca aaagaaaatt tcaattatat gttgatagtc caccagaagg    5520
ggccttggag ggaaacagta taccccacag taatgcaaaa gaggtataat ggtcctagaa    5580
gtgatagggt tgtggacaac tgcaattatt cacattaact gttcaaatgt aaagatcata    5640
aggagtgggc acccactatt gaaaagaggt ggggcatcct tgtctagggc acaagaacca    5700
acataaatgc aattatgcat gtcaacaagc caagaaaagg ggacttaggg ggtcagcaac    5760
cctggtatac tgcaaatgga gggtgagaag gtagaacttt gtttaattag gatgaaccat    5820
gtggtgatta catacattaa tgtccaaggg acattgttgt ggtcaattaa aaccatgtac    5880
tttggacaaa tataagaatc ttaaaaagta gtgggtactc cttgttgaaa agcaaaggga    5940
gtccatgaga aggtgccctt atctagtaca caagaatata gacaagccaa gcaaagaggc    6000
ctcagtgatc agcaccccag ctatactgca aaggggtct gagagtagga ctttattcaa    6060
ataggataag ccatgtgcag ttatgcacat aaatttccaa gatgcatggt tgtggtcact    6120
tacaattgtg caccttgatt gtccaaatgt aagggtctta tggagtgagc actccctgct    6180
gggaggaaaa gaaagattat gcgtagatgg gatgggcag aggaggcttc cttgtctagt    6240
acacagaaac ctggacaaat ataatcacac acataacagg ccaggaaaat gggccttggt    6300
tatcagcacc cctgctgtac tgcaaaaggg gtctgagagt aaggccttat tcagatgaga    6360
taggccgtgt gcagttacac acattattga ccaaggtgca tggctgcggt cacttagaat    6420
tgtgcacctt gactgtccaa atgtaaggtt cttatggagc tggcactccc tgccagaagg    6480
gaaaggaaga ttgagggtgg ggtggggcag gggaggcttc catgtcttat acactggaac    6540
ccagacaaat ataatcacat acgttaacag gccaggaaga ggggccttgg ttatcagcac    6600
acctactgta ctgcaaaagg ggtctgagag taggacctta ttcagatggg atgggccatg    6660
tgcagttaca cacatttatg tccaaggtgc atggttgtgg tcacatacaa ttgtgcacct    6720
tgactgtcca aatgtaaggg tcttatggag cgggtacttc ctgccagaag gaaaggaaga    6780
ttggggggtgg agtgtggcag gggaggcttc catgtctatt acacaggaac tggaacaaat    6840
ataatcacac acataacagg ccaggaaaag gggccttggt gatcagcacc cctgctgtac    6900
tgcaaaaagg gtctgagagt aggaccttat tcagatggga tgggccatgt gcagttatgc    6960
acattcatgt ccaaggtgag tgcctatgct cacttacaat tgtgcacctt gattgtccaa    7020
atgtaagggt atatggagtg gacactccct ggtggaaggg aaaggaagat tggaggtggg    7080
gtgtggcagg ggaggctttc atgtctatta cacagaaact gggataaata taatcacaca    7140
cataacaggc caagaaaaag ggccttggtg attcagtacc cctgctgtac tgcaaaggca    7200
tctgagagta ggtccttatt cagatgggat gggccatgtg cagttacgca cattaatgtc    7260
caataatgtc caaggtgcat ggctgtggtc acttataatt gtgcaccttg attgtccaaa    7320
tgtaatgatc ttatggaggg ggcactccct gctggaaggg aaaggaagac tgggagtggg    7380
ggtgggggcg gggggaaggc ttccttgtct aatacacagg aacccagaca aatataatca    7440
cgcacataac aggccaagaa aaggggcctt ggtgatcagc acccctgctg tactgcaaaa    7500
ggggtctgag agtaggacct tattcagatg gaatgggcaa agtggttatg cacattaatg    7560
tccaaggtgt atgcctgtgg tcacttacaa ctgtgcacct tgattgtcca aacgtaagcg    7620
```

```
tcttatggag agggcactcc tgccggaagg gaaaggaaga ttgggggtgg agtgtggcag    7680
gggaggcttc catgtctaat acacaggaac cgggacaaac ataatcacac gcataccagg    7740
ccaggaaaaa gggccttggt gatcagcacc cctgctgtac tgcaaaaggg gtctgagagt   7800
aggattttat tcagataggt tgagctgtgt gtagttatgc aaatccatgt ctaaggtgca    7860
tggttgtgtt cacttaacaa ttacgcacct tgactgtcca aatgtgagag tcttatggag    7920
tgggcactcc ctgctggaag ggaaaggtga gactgaggta tgtggagagg accctccttt    7980
tctagtgcat aggatcccag acgattataa tcacacacaa catgccaaga aaggggact     8040
gcgttatcag caaccttct gtattgcaaa aggggtcgga gagtaggacc ttattcacat     8100
ggaatgagca gtgtgcgatt acgcacataa atgtccaaga tgcatgcttg tggtcactta    8160
caattgtgca cctagactct ccaaataaaa gggtcttatg gggtgggcac ttcctgctgg    8220
aagggaaaag tggggatgag gggagcactt tccttctcta gtgcatagca acctcgacaa    8280
atacaatcac acatattggg aggccaattg ccaacgatc atctgtgatc cattctggtc     8340
cttgccacgg ctcaccacca tgtccacacc aagcaggcct ggagcactgc ccatggcaac    8400
agtgcagtgc agggcagacc agaggggggt aggggggtag ggggtaggg gggtggggag     8460
gtgggggtg ggggtgggg gtgggagtt gggggggttg ggggtgggg ggggaggtat        8520
acttagcctt aggtgaggca ccaatacaga ggaatggagg gaggttcaga ccacacagcc    8580
agatatccag cactgcaaga ggcagcactg gacaggaggg gacaaataag aggggacaga    8640
ggtggaaagg ctaaatgtcc ttgaaaagac cttgaaaaca cctggtgtac cgcccactgg    8700
gagacataca cgtggcccct ccacttcttt ctcctgactg gctaaagaca gctgcgaagt    8760
gccatgctaa ttcacccagg tcttcgctga gtagctggac agtgtgtcat cagtctaatt    8820
ccatcttctg ctctaattgg ctgtgatcaa ttccaccccc atttctaatt ggttgggtta    8880
tgcagcaatc cagcactgtc catcccacct tttctcccgc tctgcgtggc actaggcggc    8940
aaacccgcc atctttaaca atgcggcaag cccgccatga tgtccacgtg acaaaagcca    9000
tgatatacat atgacaacgc ctgccatatt gtccctgcgg caaaacccaa cacgaaaagc    9060
acacagcaaa gacaaagagg cccgccatgt tttacactgc ggcaagacct tcagccgcca    9120
tcttttcctg tgtgaccgca catgtccacc accatgctaa ccacttaaca aagcctcgcc    9180
catcatgatg tggccttccc gccacttgaa cactgcgaca gaactggatc cgccattttg    9240
gacaacctaa caaagcacag cccgccatgc tgagcaatgc cgcaatgtca aaatcgccat    9300
tttaagccct gcaccttagt ctttcctaac cttccatttt taactagtcc cttgtactga    9360
taaaagatga ttcttactgc ctcccgatac aacaatcacg caaagctcct aacaagcccc    9420
aaatcaattc attcagatag gtttagctca tgcaatgcac atgacttcct ctgcctgacc    9480
tgctatcatc catcttgcct ccctagttta acttagcaca aacgactagc cctaagccga    9540
gttatgcggc aagtctaaaa tggcggccac ttttcctcca caatctgaac acgcccttag    9600
cttaactgca gagtcattct ctgccaaagc ggtaggtaca ctcacacacc accaaatgat    9660
cagcagcaaa aaaagtgta gatattccag agagtgcaac aacccacaaa accaacattt    9720
tttcatccat aaaaagcacc gatgggcgat gaaaaaaaaa aatcaaagca ggtatccgcg    9780
gccccgatgg gcagaaaaac aaaattaaa gcaggtatcc gaggccccga tgggcaagga    9840
aaataaaaaa aaaaaaagca ggtatccgaa gccccgatgg gccaaaaaaa gaaaattttt    9900
aaaaagcaga tatccgtcac cccgatgggc cagagtgttg ggggttcaga ggggaaggga    9960
atcagcaggt atccgatacc ccgatgggct aaggaaaaaa aaataaaaag caggtatccg   10020
```

```
cggccccgat gggcgaataa aaaagaatta aaaggcaggt atccacggcc ccgttgggca    10080
aagaaaaaat aataaaacca ggtatccgca gccccgatgg gcaaaatata gaaagagag    10140 tggaagagta aaaactgat ccacaaaaaa cagagatgtc accaaaaatg attccaaaga    10200
aaaattcctt aaatattaaa aattgcctca aatattccaa aatactttct ttaaaaaaat    10260
atggaggacg tgtcaagaag acactaggag aaagtataga atttaaaaaa atattttatg    10320
gaatttaggt gattttttta aagaaatacg ccataaaggg tgttgggga ctagaaaatg     10380 ttctagaatc tgcagaattc caccacactg gactagtgga tccgagctcg gtaccaagct    10440
taagtttaaa cgctagagtc cggaggctgg atcggtcccg tgtcttcta tggaggtcaa     10500 aacagcgtgg atggcgtctc caggcgatct gacggttcac taaacgagct cgtcgacgat    10560
ctctatcact gatagggaga tctctatcac tgatagggag agctctgctt atatagacct    10620
cccaccgtac acgcctaccg cccatttgcg tcaatgggc ggagttgtta cgacattttg      10680
gaaagtcccg ttgattttgg tgccaaaaca aactcccatt gacgtcaatg gggtggagac    10740
ttggaaatcc ccgtgagtca aaccgctatc cacgcccatt gatgtactgc caaaaccgca    10800
tcaccatggt aatagcgatg actaatacgt agatgtactg ccaagtagga aagtcccata    10860
aggtcatgta ctgggcataa tgccaggcgg gccatttacc gtcattgacg tcaataggg     10920 gcgtacttgg catatgatac acttgatgta ctgccaagtg gcagtttac cgtaaatact     10980 ccacccattg acgtcaatgg aaagtccta ttggcgttac tatgggaaca tacgtcatta    11040
ttgacgtcaa tgggcgggg tcgttgggcg gtcagccagg cgggccattt accgtaagtt     11100
atgtaacgcg gaactccata tatgggctat gaactaatga ccccgtaatt gattactatt    11160
aataactagt caataatcaa tgtcaacgcg tatatctggc ccgtacatcg agctttacta    11220
gggacaggat tggtgacaga aaagccccat ccttaggcct cctccttcct agtctcctga    11280
tattgggtct aaccccccacc tcctgttagg cagattcctt atctggtgac acacccccat    11340
ttcctggagc catctctctc cttgccagaa cctctaaggt ttgcttacga tggagccaga    11400
gaggatcctg ggagggagag cttggcaggg ggtgggaggg aaggggggga tgcgtgacct    11460
gcccggttct cagtggccac cctgcgctac cctctcccag aacctgagct gctctgacgc    11520
ggctgtctgg tgcgtttcac tgatcctggt gctgcagctt ccttacactt cccaagagga    11580
gaagcagttt ggaaaaacaa aatcagaata agttggtcct gagttctaac tttggctctt    11640 caccttctcta gtccccaatt tatattgttc ctccgtgcgt cagttttacc tgtgagataa    11700
ggccagtagc cagcccgtc ctggcaggc tgtggtgagg aggggggtgt ccgtgtgaa      11760 aactcccttt gtgagaatgg tgcgtcctag gtgttcacca ggtcgtggcc gcctctactc    11820
cctttctctt tctccatcct tctttcctta aagagtcccc agtgctatct gggacatatt    11880
cctccgccca gagcagggtc ccgcttccct aaggccctgc tctgggcttc tgggtttgag    11940
tccttggcaa gccaggaga ggcgctcagg cttccctgtc cccttcctc gtccaccatc      12000 tcatgcccct ggctctcctg ccccttccct acaggggttc ctggctctgc tctaagggca    12060
agggcgaatt cgcggccgct aaattcaatt cgccctatag tgagtcgtat tacaattcac    12120
tggccgtcgt tttacaacgt cgtgactggg aaaaccctgg cgttacccaa cttaatcgcc    12180
ttgcagcaca tccccctttc gccagctggc gtaatagcga gaggcccgc accgatcgcc     12240 cttcccaaca gttgcgcagc ctatacgtac ggcagtttaa ggtttacacc tataaaagag    12300
agagccgtta tcgtctgttt gtggatgtac agagtgatat tattgacacg ccggggcgac    12360
```

```
ggatggtgat ccccctggcc agtgcacgtc tgctgtcaga taaagtctcc cgtgaacttt   12420
acccggtggt gcatatcggg gatgaaagct ggcgcatgat gaccaccgat atggccagtg   12480
tgccggtctc cgttatcggg gaagaagtgg ctgatctcag ccaccgcgaa aatgacatca   12540
aaaacgccat taacctgatg ttctggggaa tataaatgtc aggcatgaga ttatcaaaaa   12600
ggatcttcac ctagatcctt ttcacgtaga aagccagtcc gcagaaacgg tgctgacccc   12660
ggatgaatgt cagctactgg gctatctgga caagggaaaa cgcaagcgca aagagaaagc   12720
aggtagcttg cagtgggctt acatggcgat agctagactg ggcggtttta tggacagcaa   12780
gcgaaccgga attgccagct ggggcgccct ctggtaaggt tgggaagccc tgcaaagtaa   12840
actggatggc tttcttgccg ccaaggatct gatggcgcag gggatcaagc tctgatcaag   12900
agacaggatg aggatcgttt cgcatgattg aacaagatgg attgcacgca ggttctccgg   12960
ccgcttgggt ggagaggcta ttcggctatg actgggcaca acagacaatc ggctgctctg   13020
atgccgccgt gttccggctg tcagcgcagg ggcgcccggt tctttttgtc aagaccgacc   13080
tgtccggtgc cctgaatgaa ctgcaagacg aggcagcgcg gctatcgtgg ctggccacga   13140
cgggcgttcc ttgcgcagct gtgctcgacg ttgtcactga agcgggaagg gactggctgc   13200
tattgggcga agtgccgggg caggatctcc tgtcatctca ccttgctcct gccgagaaag   13260
tatccatcat ggctgatgca atgcggcggc tgcatacgct tgatccggct acctgcccat   13320
tcgaccacca agcgaaacat cgcatcgagc gagcacgtac tcggatggaa gccggtcttg   13380
tcgatcagga tgatctggac gaagagcatc aggggctcgc gccagccgaa ctgttcgcca   13440
ggctcaaggc gagcatgccc gacggcgagg atctcgtcgt gacccatggc gatgcctgct   13500
tgccgaatat catggtggaa aatggccgct tttctggatt catcgactgt ggccggctgg   13560
gtgtggcgga ccgctatcag gacatagcgt tggctacccg tgatattgct gaagagcttg   13620
gcggcgaatg ggctgaccgc ttcctcgtgc tttacggtat cgccgctccc gattcgcagc   13680
gcatcgcctt ctatcgcctt cttgacgagt tcttctgaat tattaacgct tacaatttcc   13740
tgatgcggta ttttctcctt acgcatctgt gcggtatttc acaccgcatc aggtggcact   13800
tttcggggaa atgtgcgcgg aacccctatt tgtttatttt tctaaataca ttcaaatatg   13860
tatccgctca tgagattatc aaaaaggatc ttcacctaga tccttttaaa ttaaaaatga   13920
agttttaaat caatctaaag tatatatgag taaacttggt ctgacagtta ccaatgctta   13980
atcagtgagg cacctatctc agcgatctgt ctatttcgtt catccatagt tgcctgactc   14040
cccgtcgtgt agataactac gatacgggag ggcttaccat ctggccccag tgctgcaatg   14100
ataccgcgag acccacgctc accggctcca gatttatcag caataaacca gccagccgga   14160
agggccgagc gcagaagtgg tcctgcaact ttatccgcct ccatccagtc tattaattgt   14220
tgccgggaag ctagagtaag tagttcgcca gttaatagtt tgcgcaacgt tgttgccatt   14280
gctacaggca tcgtggtgtc acgctcgtcg tttggtatgg cttcattcag ctccggttcc   14340
caacgatcaa ggcgagttac atgatccccc atgttgtgca aaaaagcggt tagctccttc   14400
ggtcctccga tcgttgtcag aagtaagttg gccgcagtgt tatcactcat ggttatggca   14460
gcactgcata attctcttac tgtcatgcca tccgtaagat gcttttctgt gactggtgag   14520
tactcaacca agtcattctg agaatagtgt atgcggcgac cgagttgctc ttgcccggcg   14580
tcaatacggg ataataccgc gccacatagc agaactttaa aagtgctcat cattggaaaa   14640
cgttcttcgg ggcgaaaact ctcaaggatc ttaccgctgt tgagatccag ttcgatgtaa   14700
cccactcgtg cacccaactg atcttcagca tcttttactt tcaccagcgt ttctgggtga   14760
```

-continued

```
gcaaaaacag gaaggcaaaa tgccgcaaaa aagggaataa gggcgacacg gaaatgttga   14820
atactcatac tcttcctttt tcaatattat tgaagcattt atcagggtta ttgtctcatg   14880
accaaaatcc cttaacgtga gttttcgttc cactgagcgt cagacccgt agaaaagatc    14940
aaaggatctt cttgagatcc ttttttttctg cgcgtaatct gctgcttgca acaaaaaaaa  15000
ccaccgctac cagcggtggt ttgtttgccg gatcaagagc taccaactct ttttccgaag   15060
gtaactggct tcagcagagc gcagatacca aatactgttc ttctagtgta gccgtagtta   15120
ggccaccact tcaagaactc tgtagcaccg cctacatacc tcgctctgct aatcctgtta   15180
ccagtggctg ctgccagtgg cgataagtcg tgtcttaccg ggttggactc aagacgatag   15240
ttaccggata aggcgcagcg gtcgggctga acggggggtt cgtgcacaca gcccagcttg   15300
gagcgaacga cctacaccga actgagatac ctacagcgtg agctatgaga aagcgccacg   15360
cttcccgaag ggagaaaggc ggacaggtat ccggtaagcg gcagggtcgg aacaggagag   15420
cgcacgaggg agcttccagg gggaaacgcc tggtatcttt atagtcctgt cgggtttcgc   15480
cacctctgac ttgagcgtcg attttttgtga tgctcgtcag ggggggcggag cctatggaaa  15540
aacgccagca acgcggcctt tttacggttc ctggccttt gctggccttt tgctcacatg    15600
ttctttcctg cgttatcccc tgattctgtg gataaccgta ttaccgcctt tgagtgagct   15660
gataccgctc gccgcagccg aacgaccgag cgcagcgagt cagtgagcga ggaagcggaa   15720
g                                                                    15721
```

<210> SEQ ID NO 58
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Ser Thr Arg Ile Ser Gly Pro Tyr Ile Gly Pro Arg Gly Gln Glu
1               5                   10                  15

His Ser Leu Cys Pro Thr His Pro Pro Thr Val Gly Arg Gly Thr Leu
            20                  25                  30

Gly Asn Pro Val Cys Pro Glu Pro Gln His Ser Gly Ser Leu Gly Ser
        35                  40                  45

Leu Cys Leu Pro Asp His Thr Leu Met Pro Ser Leu Pro Leu Pro Ala
    50                  55                  60

His Ser Gly Ser Gly Pro Asp Arg Leu Arg Arg Pro Thr Pro Val Pro
65                  70                  75                  80

Tyr Ser Ala Val His Leu Arg Pro Ala His Ala Leu Pro Arg Arg Leu
                85                  90                  95

His Leu Leu Ala Ala Arg His Val Gly His Arg His Arg His Val Ser
            100                 105                 110

His Glu Leu Gly Leu Ser Leu Pro His Arg Pro Ala Ala Leu Pro
        115                 120                 125

Arg Leu Ile Thr Gly Ala Gly Arg Ala Leu Pro Asp Arg Leu Ala Leu
    130                 135                 140

Leu Pro Ser Ile Leu Arg Arg Leu Gly Arg Phe Leu Pro Val Leu His
145                 150                 155                 160

Gly Gly Arg Arg Glu Ile Ala Pro Ala His Pro Ala Ala Leu His Gln
                165                 170                 175
```

Arg Ile His Arg Arg Arg Ala Ala Gln Pro Gln Pro Pro Gln Pro Glu
            180                 185                 190

Arg Arg Gly Gly Asp Arg Gly Gln Pro
            195                 200

<210> SEQ ID NO 59
<211> LENGTH: 20607
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

| | | | | | |
|---|---|---|---|---|---|
| gggcgaattg | ggcccgacgt | cgcatgctcc | cggccgccat | ggccgcgggg | catctctctc | 60 |
| cttcctccag | tgtctgcaag | cacacacaca | cacacacaca | cacacacaca | cacacacaca | 120 |
| cacacacatg | cgcgcgagca | cctaactaaa | aataaaatag | ctgtaaatga | aacacgtat | 180 |
| tcgaatagag | cacttgaatt | tgaacatatc | taaaaggccc | atgtcttttt | tattacagag | 240 |
| cgtatacaaa | gcgagacagg | gagggatgga | aggagaaggg | gaggagggag | agagaacctg | 300 |
| acctctcgta | gaaagacgcc | acactatctc | agatcttcca | catactctgc | ccccagcagc | 360 |
| tgagactgta | acattactcc | tgcgcttatg | cccatgacaa | atcacggact | cactcgggat | 420 |
| tccggtaacg | tggtaccatt | accacattac | catgtaagaa | ctgggacaga | ctggcagagc | 480 |
| atgttcagac | acggctctga | aacgtggtga | cctctccttc | attttttcc | agtggattca | 540 |
| cctttttttgt | ctcaggacaa | atgaagcaag | agggataatg | ggcagagtca | cttgtttgtg | 600 |
| tccagtgtat | tgcatcagat | gacaacaggc | cgattgtgtg | tgtgcctaat | gctctccctc | 660 |
| ctgcctcggc | ttctccctag | actgtataaa | tctaactgga | aaaaaaaaat | ggagtagagc | 720 |
| ttcctgttaa | ctctcaagca | tgtcatggct | ctctgtaagc | aaaacaagtg | acacagagtt | 780 |
| tgctcataga | ggtccccggt | gagggcgcag | agatgaaccc | tgaggaatga | ggtgtggcct | 840 |
| gctggctgga | ggagaggcta | gagggcagcc | taccagggca | gcctaccaga | gccactgttg | 900 |
| gtttacagcc | tttgcctgcc | cacatgtctg | acttgctttg | aaaagattaa | caggagtgtt | 960 |
| tgtttgaaag | tcagactcct | ggtttcctca | ttagtagagg | gatttgctgc | agacttgggc | 1020 |
| tgtgcttata | aactctaatt | acctctctga | tgaggagtct | atttctctca | cattcagccc | 1080 |
| aaatgtacac | aagagttcct | tttgtaaaat | cgtgttagag | caataaaaga | ttattgagag | 1140 |
| ggggtggagg | gggagaggga | gaaacaagaa | cacaagcccg | agctctccgt | gctgaaataa | 1200 |
| taggcttgga | acagaaagaa | gttgatcaca | gcccatgcct | tccaaaaaaa | aaaaaagatt | 1260 |
| aatccacccg | ggtagctttc | ctttcaaagg | aagcttttcg | atcccctcaa | gtttctctct | 1320 |
| agcaggctca | actctgtacc | tgaatttgag | aatttaacat | tttgaacact | tagttcgtgc | 1380 |
| ctctgccctg | tgttgttgct | gctgctgagc | cgtgctggtg | cgaacagtat | agtcgcagcc | 1440 |
| tgccctcctc | tgactgacag | acacaagcta | cccgaaacac | cgtcctaact | cactgtggca | 1500 |
| gctggtgggc | ggatgtgcat | cccttcctaa | ccattctcag | ttatttcgca | atgtctggag | 1560 |
| attcttttgg | atgtcaaagt | agcgggcagg | gggtcggcag | ggaggccact | agaggcatct | 1620 |
| tgtgggtaaa | gaaggaagat | gccaccaaac | agttatcagt | ctccaaacac | ccgctagaca | 1680 |
| taatacagcc | caaagatgcc | agcagtggca | cttttggcaa | gggaaccctc | ctgtccctcc | 1740 |
| tgtcccctgg | tctgcctcaa | aggcagcatg | cacacgtgcc | aagtcagag | ggagccggtg | 1800 |
| aagcaagggc | agtctgtaga | actgtaaatt | caaaatgaat | cttgtaaaga | aagtctgtca | 1860 |

```
tttctggaca aaacaagttt tgctatccat ttgtgttaga agctagtgag tgacacagca   1920
gctggagcca tgactcagtg gtttagagca tgcactgctc tgggggatgt tggcacccac   1980
ttctagcctc tgggggcact gcacacacac aggctcataa ccacacaagc ataatcacaa   2040
gtaaaattac ctttaagaag aaaacagtga ctcaggtctt agataaagac gagacatgaa   2100
gtcaaatgtc taaggttact atagatggga acaagtcaga aggcagagac agaggcaagt   2160
gatgtgtcaa tcaccgacat tcacgtcgtc cctaccacaa cacgcactgc acctaataat   2220
aggaaattag ccaactttca agggatcaga gtctacaaaa atgacagttt tctattatcc   2280
aacctgacta ctaagtgcaa tgacataata ttgttattat aacatactta acatataata   2340
ttctactatc aacatatcag tggatgcatg acctcagtta ttttaatgtt atgccattgt   2400
atattgttat attaatattg ttatgccaat gtactgatta tattagcaat ataccagtca   2460
gtattgatgc tttcattaga ggataggctt ttttttctcc cccagtaaag gaccaaagag   2520
aagttgttaa gctttggaca ctctgttgtc ctggtcactc aacagcaata ggagctactt   2580
agcgcccatg aaagtgcaca caggtgccaa cttgtgctat aggttgaagc tatgtcgcaa   2640
cagagtagaa atacaatttt tgtgtgtttt tattttagt cttacaacca tttgaaaagg   2700
taaaattcat tcttaattcc tagaacacat aaaacttctc cccagccaga cttagccaat   2760
gagctacagt ttgccaacct gggatctaac atttatgtgt attggaaact ttacactaca   2820
gtgtgtgtga caggtaccta tatggtacat atgctacggc gtgtcaggat ataccata    2880 tgccgcccac cactccctgc aatgcatctg ccattgctct gtgtcacact gtttgacatc   2940
tgtcatgtca aacatgctgg gggaagccca cttcttgcta gatagtcccc gccacccacc   3000
attccctggc agcagccctc tgcatagaat ctcatcttct taagtgacag tatcttgggt   3060
agttatctgt cctgttgact tctaggtaag tgtacatctc aggcaggaat attctcagtg   3120
gttccctcct ccctgggcag ggagctgtgg gcagtccagt ctgttgggtg ggtgcactct   3180
ccgtgctccc tcctccatgg tcagggccag tctgggcact cttctgtgtc ctgagtagga   3240
gcactccctg tgccaccccc atcccccacc catagtcatt ctgtgcaatc ttgtgtgacc   3300
tggttggaaa cagtcttggt ggtctggac actctgagca gtcctgtgtc ctgggtggga   3360
gcaattttgc ggtccccct tccacaggca ggggcagtgt gttgtggggg gagcactctc   3420
tgtgtagccc cctacatggg cagaggcact ctccgtggtc cccccccccc gggcagaagc   3480
actctgggta gtcctgtgtg ttagggcagg atcacatgct gtgcccccac tccgtgggca   3540
ggagcactct gggtagtcct gtgtcttagg gcaggtgcac ttgccgtgct cccctccccg   3600
tgggcagggt cactctctgt ggccccccc tccatgggca ggggtactct gggtagtcca   3660
gtatttgggg caggggtatt ctctatgccc ccccccccca tgagcagggc cagtctgggc   3720
aatcctgtgt cctaggtggg agcacttccg gtttccccct ccatggatgg ggcacttttg   3780
gcagtcagtg tgttggggtg ggagcactct ctggtcgct ccctccatgg gcagaagcac   3840
tctgattagt cctttgtcat agggcaggag cactcgctgt gcccccccc ccgcccccgg   3900 ggcaagggca ctctctgtgg tccctctcca tgggcaggga cactctctgg gcaagtccag   3960
tgtgttggag agggagcact ctttgtgtca gaggcactct ccgtgatcgc ggcctacaga   4020
catgataaga tacattgatg agtttggaca aaccacaact agaatgcagt gaaaaaaatg   4080 cttatttttgt gaaatttgtg atgctattgc tttatttgta accattataa gctgcaataa   4140
acaagttggg gtgggcgaag aactccagca tgagatcccc gcgctggagg atcatccagc   4200
cggcgtcccg gaaaacgatt ccgaagccca acctttcata gaaggcggcg gtggaatcga   4260
```

```
aatctcgtag cacgtgctat tcctttgccc tcggacgagt gctggggcgt cggtttccac   4320
tatcggcgag tacttctaca cagccatcgg tccagacggc cgcgcttctg cgggcgattt   4380
gtgtacgccc gacagtcccg gctccggatc ggacgattgc gtcgcatcga ccctgcgccc   4440
aagctgcatc atcgaaattg ccgtcaacca agctctgata gagttggtca agaccaatgc   4500
ggagcatata cgcccggagc cgcggcgatc ctgcaagctc cggatgcctc cgctcgaagt   4560
agcgcgtctg ctgctccata caagccaacc acggcctcca gaagaagatg ttggcgacct   4620
cgtattggga atccccgaac atcgcctcgc tccagtcaat gaccgctgtt atgcggccat   4680
tgtccgtcag gacattgttg gagccgaaat ccgcgtgcac gaggtgccgg acttcggggc   4740
agtcctcggc ccaaagcatc agctcatcga gagcctgcgc gacggacgca ctgacggtgt   4800
cgtccatcac agtttgccag tgatacacat ggggatcagc aatcgcgcat atgaaatcac   4860
gccatgtagt gtattgaccg attccttgcg gtccgaatgg gccgaacccg ctcgtctggc   4920
taagatcggc cgcagcgatc gcatccatgg cctccgcgac cggctgcaga acagcgggca   4980
gttcggtttc aggcaggtct tgcaacgtga caccctgtgc acggcgggag atgcaatagg   5040
tcaggctctc gctgaattcc ccaatgtcaa gcacttccgg aatcgggagc gcggccgatg   5100
caaagtgccg ataaacataa cgatctttgt agaaaccatc ggcgcagcta tttacccgca   5160
ggacatatcc acgccctcct acatcgaagc tgaaagcacg agattcttcg ccctccgaga   5220
gctgcatcag gtcggagacg ctgtcgaact tttcgatcag aaacttctcg acagacgtcg   5280
cggtgagttc aggcttttc atcacgtgct gatcagatcc gaaaatggat atacaagctc   5340
ccgggagctt tttgcaaaag cctaggcctc caaaaaagcc tcctcactac ttctggaata   5400
gctcagaggc agaggcggcc tcggcctctg cataaataaa aaaaattagt cagccatggg   5460
gcggagaatg ggcggaactg ggcggagtta ggggcgggat gggcggagtt aggggcggga   5520
ctatggttgc tgactaattg agatgcatgc tttgcatact tctgcctgct ggggagcctg   5580
gggactttcc acacctggtt gctgactaat tgagatgcat gctttgcata cttctgcctg   5640
ctggggagcc tggggacttt ccacacccta actgacacac attccacaga attaattcgc   5700
gttaaatttt tgttaaatca gctcattttt taaccaatag gccgaaatcg gcaaaatccc   5760
ttataaatca aaagaataga ccagataggg ttgagtgtt gttccagttt ggaacaagag   5820
tccactatta agaacgtgg actccaacgt caaagggcga aaaaccgtct atcagggcga   5880
tggcccacta cgtgaaccat caccctaatc aagtttttg gggtcgaggt gccgtaaagc   5940
actaaatcgg aaccctaaag ggagcccccg atttagagct tgacggggaa agccggcgaa   6000
cgtggcgaga aggaaggga agaaagcgaa aggagcgggc gctagggcgc tggcaagtgt   6060
agcggtcacg ctgcgcgtaa ccaccacacc cgccgcgctt aatgcgccgc tacagggcgc   6120
gtggggatac cccctagagc cccagctggt tctttccgcc tcagaagcca tagagcccac   6180
cgcatcccca gcatgcctgc tattgtcttc ccaatcctcc cccttgctgt cctgcccac   6240 cccaccccc agaatagaat gacacctact cagacaatgc gatgcaattt cctcatttta   6300
ttaggaaagg acagtgggag tggcaccttc cagggtcaag gaaggcacgg ggagggca   6360 aacaacagat ggctggcaac tagaaggcac agtcgaggct gatcagcggg tttaaacggg   6420
ccctctagac tcgagcggcc cgaagtcggc catatccaga gcgccgtagg gggcggagtc   6480
gtggggggta atcccggac ccggggaatc ccgtccccc aacatgtcca gatcgaaatc   6540
gtctagcgcg tcggcatgcg ccatcgccac gtcctcgccg tctaagtgga gctcgtcccc   6600
```

```
caggctgaca tcggtcgggg gggccgtcga cggtatcgcg cgcagcaaca tgcatgtaca    6660
cacacacata catacactca tacacaatag ctcccaaaaa agacctaagt actcggcggc    6720
tacaaagcac ccttcacact agagaaagct cttttcttac taggaaaatc tctctttgaa    6780
gtgtacgttt aaaggaatga ttagatcctg gcagacatat tttaaaatgt aaagtgggga    6840
aacaggttct atcatctcta aaataaattc ccactttagg aattttcaag ctacttcaaa    6900
ttattgccag agtttaatgg tggatagaat gaattaatta aatgtgatgg cctatataat    6960
tttcaaaggc gacttgacat gttctcaaat ttaatccatc cagtcacctt ttaaaaataa    7020
gcaaggactg gtgaccaatg tcagacaaaa tataatgatt agaaggctta ggtcatcttc    7080
caaaaagtta atcatactaa aggccacaca aagattgact ttttcgtttt gttaaacttg    7140
tagtaaagac caagcaaaga tacttgtctt aaacattctg caatagttgc actgatcttt    7200
ccacagactc atcaccctca gtacactgag acactgctta gtcttcagaa acatgacaca    7260
aatggctatt tttacttcac aaaagctaat gatctcacag tcaatccacc ttgcaatcca    7320
aatgcctttc ttaaggaata aaattatcaa taacttttct ggcagttggt cctgtacagt    7380
agcaatatac aaaatcgggc ttaaagtttc ttaagcagac agttggctcc ttcctggagg    7440
aagaatggaa agaaaagtgc taagcttcct tctcaggaag acaattttca gttcatactg    7500
taaaggaaag ccccaagtaa aaggtggcaa tccaactccc tgagctactt gcctgcaata    7560
ttttgcacaa taaagcatta ataaaggtag gcaagaatgg ttcctggccc tagaatgtgc    7620
cagcagttgg aattggaata atttagaagt gcaagttaaa gattgaaggc tcatccacct    7680
agttttggcc tgcttttgct attcagtgta taaatacacc aaaatttatt aatgacacat    7740
agggtgtttg gggtaattaa cattacccag aataatgtaa gaattcgagg tgtctctgtt    7800
cagtgggagc aaggagaagg caactgagac actgtagcca tatgaagtga gtaaactggt    7860
gttgttgact ttaagtcaag agaagggctt tgcccagtca atactgttca aacaaagagg    7920
caaaagggat ggcatgatgg aattgagaaa gggcacaaac tcttccttaa tgatgggttt    7980
gtgagaatta gtgattcaga aaagtggtca atggacaaac tagaggccgg gcaaaaggaa    8040
cactataaag tgtgagattg tgactatttta ggattgtata tattaaagca atgcaaaaag    8100
ggtcgaaatc cgggtcattg ttgggtgtac atactgctgt actttattat atcattggga    8160
aactagcagg ggatttgctc aagttggagt agaaaataaa ccatccagaa ctgccattgt    8220
gcctattaag agtcccaaaa tcagtttaag gaagagagca ggtcattcgt cagagcccct    8280
gtgctcattg acagtaccgg gtagtttcgg gggctcagca acctctgcaa taatgtaaag    8340
gggacaaaat attccagaca ttcatagtta taaatacgca taacttagca attaattctg    8400
ggactcagta gccttgatgg tatgcaaaga gagcacacag gtccttgaca ttttttgcata    8460 gtaatcatcc aaatgctgag gttactaata gttactacca ctcagcagcc ccagtcaaaa    8520
ggtaggcatt tcagaacctt tgctgccgca caggtcatat gtgtaagggt acagattaat    8580
attgacaaga gaagtgctca gaaataatta atatgcctct ggtgtcaaaa gagtacaagg    8640
atgtaaaatc caactccaaa ggtaatgatg gacaactaac tgcattaatg cacttaagtc    8700
caaatgaaga gcacttcgta caaccctctt tctgctttaa agcggagaag agggtacagt    8760
agttcttaga gaagtgctta gacatgtgaa ctttccaaat gaaagtcttg agcttattat    8820
cacttcctgc tgaaggtgct aaggaagtga gtgggatcct ttcaagtgca cagagcaggt    8880
ggcagtgcat acgcatacat ttaatatatg ataacagtcc aaaagaatgc ggccttgttg    8940
atcagcatat cctgatatag tgcaaatgaa aggcgaagga gtatggcctt tgtttactgg    9000
```

```
caaagacaaa ggaagattca ctgtatatta atggtccact agcagggacc ttgggagata    9060
aacggtatcc cttgcaggag tgcaagagat acaatggtcc gaaaagtaat aaggttgtgg    9120
ataagtgtaa ttttacacat taactggcca agtatttta ttaaaatgaa tggatcatgt     9180
ccctgttata tacattaatg ttcaagggac atgttatcaa ttaaaaaccc catcctttat    9240
gcaaatatta agtctttaaa gtaatagtcc tggaaattaa agagtggaaa ggaggggaca    9300
gccttatcca gtgtccagga agatgaagaa gccaaaagat tagtgaccct tgctgtactg    9360
caaagggtt tgagagtagg atcgtatcca aatggaatga gatgtgtgca gtaaatgcat      9420
actaatatgc aaggtacatg tttatggcca ttacagtttt acgctgttca ggtttccttc    9480
tgtagtgaac agaaaaggcc tactacaatc agtcattatt attagcaagc cacaaaatgg    9540
gaccttatag gtcaacacca cttctgtact tcaaagttaa gagtaaaatt gatcctacta    9600
aaattgccag tatgtacata aatagtttga ggaagggggtt tcaagtgcac agcacataca   9660
taattccata aagcaaagag gatatgaatg atcagagaca gaagtcttac cttgaaggac    9720
cattgaccgt attggaatcg tttcaatcta tagtctcatg aaagaagctt tatattagtg    9780
agcctctttg ctttgctaag tacaggagtc ctgatctaaa aggcacaact gtggacatga    9840
gaatatgtac aatagagtta acactgtgca catttactat gttaaggatc ttaaatactg    9900
ctgcaataca aataagtctt caccagatgc agattactac agtgaaatga catatgcaca    9960
ttcacaatat gaaagactgc atgcagggca tagtggtagg aaccagatat gccaacactt   10020
gttaaacgca ggctagatcc tgagctcaag gctagcctgg gttatatgct aagttccagg   10080
ccagcctgga agttaaaaac aggacagatc aaaggtcttc ttgattacca acaaaatgac   10140
ttgacttagt ttggtttctt tatccaatgc ttaggaagag ggacaaatgc agctgtgcac   10200
acaacaggca caaatatgtt tacattacag gtggcaatgc ctgtaagtcc cgcccagccc   10260
aggctacata agaggctgtt ctctcaaacc accacacggt ggggctgtag ctctatgaca   10320
gtgctttact agcgtacaca agactcaagg tttgattccc cagcacagca gaaagaccag   10380
aacagagaag tggtctcatt ggttggcacc cttgattgtc acccattagg gtatgagggt   10440
atgggatctt ggttactaac agaaggggac ttgaacaact gcaattttgc acaattgtgt   10500
aagaggcatt aagtaatcag caccctcttt acataaagca agggtagtat taggaccttg   10560
agaaaagact caattcctag tcaggattat ccacataaaa tgttccagtg cagaggtttt   10620
tggctgaaat aagaaagcat gtgagactag tatacaatat catgagcaaa taaatgtatc   10680
tccatcagtt agaaagatgt gacctggggc gatagcaccc atgacagcat gccaacagta   10740
tatagtattc taccccctt aatggccaat gccttgaaaa ttgggactga gcactttaac     10800
tgtctgataa cagacctgtg tttgcccctt tgctaaatgc acacagggct ggactagcta   10860
aagtctaatc caatggacaa aatatttctg acagaattat tcagtactca aggtaataca   10920
tgagaaaaga cgactgaaca ctgccttagaa acttgggact gtgactacta cagcaatgac  10980
agaatggttt tcttttcctta aaggaaagga gacttgagag atgatacctc catggatccg   11040
acatcatcca acacttcagt gttagaattg caagcatgcg ctctcccgac ctgggcaggc   11100
acttcgaaaa aatgatgact aaagacacac gtgaagtacc aagcgaaact cacgtcctta   11160
tgggacagtg actcatcaca gtctaattcc atcctggcca ccaagcaata atgcacattt   11220
ctaactggaa gtcaagcaaa caccaacact ttcacacttg tgcccatttc tgacgagtta   11280
cgtcaagtgg caaccaacac ttccacttag ccttgcctca gcttcgagtg gcacaaggta   11340
```

```
ggaccaacca cacccctacca taatgcacca agtgtaccct cgggcaaagc ccgccaagta   11400
gctaaagccc gccaaaaaaa aaatcactga aagaaaccac tagagggcag gtcacatgac   11460
ttccgccatc ttagacacat tcaagagcat gtgccacctc tccaggctaa ctcagacatg   11520
aagctgacat gtgacacaca aagcccttttg cgttataccg caccaagaac ttgagccgcc   11580
atctttcct gtacgaccta aatgtcctat aatccattgc tacacaccag aacaaagatt   11640
gggctgtcga gcctcgggtg gagccccga gccgccattt tatagacttc tgagcagccc   11700
ttaaagccac gggggaccgc gccaggggtc catatgcaca cacccctgc ccaatcccca   11760
cacccacgct gagccctatc ccctagtcct ctgcggcttc cgcgcaacac cgcacactaa   11820
tacgagcact ccttggcttt ctacttccgg ctagcacaac cccgcaaatg ctaccacaaa   11880
tcaaggcgaa tcccgcaacc ccgcacatat aaagaaagcc tttagctagc gcagcgcaat   11940
tggttgcttt tatccagtcc gctgtgctcc tcggtgtcct aattcttggc gtaactggct   12000
cgagaatagc cgtatcacgc agaagccata atggcggacg cgggctctcc acgccctgaa   12060
cacccactca gtttaagagc aaagtcgttt ttctaagcca taggttcact cacacagcac   12120
caaacgatca gcagcaacag tacacgcaaa taagaggcat agatattcca ggtagtgcaa   12180
taactcacaa aaccatatt ccatccacca agcgccccgt tgggccgtga aaaaaaaaat   12240
ttaaagcagg tatccacagc cccgatgggc aaagaaaaa gaaaaaaaaa taataacagc   12300
aggtatccga ggcccgttg ggcatgggaa aaaaagacta aacgcaggta tccgaggtcc   12360
cgatggaccg agaaaggttt ttttttttt tttttttt ttacaaaag caggtatcca   12420
tggcccccgat gggctaagga gaagaaaaaa agaataaaag caggtatcca cagcccagat   12480
gggcaagttt agaaaaaaaa ataataagaa aaaaaagaa tgaaaaggca ggtaagtatc   12540
caaaaccccg ttgggcatgg aatggcgggg aggacacaca ggtatccgtg gccccgatgg   12600
gcaagaatat ataaacaatg aaagaaaggt aagtccacca tacacacaca agtatcaacc   12660
aaaaggcaca acaaagaaat attccttaaa aatgaaaaat tgactgaaaa tattacaaat   12720
atcaaaaagt atggaggaca tgtcaaaaaa aaatcttac cagaacatat caaaacgtca   12780
aaaatctcgt ggaattttga tatgttttct taaataagcc ataaggcttg gtggtagggg   12840
aactaaaaat gttcccccaa agctccttag atggagagaa accacggaag aaccgcacat   12900
ccacgggaaa cgagcaaaca tggctggagc aagccgttgc acgcctttaa ctgatccgcg   12960
gaggctggat cggtcccggt gtcttctatg gaggtcggat ccgagctcgg taccaagctt   13020
aagtttaaac gctagagtcc ggaggctgga tcggtcccgg tgtcttctat ggaggtcaaa   13080
acagcgtgga tggcgtctcc aggcgatctg acggttcact aaacgagctc gtcgacgatc   13140
tctatcactg atagggagat ctctatcact gatagggaga gctctgctta tatagacctc   13200
ccaccgtaca cgcctaccgc ccatttgcgt caatggggcg gagttgttac gacattttgg   13260
aaagtcccgt tgattttggt gccaaaacaa actcccattg acgtcaatgg ggtggagact   13320
tggaaatccc cgtgagtcaa accgctatcc acgcccattg atgtactgcc aaaaccgcat   13380
caccatggta atagcgatga ctaatacgta gatgtactgc caagtaggaa agtcccataa   13440
ggtcatgtac tgggcataat gccaggcggg ccatttaccg tcattgacgt caataggggg   13500
cgtacttggc atatgataca cttgatgtac tgccaagtgg gcagtttacc gtaaatactc   13560
cacccattga cgtcaatgga aagtccctat tggcgttact atgggaacat acgtcattat   13620
tgacgtcaat gggcggggt cgttggcgg tcagccaggc gggccattta ccgtaagtta   13680
tgtaacgcgg aactccatat atgggctatg aactaatgac cccgtaattg attactatta   13740
```

-continued

```
ataactagtc aataatcaat gtcaacgcgt atatctggcc cgtacatcgg gccgcgtggg    13800
caggagcact cgctgtgccc cacccaccca cccaccgtgg gcaggggcac cctgggcaat    13860
cctgtgtgtc ctgagccgca gcactctggc agtctaggaa gcctgtgcct ccctgaccac    13920
acactcatgc cttctcttcc tctgcccgcc cacagcggct ccggacctga ccgccttcgg    13980
cgacccacgc cagttcccta ctctgccgtc catctccgac ccgcgcatgc actacccagg    14040
cgccttcacc tactcgccgc ccgtcacgtc gggcatcggc atcggcatgt cagccatgag    14100
ctcggcctct cgctaccaca ccgccctgcc gccgccctac cccggctcat cacaggcgca    14160
ggccgggccc ttccagaccg gctcgccctc ctaccatcta tactacgcg cctcggccga    14220 ttcctaccag ttctccatgg tgggcggaga gagatcgccc ccgcgcatcc tgccgccctg    14280
caccaacgca tccaccggcg ccgcgctgct caacccagc ctccccagcc agagcgacgt    14340
ggtggagacc gagggcagcc atagcaactc gcccaccaac atgccccccg cgcgcctgga    14400
ggaggccgtg tggcggccct actgagctga gcgccatcgc catcgaggga ctgggcctgc    14460
cgtccatgca cagacccgc caggagggcc cttggaggcc accaggaaga atcccggagg    14520
gaaactgtga atgcttctga tttagcaatg ctgtgaataa agaaagatt ttatacccctt    14580 gacttcactt tttaaccacg ttgtttattc caaagagtgt ggaatgtttt cggttcgggg    14640
tggggaagac gcagcccatc ctgtttggca tctatttctt atttcggagt tttcttttcc    14700
gcaccttatc gattgcaaaa atgcctgttt gcatctgggt ggtcatttat ttttaagtgt    14760
gtatagattt gagcttgctt ttttttcttc ctttgaccaa ctcaaagaaa taaaattccc    14820
ttctctgtaa ggtttatta acttttagac tttcatgtag ctgggggttt tatttgtgtt    14880
tggtttttgt ttttatttt aaagagacag ctacagcttt gggtcatttt ttaactactg    14940
tatttccaca aagaaatccc tagatattta tgtatcttga tgtttgaaca tttacatatg    15000
tgttgatact ttttaatta tttaaatgta cttatattaa gaaagatatc aagtactaca    15060 tttttctta taatagccaa agttaaatat tattgcgttg aagatgtctg gaaaaaaag    15120 agatcgcttg gttaactaga aatattgttt acattaaact ccctttatgt tattcaaaca    15180
agttggtagg taacgcagca atgttttaa ttggattgta gacactgagg gtcactccaa    15240
ggtcagaagt acaaaatttt ctgctaggct caacaaatag tctcataccct ggctccttcc    15300 cttcaaaaag agaggcaaac tctgtcctga aagggttcag agaggtgcca aggatttgct    15360
ctgaagagga tttcattttg gcctggagat atacttgccc caaggcctcc tcattctggc    15420
atgctttatc acagagctca accaagtaag ctgttggtca ggggtttact tacatagtat    15480
ttacatagac ccaaaccact gaatgtgatt tttaaattgc cttccattaa tagtacccgt    15540
tcattgatga aaaccaaaac ttgaggctgt accccaaaga tccaaataga agagttaaga    15600
ccaggtgtct ttgaggccta aaggctgagt tttaagagag tgtaccccaa aagtctgaag    15660
gagccggttt ccttctccca gtcttagtgg aatcagtcat gggaggcaga tgccacgccc    15720
acctgtgcag gatgctcctc agaagctgcc ccttcaccag catcttctcc caccaggccg    15780
agcccctgac ctttggggtg catcagtgtg atagatcctg gtctctgcag tccgccatgg    15840
ctacggttca gatgtgcatc gtgtcactgt aaatgtaatg gtactgttgt tacagtggag    15900
gacttggtca aaatccagtt gttctacaac gtatgaagcc taaccgctgg ttctgacata    15960
catgtgctca aaatgatctg gttgtttgga ttttcttttt gttgttttgt tttttaatgt    16020
acctcttaaa ttagttgaag tgatgtcagg tcaactccga agagcgtttg aaagcaggac    16080
```

```
ttcagcacag tgtttgattt ttttattatt attaatatta ttttataaat ttaagcattc    16140
agattagatc tttggctgca ggcagcaaaa acggctggac ttatttaaaa aaaatacagc    16200
ttgttttttg agttatctat atctatatct atatgttgat tctttgtctt acatagagca    16260
gcagcacttt ggtaacctgt gataccaggt tgctcttgtc tggagaagag cgctagcagg    16320
attcagagaa actcagaata gatcttcata tcagccatac cttcctcctc catccggtct    16380
ccactcagtt attccacaga acactttgac agctgtgttg tcagaaaaat aaaaaaaaat    16440
ttaatttctc aaaaggagtt tgtttctcca acattagatg ttcctcttac cataggctgc    16500
cgtatctggc ctgagaaaac ggtagggaag gacgaaggaa agagatttct atttttttcat   16560 attaattttg atatctaaag atacgctagc cctcagagga gcagataatc tcacacattg    16620
aattttcgcc ctgggcacca tgcatcaaga aggcttgtca ctgtgttaga gccatttagt    16680
gcttcctaaa cttttatcaa cataggcagt atttagtctc agagaaaaaa aaatccatca    16740
ggcacatgta gtcttggaga tagattccac ggggcaggta tttctctacc tgagaaattg    16800
tgttcattgc cttcgggtgc ttccagcggt ctcctcattc gctgtcttca aggaagaccc    16860
ataagccaat tctgagataa tggagctgtt gggaatactg gtccagagaa agaaaaatgg    16920
gataagccat tcttactgct tattcaagcc cctatttata attttaacac actttccatt    16980
ccttctggtt ttctcgccgt ctatatcctc ccaatagccc ttctcacttt tcttttccct    17040
cctgcaaaca cacacacaca cacacacaca cacacacata aggcacacac acacacatcc    17100
tctcccccat accaagtgtc cagaacacag aaagtccagt tcttctccgt ttattaaaga    17160
acagggtgag tcagccattc tcttgctcac gggtttttt ccccaacaga acagaggcgt     17220
tgccagccat tttgggtctg ctttctgtcc agatactgca gcaaaaactc ttgaggatca    17280
caacccgttg gctgagcagc tgtgctgctg cccaaacgtc ctgcgcagac aaacgcacgc    17340
tgggaccgga aggggtgtct ctccttctgc ctctttctct tcatacgttt ctctcgaaag    17400
gcctcaactg aggactgcaa atttctttct tgaaataact ttcccccagg gacattcggt   17460
cttagggatt ttttggtttt gatgggtttt gttttgtttt ggttttttg gttcttctca    17520 ttttctttgt aggagaaggc atgagatgtt gagggtcttt catacatgaa aataaatagt    17580
ttgacagcaa tctcagaata tattttttcc ttatttgaac aaagtactgt tttgtttact    17640
ctacagtaca cctttatttg gtgggtttgg ctgttggtcg ggtcgaccat atgggagagc    17700
tcccaacgcg ttggatgcat agcttgagta ttctatagtg tcacctaaat agcttggcgt    17760
aatcatggtc atagctgttt cctgtgtgaa attgttatcc gctcacaatt ccacacaaca    17820
tacgagccgg aagcataaag tgtaaagcct ggggtgccta atgagtgagc taactcacat    17880
taattgcgtt gcgctcactg cccgctttcc agtcgggaaa cctgtcgtgc cagctgcatt    17940
aatgaatcgg ccaacgcgcg gggagaggcg gtttgcgtat gggcgctct tccgcttcct    18000 cgctcactga ctcgctgcgc tcggtcgttc ggctgcggcg agcggtatca gctcactcaa    18060
aggcggtaat acggttatcc acagaatcag gggataacgc aggaaagaac atgtgagcaa    18120
aaggccagca aaaggccagg aaccgtaaaa aggccgcgtt gctggcgttt ttccataggc    18180
tccgcccccc tgacgagcat cacaaaaatc gacgctcaag tcagaggtgg cgaaacccga    18240
caggactata aagataccag gcgtttcccc ctggaagctc cctcgtgcgc tctcctgttc    18300
cgaccctgcc gcttaccgga tacctgtccg cctttctccc ttcgggaagc gtggcgcttt    18360
ctcatagctc acgctgtagg tatctcagtt cggtgtaggt cgttcgctcc aagctgggct    18420
gtgtgcacga accccccgtt cagcccgacc gctgcgcctt atccggtaac tatcgtcttg    18480
```

```
agtccaaccc ggtaagacac gacttatcgc cactggcagc agccactggt aacaggatta   18540
gcagagcgag gtatgtaggc ggtgctacag agttcttgaa gtggtggcct aactacggct   18600
acactagaag aacagtattt ggtatctgcg ctctgctgaa gccagttacc ttcggaaaaa   18660
gagttggtag ctcttgatcc ggcaaacaaa ccaccgctgg tagcggtggt ttttttgttt   18720
gcaagcagca gattacgcgc agaaaaaaag gatctcaaga agatcctttg atcttttcta   18780
cggggtctga cgctcagtgg aacgaaaact cacgttaagg gattttggtc atgagattat   18840
caaaaaggat cttcacctag atccttttaa attaaaaatg aagttttaaa tcaatctaaa   18900
gtatatatga gtaaacttgg tctgacagtt accaatgctt aatcagtgag gcacctatct   18960
cagcgatctg tctatttcgt tcatccatag ttgcctgact ccccgtcgtg tagataacta   19020
cgatacggga gggcttacca tctggcccca gtgctgcaat gataccgcga gacccacgct   19080
caccggctcc agatttatca gcaataaacc agccagccgg aagggccgag cgcagaagtg   19140
gtcctgcaac tttatccgcc tccatccagt ctattaattg ttgccgggaa gctagagtaa   19200
gtagttcgcc agttaatagt ttgcgcaacg ttgttgccat tgctacaggc atcgtggtgt   19260
cacgctcgtc gtttggtatg gcttcattca gctccggttc ccaacgatca aggcgagtta   19320
catgatcccc catgttgtgc aaaaaagcgg ttagctcctt cggtcctccg atcgttgtca   19380
gaagtaagtt ggccgcagtg ttatcactca tggttatggc agcactgcat aattctctta   19440
ctgtcatgcc atccgtaaga tgcttttctg tgactggtga gtactcaacc aagtcattct   19500
gagaatagtg tatgcggcga ccgagttgct cttgcccggc gtcaatacgg gataataccg   19560
cgccacatag cagaacttta aaagtgctca tcattggaaa acgttcttcg ggcgaaaac    19620
tctcaaggat cttaccgctg ttgagatcca gttcgatgta acccactcgt gcacccaact   19680
gatcttcagc atcttttact ttcaccagcg tttctgggtg agcaaaaaca ggaaggcaaa   19740
atgccgcaaa aaagggaata agggcgacac ggaaatgttg aatactcata ctcttccttt   19800
ttcaatatta ttgaagcatt tatcagggtt attgtctcat gagcggatac atatttgaat   19860
gtatttagaa aaataaacaa ataggggttc cgcgcacatt tccccgaaaa gtgccacctg   19920
atgcggtgtg aaataccgca cagatgcgta aggagaaaat accgcatcag gaaattgtaa   19980
gcgttaatat tttgttaaaa ttcgcgttaa attttgtta  aatcagctca ttttttaacc   20040
aataggccga atcggcaaa  atcccttata aatcaaaaga atagaccgag ataggggttga  20100
gtgttgttcc agtttggaac aagagtccac tattaaagaa cgtggactcc aacgtcaaag   20160
ggcgaaaaac cgtctatcag ggcgatggcc cactacgtga accatcaccc taatcaagtt   20220
ttttggggtc gaggtgccgt aaagcactaa atcggaaccc taaagggagc ccccgattta   20280
gagcttgacg gggaaagccg gcgaacgtgg cgagaaagga agggaagaaa gcgaaaggag   20340
cgggcgctag ggcgctggca agtgtagcgg tcacgctgcg cgtaaccacc acacccgccg   20400
cgcttaatgc gccgctacag ggcgcgtcca ttcgccattc aggctgcgca actgttggga   20460
agggcgatcg gtgcgggcct cttcgctatt acgccagctg gcgaaagggg gatgtgctgc   20520
aaggcgatta agttgggtaa cgccaggggt ttcccagtca cgacgttgta aaacgacggc   20580
cagtgaattg taatacgact cactata                                       20607
```